(12) United States Patent
Bartlett et al.

(10) Patent No.: US 11,851,438 B2
(45) Date of Patent: Dec. 26, 2023

(54) 1'-CYANO NUCLEOSIDE ANALOGS AND METHODS FOR TREATMENT OF VIRAL INFECTIONS

(71) Applicant: Gilead Sciences, Inc., Foster City, CA (US)

(72) Inventors: Mark J. Bartlett, Castro Valley, CA (US); Daniel H. Byun, Foster City, CA (US); Yifan Deng, Milpitas, CA (US); Jennifer L. Cosman Ellis, Foster City, CA (US); Rao V. Kalla, Cupertino, CA (US); Richard L. Mackman, Millbrae, CA (US); Dustin S. Siegel, Half Moon Bay, CA (US); Xianhuang Zeng, Redwood City, CA (US)

(73) Assignee: Gilead Sciences, Inc., Foster City, CA (US)

(*) Notice: Subject to any disclaimer, the term of this patent is extended or adjusted under 35 U.S.C. 154(b) by 0 days.

(21) Appl. No.: 18/117,878

(22) Filed: Mar. 6, 2023

(65) Prior Publication Data

US 2023/0279014 A1 Sep. 7, 2023

Related U.S. Application Data

(63) Continuation of application No. 18/115,955, filed on Mar. 1, 2023.

(60) Provisional application No. 63/434,993, filed on Dec. 23, 2022, provisional application No. 63/424,083, filed on Nov. 9, 2022, provisional application No. 63/390,421, filed on Jul. 19, 2022, provisional application No. 63/315,769, filed on Mar. 2, 2022.

(51) Int. Cl.
*A61K 31/341* (2006.01)
*C07D 307/20* (2006.01)
*C07D 487/04* (2006.01)
*A61P 31/14* (2006.01)

(52) U.S. Cl.
CPC ............ *C07D 487/04* (2013.01); *A61P 31/14* (2018.01)

(58) Field of Classification Search
CPC ............................. A61K 31/341; C07D 307/20
USPC .......................................... 514/473; 549/476
See application file for complete search history.

(56) References Cited

U.S. PATENT DOCUMENTS

| | | | |
|---|---|---|---|
| 4,816,570 A | 3/1989 | Farquhar | |
| 4,968,788 A | 11/1990 | Farquhar | |
| 5,663,159 A | 9/1997 | Starrett, Jr. et al. | |
| 5,792,756 A | 8/1998 | Starrett, Jr. et al. | |
| 6,312,662 B1 | 11/2001 | Erion et al. | |
| 6,475,985 B1 | 11/2002 | Wagner et al. | |
| 6,476,030 B1 | 11/2002 | Carling et al. | |
| 6,656,915 B1 | 12/2003 | Bantia et al. | |
| 6,909,011 B2 | 6/2005 | Skranc et al. | |
| 7,078,403 B1 | 7/2006 | Wu et al. | |
| 7,105,493 B2 | 9/2006 | Sommadossi et al. | |
| 7,125,855 B2 | 10/2006 | Bhat et al. | |
| 7,166,604 B2 | 1/2007 | Watson et al. | |
| 7,176,203 B2 | 2/2007 | Chambers et al. | |
| 7,268,119 B2 | 9/2007 | Cook et al. | |
| 7,285,658 B2 | 10/2007 | Cook et al. | |
| 7,368,437 B1 | 5/2008 | Bojack et al. | |
| 7,390,791 B2 | 6/2008 | Becker et al. | |
| 7,429,571 B2 | 9/2008 | Chand et al. | |
| 7,514,410 B2 | 4/2009 | Babu et al. | |
| 7,560,434 B2 | 7/2009 | Babu et al. | |
| 7,598,230 B2 | 10/2009 | Cook et al. | |
| 7,608,597 B2 | 10/2009 | Sommadossi et al. | |
| 7,713,941 B2 | 5/2010 | Cook et al. | |
| 7,803,788 B2 | 9/2010 | Becker et al. | |
| 7,807,653 B2 | 10/2010 | Cook et al. | |
| 7,842,672 B2 | 11/2010 | Boojamra et al. | |
| 7,951,787 B2 | 5/2011 | McGuigan | |
| 7,973,013 B2 | 7/2011 | Cho et al. | |
| 7,994,139 B2 | 8/2011 | Babu et al. | |
| 8,008,264 B2 | 8/2011 | Butler et al. | |
| 8,012,941 B2 | 9/2011 | Cho et al. | |
| 8,012,942 B2 | 9/2011 | Butler et al. | |
| 8,071,568 B2 | 12/2011 | Narjes et al. | |
| 8,119,607 B2 | 2/2012 | Francom et al. | |
| 8,242,085 B2 | 8/2012 | Babu et al. | |
| 8,318,682 B2 | 11/2012 | Butler et al. | |
| 8,415,308 B2 | 4/2013 | Cho et al. | |

(Continued)

FOREIGN PATENT DOCUMENTS

| | | |
|---|---|---|
| CN | 110330540 | 10/2019 |
| CN | 110776512 | 2/2020 |

(Continued)

OTHER PUBLICATIONS

Adlington et al., "Synthesis of novel C-nucleosides with potential applications in combination and parallel synthesis," Tetrahedron Letters, 2000, 41:575-578.

(Continued)

*Primary Examiner* — Douglas M Willis
(74) *Attorney, Agent, or Firm* — Fish & Richardson P.C.

(57) ABSTRACT

1'-Cyano nucleoside analogs of Formula I and methods of using said compounds, singly or in combination with additional agents, and salts or pharmaceutical compositions of said compounds for the treatment of viral infections are disclosed.

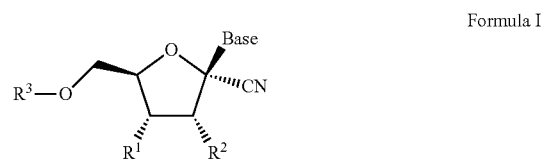

Formula I

16 Claims, 2 Drawing Sheets

(56) References Cited

U.S. PATENT DOCUMENTS

| | | |
|---|---|---|
| 8,455,451 B2 | 6/2013 | Cho et al. |
| 8,853,171 B2 | 10/2014 | Butler et al. |
| 8,871,737 B2 | 10/2014 | Smith et al. |
| 8,889,159 B2 | 11/2014 | Clearly et al. |
| 8,980,865 B2 | 3/2015 | Wang |
| 9,090,642 B2 | 7/2015 | Cho et al. |
| 9,243,022 B2 | 1/2016 | Beigelman et al. |
| 9,249,174 B2 | 2/2016 | Beigelman et al. |
| 9,278,990 B2 | 3/2016 | Smith et al. |
| 9,388,208 B2 | 7/2016 | Clarke et al. |
| 9,393,256 B2 | 7/2016 | Ray et al. |
| 9,452,154 B2 | 9/2016 | Delaney et al. |
| 9,481,703 B2 | 11/2016 | Kalayanov et al. |
| 9,487,544 B2 | 11/2016 | Cho et al. |
| 9,504,701 B2 | 11/2016 | Casola et al. |
| 9,540,411 B2 | 1/2017 | Kalayanov et al. |
| 9,549,941 B2 | 1/2017 | Cleary et al. |
| 9,605,018 B2 | 3/2017 | Wang et al. |
| 9,616,076 B2 | 4/2017 | Casola et al. |
| 9,701,682 B2 | 7/2017 | Clarke et al. |
| 9,724,360 B2 | 8/2017 | Chun et al. |
| 9,828,408 B2 | 11/2017 | Kalayanov |
| RE46,762 E | 3/2018 | Butler et al. |
| 9,949,994 B2 | 4/2018 | Chun et al. |
| 10,023,600 B2 | 7/2018 | Butler et al. |
| 10,034,893 B2 | 7/2018 | Luly et al. |
| 10,059,716 B2 | 8/2018 | Clarke et al. |
| 10,065,958 B2 | 9/2018 | Mackman et al. |
| 10,251,898 B2 | 4/2019 | Chun et al. |
| 10,251,904 B2 | 4/2019 | Clarke et al. |
| 10,377,761 B2 | 8/2019 | Clarke et al. |
| RE47,589 E | 9/2019 | McGuigan |
| 10,675,296 B2 | 6/2020 | Larson |
| 10,682,368 B2 | 6/2020 | Perron et al. |
| 10,695,357 B2 | 6/2020 | Chun et al. |
| 10,695,361 B2 | 6/2020 | Clarke et al. |
| 10,696,679 B2 | 6/2020 | Mackman et al. |
| 10,836,787 B2 | 11/2020 | Brak et al. |
| 10,988,498 B2 | 4/2021 | Butler et al. |
| 11,007,208 B2 | 5/2021 | Clarke et al. |
| 11,260,070 B2 | 3/2022 | Perron et al. |
| 11,266,666 B2 | 3/2022 | Chun et al. |
| 11,266,681 B2 | 3/2022 | Larson et al. |
| 11,344,565 B2 | 5/2022 | Axt et al. |
| 11,377,456 B2 | 7/2022 | Souza et al. |
| 11,382,926 B2 | 7/2022 | Clarke et al. |
| 11,491,169 B2 | 11/2022 | Cihlar |
| 11,492,353 B2 | 11/2022 | Mackman et al. |
| 11,541,071 B1 | 1/2023 | Liang et al. |
| 11,597,742 B2 | 3/2023 | Brak et al. |
| 11,613,553 B2 | 3/2023 | Badalov et al. |
| 11,660,307 B2 | 5/2023 | Cihlar et al. |
| 11,701,372 B2 | 7/2023 | Ellis et al. |
| 2003/0050229 A1 | 3/2003 | Sommadossi et al. |
| 2003/0092775 A1 | 5/2003 | Ernst et al. |
| 2004/0006002 A1 | 1/2004 | Sommadossi et al. |
| 2004/0023901 A1 | 2/2004 | Cook et al. |
| 2004/0063658 A1 | 4/2004 | Roberts et al. |
| 2004/0067901 A1 | 4/2004 | Bhat et al. |
| 2004/0138170 A1 | 7/2004 | Montgomery et al. |
| 2005/0187180 A1 | 8/2005 | Loeb et al. |
| 2005/0209166 A1 | 9/2005 | Eckhardt et al. |
| 2005/0215513 A1 | 9/2005 | Boojamra et al. |
| 2005/0250728 A1 | 11/2005 | Bantia et al. |
| 2006/0058303 A1 | 3/2006 | Chambers et al. |
| 2006/0142238 A1 | 6/2006 | McGuigan |
| 2006/0241064 A1 | 10/2006 | Roberts et al. |
| 2008/0107628 A1 | 5/2008 | Boojamra et al. |
| 2008/0161324 A1 | 7/2008 | Johansen et al. |
| 2008/0280842 A1 | 11/2008 | MacCoss et al. |
| 2009/0004138 A1 | 1/2009 | Francom et al. |
| 2009/0221524 A1 | 9/2009 | Kotra et al. |
| 2009/0233879 A1 | 9/2009 | Reddy et al. |
| 2009/0317361 A1 | 12/2009 | Cho et al. |
| 2010/0015094 A1 | 1/2010 | Babu et al. |
| 2010/0016251 A1 | 1/2010 | Sofia et al. |
| 2010/0021425 A1 | 1/2010 | Butler et al. |
| 2010/0035835 A1 | 2/2010 | Narjes et al. |
| 2010/0035836 A1 | 2/2010 | Francom et al. |
| 2010/0065512 A1 | 3/2010 | Bjorsvik |
| 2010/0203015 A1 | 8/2010 | Butler et al. |
| 2010/0234584 A1 | 9/2010 | Chang |
| 2010/0249068 A1 | 9/2010 | Beigelman et al. |
| 2010/0291031 A2 | 11/2010 | Francom et al. |
| 2010/0298257 A1 | 11/2010 | Ross et al. |
| 2010/0305202 A1 | 12/2010 | Hwang et al. |
| 2011/0070194 A1 | 3/2011 | Cho et al. |
| 2011/0084230 A1 | 4/2011 | Knochel et al. |
| 2011/0230654 A1 | 9/2011 | Butler et al. |
| 2011/0257122 A1 | 10/2011 | Sofia et al. |
| 2011/0293563 A1 | 12/2011 | Butler et al. |
| 2012/0009147 A1 | 1/2012 | Cho et al. |
| 2012/0020921 A1 | 1/2012 | Cho et al. |
| 2012/0027752 A1 | 2/2012 | Mackman et al. |
| 2012/0071434 A1 | 3/2012 | Smith et al. |
| 2012/0107274 A1 | 5/2012 | Clarke et al. |
| 2013/0034521 A1 | 2/2013 | Butler et al. |
| 2013/0143835 A1 | 6/2013 | Eneroth et al. |
| 2013/0281686 A1 | 10/2013 | Cho et al. |
| 2013/0315868 A1 | 11/2013 | Mayes |
| 2013/0344028 A2 | 12/2013 | Butler et al. |
| 2014/0219958 A1 | 8/2014 | Luly et al. |
| 2015/0031687 A1 | 1/2015 | Guo et al. |
| 2015/0111839 A1 | 4/2015 | Mackman et al. |
| 2015/0133395 A1 | 5/2015 | Clarke et al. |
| 2015/0152116 A1 | 6/2015 | Mackman et al. |
| 2015/0210682 A1 | 7/2015 | Han et al. |
| 2015/0252057 A1 | 9/2015 | Guo et al. |
| 2016/0058779 A1 | 3/2016 | Casola et al. |
| 2016/0122344 A1 | 5/2016 | Han et al. |
| 2016/0122356 A1 | 5/2016 | Axt et al. |
| 2016/0122374 A1 | 5/2016 | Chun |
| 2016/0176899 A1 | 6/2016 | Schwitter et al. |
| 2016/0220586 A1 | 8/2016 | Andre et al. |
| 2016/0237090 A1 | 8/2016 | Hu et al. |
| 2017/0071964 A1 | 3/2017 | Clark et al. |
| 2018/0346504 A1 | 12/2018 | Brak et al. |
| 2019/0083525 A1 | 3/2019 | Larson |
| 2020/0197422 A1 | 6/2020 | Axt et al. |
| 2020/0360420 A1 | 11/2020 | Larson |
| 2020/0376014 A1 | 12/2020 | Perron et al. |
| 2021/0052613 A1 | 2/2021 | Chun et al. |
| 2021/0061806 A1 | 3/2021 | Mackman et al. |
| 2021/0283150 A1 | 9/2021 | Cihlar et al. |
| 2021/0309689 A1 | 10/2021 | Badalov et al. |
| 2021/0330685 A1 | 10/2021 | Ellis et al. |
| 2021/0393653 A1 | 12/2021 | Cihlar et al. |
| 2021/0393659 A1 | 12/2021 | Clarke et al. |
| 2021/0403497 A1 | 12/2021 | Butler et al. |
| 2022/0081462 A1 | 3/2022 | Chun et al. |
| 2022/0175805 A1 | 6/2022 | Cihlar |
| 2022/0280549 A1 | 9/2022 | Larson et al. |
| 2022/0354873 A1 | 11/2022 | Axt et al. |
| 2022/0356196 A1 | 11/2022 | Byun et al. |
| 2023/0027727 A1 | 1/2023 | Clarke et al. |
| 2023/0040586 A1 | 2/2023 | Byun et al. |
| 2023/0125751 A1 | 4/2023 | Mackman et al. |
| 2023/0151043 A1 | 5/2023 | Bunyan et al. |
| 2023/0233587 A1 | 7/2023 | Cihlar |

FOREIGN PATENT DOCUMENTS

| | | |
|---|---|---|
| CN | 111171078 | 5/2020 |
| CN | 111205294 | 5/2020 |
| CN | 111205327 | 5/2020 |
| CN | 111233869 | 6/2020 |
| CN | 111265532 | 6/2020 |
| CN | 111440176 | 7/2020 |
| CN | 111548384 | 8/2020 |
| CN | 111961057 | 11/2020 |
| CN | 202011613943.3 | 12/2020 |
| CN | 112778310 | 5/2021 |
| CN | 202110562244.9 | 5/2021 |
| CN | 113754665 | 6/2021 |

(56) References Cited

FOREIGN PATENT DOCUMENTS

| | | |
|---|---|---|
| CN | 113185519 | 7/2021 |
| CN | 113248508 | 8/2021 |
| CN | 113292565 | 8/2021 |
| CN | 113387954 | 9/2021 |
| CN | 113735862 | 9/2021 |
| CN | 113698405 | 11/2021 |
| CN | 114292272 | 12/2021 |
| CN | 113999237 | 1/2022 |
| CN | 114181258 | 3/2022 |
| CN | 114409655 | 4/2022 |
| CN | 114437159 | 5/2022 |
| CN | 114621229 | 6/2022 |
| CN | 114765979 | 7/2022 |
| CN | 115521316 | 12/2022 |
| CN | 115583954 | 1/2023 |
| CN | 116172966 | 5/2023 |
| IN | 202121023147 | 5/2021 |
| IN | 202134041493 | 9/2021 |
| IN | 202011021676 | 11/2021 |
| JP | 2005185235 | 7/2005 |
| JP | 2005187428 | 7/2005 |
| WO | WO1991019721 | 12/1991 |
| WO | WO1999045029 | 9/1999 |
| WO | WO2000056734 | 9/2000 |
| WO | WO2000075157 | 12/2000 |
| WO | WO2001032153 | 5/2001 |
| WO | WO2001060315 | 8/2001 |
| WO | WO2001090121 | 11/2001 |
| WO | WO2001091737 | 12/2001 |
| WO | WO2001092282 | 12/2001 |
| WO | WO2002008241 | 1/2002 |
| WO | WO2002018404 | 3/2002 |
| WO | WO2002032920 | 4/2002 |
| WO | WO2002057287 | 7/2002 |
| WO | WO2002057425 | 7/2002 |
| WO | WO2003093272 | 11/2003 |
| WO | WO2003093273 | 11/2003 |
| WO | WO2003100009 | 12/2003 |
| WO | WO2004046159 | 6/2004 |
| WO | WO2004046331 | 6/2004 |
| WO | WO2004112687 | 12/2004 |
| WO | WO2005009418 | 2/2005 |
| WO | WO2005092877 | 10/2005 |
| WO | WO2005123087 | 12/2005 |
| WO | WO2006031725 | 3/2006 |
| WO | WO2006050161 | 5/2006 |
| WO | WO2006064033 | 6/2006 |
| WO | WO2006065335 | 6/2006 |
| WO | WO2006121820 | 11/2006 |
| WO | WO2006135978 | 12/2006 |
| WO | WO2007027248 | 3/2007 |
| WO | WO2007056170 | 5/2007 |
| WO | WO2007062542 | 6/2007 |
| WO | WO2007064883 | 6/2007 |
| WO | WO2007064931 | 6/2007 |
| WO | WO2007065289 | 6/2007 |
| WO | WO2007065829 | 6/2007 |
| WO | WO2007095269 | 8/2007 |
| WO | WO2007097991 | 8/2007 |
| WO | WO2007113294 | 10/2007 |
| WO | WO2007135134 | 11/2007 |
| WO | WO2008005542 | 1/2008 |
| WO | WO2008011406 | 1/2008 |
| WO | WO2008055870 | 5/2008 |
| WO | WO2008079206 | 7/2008 |
| WO | WO2008082601 | 7/2008 |
| WO | WO2008085508 | 7/2008 |
| WO | WO2008089105 | 7/2008 |
| WO | WO2008116064 | 9/2008 |
| WO | WO2008121634 | 10/2008 |
| WO | WO2008141079 | 11/2008 |
| WO | WO2009009951 | 1/2009 |
| WO | WO2009018609 | 2/2009 |
| WO | WO2009131926 | 10/2009 |
| WO | WO2009132123 | 10/2009 |
| WO | WO2009132135 | 10/2009 |
| WO | WO2010002877 | 1/2010 |
| WO | WO2010036407 | 4/2010 |
| WO | WO2010039548 | 4/2010 |
| WO | WO2010093608 | 8/2010 |
| WO | WO2010099458 | 9/2010 |
| WO | WO2010108140 | 9/2010 |
| WO | WO2010135569 | 11/2010 |
| WO | WO2011011303 | 1/2011 |
| WO | WO2010111381 | 3/2011 |
| WO | WO2011035231 | 3/2011 |
| WO | WO2011035250 | 3/2011 |
| WO | WO2011080568 | 7/2011 |
| WO | WO2011100131 | 8/2011 |
| WO | WO2011123645 | 10/2011 |
| WO | WO2011123668 | 10/2011 |
| WO | WO2011123672 | 10/2011 |
| WO | WO2011150288 | 12/2011 |
| WO | WO2012012465 | 1/2012 |
| WO | WO2012012776 | 1/2012 |
| WO | WO2012039787 | 3/2012 |
| WO | WO2012039791 | 3/2012 |
| WO | WO2012051570 | 4/2012 |
| WO | WO2012040127 | 5/2012 |
| WO | WO2012121764 | 9/2012 |
| WO | WO2012142523 | 10/2012 |
| WO | WO2012158643 | 11/2012 |
| WO | WO2013084165 | 6/2013 |
| WO | WO2014033617 | 3/2014 |
| WO | WO2014042433 | 3/2014 |
| WO | WO2014078463 | 5/2014 |
| WO | WO2014078778 | 5/2014 |
| WO | WO2014116755 | 7/2014 |
| WO | WO2014169280 | 10/2014 |
| WO | WO2014209979 | 12/2014 |
| WO | WO2016107833 | 12/2014 |
| WO | WO2015054465 | 4/2015 |
| WO | WO2015069939 | 5/2015 |
| WO | WO2015173164 | 11/2015 |
| WO | WO2015200205 | 12/2015 |
| WO | WO2015200219 | 12/2015 |
| WO | WO2016012470 | 1/2016 |
| WO | WO2016023877 | 2/2016 |
| WO | WO2016069825 | 5/2016 |
| WO | WO2016069826 | 5/2016 |
| WO | WO2016069827 | 5/2016 |
| WO | WO2016102438 | 6/2016 |
| WO | WO2016107832 | 7/2016 |
| WO | WO2016120186 | 8/2016 |
| WO | WO2016128335 | 8/2016 |
| WO | WO2017049060 | 3/2017 |
| WO | WO2017165489 | 9/2017 |
| WO | WO2017184668 | 10/2017 |
| WO | WO2018085307 | 5/2018 |
| WO | WO2018121678 | 7/2018 |
| WO | WO2018145148 | 8/2018 |
| WO | WO2018204198 | 11/2018 |
| WO | WO2019014247 | 1/2019 |
| WO | WO2019053696 | 3/2019 |
| WO | WO2022098371 | 11/2020 |
| WO | WO2021021717 | 2/2021 |
| WO | WO2021040356 | 3/2021 |
| WO | WO2021050961 | 3/2021 |
| WO | WO2021147236 | 7/2021 |
| WO | WO2021175296 | 9/2021 |
| WO | WO2021195661 | 9/2021 |
| WO | WO2022142477 | 9/2021 |
| WO | WO2021202907 | 10/2021 |
| WO | WO2021207049 | 10/2021 |
| WO | WO2021213288 | 10/2021 |
| WO | WO2021222807 | 11/2021 |
| WO | WO2022143473 | 12/2021 |
| WO | WO2022008642 | 1/2022 |
| WO | WO2022029704 | 2/2022 |
| WO | WO2022047065 | 3/2022 |
| WO | WO2022047441 | 3/2022 |
| WO | WO2022165386 | 8/2022 |
| WO | WO2022174194 | 8/2022 |
| WO | WO2022217153 | 10/2022 |

(56) References Cited

FOREIGN PATENT DOCUMENTS

| WO | WO2022217154 | 10/2022 |
| WO | WO2022217155 | 10/2022 |
| WO | WO2022218274 | 10/2022 |
| WO | WO2022222994 | 10/2022 |
| WO | WO2022251663 | 12/2022 |
| WO | WO2022265964 | 12/2022 |
| WO | WO2023022216 | 2/2023 |
| WO | WO2023078416 | 5/2023 |

OTHER PUBLICATIONS

Agostini et al., "Coronavirus Susceptibility to the Antiviral Remdesivir (GS5734) Is Mediated by the Viral Polymerase and the Proofreading Exoribonuclease", MBIO, Mar. 6, 2018, 9(2):1-15.

Alessandrini, et al., Synthesis of Differently Protected 1-C-methyl-ribofuranoses Intermediates for the Preparation of Biologically Active 1'-C-methyl-ribonucleosides, Journal of Carbohydrate Chemistry, 2008, pp. 332-344, vol. 27, No. 5.

Ali, et al., Quantitative structure-activity relationships (QSAR) of two series of O-aryl or N-acyl O-ethyl phosphoramidate and phosphorodiamidate fungicides incorporating amino acid ethyl esters, Bulletin of Environmental Contamination and Toxicology, 2000, pp. 415-420, vol. 65, No. 4.

Anonymous [online], "University of Alabama & Multi-Center Collaboration Help Develop Remdesivir with Gilead Thanks to $37.5m from NIH," TrialSiteNews.com, retrieved on Mar. 13, 2023, URL <https://www.trialsitenews.com/a/university-of-alabama-multi-center-collaboration-help-develop-remdesivir-with-gilead-thanks-to-37-5m-from-nih>, Mar. 1, 2020, 5 pages.

Anonymous, "Gillings research on broad-spectrum antiviral could aid public health response to coronavirus outbreaks", -UNC Gillings School of Global Public Health, Jan. 10, 2020, retrieved on May 13, 2021, retrieved from URL <"https://sph.unc.edu/sph-news/gillings-research-on-broad-spectrum-antiviral-could-aid-public-health-response-to-coronavirus-outbreaks/">, 5 pages.

Arimilli, et al., Synthesis, In Vitro Biological Evaluation and Oral Bioavailability of 9-[2-(phosphonomethoxy)propyl]adenine (PMPA) Prodrugs, Antiviral Chemistry & Chemotherapy, 1997, pp. 557-564, vol. 8, No. 6.

Asbun, et al., Synthesis of 5-substituted Pyrimidines. II, Journal of Organic Chemistry, 1968, pp. 140-142, vol. 31.

Ballini, et al., Enantioselective Synthesis of the Lactone Moiety of the Mevinic Acids using D-Xylose as a Chiral Precursor, Journal of the Chemical Society, Perkin Transactions 1, 1991, pp. 490-491.

Balzarini, et al., Inhibition of Feline (FIPV) and Human (SARS) Coronavirus by Semisynthetic Derivatives of Glycopeptide Antibiotics, Antiviral Research, 2006, pp. 20-33, vol. 72.

Bandini, et al., Indium tribromide: a highly effective catalyst for the addition of trimethylsilyl cyanide to α-hetero-substituted ketone, Tetrahedron Letters, 2001, pp. 3041-3043. vol. 42.

Barker, et al., 2,3,5-Tri-O-benzyl-D-ribosyl and -L-arabinosyl Bromides, Journal of Organic Chemistry, 1961, pp. 4605-4609, vol. 26, No. 11.

Barl, et al., The halogen/magnesium-exchange using iPrMgCl•LiCl and related exchange reagents, Heterocycles, Jan. 2014, pp. 827-844, vol. 88, No. 2.

Beer et al., "Characteristics of Filoviridae: Marburg and Ebola Viruses," Naturwissenschaften, 1999, 86:8-17.

Behzadi et al., "Overview of Current Therapeutics and Novel Candidates Against Influenza Respiratory Syncytial Virus, and Middle East Respiratory Syndrome Coronavirus Infections," Frontiers in Microbiology, Jun. 2019, 10:1327, pp. 1-16.

Belokon et al., "Optimized catalysts for the asymmetric addition of trimethylsilyl cyanide to aldehydes and ketones," Tetrahedron, 2001, 57: 771-779.

Benksim et al., "A Novel Stereospecific Synthesis of Glycosyl Cyanides from 1,2-O-sulfinyl Derivatives," Organic Letters, 2004, 6(22): 3913-3915.

Benzaria et al., "Synthesis, In Vitro Antiviral Evaluation, and Stability Studies of Bis(S-acyl-2-thioethyl) Ester Derivatives of 9-[2-(phosphonomethoxy)ethyl]adenine (PMEA) as Potential PMEA prodrugs with Improved Oral Bioavailability," J. Med. Chem., 1996, 39(25): 4958-4965.

Bio et al., "Practical Synthesis of a Potent Hepatitis C Virus RNA Replication Inhibitor," J. Org. Chem., 2004, 69(19): 6257-6266.

Bobeck et al., "Advances in Nucleoside Monophosphate Prodrugs as Anti-HCV Agents," Antiviral Therapy, 2010, 15: 935-950.

Bobrowski et al., "Synergistic and Antagonistic Drug Combinations against SARS-CoV-2", Molecular Therapy, Feb. 2021, 29(2):873-885.

Bojack, et al., Design and Synthesis of Inhibitors of Adenosine and AMP Deaminases, Organic Letters, 2001, pp. 839-842, vol. 3, No. 6.

Bowie et al., "RIG-I: tri-ing to discriminate between self and non-self RNA," Trends in Immunology, Apr. 2007, 28(4): 147-150.

Boyer, et al., Pathogenesis, diagnosis and management of hepatitis C, Journal of Hepatology, 2000, pp. 98-112, vol. 32.

Bozza, Zika Outbreak, Brazil 2015, ISARIC, 2015, 28 pages.

Bradley et al., "The Management of Community-Acquired Pneumonia in Infants and Children Older Than 3 Months of Age: Clinical Practice Guidelines by the Pediatric Infectious Diseases Society and the Infectious Diseases Society of America", Pediatric Community Pneumonia Guidelines, Clinical Infectious Diseases, Oct. 2011, 53(7):e25-e76.

Brands et al., "Crystallization-Induced Diastereomer Transformations," Chem. Rev., 2006, 106(7): 2711-2733.

Brittain, Polymorphism in Pharmaceutical Solids, 2nd Edition, 2009, pp. 183-226, Informa Healthcare USA, Inc.

Brotschi et al., "Bipyridyl and biphenyl DNA: A recognition motif based on interstrand aromatic stacking," Chemistry—A European Journal, 2005, 11(6):1911-1923.

Brown et al., "Broad spectrum antiviral remdesivir inhibits human endemic and zoonotic deltacoronaviruses with a highly divergent RNA dependent RNA polymerase", Antiviral Research, Jun. 21, 2019, 169:1-31.

Brown, "Progress towards improving antiviral therapy for hepatitis C virus polymerase inhibitors", Part O: Nucleoside analogues, 2009, 18: 709-725.

Bullard-Feibelman et al., "The FDA-approved drug Sofosbuvir inhibits Zika Virus infection," Antiviral Res., Jan. 1, 2018, 137: 134-140.

Burns, "A Glimmer of Hope for Fatal Feline Disease," JAVMAnews, Dec. 15, 2017, 5 pages.

Butora et al., "Synthesis and HCV inhibitory properties of 9-deaza- and 7,9-dideaza-7-oxa-2'-C-methyladenosine," Bioorganic & Medicinal Chemistry, 2007, 15(15):5219-5229.

Cabirol et al., Robust and Efficient, yet Uncatalyzed, Synthesis of Triarylsilyl-protected Cyanohydrins from Ketones, 2008, pp. 2446-2449, vol. 73.

Caira, "Crystalline Polymorphism of Organic Compounds," Topics in Current Chemistry, 1998, 198: 163-208.

Cales et al., "Treatment of liver fibrosis: clinical aspects," Gastroentérologie Clinique et Biologique, 2009, 33(10-11): 958-966.

Calisher et al., "Antigenic Relationships between Flaviviruses as Determined by Cross-neutralization Tests with Polyclonal Antisera," Journal of General Virology, 1989, 70: 37-43.

Camps, "Studies on Structurally Simple-αβ-butenolides-II," Tetrahedron, 1982, 38(15): 2395-2402.

Carey et al., "Addition, Condensation and Substitution Reactions of Carbonyl Compounds," Advanced Organic Chemistry: Part B: Reaction and Synthesis, Springer Science & Business Media, 2007, pp. 629-711.

Carroll, "Robust Antiviral Efficacy upon Administration of a Nucleoside Analog to Hepatitis C Virus-Infected Chimpanzees," Antimicrobial Agents and Chemotherapy, 2009, 53(3): 926-934.

Carryer et al., "The effect of cortisone on bronchial asthma and hay fever occurring in subjects sensitive to ragweed pollen", Journal of Allergy, Jul. 1950, 21(4): 282-287.

(56) References Cited

OTHER PUBLICATIONS

CAS No. 1476-52-4, "Desethyl Chloroquine", ChemSRc, retrieved on Jul. 29, 2021, retrieved from URL <"https://www.chemsrc.com/en/cas/1476-52-4_1032909.html">, 5 pages.
CAS No. 4298-15-1, "2-[4-[(7-chloroquinolin-4-yl)amino]pentylamino]ethanol", ChemSRc, retrieved on Jul. 29, 2021, retrieved from URL <"https://www.chemsrc.com/en/cas/4298-15-1_589766.html">, 4 pages.
CAS No. 54-05-7, "Chloroquine", ChemSRc, retrieved on Jul. 29, 2021, retrieved from URL <"https://www.chemsrc.com/en/cas/54-05-7_419322.html">, 16 pages.
CAS Registry No. 1809249-37-3, "L-Alanine, N-[(S)-hydroxyphenoxyphosphinyl]-, 2-ethylbutyl ester, 6-ester with 2-C-(4-aminopyrrolo[2,1-f][1,2,4]triazin-7-yl)-2,5-anhydro-D-altrononitrile", American Cemical Society, retrieved on Jul. 27, 2021, retrieved from URL <"https://commonchemistry.cas.org/detail?cas_rn=1809249-37-3">, 3 pages.
Chapman et al., "RSV604, a Novel Inhibitor of Respiratory Syncytial Virus Replication," Antimicrobial Agents and Chemotherapy, 2007, 51(9): 3346-3353.
Cho et al., "Discovery of the First C-Nucleoside HCV Polymerase Inhibitor (GS-6620) with Demonstrated Antiviral Response in HCV Infected Patients," J. Med. Chem., 2014, 57(5): 1812-1825.
Cho et al., "Synthesis and antiviral Activity of a Series of 1'-Substituted 4-aza-7,9-dideazaadenosine C-Nucleosides", Bioorganic & Medicinal Chemistry Letters, 2012, 22(8):2705-2707.
Cihlar et al., "Design and Profiling of GS-9148, a Novel Nucleotide Analog Active against Nucleoside-resistant Variants of Human Immunodeficiency Virus Type 1, and Its Orally Bioavailable Phosphonoamidate Prodrug, GS-9131," Antimicrobial Agents and Chemotherapy, 2008, 52(2): 655-665.
Clark et al., "Design, Synthesis, and Antiviral Activity of 2'-Deoxy-2'-fluoro-2'-C-methylcytidine, a Potent Inhibitor of Hepatitis C Virus Replication," Journal of Medicinal Chemistry, 2005, 48(17): 5504-5508.
Clarke et al., "Discovery of beta-D-2'-Deoxy-2'-alpha-Fluoro-4'-alpha-Cyano-5-aza-7,9-Dideaza Adenosine as a Potent Nucleoside Inhibitor of Respiratory Syncytial Virus with Excellent Selectivity Over Mitochondrial RNA and DNA Polymerases," Bioorganic & Medicinal Chemistry Letters, Apr. 29, 2015, 25: 2484-2487.
Colacino et al., "Synthesis and Biological Evaluation of Some 5-Nitro- and 5-Amino Derivatives of 2'-Deoxycytidine, 2',3'-Dideoxyuridine, and 2',3'-Dideoxycytidine," Nucleoside, Nucleotides & Nucleic Acids, 2003, 22(11): 2013-2026.
Cox et al., "Oral prodrug of remdesivir parent GS-441524 is efficacious against SARS-CoV-2 in ferrets," Nature Communications, Nov. 2021, 12(1):1-11.
Cox et al., "Therapeutically administered ribonucleoside analogue MK-4482/EIDD-2801 blocks SARS-CoV-2 transmission in ferrets," Nature Microbiology, 2020, 6(1):11-18.
Dai et al., "Synthesis of 2'-C-β-Fluoromethyluridine," Organic Letters, 2003, 5(6):807-810.
Damont et al., "Synthesis of 1'-C-Fluoromethyladenosine," Nucleosides, Nucleotides, and Nucleic Acids, 2007, 26:1431-1434.
De Clercq, "Antiviral Drugs: Current State of the Art," J. Clin. Virol., 2001, 22(1):73-89.
De Clercq, "Molecular Targets for Antiviral Agents," The Journal of Pharmacology and Experimental Therapeutics, 2001, 297(1): 1-10.
De Francesco et al., "Approaching a New Era for Hepatitis C Virus Therapy: Inhibitors of the NS3-4A Serine Protease and the NS5B RNA-Dependent RNA Polymerase," Antiviral Research, 2003, 58(1): 1-16.
De Las Heras, "Synthesis of Ribosyl and Arabinosyl Cyanides by Reaction of 1-O-Acyl Sugars with Trimethylsilyl Cyanide," Journal of the Chemical Society, Perkin Transactions 1, 1982, pp. 903-907.
De Lombaert et al., "N-Phosphonomethyl Dipeptides and Their Phosphonate Prodrugs, a New Generation of Neutral Endopeptidase (NEP, EC 3.4.24.11) Inhibitors," J. Med. Chem., 1994, 37(4): 498-511.

Di Bisceglie et al., "The Unmet Challenges of Hepatitis C," Scientific American, Oct. 1999, pp. 80-85.
Dinnon et al., "A mouse-adapted model of SARS-CoV-2 to test COVID-19 countermeasures," Nature, Aug. 2020, 586: 560-566.
Dolzhenko et al., "Pyrazolo[1,5-a][1,3,5]Triazines(5-Aza-9-Deazapurines): Synthesis and Biological Activity," Heterocycles, 2008, 75(7): 1575-1622.
Domingo et al., "The quasispecies (extremely heterogeneous) nature of viral RNA genome populations: biological relevance—a review," Gene, 1985, 40: 1-8.
Dondoni et al., "Thiazole-Based Synthesis of Formyl C-Glycosides," Journal of Organic Chemistry, 1994, 59: 6404-6414.
Dudfield et al., "Synthesis of C-ribosyl imidazo[2,1-f][1,2,4]triazines as inhibitors of adenosine and AMP deaminases," J. Chem. Soc, Perkin Trans I, 1999, pp. 2929-2936.
Dudfield et al., "Synthesis of C-ribosyl 1,2,4-triazolo[3,4-f][1,2,4]triazines as Inhibitors of Adenosine and AMP Deaminasses," J. Chem. Soc., Perkin Trans. 1, 1999, pp. 2937-2942.
Durcan et al., "Hydroxychloroquine Blood Levels in Systemic Lupus Erythematosus: Clarifying Dosing Controversies and Improving Adherence", Journal of Rheumatology, 2015, 42(11):2092-2097.
Dymock et al., "Novel approaches to the treatment of hepatitis C virus infection," Antiviral Chemistry & Chemotherapy, 2000, 11(2): 79-96.
El Safadi et al., "5-Modified-2'-dU and 2'-dC as Mutagenic Anti HIV-1 Proliferation Agents: Synthesis and Activity," Journal of Medicinal Chemistry, 2010, 53(4): 1534-1545.
Farquhar et al., "Biologically Reversible Phosphate-Protective Groups," Journal of Pharmaceutical Sciences, 1983, 72(3): 324-325.
Fauquet et al., "Abbreviations for vertebrate virus species names", Archives of Virology, Dec. 31, 1999, pp. 1865-1880.
fda.gov [online], "Remdesivir by Gilead Sciences: FDA Warns of Newly Discovered Potential Drug Interaction That May Reduce Effectiveness of Treatment," Jun. 15, 2020, retrieved on Sep. 2, 2022, retrieved from URL <https://www.fda.gov/safety/medical-product-safety-information/remdesivir-gilead-sciences-fda-warns-newly-discovered-potential-drug-interaction-may-reduce>, 2 pages.
Flint et al., "Functional analysis of cell surface-expressed hepatitis C virus E2 glycoprotein," J. Virol., Aug. 1999, 73(8): 6782-6790.
Foster et al., "Deuterium isotope effects in studies of drug metabolism," Trends in Pharmacological Sciences, Jan. 1984, 5:524-527.
Franchetti et al., "Antitumor Activity of C-Methyl-β-D-ribofuranosyladenine Nuceoside Ribonuceotide Reductase Inhibitors," J. Med. Chem. 2005, 48: 4983-4989.
Freeman et al., "3 Prodrug Design for Phosphates and Phosphonates," Progress in Medicinal Chemistry, 1997, 34: 111-147.
Fukumoto et al., "Viral Dynamics of Hepatitis C Early After Orthotopic Liver Transplantation: Evidence for Rapid Turnover of Serum Virions," Hepatology, 1996, 24: 1351-1354.
Garcia et al., "Synthesis of (2,3,4,6-tetra-O-acetyl-alpha-D-glycopyranosyl)thiophene derivatives as new C-nucleoside analogues," J. Carbohydrate Chemistry, 2001, 20(7/8): 681-687.
Gardelli et al., "Phosphoramidate Prodrugs of 2'-C-Methylcytidine for Therapy of Hepatitis C Virus Infection," Journal of Medicinal Chemistry, 2009, 52(17): 5394-5407.
George et al., "Preparation of silyl-and germylmetallic compounds," Journal of the American Chemical Society, Jan. 1960, 82(2):403-6.
Gleeson et al., "Prediction of the Potency of Inhibitors of Adenosine Deaminase by QM/MM Calculations." Chem. Commun., 2003, pp. 2180-2181.
Gordon et al., "Remdesivir is a direct-acting antiviral that inhibits RNA-dependent RNA polymerase from severe acute respiratory syndrome coronavirus 2 with high potency," J. Biol. Chem., 2020, 295(20):6785-6797.
Gordon et al., "The antiviral compound remdesivir potently inhibits RNA-dependent RNA polymerase from Middle East respiratory syndrome coronavirus," Journal of Biol. Chemistry, 2020, 295(15):4773-4779.
Gordon et al., Control of Hepatitis C: A Medicinal Chemistry Perspective, J. Med. Chem., 2005, pp. 1-20, vol. 48, No. 1.

(56) References Cited

OTHER PUBLICATIONS

Greene et al., "Protective Groups in Organic Synthesis," John Wiley & Sons., 1991, pp. 118-142.

Greene et al., "Protective Groups in Organic Synthesis," published by John Wiley & Sons, v Inc., 1991, pp. 1-4, 10-14, 47-53 and 100-103.

Grein et al., "Compassionate Use of Remdesivir for Patients with Severe Covid-19", The New England Journal of Medicine, Apr. 2020, 382(24): 2327-2336.

Gudmundsson et al., "Synthesis of imidazo[1,2-a]pyridine C-Nucleosides with an Unexpected Site of Ribosylation," Journal of Organic Chemistry, 1997, 62: 3453-3459.

Gudmundsson et al., "The Condensation of 2,6-dichloroimidazo[1,2-a]pyridine C-nucleoside with an Unexpected Site of Ribosylation," Tetrahedron Letters, 1996, 7(14): 2365-2368.

Gunic et al., "Cyclic monophosphate prodrugs of base-modified 2'-C-methyl ribonucleosides as potent inhibitors of hepatitis C virus RNA replication," Bioorganic & Medicinal Chemistry Letters, 2007, 17: 2452-2455.

Hamann et al., "Synthesis and antiviral evaluation of 7,9-dideaza-8-thiapurine C-nucleoside derivatives," Collection Symposium Series, 2008, 10: 347-349.

Hamann et al., "Synthesis and antiviral evaluation of thieno[3,4-d]pyrimidine C-nucleoside analogues of 2',3'-dideoxy- and 2',3'-dideoxy-2',3'-didehydro-adenosine and -inosine," Bioorganic & Medicinal Chemistry, 2009, 17: 2321-2326.

Han et al., "Synthesis of 1-Chloroacetyl-1-dehydroxy-2,3,5-tri-O-benzoyl-β-D-ribofuranose. A Potentially Versatile Intermediate for the Synthesis of C-Nucleosides," Synthetic Communications, 1992, 22(19): 2815-2822.

Haraguchi et al., "Stereoselective Synthesis of 1'-C-Branched Uracil Nucleosides From Uridine," Nucleosides & Nucleotides, 1995, 14(3-5): 417-420.

Harcourt et al., "Molecular Characterization of the Polymerase Gene and Genomic Termini of Nipah Virus," Virology, 2001, 287: 192-201.

Harki et al., "Synthesis and Antiviral Activity of 5-Substituted Cytidine Analogues: Identification of Potent Inhibitor of Viral RNA-Dependent RNA Polymerases," Journal of Medicinal Chemistry, 2006, 49(21): 6166-6169.

Hayashi et al., "C-Nucleosides, A Synthesis of 2-Substituted 7-(b-D-Ribofuranosyl)-Pyrrolo[2,1-f]-1,2,4-Triazines. A New Type of "Purine Like" C-Nucleoside," Heterocycles, 1992, 34(3): 569-574.

Hecker et al., "Liver Targeted Prodrugs of 2'-C-Methyladenosine for Therapy of Hepatitis C Virus Infection," J. Med. Chem., 2007, 50(16): 3891-3896.

Hoffmann et al., "When, in the context of drug design, can a fluorine atom successfully substitute a hydroxyl group?," International Journal of Quantum Chemistry, 2002, 89: 419-427.

Holshue et al., "First Case of 2019 Novel Coronavirus in the United States", The New England Journal of Medicine, Jan. 2020, 9 pages.

Huang et al., "Recent development of therapeutics for chronic HCV infection," Antiviral Research, Sep. 2006, 71(2-3): 351-362.

Itoh et al., "Divergent and Stereocontrolled Approach to the Synthesis of Uracil Nucleosides Branched at the Anomeric Position," J. Org. Chem, 1995, 60: 656-662.

Jasko et al., "5'-Phosphonates of Ribonucleosides and 2'-Deoxyribonucleosides: Synthesis and Antiviral Activity," Nucleosides & Nucleotides, 1993, 12(8): 879-893.

Jonckers et al., "2'Deoxy-2'-spirocyclopropylcytidine Revisited: A New and Selective Inhibitor of the Hepatitis C Virus NS5B Polymerase," Journal of Medicinal Chemistry, Nov. 2010, 53(22)8150-60.

Jones et al., "Di- and Triester Prodrugs of the Varicella-Zoster Antiviral Agent 6-Methoxypurine Arabinoside," Journal of Medicinal Chemistry, Jan. 1992, 35(1):56-63.

Joseph [online], "As the coronavirus spreads, a drug that once raised the world's hopes is given a second shot," StatNews.com, retrieved on Mar. 13, 2023, URL <https://www.statnews.com/2020/03/16/remdesivir-surges-ahead-against-coronavirus>, Mar. 16, 2020, 11 pages.

Kabat et al., "Nucleosides, CXLVIII, Synthesis of 6-(β-D-Ribofuranosyl)picolinamide: A Novel C-Nucleoside from D-Ribonolactone", Chemical & Pharmaceutical Bulletin, 1988, pp. 634-640, vol. 36, No. 2.

Kaewkhao et al., "High sensitivity methods to quantify chloroquine and its metabolite in human blood samples using LC-MS/MS", Bioanalysis, Mar. 2019, 11(5):333-347.

Kalil et al., "Baricitinib plus Remdesivir for hospitalized adults with Covid-19," New England Journal of Medicine, Dec. 11, 2020, 13 pages.

Khamnei et al., "Neighboring Group Catalysis in the Design of Nucleotide Prodrugs," J. Med. Chem., 1996, 39(20): 4109-4115.

Khan et al., "Coronaviruses disease 2019 (COVID-19): Causative agent, mental health concerns, and potential management options," Journal of Infection and Public Health, Dec. 2020, 13(12):1840-1844.

Kim et al., "Reversal of the Progression of Fatal Coronavirus Infection in Cats by a Broad-Spectrum Coronavirus Protease Inhibitor," PLOS Pathogens, Mar. 30, 2016, 18 pages.

Kim et al., "Synthesis and Evaluation of 2-Amino-6-fluoro-9-(4-hydroxy-3-hydroxymethylbut-1-yl) purine Mono- and Diesters as Potential Prodrugs of Penciclovir," Bioorganic & Medicinal Chemistry, Mar. 1999, 7(3):565-70.

Kim et al., "Synthesis and Evaluation of 2-Amino-9-(1,3-dihydroxy-2-propoxymethyl)-6-fluoropurine Mono- and Diesters as Potential Prodrugs of Ganciclovir," Journal of Medicinal Chemistry, Jan. 1999, 42(2):324-28.

Klumpp et al., "Chapter 20: Discovery and Clinical Evaluation of the Nucleoside Analog Balapiravir (R1626) for the Treatment of HCV Infection," Antiviral Drugs: From Basic Discovery through Clinical Trials, Jun. 20, 2011, pp. 287-304.

Klumpp et al., "The Novel Nucleoside Analog R1479 (4'-Azidocytidine) is a Potent Inhibitor of NS5B-dependent RNA Synthesis and Hepatitis C virus Replication in Cell Culture," Journal of Biological Chemistry, 2006, 281(7): 3793-3799.

Knaggs et al., A QSAR Study Investigating the Effect of L-Alanine Ester Variation on the Anti-HIV Activity of Some Phosphoramidate Derivatives of d4T, Bioorganic & Medicinal Chemistry Letters, 2000, 10: 2075-2078.

Knutsen et al., "Synthesis of Imidazo-fused Bridgehead-nitrogen C-Nucleosides : Coupling-Elimination Reactions of 2,5-Anhydro-3,4,6-tri-O-benzoyl-D-allonic Acid," J. Chem. Soc. Perkin Trans I, 1985, pp. 621-630.

Knutsen et al., "Synthesis of Imidazo-fused Bridgehead-nitrogen C-Nucleosides via Dehydrative Coupling Reactions of 2,5-Anhydro-3,4,6-tri-O-benzoyl-D-allonic Acid," J. Chem. Soc. Perkin Trans I, 1984, pp. 229-238.

Kobe et al., "Use of Distance Geometry Approach for the In Vitro Antiviral Activity Evaluation of N-bridgehead C-nucleosides," European J. Med. Chem., 1992, 27(3):259-266.

Koplon [online], "$37.5 million grant will address research of high-priority infections," UAB News, retrieved on Mar. 13, 2023, URL <https://www.uab.edu/news/health/item/10307-37-5-million-grant-will-address-research-of-high-priority-infections>, Mar. 20, 2019, 1 page.

Kulli, "K Banhatti Polynomials of Remdesivir, Chloroquine, Hydroxychloroquine: Research Advances for the Prevention and Treatment of COVID-19," SSRG International Journal of Applied Chemistry, May-Aug. 2020, 7(2):48-55.

Kushner et al., "Pharmacological uses and perspectives of heavy water and deuterated compounds," Canadian Journal of Physiology and Pharmacology, Feb. 1999, 77(2):79-88.

Kuzik et al., "Nebulized Hypertonic Saline in the Treatment of Viral Bronchiolitis in Infants", The Journal of Pediatrics, Sep. 2007, 151(3):266-270.e1.

Lefebvre et al., "Mononucleoside Phosphotriester Derivatives with S-Acyl-2-thioethyl Bioreversible Phosphate-Protecting Groups: Intracellular Delivery of 3'-Azido-2',3'-dideoxythymidine 5'-Monophosphate," Journal of Medicinal Chemistry, 1995, 38(20): 3941-3950.

(56) References Cited

OTHER PUBLICATIONS

Lefebvre et al., "Synthesis, Decomposition Pathways and 'In Vitro' Evaluation of Bioreversible Phosphotriesters of Azt, Nucleosides," Nucleotides & Nucleic Acids, 1995, 14(3-5): 763-766.

Leyssen et al., "Molecular strategies to inhibit the replication of RNA Viruses," Antiviral Research, 2008, 78:9-25.

Lindell et al., "Synthesis and Biochemical Testing of 3-(Carboxyphenylethyl)imidazo[2,1-f][1,2,4]triazines as Inhibitors of AMP Deaminase," ACS Medicinal Chemistry Letters, 2010, 1(6): 286-289.

Liu et al., "Hydroxychloroquine, a less toxic derivative of chloroquine, is effective in inhibiting SARS-CoV-2 infection in vitro," Cell Discovery, Mar. 18, 2020, 6:16, 4 pages.

Lo et al., "GS-5734 and its parent nucleoside analog inhibit Filo-, Pneumo-, and Paramyxoviruses," Scientific Reports, 2017, 7(43395):1-7.

Lovelette, "1,2,4-Triazines. Synthesis of selected members of the s-triazolo[3,4-f][1,2,4]triazine and tetrazolo[1,5-f][1,2,4]triazine ring systems," Journal of Heterocyclic Chemistry, 1979, 16: 555-560.

Lu, Chengping, Veterinary Microbiology 5th edition, Jan. 31, 2013, p. 431, China Agriculure Press (No English Translation available).

Martell et al., "Hepatitis C Virus (HCV) Circulates as a Population of Different but Closely Related Genomes: Quasispecies Nature of HCV Genome Distribution," Journal of Virology, 1992, 6695: 3225-3229.

Martin et al., "Hint2, A Mitochondrial Apoptotic Sensitizer Down-Regulated in Hepatocellular Carcinoma," Gastroenterology, Jun. 2006, 130(7):2179-2188.

Mason et al., "Polyadenylation-dependent screening assay for respiratory syncytial virus RNA transcriptase activity and identification of an inhibitor," Nucleic Acids Research, 2004, 32(16): 4758-4767.

Matulic-Adamic et al., "Synthesis of 3-(β-D-Ribofuranosyl)-2-Fluoropyridine and 3-(β-D-Ribofuranosyl)-Pyridin-2-one," Tetrahedron Letters, 1997, 38(2): 203-206.

Matulic-Adamic et al., "Synthesis of 5-(β-D-Ribofuranosyl)-Pyridin-2-one: a 'Deletion-Modified' Analogue of Uridine," Tetrahedron Letters, 1997, 38(10): 1669-1672.

McGuigan et al. "Application of Phosphoramidate ProTide Technology Significantly Improves Antiviral Potency of Carbocyclic Adenosine Derivatives," J. Med. Chem., 2006, 49: 7215-7226.

McGuigan et al., "Aryl Phosphoramidate Derivatives of d4T Have Improved Anti-HIV Efficacy in Tissue Culture and May Act by the Generation of a Novel Intracellular Metabolite," J. Med. Chem., 1996, 39: 1748-1753.

McGuigan et al., "Design, synthesis and biological evaluation of phosphorodiamidate prodrugs of antiviral and anticancer nucleosides," European Journal of Medical Chemistry, 2013, 70:326-340.

McGuigan et al., "Intracellular Delivery of Bioactive AZT Nucleotides by Aryl Phosphate Derivatives of AZT," J. Med. Chem., 1993, 36(8): 1048-1052.

Mehellou et al., ""Aryloxy Phosphoramidate Triesters: a Technology for Delivering Monophosphorylated Nucleosides and Sugars into Cells,"" ChemMedChem, 2009, 4:1779-1791.

Meppen et al., "Cyclic phosphoramidates as prodrugs of 2'-C-methylcytidine," European Journal of Medicinal Chemistry, 2009, 49(9): 3765-3770.

Meppen et al., "Medi-404—A Prodrug Approach for the Treatment of HCV Infection," Abstracts of papers, 236th ACS National Meeting, Philadelphia, PA, United States, Aug. 17-21, 2008, 1 page.

Metobo et al., "Practical synthesis of 1'-substituted Tubercidin C-nucleoside analogs," Tetrahedron Letters, Feb. 2012, 53(5):484-486.

Migliaccio et al., "Characterization of Resistance to Non-obligate Chain-terminating Ribonucleoside Analogs That Inhibit Hepatitis C Virus Replication in vitro," The Journal of Biological Chemistry, 2003, 278(49): 49164-49170.

Mitchell et al., "Bioreversible Protection for the Phospho Group: Bioactivation of the Di(4-acyloxybenzyl) and Mono(4-acyloxybenzyl) Phosphoesters of Methylphosphonate and Phosphonoacetate," J. Chem. Soc., Perkin Trans. 1, 1992, pp. 2345-2353.

Mitchell et al., "Synthesis of C-Nucleoside Isosteres of 9-(2-Hydroxyethoxymethyl)guanine (Acyclovir)," J. Het. Chem., 1984, 21(3): 697-699.

Moennig et al., "The Pestiviruses", Advances in Virus Research, 1992, 41: 53-98.

Moorman et al., "5'-ester prodrugs of the varicella-zoster antiviral agent, 6-methoxypurine arabinoside," Antiviral Chemistry & Chemotherapy, Jun. 1992, 3(3):141-46.

Moradpour et al., "Replication of hepatitis C virus," Nature Reviews Microbiology, 2007, 5(6): 453-463.

Morris, "Mechanisms of action and therapeutic role of corticosteroids in asthma", J. Allergy Clin. Immunol., Jan. 1985, 75(1 Pt):1-13.

Moscow et al., "Reduced Folate Carrier Gene (RFC1) Expression and Anti-Folate Resistance in Transfected and Non-Selected Cell Lines," International Journal of Cancer, 1997, 72: 184-190.

Mossel et al., "Exogenous ACE2 expression allows refractory cell lines to support severe acute respiratory syndrome coronavirus replication," Journal of Virology, Mar. 15, 2005, 79(6):3846-50.

Munster et al., "Hydroxychloroquine concentration-response relationships in patients with rheumatoid arthritis", Arthritis Rheumatology, Jun. 2002, 46(6):1460-1469.

Murakami et al., "Mechanism of Activation of Beta-D-2'-Fluoro-2'-C-Methylcytidine and Inhibition of Hepatitis C Virus NS5B RNA Polymerase", Antimicrob Agents Chemother., Feb. 2007, 51(2):503-509.

Murakami et al., "Mechanism of Activation of PSI-7851 and Its Diastereoisomer PSI-7977", The Journal of Biological Chemistry, 2010, 285(45):34337-34347.

Murphy et al., "The Nucleoside Analog GS-441524 Strongly Inhibits Feline Infectious Peritonisitis (FIP) Virus in Tissue Culture and Experimental Cat Infection Studies", Veterinary Microbiology, 2018, 219:226-233.

Neumann et al., "Hepatitis C Viral Dynamics in Vivo and the Antiviral Efficacy of Interferon-α Therapy", Science, 1998, 282:103-107.

Nilsson et al., "Discovery of 4'-azido-2'-deoxy-2'-C-methyl cytidine and prodrugs thereof: A potent inhibitor of Hepatitis C virus replication," Bioorganic & Medicinal Chemistry Letters, May 2012, 22(9):3265-68.

Nishimura et al., "Synthesis of pyrrolo[2,1-f][1,2,4]triazine C-nucleosides. Isosteres of sangivamycin, tubercidin, and toyocamycin," Carbohydrate Research, 2001, 331:77-82.

Ogura et al., "Reaction of Ethynyl Compounds with Lactones," Journal of Organic Chemistry, 1972, 37(1): 72-75.

Olsen et al., "A 7-Deaza-Adenosine Analog Is a Potent and Selective Inhibitor of Hepatitis C Virus Replication with Excellent Pharmacokinetic Properties," Antimicrobial agents and Chemotherapy, 2004, 3944-3953.

Otter et al., "Conformational Properties of Purine-Like C-Nucleosides," Nucleosides & Nucleotides, 1996, 15(1-3): 793-807.

Owusu et al., "A Comparison Analysis on Remdesivir, Favipiravir, Hydroxychloroquine, Chloroquine and Azithromycin in the Treatment of Corona Virus Disease 2019 (COVID-19)—A Review," World Journal of Pharmacy and Pharmaceutical Sciences, May 2020, 9(5):121-133.

Pankiewicz et al., "C-Nucleoside Analogues of Nicotinamide Mononucleotide (NMN)," Nucleosides and Nucleotides, 1988, 7(5 &6): 589-593.

Pankiewicz et al., "Efficient Synthesis of 5-(β-D-Ribofuranosyl)nicotinamide and its α-Isomer," Journal of Organic Chemistry, 1988, 53: 3473-3479.

Patani et al., "Bioisosterism: a rational approach in drug design," Chem. Rev., 1996, 96:3147-3176.

Patil et al., "4-Aza-7,9-Dideazaadenosine, a New Cytotoxic Synthetic C-Nucleoside Analogue of Adenosine," Tetrahedron Letters, 1994, 35(30): 5339-5342.

Patil et al., "C-Glycosylation of Substituted Heterocycles under Friedel-Crafts Conditions (II): Robosylation of Multi-

(56) References Cited

OTHER PUBLICATIONS

Functionalized Thiophenes and Furans for the Synthesis of Purine-Like C-Nucleosides," Nucleosides & Nucleotides, 1990, 9(7):937-956.

Patil et al., "Synthesis of Pyrrolo[2,1-f][1,2,4]triazine Congeners of Nucleic Acid Purines via the N-Amination of 2-Substituted Pyrroles," J. Het. Chem., 1994, 31:781-786.

Patil et al., "Synthesis of some new thieno[3,4-d]pyrimidines and their C-nucleosides," Journal of Heterocyclic Chemistry, 1993, 30(2): 509-515.

Pelet et al., "High throughput screening assay for negative single stranded RNA virus polymerase inhibitors," J. Virol. Methods, Sep. 2005, 128(1-2): 29-36.

Perrone et al., "Application of the Phosphoramidate ProTide Approach to 4'-Azidouridine Confers Sub-micromolar Potency versus Hepatitis C Virus on an Inactive Nucleoside", Journal of Medicinal Chemistry, 2007, 50(8):1840-1849.

Perrone et al., "First Example of Phosphoramidate Approach Applied to a 4'-Substituted Purine Nucleoside (4'-Azidoadenosine): Conversion of an Inactive Nucleoside to a Submicromolar Compound versus Hepatitis C Virus," Journal of Medicinal Chemistry, Oct. 2007, 50(22): 5463-5470.

Peterson et al., "Prodrug approaches to improving the oral absorption of antiviral nucleotide analogues," Expert Opinion, Drug Deliv., 2009, 6(4): 405-420.

Piccirilli et al., "A Direct Route to 3-(D-Ribofuranosyl)pyridine Nucleosides," Helvetica Chimica Acta, 1991, 74: 397-406.

Pierra et al., "Synthesis and Pharmacokinetics of Valopicitabine (NM283), and Efficient Prodrug of the Potent Anti-HCV Agent 2'-C-Methylcytidine," Journal of Medicinal Chemistry, 2006, 49(22): 6614-6620.

Pizzorno et al., "In vitro evaluation of antiviral activity of single and combined repurposable drugs against SARS-CoV-2," Antiviral Research, Sep. 2020, 181:104878.

Poduch et al., "Design of Inhibitors of Orotidine Monophosphate Decarboxylase Using Bioisosteric Replacement and Determination of Inhibition Kinetics," Journal of Medicinal Chemistry, 2006, 49(16): 4937-4945.

Porter et al., "Zika virus, drug discovery, and student projects," ScienceBlogs, Mar. 9, 2016, 7 pages.

Pruijssers et al., "Remdesivir Inhibits SARS-CoV-2 in Human Lung Cells and Chimeric SARS-CoV Expressing the SARS-CoV-2 RNA Polymerase in Mice," Cell Reports, 2020, 32(107940):1-16.

Puech et al., "Intracellular Delivery of Nucleoside Monophosphates through a Reductase-mediated Activation Process," Antiviral Research, 1993, 22(4): 155-174.

Ramasamy et al., "Synthesis and Antitumor Activity of Certain 3-B-D-Ribofuranosyl-1,2,4-triazolo[3,4-f]-1,2,4-triazines Related to Formycin Prepared via Ring Closure of a 1,2,4-Triazine Precursor," J. Med. Chem., 1986, 29(11): 2231-2235.

Rao et al., "C-Glycosylation of Substituted Heterocycles under Friedel-Crafts Conditions (I): A Two-Step Synthesis of the Thieno[3,4-d]Pyrimidine C-Nucleoside Analog of Inosine," Tetrahedron Letters, 1988, 29(29): 3537-3540.

Rebeaud et al., "SARS-CoV-2 and the Use of Chloroquine as an Antiviral Treatment," Frontiers in Medicine, Apr. 24, 2020, 7:184, 6 pages.

Reddy et al., "Stereoselective Synthesis of Nucleoside Monophosphate HepDirect™ Prodrugs," Tet. Lett., 2005, 46: 4321-4324.

Remington's Pharmaceutical Science, 17th ed., Gennaro (ed)., 1985, Chapter 68, 58 pages.

Ross et al., "Synthesis of Diastereomerically Pure Nucleotide and Phosphoramidates," J. Org. Chem., 2011, 76: 8311-8319.

Sacramento et al., "The clinically approved antiviral drug Sofosbuvir inhibits Zika Virus replication," Nature, Jan. 18. 2017, 7: 40920, 12 pages.

Sahakijpijarn et al., "Development of Remdesivir as a Dry Powder for Inhalation by Thin Film Freezing," Pharmaceutics, Oct. 2020, 12(11):1002, 27 pages.

Schäfer et al., "Therapeutic treatment with an oral prodrug of the remdesivir parental nucleoside is protective against SARS-CoV-2 pathogenesis in mice," Science Translational Medicine, May 2022, 14(643), 16 pages.

Schnirring, "China releases genetic data on new coronavirus, now deadly," CIDRAP News, Jan. 2020, retrieved on Mar. 15, 2022, retrieved from URL <https://www.cidrap.umn.edu/news-perspective/2020/01/china-releases-genetic-data-new-coronavirus-now-deadly>, 3 pages.

Schul et al., "A Dengue Fever Viremia Model in Mice Shows Reduction in Viral Replication and Suppression of the Inflammatory Response after Treatment with Antiviral Drugs," Journal of Infectious Diseases, 2007, 195: 665-674.

Schultz, "Prodrugs of Biologically Active Phosphate Esters," Bioorganic & Medicinal Chemistry, 2003, 11: 885-898.

Scott et al., "Interferon-a-2b Plus Ribavirin: A Review of its Use in the Management of Chronic Hepatitis C," Drugs, 2002, 62(3): 507-556.

Sheahan et al., "Broad-spectrum antiviral GS-5734 inhibits both epidemic and zoonotic coronaviruses", Science Translational Medicine, Jun. 2017, 9(396):eaal3653, 11 pages.

Sheahan et al., "Comparative therapeutic efficacy of remdesivir and combination lopinavir, ritonavir, and interferon beta against MER-CoV," Nature Communications, 2020, 11(222):1-14.

Sheahan, "Preparing for future pandemics, today with broad-spectrum antivirals", Nature Portfolio Microbiology Community, Jan. 10, 2020, retrieved on May 13, 2021, retrieved from URL <"https://naturemicrobiologycommunity.nature.com/posts/58125-preparing-for-future-pandemics-today-with-broad-spectrum-antivirals", 13 pages.

Shekunov et al., "Crystallization processes in pharmaceutical technology and drug delivery design," Journal of Crystal Growth, 2000, 211: 122-136.

Shi et al., "Synthesis and anti-viral activity of a series of d- and 1-2'-deoxy-2'-fluororibonucleosides in the subgenomic HCV replicon system," Bioorganic & Medicinal Chemistry, Mar. 2005, 13(5):1641-1652.

Siegel et al., "Discovery and Synthesis of a Phosphoramidate Prodrug of a Pyrrolo[2,1-f][triazin-4-amino] Adenine C-Nucleoside (GS-5734) for the Treatment of Ebola and Emerging Viruses," J. Med. Chem., 2017, 60, 5, 1648-1661 Supplementary Material.

Siegel et al., "Discovery and Synthesis of a Phosphoramidate Prodrug of a Pyrrolo[2,1-f][triazin-4-amino] Adenine C-Nucleoside(GS-5734) for the Treatment of Ebola and Emerging Viruses", Journal of Medicinal Chemistry, 2017, 60(5): 1648-1661.

Silverman et al., "The Organic Chemistry of Drug Design and Drug Action," Elsevier Science, 1992, pp. 19-23.

Silverman, "The Organic Chemistry of Drug Design and Drug Action," Elsevier Science, 2nd Ed., 2004, pp. 29-34.

Sofia et al., "Discovery of a β-d-2'-Deoxy-2'-α-fluoro-2'-β-C-methyluridine Nucleotide Prodrug (PSI-7977) for the Treatment of Hepatitis C Virus," Journal of Medicinal Chemistry, Sep. 2010, 53(19):7202-7218.

Srivastav et al., "Antiviral Activity of Various 1-(2'-Deoxy-β-D-lyxofuranosyl), 1-(2'-Fluoro-β-D-xylofuranosyl), 1-(3'-Fluor-β-D-arabinofuranosyl), and 2'-Fluoro-2',3'-didehydro-2',3'-dideoxyribose Pyrimidine Nucleoside Analogues against Duck Hepatitis B Virus (DHBV) and Human Hepatitis B Virus (HBV) Replication," Journal of Medicinal Chemistry, 2010, 53(19): 7156-7166.

Stein et al., "Phosphorylation of Nucleoside Analog Antiretrovirals: A Review for Clinicians," Pharmacotherapy, Jan. 2001, 21(1):11-34.

Stella et al., "Cyclodextrins," Toxicologic Pathology, 2008, 36(1):30-42.

Streetman, "Drug Interaction Concerns for COVID-19 Treatments", Wolters Kluwer, Apr. 15, 2020, retrieved on Sep. 7, 2021, retrieved from URL <"https://www.wolterskluwer.com/en/expert-insights/drug-interaction-concerns-for-covid-19-treatments">, 10 pages.

Sun, "Remdesivir for Treatment of COVID-19: Combination of Pulmonary and IV Administration May Offer Additional Benefit", The AAPS Journal, 2020, 22(77):1-6.

(56) References Cited

OTHER PUBLICATIONS

Szente et al., "Sulfobutylether-beta-cyclodextrin-enabled antiviral remdesivir: Characterization of electrospun- and lyophilized formulations," Carbohydrate Polymers, 2021, 264:118011, 8 pages.
Tan et al., "Combination Treatment With Remdesivir and Ivermectin Exerts Highly Synergistic and Potent Antiviral Activity Against Murine Coronavirus Infection," Frontiers in Cellular and Infection Microbiology, Jul. 30, 2021, 11(700502):1-10.
Tapia et al., "Combination of a Mutagenic Agent with a Reverse Transcriptase Inhibitor Results n Systematic Inhibition of HIV-1 Infection," Virology, 2005, 338: 1-8.
Tong, "Gilead quashes microcap biotech's hope of partnering on oral Covid-19 drug," Endpoint News, Jan. 31, 2023, 2 pages.
Totura et al., "Broad-spectrum coronavirus antiviral drug discovery", Expert Opinion on Drug Discovery, Mar. 2019, 17 pages.
Towner et al., "Newly Discovered Ebola Virus Associated with Hemorrhagic Fever Outbreak in Uganda," PLoS Pathogens, 2008, 4(11): e1000212, 6 pages.
Tschesnokov et al., "Template-dependent inluibition of coronavirus RNA-dependent RNA polymerase by remdesivir reveals a second mechanism of action," J. Biol. Chem., 2020, 295(47):16156-16165.
Uchiyama et al., "O-selective Phosphorylation of Nucleosides without N-protection," J. Org. Chem., Jan. 1, 1993, 58(2): 373-379.
Vaghefi et al., "Synthesis and Antiviral Activity of Certain Nucleoside 5'-Phosphonoformate Derivatives," Journal of Medicinal Chemistry, 1986, 29(8): 1389-1393.
Venkatachalam et al., "Effect of change in nucleoside structure on the activation and antiviral activity of phosphoramidate derivatives," Bioorganic & Medicinal Chemistry, 2005, 13: 5408-5423.
Vermillion et al., "Inhaled remdesivir reduces viral burden in a nonhuman primate model of SARS-CoV-2 infection," Science Translational Medicine, Dec. 2021, 20 pages.
Vieira et al., "Development of a Large-Scale Cyanation Process Using Continuous Flow Chemistry En Route to the Synthesis of Remdesivir," Organic Process Research & Development, May 2020, 24(10):2113-2121.
Walker et al., "Plasma chloroquine and desethylchloroquine concentrations in children during and after chloroquine treatment for malaria.", British Journal Clinical Pharmacology, Dec. 1983, 16(6):701-705.
Wang et al., "ANNOVAR: functional annotation of genetic variants from high-throughput sequencing data," Nucleic Acids Research, 2010, 38(16): e164, 7 pages.
Wang et al., "Remdesivir and chloroquine effectively inhibit the recently emerged novel coronavirus (2019-nCoV) in vitro", Cell Research, 2020, 30:269-271.
Wang et al., "Remdesivir in adults with severe COVID-19: a randomised, double-blind, placebo-controlled, multicentre trial," Lancet, Apr. 29, 2020, 395:1569-1578.
Warren et al., "Protection against filovirus diseases by a novel broad-spectrum nucleoside analogue BCX4430", Nature, Apr. 2014, 508(7496):402-405.
Warren et al., "Therapeutic efficacy of the small molecules GS-5734 against Ebola Virus in rhesus monkeys", Nature, Mar. 17, 2016, 531(7594): 381-385.
Wolfel et al., "Virological assessment of hospitalized patients with Covid-2019," Nature, Apr. 2020, 581: 465-470.
Wu et al., "Synthetic Methodologies for C-Nucleosides," Synthesis, 2004, 10: 1533-1553.
Xie et al.. "A nanoluciferase SARS-CoV-2 for rapid neutralization testing and screening of anti-infective drugs for COVID-19," Nature Communications, Oct. 15, 2020, 11(1):1-11.
Xie et al., "Weinreb Amide Approach to the Practical Synthesis of a Key Remdesivir Intermediate," The Journal of Organic Chemistry, 2021, 86:5065-5072.
Xu et al., "Off-Target In Vitro Profiling Demonstrates that Remdesivir Is a Highly Selective Antiviral Agent," Antimicrobial Agents and Chemotherapy, Jan. 20, 2021, 65(2), 14 pages.

Yamanaka et al., "Metabolic Studies on BMS-200475, a New Antiviral Compound Active against Hepatitis B Virus," Antimicrobial Agents and Chemotherapy, 1999, p. 43(1): 190.
Yan et al., "Advantages of the Parent Nucleoside GS-441524 over Remdesivir for Covid-19 Treatment," ACS Medicinal Chemistry Letters, Jun. 30, 2020, 11(7):1361-1366.
Yan et al., "Gilead should ditch remdesivir and focus on its simpler and safer ancestor," STAT Health Care News, May 14, 2020, 6 pages.
Yan et al., "Pharmacokinetics of 1 Orally Administered GS-441524 in Dogs," bioRxiv Preprint, May 31, 2021, 18 pages.
Yang et al., "Lewis acid catalyzed direct cyanation of indoles and pyrroles with N-cyano-N-phenyl-p-toluenesulfonamide (NCTS)," Organic Letters, 2011, 13(20): 5608-5611.
Yates et al., "The evolution of antiviral nucleoside analogues: A review for chemists and non-chemists. PartII: Complex modifications to the nucleoside scaffold", Antiviral Research, Dec. 8, 2018, 162:5-21.
Yoon et al., "High-throughput screening-based identification of paramyxovirus inhibitors," J. Biomol. Screen., Aug. 2008, 13(7): 591-608.
Yoshimura et al., "Synthesis and Biological Evaluation of 1'-C-Cyano-Pyrimidine Nucleosides," Nucleosides & Nucleotides, 1996, 15(1-3): 305-324.
Zhang et al., "A Practical Synthesis of (2R)-3,5-di-O-benzoyl-2-fluoro-2-C-methyl-D-ribono-y-lactone", Tetrahedron: Asymmetry, 2009, 20:305-312.
Zhu et al., "A novel coronavirus from patients with pneumonia in China, 2019," New England Journal of Medicine, Jan. 24, 2020, 14 pages.
U.S. Appl. No. 13/189,373, filed Jul. 22, 2011, Richard L. Mackman.
U.S. Appl. No. 14/613,719, filed Feb. 4, 2015, Richard L. Mackman.
U.S. Appl. No. 14/579,348, filed Dec. 22, 2014, Richard L. Mackman.
U.S. Appl. No. 16/042,085, filed Jul. 23, 2018, Richard L. Mackman.
U.S. Appl. No. 16/879,491, filed May 20, 2020, Richard L. Mackman.
U.S. Appl. No. 17/854,818, filed Jun. 30, 2022, Richard L. Mackman.
U.S. Appl. No. 17/333,389, filed May 28, 2021, Tomas Cihlar.
U.S. Appl. No. 17/676,920, filed Feb. 22, 2022, Tomas Cihlar.
U.S. Appl. No. 17/222,125, filed Apr. 5, 2021, Scott Ellis.
U.S. Appl. No. 17/158,391, filed Jan. 26, 2021, Tomas Cihlar.
U.S. Appl. No. 17/198,829, filed Mar. 11, 2021, Pavel R. Badalov.
U.S. Appl. No. 18/108,480, filed Feb. 10, 2023, Pavel R. Badalov.
U.S. Appl. No. 16/031,620, filed Jul. 10, 2018, Nate Larson.
U.S. Appl. No. 16/865,209, filed May 1, 2020, Nate Larson.
U.S. Appl. No. 17/585,651, filed Jan. 27, 2022, Nate Larson.
U.S. Appl. No. 15/919,750, filed Mar. 13, 2018, Michel Joseph Perron.
U.S. Appl. No. 16/852,102, filed Apr. 17, 2020, Michel Joseph Perron.
U.S. Appl. No. 17/578,682, filed Jan. 19, 2022, Michel Joseph Perron.
U.S. Appl. No. 17/895,123, filed Aug. 25, 2022, Michel Joseph Perron.
U.S. Appl. No. 15/964,597, filed Apr. 27, 2018, Katrien Brak.
U.S. Appl. No. 17/069,248, filed Oct. 13, 2020, Katrien Brak.
U.S. Appl. No. 18/099,477, filed Jan. 20, 2023, Katrien Brak.
U.S. Appl. No. 15/267,433, filed Sep. 16, 2016, Michael O'Neil Hanrahan Clarke.
U.S. Appl. No. 16/265,016, filed Feb. 1, 2019, Michael O'Neil Hanrahan Clarke.
U.S. Appl. No. 16/863,566, filed Apr. 30, 2020, Michael O'Neil Hanrahan Clarke.
U.S. Appl. No. 17/222,066, filed Apr. 5, 2021, Michael O'Neil Hanrahan Clarke.
U.S. Appl. No. 17/748,400, filed May 19, 2022, Michael O'Neil Hanrahan Clarke.
U.S. Appl. No. 14/926,063, filed Oct. 29, 2015, Steven Donald Axt.

(56) References Cited

OTHER PUBLICATIONS

U.S. Appl. No. 16/692,966, filed Nov. 22, 2019, Steven Axt.
U.S. Appl. No. 17/665,724, filed Feb. 7, 2022, Steven Donald Axt.
U.S. Appl. No. 14/926,062, filed Oct. 29, 2015, Byoung Chun.
U.S. Appl. No. 15/246,240, filed Aug. 24, 2016, Byoung Chun.
U.S. Appl. No. 15/902,690, filed Feb. 22, 2018, Byoung Chun.
U.S. Appl. No. 16/274,049, filed Feb. 12, 2019, Byoung Chun.
U.S. Appl. No. 16/881,419, filed May 22, 2020, Byoung-Kwon Chun.
U.S. Appl. No. 17/579,650, filed Jan. 20, 2022, Byoung Kwon Chun.
U.S. Appl. No. 17/897,380, filed Aug. 29, 2022, Byoung Kwon Chun.
U.S. Appl. No. 14/746,430, filed Jun. 22, 2015, Aesop Cho.
U.S. Appl. No. 13/813,886, filed Jun. 25, 2013, Aesop Cho.
U.S. Appl. No. 12/886,248, filed Sep. 20, 2010, Thomas Butler.
U.S. Appl. No. 16/011,055, filed Jun. 18, 2018, Thomas Butler.
U.S. Appl. No. 16/988,250, filed Aug. 7, 2020, Thomas Butler.
U.S. Appl. No. 17/209,639, filed Mar. 23, 2021, Thomas Butler.
U.S. Appl. No. 12/428,176, filed Apr. 22, 2009, Thomas Butler.
U.S. Appl. No. 13/196,117, filed Aug. 2, 2011, Thomas Butler.
U.S. Appl. No. 13/649,511, filed Oct. 11, 2012, Thomas Butler.
U.S. Appl. No. 17/458,023, filed Aug. 26, 2021, Byoung-Kwon Chun.
U.S. Appl. No. 18/098,950, filed Jan. 19, 2023, Byoung-Kwon Chun.
U.S. Appl. No. 18/115,895, filed Mar. 1, 2023, Rao V. Kalla.
U.S. Appl. No. 18/115,955, filed Mar. 1, 2023, Mark J. Bartlett.
U.S. Appl. No. 18/117,858, filed Mar. 6, 2023, Mark J. Bartlett.
U.S. Appl. No. 18/117,913, filed Mar. 6, 2023, Mark J. Bartlett.
U.S. Appl. No. 17/355,813, filed Jun. 23, 2021, Daniel H. Byun.
"Molecular Nuclear Medicine," First Edition, Wang (ed.), May 31, 2001, pp. 388-391, 11 pages (with English translation).
"Veterinary Microbiology," 4th Edition, Lu (ed.), 2007, p. 304: paragraph 2, p. 408: paragraph 1, p. 419: paragraphs 1-2, 7 pages (with English translation).
Al-Aly et al., "High-dimensional characterization of post-acute sequelae of COVID-19," Nature, Jun. 2021, 594(7862): 259-64.
Al-Aly et al., "Long COVID after breakthrough SARS-CoV-2 infection," Nature Medicine. Jul. 2022, 28(7): 1461-7.
Alavi et al., "Severe SARS-CoV-2 infection in a 32-week pregnant woman treated with Remdesivir-Dexamethasone combination therapy: A case report," Clinical Case Reports, Aug. 2022, 10(8): e6241.
Aleissa et al., "New Perspectives on Antimicrobial Agents: Remdesivir Treatment for COVID-19," Antimicrobial Agents and Chemotherapy, Dec. 2020, 65(1): 18 pages.
Amstutz et al., "Effects of remdesivir in patients hospitalised with COVID-19: A systematic review and individual patient data meta-analysis of randomised controlled trials," The Lancet Respiratory Medicine, Feb. 2023, 11(5): 453-464.
Anderson et al., "The use of convalescent plasma therapy and remdesivir in the successful management of a critically ill obstetric patient with novel coronavirus 2019 infection: A case report," Case Reports in Women's Health, May 2020, 27: 3 pages.
Anoshchenko et al., "Pharmacokinetics, Safety, and Tolerability of Obeldesivir (OBV; GS-5245) in Healthy Participants," Poster P2620, Presented at European Congress of Clinical Microbiology and Infectious Diseases (ECCMID), Apr. 15-18, 2023, 1 page.
Assiri et al., "Epidemiological, Demographic, and Clinical Characteristics of 47 Cases of Middle East Respiratory Syndrome Coronavirus Disease From Saudi Arabia: A Descriptive Study," The Lancet Infectious Diseases, Sep. 2013, 13(9):752-61.
Austin, "An Introduction to Propensity Score Methods for Reducing the Effects of Confounding in Observational Studies," Multivariate behavioral research, May 2011, 46(3): 399-424.
Baker et al., "Prodrugs of 9-Beta-D-Arabinofuranosyladenine. 1. Synthesis and Evaluation of some 5'-(O-Acyl) Derivatives," Journal of Medicinal Chemistry, Dec. 1978, 21(12): 1218-1221.
Barrett et al., "Risk for Newly Diagnosed Diabetes >30 Days After SARS-CoV-2 Infection Among Persons Aged <18 Years—United States, Mar. 1, 2020-Jun. 28, 2021," MMWR Morbidity and Mortality Weekly Report, Jan. 14, 2022, 71(2): 59-65.
Beigel et al., "Remdesivir for the Treatment of Covid-19—Final Report," New England Journal of Medicine, Nov. 5, 2020, 383(19): 1813-1826.
Bhimraj et al., "Infectious Diseases Society of America guidelines on the treatment and management of patients with COVID-19," Clinical Infectious Diseases, Apr. 27, 2020, 20 pages.
Boglione et al., "Risk factors and incidence of long-COVID syndrome in hospitalized patients: does remdesivir have a protective effect?" QJM: An International Journal of Medicine, Dec. 2021, 114(12): 865-71.
Bornholdt et al., "A Two-Antibody Pan-Ebolavirus Cocktail Confers Broad Therapeutic Protection in Ferrets and Nonhuman Primates," Cell Host Microbe, Jan. 2019, 25(1): 49-58, e1-e5.
Bowe et al., "Acute and postacute sequelae associated with SARS-CoV-2 reinfection," Nature Medicine, Nov. 2022, 28(11): 2398-405.
Bowe et al., "Kidney Outcomes in Long COVID," Journal of the American Society of Nephrology, Nov. 2021, 32(11): 2851-62.
Brannan et al., "Post-exposure immunotherapy for two ebolaviruses and Marburg virus in nonhuman primates," Nature Communications, Jan. 2019, 10: 105, 10 pages.
Brookes et al., "IMPAACT 2032: Remdesivir PK and safety in pregnant and non-pregnant women with COVID-19 [CROI Abstract 676]," Abstracts from CROI 2022 Conference on Retroviruses and Opportunistic Infections, Feb. 2022. 1 page.
Budi et al., "Remdesivir for pregnancy: A systematic review of antiviral therapy for COVID-19," Heliyon, Jan. 2022,8(1): 10 pages.
Burwick et al., "Compassionate Use of Remdesivir in Pregnant Women With Severe Coronavirus Disease," Clinical Infectious Diseases, Dec. 2021, 73(1): e3996-e4004.
Bwire et al., "Sudan Ebola virus (SUDV) outbreak in Uganda, 2022: lessons learnt and future priorities for sub-Saharan Africa," BMC Medicine, Apr. 2023, 21: 144, 3 pages.
Cao et al., "The Adenosine Analog Prodrug ATV006 is Orally Bioavailable and has Preclinical Efficacy Against Parental SARS-CoV-2 and Variants," Science Translational Medicine, May 2022, 14(661), 16 pages.
Center for Disease Control and Prevention (CDC) [online], "People Who Are Immunocompromised," last updated May 11, 2023, retrieved from URL <https://www.cdc.gov/coronavirus/2019-ncov/need-extra-precautions/people-who-are-immunocompromised.html>, 4 pages.
Chang et al., "Critical Care Management of a Severe Acute Respiratory Distress Syndrome COVID-19 Patient With Control Cesarean Section," Cureus, Feb. 2022, 14(2): 4 pages.
Charytan et al., "Decreasing Incidence of Acute Kidney Injury in Patients with COVID-19 Critical Illness in New York City," Kidney International Reports, Apr. 2021, 6(4):916-27.
Chinen et al., "Critical respiratory failure in pregnancy complicated with COVID-19: A case report," Case Reports in Women's Health, Apr. 2021, 30: 4 pages.
Choi et al., "Clinical Presentation and Outcomes of Middle East Respiratory Syndrome in the Republic of Korea," Infection & Chemotherapy, Jun. 2016, 48(2): 118-26.
Chokkalingam et al., "Association of Remdesivir Treatment With Mortality Among Hospitalized Adults With COVID-19 in the United States," JAMA Network Open, Dec. 2022, 5(12), 12 pages.
Cihlar et al., "Journey of Remdesivir From the Inhibition of Hepatitis C virus to the Treatment of COVID-19," Antiviral Therapy, Mar. 2022, 27(2), 12 pages.
ClinicalTrials.gov [online], "Study of Obeldesivir in Participants With COVID-19 Who Have a High Risk of Developing Serious or Severe Illness (BIRCH)," Gilead Sciences, Trial Identifier: NCT05603143, last updated Aug. 3, 2023, retrieved on Aug. 23, 2023, retrieved from URL: <https://classic.clinicaltrials.gov/ct2/show/record/NCT05603143>, 8 pages.
Coffin et al., "Persistent Marburg Virus Infection in the Testes of Nonhuman Primate Survivors," Cell Host & Microbe, Sep. 2018, 24(1): 405-416.
Coppock et al., "COVID-19 treatment combinations and associations with mortality in a large multi-site healthcare system," PloS one, Jun. 11, 2021, 16(6): 13 pages.

(56) References Cited

OTHER PUBLICATIONS

Cross et al., Combination therapy protects macaques against advanced Marburg virus disease. Nature Communications, Mar. 2021, 12(1): 1891, 10 pages.
Cross et al., "Combination therapy with remdesivir and monoclonal antibodies protects nonhuman primates against advanced Sudan virus disease," JCI Insight, May 2022, 7(10): 1-14.
Cross et al., "Natural history of nonhuman primates after conjunctival exposure to Ebola virus," Scientific Reports, Mar. 2023, 13(1), 12 pages.
Dande et al., "Remdesivir in a pregnant patient with COVID-19 pneumonia," Journal of Community Hospital Internal Medicine Perspectives, Jan. 2021, 11(1): 103-6.
Davis et al., "Long COVID: major findings, mechanisms and recommendations," Nature Reviews Microbiology, Jan. 13, 2023, 21(3): 133-146.
De Wit et al., "Prophylactic and Therapeutic Remdesivir (GS-5734) Treatment in the Rhesus Macaque Model of MERS-CoV Infection," Proceedings of the National Academy of Sciences of the United States of America, Mar. 2020, 117(12): 6771-6776.
De Wit et al., "SARS and MERS: Recent Insights Into Emerging Coronaviruses," Nature Review, Jun. 2016; 14: 523-34.
Dehghan et al., "A Lesson for the Future; Determining the Prognosis of the Pregnant Patients with COVID-19 in the Second Trimester? A Case Report," Caspian Journal of Internal Medicine, Apr. 2022, 13(Suppl 3): 284-288.
DeWolf et al., "SARS-CoV-2 in immunocompromised individuals," Immunity, Oct. 11, 2022; 55(10): 1779-98.
Douafer et al., "Scope and limitations on aerosol drug delivery for the treatment of infectious respiratory diseases," Journal of Controlled Release, Sep. 2020, 325: 276-292.
Easterlin et al., "Extremely Preterm Infant Born to a Mother With Severe COVID-19 Pneumonia," Journal of Investigative Medicine High Impact Case Reports, Jul. 2020, 8: 1-5.
Eastman et al., "Remdesivir: A Review of Its Discovery and Development Leading to Emergency Use Authorization for Treatment of COVID-19," ACS Central Science, May 4, 2020; 6(5): 672-83.
Eid et al., "Early Administration of Remdesivir and Intensive Care Unit Admission in Hospitalized Pregnant Individuals With Coronavirus Disease 2019 (COVID-19)," Obstetrics & Gynecology, Apr. 2022, 139(4): 619-621.
ERA-EDTA Council et al., "Chronic kidney disease is a key risk factor for severe COVID-19: a call to action by the ERA-EDTA," Nephrology Dialysis Transplantation, Jan. 2021, 36(1): 87-94.
Escaffre et al., "STAT-1 Knockout Mice as a Model for Wild-Type Sudan Virus (SUDV)," Viruses, Jul. 2021, 13(7): 1-16.
European Medicines Agency, "New vaccine for prevention of Ebola virus disease recommended for approval in the European Union," Press Release, May 29, 2020, 3 pages.
Fan et al., "Safety profile of the antiviral drug remdesivir: An update," Biomedicine & Pharmacotherapy, Oct. 2020, 130: 3 pages.
Feldmann et al., "Ebola," New England Journal of Medicine, May 2020, 382: 1832-42.
Flythe et al., "Characteristics and Outcomes of Individuals With Pre-existing Kidney Disease and COVID-19 Admitted to Intensive Care Units in the United States," American Journal of Kidney Diseases, Feb. 2021, 77(2): 190-203.
Geisbert et al., "Considerations in the Use of Nonhuman Primate Models of Ebola Virus and Marburg Virus Infection," The Journal of Infectious Diseases, Oct. 2015, 212(Suppl. 2), S91-97.
Geisbert et al., "Single-injection vaccine protects nonhuman primates against infection with marburg virus and three species of ebola virus," Journal of Virology, Jul. 2009, 83(14): 7296-7304.
Gil et al., "COVID-19: Drug Targets and Potential Treatments," Journal of Medicinal Chemistry, Jun. 2020, 63(21): 12359-12386.
Goldman et al., "COVID-19 in immunocompromised populations: implications for prognosis and repurposing of immunotherapies," Journal for Immunotherapy of Cancer, Jun. 11, 2021, 9(6): 1-13.

Gordon et al., "Efficient Incorporation and Template-Dependent Polymerase Inhibition are Major Determinants for the Broad-Spectrum Antiviral Activity of Remdesivir," Journal of Biological Chemistry, Dec. 2021, 298(2): 14 pages.
Gottlieb et al., "Early Remdesivir to Prevent Progression to Severe Covid-19 in Outpatients," New England Journal of Medicine, Jan. 27, 2022, 386(4): 305-315.
Gupta et al., "Factors Associated With Death in Critically Ill Patients With Coronavirus Disease 2019 in the US," JAMA Internal Medicine, Nov. 2020, 180(11): 1436-47.
Gutierrez et al., "Remdesivir use in pregnancy during the SARS-CoV-2 pandemic," The Journal of Maternal-Fetal & Neonatal Medicine, Feb. 2022, 35(25): 9445-51.
Hadi et al., "Outcomes of COVID-19 in Solid Organ Transplant Recipients: A Propensity-matched Analysis of a Large Research Network," Transplantation, Jun. 1, 2021; 105(6): 1365-71.
Hammond et al., "Oral Nirmatrelvir for High-Risk, Nonhospitalized Adults with Covid-19," New England Journal of Medicine, Feb. 2022, 386(15): 1397-1408.
Hanson et al., "Estimated Global Proportions of Individuals With Persistent Fatigue, Cognitive, and Respiratory Symptom Clusters Following Symptomatic COVID-19 in 2020 and 2021," JAMA Network, Oct. 10, 2022; 328(16): 1604-1615.
Harvey et al., "Association of SARS-CoV-2 Seropositive Antibody Test With Risk of Future Infection," JAMA Internal Medicine, Feb. 24, 2021; 181(5): 672-679.
Hayashi et al., "Gasless laparoendoscopic single-site surgery for management of unruptured tubal pregnancy in a woman with moderate COVID-19 pneumonia after administration of remdesivir and casirivimab-imdevimab: A case report," Case Reports in Women's Health, Jan. 2022, 33: e00368.
He et al., Species Differences in Size Discrimination in the Paracellular Pathway Reflected by Oral Bioavailability of Poly(ethylene glycol) and D-peptides, Journal of Pharmaceutical Sciences, May 1998, 87(5): 626-633.
Henry et al., "Chronic kidney disease is associated with severe coronavirus disease 2019 (COVID-19) infection," International urology and nephrology, Jun. 2020, 52(6): 1193-4.
Herbert et al., "Development of an antibody cocktail for treatment of Sudan virus infection," Proceedings of the National Academy of Sciences, Feb. 2020, 117: 3768-78.
Higgs et al., "PREVAIL IV: A Randomized, Double-Blind, 2-Phase, Phase 2 Trial of Remdesivir vs Placebo for Reduction of Ebola Virus RNA in the Semen of Male Survivors," Clinical Infectious Diseases, Nov. 2021, 73(10): 1849-1856.
Hoste et al., "Assessment of renal function in recently admitted critically ill patients with normal serum creatinine," Nephrology Dialysis Transplantation, Apr. 2005, 20(4): 747-53.
Hsu et al., COVID-19 Among US Dialysis Patients: Risk Factors and Outcomes From a National Dialysis Provider, American Journal of Kidney Disease, May 2021, 77(5):748-56.
Humeniuk et al., "Pharmacokinetic, Pharmacodynamic, and Drug-Interaction Profile of Remdesivir, a SARS-CoV-2 Replication Inhibitor," Clinical pharmacokinetics, May 2021, 60(2021): 569-583.
Igbinosa et al., "Use of remdesivir for pregnant patients with severe novel coronavirus disease 2019," American Journal of Obstetrics & Gynecology, Aug. 2020, 223(5): 768-770.
Ioannou et al., "Rates and Factors Associated With Documentation of Diagnostic Codes for Long COVID in the National Veterans Affairs Health Care System," JAMA Network Open, Jul. 29, 2022, 5(7): 1-11.
Jacobson et al., "Use of dexamethasone, remdesivir, convalescent plasma and prone positioning in the treatment of severe COVID-19 infection in pregnancy: A case report," Case Reports in Women's Health, Jan. 2021, 29: 3 pages.
Jeong et al., "Detecting drug-drug interactions between therapies for COVID-19 and concomitant medications through the FDA adverse event reporting system," Frontiers in Pharmacology, Jul. 22, 2022, 13: 14 pages.
Jorgensen et al., "A review of remdesivir for COVID-19 in pregnancy and lactation," Journal of Antimicrobial Chemotherapy, Aug. 2021, 77(1): 24-30.

(56) References Cited

OTHER PUBLICATIONS

Kabinger et al., "Mechanism of Molnupiravir-Induced SARS-CoV-2 Mutagenesis," Nature Structural & Molecular Biology, Aug. 2021, 28(9): 740-746.
Kelly et al., "Post-acute sequelae of SARS-CoV-2 among previously hospitalised individuals with COVID-19: a systematic literature review and meta-analysis," European Respiratory Journal, 2022, 60(Suppl. 66): 4430.
Ksiazek et al., "A Novel Coronavirus Associated with Severe Acute Respiratory Syndrome," New England Journal of Medicine, May 2003, 348(20): 1953-66.
Kuang et al., "Reversion of Ebolavirus Disease from a Single Intramuscular Injection of a Pan-Ebolavirus Immunotherapeutic," Pathogens, Jun. 2022, 11(6): 655, 14 pages.
Kudose et al., "Longitudinal Outcomes of COVID-19-Associated Collapsing Glomerulopathy and Other Podocytopathies," Journal of the American Society of Nephrology, Nov. 2021; 32(11): 2958-69.
Lafont et al., "Targeted SARS-CoV-2 treatment is associated with decreased mortality in immunocompromised patients with COVID-19," Journal of Antimicrobial Chemotherapy, Jul. 25, 2022, 77(10): 2688-92.
Languon et al., "Filovirus Disease Outbreaks: A Chronological Overview," Virology: Research and Treatment, Jun. 2019, 10: 1-12.
Lat et al., "Therapeutic options in the treatment of severe acute respiratory syndrome coronavirus 2 in pregnant patient," American Journal of Obstetrics & Gynecology MFM, Nov. 2020, 2(4): 100224.
Li et al., "Key Metabolic Enzymes Involved in Remdesivir Activation in Human Lung Cells," Antimicrobial Chemotherapy, Aug. 2021, 65(9): 17 pages.
Liu et al., "Ebola virus persistence and disease recrudescence in the brains of antibody-treated nonhuman primate survivors," Science Translational Medicine, Feb. 2022, 14(631), 13 pages.
Liu et al., "Physiologically-based pharmacokinetic modeling of remdesivir and its metabolites in pregnant women with COVID-19," CPT: Pharmacometrics & Systems Pharmacology, Dec. 2022, 12(2): 148-53.
MacKenna et al., "Risk of severe COVID-19 outcomes associated with immune-mediated inflammatory diseases and immune-modifying therapies: a nationwide cohort study in the OpenSAFELY platform," The Lancet Rheumatology, Jun. 8, 2022, 4(7): e490-e506.
Mackman et al., "Chapter 22: Veklury® (Remdesivir), A Nucleotide Prodrug Approved for the treatment of COVID-19," 2022 Medicinal Chemistry Reviews, Dec. 2022, 57: 545-569.
Mackman et al., "Prodrugs of a 1'-CN-4-Aza-7,9-dideazaadenosine C-Nucleoside Leading to the Discovery of Remdesivir (GS-5734) as a Potent Inhibitor of Respiratory Syncytial Virus with Efficacy in the African Green Monkey Model of RSV," Journal of Medicinal Chemistry, Apr. 2021, 64(8): 5001-5017.
Maldarelli et al., "Remdesivir Treatment for Severe COVID-19 in Third-Trimester Pregnancy: Case Report and Management Discussion," Open Forum Infectious Diseases, Sep. 2020, 7(9): 4 pages.
Marikawa et al., "Remdesivir impairs mouse preimplantation embryo development at therapeutic concentrations," Reproductive Toxicology, Aug. 2022, 111: 135-47.
Markham, "REGN-EB3: First Approval," Drugs, Jan. 2021, 81: 175-178.
Martin et al., "Genetic Conservation of SARS-CoV-2 RNA Replication Complex in Globally Circulating Isolates and Recently Emerged Variants from Humans and Minks Suggests Minimal Pre-Existing Resistance to Remdesivir," Antiviral Research, Apr. 2021, 188: 7 pages.
Marzban-Rad et al., "The use of remdesivir among pregnant women and associated clinical outcomes in the mother and the child," Annals of Medicine and Surgery, May 2022, 77: 3 pages.
McCoy et al., "Compassionate use of remdesivir for treatment of severe coronavirus disease 2019 in pregnant women at a United States academic center," American Journal of Obstetrics & Gynecology MFM, Aug. 2020, 2(Suppl 3): 4 pages.

MotherToBaby, "Remdesivir (Veklury®): Fact Sheet," Otis, May 2022, 4 pages.
Mozaffari et al., "Remdesivir Treatment in Hospitalized Patients With Coronavirus Disease 2019 (COVID-19): A Comparative Analysis of In-hospital All-cause Mortality in a Large Multicenter Observational Cohort," Clinical Infectious Diseases, Jul. 2022, 75(1): e450-e458.
Mulangu et al., "A Randomized, Controlled Trial of Ebola Virus Disease Therapeutics," New England Journal of Medicine, Dec. 2019; 381(24): 2293-303.
Naqvi et al., "Tocilizumab and Remdesivir in a Pregnant Patient With Coronavirus Disease 2019 (COVID-19)," Obstetrics & Gynecology, Nov. 2020, 136(5): 1025-9.
Nasrallah et al., "Pharmacological treatment in pregnant women with moderate symptoms of coronavirus disease 2019 (COVID-19) pneumonia," The Journal of Maternal-Fetal & Neonatal Medicine Mar. 2021, 35(25): 5970-5977.
National Institute of Diabetes and Digestive and Kidney Diseases (NIDDK), "2009 CKD-EPI Creatinine Calculator," Chronic Kidney Disease Epidemiology Collaboration (CKD-EPI) equation, last reviewed Dec. 2022, retrieved from URL <https://www.niddk.nih.gov/health-information/professionals/clinical-tools-patient-management/kidney-disease/laboratory-evaluation/glomerular-filtration-rate-calculators/historical>, 2 pages.
Nevalainen et al., "Effect of remdesivir post hospitalization for COVID-19 infection from the randomized Solidarity Finland trial," Nature Communications, Oct. 2022, 13(1): 6152.
Nguyen et al., "Favipiravir pharmacokinetics in Ebola-Infected patients of the JIKI trial reveals concentrations lower than targeted," PLoS Neglected Tropical Diseases, Feb. 2017, 11(2), 18 pages.
NIH [online], "COVID-19 Treatment Guidelines: Antiviral Agents, Including Antibody Products," last updated Jul. 21, 2023, retrieved from URL https://www.covid19treatmentguidelines.nih.gov/therapies/antivirals-including-antibody-products/summary-recommendations/, 3 pages.
NIH [online], "COVID-19 Treatment Guidelines: Special Considerations During Pregnancy and After Delivery," last updated Apr. 20, 2023, retrieved from URL <https://www.covid19treatmentguidelines.nih.gov/special-populations/pregnancy/>, 8 pages.
NIH [online], "COVID-19 Treatment Guidelines: Special Considerations in People Who Are Immunocompromised," last updated Jul. 21, 2023, retrieved from URL <https://www.covid19treatmentguidelines.nih.gov/special-populations/immunocompromised/>, 12 pages.
O'Mahoney, "The prevalence and long-term health effects of Long Covid among hospitalised and non-hospitalised populations: A systematic review and meta-analysis," EClinicalMedicine, Dec. 1, 2022, 55: 1-10.
Owen et al., "An oral SARS-CoV-2 Mpro Inhibitor Clinical Candidate for the Treatment of COVID-19," Science, Nov. 2021, 374(6575): 1586-1593.
Ozturk et al., "Mortality analysis of COVID-19 infection in chronic kidney disease, haemodialysis and renal transplant patients compared with patients without kidney disease: a nationwide analysis from Turkey," Nephrology Dialysis Transplantation, Dec. 2020, 35(12): 2083-95.
Pagan et al., "Management of Critically Ill Pregnant Patients with COVID-19 Infection in a Rural State," American Journal of Perinatology, Jan. 2022, 39(2): 165-71.
Patel et al., "Analysis of MarketScan Data for Immunosuppressive Conditions and Hospitalizations for Acute Respiratory Illness, United States," Emerging Infectious Diseases, Apr. 29, 2020; 26(8): 1720-30.
Perlis et al., "Prevalence and Correlates of Long COVID Symptoms Among US Adult," JAMA Network Open, Oct. 27, 2022; 5(10): 1-11.
Pierce-Williams et al., "Clinical course of severe and critical coronavirus disease 2019 in hospitalized pregnancies: a United States cohort study," American Journal of Obstetrics & Gynecology MFM, Aug. 2020, 2(3): 12 pages.
Pilcer et al., "Formulation strategy and use of excipients in pulmonary drug delivery," International Journal of Pharmaceutics, Jun. 2010, 392(1-2): 1-19.

(56) References Cited

OTHER PUBLICATIONS

Pitts et al., "Intravenous Delivery of GS-441524 is Efficacious in the African Green Monkey Model of SARS-CoV-2 Infection," Antiviral Research, Jul. 2022, 203: 9 pages.

Pitts et al., "Remdesivir and GS-441524 Retain Antiviral Activity against Delta, Omicron, and Other Emergent SARS-CoV-2 Variants," Antimicrobial agents and chemotherapy, May 9, 2022, 66(6): 13 pages.

Porter et al., "Remdesivir (GS-5734) Is Efficacious in Cynomolgus Macaques Infected With Marburg Virus," The Journal of Infectious Diseases, Jun. 2020, 222(11): 1894-1901.

Prasad et al., "Resistance of Cynomolgus Monkeys to Nipah and Hendra Virus Disease Is Associated With Cell-Mediated and Humoral Immunity," The Journal of Infectious Diseases, May 2020, 221(Suppl. 4): S436-447.

Rahim et al., "Postexposure Protective Efficacy of T-705 (Favipiravir) Against Sudan Virus Infection in Guinea Pigs," The Journal of Infectious Diseases, Jul. 2018, 218(Suppl. 5): S649-S657.

Rajme-Lopez et al., "Early Outpatient Treatment With Remdesivir in Patients at High Risk for Severe COVID-19: A Prospective Cohort Study," Open Forum Infectious Diseases, Oct. 6, 2022, 9(10): 1-6.

Ronco et al., "Kidney Involvement in COVID-19 and Rationale for Extracorporeal Therapies," Nature Reviews Nephrology, Apr. 2020, 16: 308-310.

Rosner-Tenerowicz et al. "Placental pathology in a pregnant woman with severe COVID-19 and successful ECMO treatment: a case report," BMC Pregnancy and Childbirth, Nov. 2021, 21: 760, 6 pages.

Saroyo et al., "Remdesivir Treatment for COVID 19 in Pregnant Patients with Moderate to Severe Symptoms: Serial Case Report," Infectious Disease Reports, May 2021, 13(2): 437-443.

Schäfer et al., "Therapeutic efficacy of an oral nucleoside analog of remdesivir against SARS-CoV-2 pathogenesis in mice," bioRxiv Preprint, Sep. 17, 2021, 36 pages.

Schindell et al., "Persistence and Sexual Transmission of Filoviruses," Viruses, Dec. 2018, 10(12), 22 pages.

Schnettler et al., "Severe acute respiratory distress syndrome in coronavirus disease 2019-infected pregnancy: obstetric and intensive care considerations," American Journal of Obstetrics & Gynecology MFM, Aug. 2020, 2(Suppl 3): 10 pages.

Shetty et al., "COVID-19-Associated Glomerular Disease," Journal of the American Society of Nephrology, Jan. 2021, 32(1): 33-40.

Singh et al., "Treatment With Remdesivir in Two Pregnant Patients With COVID-19 Pneumonia," Cureus, May 2021, 13(5): 6 pages.

Song et al., "Risk and Outcome of Breakthrough COVID-19 Infections in Vaccinated Patients With Cancer: Real-World Evidence From the National COVID Cohort Collaborative," Journal of Clinical Oncology, May 1, 2022, 40(13): 1414-1427.

Spinelli et al., "COVID-19 Outcomes and Risk Factors Among People Living with HIV," Current HIV/AIDS Reports, Aug. 5, 2022, 19(5): 425-32.

Spinner et al., "Effect of Remdesivir vs Standard Care on Clinical Status at 11 Days in Patients With Moderate COVID-19: A Randomized Clinical Trial," Jama, Sep. 2020, 324(11): 1048-1057.

Swank et al., "Persistent Circulating Severe Acute Respiratory Syndrome Coronavirus 2 Spike Is Associated With Post-acute Coronavirus Disease 2019 Sequelae," Clinical Infectious Diseases, Sep. 2, 2022, 76(3): e487-e490.

Taki et al., "Ebanga™: The most recent FDA-approved drug for treating Ebola," Frontiers in Pharmacology, Mar. 2023, 14: 1-8.

Tao et al., "Comparison of Anti-SARS-CoV-2 Activity and Intracellular Metabolism of Remdesivir and its Parent Nucleoside," Current Research in Pharmacology and Drug Discovery, 2021, 2, 7 pages.

Taylor et al., "Neutralizing Monoclonal Antibodies for Treatment of COVID-19," Nature Reviews Immunology, Apr. 2021, 21(6): 382-393.

Taylor, "Aulton's Pharmaceutics: The Design and Manufacture of Medicines; Chapter 37: Pulmonary Drug Delivery," 5th ed., Aulton et al (ed), 2018: 653-670.

The Recovery Collaborative Group, "Dexamethasone in Hospitalized Patients with Covid-19," New England Journal of Medicine, Feb. 2020, 384(8): 693-704.

Thi et al., "Rescue of non-human primates from advanced Sudan ebolavirus infection with lipid encapsulated siRNA," Nature Microbiology, Aug. 2016, 1: 16142, 21 pages.

US Department of Health and Human Services [online] ,"What is Long COVID?" retrieved on Jul. 24, 2023, retrieved from URL <https://www.covid.gov/longcovid/definitions>, 2 pages.

U.S. Food and Drug Administration (FDA), "First FDA-approved vaccine for the prevention of Ebola virus disease, marking a critical milestone in public health preparedness and response," Press Release, Dec. 19, 2019, 3 pages.

Vandesompele et al., "Accurate normalization of real-time quantitative RT-PCR data by geometric averaging of multiple internal control genes," Genome Biology, Jun. 2002, 3(7): 1-12.

Vangeel et al., "Remdesivir, Molnupiravir and Nirmatrelvir remain active against SARS-CoV-2 Omicron and other variants of concern," Antiviral Research, Jan. 2022, 198: 3 pages.

V'kovski et al., "Coronavirus Biology and Replication: Implications for SARS-CoV-2," Nature Reviews Microbiology, Oct. 2021, 19(3): 155-170.

Wang et al., "Analyses of Risk, Racial Disparity, and Outcomes Among US Patients With Cancer and COVID-19 Infection," JAMA Oncology, Dec. 10, 2021, 7(2): 220-227.

Wang et al., "Preclinical Pharmacokinetics and In Vitro Properties of GS-441524, a Potential Oral Drug Candidate for COVID-19 Treatment," Frontiers in Pharmacology, Aug. 2022, 13: 16 pages.

Warfield et al., "Homologous and heterologous protection of non-human primates by Ebola and Sudan virus-like particles," PLoS One, Mar. 2015, 10(3): 16 pages.

Wec et al., "Development of a Human Antibody Cocktail that Deploys Multiple Functions to Confer Pan-Ebolavirus Protection," Cell Host Microbe, Jan. 2019, 25(1): 39-48, e1-e5.

Wei et al., "Potency and Pharmacokinetics of GS-441524 Derivatives Against SARS-CoV-2," Bioorganic & Medicinal Chemistry, Sep. 2021, 46: 12 pages.

Williamson et al., "Factors associated with COVID-19-related death using OpenSAFELY," Nature, Aug. 2020, 584(7821): 430-6.

Woolsey et al., "A highly attenuated Vesiculovax vaccine rapidly protects nonhuman primates against lethal Marburg virus challenge," PLoS Neglected Tropical Diseases, May 2022, 16(5), 27 pages.

Woolsey et al., "Bundibugyo ebolavirus Survival Is Associated with Early Activation of Adaptive Immunity and Reduced Myeloid-Derived Suppressor Cell Signaling," mBio, Aug. 2021, 12(4), 20 pages.

Woolsey et al., "Natural history of Sudan ebolavirus infection in rhesus and cynomolgus macaques," Emerging Microbes & Infections, Jun. 2022, 11(1): 1635-46.

World Health Organization (WHO) [online], "A clinical case definition of post COVID-19 condition by a Delphi consensus," Oct. 6, 2021, retrieved from URL <https://www.who.int/publications/i/item/WHO-2019-nCoV-Post_COVID-19_condition-Clinical_case_definition-2021.1>, 27 pages.

World Health Organization (WHO) [online], "Clinical management of COVID-19: living guideline," Jan. 12, 2023, retrieved from URL <https://app.magicapp.org/#/guideline/j1WBYn>, 183 pages.

World Health Organization (WHO) [online], "Post COVID-19 condition (Long COVID)," Dec. 7, 2022, retrieved from URL <https://www.who.int/europe/news-room/fact-sheets/item/post-covid-19-condition>, 2 pages.

World Health Organization (WHO) [online], "Therapeutics and COVID-19: Living Guideline," Jul. 14, 2022, updated Jan. 13, 2023, retrieved from URL <https://www.who.int/publications/i/item/WHO-2019-nCoV-therapeutics-2022.4>, 142 pages.

World Health Organization (WHO), "Ebola haemorrhagic fever in Zaire, 1976: Report of an International Commission," Bulletin of the World Health Organization, 1978, 56(2): 271-293.

Wu et al., "AKI and Collapsing Glomerulopathy Associated with COVID-19 and APOL1 High-Risk Genotype," Journal of the American Society of Nephrology, Aug. 2020, 31(8):1688-95.

(56) References Cited

OTHER PUBLICATIONS

Xie et al., "Engineering SARS-CoV-2 using a reverse genetic system," Nature protocols, Jan. 29, 2021, 16(3): 1761-1784.

Xie et al., "Long-term cardiovascular outcomes of COVID-19," Nature Medicine, Mar. 2022, 28(3): 583-90.

Yamamoto et al., "High-Dose Corticosteroids for a Pregnant Woman Critically Ill With Coronavirus Disease 2019," Cureus, Aug. 2021, 13(8): 5 pages.

Yang et al., "Biotransformation and transplacental transfer of the anti-viral remdesivir and predominant metabolite, GS-441524 in pregnant rats," EBioMedicine, Jul. 2022, 81: 11 pages.

Youssef et al., "Brief Report: Rapid Clinical Recovery From Critical Coronavirus Disease 2019 With Respiratory Failure in a Pregnant Patient Treated With IV Vasoactive Intestinal Peptide," Critical Care Explorations, Jan. 2022, 4(1): e0607.

Zeng et al., "Identification and pathological characterization of persistent asymptomatic Ebola virus infection in rhesus monkeys," Nature Microbiology, Jul. 2017, 2(1), 11 pages.

Zhang et al., "Pharmacokinetics & Safety of Remdesivir in Renal Impairment," Poster # 083, Presented at 2022 American College of Clinical Pharmacology Annual Meeting, Sep. 11, 2022, 1 page.

PCT International Search Report and Written Opinion in International Appln. No. PCT/US2023/014299, dated Jun. 1, 2023, 24 pages.

PCT Invitation to Pay Additional Fees in International Appln. No. PCT/US2023/014299, dated Apr. 28, 2023, 11 pages.

1'-CYANO NUCLEOSIDE ANALOGS AND METHODS FOR TREATMENT OF VIRAL INFECTIONS

CROSS-REFERENCES TO RELATED APPLICATIONS

This Application is a continuation of U.S. Ser. No. 18/115,955, filed on Mar. 1, 2023, which claims the benefit of U.S. Provisional Application No. 63/315,769, filed on Mar. 2, 2022, U.S. Provisional Application No. 63/390,421, filed on Jul. 19, 2022, U.S. Provisional Application No. 63/424,083, filed on Nov. 9, 2022, and U.S. Provisional Application No. 63/434,993, filed on Dec. 23, 2022. The entire contents of these applications are incorporated herein by reference in their entirety.

BACKGROUND

There is a need for compounds and methods for treating viral infections, for example paramyxoviridae, pneumoviridae, picornaviridae, flaviviridae, filoviridae, arenaviridae, orthomyxovirus, and coronaviridae infections. The present disclosure addresses these and other needs.

The oral route is a preferred route for daily drug administration, due to its advantages, such as non-invasiveness, patient compliance, and convenience of drug administration. Nevertheless, oral administration can be limited due to poor physicochemical properties of the drug molecule, including low aqueous solubility between pH2 and pH7, instability, low permeability, and rapid metabolism, all of which can combine to result in low and irregular oral bioavailability. Oral bioavailability (F %) is the fraction of an oral administered drug that reaches systemic circulation relative to the same dose delivery by intravenous administration. After intravenous administration, a drug is directly and fully available in the bloodstream and can be distributed via systemic circulation to the point where a pharmacological effect takes place. If a drug is administered orally, it has to survive the intestinal fluid, cross further barriers such as the gastero-intestinal (GI) cell layer and then the liver in order to reach the systemic circulation, which can significantly reduce the amount of administered drug that reaches the bloodstream. Oral bioavailability is therefore an important property in drug design and development. A high oral bioavailability reduces the required amount of an administered drug that would be necessary to achieve a desired pharmacological effect and therefore could reduce the risk of side-effects and toxicity during the absorption process. The present disclosure also provides compounds with combined solubility, stability and permeability properties leading to improved oral bioavailability.

SUMMARY

The instant disclosure provides a compound of Formula I:

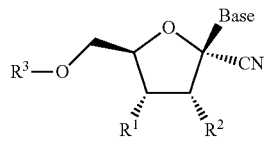

Formula I or a pharmaceutically acceptable salt thereof, wherein $R^1$, $R^2$, $R^3$, and Base are defined herein.

Also provided herein is a pharmaceutical composition comprising a compound disclosed herein (e.g., a compound of Formula I), or a pharmaceutically acceptable salt thereof, and one or more pharmaceutically acceptable excipients.

Also provided herein is a method of treating or preventing a viral infection in a human in need thereof, wherein the method comprises administering to the human a compound disclosed herein (e.g., a compound of Formula I), or a pharmaceutically acceptable salt thereof, or a pharmaceutical composition described herein.

Also provided herein is a use of a compound disclosed herein (e.g., a compound of Formula I), or a pharmaceutically acceptable salt thereof, for the manufacture of a medicament for the treatment or prevention of a viral infection in a human in need thereof.

Also provided herein is a composition comprising a compound described herein (e.g., a compound of Formula I), or a pharmaceutically acceptable salt thereof, for use in treatment or prevention of a viral infection in a human in need thereof.

DETAILED DESCRIPTION OF THE INVENTION

I. General

Figure 1:
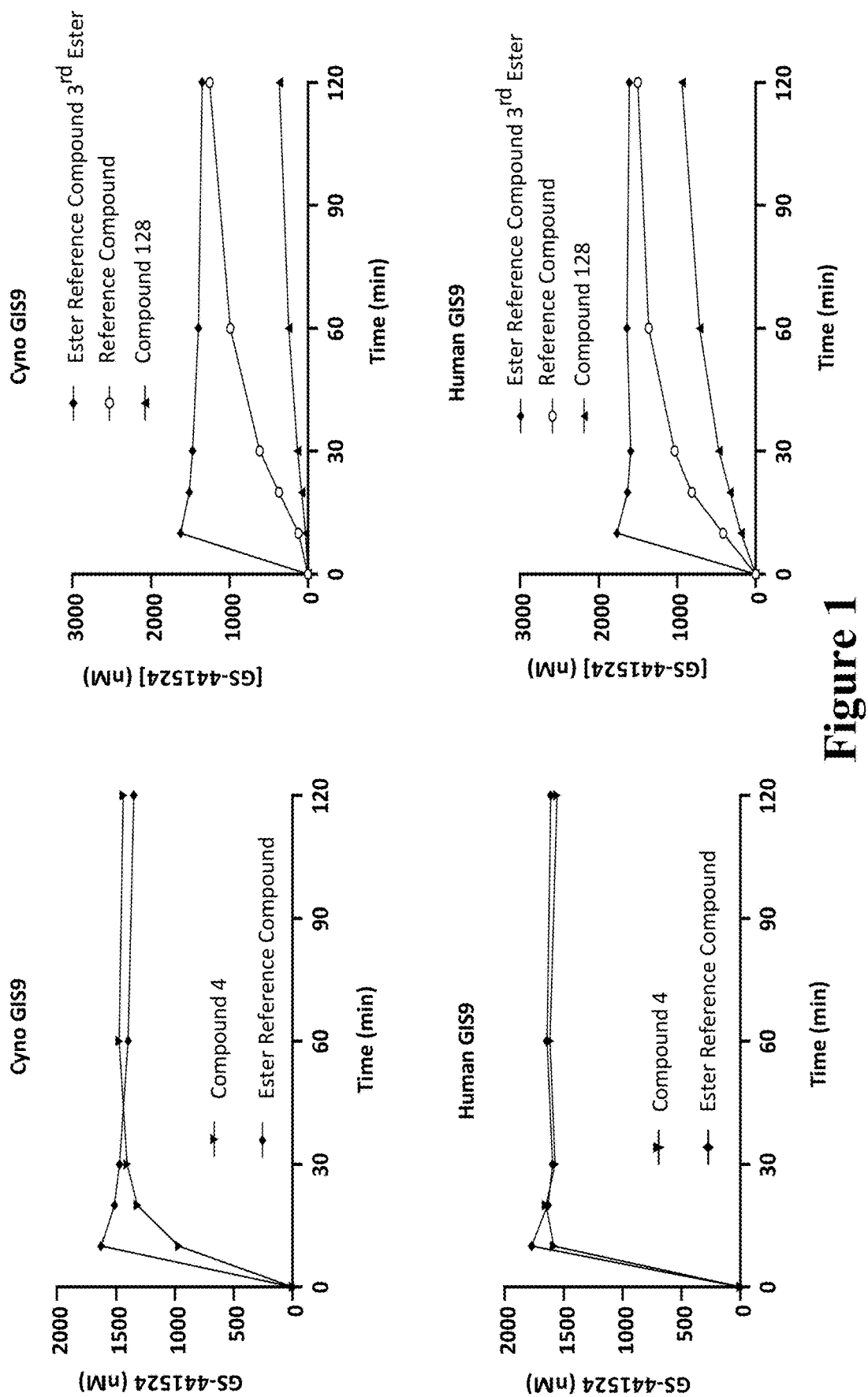
FIG. 1: Shows GI stability of Compound 4, Compound 128, Ester Reference Compound, and $3^{rd}$ Ester Reference Compound.

The invention relates generally to methods and compounds for treating or preventing viral infections, for example paramyxoviridae, pneumoviridae, picornaviridae, flaviviridae, filoviridae, arenaviridae, orthomyxovirus, and coronaviridae infections.

II. Definitions

Unless stated otherwise, the following terms and phrases as used herein are intended to have the following meanings:

"Alkyl" refers to an unbranched or branched saturated hydrocarbon chain. For example, an alkyl group can have 1 to 20 carbon atoms (i.e., $C_1$-$C_{20}$ alkyl), 1 to 8 carbon atoms (i.e., $C_1$-$C_8$ alkyl), 1 to 6 carbon atoms (i.e., $C_1$-$C_6$ alkyl), or 1 to 3 carbon atoms (i.e., $C_1$-$C_3$ alkyl). Examples of suitable alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2$ CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), and 3,3-dimethyl-2-butyl (—CH(CH$_3$)C(CH$_3$)$_3$).

"Alkenyl" refers to an aliphatic group containing at least one carbon-carbon double bond and having from 2 to 20 carbon atoms (i.e., C$_{2-20}$ alkenyl), 2 to 8 carbon atoms (i.e., C$_{2-8}$ alkenyl), 2 to 6 carbon atoms (i.e., C$_{2-6}$ alkenyl), or 2 to 4 carbon atoms (i.e., C$_{2-4}$ alkenyl). Examples of alkenyl groups include ethenyl, propenyl, butadienyl (including 1,2-butadienyl and 1,3-butadienyl).

"Alkynyl" refers to an aliphatic group containing at least one carbon-carbon triple bond and having from 2 to 20 carbon atoms (i.e., C$_{2-20}$ alkynyl), 2 to 8 carbon atoms (i.e., C$_{2-8}$ alkynyl), 2 to 6 carbon atoms (i.e., C$_{2-6}$ alkynyl), or 2 to 4 carbon atoms (i.e., C$_{2-4}$ alkynyl). The term "alkynyl" also includes those groups having one triple bond and one double bond.

"Haloalkyl" is an alkyl group, as defined above, in which one or more hydrogen atoms of the alkyl group is replaced with a halogen atom. The alkyl portion of a haloalkyl group can have 1 to 20 carbon atoms (i.e., C$_1$-C$_{20}$ haloalkyl), 1 to 12 carbon atoms (i.e., C$_1$-C$_{12}$ haloalkyl), 1 to 8 carbon atoms (i.e., C$_1$-C$_8$ haloalkyl), 1 to 6 carbon atoms (i.e., C$_1$-C$_6$ alkyl) or 1 to 3 carbon atoms (i.e., C$_1$-C$_3$ alkyl). Examples of suitable haloalkyl groups include, but are not limited to, —CF$_3$, —CHF$_2$, —CFH$_2$, —CH$_2$CF$_3$, and the like.

"Aryl" means an aromatic hydrocarbon radical derived by the removal of one hydrogen atom from a single carbon atom of a parent aromatic ring system. For example, an aryl group can have 6 to 20 carbon atoms, 6 to 14 carbon atoms, or 6 to 10 carbon atoms. Typical aryl groups include, but are not limited to, radicals derived from benzene (e.g., phenyl), substituted benzene, naphthalene, anthracene, biphenyl, and the like.

"Heteroaryl" refers to an aromatic group having a single ring, multiple rings, or multiple fused rings, with one or more ring heteroatoms independently selected from nitrogen, oxygen, and sulfur. As used herein, heteroaryl includes 1 to 20 ring atoms (i.e., 1 to 20 membered heteroaryl), 3 to 12 ring atoms (i.e., 3 to 12 membered heteroaryl) or 3 to 8 carbon ring atoms (3 to 8 membered heteroaryl) or 5 to 6 ring atoms (5 to 6 membered heteroaryl). Examples of heteroaryl groups include pyrimidinyl, purinyl, pyridyl, pyridazinyl, benzothiazolyl, and pyrazolyl. Heteroaryl does not encompass or overlap with aryl as defined above.

"Carbocyclyl" or "carbocyclic ring" refers to a non-aromatic hydrocarbon ring consisting of carbon and hydrogen atoms, having from three to twenty carbon atoms, in certain embodiments having from three to fifteen carbon atoms, in certain embodiments having from three to ten carbon atoms, from three to eight carbon atoms, from three to seven carbon atoms, or from 3 to 6 carbon atoms and which is saturated or partially unsaturated and attached to the rest of the molecule by a single bond. Carbocyclic rings include, for example, cyclopropane, cyclobutane, cyclopentane, cyclopentene, cyclohexane, cyclohexene, 1,3-cyclohexadiene, 1,4-cyclohexadiene, cycloheptane, cycloheptene, and cyclooctane. Carbocyclic rings include cycloalkyl groups.

"Cycloalkyl" refers to a saturated cyclic alkyl group having a single ring or multiple rings including fused, bridged, and spiro ring systems. As used herein, cycloalkyl has from 3 to 20 ring carbon atoms (i.e., C$_{3-20}$ cycloalkyl), 3 to 12 ring carbon atoms (i.e., C$_{3-12}$ cycloalkyl), 3 to 10 ring carbon atoms (i.e., C$_{3-10}$ cycloalkyl), 3 to 8 ring carbon atoms (i.e., C$_{3-8}$ cycloalkyl), or 3 to 6 ring carbon atoms (i.e., C$_{3-6}$ cycloalkyl). Examples of cycloalkyl groups include cyclopropyl, cyclobutyl, cyclopentyl, cyclohexyl, cycloheptyl, and cyclooctyl.

"Heterocycle" or "heterocyclyl" as used herein includes by way of example and not limitation those heterocycles described in Paquette, Leo A.; *Principles of Modern Heterocyclic Chemistry* (W. A. Benjamin, New York, 1968), particularly Chapters 1, 3, 4, 6, 7, and 9; *"The Chemistry of Heterocyclic Compounds. A Series of Monographs"* (John Wiley & Sons, New York, 1950 to present), in particular Volumes 13, 14, 16, 19, and 28; and *J. Am. Chem. Soc.* (1960) 82:5566. For example, "heterocycle" includes a "carbocycle" as defined herein, wherein one or more (e.g. 1, 2, 3, or 4) carbon atoms have been replaced with a heteroatom (e.g. O, N, or S). As used herein, heterocycle or heterocyclyl has from 3 to 20 ring atoms, 3 to 12 ring atoms, 3 to 10 ring atoms, 3 to 8 ring atoms, or 3 to 6 ring atoms. Ring-forming carbon atoms and heteroatoms of a heterocyle group can be optionally oxidized to form an oxo or sulfido group or other oxidized linkage (e.g., C(O), S(O), C(S), or S(O)$_2$. N-oxide etc.) or a nitrogen atom can be quaternized. The terms "heterocycle" or "heterocyclyl" includes saturated rings and partially unsaturated rings. Substituted heterocyclyls include, for example, heterocyclic rings substituted with any of the substituents disclosed herein including carbonyl groups. A non-limiting example of a carbonyl substituted heterocyclyl is:

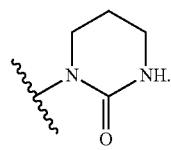

Example heterocycles include, but are not limited to, tetrahydrofuranyl azetidinyl, and 2-oxo-1,3-dioxol-4-yl.

The term "optionally substituted" in reference to a particular moiety of the compound described herein such as the compound of Formula I (e.g., an optionally substituted aryl group) refers to a moiety wherein all substituents are hydrogen or wherein one or more of the hydrogens of the moiety may be replaced by the listed substituents.

Unless otherwise specified, the carbon atoms of the compounds of Formula I are intended to have a valence of four. If in some chemical structure representations, carbon atoms do not have a sufficient number of variables attached to produce a valence of four, the remaining carbon substituents needed to provide a valence of four should be assumed to be hydrogen.

The term "treating", as used herein, unless otherwise indicated, means reversing, alleviating, or inhibiting the progress of the disorder or condition to which such term applies, or one or more symptoms of such disorder or condition. The term "treatment", as used herein, refers to the act of treating, as "treating" is defined immediately above.

"Prevention" or "preventing" means any treatment of a disease or condition that causes the clinical symptoms of the disease or condition not to develop. The compounds and compositions disclosed herein may, in some embodiments, be administered to a subject (including a human) who is at risk of having the disease or condition. As used herein, the terms "preventing" and "prevention" encompass the administration of a compound, composition, or pharmaceutically acceptable salt according to the embodiments disclosed herein pre- or post-exposure of the individual to a virus, but before the appearance of symptoms of the viral infection, and/or prior to the detection of the virus in the blood. The terms also refer to prevention of the appearance of symptoms of the disease and/or to prevent the virus from reaching detectible levels in the blood. The terms include both pre-exposure prophylaxis (PrEP), as well as post-exposure prophylaxis (PEP) and event driven or "on demand" prophylaxis. The terms also refer to prevention of perinatal transmission of a virus from mother to baby, by administration to the mother before giving birth and to the child within the first days of life. The terms also refer to prevention of transmission of a virus through blood transfusion.

The term "therapeutically effective amount", as used herein, is the amount of a compound described herein (e.g., a compound of Formula I) present in a composition described herein that is needed to provide a desired level of drug in the secretions and tissues of the airways and lungs, or alternatively, in the bloodstream of a subject to be treated to give an anticipated physiological response or desired biological effect when such a composition is administered by the chosen route of administration. The precise amount will depend upon numerous factors, for example the particular compound described herein (e.g., the compound of Formula I), the specific activity of the composition, the delivery device employed, the physical characteristics of the composition, its intended use, as well as patient considerations such as severity of the disease state, patient cooperation, etc., and can readily be determined by one skilled in the art based upon the information provided herein.

III. Compounds

Any reference to the compounds of the invention described herein also includes a reference to a pharmaceutically acceptable salt thereof. Examples of pharmaceutically acceptable salts of the compounds of the invention include salts derived from an appropriate base, such as an alkali metal or an alkaline earth (for example, $Na^+$, $Li^+$, $K^+$, $Ca^{+2}$ and $Mg^{+2}$), ammonium and $NR_4^+$ (wherein R is defined herein). Pharmaceutically acceptable salts of a nitrogen atom or an amino group include (a) acid addition salts formed with inorganic acids, for example, hydrochloric acid, hydrobromic acid, sulfuric acid, sulfamic acids, phosphoric acid, nitric acid and the like; (b) salts formed with organic acids such as, for example, acetic acid, oxalic acid, tartaric acid, succinic acid, maleic acid, fumaric acid, gluconic acid, citric acid, malic acid, ascorbic acid, benzoic acid, isethionic acid, lactobionic acid, tannic acid, palmitic acid, alginic acid, polyglutamic acid, naphthalenesulfonic acid, methanesulfonic acid, p-toluenesulfonic acid, benzenesulfonic acid, naphthalenedisulfonic acid, polygalacturonic acid, malonic acid, sulfosalicylic acid, glycolic acid, 2-hydroxy-3-naphthoate, pamoate, salicylic acid, stearic acid, phthalic acid, mandelic acid, lactic acid, ethanesulfonic acid, lysine, arginine, glutamic acid, glycine, serine, threonine, alanine, isoleucine, leucine and the like; and (c) salts formed from elemental anions for example, chlorine, bromine, and iodine. Pharmaceutically acceptable salts of a compound of a hydroxy group include the anion of said compound in combination with a suitable cation such as $Na^+$ and $NR_4^+$.

In some embodiments, R is H, ($C_1$-$C_8$) alkyl, ($C_2$-$C_5$) alkenyl, ($C_2$-$C_5$) alkynyl, $C_6$-$C_{20}$ aryl, or $C_2$-$C_{20}$ heterocyclyl.

For therapeutic use, salts of active ingredients of the compounds of the invention will be pharmaceutically acceptable, i.e., they will be salts derived from a pharmaceutically acceptable acid or base. However, salts of acids or bases which are not pharmaceutically acceptable may also find use, for example, in the preparation or purification of a pharmaceutically acceptable compound. All salts, whether or not derived form a pharmaceutically acceptable acid or base, are within the scope of the present invention.

It is also to be understood that the compositions herein comprise compounds of the invention in their un-ionized, as well as zwitterionic form, and combinations with stoichiometric amounts of water as in hydrates.

It is to be noted that all enantiomers, diastereomers, racemic mixtures, tautomers, polymorphs, and pseudopolymorphs of compounds described herein (e.g., compounds within the scope of Formula I) and pharmaceutically acceptable salts thereof are embraced by the present invention. All mixtures of such enantiomers and diastereomers are within the scope of the present invention.

The compounds of the invention, exemplified by Formula I may have chiral centers, e.g., chiral carbon or phosphorus atoms. The compounds of the invention thus include racemic mixtures of all stereoisomers, including enantiomers, diastereomers, and atropisomers. In addition, the compounds of the invention include enriched or resolved optical isomers at any or all asymmetric, chiral atoms. In other words, the chiral centers apparent from the depictions are provided as the chiral isomers or racemic mixtures. Both racemic and diastereomeric mixtures, as well as the individual optical isomers isolated or synthesized, substantially free of their enantiomeric or diastereomeric partners, are all within the scope of the invention. The racemic mixtures are separated into their individual, substantially optically pure isomers through appropriate techniques such as, for example, the separation of diastereomeric salts formed with optically active adjuncts, e.g., acids or bases followed by conversion back to the optically active substances. In most instances, the desired optical isomer is synthesized by means of stereospecific reactions, beginning with the appropriate stereoisomer of the desired starting material.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l, D and L, or (+) and (−) are employed to designate the sign of rotation of plane-polarized light by the compound, with S, (−), or l meaning that the compound is levorotatory while a compound prefixed with R, (+), or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The compounds of the invention may also exist as tautomeric isomers in certain cases. Although only one delocalized resonance structure may be depicted, all such forms are contemplated within the scope of the invention. For example, ene-amine tautomers can exist for purine, pyrimidine, imidazole, guanidine, amidine, and tetrazole systems and all their possible tautomeric forms are within the scope of the invention.

Any formula or structure given herein, including Formula I compounds, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl and $^{125}$I. Various isotopically labeled compounds of the present disclosure, for example those into which radioactive isotopes such as $^3$H, $^{13}$C and $^{14}$C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also includes compounds (e.g., compounds of Formula I) in which from 1 to x hydrogens attached to a carbon atom is/are replaced by deuterium, in which x is the number of hydrogens in the molecule. Such compounds exhibit increased resistance to metabolism and are thus useful for increasing the half-life of any compound described herein (e.g., compounds of Formula I) when administered to a mammal, particularly a human. See, for example, Foster, "Deuterium Isotope Effects in Studies of Drug Metabolism", Trends Pharmacol. Sci. 5(12):524-527 (1984). In view of the present disclosure, such compounds are synthesized by means known in the art, for example by employing starting materials in which one or more hydrogens have been replaced by deuterium.

Deuterium labeled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}$F labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in the compound of Formula I.

In some embodiments, the carbon bonded to the 5 position on the tetrahydrofuranyl ring of Formula I is substituted with one or two deuterium atoms. In some embodiments, the compound of Formula I is

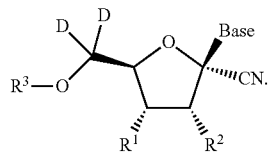

In some embodiments, the compound of Formula I is

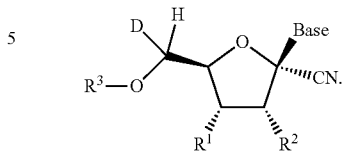

In some embodiments, a carbon of the Base of Formula I is substituted with one or more deuterium atoms. In some embodiments, Base is

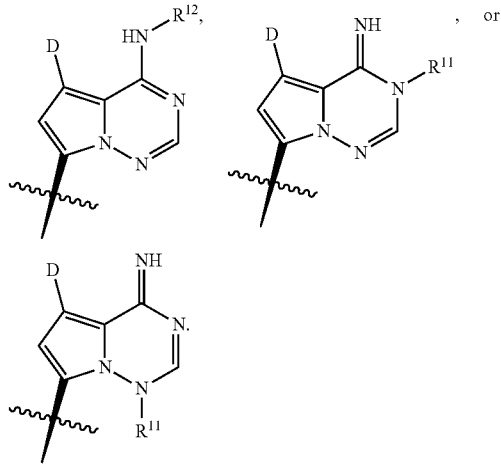

In some embodiments, a carbon on $R^{12}$ of the Base of Formula I is substituted with one or more deuterium atoms. In some embodiments, a carbon on $R^{11}$ of the Base of Formula I is substituted with one or more deuterium atoms. In some embodiments, a carbon on $R^1$ of Formula I is substituted with one or more deuterium atoms. In some embodiments, a carbon on $R^2$ of Formula I is substituted with one or more deuterium atoms. In some embodiments, a carbon on $R^3$ of Formula I is substituted with one or more deuterium atoms.

In some embodiments, the compound of Formula I is

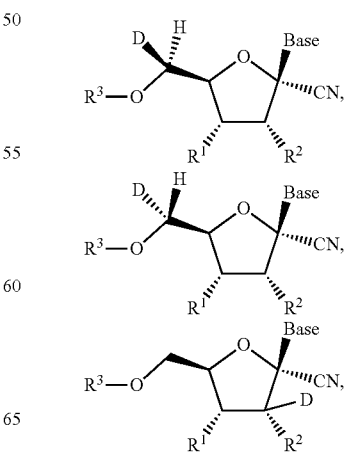

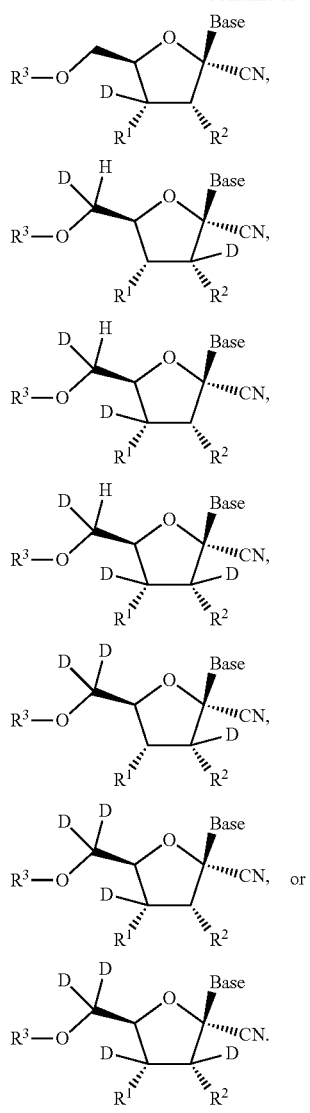
In some embodiments, Base is
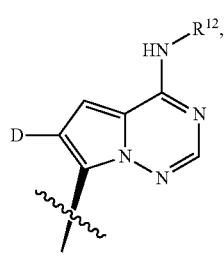
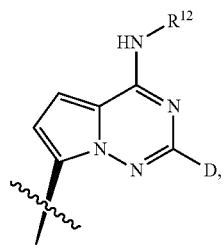
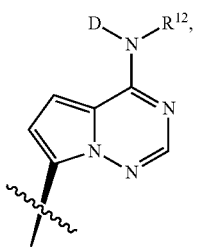
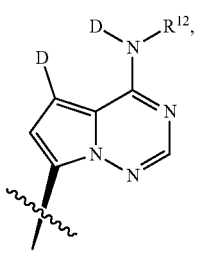
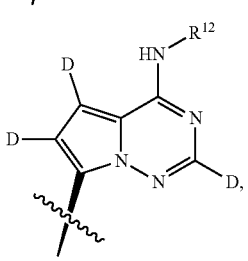
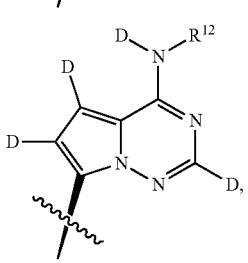
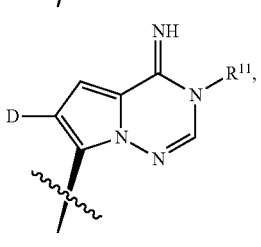
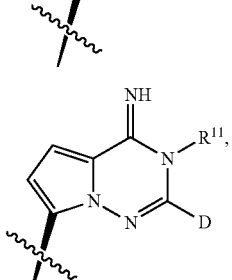
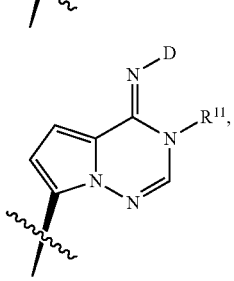

-continued

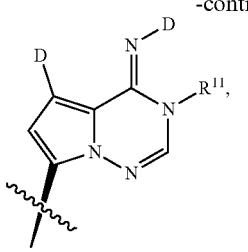

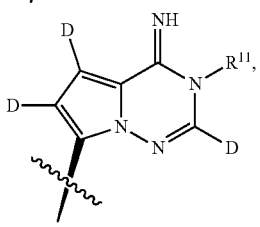

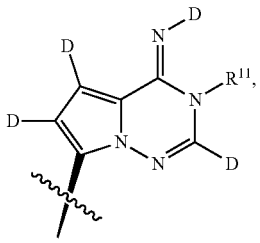

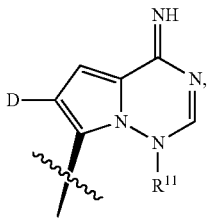

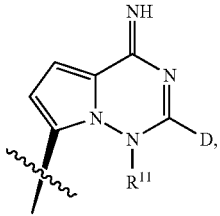

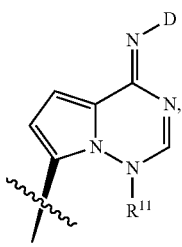

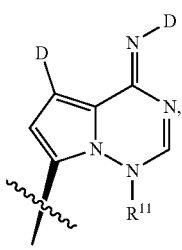

-continued

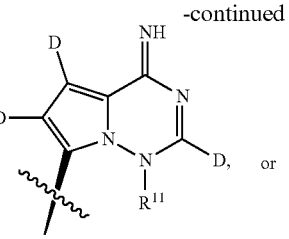 or

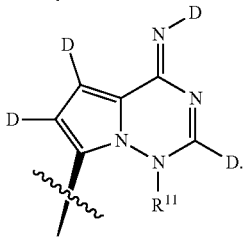

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

Whenever a compound described herein is substituted with more than one of the same designated group, e.g., "R" or "R", then it will be understood that the groups may be the same or different, i.e., each group is independently selected.

Wavy lines, ～～, indicate the site of covalent bond attachments to the adjoining substructures, groups, moieties, or atoms.

IV. Compounds

In certain embodiments, provided herein is a compound of Formula I:

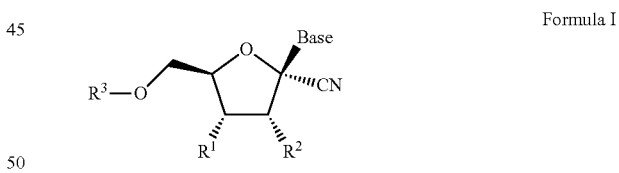

Formula I or a pharmaceutically acceptable salt thereof, wherein:
  $R^1$ is —OH, —OC(=O)$R^4$, —OC(=O)O$R^4$, or —OP(=O)(OH)(O$R^4$);
  $R^2$ is —OH, —OC(=O)$R^5$, —OC(=O)O$R^5$, or —OP(=O)(OH)(O$R^5$); or
  $R^1$ and $R^2$ are taken together to form —OC(=O)O—, —OP(=O)(OH)O—, or —OCH$R^6$O—;
  $R^3$ is —C(=O)O$R^7$;
  $R^4$, $R^5$, and $R^7$ are each independently $C_1$-$C_{20}$ alkyl, $C_2$-$C_8$ alkenyl, $C_2$-$C_8$ alkynyl, $C_3$-$C_{10}$ carbocyclyl, $C_6$-$C_{10}$ aryl, 4 to 8 membered heterocyclyl containing 1, 2, or 3 heteroatoms selected from N, O, and S, or 5 to 6 membered heteroaryl containing 1, 2, or 3 heteroatoms selected from N, O, and S;
  wherein $C_1$-$C_{20}$ alkyl, $C_2$-$C_8$ alkenyl, $C_2$-$C_8$ alkynyl, $C_3$-$C_{10}$ carbocyclyl, $C_6$-$C_{10}$ aryl, 4 to 8 membered heterocyclyl, or 5 to 6 membered heteroaryl of $R^4$, $R^5$, and $R^7$ are each, independently, optionally substituted with one, two, or three substituents independently selected from the group consisting of $C_1$-$C_8$ alkyl, halogen, cyano, carbonyl, —$N_3$, —$OR^8$, —$NR^9R^{10}$, —OP(=O)(OH)$_2$, —OP(=O)($OR^8$)$_2$, $C_3$-$C_8$ carbocyclyl, 4 to 6 membered heterocyclyl containing 1, 2, or 3 heteroatoms selected from N, O, and S, 5 to 6 membered heteroaryl containing 1, 2, or 3 heteroatoms selected from N, O, and S, and phenyl;

wherein substituent $C_3$-$C_8$ carbocyclyl of $R^4$, $R^5$, and $R^7$ is optionally substituted with one, two, or three substituents independently selected from $C_1$-$C_8$ alkyl, halogen, —$CF_3$, cyano, —$CH_2CN$, and phenyl, wherein substituent 4 to 6 membered heterocyclyl of $R^4$, $R^5$, and $R^7$ is optionally substituted with one, two, or three substituents independently selected from carbonyl and $C_1$-$C_6$ alkyl, and wherein substituent phenyl of $R^4$, $R^5$, and $R^7$ is optionally substituted with one, two or three substituents independently selected from halo, cyano, $C_1$-$C_6$ alkyl, and —$OR^8$;

$R^6$ is H, $C_1$-$C_6$ alkyl, $C_1$-$C_6$ alkoxy, 5 to 6 membered heteroaryl containing 1, 2, or 3 heteroatoms selected from N, O, and S, or $C_6$-$C_{10}$ aryl;

wherein 5 to 6 membered heteroaryl and $C_6$-$C_{10}$ aryl of $R^6$ are each, independently, optionally substituted with one, two, or three substituents independently selected from halo, cyano, $C_1$-$C_6$ alkoxy, and $C_1$-$C_6$ alkyl;

each $R^8$ is independently H, $C_1$-$C_6$ alkyl, $C_1$-$C_6$ haloalkyl, $C_3$-$C_6$ cycloalkyl, and 4 to 6 membered heterocyclyl;

wherein $C_1$-$C_6$ alkyl of $R^8$ is optionally substituted with $C_3$-$C_6$ cycloalkyl or 4 to 6 membered heterocyclyl;

each $R^9$ is independently H, $C_1$-$C_6$ alkyl, $C_1$-$C_6$ haloalkyl, and $C_3$-$C_6$ cycloalkyl;

each $R^{10}$ is independently H, $C_1$-$C_6$ alkyl, $C_1$-$C_6$ haloalkyl, and $C_3$-$C_6$ cycloalkyl;

Base is

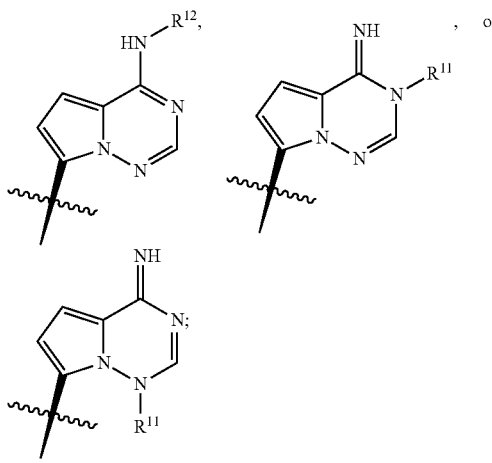

$R^{11}$ is $C_1$-$C_6$ alkyl optionally substituted with —OP(=O)(OH)($OR^{14}$);

$R^{12}$ is H, $C_1$-$C_6$ alkyl, —C(=O)$R^{13}$, or —C(=O)$OR^{13}$;

each $R^{13}$ is independently H or $C_1$-$C_8$ alkyl; wherein $C_1$-$C_8$ alkyl of $R^{13}$ is optionally substituted with one, two, or three substituents independently selected from halogen, cyano, —OP(=O)(OH)($OR^{14}$), and phenyl, wherein substituent phenyl of $R^{13}$ is optionally substituted with —OP(=O)(OH)($OR^{14}$); and each $R^{14}$ is independently H, $C_1$-$C_8$ alkyl, $C_3$-$C_8$ carbocyclyl, $C_6$-$C_{10}$ aryl, or 5 to 6 membered heteroaryl containing 1, 2, or 3 heteroatoms selected from N, O, and S; wherein $C_1$-$C_8$ alkyl of $R^{14}$ is optionally substituted with one, two or three substituents independently selected from the group consisting of halogen, cyano, and phenyl.

In certain embodiments, provided herein is a compound of Formula I:

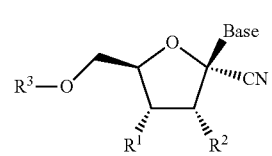

Formula I or a pharmaceutically acceptable salt thereof, wherein:
$R^1$ is —OH, —OC(=O)$R^4$, or —OC(=O)$OR^4$;
$R^2$ is —OH, —OC(=O)$R^5$, or —OC(=O)$OR^5$; or
$R^1$ and $R^2$ are taken together to form —OC(=O)O—, —OP(=O)(OH)O—, or —OCHR$^6$O—;
$R^3$ is —C(=O)$OR^7$;
$R^4$, $R^5$, and $R^7$ are each independently $C_1$-$C_{20}$ alkyl, $C_2$-$C_8$ alkenyl, $C_2$-$C_8$ alkynyl, $C_3$-$C_8$ carbocyclyl, $C_6$-$C_{10}$ aryl, 4 to 6 membered heterocyclyl containing 1, 2, or 3 heteroatoms selected from N, O, and S, or 5 to 6 membered heteroaryl containing 1, 2, or 3 heteroatoms selected from N, O, and S;

wherein $C_1$-$C_{20}$ alkyl, $C_2$-$C_8$ alkenyl, $C_2$-$C_8$ alkynyl, $C_3$-$C_8$ carbocyclyl, $C_6$-$C_{10}$ aryl, 4 to 6 membered heterocyclyl, or 5 to 6 membered heteroaryl of $R^4$, $R^5$, and $R^7$ are each, independently, optionally substituted with one, two, or three substituents independently selected from the group consisting of $C_1$-$C_8$ alkyl, halogen, cyano, carbonyl, —$N_3$, —$OR^8$, —$NR^9R^{10}$, —OP(=O)(OH)$_2$, —OP(=O)($OR^8$)$_2$, $C_3$-$C_8$ carbocyclyl, 4 to 6 membered heterocyclyl containing 1, 2, or 3 heteroatoms selected from N, O, and S, 5 to 6 membered heteroaryl containing 1, 2, or 3 heteroatoms selected from N, O, and S, and phenyl;

wherein substituent $C_3$-$C_8$ carbocyclyl of $R^4$, $R^5$, and $R^7$ is optionally substituted with one, two, or three substituents independently selected from $C_1$-$C_8$ alkyl, halogen, —$CF_3$, cyano, —$CH_2CN$, and phenyl, wherein substituent 4 to 6 membered heterocyclyl of $R^4$, $R^5$, and $R^7$ is optionally substituted with one, two, or three substituents independently selected from carbonyl and $C_1$-$C_6$ alkyl, and wherein substituent phenyl of $R^4$, $R^5$, and $R^7$ is optionally substituted with one, two or three substituents independently selected from halo, cyano, $C_1$-$C_6$ alkyl, and —$OR^8$;

$R^6$ is H, $C_1$-$C_6$ alkyl, $C_1$-$C_6$ alkoxy, 5 to 6 membered heteroaryl containing 1, 2, or 3 heteroatoms selected from N, O, and S, or $C_6$-$C_{10}$ aryl;

wherein 5 to 6 membered heteroaryl and $C_6$-$C_{10}$ aryl of $R^6$ are each, independently, optionally substituted with one, two, or three substituents independently selected from halo, cyano, $C_1$-$C_6$ alkoxy, and $C_1$-$C_6$ alkyl;

each $R^8$ is independently H, $C_1$-$C_6$ alkyl, $C_1$-$C_6$ haloalkyl, and $C_3$-$C_6$ cycloalkyl;
each $R^9$ is independently H, $C_1$-$C_6$ alkyl, $C_1$-$C_6$ haloalkyl, and $C_3$-$C_6$ cycloalkyl;
each $R^{10}$ is independently H, $C_1$-$C_6$ alkyl, $C_1$-$C_6$ haloalkyl, and $C_3$-$C_6$ cycloalkyl;
Base is

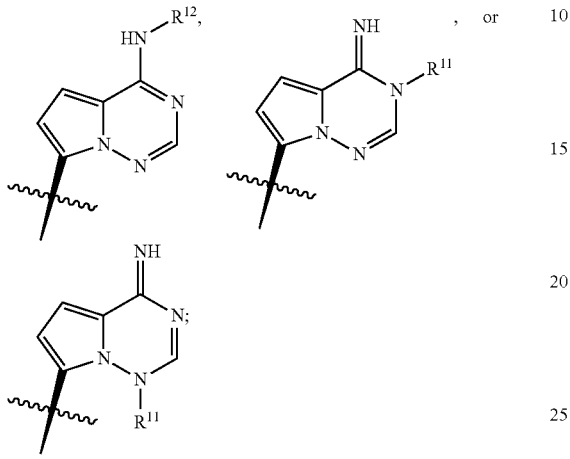

$R^{11}$ is $C_1$-$C_6$ alkyl optionally substituted with —OP(=O)(OH)(OR$^{14}$);
$R^{12}$ is H, $C_1$-$C_6$ alkyl, —C(=O)R$^{13}$, or —C(=O)OR$^{13}$;
each $R^{13}$ is independently H or $C_1$-$C_8$ alkyl; wherein $C_1$-$C_8$ alkyl of $R^{13}$ is optionally substituted with one, two, or three substituents independently selected from halogen, cyano, —OP(=O)(OH)(OR$^{14}$), and phenyl, wherein substituent phenyl of $R^{13}$ is optionally substituted with —OP(=O)(OH)(OR$^{14}$); and
each $R^{14}$ is independently H, $C_1$-$C_8$ alkyl, $C_3$-$C_8$ carbocyclyl, $C_6$-$C_{10}$ aryl, or 5 to 6 membered heteroaryl containing 1, 2, or 3 heteroatoms selected from N, O, and S; wherein $C_1$-$C_8$ alkyl of $R^{14}$ is optionally substituted with one, two or three substituents independently selected from the group consisting of halogen, cyano, and phenyl.

In certain embodiments, provided herein is a compound of Formula I:

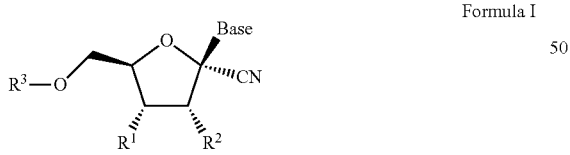

Formula I or a pharmaceutically acceptable salt thereof, wherein:
$R^1$ is —OH, —OC(=O)R$^4$, or —OC(=O)OR$^4$;
$R^2$ is —OH, —OC(=O)R$^5$, or —OC(=O)OR$^5$; or
$R^1$ and $R^2$ are taken together to form —OC(=O)O—, —OP(=O)(OH)O—, or —OCHR$^6$O—;
$R^3$ is —C(=O)OR$^7$;
$R^4$, $R^5$, and $R^7$ are each independently $C_1$-$C_8$ alkyl, $C_2$-$C_8$ alkenyl, $C_2$-$C_8$ alkynyl, $C_3$-$C_8$ carbocyclyl, $C_6$-$C_{10}$ aryl, 4 to 6 membered heterocyclyl containing 1, 2, or 3 heteroatoms selected from N, O, and S, or 5 to 6 membered heteroaryl containing 1, 2, or 3 heteroatoms selected from N, O, and S;

wherein $C_1$-$C_8$ alkyl, $C_2$-$C_8$ alkenyl, $C_2$-$C_8$ alkynyl, $C_3$-$C_8$ carbocyclyl, $C_6$-$C_{10}$ aryl, 4 to 6 membered heterocyclyl, or 5 to 6 membered heteroaryl of $R^4$, $R^5$, and $R^7$ are each, independently, optionally substituted with one, two, or three substituents independently selected from the group consisting of $C_1$-$C_8$ alkyl, halogen, cyano, carbonyl, —N$_3$, —OR$^8$, —NR$^9$R$^{10}$, —OP(=O)(OH)$_2$, $C_3$-$C_8$ carbocyclyl, 4 to 6 membered heterocyclyl containing 1, 2, or 3 heteroatoms selected from N, O, and S, 5 to 6 membered heteroaryl containing 1, 2, or 3 heteroatoms selected from N, O, and S, and phenyl;
wherein substituent 4 to 6 membered heterocyclyl of $R^4$, $R^5$, and $R^7$ is optionally substituted with one, two, or three substituents independently selected from carbonyl and $C_1$-$C_6$ alkyl, and wherein substituent phenyl of $R^4$, $R^5$, and $R^7$ is optionally substituted with one, two or three substituents independently selected from halo, cyano, and $C_1$-$C_6$ alkyl;
$R^6$ is H, $C_1$-$C_6$ alkyl, $C_1$-$C_6$ alkoxy, 5 to 6 membered heteroaryl containing 1, 2, or 3 heteroatoms selected from N, O, and S, or $C_6$-$C_{10}$ aryl;
wherein 5 to 6 membered heteroaryl and $C_6$-$C_{10}$ aryl of $R^6$ are each, independently, optionally substituted with one, two, or three substituents independently selected from halo, cyano, $C_1$-$C_6$ alkoxy, and $C_1$-$C_6$ alkyl:
each $R^8$ is independently H, $C_1$-$C_6$ alkyl, $C_1$-$C_6$ haloalkyl, and $C_3$-$C_6$ cycloalkyl;
each $R^9$ is independently H, $C_1$-$C_6$ alkyl, $C_1$-$C_6$ haloalkyl, and $C_3$-$C_6$ cycloalkyl;
each $R^{10}$ is independently H, $C_1$-$C_6$ alkyl, $C_1$-$C_6$ haloalkyl, and $C_3$-$C_6$ cycloalkyl;
Base is

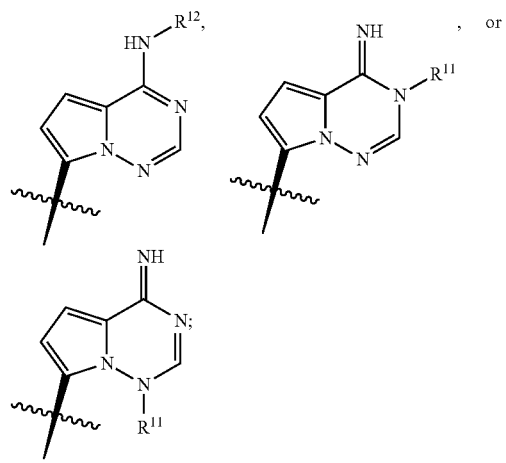

$R^{11}$ is $C_1$-$C_6$ alkyl optionally substituted with —OP(=O)(OH)(OR$^{14}$);
$R^{12}$ is H, $C_1$-$C_6$ alkyl, —C(=O)R$^{13}$ or —C(=O)OR$^{13}$;
each $R^{13}$ is independently H or $C_1$-$C_8$ alkyl; wherein $C_1$-$C_8$ alkyl of $R^{13}$ is optionally substituted with one, two, or three substituents independently selected from halogen, cyano, —OP(=O)(OH)(OR$^{14}$), and phenyl, wherein substituent phenyl of $R^{13}$ is optionally substituted with —OP(=O)(OH)(OR$^{14}$); and
each $R^{14}$ is independently H, $C_1$-$C_8$ alkyl, $C_3$-$C_8$ carbocyclyl, $C_6$-$C_{10}$ aryl, or 5 to 6 membered heteroaryl containing 1, 2, or 3 heteroatoms selected from N, O, and S; wherein $C_1$-$C_8$ alkyl of $R^{14}$ is optionally substituted with one, two or three substituents independently selected from the group consisting of halogen, cyano, and phenyl.

In certain embodiments, provided herein is a compound of Formula I:

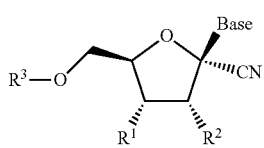

Formula I or a pharmaceutically acceptable salt thereof, wherein:

$R^1$ is —OH, —OC(=O)$R^4$, or —OC(=O)O$R^4$;

$R^2$ is —OH, —OC(=O)$R^5$, or —OC(=O)O$R^5$; or $R^1$ and $R^2$ are taken together to form —OC(=O)O—, —OP(=O)(OH)O—, or —OCH$R^6$O—;

$R^3$ is —C(=O)O$R^7$;

$R^4$, $R^5$, and $R^7$ are each independently $C_1$-$C_8$ alkyl, $C_2$-$C_8$ alkenyl, $C_2$-$C_8$ alkynyl, $C_3$-$C_8$ carbocyclyl, $C_6$-$C_{10}$ aryl, 4 to 6 membered heterocyclyl containing 1, 2, or 3 heteroatoms selected from N, O, and S, or 5 to 6 membered heteroaryl containing 1, 2, or 3 heteroatoms selected from N, O, and S;

wherein $C_1$-$C_8$ alkyl, $C_2$-$C_8$ alkenyl, $C_2$-$C_8$ alkynyl, $C_3$-$C_8$ carbocyclyl, $C_6$-$C_{10}$ aryl, 4 to 6 membered heterocyclyl, or 5 to 6 membered heteroaryl of $R^4$, $R^5$, and $R^7$ are each, independently, optionally substituted with one, two, or three substituents independently selected from the group consisting of halogen, cyano, carbonyl, —N$_3$, —O$R^8$, —N$R^9R^{10}$, —OP(=O)(OH)$_2$, $C_3$-$C_8$ carbocyclyl, 4 to 6 membered heterocyclyl containing 1, 2, or 3 heteroatoms selected from N, O, and S, 5 to 6 membered heteroaryl containing 1, 2, or 3 heteroatoms selected from N, O, and S, and phenyl;

wherein 4 to 6 membered heterocyclyl is optionally substituted with one, two, or three substituents independently selected from carbonyl and $C_1$-$C_6$ alkyl, and wherein phenyl is optionally substituted with one, two or three substituents independently selected from halo, cyano, and $C_1$-$C_6$ alkyl;

$R^6$ is H, $C_1$-$C_6$ alkyl, $C_1$-$C_6$ alkoxy, 5 to 6 membered heteroaryl containing 1, 2, or 3 heteroatoms selected from N, O, and S, or $C_6$-$C_{10}$ aryl;

wherein 5 to 6 membered heteroaryl and $C_6$-$C_{10}$ aryl are each, independently, optionally substituted with one, two, or three substituents independently selected from halo, cyano, $C_1$-$C_6$ alkoxy, and $C_1$-$C_6$ alkyl;

each $R^8$ is independently H, $C_1$-$C_6$ alkyl, $C_1$-$C_6$ haloalkyl, and $C_3$-$C_6$ cycloalkyl;

each $R^9$ is independently H, $C_1$-$C_6$ alkyl, $C_1$-$C_6$ haloalkyl, and $C_3$-$C_6$ cycloalkyl;

each $R^{10}$ is independently H, $C_1$-$C_6$ alkyl, $C_1$-$C_6$ haloalkyl, and $C_3$-$C_6$ cycloalkyl;

Base is

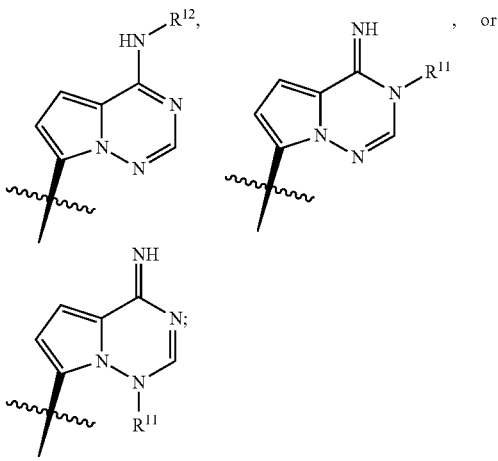

$R^{11}$ is $C_1$-$C_6$ alkyl optionally substituted with —OP(=O)(OH)(O$R^{14}$);

$R^{12}$ is H, $C_1$-$C_6$ alkyl, —C(=O)$R^{13}$ or —C(=O)O$R^{13}$; and each $R^{13}$ is independently H or $C_1$-$C_8$ alkyl; wherein $C_1$-$C_8$ alkyl of $R^{13}$ is optionally substituted with one, two, or three substituents independently selected from halogen, cyano, —OP(=O)(OH)(O$R^{14}$), and phenyl, wherein phenyl is optionally substituted with —OP(=O)(OH)(O$R^{14}$); and each $R^{14}$ is independently H, $C_1$-$C_8$ alkyl, $C_3$-$C_8$ carbocyclyl, $C_6$-$C_{10}$ aryl, or 5 to 6 membered heteroaryl containing 1, 2, or 3 heteroatoms selected from N, O, and S; wherein $C_1$-$C_8$ alkyl of $R^{14}$ is optionally substituted with one, two or three substituents independently selected from the group consisting of halogen, cyano, and phenyl.

In some embodiments, $R^1$ is —OH. In some embodiments, $R^1$ is —OC(=O)$R^4$. In some embodiments, $R^1$ is —OC(=O)O$R^4$.

In some embodiments, $R^1$ is —OP(=O)(OH)(O$R^4$).

In some embodiments, $R^2$ is —OH. In some embodiments, $R^2$ is —OC(=O)$R^5$. In some embodiments, $R^2$ is —OC(=O)O$R^5$.

In some embodiments, $R^2$ is —OP(=O)(OH)(O$R^5$).

In some embodiments, $R^1$ and $R^2$ are both —OH. In some embodiments, $R^1$ is —OC(=O)$R^4$ and $R^2$ is —OC(=O)$R^5$. In some embodiments, $R^1$ is OH, and $R^2$ is —OC(=O)$R^5$ or —OC(=O)O$R^5$. In some embodiments, $R^1$ is —OC(=O)$R^4$ or —OC(=O)O$R^4$, and $R^2$ is OH. In some embodiments, $R^1$ and $R^2$ are taken together to form —OC(=O)O— In some embodiments, $R^1$ and $R^2$ are taken together to form —OP(=O)(OH)O—. In some embodiments, $R^1$ and $R^2$ are taken together to form —OCH$R^6$O—.

In some embodiments, $R^1$ is OH and $R^2$ is —OC(=O)$R^5$. In some embodiments, $R^1$ is OH and $R^2$ is OC(=O)O$R^5$. In some embodiments, $R^1$ is —OC(=O)$R^4$ and $R^2$ is OH. In some embodiments, $R^1$ is —OC(=O)O$R^4$ and $R^2$ is OH In some embodiments, $R^1$ is —OC(=O)O$R^4$ and $R^2$ is OC(=O)O$R^5$. In some embodiments, $R^1$ is —OC(=O)$R^4$ and $R^2$ is OC(=O)O$R^5$. In some embodiments. $R^1$ is —OC(=O)O$R^4$ and $R^2$ is OC(=O)$R^5$.

In some embodiments, $R^1$ is —OP(=O)(OH)(O$R^4$) and $R^2$ is —OH.

In some embodiments, $R^1$ is —OC(=O)CH$_3$. In some embodiments $R^2$ is —OC(=O)CH$_3$. In some embodiments, $R^1$ and $R^2$ are both —OC(=O)CH$_3$.

In some embodiments, $R^1$ is OH, OC(O)CH(CH$_3$)$_2$, or OC(O)CH$_3$, $R^2$ is OH, OC(O)CH(CH$_3$)$_2$, or OC(O)CH$_3$, or $R^1$ and $R^2$ are taken together to form —OC(=O)O—.

In some embodiments, $R^4$ is C$_1$-C$_8$ alkyl, C$_2$-C$_8$ alkenyl, or C$_2$-C$_8$ alkynyl; wherein C$_1$-C$_8$ alkyl, C$_2$-C$_8$ alkenyl, and C$_2$-C$_8$ alkynyl of $R^4$ are each, independently, optionally substituted with one, two, or three substituents independently selected from the group consisting of halogen, cyano, —N$_3$, —OR$^8$, —NR$^9$R$^{10}$, —OP(=O)(OH)$_2$, C$_3$-C$_8$ carbocyclyl and phenyl; wherein substituent phenyl of $R^4$ is optionally substituted with one, two or three substituents independently selected from halo, cyano, and C$_1$-C$_6$ alkyl.

In some embodiments, $R^4$ is C$_1$-C$_8$ alkyl, C$_2$-C$_8$ alkenyl, or C$_2$-C$_8$ alkynyl; wherein C$_1$-C$_8$ alkyl, C$_2$-C$_8$ alkenyl, and C$_2$-C$_8$ alkynyl of $R^4$ are each, independently, optionally substituted with one, two, or three substituents independently selected from the group consisting of halogen, cyano, —N$_3$, —OR$^8$, —NR$^9$R$^{10}$, —OP(=O)(OH)$_2$, C$_3$-C$_8$ carbocyclyl and phenyl; wherein phenyl is optionally substituted with one, two or three substituents independently selected from halo, cyano, and C$_1$-C$_6$ alkyl.

In some embodiments, $R^4$ is C$_1$-C$_8$ alkyl optionally substituted with one, two, or three substituents independently selected from the group consisting of halogen, cyano, —N$_3$, —OR$^8$, —NR$^9$R$^{10}$, —OP(=O)(OH)$_2$, C$_3$-C$_8$ carbocyclyl and phenyl. In some embodiments, $R^4$ is C$_1$-C$_8$ alkyl. In some embodiments, $R^4$ is C$_1$-C$_6$ alkyl. In some embodiments, $R^4$ is C$_1$-C$_3$ alkyl. In some embodiments, $R^4$ is —CH$_3$, —CH$_2$CH$_3$, —(CH$_2$)$_2$CH$_3$, —CH(CH$_3$)$_2$, —(CH$_2$)$_3$CH$_3$, or —C(CH$_3$)$_3$. In some embodiments, $R^4$ is —CH$_3$ or —CH(CH$_3$)$_2$.

In some embodiments, $R^4$ is —CH$_3$, —CH$_2$CH$_3$, —(CH$_2$)$_2$CH$_3$, —CH(CH$_3$)$_2$, —(CH$_2$)$_3$CH$_3$, —C(CH$_3$)$_3$, or —C(CH$_3$)$_2$CH$_2$CH$_3$.

In some embodiments, $R^4$ is C$_1$-C$_{20}$ alkyl substituted with one, two, or three substituents independently selected from the group consisting of carbonyl, —OR$^8$, —NR$^9$R$^{10}$, and —OP(=O)(OH)$_2$. In some embodiments, $R^4$ is C$_2$-C$_8$ alkyl substituted with carbonyl and —OR$^8$. In some embodiments, $R^4$ is

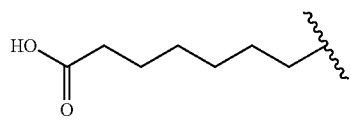

In some embodiments $R^4$ is C$_2$-C$_8$ alkenyl. In some embodiments, $R^4$ is C$_4$ alkenyl. In some embodiments, $R^4$ is

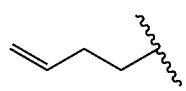

In some embodiments, $R^5$ is C$_1$-C$_8$ alkyl, C$_2$-C$_8$ alkenyl, or C$_2$-C$_8$ alkynyl; wherein C$_1$-C$_8$ alkyl, C$_2$-C$_8$ alkenyl, and C$_2$-C$_8$ alkynyl of $R^4$ are each, independently, optionally substituted with one, two, or three substituents independently selected from the group consisting of halogen, cyano, —N$_3$, —OR$^8$, —NR$^9$R$^{10}$, —OP(=O)(OH)$_2$, C$_3$-C$_8$ carbocyclyl and phenyl; wherein substituent phenyl of $R^5$ is optionally substituted with one, two or three substituents independently selected from halo, cyano, and C$_1$-C$_6$ alkyl.

In some embodiments, $R^5$ is C$_1$-C$_8$ alkyl, C$_2$-C$_8$ alkenyl, or C$_2$-C$_8$ alkynyl; wherein C$_1$-C$_8$ alkyl, C$_2$-C$_8$ alkenyl, and C$_2$-C$_8$ alkynyl of $R^4$ are each, independently, optionally substituted with one, two, or three substituents independently selected from the group consisting of halogen, cyano, —N$_3$, —OR$^8$, —NR$^9$R$^{10}$, —OP(=O)(OH)$_2$, C$_3$-C$_8$ carbocyclyl and phenyl; wherein phenyl is optionally substituted with one, two or three substituents independently selected from halo, cyano, and C$_1$-C$_6$ alkyl.

In some embodiments, $R^5$ is C$_1$-C$_8$ alkyl optionally substituted with one, two, or three substituents independently selected from the group consisting of halogen, cyano, —N$_3$, —OR$^8$, —NR$^9$R$^{10}$, —OP(=O)(OH)$_2$, C$_3$-C$_8$ carbocyclyl and phenyl. In some embodiments, $R^5$ is C$_1$-C$_8$ alkyl. In some embodiments, $R^5$ is C$_1$-C$_6$ alkyl. In some embodiments, $R^5$ is C$_1$-C$_3$ alkyl. In some embodiments, $R^5$ is —CH$_3$, —CH$_2$CH$_3$, —(CH$_2$)$_2$CH$_3$, —CH(CH$_3$)$_2$, —(CH$_2$)$_3$CH$_3$, or —C(CH$_3$)$_3$. In some embodiments, $R^5$ is —CH$_3$ or —CH(CH$_3$)$_2$.

In some embodiments, $R^5$ is —CH$_3$, —CH$_2$CH$_3$, —(CH$_2$)$_2$CH$_3$, —CH(CH$_3$)$_2$, —(CH$_2$)$_3$CH$_3$, —C(CH$_3$)$_3$, or —C(CH$_3$)$_2$CH$_2$CH$_3$.

In some embodiments, $R^5$ is C$_1$-C$_{20}$ alkyl substituted with one, two, or three substituents independently selected from the group consisting of carbonyl, —OR$^8$, —NR$^9$R$^{10}$, and —OP(=O)(OH)$_2$. In some embodiments, $R^5$ is C$_2$-C$_8$ alkyl substituted with carbonyl and —OR$^8$. In some embodiments, $R^5$ is

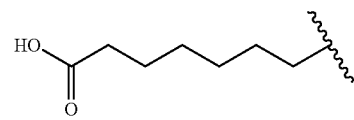

In some embodiments $R^5$ is C$_2$-C$_8$ alkenyl. In some embodiments, $R^5$ is C$_4$ alkenyl. In some embodiments, $R^5$ is

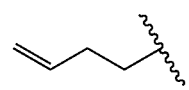

In some embodiments, $R^4$ and $R^5$ are the same. In some embodiments, $R^4$ and $R^5$ are different. In some embodiments, $R^4$ is C$_1$-C$_8$ alkyl and $R^5$ is C$_1$-C$_8$ alkyl. In some embodiments, $R^4$ is —CH$_3$ or —CH(CH$_3$)$_2$ and $R^5$ is —CH$_3$ or —CH(CH$_3$)$_2$. In some embodiments, $R^4$ is —CH$_3$ and $R^5$ is —CH$_3$. In some embodiments, $R^4$ is —CH(CH$_3$)$_2$ and $R^5$ is —CH(CH$_3$)$_2$.

In some embodiments, $R^6$ is H. In some embodiments, $R^6$ is C$_1$-C$_6$ alkyl. In some embodiments, $R^6$ is —CH$_3$, —CH$_2$CH$_3$, —(CH$_2$)$_2$CH$_3$, —CH(CH$_3$)$_2$, —(CH$_2$)$_3$CH$_3$, or —C(CH$_3$)$_3$. In some embodiments. $R^6$ is C$_1$-C$_6$ alkoxy. In some embodiments, $R^6$ is —OCH$_3$.

In some embodiments, $R^6$ is 5 to 6 membered heteroaryl containing 1, 2, or 3 heteroatoms selected from N, O, and S optionally substituted with one, two, or three substituents independently selected from halo, cyano, C$_1$-C$_6$ alkoxy, and C$_1$-C$_6$ alkyl. In some embodiments, $R^6$ is 5 to 6 membered heteroaryl containing 1, 2, or 3 heteroatoms selected from N, O, and S substituted with one, two, or three substituents independently selected from halo, cyano, C$_1$-C$_6$ alkoxy, and C$_1$-C$_6$alkyl. In some embodiments, $R^6$ is 5 to 6 membered heteroaryl containing 1, 2, or 3 heteroatoms selected from N, O, and S.

In some embodiments, $R^6$ is $C_6$-$C_{10}$ aryl optionally substituted with one, two, or three substituents independently selected from halo, cyano, $C_1$-$C_6$ alkoxy, and $C_1$-$C_6$ alkyl. In some embodiments, $R^6$ is $C_6$-$C_{10}$ aryl substituted with one, two, or three substituents independently selected from halo, cyano, $C_1$-$C_6$ alkoxy, and $C_1$-$C_6$ alkyl. In some embodiments, $R^6$ is $C_6$-$C_{10}$ aryl. In some embodiments, $R^6$ is phenyl.

In some embodiments, $R^7$ is $C_1$-$C_{20}$ alkyl, $C_2$-$C_8$ alkenyl, $C_3$-$C_{10}$ carbocyclyl, $C_6$-$C_{10}$ aryl, 4 to 8 membered heterocyclyl containing 1, 2, or 3 heteroatoms selected from N, O, and S or 5 to 6 membered heteroaryl containing 1, 2, or 3 heteroatoms selected from N, O, and S; wherein $C_1$-$C_{20}$ alkyl, $C_3$-$C_8$ carbocyclyl, $C_6$-$C_{10}$ aryl, 4 to 6 membered heterocyclyl, or 5 to 6 membered heteroaryl of $R^7$ are each optionally substituted with one, two, or three substituents independently selected from the group consisting of $C_1$-$C_8$ alkyl, halogen, cyano, carbonyl, —$N_3$, —$OR^8$, —$NR^9R^{10}$, —OP(=O)(OH)$_2$, —OP(=O)(OR$^8$)$_2$, $C_3$-$C_8$ carbocyclyl, 4 to 6 membered heterocyclyl containing 1, 2, or 3 heteroatoms selected from N, O, and S, 5 to 6 membered heteroaryl containing 1, 2, or 3 heteroatoms selected from N, O, and S, and phenyl; wherein substituent $C_3$-$C_8$ carbocyclyl of $R^7$ is optionally substituted with one, two, or three substituents independently selected from $C_1$-$C_8$ alkyl, halogen, —$CF_3$, cyano. —$CH_2CN$, and phenyl, wherein substituent 4 to 6 membered heterocyclyl of $R^7$ is optionally substituted with one, two, or three substituents independently selected from carbonyl and $C_1$-$C_6$ alkyl, and wherein substituent phenyl of $R^7$ is optionally substituted with one, two or three substituents independently selected from halo, cyano. $C_1$-$C_6$ alkyl, and $OR^8$.

In some embodiments, $R^7$ is $C_1$-$C_{20}$ alkyl, $C_2$-$C_8$ alkenyl, $C_3$-$C_8$ carbocyclyl, $C_6$-$C_{10}$ aryl, 4 to 6 membered heterocyclyl containing 1, 2, or 3 heteroatoms selected from N, O, and S or 5 to 6 membered heteroaryl containing 1, 2, or 3 heteroatoms selected from N, O, and S; wherein $C_1$-$C_{20}$ alkyl, $C_3$-$C_8$ carbocyclyl, $C_6$-$C_{10}$ aryl, 4 to 6 membered heterocyclyl, or 5 to 6 membered heteroaryl of $R^7$ are each optionally substituted with one, two, or three substituents independently selected from the group consisting of $C_1$-$C_8$ alkyl, halogen, cyano, carbonyl, —$N_3$, —$OR^8$, —$NR^9R^{10}$, —OP(=O)(OH)$_2$, —OP(=O)(OR$^8$)$_2$, $C_3$-$C_8$ carbocyclyl, 4 to 6 membered heterocyclyl containing 1, 2, or 3 heteroatoms selected from N, O, and S, 5 to 6 membered heteroaryl containing 1, 2, or 3 heteroatoms selected from N, O, and S, and phenyl; wherein substituent $C_3$-$C_8$ carbocyclyl of $R^7$ is optionally substituted with one, two, or three substituents independently selected from $C_1$-$C_8$ alkyl, halogen, —$CF_3$, cyano, —$CH_2CN$, and phenyl, wherein substituent 4 to 6 membered heterocyclyl of $R^7$ is optionally substituted with one, two, or three substituents independently selected from carbonyl and $C_1$-$C_6$ alkyl, and wherein substituent phenyl of $R^7$ is optionally substituted with one, two or three substituents independently selected from halo, cyano, $C_1$-$C_6$ alkyl, and $OR^3$.

In some embodiments, $R^7$ is $C_1$-$C_{20}$ alkyl, $C_3$-$C_8$ carbocyclyl, $C_6$-$C_{10}$ aryl, 4 to 6 membered heterocyclyl containing 1, 2, or 3 heteroatoms selected from N, O, and S or 5 to 6 membered heteroaryl containing 1, 2, or 3 heteroatoms selected from N, O, and S; wherein $C_1$-$C_{20}$ alkyl, $C_3$-$C_8$ carbocyclyl, $C_6$-$C_{10}$ aryl, 4 to 6 membered heterocyclyl, or 5 to 6 membered heteroaryl of $R^7$ are each optionally substituted with one, two, or three substituents independently selected from the group consisting of $C_1$-$C_8$ alkyl, halogen, cyano, carbonyl, —$N_3$, —$OR^8$, —$NR^9R^{10}$, —OP(=O)(OH)$_2$, —OP(=O)(OR$^8$)$_2$, $C_3$-$C_8$ carbocyclyl, 4 to 6 membered heterocyclyl containing 1, 2, or 3 heteroatoms selected from N, O, and S, 5 to 6 membered heteroaryl containing 1, 2, or 3 heteroatoms selected from N, O, and S, and phenyl; wherein substituent $C_3$-$C_8$ carbocyclyl of $R^7$ is optionally substituted with one, two, or three substituents independently selected from $C_1$-$C_8$ alkyl, halogen, —$CF_3$, cyano, —$CH_2CN$, and phenyl, wherein substituent 4 to 6 membered heterocyclyl of $R^7$ is optionally substituted with one, two, or three substituents independently selected from carbonyl and $C_1$-$C_6$ alkyl, and wherein substituent phenyl of $R^7$ is optionally substituted with one, two or three substituents independently selected from halo, cyano, $C_1$-$C_6$ alkyl, and $OR^8$.

In some embodiments, $R^7$ is $C_1$-$C_{20}$ alkyl, $C_3$-$C_8$ carbocyclyl, $C_6$-$C_{10}$ aryl, 4 to 6 membered heterocyclyl containing 1, 2, or 3 heteroatoms selected from N, O, and S or 5 to 6 membered heteroaryl containing 1, 2, or 3 heteroatoms selected from N, O, and S; wherein $C_1$-$C_{20}$ alkyl, $C_3$-$C_8$ carbocyclyl. $C_6$-$C_{10}$ aryl, 4 to 6 membered heterocyclyl, or 5 to 6 membered heteroaryl of $R^7$ are each optionally substituted with one, two, or three substituents independently selected from the group consisting of $C_1$-$C_8$ alkyl, —$OR^8$, —$NR^9R^{10}$, —OP(=O)(OH)$_2$, —OP(=O)(OR$^8$)$_2$, $C_3$-$C_8$ carbocyclyl, 4 to 6 membered heterocyclyl containing 1, 2, or 3 heteroatoms selected from N, O, and S, 5 to 6 membered heteroaryl containing 1, 2, or 3 heteroatoms selected from N, O, and S, and phenyl; wherein substituent $C_3$-$C_8$ carbocyclyl of $R^7$ is optionally substituted with one, two, or three substituents independently selected from $C_1$-$C_8$ alkyl, halogen, —$CF_3$, cyano, —$CH_2CN$, and phenyl, wherein substituent 4 to 6 membered heterocyclyl of $R^7$ is optionally substituted with one, two, or three substituents independently selected from carbonyl and $C_1$-$C_6$ alkyl, and wherein substituent phenyl of $R^7$ is optionally substituted with one, two or three substituents independently selected from halo, cyano, $C_1$-$C_6$ alkyl, and $OR^8$.

In some embodiments, $R^7$ is $C_1$-$C_8$ alkyl, $C_3$-$C_8$ carbocyclyl, $C_6$-$C_{10}$ aryl, 4 to 6 membered heterocyclyl containing 1, 2, or 3 heteroatoms selected from N, O, and S or 5 to 6 membered heteroaryl containing 1, 2, or 3 heteroatoms selected from N, O, and S; wherein $C_1$-$C_8$ alkyl, $C_3$-$C_8$ carbocyclyl, $C_6$-$C_{10}$ any, 4 to 6 membered heterocyclyl, and 5 to 6 membered heteroaryl of $R^7$ are each optionally substituted with one, two, or three substituents independently selected from the group consisting of $C_1$-$C_8$ alkyl, —$OR^8$, —OP(=O)(OH)$_2$, $C_3$-$C_8$ carbocyclyl, 4 to 6 membered heterocyclyl containing 1, 2, or 3 heteroatoms selected from N, O, and S, 5 to 6 membered heteroaryl containing 1, 2, or 3 heteroatoms selected from N, O, and S, and phenyl; wherein substituent 4 to 6 membered heterocyclyl of $R^7$ is optionally substituted with one, two, or three substituents independently selected from carbonyl and $C_1$-$C_6$ alkyl and wherein substituent phenyl of $R^7$ is optionally substituted with one, two, or three substituents independently selected from halo, cyano, and $C_1$-$C_6$ alkyl.

In some embodiments, $R^7$ is $C_1$-$C_8$ alkyl, $C_3$-$C_8$ carbocyclyl, $C_6$-$C_{10}$ aryl, 4 to 6 membered heterocyclyl containing 1, 2, or 3 heteroatoms selected from N, O, and S or 5 to 6 membered heteroaryl containing 1, 2, or 3 heteroatoms selected from N, O, and S; wherein $C_1$-$C_8$ alkyl, $C_3$-$C_8$ carbocyclyl, $C_6$-$C_{10}$ aryl, 4 to 6 membered heterocyclyl, and 5 to 6 membered heteroaryl of $R^7$ are each optionally substituted with one, two, or three substituents independently selected from the group consisting of —$OR^8$, —OP(=O)(OH)$_2$, $C_3$-$C_8$ carbocyclyl, 4 to 6 membered heterocyclyl containing 1, 2, or 3 heteroatoms selected from N, O, and S, 5 to 6 membered heteroaryl containing 1, 2, or 3 heteroatoms selected from N, O, and S, and phenyl; wherein substituent $C_3$-$C_8$ carbocyclyl of $R^7$ is optionally substituted with one, two, or three substituents independently selected from $C_1$-$C_8$ alkyl, halogen, —$CF_3$, cyano, —$CH_2CN$, and phenyl, wherein substituent 4 to 6 membered heterocyclyl of $R^7$ is optionally substituted with one, two, or three substituents independently selected from carbonyl and $C_1$-$C_6$ alkyl, and wherein substituent phenyl of $R^7$ is optionally substituted with one, two or three substituents independently selected from halo, cyano, $C_1$-$C_6$alkyl, and $OR^8$.

In some embodiments, $R^7$ is $C_1$-$C_8$ alkyl, $C_3$-$C_8$ carbocyclyl, $C_6$-$C_{10}$ aryl, 4 to 6 membered heterocyclyl containing 1, 2, or 3 heteroatoms selected from N, O, and S or 5 to 6 membered heteroaryl containing 1, 2, or 3 heteroatoms selected from N, O, and S; wherein $C_1$-$C_8$ alkyl, $C_3$-$C_8$ carbocyclyl, $C_6$-$C_{10}$ aryl, 4 to 6 membered heterocyclyl, and 5 to 6 membered heteroaryl of $R^7$ are each optionally substituted with one, two, or three substituents independently selected from the group consisting of —$OR^8$, —OP(=O)(OH)$_2$, $C_3$-$C_8$ carbocyclyl, 4 to 6 membered heterocyclyl containing 1, 2, or 3 heteroatoms selected from N, O, and S, 5 to 6 membered heteroaryl containing 1, 2, or 3 heteroatoms selected from N, O, and S, and phenyl; wherein substituent 4 to 6 membered heterocyclyl of $R^7$ is optionally substituted with one, two, or three substituents independently selected from carbonyl and $C_1$-$C_6$ alkyl and wherein substituent phenyl of $R^7$ is optionally substituted with one, two, or three substituents independently selected from halo, cyano, and $C_1$-$C_6$ alkyl.

In some embodiments, $R^7$ is $C_1$-$C_8$ alkyl, $C_3$-$C_8$ carbocyclyl, $C_6$-$C_{10}$ aryl, 4 to 6 membered heterocyclyl containing 1, 2, or 3 heteroatoms selected from N, O, and S or 5 to 6 membered heteroaryl containing 1, 2, or 3 heteroatoms selected from N, O, and S; wherein $C_1$-$C_8$ alkyl, $C_3$-$C_8$ carbocyclyl, $C_6$-$C_{10}$ aryl, 4 to 6 membered heterocyclyl, and 5 to 6 membered heteroaryl of $R^7$ are each optionally substituted with one, two, or three substituents independently selected from the group consisting of —$OR^8$, —OP(=O)(OH)$_2$, $C_3$-$C_8$ carbocyclyl, 4 to 6 membered heterocyclyl containing 1, 2, or 3 heteroatoms selected from N, O, and S, 5 to 6 membered heteroaryl containing 1, 2, or 3 heteroatoms selected from N, O, and S, and phenyl; wherein 4 to 6 membered heterocyclyl is optionally substituted with one, two or three substituents independently selected from carbonyl and $C_1$-$C_6$ alkyl and wherein phenyl is optionally substituted with one, two, or three substituents independently selected from halo, cyano, and $C_1$-$C_6$ alkyl.

In some embodiments, R is $C_1$-$C_8$ alkyl, $C_3$-$C_8$ carbocyclyl, $C_6$-$C_{10}$ aryl, 4 to 6 membered heterocyclyl containing 1, 2, or 3 heteroatoms selected from N, O, and S or 5 to 6 membered heteroaryl containing 1, 2, or 3 heteroatoms selected from N, O, and S; wherein $C_1$-$C_8$ alkyl, $C_3$-$C_8$ carbocyclyl, $C_6$-$C_{10}$ aryl, 4 to 6 membered heterocyclyl, and 5 to 6 membered heteroaryl of $R^7$ are each optionally substituted with one, two, or three substituents independently selected from the group consisting of $C_1$-$C_8$ alkyl, —$OR^8$, —OP(=O)(OH)$_2$, $C_3$-$C_8$ carbocyclyl and phenyl; wherein substituent phenyl of $R^7$ is optionally substituted with one, two, or three substituents independently selected from halo, cyano, and $C_1$-$C_6$ alkyl.

In some embodiments, R is $C_1$-$C_8$ alkyl, $C_3$-$C_8$ carbocyclyl, $C_6$-$C_{10}$ aryl, 4 to 6 membered heterocyclyl containing 1, 2, or 3 heteroatoms selected from N, O, and S or 5 to 6 membered heteroaryl containing 1, 2, or 3 heteroatoms selected from N, O, and S; wherein $C_1$-$C_8$ alkyl, $C_3$-$C_8$ carbocyclyl, $C_6$-$C_{10}$ aryl, 4 to 6 membered heterocyclyl, and 5 to 6 membered heteroaryl of $R^7$ are each optionally substituted with one, two, or three substituents independently selected from the group consisting of —$OR^8$, —OP(=O)(OH)$_2$, $C_3$-$C_8$ carbocyclyl and phenyl; wherein substituent phenyl of $R^7$ is optionally substituted with one, two, or three substituents independently selected from halo, cyano, and $C_1$-$C_6$ alkyl.

In some embodiments, R is $C_1$-$C_8$ alkyl, $C_3$-$C_8$ carbocyclyl, $C_6$-$C_{10}$ aryl, 4 to 6 membered heterocyclyl containing 1, 2, or 3 heteroatoms selected from N, O, and S or 5 to 6 membered heteroaryl containing 1, 2, or 3 heteroatoms selected from N, O, and S; wherein $C_1$-$C_8$ alkyl, $C_3$-$C_8$ carbocyclyl, $C_6$-$C_{10}$ aryl, 4 to 6 membered heterocyclyl, and 5 to 6 membered heteroaryl of $R^7$ are each optionally substituted with one, two, or three substituents independently selected from the group consisting of —$OR^8$, —OP(=O)(OH)$_2$, $C_3$-$C_8$ carbocyclyl and phenyl; wherein phenyl is optionally substituted with one, two, or three substituents independently selected from halo, cyano, and $C_1$-$C_6$ alkyl.

In some embodiments, $R^7$ is $C_1$-$C_8$ alkyl, $C_3$-$C_8$ carbocyclyl, $C_6$-$C_{10}$ aryl, 4 to 6 membered heterocyclyl containing 1, 2, or 3 heteroatoms selected from N, O, and S or 5 to 6 membered heteroaryl containing 1, 2, or 3 heteroatoms selected from N, O, and S; wherein $C_1$-$C_8$ alkyl $C_3$-$C_8$ carbocyclyl, $C_6$-$C_{10}$ aryl, 4 to 6 membered heterocyclyl containing 1, 2, or 3 heteroatoms selected from N, O, and S, and 5 to 6 membered heteroaryl containing 1, 2, or 3 heteroatoms selected from N, O, and S of $R^7$ are each optionally substituted with one, two, or three substituents independently selected from the group consisting of $C_1$-$C_8$ alkyl, —$OR^8$, —OP(=O)(OH)$_2$, $C_3$-$C_8$ carbocyclyl, 4 to 6 membered heterocyclyl containing 1, 2, or 3 heteroatoms selected from N, O, and S, 5 to 6 membered heteroaryl containing 1, 2, or 3 heteroatoms selected from N, O, and S, and phenyl; wherein substituent 4 to 6 membered heterocyclyl of $R^7$ is optionally substituted with one, two, or three substituents independently selected from carbonyl and $C_1$-$C_6$ alkyl.

In some embodiments, $R^7$ is $C_1$-$C_8$ alkyl, $C_3$-$C_8$ carbocyclyl, $C_6$-$C_{10}$ aryl, 4 to 6 membered heterocyclyl containing 1, 2, or 3 heteroatoms selected from N, O, and S or 5 to 6 membered heteroaryl containing 1, 2, or 3 heteroatoms selected from N, O, and S; wherein $C_1$-$C_8$ alkyl $C_3$-$C_8$ carbocyclyl, $C_6$-$C_{10}$ aryl, 4 to 6 membered heterocyclyl containing 1, 2, or 3 heteroatoms selected from N, O, and S, and 5 to 6 membered heteroaryl containing 1, 2, or 3 heteroatoms selected from N, O, and S of $R^7$ are each optionally substituted with one, two, or three substituents independently selected from the group consisting of —$OR^8$, —OP(=O)(OH)$_2$, $C_3$-$C_8$ carbocyclyl, 4 to 6 membered heterocyclyl containing 1, 2, or 3 heteroatoms selected from N, O, and S, 5 to 6 membered heteroaryl containing 1, 2, or 3 heteroatoms selected from N, O, and S, and phenyl; wherein substituent 4 to 6 membered heterocyclyl of $R^7$ is optionally substituted with one, two, or three substituents independently selected from carbonyl and $C_1$-$C_6$ alkyl.

In some embodiments, $R^7$ is $C_1$-$C_8$ alkyl, $C_3$-$C_8$ carbocyclyl, $C_6$-$C_{10}$ aryl, 4 to 6 membered heterocyclyl containing 1, 2, or 3 heteroatoms selected from N, O, and S or 5 to 6 membered heteroaryl containing 1, 2, or 3 heteroatoms selected from N, O, and S; wherein $C_1$-$C_8$ alkyl $C_3$-$C_8$ carbocyclyl, $C_6$-$C_{10}$ aryl, 4 to 6 membered heterocyclyl containing 1, 2, or 3 heteroatoms selected from N, O, and S, and 5 to 6 membered heteroaryl containing 1, 2, or 3 heteroatoms selected from N, O, and S are optionally substituted with one, two, or three substituents independently selected from the group consisting of —$OR^8$, —OP(=O)(OH)$_2$, $C_3$-$C_8$ carbocyclyl, 4 to 6 membered heterocyclyl containing 1, 2, or 3 heteroatoms selected from N, O, and S, 5 to 6 membered heteroaryl containing 1, 2, or 3 heteroatoms selected from N, O, and S. and phenyl; wherein 4 to 6 membered heterocyclyl is optionally substituted with one, two, or three substituents independently selected from carbonyl and $C_1$-$C_6$ alkyl.

In some embodiments, $R^7$ is $C_1$-$C_8$ alkyl, $C_3$-$C_8$ carbocyclyl, $C_6$-$C_{10}$ aryl, 4 to 6 membered heterocyclyl containing 1, 2, or 3 heteroatoms selected from N, O, and S or 5 to 6 membered heteroaryl containing 1, 2, or 3 heteroatoms selected from N, O, and S; wherein $C_1$-$C_8$ alkyl, $C_3$-$C_8$ carbocyclyl, $C_6$-$C_{10}$ aryl, 4 to 6 membered heterocyclyl containing 1, 2, or 3 heteroatoms selected from N, O, and S, and 5 to 6 membered heteroaryl containing 1, 2, or 3 heteroatoms selected from N, O, and S of $R^7$ are each optionally substituted with one, two, or three substituents independently selected from the group consisting of $C_1$-$C_8$ alkyl, —$OR^8$, —OP(=O)(OH)$_2$, $C_3$-$C_8$ carbocyclyl, 4 to 6 membered heterocyclyl containing 1, 2, or 3 heteroatoms selected from N, O, and S, 5 to 6 membered heteroaryl containing 1, 2, or 3 heteroatoms selected from N, O, and S, and phenyl.

In some embodiments, $R^7$ is $C_1$-$C_8$ alkyl, $C_3$-$C_8$ carbocyclyl, $C_6$-$C_{10}$ aryl, 4 to 6 membered heterocyclyl containing 1, 2, or 3 heteroatoms selected from N, O, and S or 5 to 6 membered heteroaryl containing 1, 2, or 3 heteroatoms selected from N, O, and S; wherein $C_1$-$C_8$ alkyl, $C_3$-$C_8$ carbocyclyl, $C_6$-$C_{10}$ aryl, 4 to 6 membered heterocyclyl containing 1, 2, or 3 heteroatoms selected from N, O, and S, and 5 to 6 membered heteroaryl containing 1, 2, or 3 heteroatoms selected from N, O, and S of $R^7$ are each optionally substituted with one, two, or three substituents independently selected from the group consisting of —$OR^8$, —OP(=O)(OH)$_2$, $C_3$-$C_8$ carbocyclyl, 4 to 6 membered heterocyclyl containing 1, 2, or 3 heteroatoms selected from N, O, and S, 5 to 6 membered heteroaryl containing 1, 2, or 3 heteroatoms selected from N, O, and S, and phenyl.

In some embodiments, $R^7$ is $C_1$-$C_8$ alkyl, $C_3$-$C_8$ carbocyclyl, $C_6$-$C_{10}$ aryl, 4 to 6 membered heterocyclyl containing 1, 2, or 3 heteroatoms selected from N, O, and S or 5 to 6 membered heteroaryl containing 1, 2, or 3 heteroatoms selected from N, O, and S; wherein $C_1$-$C_8$ alkyl, $C_3$-$C_8$ carbocyclyl, $C_6$-$C_{10}$ aryl, 4 to 6 membered heterocyclyl containing 1, 2, or 3 heteroatoms selected from N, O, and S, and 5 to 6 membered heteroaryl containing 1, 2, or 3 heteroatoms selected from N, O, and S are optionally substituted with one, two, or three substituents independently selected from the group consisting of —$OR^8$, —OP(=O)(OH)$_2$, $C_3$-$C_8$ carbocyclyl, 4 to 6 membered heterocyclyl containing 1, 2, or 3 heteroatoms selected from N, O, and S, 5 to 6 membered heteroaryl containing 1, 2, or 3 heteroatoms selected from N, O, and S, and phenyl.

In some embodiments, $R^7$ is $C_1$-$C_8$ alkyl, $C_3$-$C_8$ carbocyclyl, $C_6$-$C_{10}$ aryl, 4 to 6 membered heterocyclyl containing 1, 2, or 3 heteroatoms selected from N, O, and S or 5 to 6 membered heteroaryl containing 1, 2, or 3 heteroatoms selected from N, O, and S; wherein $C_1$-$C_8$ alkyl, $C_3$-$C_8$ carbocyclyl, $C_6$-$C_{10}$ aryl, 4 to 6 membered heterocyclyl containing 1, 2, or 3 heteroatoms selected from N, O, and S, and 5 to 6 membered heteroaryl containing 1, 2, or 3 heteroatoms selected from N, O, and S of $R^7$ are each optionally substituted with one, two, or three substituents independently selected from the group consisting of $C_1$-$C_8$ alkyl, —$OR^8$, —OP(=O)(OH)$_2$, $C_3$-$C_8$ carbocyclyl and phenyl.

In some embodiments, $R^7$ is $C_1$-$C_8$ alkyl, $C_3$-$C_8$ carbocyclyl, $C_6$-$C_{10}$ aryl, 4 to 6 membered heterocyclyl containing 1, 2, or 3 heteroatoms selected from N, O, and S or 5 to 6 membered heteroaryl containing 1, 2, or 3 heteroatoms selected from N, O, and S; wherein $C_1$-$C_8$ alkyl, $C_3$-$C_8$ carbocyclyl, $C_6$-$C_{10}$ aryl, 4 to 6 membered heterocyclyl containing 1, 2, or 3 heteroatoms selected from N, O, and S, and 5 to 6 membered heteroaryl containing 1, 2, or 3 heteroatoms selected from N, O, and S of $R^7$ are each optionally substituted with one, two, or three substituents independently selected from the group consisting of —$OR^8$, —OP(=O)(OH)$_2$, $C_3$-$C_8$ carbocyclyl and phenyl.

In some embodiments, $R^7$ is $C_1$-$C_8$ alkyl, $C_3$-$C_8$ carbocyclyl, $C_6$-$C_{10}$ aryl, 4 to 6 membered heterocyclyl containing 1, 2, or 3 heteroatoms selected from N, O, and S or 5 to 6 membered heteroaryl containing 1, 2, or 3 heteroatoms selected from N, O, and S; $C_1$-$C_8$ alkyl, $C_3$-$C_8$ carbocyclyl, $C_6$-$C_{10}$ aryl, 4 to 6 membered heterocyclyl containing 1, 2, or 3 heteroatoms selected from N, O, and S, and 5 to 6 membered heteroaryl containing 1, 2, or 3 heteroatoms selected from N, O, and S is optionally substituted with one, two, or three substituents independently selected from the group consisting of —$OR^8$, —OP(=O)(OH)$_2$, $C_3$-$C_8$ carbocyclyl and phenyl.

In some embodiments, $R^7$ is $C_1$-$C_8$ alkyl, $C_3$-$C_8$ carbocyclyl, $C_6$-$C_{10}$ aryl, 4 to 6 membered heterocyclyl containing 1, 2, or 3 heteroatoms selected from N, O, and S or 5 to 6 membered heteroaryl containing 1, 2, or 3 heteroatoms selected from N, O, and S; wherein $C_1$-$C_8$ alkyl of $R^7$ is optionally substituted with one, two, or three substituents independently selected from the group consisting of $C_1$-$C_8$ alkyl, —$OR^8$, —OP(=O)(OH)$_2$, $C_3$-$C_8$ carbocyclyl, 4 to 6 membered heterocyclyl containing 1, 2, or 3 heteroatoms selected from N, O, and S, 5 to 6 membered heteroaryl containing 1, 2, or 3 heteroatoms selected from N, O, and S. and phenyl; wherein substituent 4 to 6 membered heterocyclyl of $R^7$ is optionally substituted with one, two, or three substituents independently selected from carbonyl and $C_1$-$C_6$ alkyl.

In some embodiments, $R^7$ is $C_1$-$C_8$ alkyl, $C_3$-$C_8$ carbocyclyl, $C_6$-$C_{10}$ aryl, 4 to 6 membered heterocyclyl containing 1, 2, or 3 heteroatoms selected from N, O, and S or 5 to 6 membered heteroaryl containing 1, 2, or 3 heteroatoms selected from N, O, and S; wherein $C_1$-$C_8$ alkyl of $R^7$ is optionally substituted with one, two, or three substituents independently selected from the group consisting of —$OR^8$, —OP(=O)(OH)$_2$, $C_3$-$C_8$ carbocyclyl, 4 to 6 membered heterocyclyl containing 1, 2, or 3 heteroatoms selected from N, O, and S, 5 to 6 membered heteroaryl containing 1, 2, or 3 heteroatoms selected from N, O, and S, and phenyl; wherein substituent 4 to 6 membered heterocyclyl of $R^7$ is optionally substituted with one, two, or three substituents independently selected from carbonyl and $C_1$-$C_6$ alkyl.

In some embodiments, $R^7$ is $C_1$-$C_8$ alkyl, $C_3$-$C_8$ carbocyclyl, $C_6$-$C_{10}$ aryl, 4 to 6 membered heterocyclyl containing 1, 2, or 3 heteroatoms selected from N, O, and S or 5 to 6 membered heteroaryl containing 1, 2, or 3 heteroatoms selected from N, O, and S; wherein $C_1$-$C_8$ alkyl is optionally substituted with one, two, or three substituents independently selected from the group consisting of —$OR^8$, —OP(=O)(OH)$_2$, $C_3$-$C_8$ carbocyclyl, 4 to 6 membered heterocyclyl containing 1, 2, or 3 heteroatoms selected from N, O, and S, 5 to 6 membered heteroaryl containing 1, 2, or 3 heteroatoms selected from N, O, and S, and phenyl; wherein 4 to 6 membered heterocyclyl is optionally substituted with one, two, or three substituents independently selected from carbonyl and $C_1$-$C_6$ alkyl.

In some embodiments, $R^7$ is $C_1$-$C_8$ alkyl, $C_3$-$C_8$ carbocyclyl, $C_6$-$C_{10}$ aryl, 4 to 6 membered heterocyclyl containing 1, 2, or 3 heteroatoms selected from N, O, and S or 5 to 6 membered heteroaryl containing 1, 2, or 3 heteroatoms selected from N, O, and S; wherein $C_1$-$C_8$ alkyl of $R^7$ is optionally substituted with one, two, or three substituents independently selected from the group consisting of —$OR^8$, —OP(=O)(OH)$_2$, $C_3$-$C_8$ carbocyclyl, 4 to 6 membered heterocyclyl containing 1, 2, or 3 heteroatoms selected from N, O, and S, 5 to 6 membered heteroaryl containing 1, 2, or 3 heteroatoms selected from N, O, and S, and phenyl.

In some embodiments, $R^7$ is $C_1$-$C_8$ alkyl, $C_3$-$C_8$ carbocyclyl, $C_6$-$C_{10}$ aryl, 4 to 6 membered heterocyclyl containing 1, 2, or 3 heteroatoms selected from N, O, and S or 5 to 6 membered heteroaryl containing 1, 2, or 3 heteroatoms selected from N, O, and S; wherein $C_1$-$C_8$ alkyl is optionally substituted with one, two, or three substituents independently selected from the group consisting of —$OR^8$, —OP(=O)(OH)$_2$, $C_3$-$C_8$ carbocyclyl, 4 to 6 membered heterocyclyl containing 1, 2, or 3 heteroatoms selected from N, O, and S, 5 to 6 membered heteroaryl containing 1, 2, or 3 heteroatoms selected from N, O, and S, and phenyl.

In some embodiments, $R^7$ is $C_1$-$C_8$ alkyl, $C_3$-$C_8$ carbocyclyl, $C_6$-$C_{10}$ aryl, 4 to 6 membered heterocyclyl containing 1, 2, or 3 heteroatoms selected from N, O, and S or 5 to 6 membered heteroaryl containing 1, 2, or 3 heteroatoms selected from N, O, and S; wherein $C_1$-$C_8$ alkyl of $R^7$ is optionally substituted with one, two, or three substituents independently selected from the group consisting of —$OR^8$, —OP(=O)(OH)$_2$, $C_3$-$C_8$ carbocyclyl and phenyl.

In some embodiments, $R^7$ is $C_1$-$C_8$ alkyl, $C_3$-$C_8$ carbocyclyl, $C_6$-$C_{10}$ aryl, 4 to 6 membered heterocyclyl containing 1, 2, or 3 heteroatoms selected from N, O, and S or 5 to 6 membered heteroaryl containing 1, 2, or 3 heteroatoms selected from N, O, and S; wherein $C_1$-$C_8$ alkyl is optionally substituted with one, two, or three substituents independently selected from the group consisting of —$OR^8$, —OP(=O)(OH)$_2$, $C_3$-$C_8$ carbocyclyl and phenyl.

In some embodiments, $R^7$ is $C_1$-$C_8$ alkyl, $C_2$-$C_8$ alkenyl, or $C_2$-$C_8$ alkynyl; wherein $C_1$-$C_8$ alkyl, $C_2$-$C_8$ alkenyl, or $C_2$-$C_8$ alkynyl of $R^7$ are each, independently, optionally substituted with one, two, or three substituents independently selected from the group consisting of halogen, cyano, —$N_3$, —$OR^8$, —$NR^9R^{10}$, —OP(=O)(OH)$_2$, $C_3$-$C_8$ carbocyclyl and phenyl; wherein phenyl is optionally substituted with one, two or three substituents independently selected from halo, cyano, and $C_1$-$C_6$ alkyl.

In some embodiments, $R^7$ is $C_1$-$C_8$ alkyl, $C_2$-$C_8$ alkenyl, or $C_2$-$C_8$ alkynyl; wherein $C_1$-$C_8$ alkyl, $C_2$-$C_8$ alkenyl, or $C_2$-$C_8$ alkynyl are each, independently, optionally substituted with one, two, or three substituents independently selected from the group consisting of halogen, cyano, —$N_3$, —$OR^8$, —$NR^9R^{10}$, —OP(=O)(OH)$_2$, $C_3$-$C_8$ carbocyclyl and phenyl; wherein phenyl is optionally substituted with one, two or three substituents independently selected from halo, cyano, and $C_1$-$C_6$ alkyl.

In some embodiments, $R^7$ is $C_1$-$C_{20}$ alkyl optionally substituted with one, two, or three substituents independently selected from the group consisting of $C_1$-$C_8$ alkyl, halogen, cyano, carbonyl, —$N_3$, —$OR^8$, —$NR^9R^{10}$, —OP(=O)(OH)$_2$, —OP(=O)($OR^8$)$_2$, $C_3$-$C_8$ carbocyclyl, 4 to 6 membered heterocyclyl containing 1, 2, or 3 heteroatoms selected from N, O, and S, 5 to 6 membered heteroaryl containing 1, 2, or 3 heteroatoms selected from N, O, and S, and phenyl; wherein substituent $C_3$-$C_8$ carbocyclyl of $R^7$ is optionally substituted with one, two, or three substituents independently selected from $C_1$-$C_8$ alkyl, halogen, —$CF_3$, cyano, —$CH_2CN$, and phenyl, wherein substituent 4 to 6 membered heterocyclyl of $R^7$ is optionally substituted with one, two, or three substituents independently selected from carbonyl and $C_1$-$C_6$ alkyl, and wherein substituent phenyl of $R^7$ is optionally substituted with one, two or three substituents independently selected from halo, cyano, $C_1$-$C_6$alkyl, and $OR^3$.

In some embodiments, $R^7$ is $C_1$-$C_{20}$ alkyl optionally substituted with one, two, or three substituents independently selected from the group consisting of halogen, cyano, —$N_3$, —$OR^8$, —$NR^9R^{10}$, —OP(=O)(OH)$_2$, $C_3$-$C_8$ carbocyclyl, 4 to 6 membered heterocyclyl containing 1, 2, or 3 heteroatoms selected from N, O, and S, 5 to 6 membered heteroaryl containing 1, 2, or 3 heteroatoms selected from N, O, and S, and phenyl; wherein substituent 4 to 6 membered heterocyclyl of $R^7$ is optionally substituted with one, two, or three substituents independently selected from carbonyl and $C_1$-$C_6$ alkyl and wherein substituent phenyl of $R^7$ is optionally substituted with one, two or three substituents independently selected from halo, cyano, and $C_1$-$C_6$ alkyl.

In some embodiments, $R^7$ is $C_1$-$C_8$ alkyl optionally substituted with one, two, or three substituents independently selected from the group consisting of halogen, cyano, —$N_3$, —$OR^5$, —$NR^9R^{10}$, —OP(=O)(OH)$_2$, $C_3$-$C_8$ carbocyclyl, 4 to 6 membered heterocyclyl containing 1, 2, or 3 heteroatoms selected from N, O, and S, 5 to 6 membered heteroaryl containing 1, 2, or 3 heteroatoms selected from N, O, and S, and phenyl; wherein substituent 4 to 6 membered heterocyclyl of $R^7$ is optionally substituted with one, two, or three substituents independently selected from carbonyl and $C_1$-$C_6$ alkyl and wherein substituent phenyl of $R^7$ is optionally substituted with one, two or three substituents independently selected from halo, cyano, and $C_1$-$C_6$ alkyl.

In some embodiments, $R^7$ is $C_1$-$C_8$ alkyl optionally substituted with one, two, or three substituents independently selected from the group consisting of halogen, cyano, —$N_3$, —$OR^8$, —$NR^9R^{10}$, —OP(=O)(OH)$_2$, $C_3$-$C_8$ carbocyclyl, 4 to 6 membered heterocyclyl containing 1, 2, or 3 heteroatoms selected from N, O, and S, 5 to 6 membered heteroaryl containing 1, 2, or 3 heteroatoms selected from N, O, and S, and phenyl; wherein 4 to 6 membered heterocyclyl is optionally substituted with one, two, or three substituents independently selected from carbonyl and $C_1$-$C_6$ alkyl and wherein phenyl is optionally substituted with one, two or three substituents independently selected from halo, cyano, and $C_1$-$C_6$ alkyl.

In some embodiments, $R^7$ is $C_1$-$C_8$ alkyl optionally substituted with one, two, or three substituents independently selected from the group consisting of halogen, cyano, carbonyl, —$N_3$, —$OR^8$, —$NR^9R^{10}$, —OP(=O)(OH)$_2$, $C_3$-$C_8$ carbocyclyl and phenyl; wherein substituent $C_3$-$C_8$ carbocyclyl of $R^7$ is optionally substituted with one, two or three substituents independently selected from halo, cyano, and $C_1$-$C_6$ alkyl and wherein substitutent phenyl of $R^7$ is optionally substituted with one, two or three substituents independently selected from halo, cyano, and $C_1$-$C_6$ alkyl.

In some embodiments, $R^7$ is $C_1$-$C_8$ alkyl optionally substituted with one, two, or three substituents independently selected from the group consisting of halogen, cyano, —$N_3$, —$OR^8$, —$NR^9R^{10}$, —OP(=O)(OH)$_2$, $C_3$-$C_8$ carbocyclyl and phenyl; wherein substituent phenyl of $R^7$ is optionally substituted with one, two or three substituents independently selected from halo, cyano, and $C_1$-$C_6$ alkyl.

In some embodiments, $R^7$ is $C_1$-$C_8$ alkyl optionally substituted with one, two, or three substituents independently selected from the group consisting of halogen, cyano, —$N_3$, —$OR^8$, —$NR^9R^{10}$, —OP(=O)(OH)$_2$, $C_3$-$C_8$ carbocyclyl and phenyl; wherein phenyl is optionally substituted with one, two or three substituents independently selected from halo, cyano, and $C_1$-$C_6$ alkyl.

In some embodiments, $R^7$ is $C_1$-$C_6$ alkyl optionally substituted with one, two, or three substituents independently selected from the group consisting of halogen, cyano, —$N_3$, —$OR^8$, —$NR^9R^{10}$, —$OP(=O)(OH)_2$, $C_3$-$C_8$ carbocyclyl and phenyl; wherein substituent phenyl of $R^7$ is optionally substituted with one, two or three substituents independently selected from halo, cyano, and $C_1$-$C_6$ alkyl.

In some embodiments, $R^7$ is $C_1$-$C_6$ alkyl optionally substituted with one, two, or three substituents independently selected from the group consisting of halogen, cyano, —$N_3$, —$OR^8$, —$NR^9R^{10}$, —$OP(=O)(OH)_2$, $C_3$-$C_8$ carbocyclyl and phenyl; wherein phenyl is optionally substituted with one, two or three substituents independently selected from halo, cyano, and $C_1$-$C_6$ alkyl.

In some embodiments, $R^7$ is $C_1$-$C_8$ alkyl optionally substituted with one substituent selected from the group consisting of —$OR^8$, —$OP(=O)(OH)_2$, —$OP(=O)(OR^8)_2$, $C_3$-$C_8$ carbocyclyl and phenyl.

In some embodiments, $R^7$ is $C_1$-$C_8$ alkyl optionally substituted with one substituent selected from the group consisting of —$OR^8$, —$OP(=O)(OH)_2$, $C_3$-$C_8$ carbocyclyl and phenyl. In some embodiments, $R^7$ is $C_1$-$C_6$ alkyl optionally substituted with one substituent selected from the group consisting of —$OR^8$, —$OP(=O)(OH)_2$, $C_3$-$C_8$ carbocyclyl and phenyl.

In some embodiments, $R^7$ is $C_1$-$C_8$ alkyl substituted with halogen. In some embodiments, $R^7$ is $C_1$-$C_8$ alkyl substituted with —F or —Cl. In some embodiments, $R^7$ is

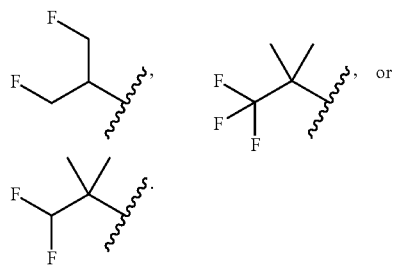

In some embodiments, $R^7$ is

In some embodiments, $R^7$ is $C_1$-$C_8$ alkyl substituted with —$OR^8$. In some embodiments, $R^7$ is $C_2$-$C_4$ alkyl substituted with —$OR^8$. In some embodiments, $R^7$ is $C_2$-$C_4$ alkyl substituted with —$OCH_3$. In some embodiments, $R^7$ is

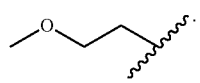 [SMILES: *CCOC]

In some embodiments, $R^7$ is

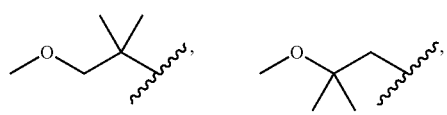

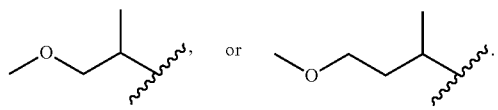

In some embodiments, $R^7$ is

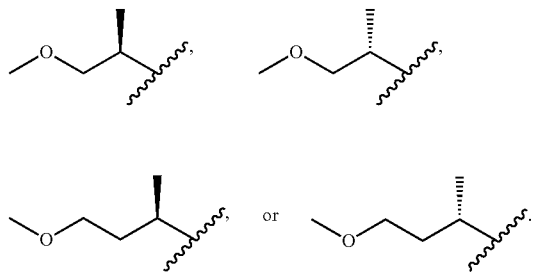

In some embodiments, $R^7$ is $C_1$-$C_8$ alkyl substituted with —$NR^9R^{10}$. In some embodiments, $R^7$ is $C_1$-$C_8$ alkyl substituted with —$N(CH_3)_2$.

In some embodiments, $R^7$ is $C_1$-$C_8$ alkyl substituted with carbonyl.

In some embodiments, $R^7$ is $C_1$-$C_8$ alkyl substituted with carbonyl and —$OR^8$. In some embodiments, $R^7$ is $C_1$-$C_8$ alkyl substituted with carbonyl and —$OCH_2CH_3$. In some embodiments, $R^7$ is

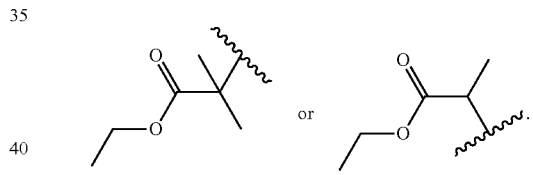

In some embodiments, $R^7$ is

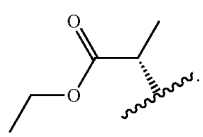 [SMILES: *[C@@H](C)C(=O)OCC]

In some embodiments, $R^7$ is $C_1$-$C_8$ alkyl substituted with carbonyl and —$NR^9R^{10}$. In some embodiments, $R^7$ is $C_1$-$C_8$ alkyl substituted with carbonyl and —$N(CH_3)_2$. In some embodiments, $R^7$ is

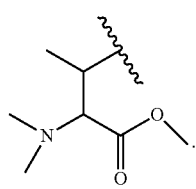

In some embodiments, $R^7$ is

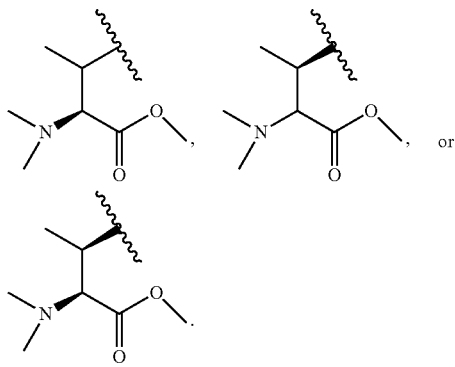

In some embodiments, $R^7$ is $C_1$-$C_8$ alkyl substituted with carbonyl and —OC(CH$_3$)$_3$. In some embodiments, $R^7$ is

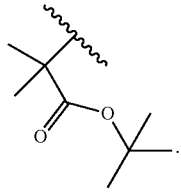 [SMILES: *C(C)(C)C(=O)OC(C)(C)C]

In some embodiments, $R^7$ is $C_1$-$C_8$ alkyl substituted with carbonyl and —OH. In some embodiments, $R^7$ is

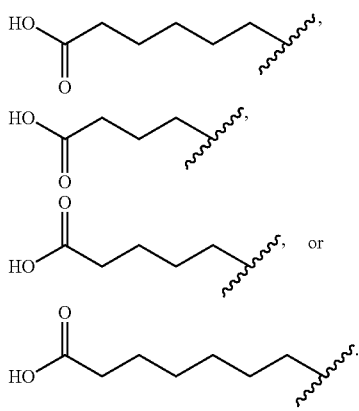

In some embodiments, $R^7$ is $C_1$-$C_8$ alkyl substituted with carbonyl, —NR$^9$R$^{10}$, and —OR$^8$. In some embodiments, $R^7$ is $C_1$-$C_8$ alkyl substituted with carbonyl, —N(CH$_3$)$_2$, and —OCH$_3$. In some embodiments, $R^7$ is $C_1$-$C_8$ alkyl substituted with carbonyl, —N(CH$_3$)$_2$, and —OCH(CH$_3$). In some embodiments, $R^7$ is $C_1$-$C_8$ alkyl substituted with carbonyl, —N(CH$_3$)$_2$, and —OCH$_2$C(CH$_3$)$_3$. In some embodiments, $R^7$ is $C_1$-$C_8$ alkyl substituted with carbonyl, —N(CH$_3$)$_2$, and

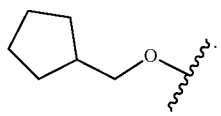 [SMILES: *OCC1CCCC1]

In some embodiments, $R^7$ is $C_1$-$C_8$ alkyl substituted with carbonyl, —N(CH$_3$)$_2$ and

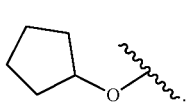 [SMILES: *OC1CCCC1]

In some embodiments, $R^7$ is $C_1$-$C_8$ alkyl substituted with carbonyl, —N(CH$_3$)$_2$, and

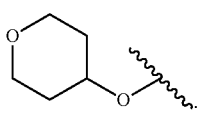 [SMILES: *OC1CCOCC1]

In some embodiments, $R^7$ is

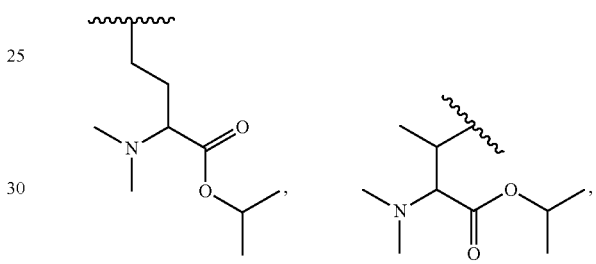

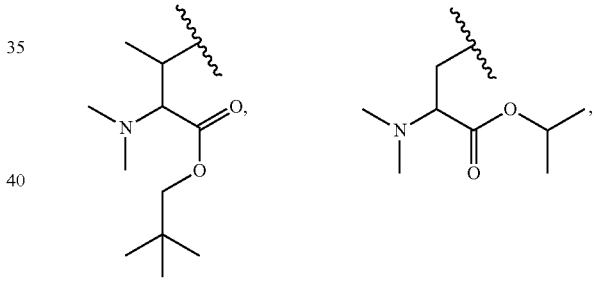

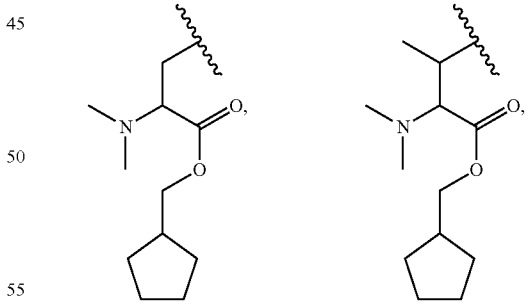

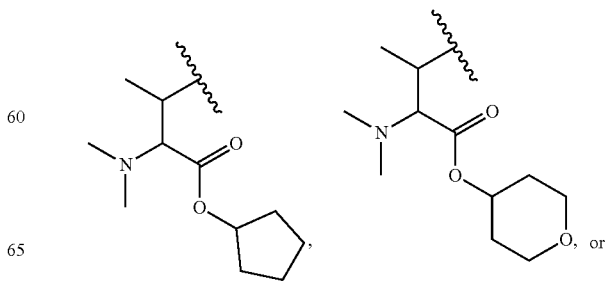

-continued

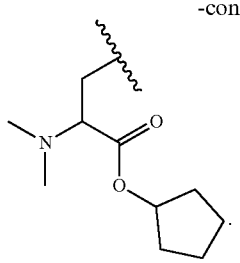

In some embodiments, R$^7$ is

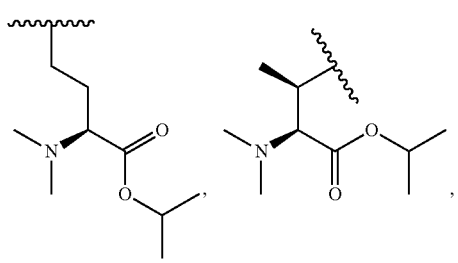

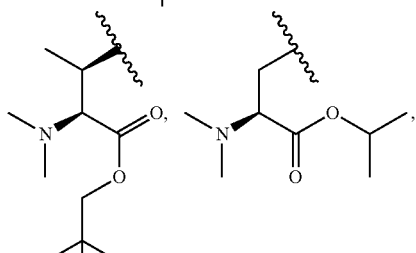

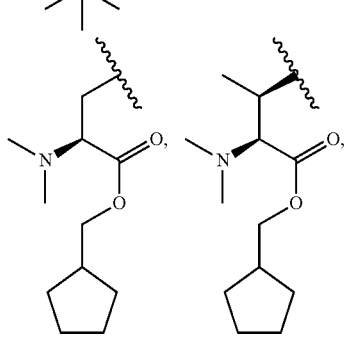

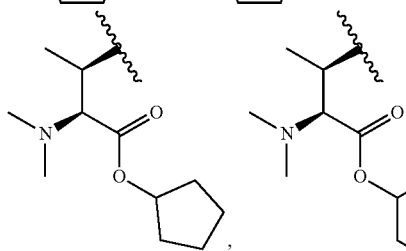

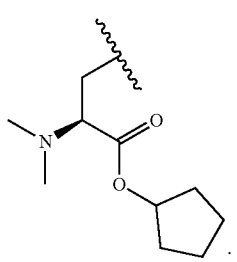

In some embodiments, R$^7$ is C$_1$-C$_8$ alkyl substituted with 5 to 6 membered heteroaryl containing 1, 2, or 3 heteroatoms selected from N, O, and S. In some embodiments, R$^7$ is alkyl substituted with pyridinyl, pyrimidinyl, or imidazolyl. In some embodiments, R$^7$ is

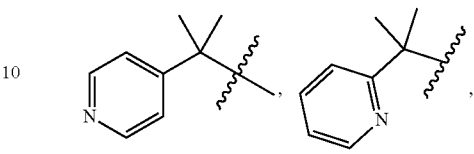

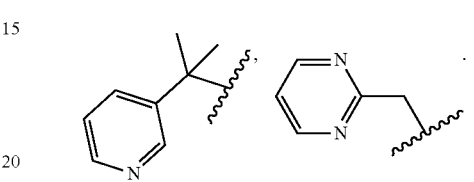

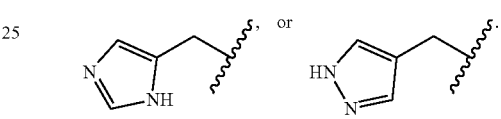

In some embodiments, R$^7$ is C$_1$-C$_8$ alkyl substituted with phenyl wherein substituent phenyl of R$^7$ is optionally substituted with one, two or three substituents independently selected from halo, cyano, C$_1$-C$_6$ alkyl, and OR$^8$. In some embodiments, R$^7$ is C$_1$-C$_8$ alkyl substituted with phenyl wherein substituent phenyl of R$^7$ is substituted with OR$^8$. In some embodiments, R$^7$ is

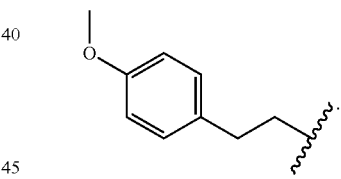

In some embodiments, R$^7$ is C$_1$-C$_8$ alkyl substituted with phenyl. In some embodiments, R$^7$ is C$_1$-C$_4$ alkyl substituted with phenyl. In some embodiments, R$^7$ is

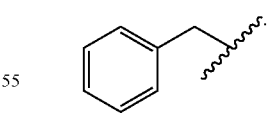

In some embodiments, R$^7$ is

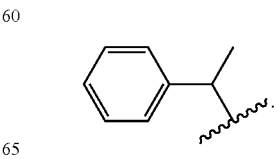

In some embodiments, $R^7$ is or

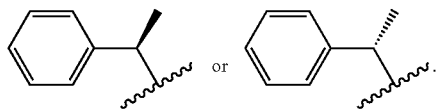

In some embodiments, $R^7$ is $C_1$-$C_8$ alkyl substituted with $C_3$-$C_8$ carbocyclyl wherein substituent $C_3$-$C_8$ carbocyclyl of $R^7$ is optionally substituted with one, two, or three substituents independently selected from $C_1$-$C_8$ alkyl, halogen, —$CF_3$, cyano, —$CH_2CN$, and phenyl. In some embodiments. $R^7$ is

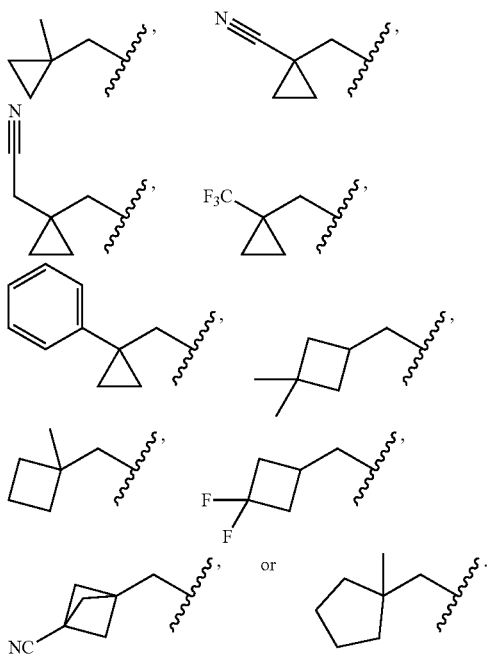

In some embodiments, $R^7$ is $C_1$-$C_8$ alkyl substituted with $C_3$-$C_8$ carbocyclyl. In some embodiments. $R^7$ is $C_2$-$C_4$ alkyl substituted with $C_4$-$C_7$ carbocyclyl. In some embodiments, $R^7$ is $C_2$-$C_4$ alkyl substituted with

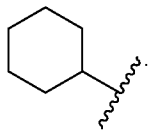 [SMILES: *C1CCCCC1]

In some embodiments, $R^7$ is

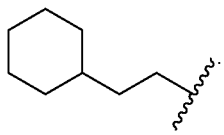 [SMILES: *CCC1CCCCC1]

In some embodiments, $R^7$ is

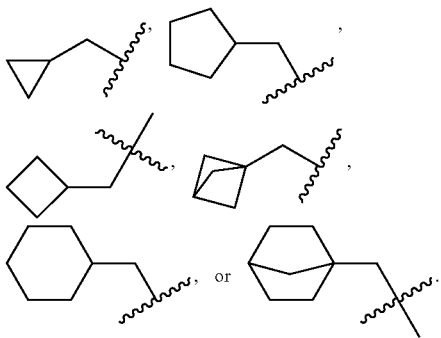

In some embodiments, $R^7$ is $C_{2-4}$ alkyl substituted with

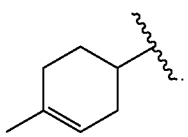 [SMILES: *C1CC=C(C)CC1]

In some embodiments. $R^7$ is

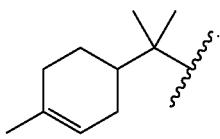 [SMILES: *C(C)(C)C1CC=C(C)CC1]

In some embodiments, $R^7$ is $C_1$-$C_8$ alkyl substituted with 4 to 6 membered heterocyclyl containing 1, 2, or 3 heteroatoms selected from N, O, and S. In some embodiments, $R^7$ is

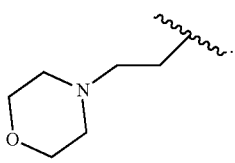 [SMILES: *CCN1CCOCC1]

In some embodiments $R^7$ is $C_1$-$C_8$ alkyl substituted with 4 to 6 membered heterocyclyl containing 1, 2, or 3 heteroatoms selected from N, O, and S wherein substituent 4 to 6 membered heterocyclyl of $R^7$ is substituted with one, two, or three substituents independently selected from the group consisting of $C_1$-$C_8$ alkyl and carbonyl. In some embodiments, $R^7$ is

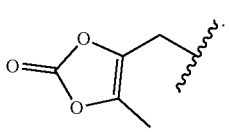

In some embodiments, $R^7$ is $C_1$-$C_8$ alkyl substituted with —OP(=O)(OH)$_2$. In some embodiments, $R^7$ is $C_1$-$C_4$ alkyl substituted with —OP(=O)(OH)$_2$. In some embodiments, $R^7$ is

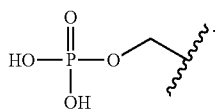

In some embodiments, $R^7$ is $C_1$-$C_8$ alkyl substituted with —OP(=O)(OR$^8$)$_2$. In some embodiments, $R^7$ is

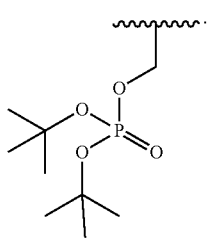 [SMILES: *COP(=O)(OC(C)(C)C)OC(C)(C)C]

In some embodiments, $R^7$ is $C_1$-$C_{20}$ alkyl. In some embodiments, $R^7$ is

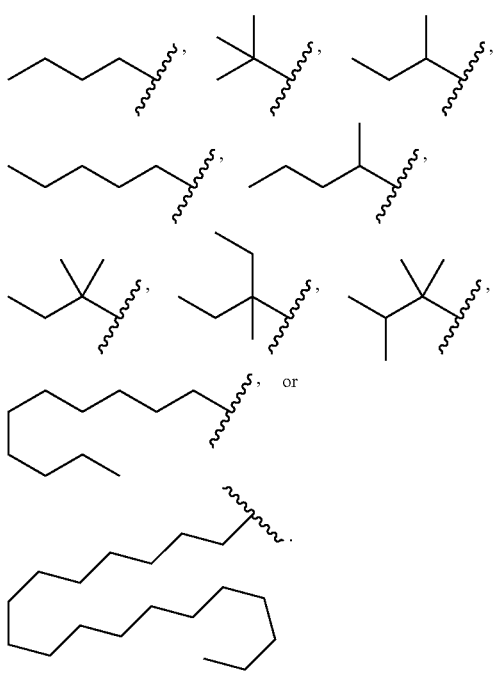

In some embodiments, $R^7$ is

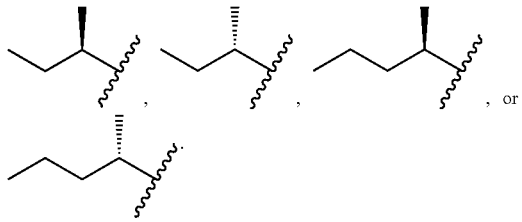

In some embodiments, $R^7$ is $C_1$-$C_8$ alkyl. In some embodiments, $R^7$ is $C_1$-$C_6$ alkyl. In some embodiments, $R^7$ is

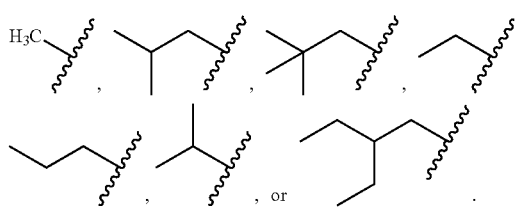

In some embodiments, $R^7$ is

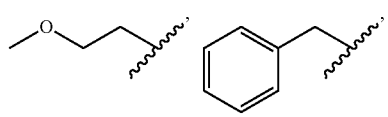

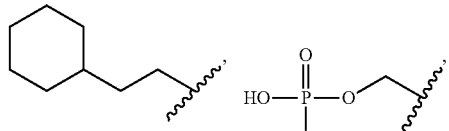

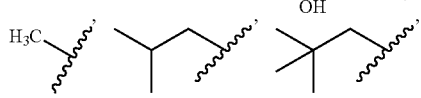

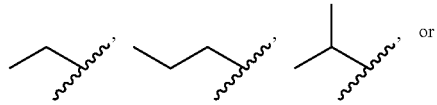

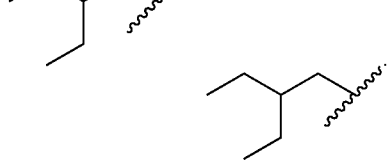

In some embodiments, $R^7$ is $C_1$-$C_3$ alkyl. In some embodiments, $R^7$ is

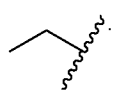

In some embodiments. $R^7$ is

In some embodiments, $R^7$ is $C_1$-$C_3$ alkyl and $R^1$ and $R^2$ are both —OC(=O)CH$_3$. In some embodiments, $R^7$ is

and $R^1$ and $R^2$ are both —OC(=O)CH$_3$. In some embodiments, $R^7$ is

and $R^1$ and $R^2$ are both $-OC(=O)CH_3$.
In some embodiments, $R^7$ is
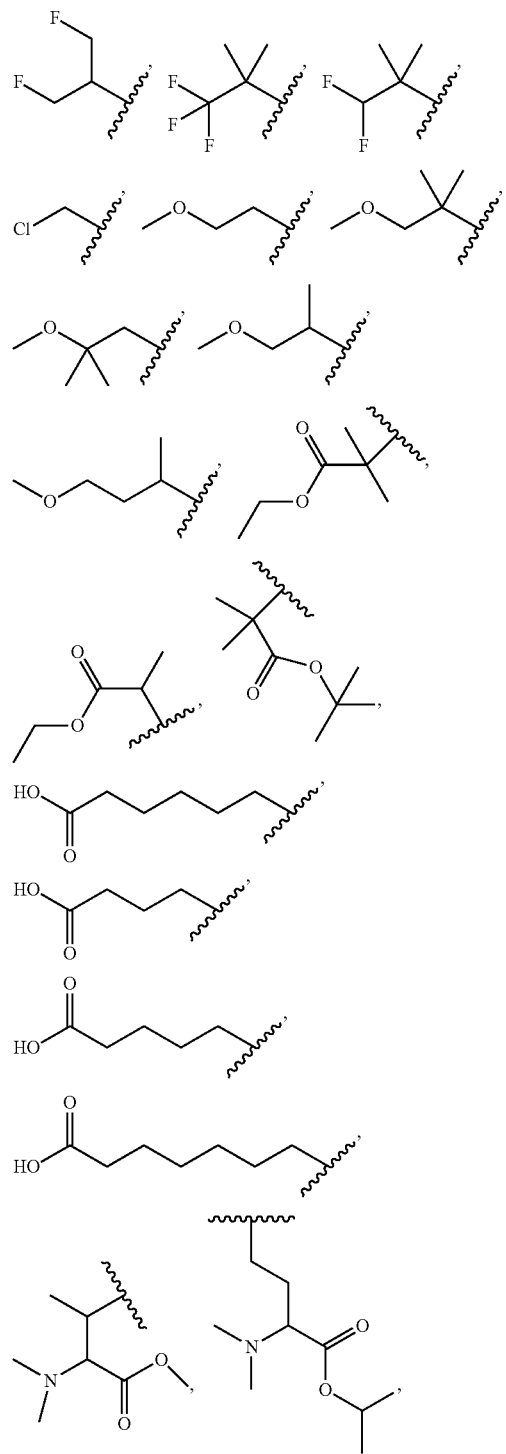
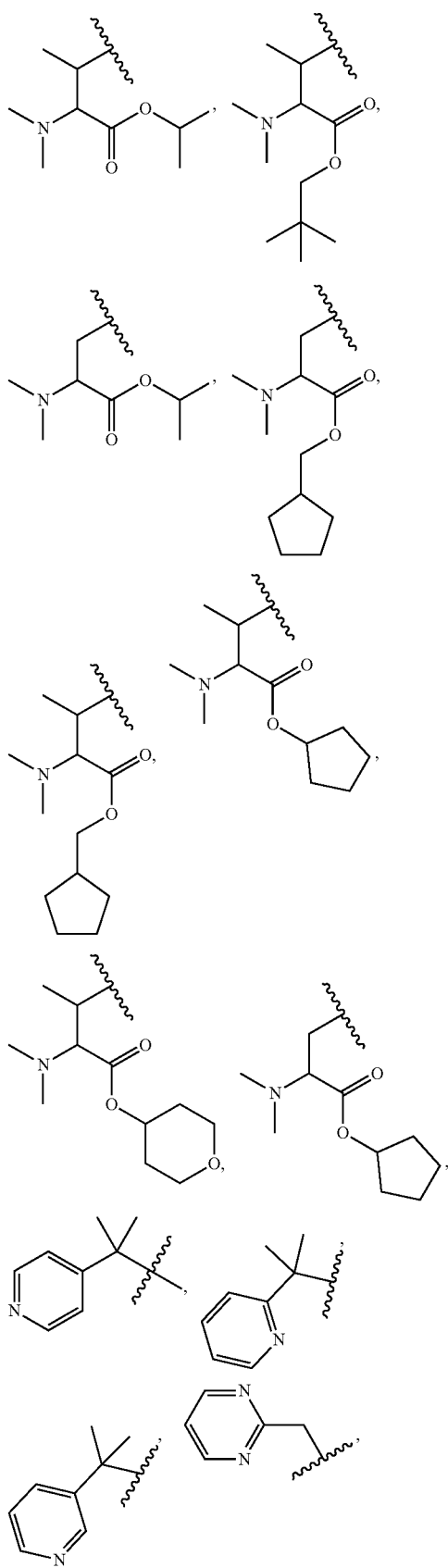

-continued
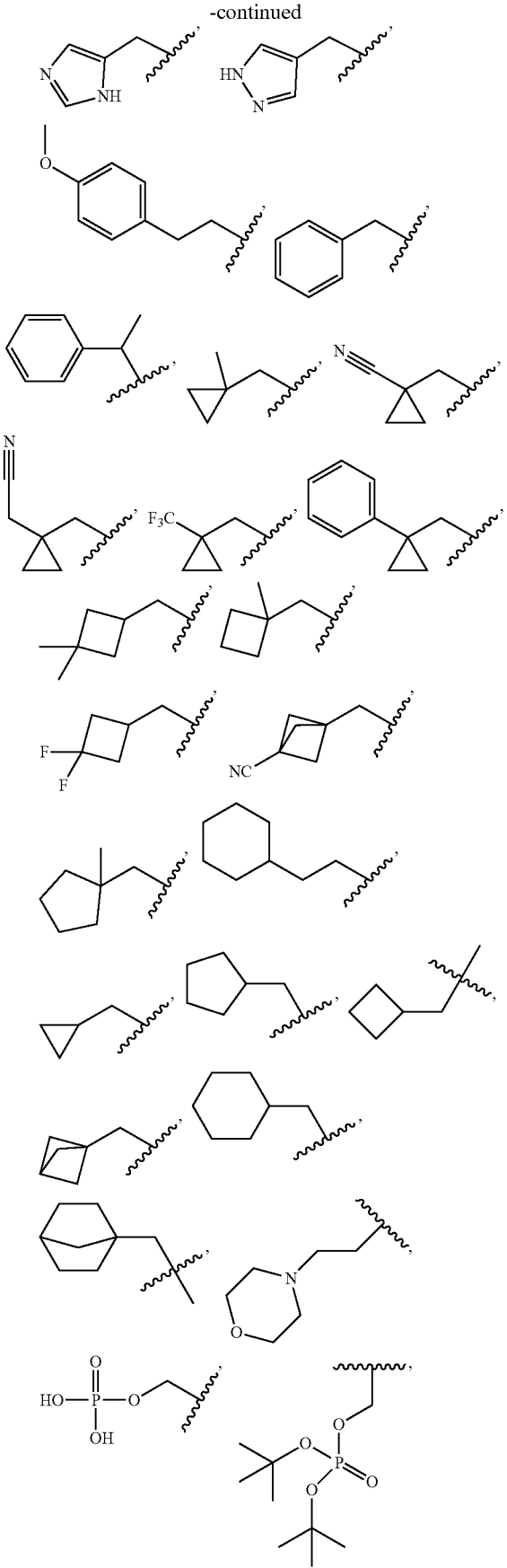
-continued
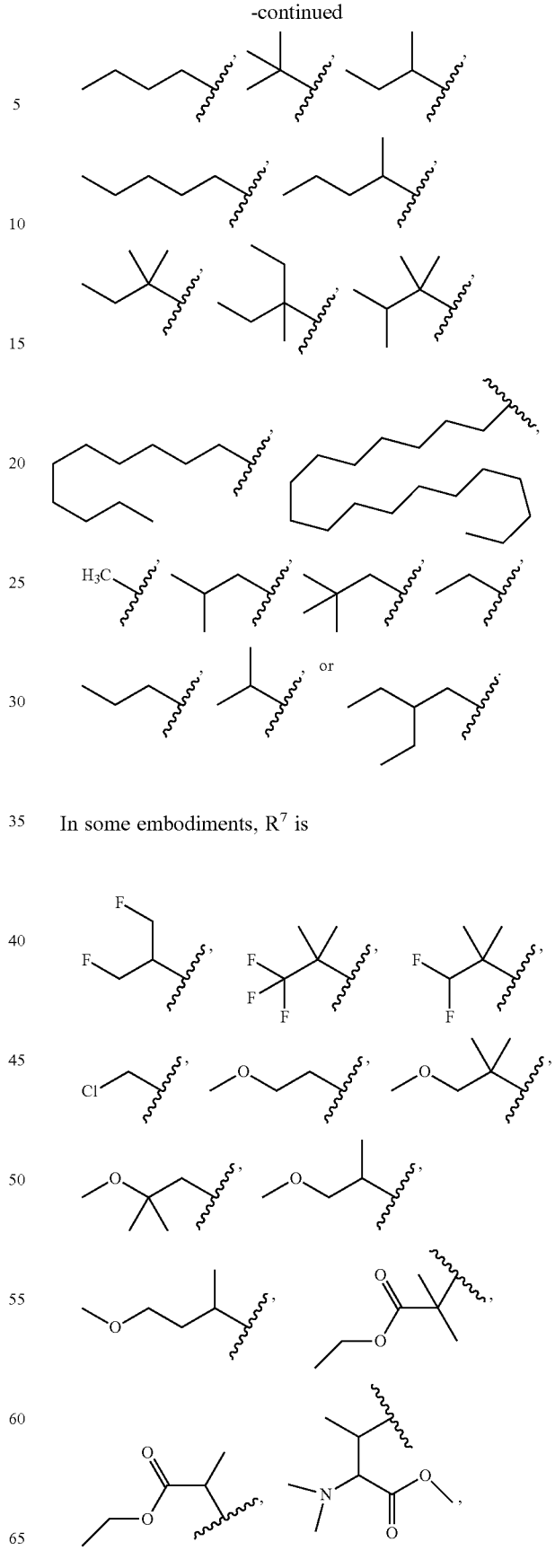
In some embodiments, R$^7$ is

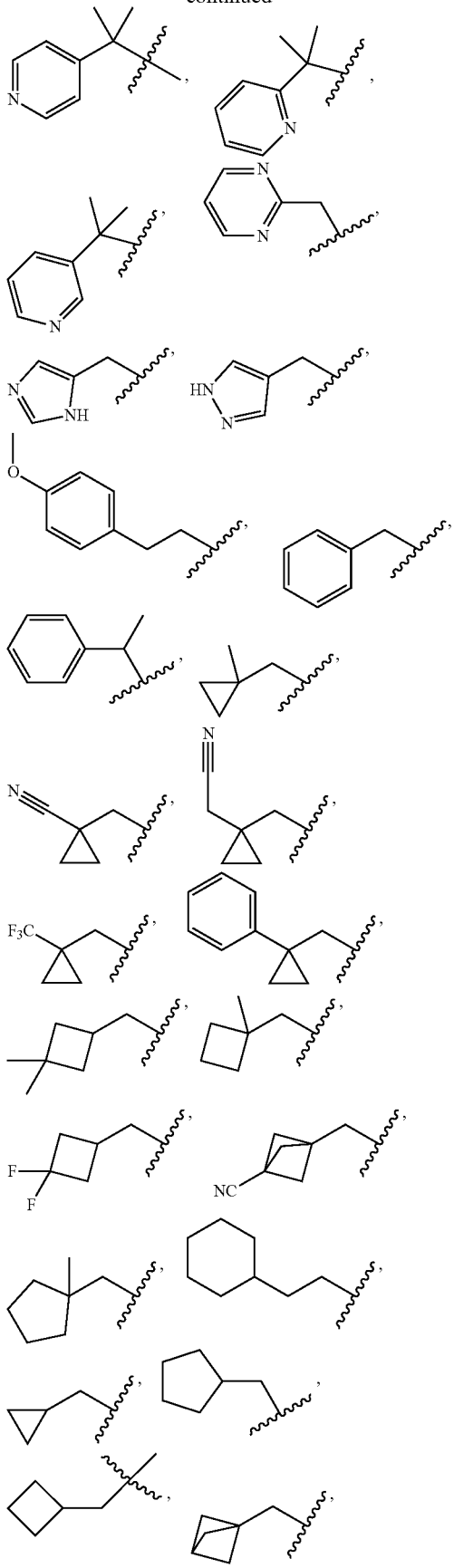
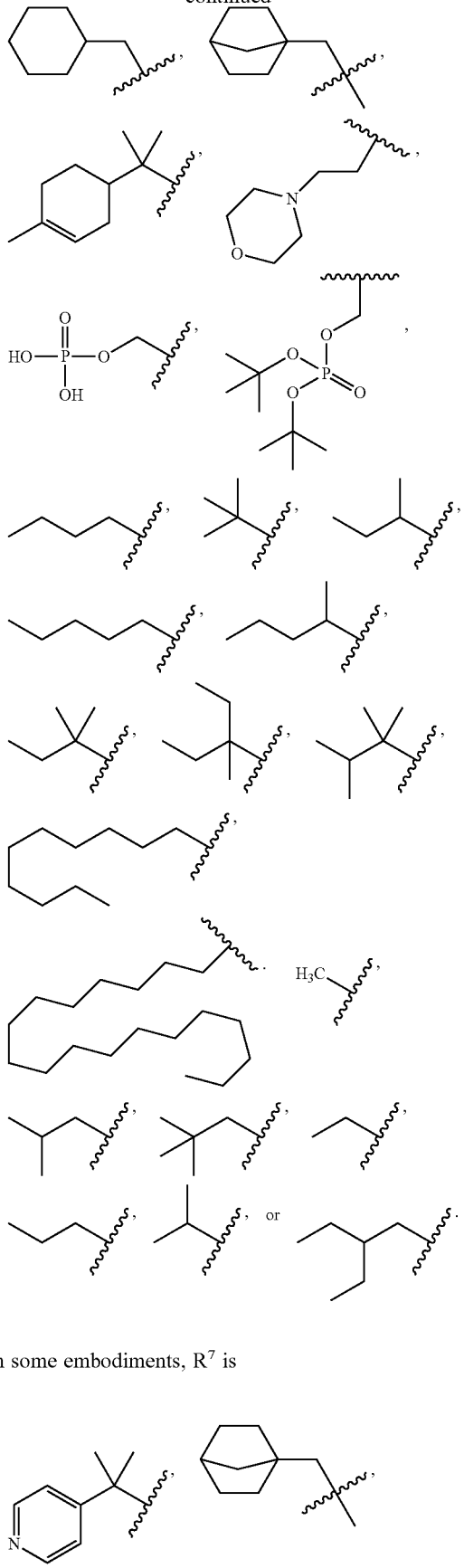
In some embodiments, R⁷ is

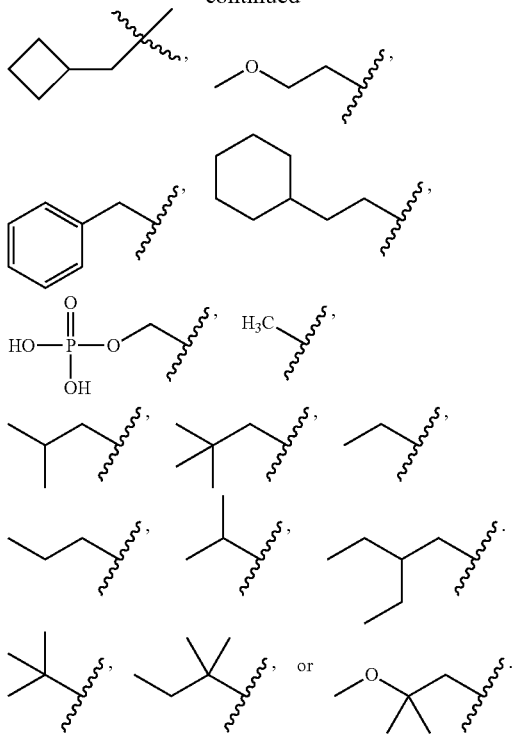

In some embodiments, $R^7$ is $C_2$-$C_8$ alkenyl. In some embodiments, $R^7$ is

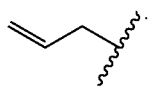 [SMILES: *CC=C]

In some embodiments, $R^7$ is $C_3$-$C_{10}$ carbocyclyl optionally substituted with one, two, or three substituents independently selected from the group consisting of $C_1$-$C_8$ alkyl, halogen, cyano, —$N_3$, —$OR^9$, —$NR^9R^{10}$, —OP(=O)(OH)$_2$, $C_3$-$C_8$ carbocyclyl and phenyl; wherein substituent phenyl $R^7$ is optionally substituted with one, two or three substituents independently selected from halo, cyano, and $C_1$-$C_6$ alkyl.

In some embodiments, $R^7$ is $C_3$-$C_8$ carbocyclyl optionally substituted with one, two, or three substituents independently selected from the group consisting of $C_1$-$C_8$ alkyl, halogen, cyano, —$N_3$, —$OR^9$, —$NR^9R^{10}$, —OP(=O)(OH)$_2$, $C_3$-$C_8$ carbocyclyl and phenyl; wherein substituent phenyl $R^7$ is optionally substituted with one, two or three substituents independently selected from halo, cyano, and $C_1$-$C_6$alkyl.

In some embodiments, $R^7$ is $C_3$-$C_8$ carbocyclyl optionally substituted with one, two, or three substituents independently selected from the group consisting of halogen, cyano, —$N_3$, —$OR^8$, —$NR^9R^{10}$, —OP(=O)(OH)$_2$, $C_3$-$C_8$ carbocyclyl and phenyl; wherein substituent phenyl $R^7$ is optionally substituted with one, two or three substituents independently selected from halo, cyano, and $C_1$-$C_6$ alkyl.

In some embodiments, $R^7$ is $C_3$-$C_8$ carbocyclyl optionally substituted with one, two, or three substituents independently selected from the group consisting of halogen, cyano, —$N_3$, —$OR^8$, —$NR^9R^{10}$, —OP(=O)(OH)$_2$, $C_3$-$C_8$ carbocyclyl and phenyl; wherein phenyl is optionally substituted with one, two or three substituents independently selected from halo, cyano, and $C_1$-$C_6$ alkyl.

In some embodiments, $R^7$ is $C_3$-$C_8$ carbocyclyl optionally substituted with one, two, or three substituents independently selected from the group consisting of $C_1$-$C_8$ alkyl, halogen, cyano, —$N_3$, —$OR^8$, —$NR^9R^{10}$, —OP(=O)(OH)$_2$, $C_1$-$C_8$ carbocyclyl and phenyl.

In some embodiments, $R^7$ is $C_3$-$C_8$ carbocyclyl optionally substituted with one, two, or three substituents independently selected from the group consisting of halogen, cyano, —$N_3$, —$OR^8$, —$NR^9R^{10}$, —OP(=O)(OH)$_2$, $C_3$-$C_8$ carbocyclyl and phenyl.

In some embodiments, $R^7$ is $C_3$-$C_8$ carbocyclyl optionally substituted with one, two, or three substituents independently selected from the group consisting of $C_1$-$C_8$ alkyl, —$OR^8$, —$NR^9R^{10}$, $C_3$-$C_8$ carbocyclyl and phenyl.

In some embodiments, $R^7$ is $C_3$-$C_8$ carbocyclyl optionally substituted with one, two, or three substituents independently selected from the group consisting of —$OR^8$, —$NR^9R^{10}$, $C_3$-$C_8$ carbocyclyl and phenyl.

In some embodiments, $R^7$ is $C_3$-$C_8$ carbocyclyl substituted with one, two, or three substituents independently selected from the group consisting of $C_1$-$C_8$ alkyl and halogen. In some embodiments, $R^7$ is

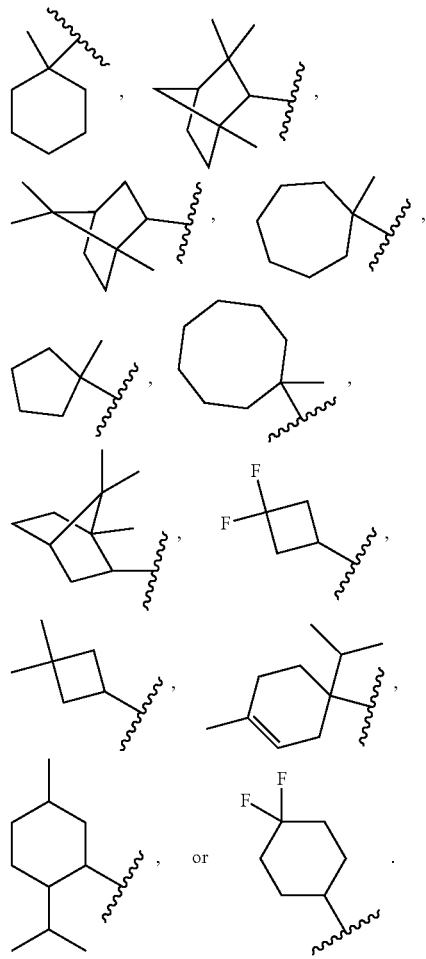

In some embodiments, $R^7$ is
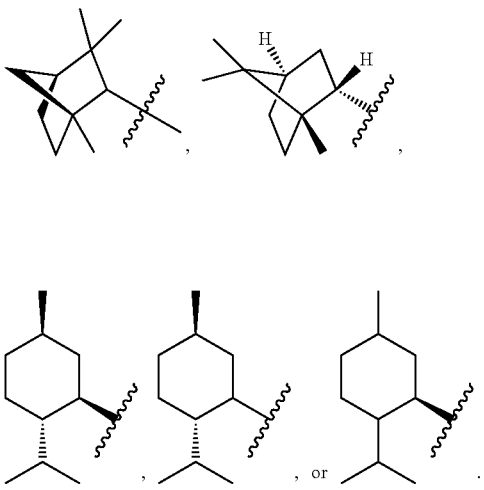
In some embodiments, $R^7$ is
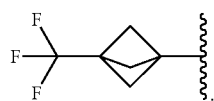
In some embodiments, $R^7$ is $C_3$-$C_{10}$ carbocyclyl. In some embodiments, $R^7$ is
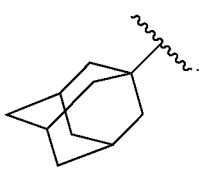 [SMILES: *C12CC3CC(CC(C3)C1)C2]
In some embodiments, $R^7$ is $C_3$-$C_8$ carbocyclyl. In some embodiments, $R^7$ is
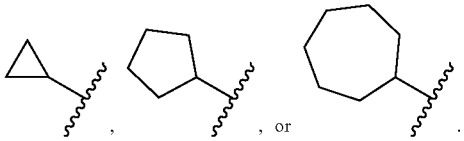
In some embodiments, $R^7$ is
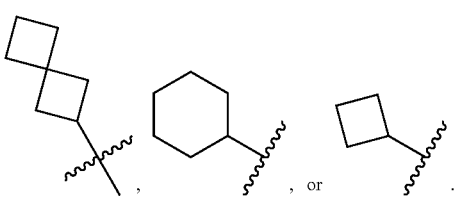
In some embodiments, $R^7$ is
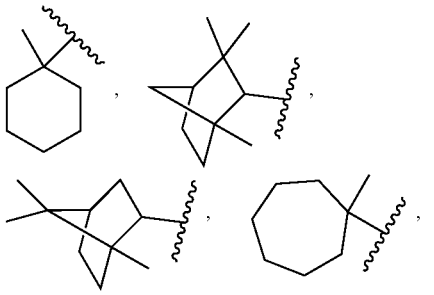
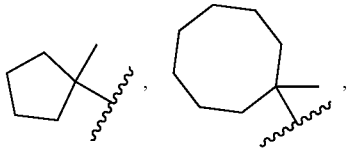
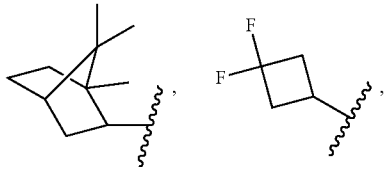
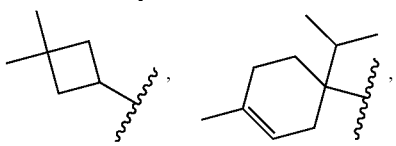
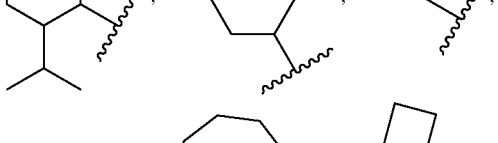
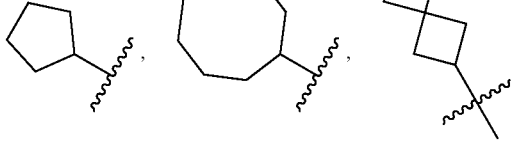
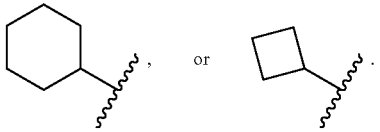
In some embodiments, $R^7$ is
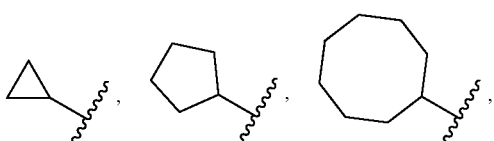
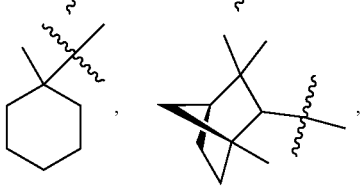

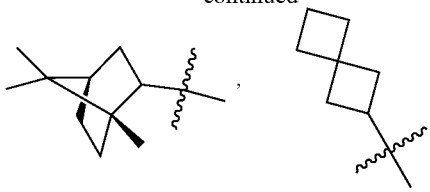

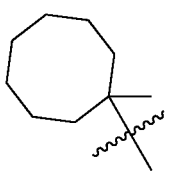

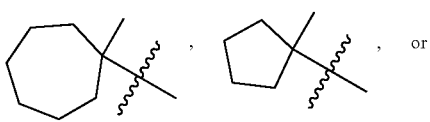

In some embodiments, $R^7$ is $C_6$-$C_{10}$ aryl optionally substituted with one, two, or three substituents independently selected from the group consisting of $C_1$-$C_8$ alkyl, halogen, cyano, —$N_3$, —$OR^8$, —$NR^9R^{10}$, —$OP(=O)(OH)_2$, $C_3$-$C_8$ carbocyclyl and phenyl, wherein substituent phenyl of $R^7$ is optionally substituted with one, two or three substituents independently selected from halo, cyano, and $C_1$-$C_6$ alkyl.

In some embodiments, $R^7$ is $C_6$-$C_{10}$ aryl optionally substituted with one, two, or three substituents independently selected from the group consisting of halogen, cyano, —$N_3$, —$OR^8$, —$NR^9R^{10}$, —$OP(=O)(OH)_2$, $C_3$-$C_8$ carbocyclyl and phenyl; wherein substituent phenyl of $R^7$ is optionally substituted with one, two or three substituents independently selected from halo, cyano, and $C_1$-$C_6$ alkyl.

In some embodiments, $R^7$ is $C_6$-$C_{10}$ aryl optionally substituted with one, two, or three substituents independently selected from the group consisting of halogen, cyano, —$N_3$, —$OR^8$, —$NR^9R^{10}$, —$OP(=O)(OH)_2$, $C_3$-$C_8$ carbocyclyl and phenyl; wherein phenyl is optionally substituted with one, two or three substituents independently selected from halo, cyano, and $C_1$-$C_6$ alkyl.

In some embodiments, $R^7$ is $C_6$-$C_{10}$ aryl optionally substituted with one, two, or three substituents independently selected from the group consisting of halogen, cyano, —$N_3$, —$OR^3$, —$NR^9R^{10}$, —$OP(=O)(OH)_2$, $C_3$-$C_8$ carbocyclyl and phenyl.

In some embodiments, $R^7$ is phenyl or naphthyl optionally substituted with one, two, or three substituents independently selected from the group consisting of halogen, cyano, —$N_3$, —$OR^8$, —$NR^9R^{10}$, —$OP(=O)(OH)_2$, $C_3$-$C_8$ carbocyclyl and phenyl.

In some embodiments, $R^7$ is phenyl optionally substituted with one, two, or three substituents independently selected from the group consisting of halogen, cyano, —$N_3$, —$OR^8$, —$NR^9R^{10}$, —$OP(=O)(OH)_2$, $C_3$-$C_8$ carbocyclyl and phenyl.

In some embodiments, $R^7$ is phenyl substituted with or three substituents independently selected from the group consisting of $C_1$-$C_8$ alkyl and —$OR^9$. In some embodiments,

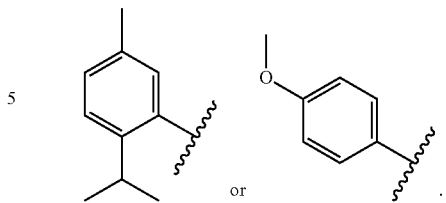

In some embodiments, $R^7$ is

In some embodiments, $R^7$ is

In some embodiments, $R^7$ is 4 to 8 membered heterocyclyl containing 1, 2, or 3 heteroatoms selected from N, O, and S optionally substituted with one, two, or three substituents independently selected from the group consisting of halogen, cyano, —$N_3$, —$OR^8$, —$NR^9R^{10}$, —$OP(=O)(OH)_2$, $C_3$-$C_8$ carbocyclyl and phenyl; wherein substituent phenyl of $R^7$ is optionally substituted with one, two or three substituents independently selected from halo, cyano, and $C_1$-$C_6$ alkyl.

In some embodiments, $R^7$ is 4 to 6 membered heterocyclyl containing 1, 2, or 3 heteroatoms selected from N, O, and S optionally substituted with one, two, or three substituents independently selected from the group consisting of halogen, cyano, —$N_3$, —$OR^8$, —$NR^9R^{10}$, —$OP(=O)(OH)_2$, $C_3$-$C_8$ carbocyclyl and phenyl; wherein substituent phenyl of $R^7$ is optionally substituted with one, two or three substituents independently selected from halo, cyano, and $C_1$-$C_6$ alkyl.

In some embodiments, $R^7$ is 4 to 6 membered heterocyclyl containing 1, 2, or 3 heteroatoms selected from N, O, and S optionally substituted with one, two, or three substituents independently selected from the group consisting of halogen, cyano, —$N_3$, —$OR^8$, —$NR^9R^{10}$, —$OP(=O)(OH)_2$, $C_3$-$C_8$ carbocyclyl and phenyl; wherein phenyl is optionally substituted with one, two or three substituents independently selected from halo, cyano, and $C_1$-$C_6$ alkyl.

In some embodiments, $R^7$ is 4 to 6 membered heterocyclyl containing 1, 2, or 3 heteroatoms selected from N, O, and S optionally substituted with one, two, or three substituents independently selected from the group consisting of halogen, cyano, —$N_3$, —$OR^8$, —$NR^9R^{10}$, —$OP(=O)(OH)_2$, $C_3$-$C_8$ carbocyclyl and phenyl.

In some embodiments, $R^7$ is 6 membered heterocyclyl containing 1, 2, or 3 heteroatoms selected from N, O, and S optionally substituted with one, two, or three substituents independently selected from the group consisting of halogen, cyano, —N$_3$, —OR$^8$, —NR$^9$R$^{10}$, —OP(=O)(OH)$_2$, C$_3$-C$_8$ carbocyclyl and phenyl.

In some embodiments, R$^7$ is

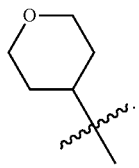 [SMILES: *C1CCOCC1]

In some embodiments, R$^7$ is 5 membered heterocyclyl containing 1, 2, or 3 heteroatoms selected from N, O, and S optionally substituted with one, two, or three substituents independently selected from the group consisting of halogen, cyano, —N$_3$, —OR$^8$, —NR$^9$R$^{10}$, —OP(=O)(OH)$_2$, C$_3$-C$_8$ carbocyclyl and phenyl.

In some embodiments, R$^7$ is 5 membered heterocyclyl containing 1, 2, or 3 heteroatoms selected from N, O, and S.
In some embodiments, R$^7$ is

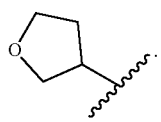

In some embodiments, R$^7$ is 4 membered heterocyclyl containing 1, 2, or 3 heteroatoms selected from N, O, and S optionally substituted with one, two, or three substituents independently selected from the group consisting of halogen, cyano, —N$_3$, —OR$^8$, —NR$^9$R$^{10}$, —OP(=O)(OH)$_2$, C$_3$-C$_8$ carbocyclyl and phenyl.

In some embodiments, R$^7$ is 4 membered heterocyclyl containing 1, 2, or 3 heteroatoms selected from N, O, and S.

In some embodiments, R$^7$ is

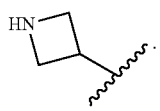

In some embodiments, R$^7$ is

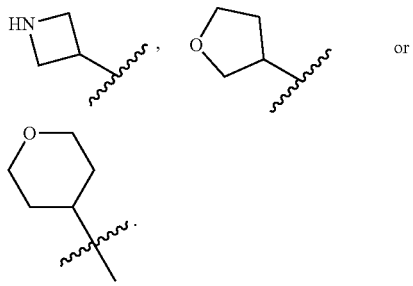

In some embodiments, R$^7$ is

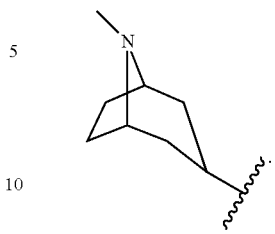

In some embodiments, R$^7$ is

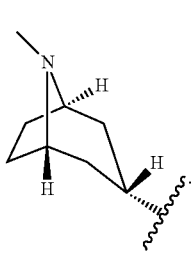 [SMILES: *[C@H]1C[C@H]2CC[C@@H](C1)N2C]

In some embodiments, R$^7$ is 5 to 6 membered heteroaryl containing 1, 2, or 3 heteroatoms selected from N, O, and S optionally substituted with one, two, or three substituents independently selected from the group consisting of halogen, cyano, —N$_3$, —OR$^8$, —NR$^9$R$^{10}$, —OP(=O)(OH)$_2$, C$_3$-C$_8$ carbocyclyl and phenyl; wherein substituent phenyl of R$^7$ is optionally substituted with one, two or three substituents independently selected from halo, cyano, and C$_1$-C$_6$ alkyl.

In some embodiments, R$^7$ is 5 to 6 membered heteroaryl containing 1, 2, or 3 heteroatoms selected from N, O, and S optionally substituted with one, two, or three substituents independently selected from the group consisting of halogen, cyano, —N$_3$, —OR$^8$, —NR$^9$R$^{10}$, —OP(=O)(OH)$_2$, C$_3$-C$_8$ carbocyclyl and phenyl; wherein phenyl is optionally substituted with one, two or three substituents independently selected from halo, cyano, and C$_1$-C$_6$ alkyl.

In some embodiments, R$^7$ is 5 to 6 membered heteroaryl containing 1, 2, or 3 heteroatoms selected from N, O, and S optionally substituted with one, two, or three substituents independently selected from the group consisting of halogen, cyano, —N$_3$, —OR$^8$, —NR$^9$R$^{10}$, —OP(=O)(OH)$_2$, C$_3$-C$_8$ carbocyclyl and phenyl.

In some embodiments, R$^7$ is 5 membered heteroaryl containing 1, 2, or 3 heteroatoms selected from N, O, and S optionally substituted with one, two, or three substituents independently selected from the group consisting of halogen, cyano, —N$_3$, —OR$^8$, —NR$^9$R$^{10}$, —OP(=O)(OH)$_2$, C$_3$-C$_8$ carbocyclyl and phenyl.

In some embodiments, R$^7$ is 5 membered heteroaryl containing 1, 2, or 3 heteroatoms selected from N, O, and S.

In some embodiments, R$^7$ is 6 membered heteroaryl containing 1, 2, or 3 heteroatoms selected from N, O, and S optionally substituted with one, two, or three substituents independently selected from the group consisting of halogen, cyano, —N$_3$, —OR$^8$, —NR$^9$R$^{10}$, —OP(=O)(OH)$_2$, C$_3$-C$_8$ carbocyclyl and phenyl.

In some embodiments, R$^7$ is 6 membered heteroaryl containing 1, 2, or 3 heteroatoms selected from N, O, and S optionally substituted with one, two, or three substituents independently selected from the group consisting of halogen, cyano, and —NR$^9$R$^{10}$.

In some embodiments, $R^7$ is 6 membered heteroaryl containing 1, 2, or 3 heteroatoms selected from N, O, and S. In some embodiments, $R^7$ is
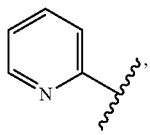, 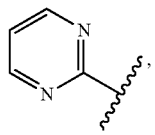, or
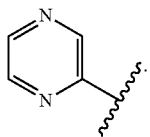.
In some embodiments, $R^7$ is
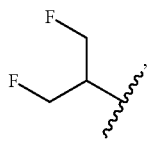 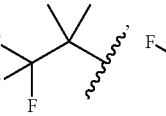 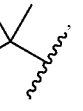
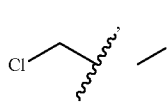  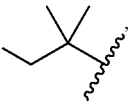
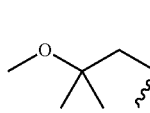 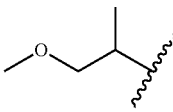
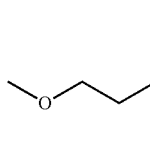 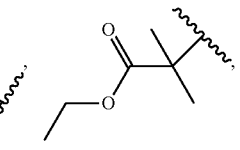
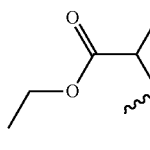 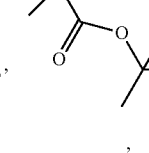
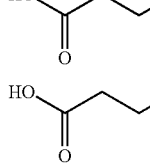 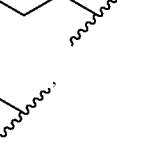
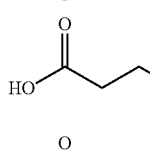 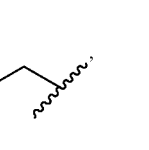
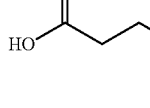 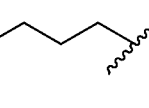
-continued
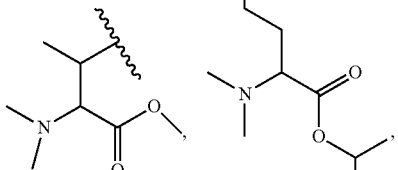
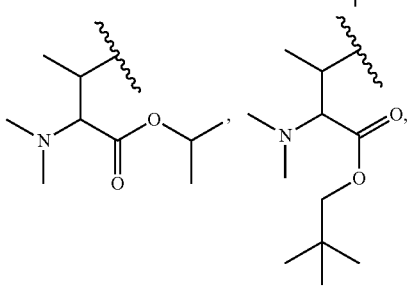
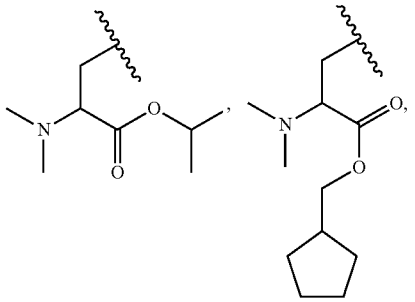
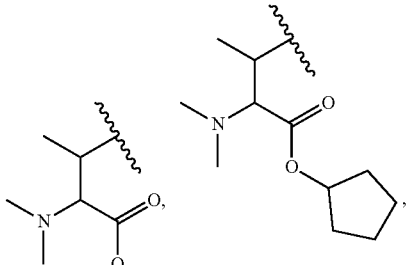
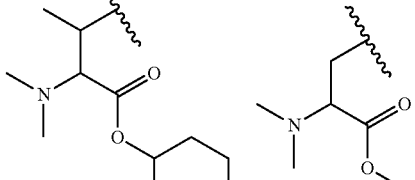
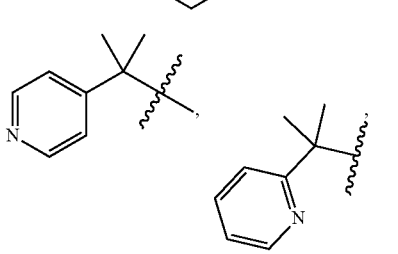

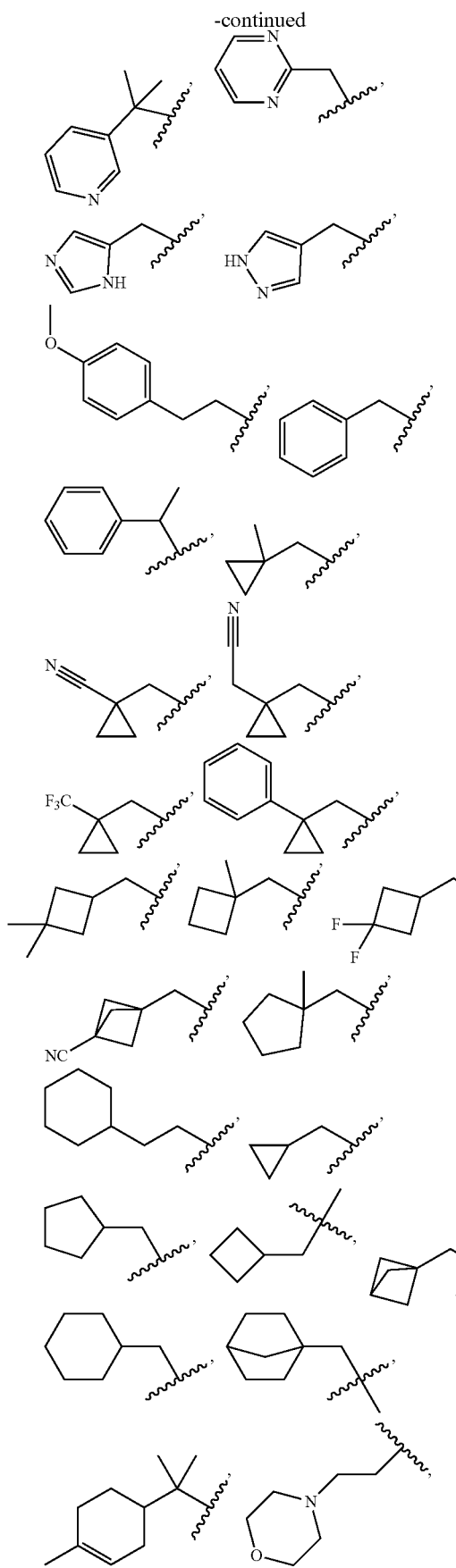
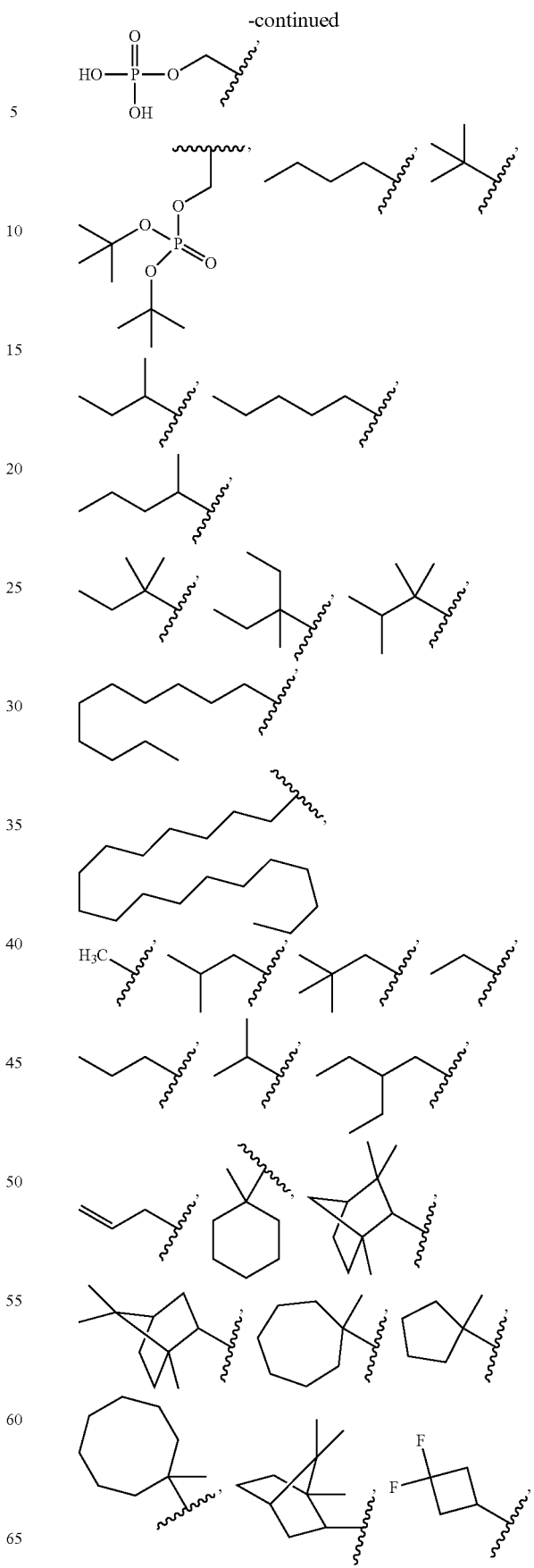

-continued
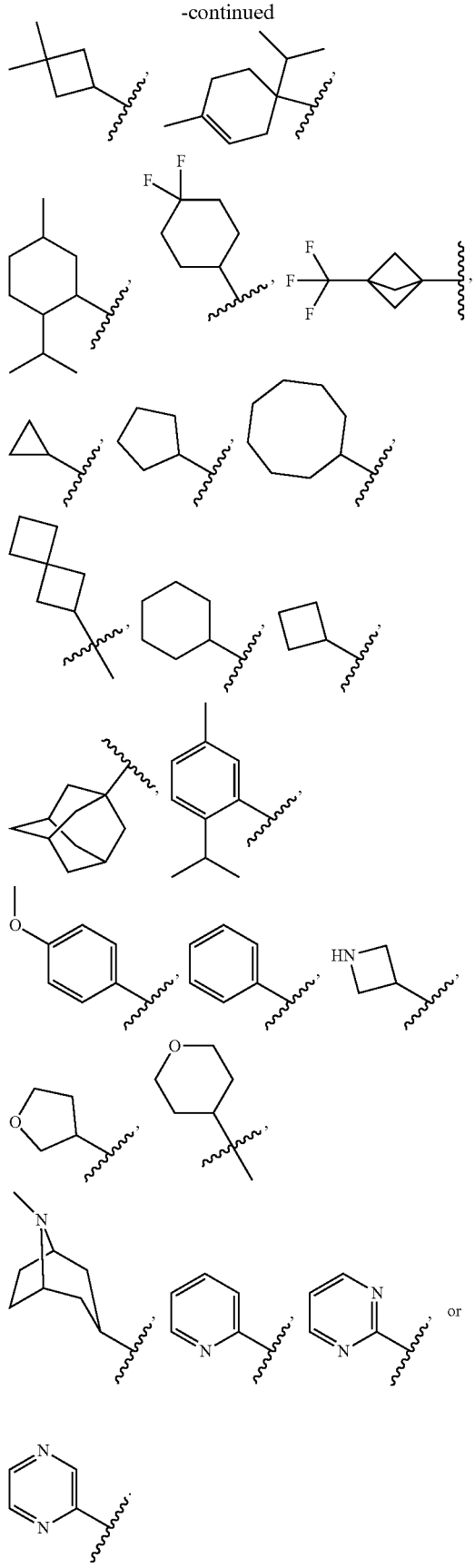
In some embodiments, R[7] is
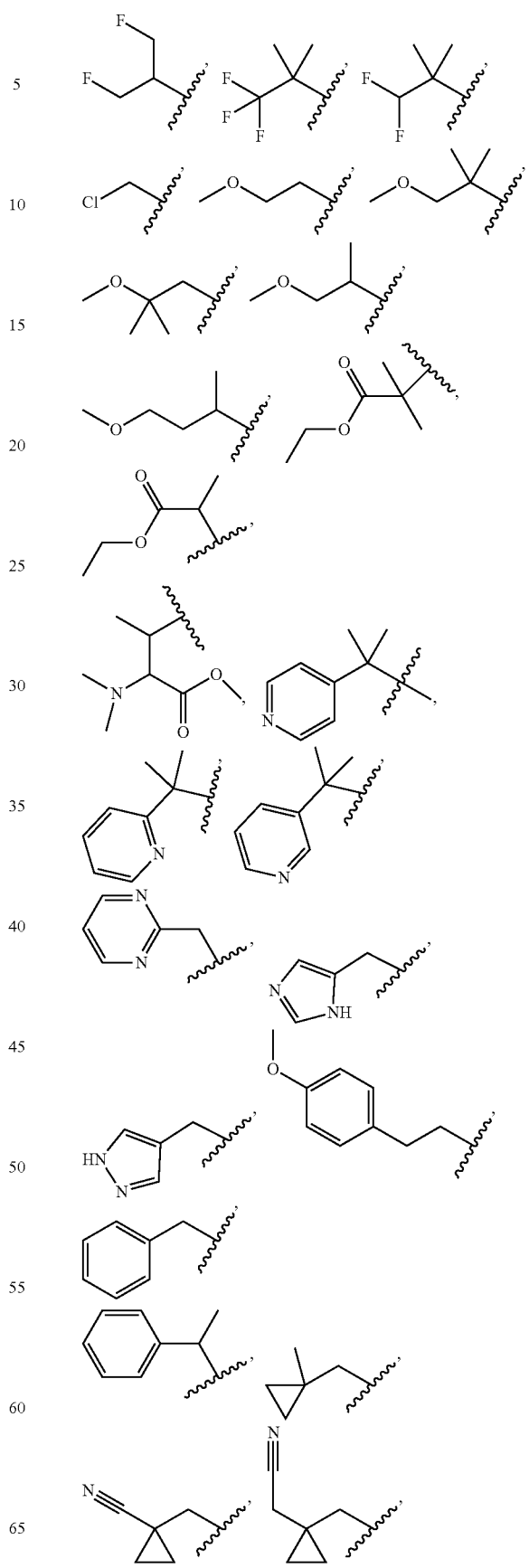

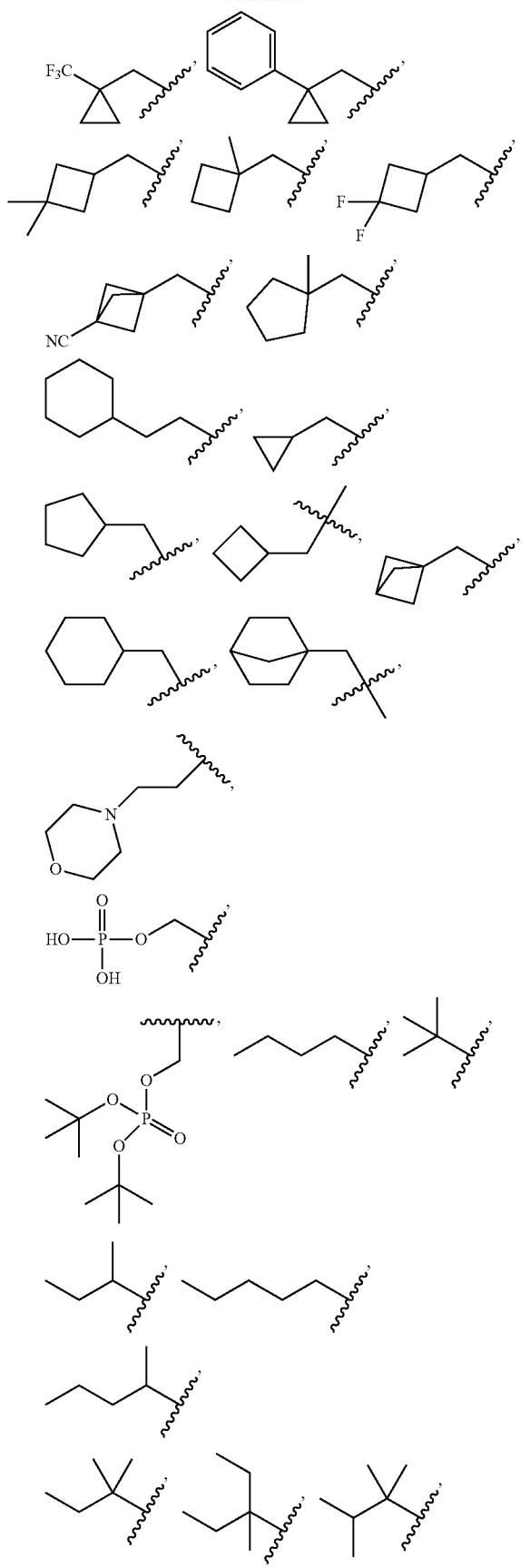
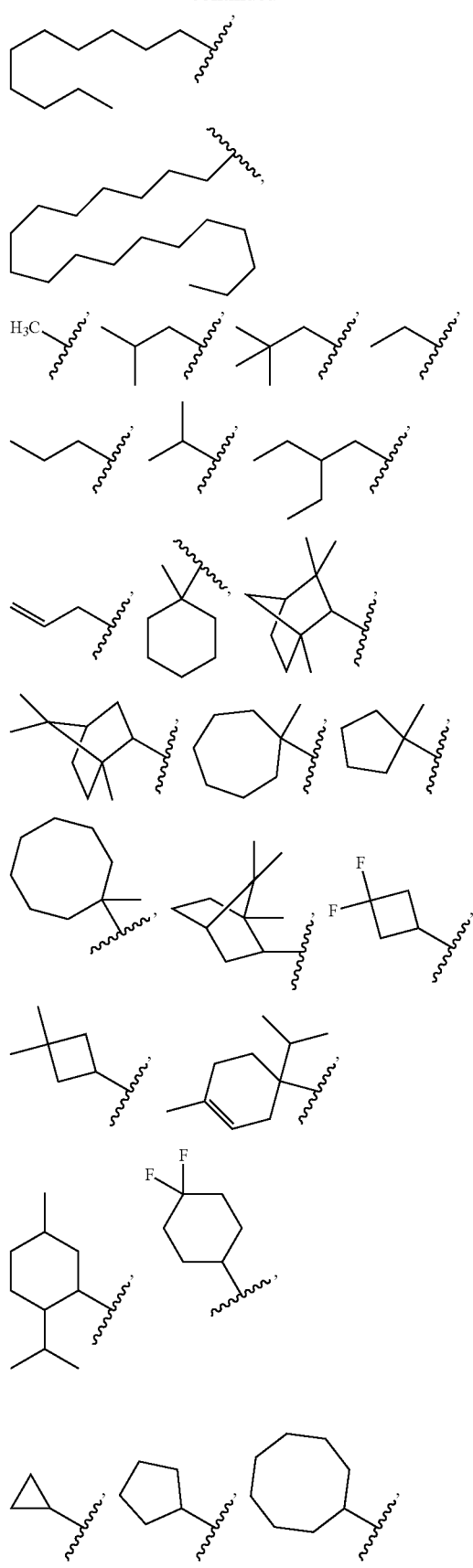

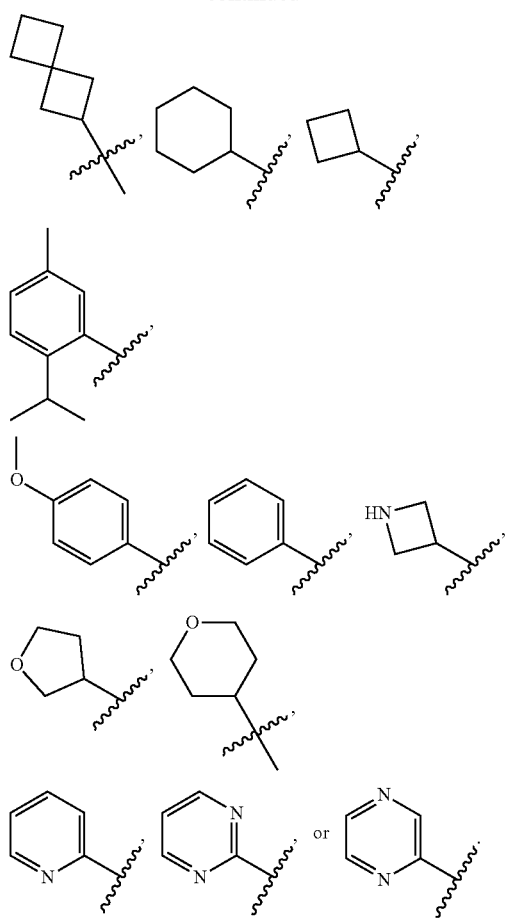
In some embodiments, R⁷ is
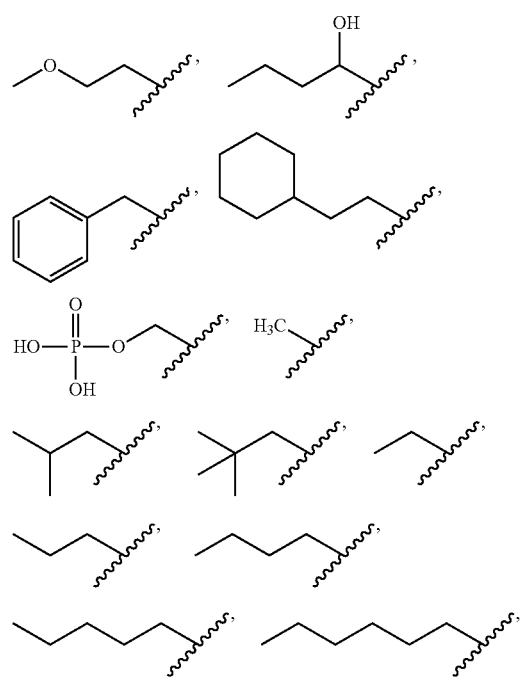
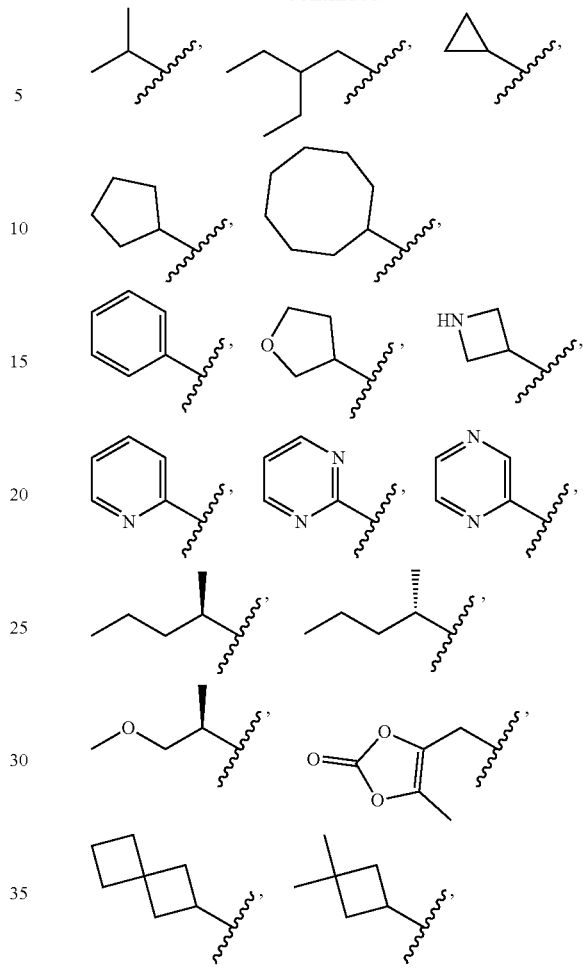
In some embodiments, R⁷ is
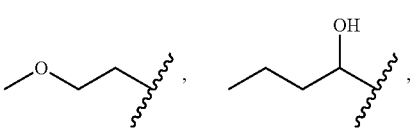

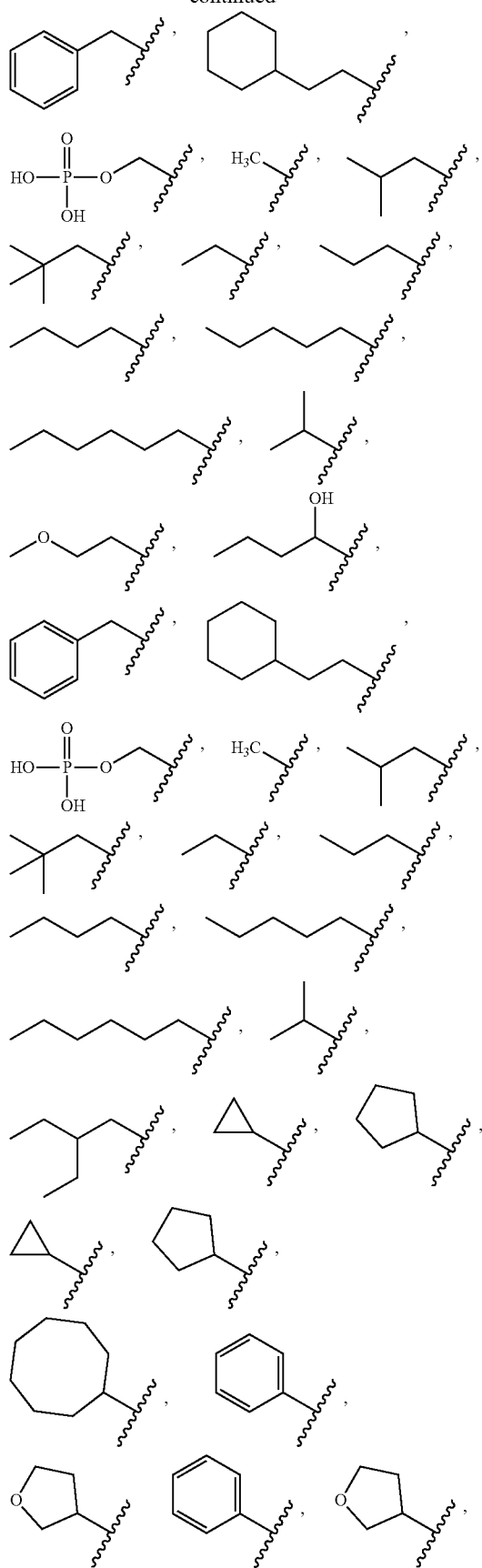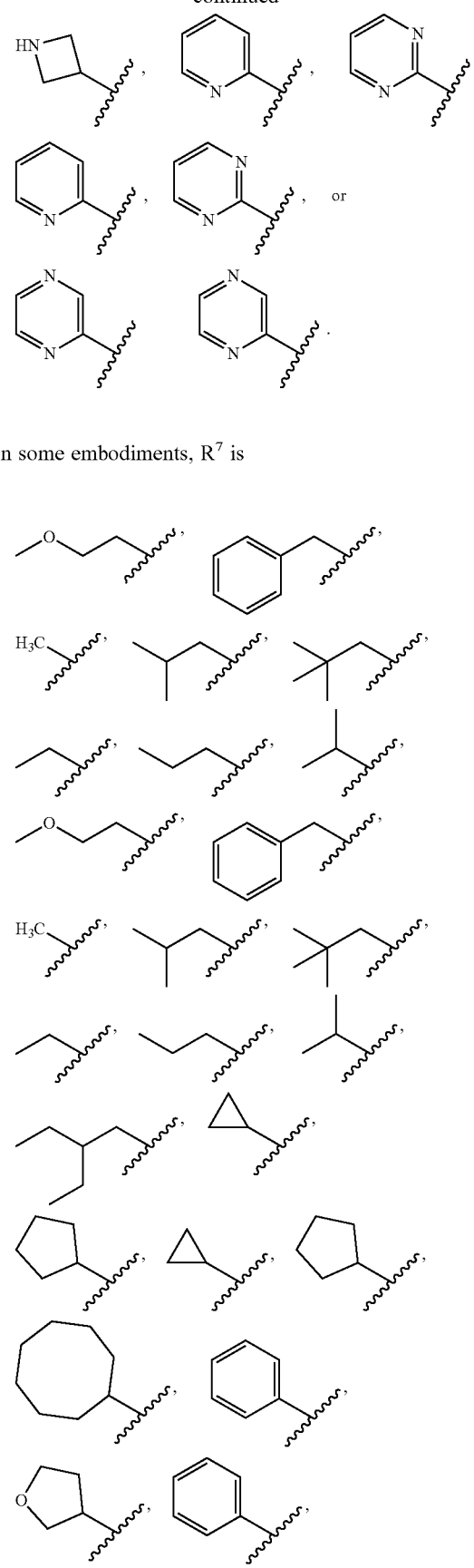
In some embodiments, $R^7$ is

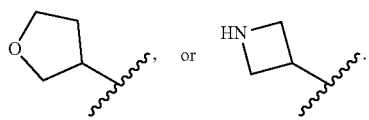

In some embodiments, $R^7$ is

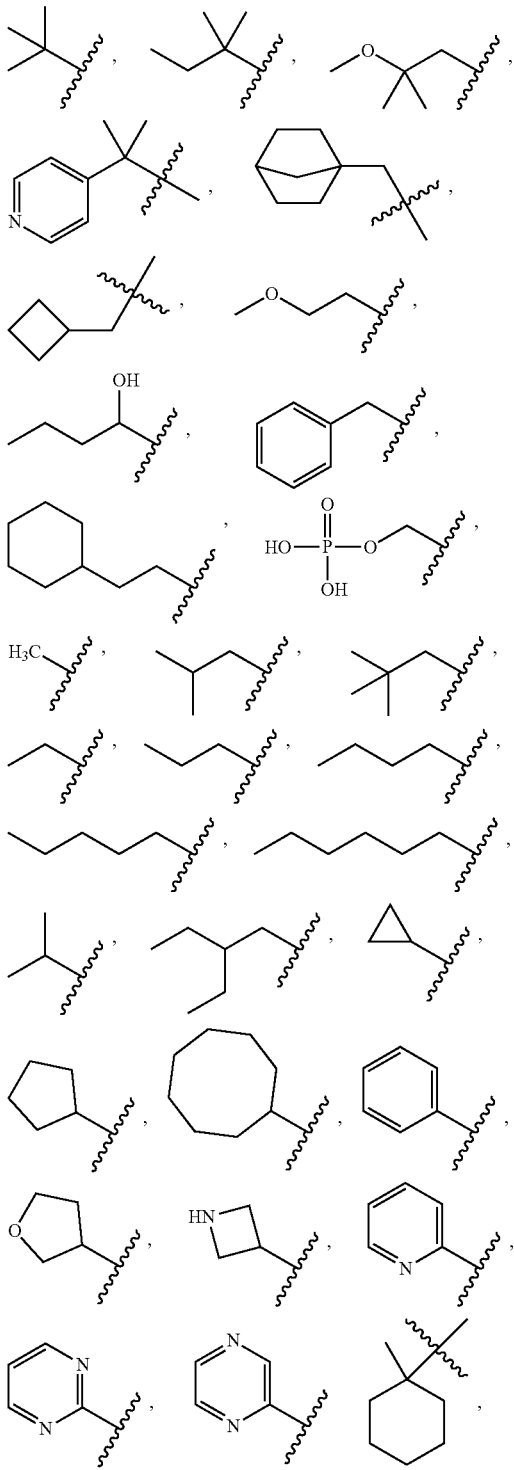

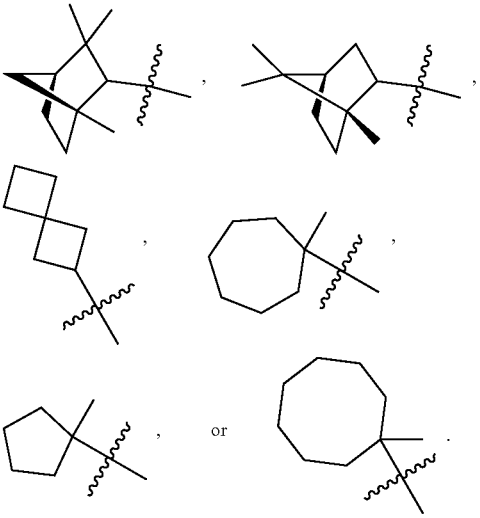

In some embodiments, $R^8$ is H. In some embodiments, $R^8$ is $C_1$-$C_6$ alkyl. In some embodiments, $R^8$ is —$CH_3$. In some embodiments, $R^a$ is $C_1$-$C_6$ haloalkyl. In some embodiments, $R^8$ is $C_3$-$C_6$ cycloalkyl.

In some embodiments, $R^8$ is

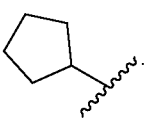 [SMILES: *C1CCCC1]

In some embodiments, $R^8$ is —$C(CH_3)_3$, —$CH(CH_3)_2$, or —$CH_2C(CH_3)_3$. In some embodiments, $R^a$ is $C_1$-$C_6$ alkyl substituted with $C_3$-$C_6$ cycloalkyl. In some embodiments, $R^8$ is

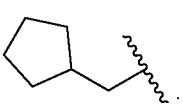 [SMILES: *CC1CCCC1]

In some embodiments, $R^8$ is 4 to 6 membered heterocyclyl. In some embodiments, $R^8$ is

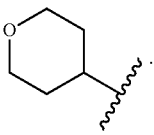 [SMILES: *C1CCOCC1]

In some embodiments, $R^9$ is H. In some embodiments, $R^9$ is $C_1$-$C_6$ alkyl. In some embodiments, $R^9$ is —$CH_3$. In some embodiments, $R^9$ is $C_1$-$C_6$ haloalkyl. In some embodiments, $R^9$ is $C_3$-$C_6$ cycloalkyl.

In some embodiments, $R^{10}$ is H. In some embodiments, $R^{10}$ is $C_1$-$C_6$ alkyl. In some embodiments, $R^{10}$ is —$CH_3$. In some embodiments, $R^{10}$ is $C_1$-$C_6$ haloalkyl. In some embodiments, $R^{10}$ is $C_3$-$C_6$ cycloalkyl.

In some embodiments, Base is

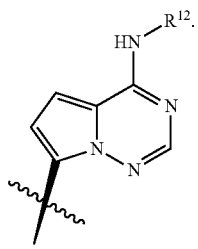

In some embodiments, Base is

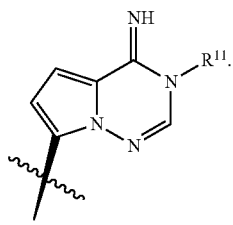

In some embodiments, Base is

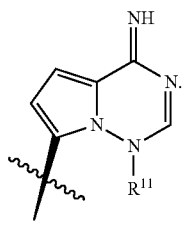

In some embodiments, Base is

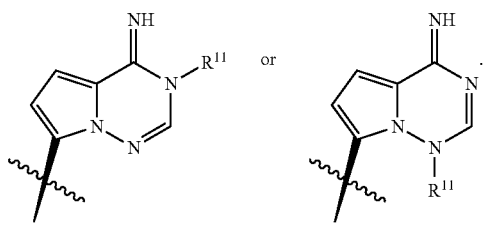

In some embodiments, $R^{11}$ is $C_1$-$C_3$ alkyl substituted with —OP(=O)(OH)(OR$^{14}$). In some embodiments, $R^{11}$ is —(CH$_2$)OP(=O)(OH)(OR$^{14}$).

In some embodiments, $R^{14}$ is H. In some embodiments, $R^{14}$ is H or $C_1$-$C_8$ alkyl; wherein $C_1$-$C_8$ alkyl of $R^{14}$ is optionally substituted with one, two or three substituents independently selected from the group consisting of halogen, cyano, and phenyl.

In some embodiments, $R^{14}$ is $C_1$-$C_8$ alkyl optionally substituted with one, two or three substituents independently selected from the group consisting of halogen, cyano, and phenyl. In some embodiments, $R^{14}$ is $C_1$-$C_3$ alkyl optionally substituted with one, two or three substituents independently selected from the group consisting of halogen, cyano, and phenyl. In some embodiments $R^{14}$ is $C_1$-$C_3$ alkyl substituted with one phenyl. In some embodiments, $R^{14}$ is

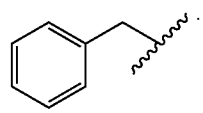 [SMILES: *Cc1ccccc1]

In some embodiments, $R^{11}$ is —(CH$_2$)OP(=O)(OH)$_2$. In some embodiments, $R^{11}$ is

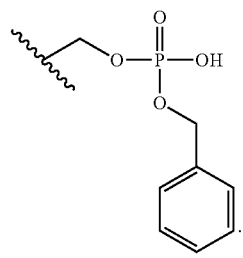 [SMILES: *COP(=O)(O)OCc1ccccc1]

In some embodiments, $R^{12}$ is H. In some embodiments, $R^{12}$ is $C_1$-$C_6$ alkyl. In some embodiments. $R^{12}$ is —C(=O)R$^{13}$. In some embodiments, $R^{12}$ is —C(=O)(CH$_2$)$_2$CH$_3$. In some embodiments, $R^{12}$ is —C(=O)OR$^{13}$. In some embodiments, $R^{12}$ is —C(=O)OCH$_2$CH(CH$_3$)$_2$. In some embodiments, $R^{12}$ is —C(=O)OCH$_2$CH(CH$_3$)$_2$ or —C(=O)(CH$_2$)$_2$CH$_3$. In some embodiments, $R^{12}$ is

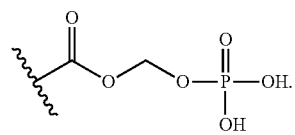 [SMILES: *C(=O)OCOP(=O)(O)O]

In some embodiments, $R^{12}$ is

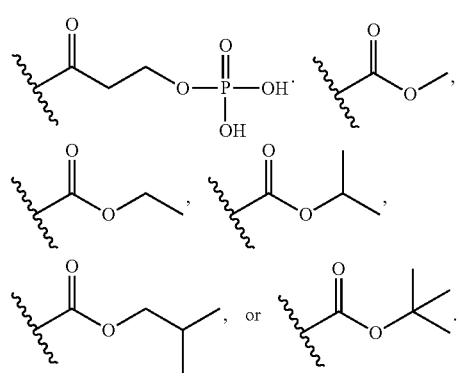

In some embodiments, $R^{12}$ is

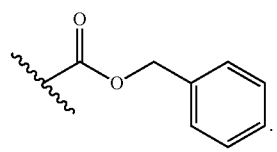 [SMILES: *C(=O)OCc1ccccc1]

In some embodiments, $R^{13}$ is $C_1$-$C_8$ alkyl; wherein $C_1$-$C_8$ alkyl of $R^{13}$ is optionally substituted with one, two, or three substituents independently selected from halogen, cyano, —OP(=O)(OH)(OR$^{14}$) and phenyl, wherein substituent phenyl of R$^{13}$ is optionally substituted with —OP(=O)(OH)(OR$^{14}$). In some embodiments, R$^{13}$ is C$_1$-C$_8$ alkyl optionally substituted with one, two, or three substituents independently selected from halogen, cyano, and phenyl; wherein substituent phenyl of R$^{13}$ is optionally substituted with —OP(=O)(OH)(OR$^{14}$).

In some embodiments, R$^{13}$ is H. In some embodiments, R$^{13}$ is C$_1$-C$_8$ alkyl; wherein C$_1$-C$_8$ alkyl of R$^{13}$ is optionally substituted with one, two, or three substituents independently selected from halogen, cyano, —OP(=O)(OH)(OR$^{14}$) and phenyl, wherein phenyl is optionally substituted with —OP(=O)(OH)(OR$^{14}$). In some embodiments, R$^{13}$ is C$_1$-C$_8$ alkyl optionally substituted with one, two, or three substituents independently selected from halogen, cyano, and phenyl; wherein phenyl is optionally substituted with —OP(=O)(OH)(OR$^{14}$). In some embodiments, R$^{13}$ is C$_1$-C$_8$ alkyl optionally substituted with one, two, or three substituents independently selected from halogen, cyano, and phenyl. In some embodiments, R$^{13}$ is C$_1$-C$_8$ alkyl. In some embodiments, R$^{13}$ is —CH$_3$, —CH$_2$CH$_3$, —(CH$_2$)$_2$CH$_3$, —CH(CH$_3$)$_2$, —(CH$_2$)$_3$CH$_3$, or —C(CH$_3$)$_3$. In some embodiments, R$^{13}$ is —CH$_2$CH(CH$_3$)$_2$ or —(CH$_2$)$_2$CH$_3$. In some embodiments, R$^{13}$ is —(CH$_2$)OP(=O)(OH)$_2$.

In some embodiments, R$^{13}$ is —(CH$_2$)CH(CH$_3$)$_2$.

In some embodiments, R$^{13}$ is C$_1$-C$_8$ alkyl substituted with phenyl. In some embodiments, R$^{13}$ is

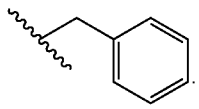

In some embodiments, Base is

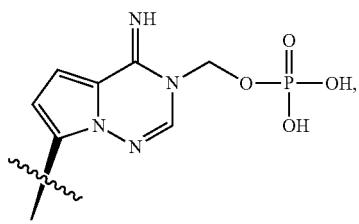

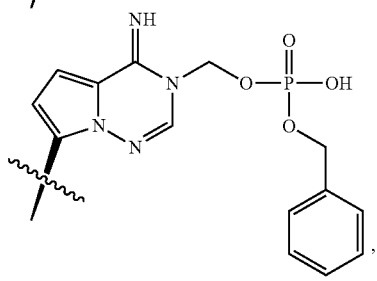

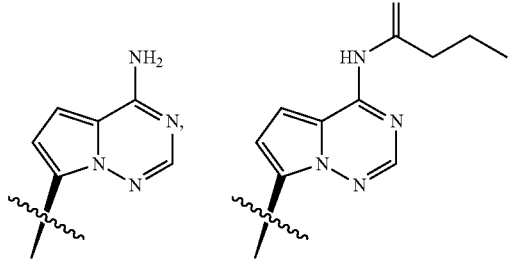

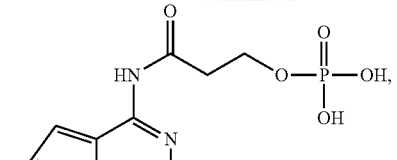

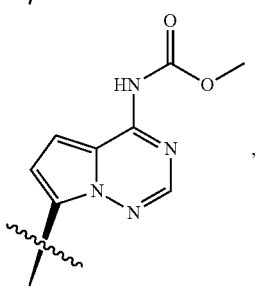

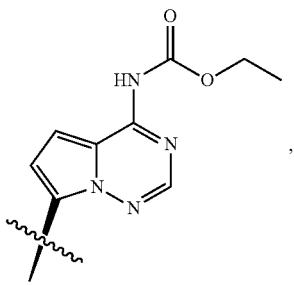

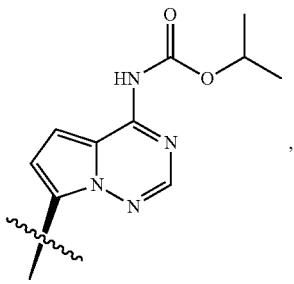

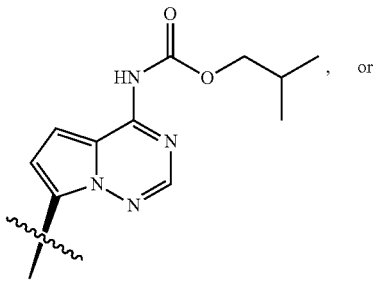

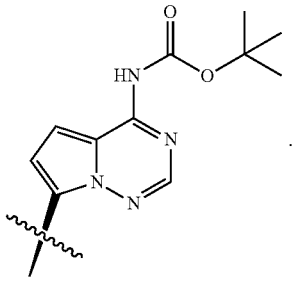

In some embodiments, Base is

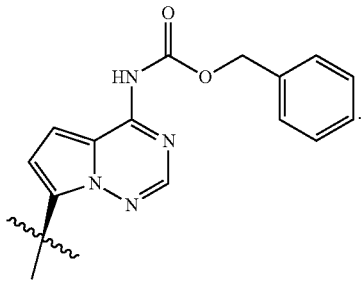

In some embodiments, Base is

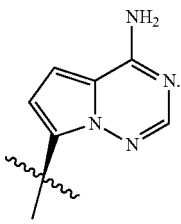

In some embodiments
R$^1$ is —OH or —OC(=O)R$^4$;
R$^2$ is —OH or —OC(=O)R$^5$;
R$^3$ is —C(=O)OR$^7$;
R$^4$ is C$_1$-C$_3$ alkyl;
R$^5$ is C$_1$-C$_3$ alkyl;
R$^7$ is C$_1$-C$_6$ alkyl or C$_6$-C$_8$ carbocyclyl;
Base is

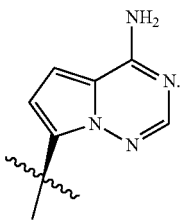

In some embodiments
R$^1$ is —OC(=O)R$^4$;
R$^2$ is —OC(=O)R$^5$;
R$^3$ is —C(=O)OR$^7$;
R$^4$ is C$_1$-C$_3$ alkyl;
R$^5$ is C$_1$-C$_3$ alkyl;
R$^7$ is C$_1$-C$_6$ alkyl;
Base is

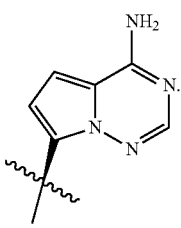

In some embodiments,
R$^1$ is —OH, —OC(=O)R$^4$, —OC(=O)OR$^4$, or —OP(=O)(OH)(OR$^4$);
R$^2$ is —OH, —OC(=O)R$^5$, or —OC(=O)OR$^5$; or
R$^1$ and R$^2$ are taken together to form —OC(=O)O—, —OP(=O)(OH)O—, or —OCHR$^6$O—;
R$^3$ is —C(=O)OR$^7$;
R$^4$ is C$_1$-C$_8$ alkyl or C$_2$-C$_8$ alkenyl, wherein the C$_1$-C$_8$ alkyl of R$^4$ is optionally substituted with one or two substituents independently selected from carbonyl and —OR$^8$;
R$^5$ is C$_1$-C$_8$ alkyl or C$_2$-C$_8$ alkenyl;
R$^7$ is C$_1$-C$_{20}$ alkyl, C$_2$-C$_8$ alkenyl, C$_3$-C$_{10}$ carbocyclyl, C$_6$-C$_{10}$ aryl, 4 to 8 membered heterocyclyl containing 1, 2, or 3 heteroatoms selected from N, O, and S, or 5 to 6 membered heteroaryl containing 1, 2, or 3 heteroatoms selected from N, O, and S;
wherein C$_1$-C$_{20}$ alkyl, C$_3$-C$_{10}$ carbocyclyl, C$_6$-C$_{10}$ aryl, or 4 to 8 membered heterocyclyl of R$^7$ are each, independently, optionally substituted with one, two, or three substituents independently selected from the group consisting of C$_1$-C$_8$ alkyl, halogen, carbonyl, —OR$^8$, —NR$^9$R$^{10}$, —OP(=O)(OH)$_2$, —OP(=O)(OR$^8$)$_2$, C$_3$-C$_8$ carbocyclyl, 4 to 6 membered heterocyclyl containing 1, 2, or 3 heteroatoms selected from N, O, and S, 5 to 6 membered heteroaryl containing 1, 2, or 3 heteroatoms selected from N, O, and S, and phenyl;
wherein substituent C$_3$-C$_8$ carbocyclyl of R$^7$ is optionally substituted with one or two substituents independently selected from C$_1$-C$_8$ alkyl, halogen, —CF$_3$, cyano, —CH$_2$CN, and phenyl,
wherein substituent 4 to 6 membered heterocyclyl of R$^7$ is optionally substituted two substituents independently selected from carbonyl and C$_1$-C$_6$ alkyl, and
wherein substituent phenyl of R$^7$ is optionally substituted with —OR$^8$;
R$^6$ is C$_1$-C$_6$ alkoxy or C$_6$-C$_{10}$ aryl;
each R$^8$ is independently H, C$_1$-C$_6$ alkyl, C$_3$-C$_6$ cycloalkyl, and 4 to 6 membered heterocyclyl;
wherein C$_1$-C$_6$ alkyl of R$^8$ is optionally substituted with C$_3$-C$_6$ cycloalkyl;
each R$^9$ and R$^{10}$ are independently C$_1$-C$_6$ alkyl;
Base is

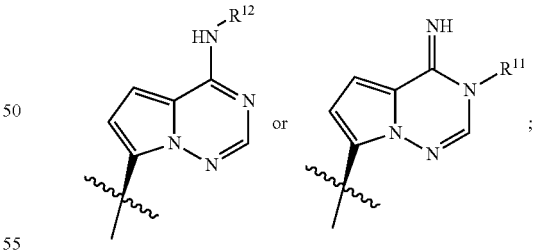

R$^{11}$ is C$_1$-C$_6$ alkyl optionally substituted with —OP(=O)(OH)(OR$^{14}$);
R$^{12}$ is H, —C(=O)R$^{13}$, or —C(=O)OR$^{13}$;
each R$^{13}$ is independently C$_1$-C$_8$ alkyl optionally substituted with phenyl or —OP(=O)(OH)(OR$^{14}$); and
each R$^{14}$ is independently H or C$_1$-C$_8$ alkyl; wherein C$_1$-C$_8$ alkyl of R$^{14}$ is optionally substituted with phenyl.
In some embodiments,
R$^1$ is —OH, —OC(=O)R$^4$, or —OC(=O)OR$^4$;
R$^2$ is —OH, —OC(=O)R$^5$, or —OC(=O)OR$^5$; or R$^1$ and R$^2$ are taken together to form —OC(=O)O—, —OP(=O)(OH)O—, or —OCHR$^6$O—;

R$^3$ is —C(=O)OR$^7$;

R$^4$ is C$_1$-C$_8$ alkyl or C$_2$-C$_8$ alkenyl, wherein the C$_1$-C$_8$ alkyl of R$^4$ is optionally substituted with one or two substituents independently selected from carbonyl and —OR$^8$;

R$^5$ is C$_2$-C$_8$ alkyl or C$_2$-C$_8$ alkenyl;

R$^7$ is C$_1$-C$_{20}$ alkyl, C$_2$-C$_8$ alkenyl, C$_3$-C$_8$ carbocyclyl, C$_6$-C$_{10}$ aryl, 4 to 6 membered heterocyclyl containing 1, 2, or 3 heteroatoms selected from N, O, and S, or 5 to 6 membered heteroaryl containing 1, 2, or 3 heteroatoms selected from N, O, and S;

wherein C$_1$-C$_{20}$ alkyl, C$_3$-C$_8$ carbocyclyl, or C$_6$-C$_{10}$ aryl of R$^7$ are each, independently, optionally substituted with one, two, or three substituents independently selected from the group consisting of C$_1$-C$_8$ alkyl, halogen, carbonyl, —OR$^9$, —NR$^9$R$^{10}$, —OP(=O)(OH)$_2$, —OP(=O)(OR$^8$)$_2$, C$_3$-C$_8$ carbocyclyl, 4 to 6 membered heterocyclyl containing 1, 2, or 3 heteroatoms selected from N, O, and S, 5 to 6 membered heteroaryl containing 1, 2, or 3 heteroatoms selected from N, O, and S, and phenyl;

wherein substituent C$_3$-C$_8$ carbocyclyl of R$^7$ is optionally substituted with one or two substituents independently selected from C$_1$-C$_8$ alkyl, halogen, —CF$_3$, cyano, —CH$_2$CN, and phenyl, wherein substituent 4 to 6 membered heterocyclyl of R$^7$ is optionally substituted two substituents independently selected from carbonyl and C$_1$-C$_6$ alkyl, and wherein substituent phenyl of R$^7$ is optionally substituted with —OR$^8$;

R$^6$ is C$_1$-C$_6$ alkoxy or C$_6$-C$_{10}$ aryl;

each R$^8$ is independently H or C$_1$-C$_6$ alkyl;

each R$^9$ and R$^{10}$ are independently C$_1$-C$_6$ alkyl;

Base is

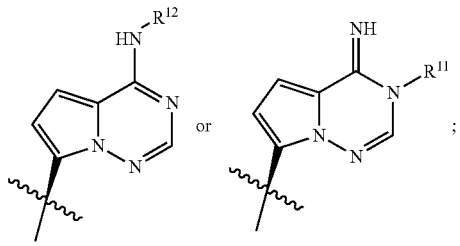

R$^{11}$ is C$_1$-C$_6$ alkyl optionally substituted with —OP(=O)(OH)(OR$^{14}$);

R$^{12}$ is H, —C(=O)R$^{13}$, or —C(=O)OR$^{13}$;

each R$^{13}$ is independently C$_1$-C$_8$ alkyl optionally substituted with phenyl or —OP(=O)(OH)(OR$^{14}$); and each R$^{14}$ is independently H or C$_1$-C$_8$ alkyl; wherein C$_1$-C$_8$ alkyl of R$^{14}$ is optionally substituted with phenyl.

In some embodiments,

R$^1$ is —OH, —OC(=O)R$^4$, or —OC(=O)OR$^4$;

R$^2$ is —OH, —OC(=O)R$^5$, or —OC(=O)OR$^5$; or

R$^1$ and R$^2$ are taken together to form —OC(=O)O—, —OP(=O)(OH)O—, or —OCHR$^6$O—;

R$^3$ is —C(=O)OR$^7$;

R$^4$ and R$^5$ are C$_1$-C$_8$ alkyl;

R$^7$ is C$_1$-C$_{20}$ alkyl, C$_2$-C$_8$ alkenyl, C$_3$-C$_8$ carbocyclyl, C$_6$-C$_{10}$ aryl, 4 to 6 membered heterocyclyl containing 1, 2, or 3 heteroatoms selected from N, O, and S, or 5 to 6 membered heteroaryl containing 1, 2, or 3 heteroatoms selected from N, O, and S;

wherein C$_1$-C$_{20}$ alkyl, C$_3$-C$_8$ carbocyclyl, or C$_6$-C$_{10}$ aryl of R$^7$ are each, independently, optionally substituted with one, two, or three substituents independently selected from the group consisting of C$_1$-C$_8$ alkyl, halogen, carbonyl, —OR$^8$, —NR$^9$R$^{10}$, —OP(=O)(OH)$_2$, —OP(=O)(OR$^8$)$_2$, C$_3$-C$_8$ carbocyclyl, 4 to 6 membered heterocyclyl containing 1, 2, or 3 heteroatoms selected from N, O, and S, 5 to 6 membered heteroaryl containing 1, 2, or 3 heteroatoms selected from N, O, and S, and phenyl;

wherein substituent C$_3$-C$_8$ carbocyclyl of R$^7$ is optionally substituted with one or two substituents independently selected from C$_1$-C$_8$ alkyl, halogen, —CF$_3$, cyano, —CH$_2$CN, and phenyl, wherein substituent 4 to 6 membered heterocyclyl of R$^7$ is optionally substituted two substituents independently selected from carbonyl and C$_1$-C$_6$ alkyl, and wherein substituent phenyl of R$^7$ is optionally substituted with —OR$^8$;

R$^6$ is C$_1$-C$_6$ alkoxy or C$_6$-C$_{10}$ aryl;

each R$^8$, R$^9$, and R$^{10}$ are independently C$_1$-C$_6$ alkyl;

Base is

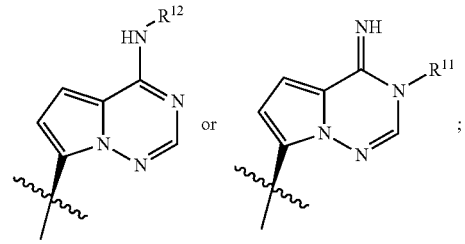

R$^{11}$ is C$_1$-C$_6$ alkyl optionally substituted with —OP(=O)(OH)(OR$^{14}$);

R$^{12}$ is H, —C(=O)R$^{13}$, or —C(=O)OR$^{13}$;

each R$^{13}$ is independently C$_1$-C$_8$ alkyl optionally substituted with —OP(=O)(OH)(OR$^{14}$); and each R$^{14}$ is independently H or C$_1$-C$_8$ alkyl; wherein C$_1$-C$_8$ alkyl of R$^{14}$ is optionally substituted with phenyl.

In some embodiments,

R$^1$ is —OH or —OC(=O)R$^4$;

R$^2$ is —OH or —OC(=O)R$^5$; or

R$^1$ and R$^2$ are taken together to form —OC(=O)O— or —OP(=O)(OH)O—;

R$^3$ is —C(=O)OR$^7$;

R$^4$, R$^5$, and R$^7$ are each independently C$_1$-C$_8$ alkyl, C$_3$-C$_8$ carbocyclyl, C$_6$-C$_{10}$ aryl, 4 to 6 membered heterocyclyl containing 1, 2, or 3 heteroatoms selected from N, O, and S or 5 to 6 membered heteroaryl containing 1, 2, or 3 heteroatoms selected from N, O, and S;

wherein C$_1$-C$_8$ alkyl of R$^7$ are each, independently, optionally substituted with one substituent selected from the group consisting of C$_1$-C$_8$ alkyl, —OR$^8$, —OP(=O)(OH)$_2$, C$_3$-C$_8$ carbocyclyl, 4 to 6 membered heterocyclyl containing 1, 2, or 3 heteroatoms selected from N, O, and S, 5 to 6 membered heteroaryl containing 1, 2, or 3 heteroatoms selected from N, O, and S, and phenyl;

wherein 4 to 6 membered heterocyclyl is optionally substituted with one, two, or three substituents independently selected from carbonyl and $C_1$-$C_6$ alkyl;
each $R^8$ is independently $C_1$-$C_6$ alkyl;
Base is

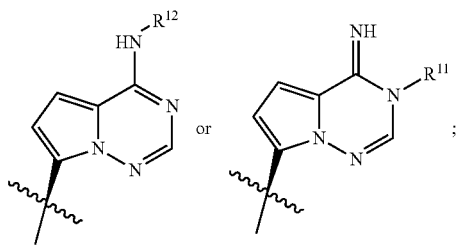

$R^{11}$ is $C_1$-$C_6$ alkyl substituted with —OP(=O)(OH)(OR$^{14}$);
$R^{12}$ is H, —C(=O)R$^{13}$ or —C(=O)OR$^{13}$;
$R^{13}$ is $C_1$-$C_8$ alkyl optionally substituted with —OP(=O)(OH)(OR$^{14}$); and
each $R^{13}$ is independently H or $C_1$-$C_8$ alkyl; wherein $C_1$-$C_8$ alkyl of $R^{14}$ is optionally substituted with phenyl.

In some embodiments,
$R^1$ is —OH or —OC(=O)R$^4$;
$R^2$ is —OH or —OC(=O)R$^5$; or
$R^1$ and $R^2$ are taken together to form —OC(=O)O— or —OP(=O)(OH)O—;
$R^3$ is —C(=O)OR$^7$;
$R^4$, $R^5$, and $R^7$ are each independently $C_1$-$C_8$ alkyl, $C_3$-$C_8$ carbocyclyl, $C_6$-$C_{10}$ aryl, 4 to 6 membered heterocyclyl containing 1, 2, or 3 heteroatoms selected from N, O, and S or 5 to 6 membered heteroaryl containing 1, 2, or 3 heteroatoms selected from N, O, and S;
wherein $C_1$-$C_8$ alkyl of $R^7$ are each, independently, optionally substituted with one substituent selected from the group consisting of —OR$^8$, —OP(=O)(OH)$_2$, $C_3$-$C_8$ carbocyclyl, 4 to 6 membered heterocyclyl containing 1, 2, or 3 heteroatoms selected from N, O, and S, 5 to 6 membered heteroaryl containing 1, 2, or 3 heteroatoms selected from N, O, and S, and phenyl;
wherein 4 to 6 membered heterocyclyl is optionally substituted with one, two, or three substituents independently selected from carbonyl and $C_1$-$C_6$ alkyl;
each $R^8$ is independently $C_1$-$C_6$ alkyl;
Base is

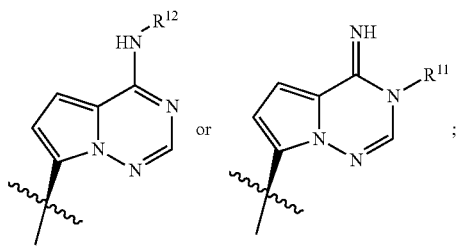

$R^{11}$ is $C_1$-$C_6$ alkyl substituted with —OP(=O)(OH)(OR$^{14}$);
$R^{12}$ is H, —C(=O)R$^{13}$ or —C(=O)OR$^{13}$;
$R^{13}$ is $C_1$-$C_8$ alkyl optionally substituted with —OP(=O)(OH)(OR$^{14}$); and
each $R^{14}$ is independently H or $C_1$-$C_8$ alkyl; wherein $C_1$-$C_8$ alkyl of $R^{14}$ is optionally substituted with phenyl.

In some embodiments,
$R^1$ is —OH or —OC(=O)R$^4$;
$R^2$ is —OH or —OC(=O)R$^5$; or
$R^1$ and $R^2$ are taken together to form —OC(=O)O—;
$R^3$ is —C(=O)OR$^7$;
$R^4$, $R^5$, and $R^7$ are each independently $C_1$-$C_8$ alkyl, $C_3$-$C_8$ carbocyclyl, $C_6$-$C_{10}$ aryl, 4 to 6 membered heterocyclyl containing 1, 2, or 3 heteroatoms selected from N, O, and S or 5 to 6 membered heteroaryl containing 1, 2, or 3 heteroatoms selected from N, O, and S;
wherein $C_1$-$C_8$ alkyl of $R^7$ are each, independently, optionally substituted with one substituent selected from the group consisting of —OR$^8$, —OP(=O)(OH)$_2$, $C_3$-$C_8$ carbocyclyl and phenyl;
each $R^8$ is independently $C_1$-$C_6$ alkyl;
Base is

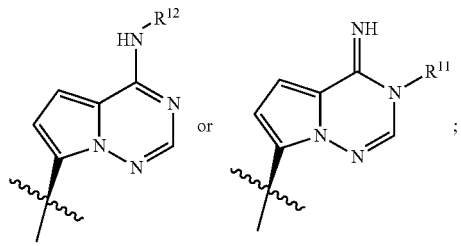

$R^{11}$ is Cd-$C_6$ alkyl substituted with —OP(=O)(OH)(OR$^{14}$);
$R^{12}$ is H, —C(=O)R$^{13}$ or —C(=O)OR$^{13}$;
$R^{13}$ is $C_1$-$C_8$ alkyl; and
each $R^{14}$ is independently H or $C_1$-$C_8$ alkyl; wherein $C_1$-$C_8$ alkyl of $R^{14}$ is optionally substituted with phenyl.

In some embodiments,
$R^1$ is —OH or —OC(=O)R$^4$;
$R^2$ is —OH or —OC(=O)R$^5$; or
$R^1$ and $R^2$ are taken together to form —OC(=O)O—;
$R^3$ is —C(=O)OR$^7$;
$R^4$, $R^5$, and $R^7$ are each independently $C_1$-$C_8$ alkyl, $C_3$-$C_8$ carbocyclyl, $C_6$-$C_{10}$ aryl, or 4 to 6 membered heterocyclyl containing 1, 2, or 3 heteroatoms selected from N, O, and S;
wherein $C_1$-$C_8$ alkyl of $R^7$ are each, independently, optionally substituted with one substituent selected from the group consisting of —OR$^8$ and phenyl;
each $R^8$ is independently $C_1$-$C_6$ alkyl;
Base is

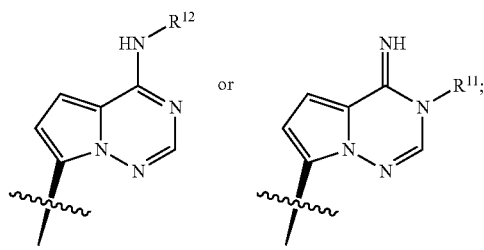

$R^{11}$ is $C_1$-$C_6$ alkyl substituted with —OP(=O)(OH)(OR$^{14}$);
$R^{12}$ is H, —C(=O)R$^{13}$ or —C(=O)OR$^{13}$;
$R^{13}$ is $C_1$-$C_8$ alkyl; and
each $R^{14}$ is independently H or $C_1$-$C_8$ alkyl; wherein $C_1$-$C_8$ alkyl of $R^{14}$ is optionally substituted with phenyl.

In some embodiments, the compound of Formula I is

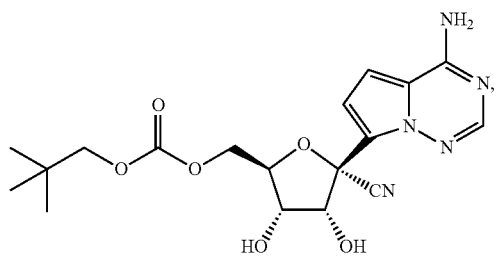 [SMILES: CC(C)(C)COC(=O)OC[C@H]1O[C@@](C#N)(c2ccc3c(N)ncnn23)[C@H](O)[C@@H]1O]

or a pharmaceutically acceptable salt thereof.

In some embodiments, the compound of Formula I is

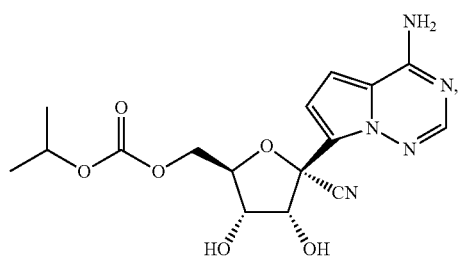 [SMILES: CC(C)OC(=O)OC[C@H]1O[C@@](C#N)(c2ccc3c(N)ncnn23)[C@H](O)[C@@H]1O]

or a pharmaceutically acceptable salt thereof.

In some embodiments, the compound of Formula I is

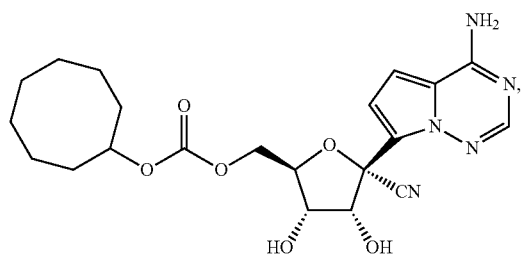 [SMILES: N#C[C@@]1(c2ccc3c(N)ncnn23)O[C@H](COC(=O)OC2CCCCCCC2)[C@@H](O)[C@H]1O]

or a pharmaceutically acceptable salt thereof.

In some embodiments, the compound of Formula I is

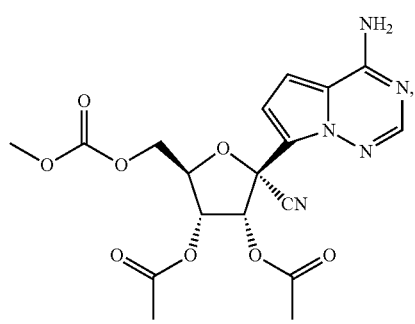 [SMILES: COC(=O)OC[C@H]1O[C@@](C#N)(c2ccc3c(N)ncnn23)[C@H](OC(C)=O)[C@@H]1OC(C)=O]

or a pharmaceutically acceptable salt thereof.

In some embodiments, the compound of Formula I is

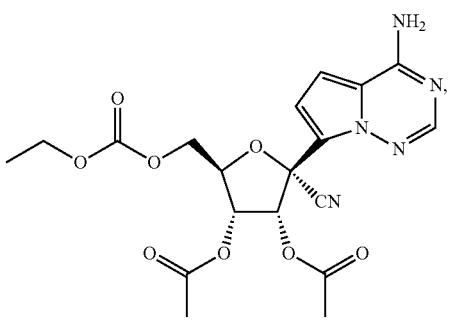 [SMILES: CCOC(=O)OC[C@H]1O[C@@](C#N)(c2ccc3c(N)ncnn23)[C@H](OC(C)=O)[C@@H]1OC(C)=O]

or a pharmaceutically acceptable salt thereof.

In some embodiments, the compound of Formula I is

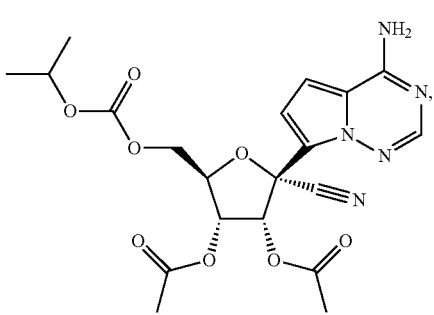 [SMILES: CC(=O)O[C@H]1[C@@H](OC(C)=O)[C@](C#N)(c2ccc3c(N)ncnn23)O[C@@H]1COC(=O)OC(C)C]

or a pharmaceutically acceptable salt thereof.

In some embodiments, the compound of Formula I is

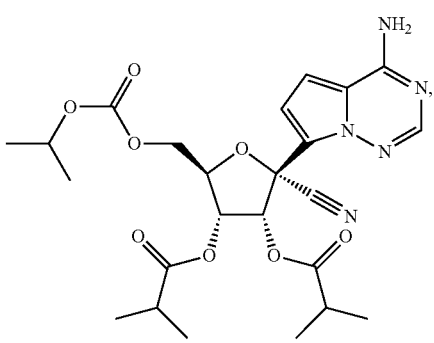 [SMILES: CC(C)OC(=O)OC[C@H]1O[C@@](C#N)(c2ccc3c(N)ncnn23)[C@H](OC(=O)C(C)C)[C@@H]1OC(=O)C(C)C]

or a pharmaceutically acceptable salt thereof.

In some embodiments, the compound of Formula I is

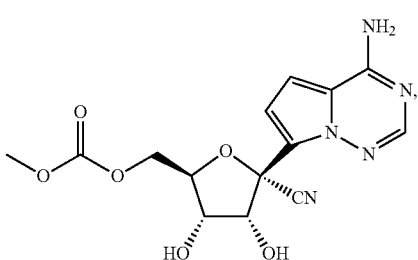 [SMILES: COC(=O)OC[C@H]1O[C@@](C#N)(c2ccc3c(N)ncnn23)[C@H](O)[C@@H]1O]

or a pharmaceutically acceptable salt thereof.

In some embodiments, the compound of Formula I is
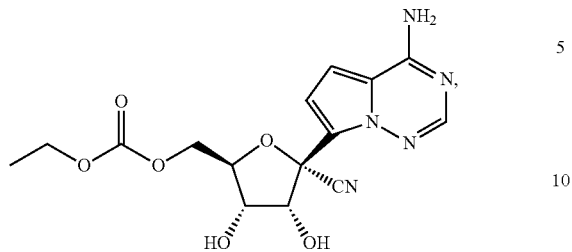
or a pharmaceutically acceptable salt thereof.
In some embodiments, the compound of Formula I is
| Example No. | Compound No. | Structure |
|---|---|---|
| Example 1 | 1 | 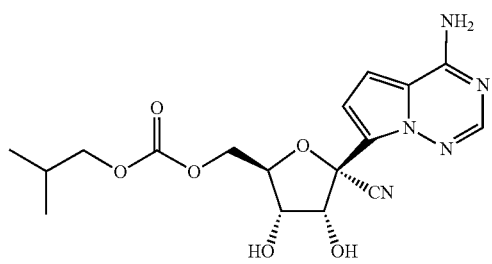 [SMILES: CC(C)COC(=O)OC[C@H]1O[C@@](C#N)(c2ccc3c(N)ncnn23)[C@H](O)[C@@H]1O] |
| Example 2 | 2 | 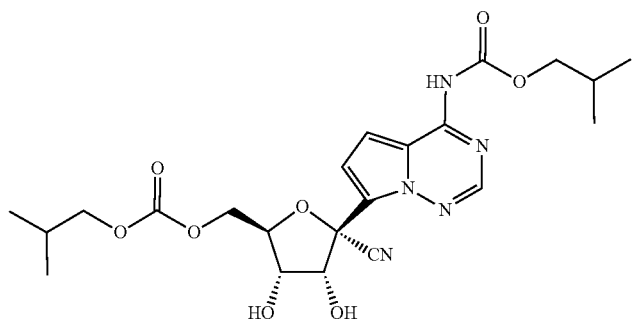 [SMILES: CC(C)COC(=O)Nc1ncnn2c([C@]3(C#N)O[C@H](COC(=O)OCC(C)C)[C@@H](O)[C@H]3O)ccc12] |
| Example 3 | 3 | 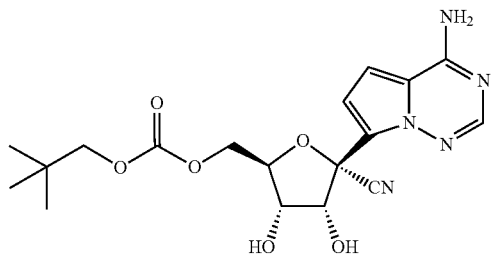 [SMILES: CC(C)(C)COC(=O)OC[C@H]1O[C@@](C#N)(c2ccc3c(N)ncnn23)[C@H](O)[C@@H]1O] |
| Example 4 | 4 | 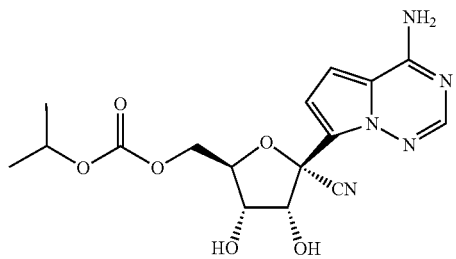 [SMILES: CC(C)OC(=O)OC[C@H]1O[C@@](C#N)(c2ccc3c(N)ncnn23)[C@H](O)[C@@H]1O] |

-continued
| Example No. | Compound No. | Structure |
|---|---|---|
| Example 5 | 5 | 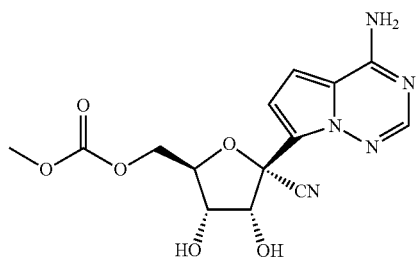 [SMILES: COC(=O)OC[C@H]1O[C@@](C#N)(c2ccc3c(N)ncnn23)[C@H](O)[C@@H]1O] |
| Example 6 | 6 | 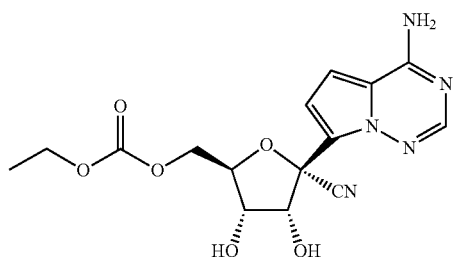 [SMILES: CCOC(=O)OC[C@H]1O[C@@](C#N)(c2ccc3c(N)ncnn23)[C@H](O)[C@@H]1O] |
| Example 7 | 7 | 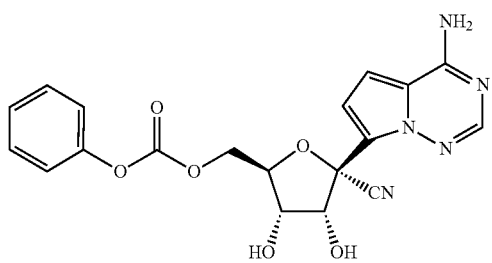 [SMILES: N#C[C@@]1(c2ccc3c(N)ncnn23)O[C@H](COC(=O)Oc2ccccc2)[C@@H](O)[C@H]1O] |
| Example 8 | 8 | 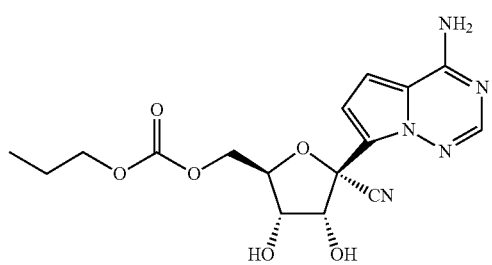 [SMILES: CCCOC(=O)OC[C@H]1O[C@@](C#N)(c2ccc3c(N)ncnn23)[C@H](O)[C@@H]1O] |
| Example 9 | 9 | 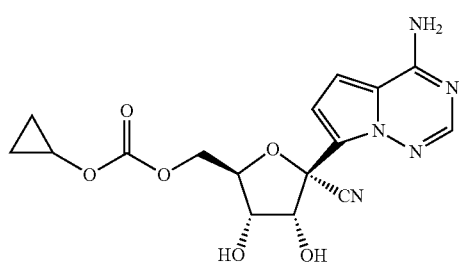 [SMILES: N#C[C@@]1(c2ccc3c(N)ncnn23)O[C@H](COC(=O)OC2CC2)[C@@H](O)[C@H]1O] |
| Example 10 | 10 | 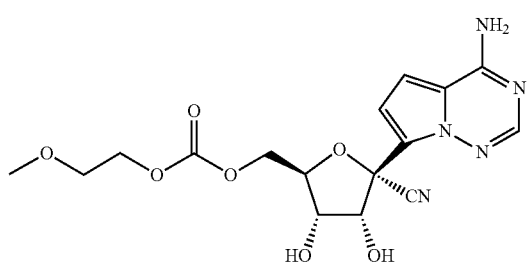 [SMILES: COCCOC(=O)OC[C@H]1O[C@@](C#N)(c2ccc3c(N)ncnn23)[C@H](O)[C@@H]1O] |

| Example No. | Compound No. | Structure |
|---|---|---|
| Example 11 | 11 | 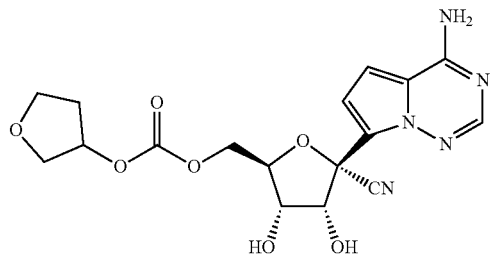 [SMILES: N#C[C@@]1(c2ccc3c(N)ncnn23)O[C@H](COC(=O)OC2CCOC2)[C@@H](O)[C@H]1O] |
| Example 12 | 12 | 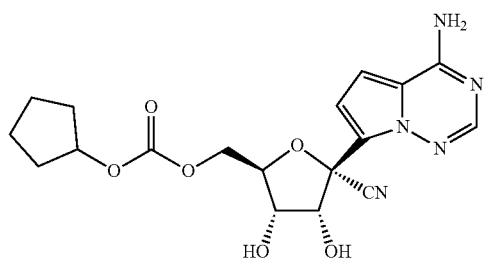 [SMILES: N#C[C@@]1(c2ccc3c(N)ncnn23)O[C@H](COC(=O)OC2CCCC2)[C@@H](O)[C@H]1O] |
| Example 13 | 13 | 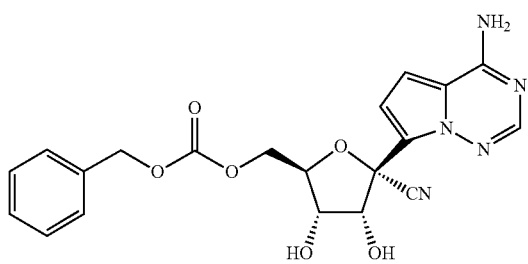 [SMILES: N#C[C@@]1(c2ccc3c(N)ncnn23)O[C@H](COC(=O)OCc2ccccc2)[C@@H](O)[C@H]1O] |
| Example 14 | 14 | 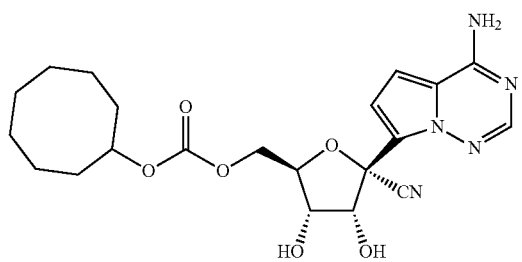 [SMILES: N#C[C@@]1(c2ccc3c(N)ncnn23)O[C@H](COC(=O)OC2CCCCCCC2)[C@@H](O)[C@H]1O] |
| Example 15 | 15 | 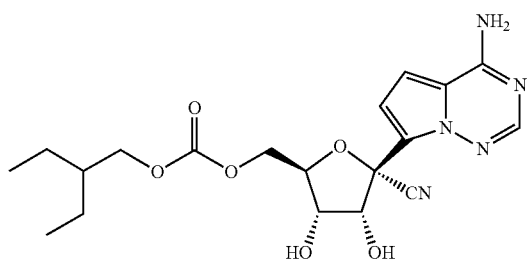 [SMILES: CCC(CC)COC(=O)OC[C@H]1O[C@@](C#N)(c2ccc3c(N)ncnn23)[C@H](O)[C@@H]1O] |

-continued
| Example No. | Compound No. | Structure |
|---|---|---|
| Example 16 | 16 | 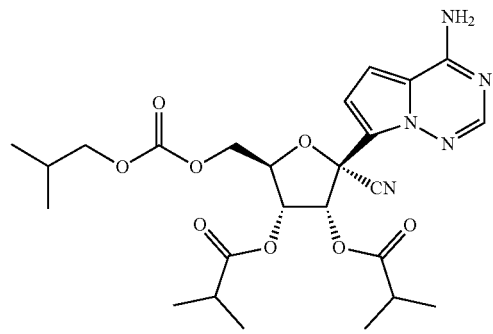 [SMILES: CC(C)COC(=O)OC[C@H]1O[C@@](C#N)(c2ccc3c(N)ncnn23)[C@H](OC(=O)C(C)C)[C@@H]1OC(=O)C(C)C] |
| Example 17 | 17 | 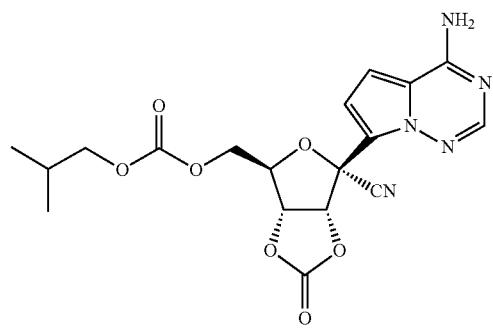 [SMILES: CC(C)COC(=O)OC[C@H]1O[C@@](C#N)(c2ccc3c(N)ncnn23)[C@@H]2OC(=O)O[C@@H]21] |
| Example 18 | 18 | 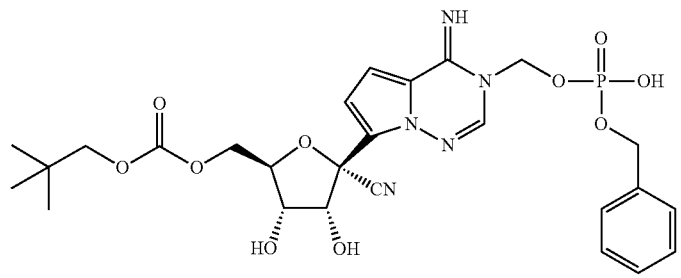 [SMILES: CC(C)(C)COC(=O)OC[C@H]1O[C@@](C#N)(c2ccc3c(=N)n(COP(=O)(O)OCc4ccccc4)cnn23)[C@H](O)[C@@H]1O] |
| Example 19 | 19 | 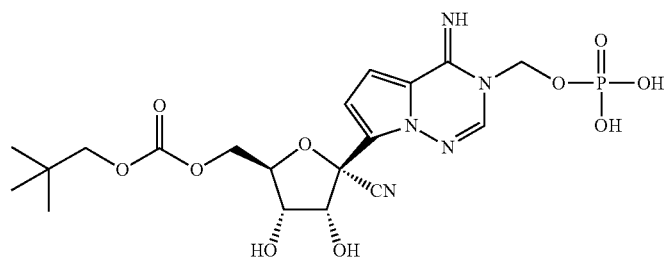 [SMILES: CC(C)(C)COC(=O)OC[C@H]1O[C@@](C#N)(c2ccc3c(=N)n(COP(=O)(O)O)cnn23)[C@H](O)[C@@H]1O] |
| Example 20 | 20 | 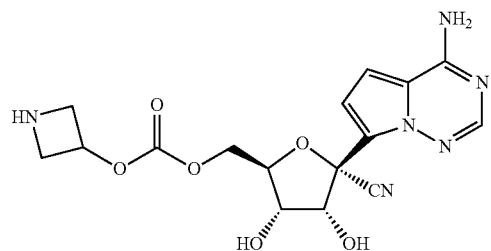 [SMILES: N#C[C@@]1(c2ccc3c(N)ncnn23)O[C@H](COC(=O)OC2CNC2)[C@@H](O)[C@H]1O] |

| Example No. | Compound No. | Structure |
|---|---|---|
| Example 21 | 21 | 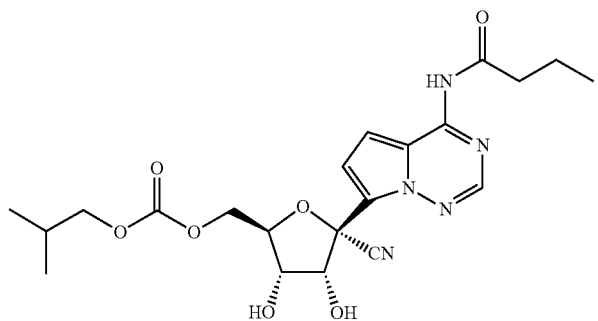 [SMILES: CCCC(=O)Nc1ncnn2c([C@]3(C#N)O[C@H](COC(=O)OCC(C)C)[C@@H](O)[C@H]3O)ccc12] |
or a pharmaceutically acceptable salt thereof.
In some embodiments, the compound of Formula I is
| Example No | Compound No | Structure |
|---|---|---|
| | 22 | 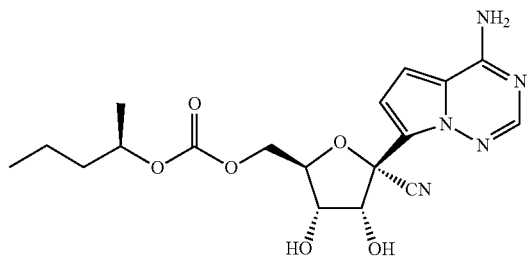 [SMILES: CCC[C@@H](C)OC(=O)OC[C@H]1O[C@@](C#N)(c2ccc3c(N)ncnn23)[C@H](O)[C@@H]1O] |
| | 23 | 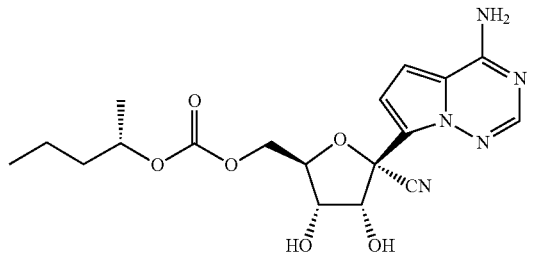 [SMILES: CCC[C@H](C)OC(=O)OC[C@H]1O[C@@](C#N)(c2ccc3c(N)ncnn23)[C@H](O)[C@@H]1O] |
| | 24 | 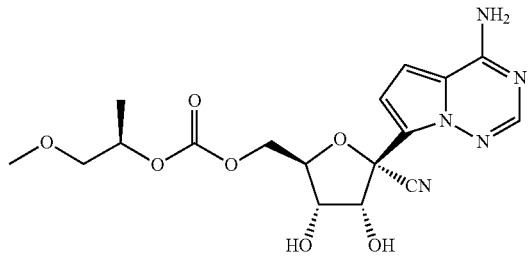 [SMILES: COC[C@@H](C)OC(=O)OC[C@H]1O[C@@](C#N)(c2ccc3c(N)ncnn23)[C@H](O)[C@@H]1O] |
| | 25 | 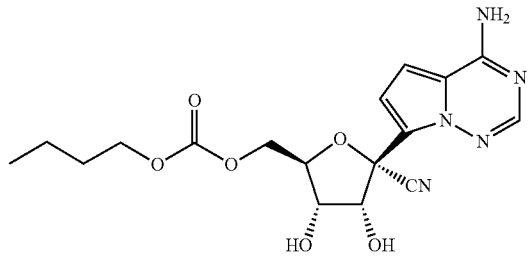 [SMILES: CCCCOC(=O)OC[C@H]1O[C@@](C#N)(c2ccc3c(N)ncnn23)[C@H](O)[C@@H]1O] |

-continued
| Example No | Compound No | Structure |
|---|---|---|
| Example 80 | 26 | 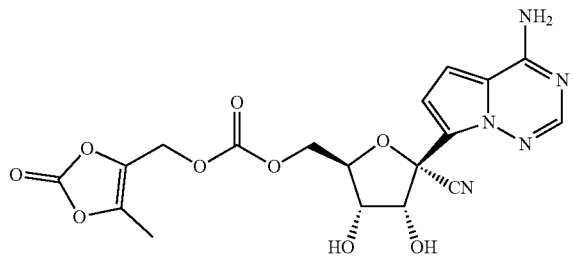 [SMILES: Cc1oc(=O)oc1COC(=O)OC[C@H]1O[C@@](C#N)(c2ccc3c(N)ncnn23)[C@H](O)[C@@H]1O] |
| Example 74 | 27 | 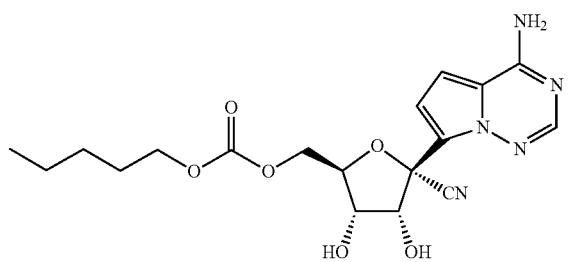 |
| | 28 | 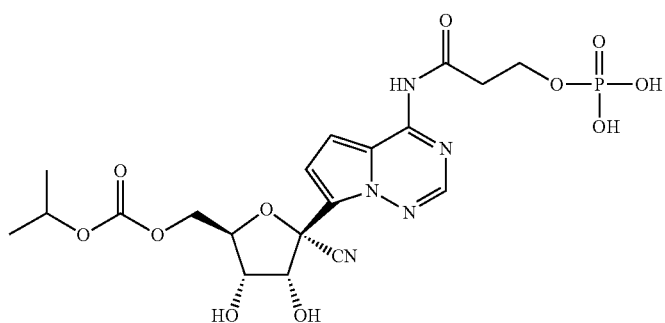 [SMILES: CC(C)OC(=O)OC[C@H]1O[C@@](C#N)(c2ccc3c(NC(=O)CCOP(=O)(O)O)ncnn23)[C@H](O)[C@@H]1O] |
| Example 30 | 29 | 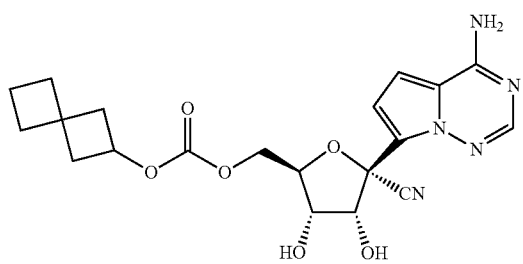 [SMILES: N#C[C@@]1(c2ccc3c(N)ncnn23)O[C@H](COC(=O)OC2CC3(CCC3)C2)[C@@H](O)[C@H]1O] |
| | 30 | 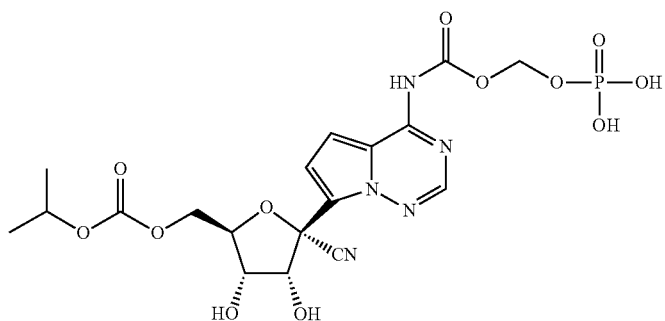 [SMILES: CC(C)OC(=O)OC[C@H]1O[C@@](C#N)(c2ccc3c(NC(=O)OCOP(=O)(O)O)ncnn23)[C@H](O)[C@@H]1O] |

-continued
| Example No | Compound No | Structure |
|---|---|---|
| Example 72 | 31 | 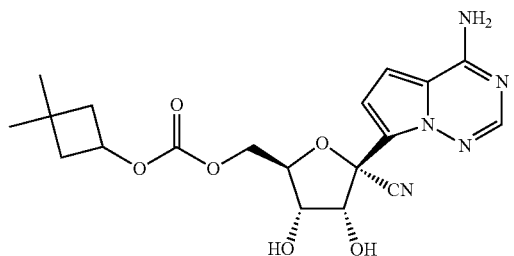 [SMILES: CC1(C)CC(OC(=O)OC[C@H]2O[C@@](C#N)(c3ccc4c(N)ncnn34)[C@H](O)[C@@H]2O)C1] |
| | 32 | 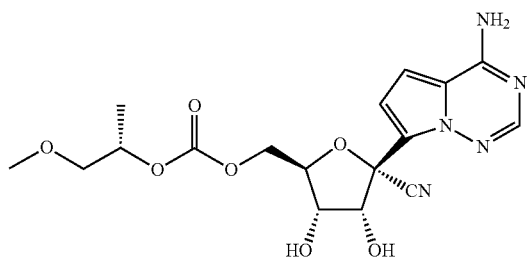 [SMILES: COC[C@H](C)OC(=O)OC[C@H]1O[C@@](C#N)(c2ccc3c(N)ncnn23)[C@H](O)[C@@H]1O] |
| | 33 | 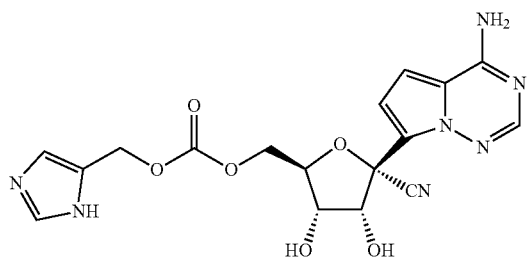 [SMILES: N#C[C@@]1(c2ccc3c(N)ncnn23)O[C@H](COC(=O)OCc2cnc[nH]2)[C@@H](O)[C@H]1O] |
| | 34 | 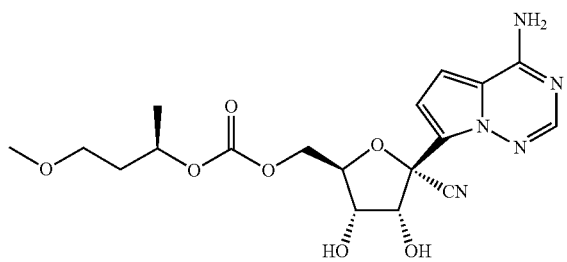 [SMILES: COCC[C@@H](C)OC(=O)OC[C@H]1O[C@@](C#N)(c2ccc3c(N)ncnn23)[C@H](O)[C@@H]1O] |
| Example 38 | 35 | 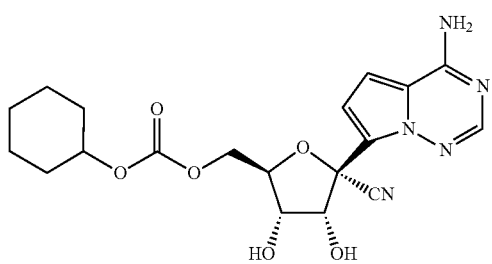 [SMILES: N#C[C@@]1(c2ccc3c(N)ncnn23)O[C@H](COC(=O)OC2CCCCC2)[C@@H](O)[C@H]1O] |
| | 36 | 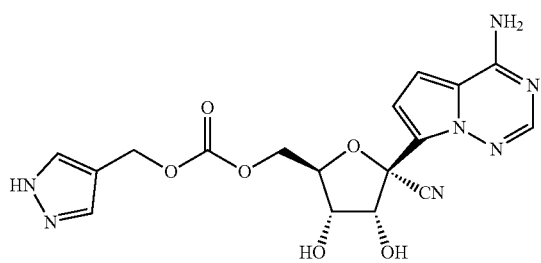 [SMILES: N#C[C@@]1(c2ccc3c(N)ncnn23)O[C@H](COC(=O)OCc2cn[nH]c2)[C@@H](O)[C@H]1O] |

-continued
| Example No | Compound No | Structure |
|---|---|---|
| Example 81 | 37 | 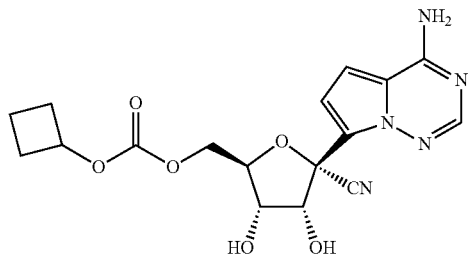 [SMILES: N#C[C@@]1(c2ccc3c(N)ncnn23)O[C@H](COC(=O)OC2CCC2)[C@@H](O)[C@H]1O] |
| | 38 | 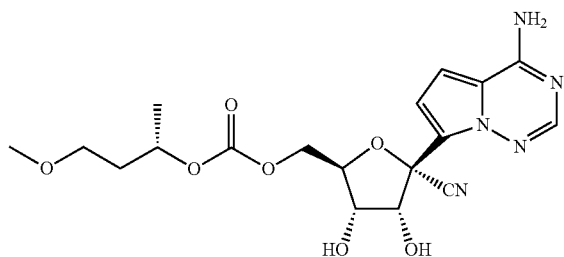 [SMILES: COCC[C@H](C)OC(=O)OC[C@H]1O[C@@](C#N)(c2ccc3c(N)ncnn23)[C@H](O)[C@@H]1O] |
| | 39 | 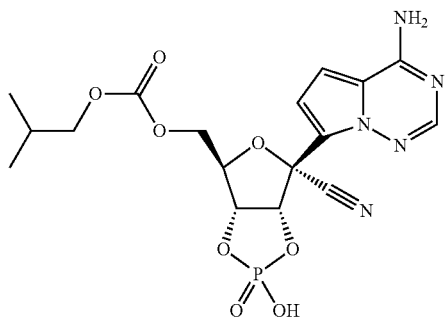 |
| Example 95 | 40 | 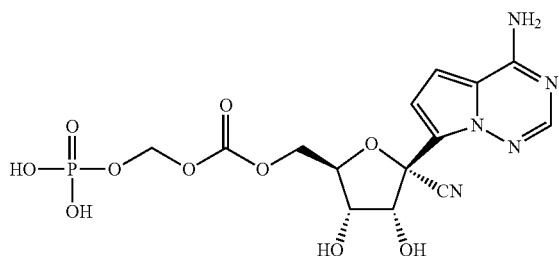 [SMILES: N#C[C@@]1(c2ccc3c(N)ncnn23)O[C@H](COC(=O)OCOP(=O)(O)O)[C@@H](O)[C@H]1O] |
| | 41 | 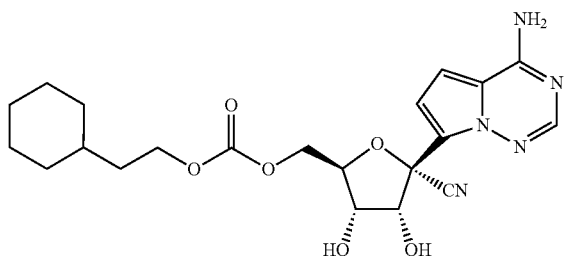 [SMILES: N#C[C@@]1(c2ccc3c(N)ncnn23)O[C@H](COC(=O)OCCC2CCCCC2)[C@@H](O)[C@H]1O] |

| Example No | Compound No | Structure |
|---|---|---|
| | 42 | 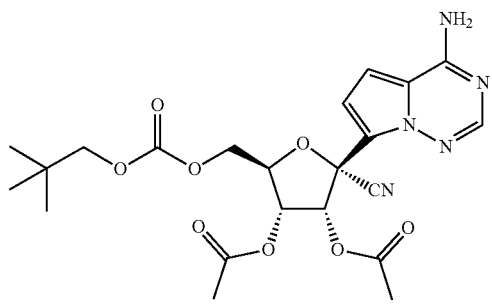 [SMILES: CC(=O)O[C@H]1[C@@H](OC(C)=O)[C@](C#N)(c2ccc3c(N)ncnn23)O[C@@H]1COC(=O)OCC(C)(C)C] |
| | 43 | 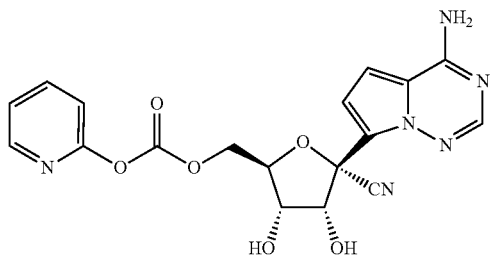 [SMILES: N#C[C@@]1(c2ccc3c(N)ncnn23)O[C@H](COC(=O)Oc2ccccn2)[C@@H](O)[C@H]1O] |
| | 44 | 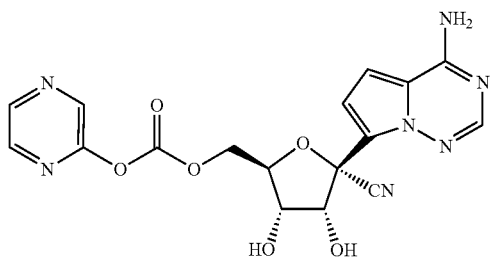 [SMILES: N#C[C@@]1(c2ccc3c(N)ncnn23)O[C@H](COC(=O)Oc2cnccn2)[C@@H](O)[C@H]1O] |
| | 45 | 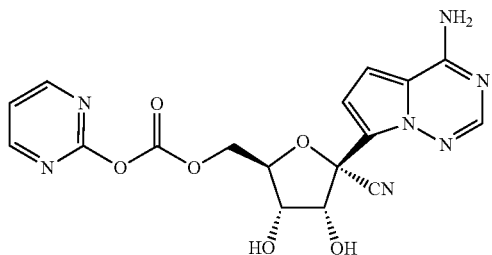 [SMILES: N#C[C@@]1(c2ccc3c(N)ncnn23)O[C@H](COC(=O)Oc2ncccn2)[C@@H](O)[C@H]1O] |
or a pharmaceutically acceptable salt thereof.
In some embodiments, the compound of Formula I is
| Example No. | Compound No. | Structure |
|---|---|---|
| Example 22 | 46 | 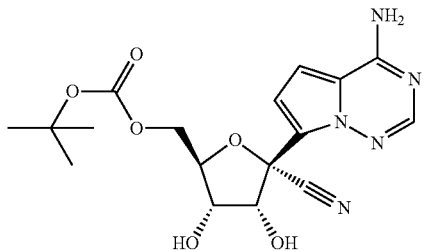 [SMILES: CC(C)(C)OC(=O)OC[C@H]1O[C@@](C#N)(c2ccc3c(N)ncnn23)[C@H](O)[C@@H]1O] |

-continued

| Example No. | Compound No. | Structure |
|---|---|---|
| Example 23 | 47 | 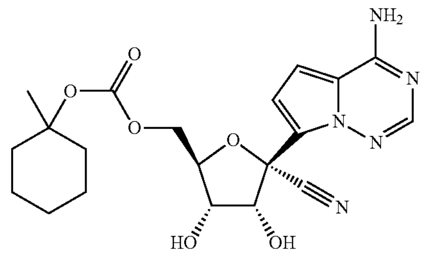 [SMILES: CC1(OC(=O)OC[C@H]2O[C@@](C#N)(c3ccc4c(N)ncnn34)[C@H](O)[C@@H]2O)CCCCC1] |
| Example 24 | 48 | 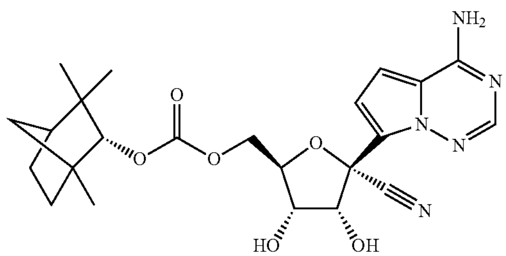 [SMILES: CC12CCC(C1)C(C)(C)[C@@H]2OC(=O)OC[C@H]1O[C@@](C#N)(c2ccc3c(N)ncnn23)[C@H](O)[C@@H]1O] |
| Example 25 | 49 | 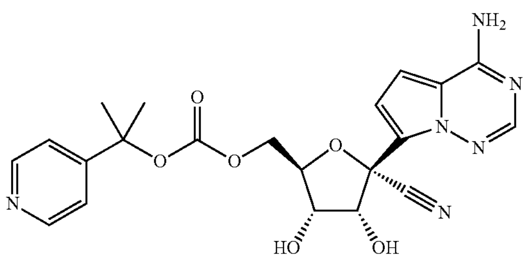 [SMILES: CC(C)(OC(=O)OC[C@H]1O[C@@](C#N)(c2ccc3c(N)ncnn23)[C@H](O)[C@@H]1O)c1ccncc1] |
| Example 26 | 50 | 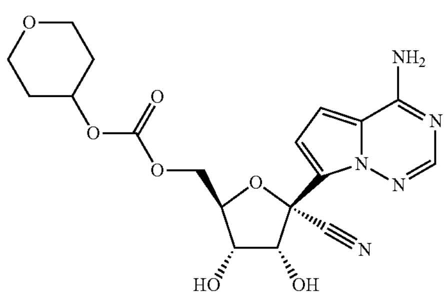 [SMILES: N#C[C@@]1(c2ccc3c(N)ncnn23)O[C@H](COC(=O)OC2CCOCC2)[C@@H](O)[C@H]1O] |
| Example 27 | 51 | 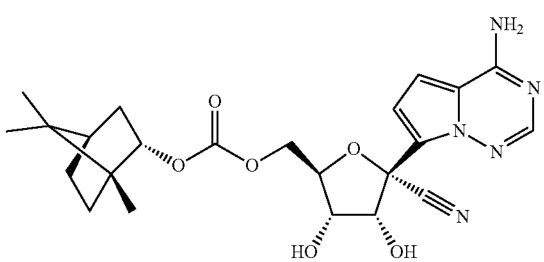 [SMILES: CC1(C)[C@@H]2CC[C@@]1(C)[C@@H](OC(=O)OC[C@H]1O[C@@](C#N)(c3ccc4c(N)ncnn34)[C@H](O)[C@@H]1O)C2] |
| Example 28 | 52 | 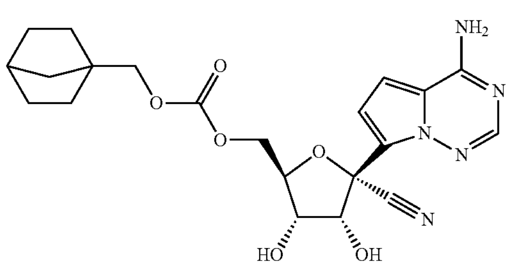 [SMILES: N#C[C@@]1(c2ccc3c(N)ncnn23)O[C@H](COC(=O)OCC23CCC(CC2)C3)[C@@H](O)[C@H]1O] |

-continued

| Example No. | Compound No. | Structure |
|---|---|---|
| Example 29 | 53 | 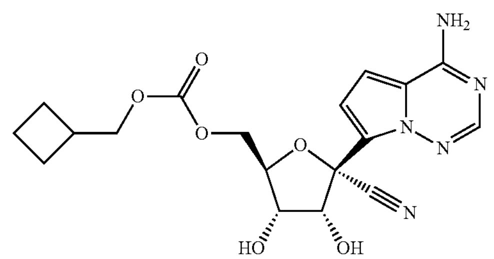 [SMILES: N#C[C@@]1(c2ccc3c(N)ncnn23)O[C@H](COC(=O)OCC2CCC2)[C@@H](O)[C@H]1O] |
| Example 31 | 54 | 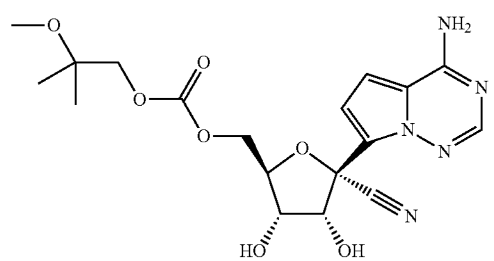 [SMILES: COC(C)(C)COC(=O)OC[C@H]1O[C@@](C#N)(c2ccc3c(N)ncnn23)[C@H](O)[C@@H]1O] |
| Example 32 | 55 | 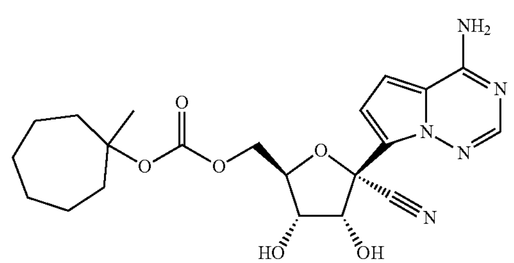 [SMILES: CC1(OC(=O)OC[C@H]2O[C@@](C#N)(c3ccc4c(N)ncnn34)[C@H](O)[C@@H]2O)CCCCCC1] |
| Example 33 | 56 | 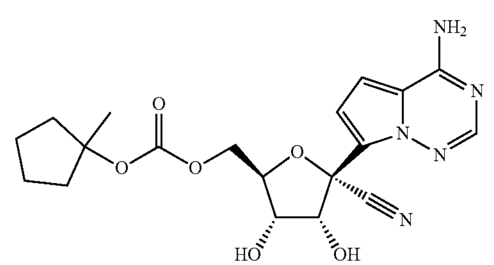 [SMILES: CC1(OC(=O)OC[C@H]2O[C@@](C#N)(c3ccc4c(N)ncnn34)[C@H](O)[C@@H]2O)CCCC1] |
| Example 34 | 57 | 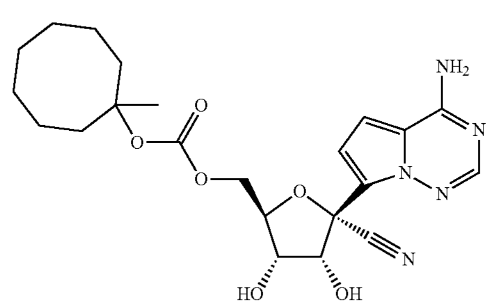 [SMILES: CC1(OC(=O)OC[C@H]2O[C@@](C#N)(c3ccc4c(N)ncnn34)[C@H](O)[C@@H]2O)CCCCCCC1] |

-continued
| Example No. | Compound No. | Structure |
|---|---|---|
| Example 35 | 58 | 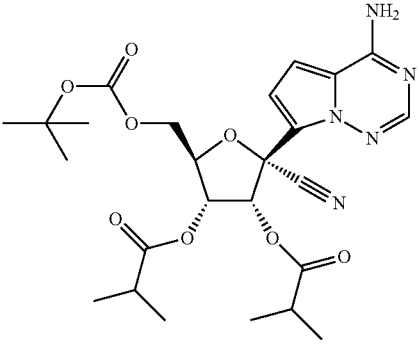 [SMILES: CC(C)C(=O)O[C@H]1[C@@H](OC(=O)C(C)C)[C@](C#N)(c2ccc3c(N)ncnn23)O[C@@H]1COC(=O)OC(C)(C)C] |
| Example 36 | 59 | 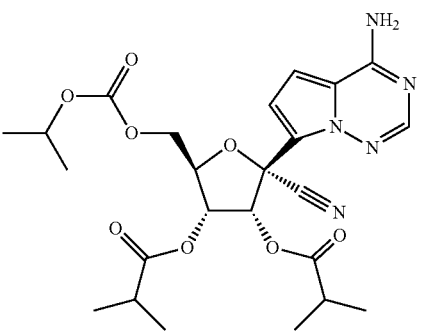 [SMILES: CC(C)OC(=O)OC[C@H]1O[C@@](C#N)(c2ccc3c(N)ncnn23)[C@H](OC(=O)C(C)C)[C@@H]1OC(=O)C(C)C] |
| Example 37 | 60 | 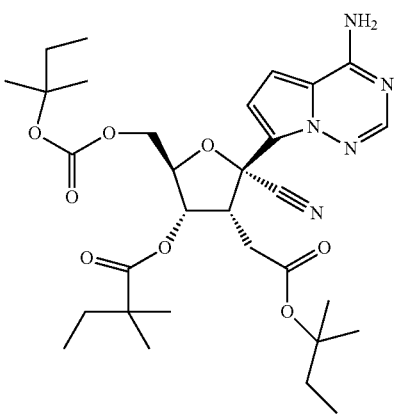 [SMILES: CCC(C)(C)OC(=O)C[C@@H]1[C@H](OC(=O)C(C)(C)CC)[C@@H](COC(=O)OC(C)(C)CC)O[C@@]1(C#N)c1ccc2c(N)ncnn12] |
| Example 39 | 62 | 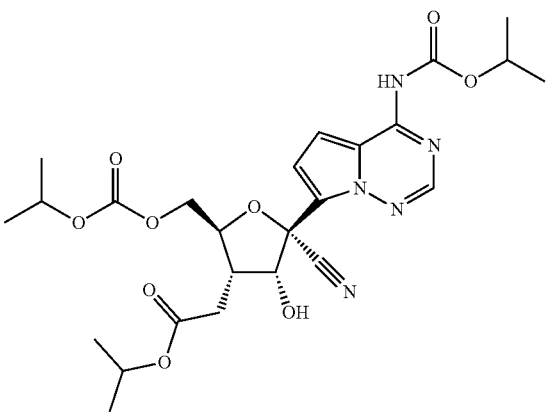 [SMILES: CC(C)OC(=O)C[C@H]1[C@@H](O)[C@](C#N)(c2ccc3c(NC(=O)OC(C)C)ncnn23)O[C@@H]1COC(=O)OC(C)C] |

-continued
| Example No. | Compound No. | Structure |
|---|---|---|
| Example 40 | 63 | 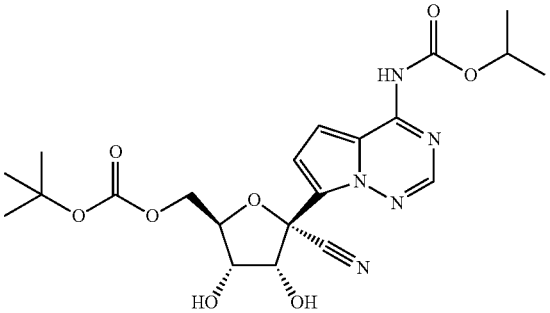 [SMILES: CC(C)OC(=O)Nc1ncnn2c([C@]3(C#N)O[C@H](COC(=O)OC(C)(C)C)[C@@H](O)[C@H]3O)ccc12] |
| Example 42 | 64 | 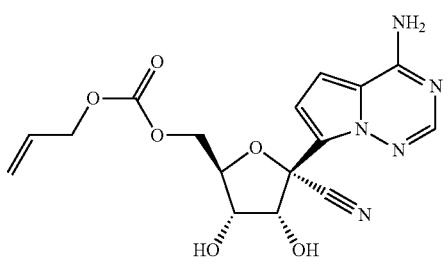 [SMILES: C=CCOC(=O)OC[C@H]1O[C@@](C#N)(c2ccc3c(N)ncnn23)[C@H](O)[C@@H]1O] |
| Example 43 | 65 | 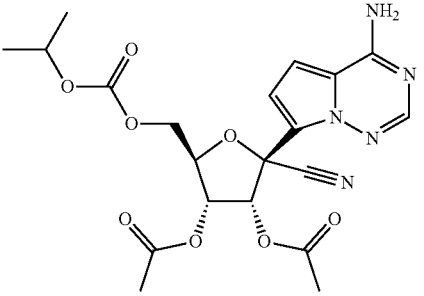 [SMILES: CC(=O)O[C@H]1[C@@H](OC(C)=O)[C@](C#N)(c2ccc3c(N)ncnn23)O[C@@H]1COC(=O)OC(C)C] |
| Example 44 | 66 | 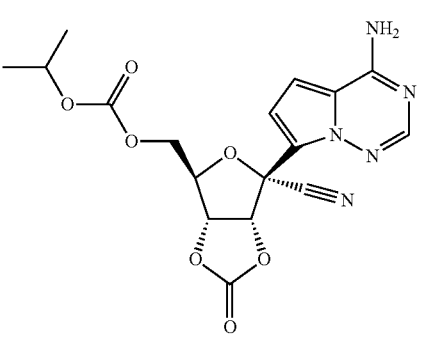 [SMILES: CC(C)OC(=O)OC[C@H]1O[C@@](C#N)(c2ccc3c(N)ncnn23)[C@@H]2OC(=O)O[C@@H]21] |
| Example 45 | 67 | 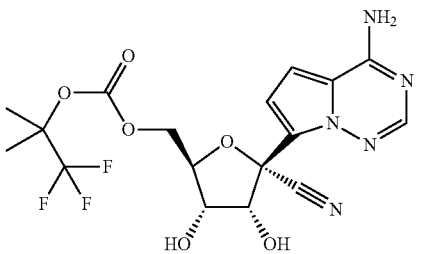 [SMILES: CC(C)(OC(=O)OC[C@H]1O[C@@](C#N)(c2ccc3c(N)ncnn23)[C@H](O)[C@@H]1O)C(F)(F)F] |

-continued
| Example No. | Compound No. | Structure |
|---|---|---|
| Example 46 | 68 | 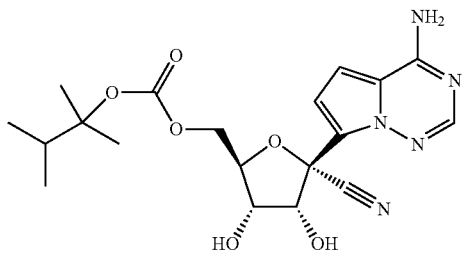 [SMILES: CC(C)C(C)(C)OC(=O)OC[C@H]1O[C@@](C#N)(c2ccc3c(N)ncnn23)[C@H](O)[C@@H]1O] |
| Example 47 | 69 | 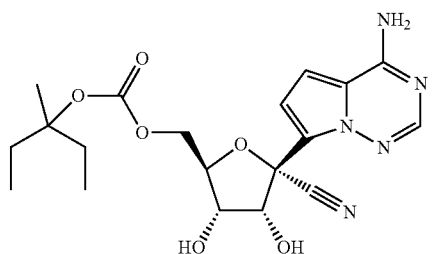 [SMILES: CCC(C)(CC)OC(=O)OC[C@H]1O[C@@](C#N)(c2ccc3c(N)ncnn23)[C@H](O)[C@@H]1O] |
| Example 48 | 70 | 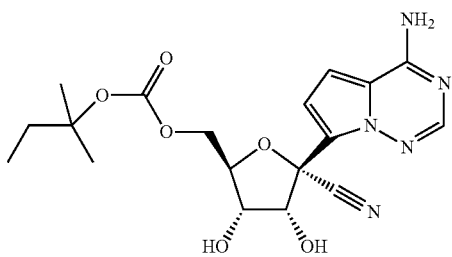 [SMILES: CCC(C)(C)OC(=O)OC[C@H]1O[C@@](C#N)(c2ccc3c(N)ncnn23)[C@H](O)[C@@H]1O] |
| Example 49 | 71 | 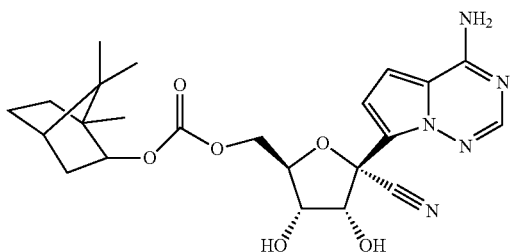 [SMILES: CC1(C)C2CCC1(C)C(OC(=O)OC[C@H]1O[C@@](C#N)(c3ccc4c(N)ncnn34)[C@H](O)[C@@H]1O)C2] |
| Example 50 | 72 | 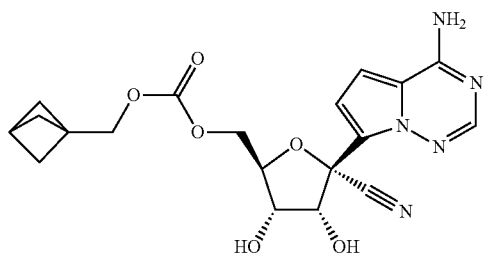 [SMILES: N#C[C@@]1(c2ccc3c(N)ncnn23)O[C@H](COC(=O)OCC23CC(C2)C3)[C@@H](O)[C@H]1O] |

-continued

| Example No. | Compound No. | Structure |
|---|---|---|
| Example 51 | 73 | 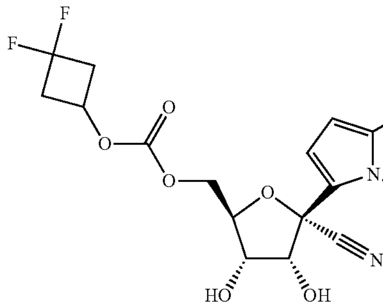 |
| Example 52 | 74 | 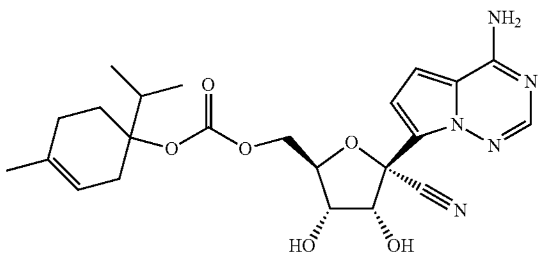 [SMILES: CC1=CCC(OC(=O)OC[C@H]2O[C@@](C#N)(c3ccc4c(N)ncnn34)[C@H](O)[C@@H]2O)(C(C)C)CC1] |
| Example 53 | 75 | 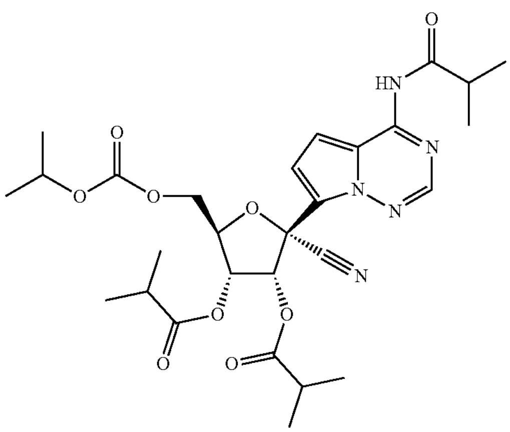 [SMILES: CC(C)OC(=O)OC[C@H]1O[C@@](C#N)(c2ccc3c(NC(=O)C(C)C)ncnn23)[C@H](OC(=O)C(C)C)[C@@H]1OC(=O)C(C)C] |
| Example 54 | 76 | 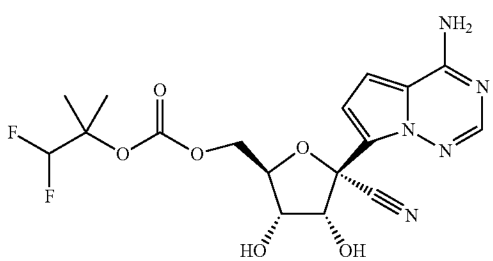 [SMILES: CC(C)(OC(=O)OC[C@H]1O[C@@](C#N)(c2ccc3c(N)ncnn23)[C@H](O)[C@@H]1O)C(F)F] |
| Example 55 | 77 | 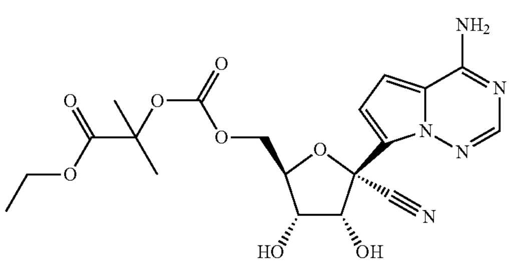 [SMILES: CCOC(=O)C(C)(C)OC(=O)OC[C@H]1O[C@@](C#N)(c2ccc3c(N)ncnn23)[C@H](O)[C@@H]1O] |

-continued

| Example No. | Compound No. | Structure |
|---|---|---|
| Example 56 | 78 | 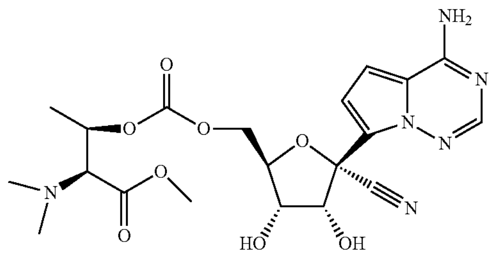 [SMILES: COC(=O)[C@H]([C@@H](C)OC(=O)OC[C@H]1O[C@@](C#N)(c2ccc3c(N)ncnn23)[C@H](O)[C@@H]1O)N(C)C] |
| Example 57 | 79 | 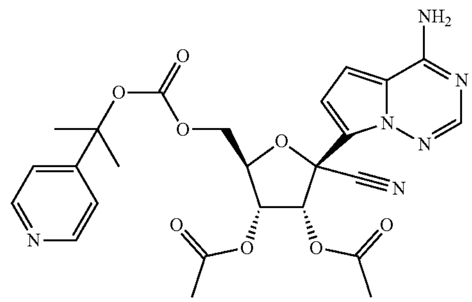 [SMILES: CC(=O)O[C@H]1[C@@H](OC(C)=O)[C@](C#N)(c2ccc3c(N)ncnn23)O[C@@H]1COC(=O)OC(C)(C)c1ccncc1] |
| Example 58 | 80 | 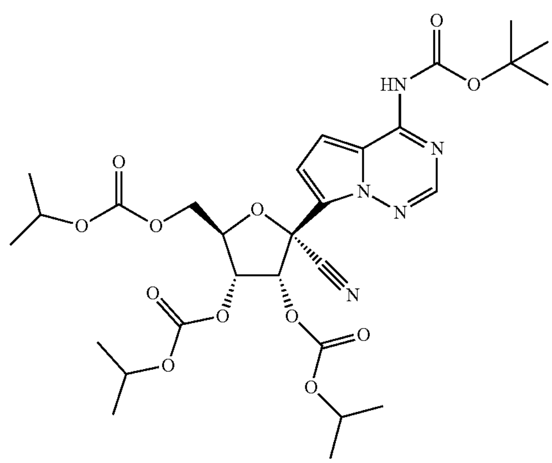 [SMILES: CC(C)OC(=O)OC[C@H]1O[C@@](C#N)(c2ccc3c(NC(=O)OC(C)(C)C)ncnn23)[C@H](OC(=O)OC(C)C)[C@@H]1OC(=O)OC(C)C] |
| Example 59 | 81 | 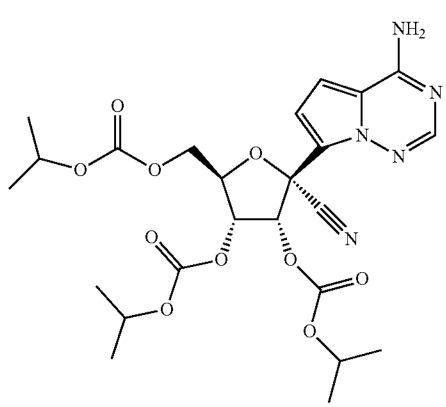 [SMILES: CC(C)OC(=O)OC[C@H]1O[C@@](C#N)(c2ccc3c(N)ncnn23)[C@H](OC(=O)OC(C)C)[C@@H]1OC(=O)OC(C)C] |

-continued

| Example No. | Compound No. | Structure |
|---|---|---|
| Example 60 | 82 | 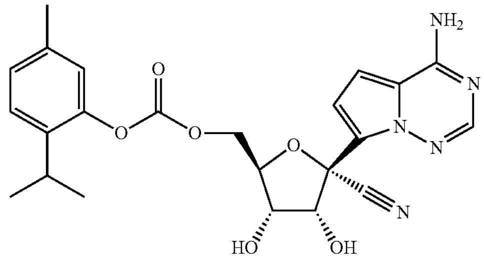 [SMILES: Cc1ccc(C(C)C)c(OC(=O)OC[C@H]2O[C@@](C#N)(c3ccc4c(N)ncnn34)[C@H](O)[C@@H]2O)c1] |
| Example 61 | 83 | 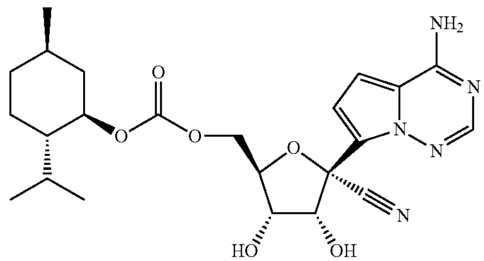 [SMILES: CC(C)[C@@H]1CC[C@@H](C)C[C@H]1OC(=O)OC[C@H]1O[C@@](C#N)(c2ccc3c(N)ncnn23)[C@H](O)[C@@H]1O] |
| Example 62 | 84 | 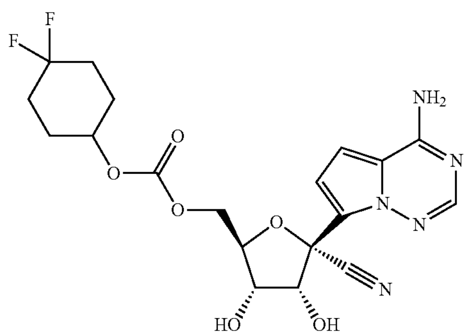 [SMILES: N#C[C@@]1(c2ccc3c(N)ncnn23)O[C@H](COC(=O)OC2CCC(F)(F)CC2)[C@@H](O)[C@H]1O] |
| Example 63 | 85 | 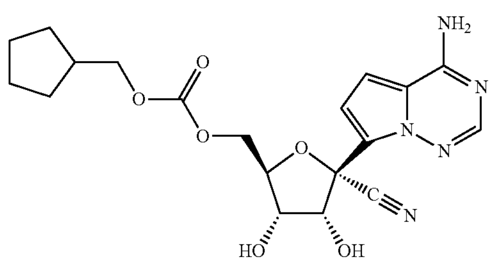 [SMILES: N#C[C@@]1(c2ccc3c(N)ncnn23)O[C@H](COC(=O)OCC2CCCC2)[C@@H](O)[C@H]1O] |
| Example 64 | 86 | 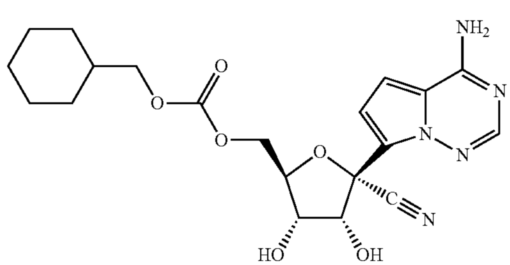 [SMILES: N#C[C@@]1(c2ccc3c(N)ncnn23)O[C@H](COC(=O)OCC2CCCCC2)[C@@H](O)[C@H]1O] |

-continued

| Example No. | Compound No. | Structure |
|---|---|---|
| Example 65 | 87 | 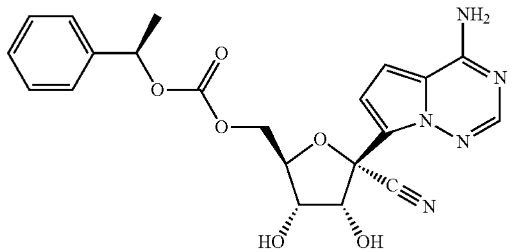 [SMILES: C[C@@H](OC(=O)OC[C@H]1O[C@@](C#N)(c2ccc3c(N)ncnn23)[C@H](O)[C@@H]1O)c1ccccc1] |
| Example 66 | 88 | 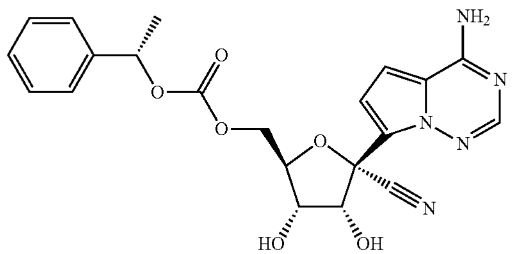 [SMILES: C[C@H](OC(=O)OC[C@H]1O[C@@](C#N)(c2ccc3c(N)ncnn23)[C@H](O)[C@@H]1O)c1ccccc1] |
| Example 67 | 89 | 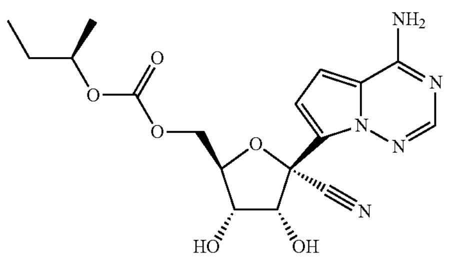 [SMILES: CC[C@@H](C)OC(=O)OC[C@H]1O[C@@](C#N)(c2ccc3c(N)ncnn23)[C@H](O)[C@@H]1O] |
| Example 68 | 90 | 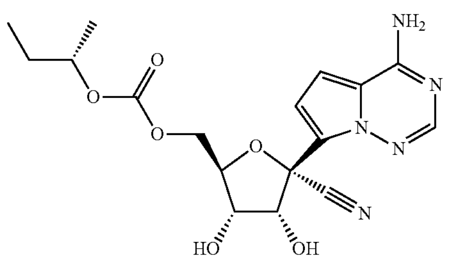 [SMILES: CC[C@H](C)OC(=O)OC[C@H]1O[C@@](C#N)(c2ccc3c(N)ncnn23)[C@H](O)[C@@H]1O] |
| Example 69 | 91 | 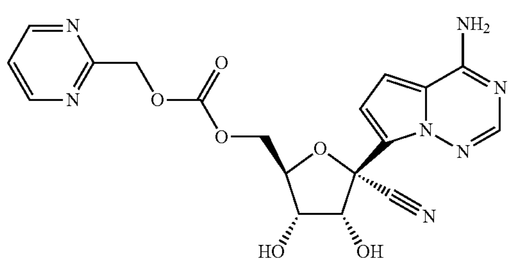 [SMILES: N#C[C@@]1(c2ccc3c(N)ncnn23)O[C@H](COC(=O)OCc2ncccn2)[C@@H](O)[C@H]1O] |
| Example 70 | 92 | 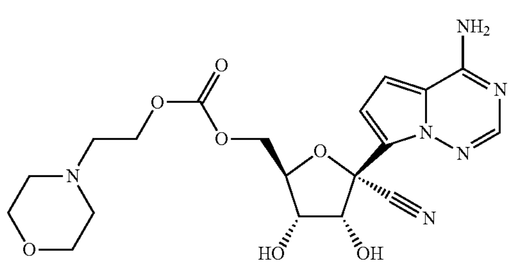 [SMILES: N#C[C@@]1(c2ccc3c(N)ncnn23)O[C@H](COC(=O)OCCN2CCOCC2)[C@@H](O)[C@H]1O] |

-continued
| Example No. | Compound No. | Structure |
|---|---|---|
| Example 71 | 93 | 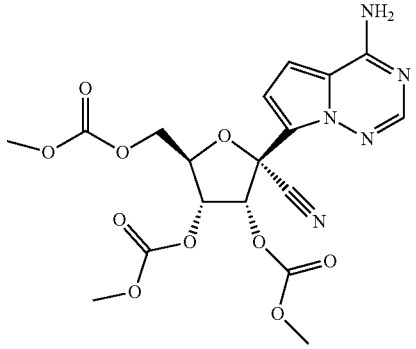 [SMILES: COC(=O)OC[C@H]1O[C@@](C#N)(c2ccc3c(N)ncnn23)[C@H](OC(=O)OC)[C@@H]1OC(=O)OC] |
| Example 73 | 94 | 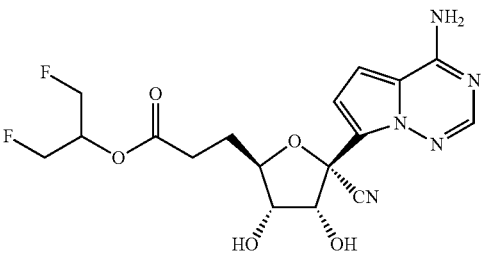 [SMILES: N#C[C@@]1(c2ccc3c(N)ncnn23)O[C@H](CCC(=O)OC(CF)CF)[C@@H](O)[C@H]1O] |
| Example 75 | 96 | 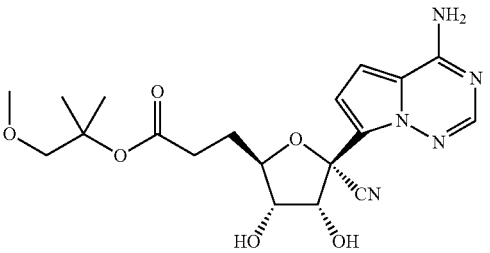 [SMILES: COCC(C)(C)OC(=O)CC[C@H]1O[C@@](C#N)(c2ccc3c(N)ncnn23)[C@H](O)[C@@H]1O] |
| Example 76 | 97 | 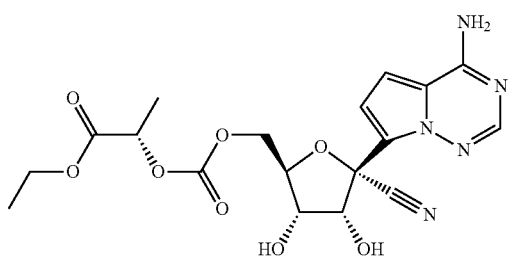 [SMILES: CCOC(=O)[C@H](C)OC(=O)OC[C@H]1O[C@@](C#N)(c2ccc3c(N)ncnn23)[C@H](O)[C@@H]1O] |
| Example 77 | 98 | 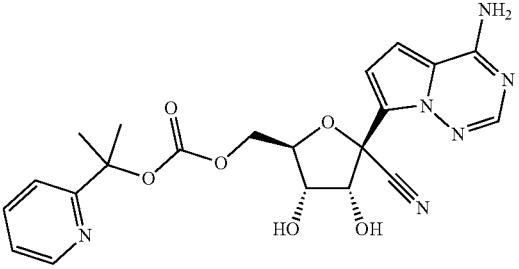 [SMILES: CC(C)(OC(=O)OC[C@H]1O[C@@](C#N)(c2ccc3c(N)ncnn23)[C@H](O)[C@@H]1O)c1ccccn1] |

| Example No. | Compound No. | Structure |
|---|---|---|
| Example 78 | 99 | 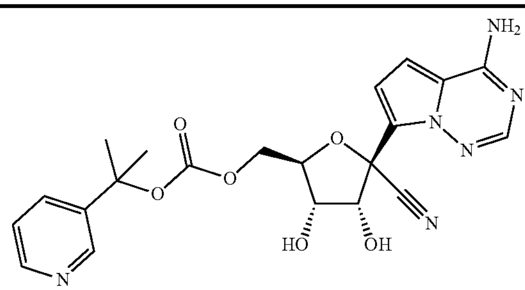 |
| Example 79 | 100 | | or a pharmaceutically acceptable salt thereof.

In some embodiments, the compound of Formula I is

| Example No. | Compound No. | Structure |
|---|---|---|
| Example 93 | 101 | 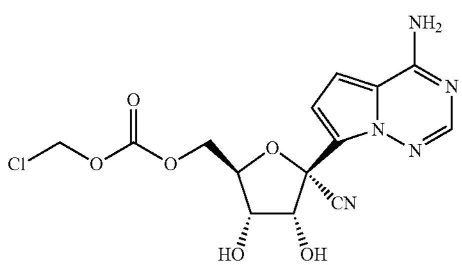 [SMILES: N#C[C@@]1(c2ccc3c(N)ncnn23)O[C@H](COC(=O)OCCl)[C@@H](O)[C@H]1O] |
| | 102 | |

-continued
| Example No. | Compound No. | Structure |
|---|---|---|
| Example 96 | 103 | 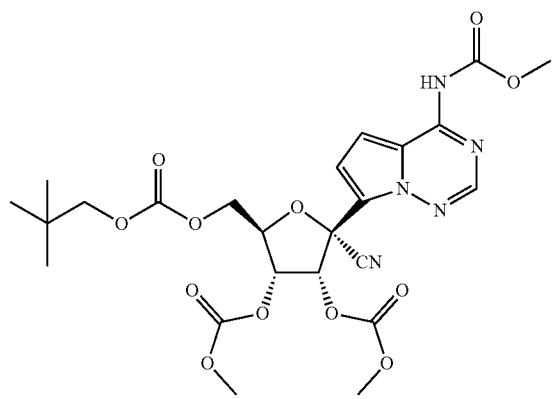 [SMILES: COC(=O)Nc1ncnn2c([C@]3(C#N)O[C@H](COC(=O)OCC(C)(C)C)[C@@H](OC(=O)OC)[C@H]3OC(=O)OC)ccc12] |
|  | 104 | 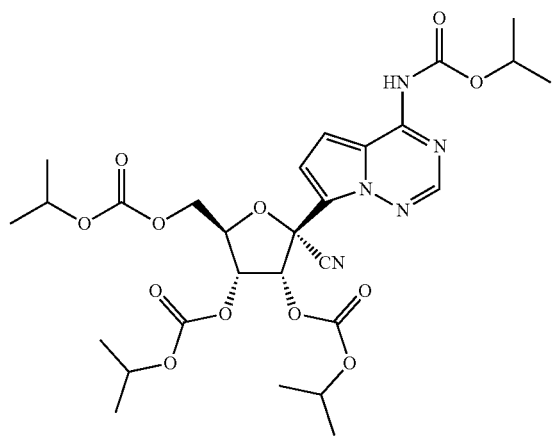 [SMILES: CC(C)OC(=O)Nc1ncnn2c([C@]3(C#N)O[C@H](COC(=O)OC(C)C)[C@@H](OC(=O)OC(C)C)[C@H]3OC(=O)OC(C)C)ccc12] |
|  | 105 | 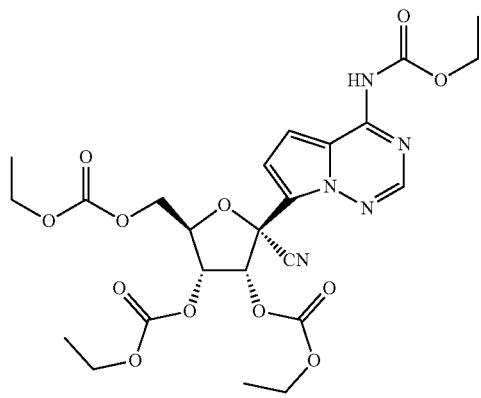 [SMILES: CCOC(=O)Nc1ncnn2c([C@]3(C#N)O[C@H](COC(=O)OCC)[C@@H](OC(=O)OCC)[C@H]3OC(=O)OCC)ccc12] |
| Example 92 | 106 | 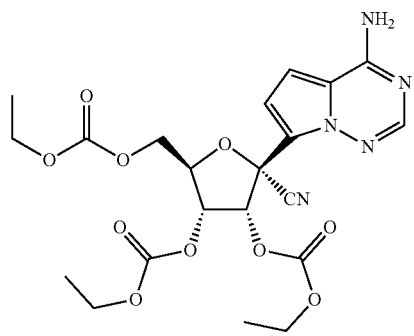 [SMILES: CCOC(=O)OC[C@H]1O[C@@](C#N)(c2ccc3c(N)ncnn23)[C@H](OC(=O)OCC)[C@@H]1OC(=O)OCC] |

| Example No. | Compound No. | Structure |
|---|---|---|
| Example 97 | 107 | 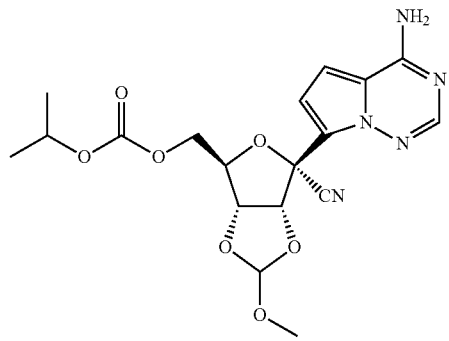 |
| | 108 | 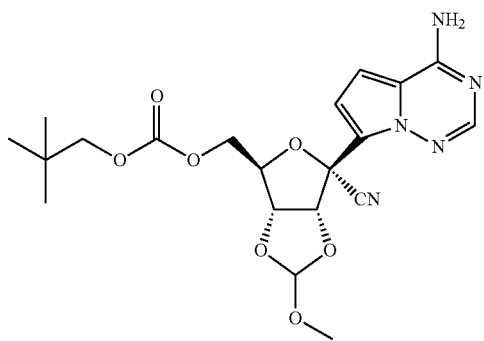 |
| | 109 | 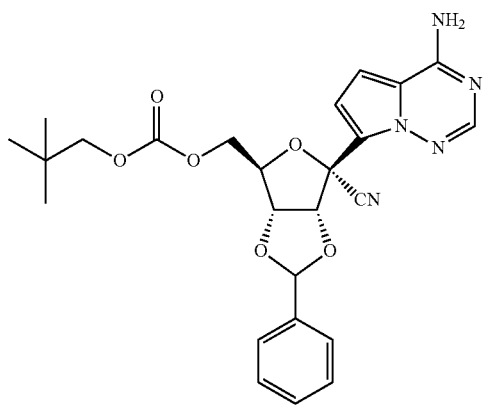 |
| Example 94 | 110 | 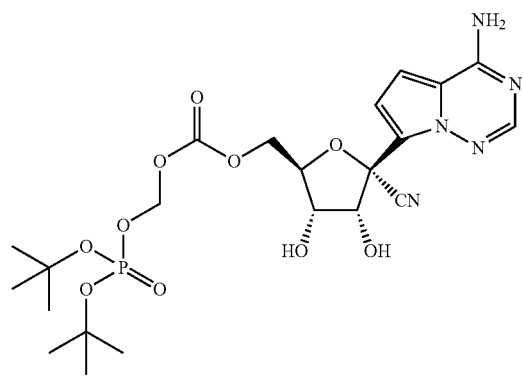 [SMILES: CC(C)(C)OP(=O)(OCOC(=O)OC[C@H]1O[C@@](C#N)(c2ccc3c(N)ncnn23)[C@H](O)[C@@H]1O)OC(C)(C)C] |

-continued

| Example No. | Compound No. | Structure |
|---|---|---|
| Example 109 | 111 | 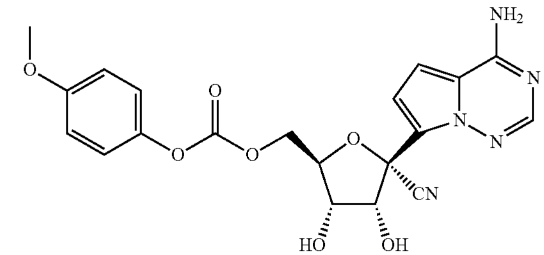 [SMILES: COc1ccc(OC(=O)OC[C@H]2O[C@@](C#N)(c3ccc4c(N)ncnn34)[C@H](O)[C@@H]2O)cc1] |
| Example 101 | 112 | 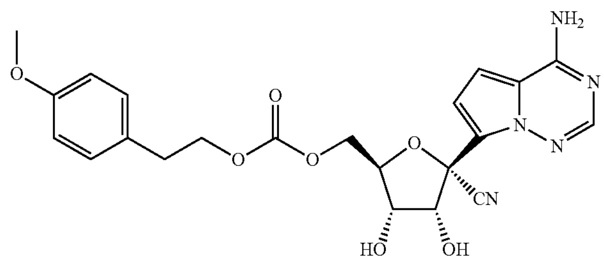 [SMILES: COc1ccc(CCOC(=O)OC[C@H]2O[C@@](C#N)(c3ccc4c(N)ncnn34)[C@H](O)[C@@H]2O)cc1] |
| Example 102 | 114 | 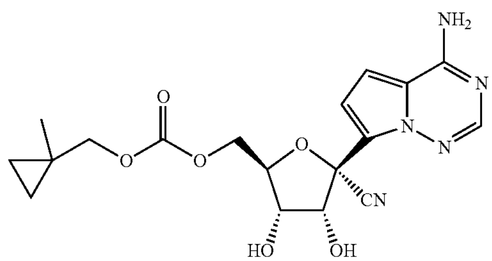 [SMILES: CC1(COC(=O)OC[C@H]2O[C@@](C#N)(c3ccc4c(N)ncnn34)[C@H](O)[C@@H]2O)CC1] |
| Example 103 | 115 | 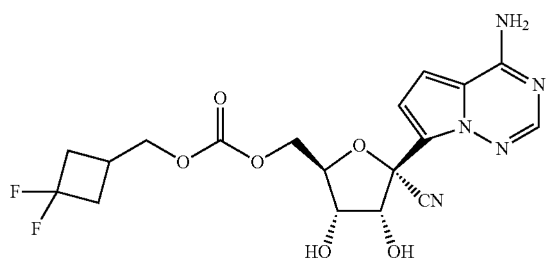 [SMILES: N#C[C@@]1(c2ccc3c(N)ncnn23)O[C@H](COC(=O)OCC2CC(F)(F)C2)[C@@H](O)[C@H]1O] |
| Example 104 | 116 | 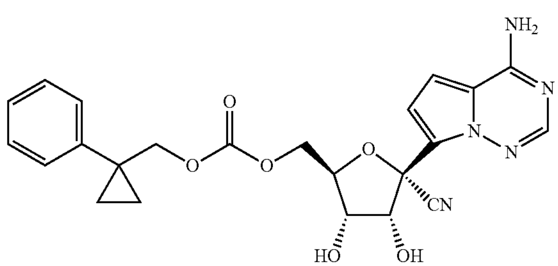 [SMILES: N#C[C@@]1(c2ccc3c(N)ncnn23)O[C@H](COC(=O)OCC2(c3ccccc3)CC2)[C@@H](O)[C@H]1O] |
| Example 105 | 117 | 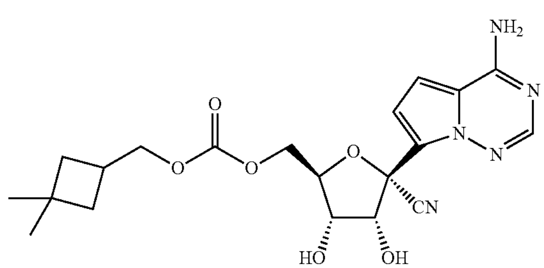 [SMILES: CC1(C)CC(COC(=O)OC[C@H]2O[C@@](C#N)(c3ccc4c(N)ncnn34)[C@H](O)[C@@H]2O)C1] |

-continued
| Example No. | Compound No. | Structure |
| --- | --- | --- |
| Example 106 | 118 | 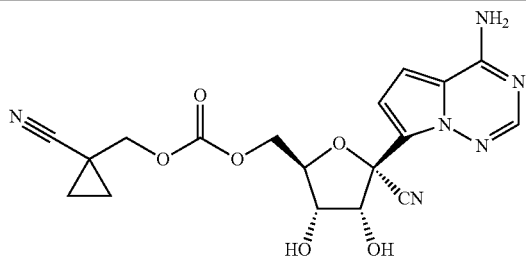 [SMILES: N#CC1(COC(=O)OC[C@H]2O[C@@](C#N)(c3ccc4c(N)ncnn34)[C@H](O)[C@@H]2O)CC1] |
| Example 107 | 119 | 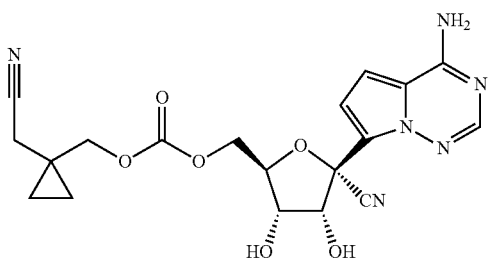 [SMILES: N#CCC1(COC(=O)OC[C@H]2O[C@@](C#N)(c3ccc4c(N)ncnn34)[C@H](O)[C@@H]2O)CC1] |
| Example 99 | 120 | 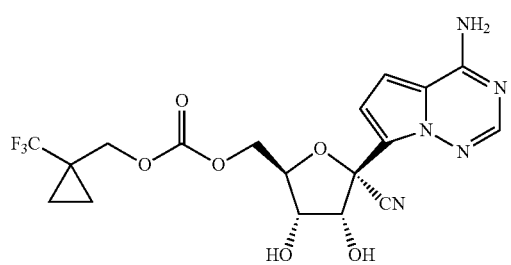 [SMILES: N#C[C@@]1(c2ccc3c(N)ncnn23)O[C@H](COC(=O)OCC2(C(F)(F)F)CC2)[C@@H](O)[C@H]1O] |
| Example 100 | 121 | 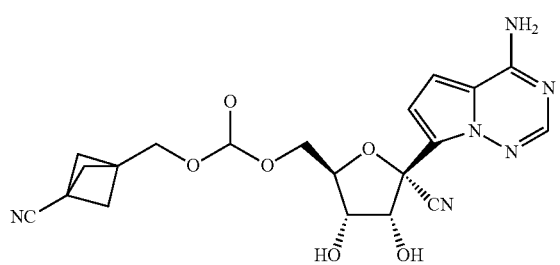 [SMILES: N#CC12CC(COC(O)OC[C@H]3O[C@@](C#N)(c4ccc5c(N)ncnn45)[C@H](O)[C@@H]3O)(C1)C2] |
| Example 108 | 122 | 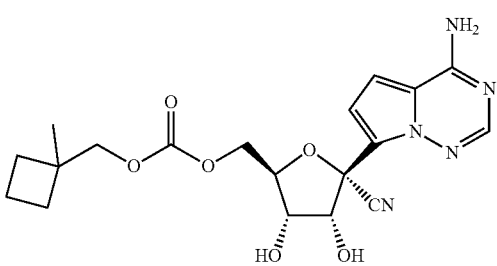 [SMILES: CC1(COC(=O)OC[C@H]2O[C@@](C#N)(c3ccc4c(N)ncnn34)[C@H](O)[C@@H]2O)CCC1] |
| Example 109 | 123 | 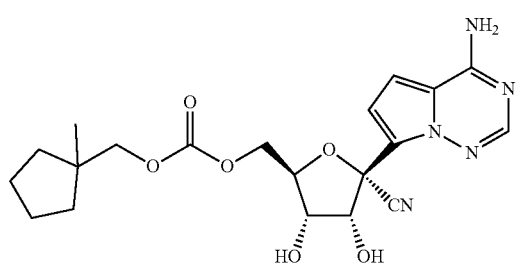 [SMILES: CC1(COC(=O)OC[C@H]2O[C@@](C#N)(c3ccc4c(N)ncnn34)[C@H](O)[C@@H]2O)CCCC1] |

| Example No. | Compound No. | Structure |
| --- | --- | --- |
| Example 113 | 124 | 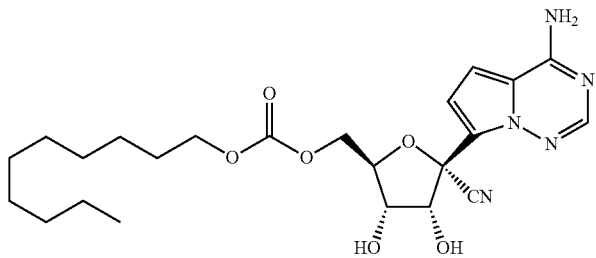 [SMILES: CCCCCCCCCCOC(=O)OC[C@H]1O[C@@](C#N)(c2ccc3c(N)ncnn23)[C@H](O)[C@@H]1O] |
| Example 98 | 125 | 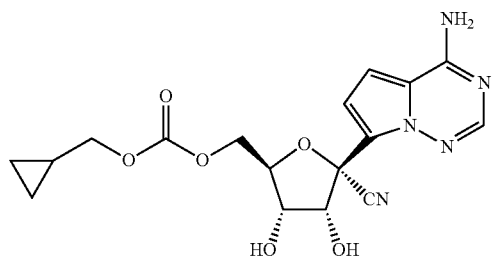 [SMILES: N#C[C@@]1(c2ccc3c(N)ncnn23)O[C@H](COC(=O)OCC2CC2)[C@@H](O)[C@H]1O] |
| Example 114 | 126 | 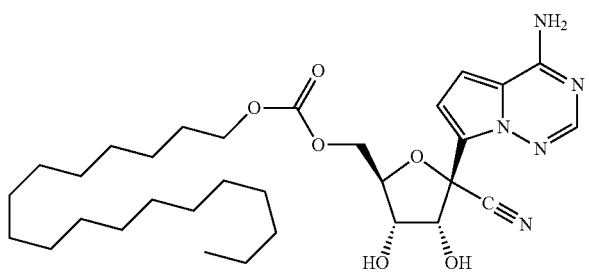 [SMILES: CCCCCCCCCCCCCCCCCCOC(=O)OC[C@H]1O[C@@](C#N)(c2ccc3c(N)ncnn23)[C@H](O)[C@@H]1O] |
or a pharmaceutically acceptable salt thereof.
  In some embodiments, the compound of Formula I is
| Example No. | Compound No. | Structure |
| --- | --- | --- |
| Example 82 | 127 | 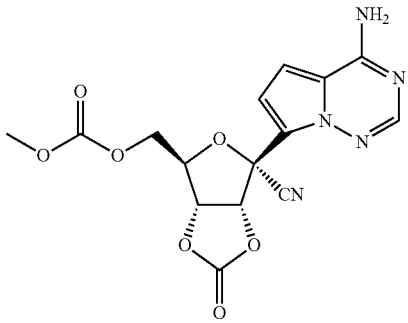 [SMILES: COC(=O)OC[C@H]1O[C@@](C#N)(c2ccc3c(N)ncnn23)[C@@H]2OC(=O)O[C@@H]21] |
| Example 83 | 128 | 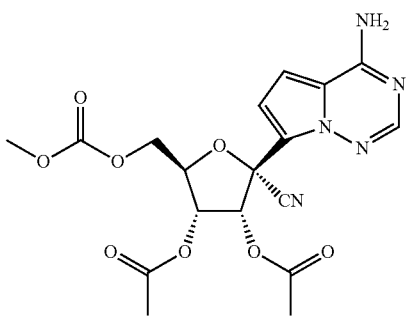 [SMILES: COC(=O)OC[C@H]1O[C@@](C#N)(c2ccc3c(N)ncnn23)[C@H](OC(C)=O)[C@@H]1OC(C)=O] |

| Example No. | Compound No. | Structure |
|---|---|---|
| Example 84 | 129 | 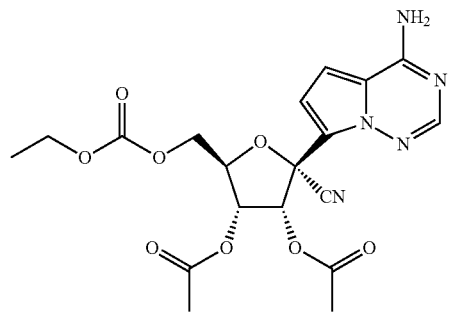 [SMILES: CCOC(=O)OC[C@H]1O[C@@](C#N)(c2ccc3c(N)ncnn23)[C@H](OC(C)=O)[C@@H]1OC(C)=O] |
| Example 85 | 130 | 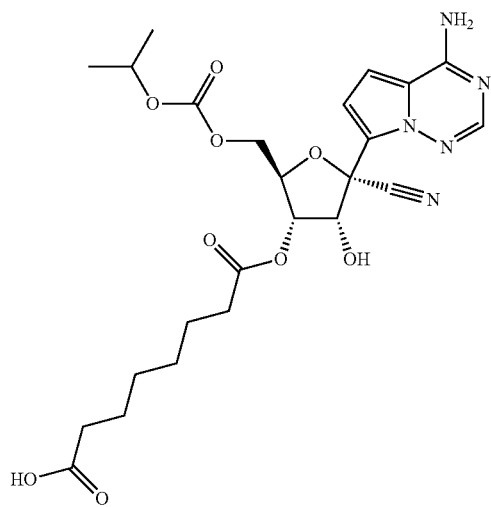 [SMILES: CC(C)OC(=O)OC[C@H]1O[C@@](C#N)(c2ccc3c(N)ncnn23)[C@H](O)[C@@H]1OC(=O)CCCCCCC(=O)O] |
| Example 86 | 131 | 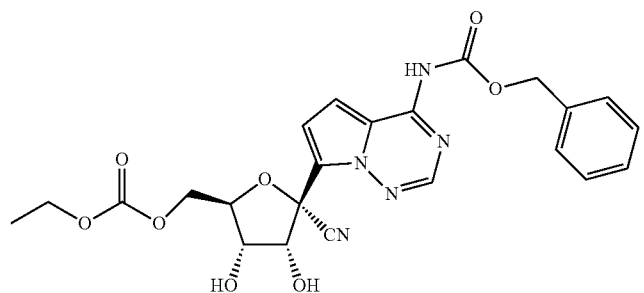 [SMILES: CCOC(=O)OC[C@H]1O[C@@](C#N)(c2ccc3c(NC(=O)OCc4ccccc4)ncnn23)[C@H](O)[C@@H]1O] |
| Example 87 | 132 | 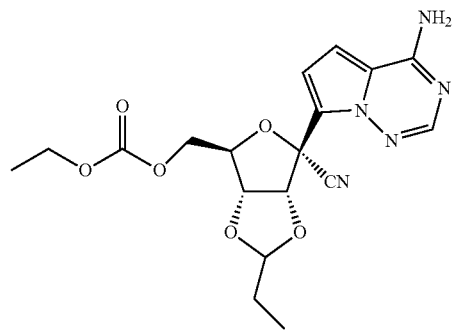 |

| Example No. | Compound No. | Structure |
|---|---|---|
| Example 88 | 133 | 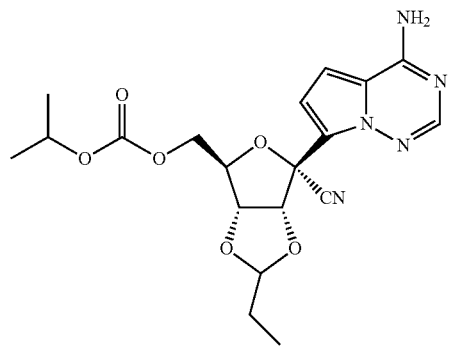 |
| Example 89 | 134 | 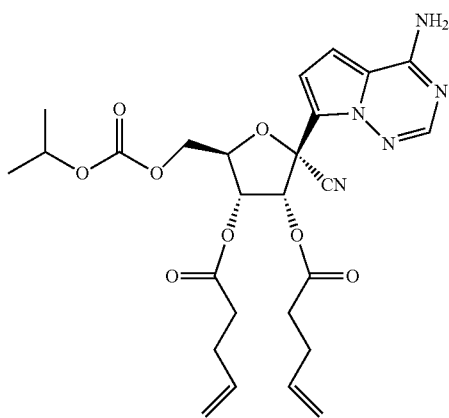 [SMILES: C=CCCC(=O)O[C@H]1[C@@H](OC(=O)CCC=C)[C@](C#N)(c2ccc3c(N)ncnn23)O[C@@H]1COC(=O)OC(C)C] |
| Example 90 | 135 | 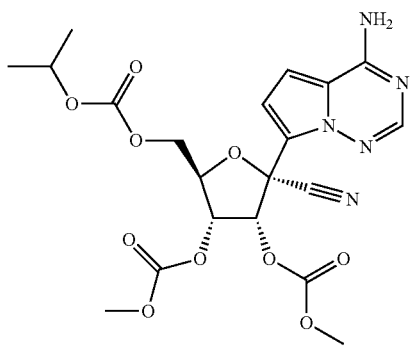 [SMILES: COC(=O)O[C@H]1[C@@H](OC(=O)OC)[C@](C#N)(c2ccc3c(N)ncnn23)O[C@@H]1COC(=O)OC(C)C] |

| Example No. | Compound No. | Structure |
|---|---|---|
| Example 91 | 136 | 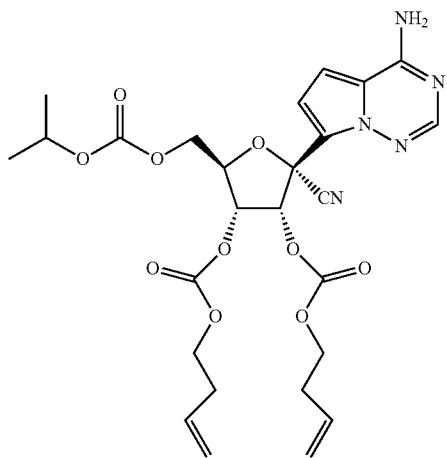 [SMILES: C=CCCOC(=O)O[C@H]1[C@@H](OC(=O)OCCC=C)[C@](C#N)(c2ccc3c(N)ncnn23)O[C@@H]1COC(=O)OC(C)C] |
or a pharmaceutically acceptable salt thereof.
In some embodiments, the compound of Formula I is
| Example No. | Compound No. | Structure |
|---|---|---|
| Example 110 | 137 | 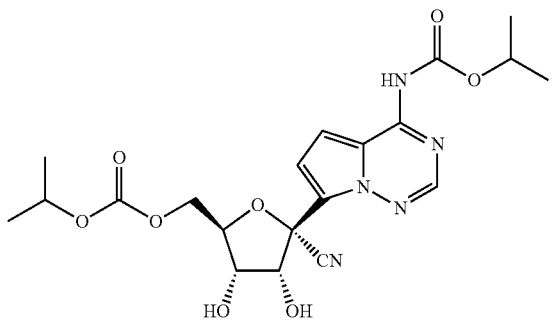 [SMILES: CC(C)OC(=O)Nc1ncnn2c([C@]3(C#N)O[C@H](COC(=O)OC(C)C)[C@@H](O)[C@H]3O)ccc12] |
| Example 111 | 138 | 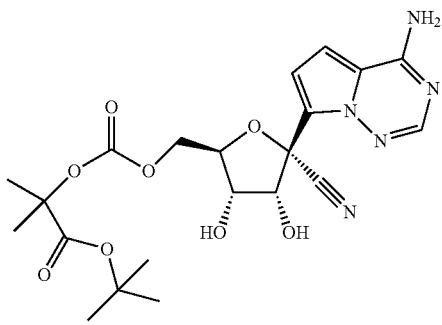 [SMILES: CC(C)(C)OC(=O)C(C)(C)OC(=O)OC[C@H]1O[C@@](C#N)(c2ccc3c(N)ncnn23)[C@H](O)[C@@H]1O] |
| Example 112 | 139 | 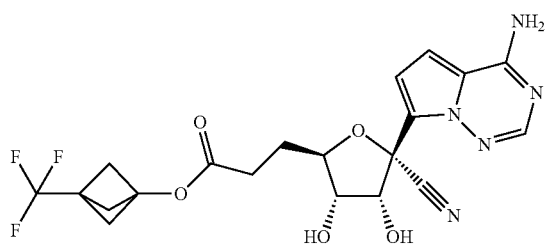 [SMILES: N#C[C@@]1(c2ccc3c(N)ncnn23)O[C@H](CCC(=O)OC23CC(C(F)(F)F)(C2)C3)[C@@H](O)[C@H]1O] |

| Example No. | Compound No. | Structure |
|---|---|---|
| Example 115 | 140 | 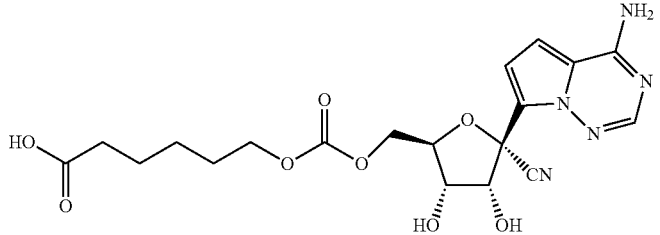 [SMILES: N#C[C@@]1(c2ccc3c(N)ncnn23)O[C@H](COC(=O)OCCCCCC(=O)O)[C@@H](O)[C@H]1O] |
| Example 116 | 141 | 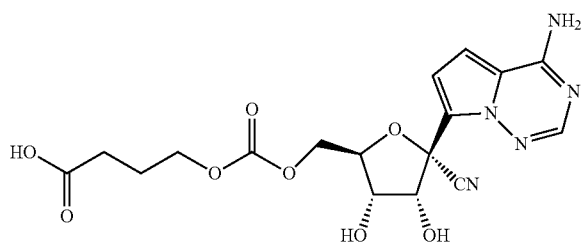 [SMILES: N#C[C@@]1(c2ccc3c(N)ncnn23)O[C@H](COC(=O)OCCCC(=O)O)[C@@H](O)[C@H]1O] |
| Example 117 | 142 | 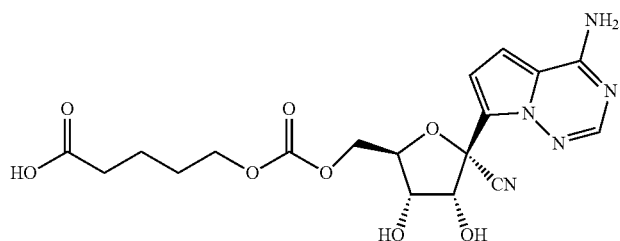 [SMILES: N#C[C@@]1(c2ccc3c(N)ncnn23)O[C@H](COC(=O)OCCCCC(=O)O)[C@@H](O)[C@H]1O] |
| Example 118 | 143 | 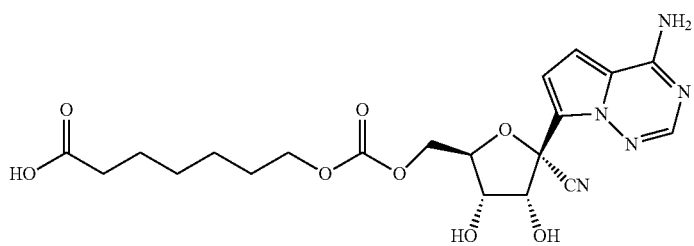 [SMILES: N#C[C@@]1(c2ccc3c(N)ncnn23)O[C@H](COC(=O)OCCCCCCC(=O)O)[C@@H](O)[C@H]1O] |
| Example 119 | 144 | 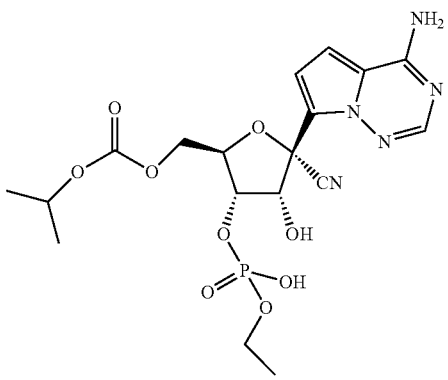 [SMILES: CCOP(=O)(O)O[C@H]1[C@@H](O)[C@](C#N)(c2ccc3c(N)ncnn23)O[C@@H]1COC(=O)OC(C)C] |

-continued
| Example No. | Compound No. | Structure |
|---|---|---|
| Example 120 | 145 | 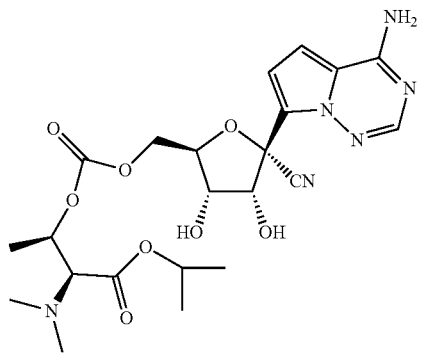 [SMILES: CC(C)OC(=O)[C@H]([C@@H](C)OC(=O)OC[C@H]1O[C@@](C#N)(c2ccc3c(N)ncnn23)[C@H](O)[C@@H]1O)N(C)C] |
| Example 121 | 146 | 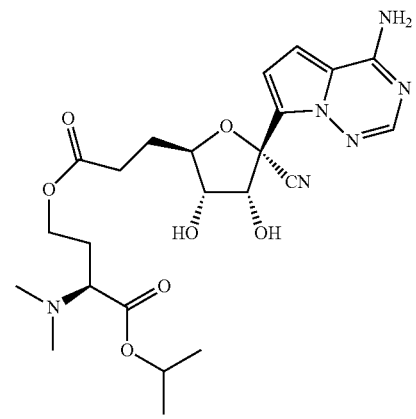 [SMILES: CC(C)OC(=O)[C@H](CCOC(=O)CC[C@H]1O[C@@](C#N)(c2ccc3c(N)ncnn23)[C@H](O)[C@@H]1O)N(C)C] |
| Example 122 | 147 | 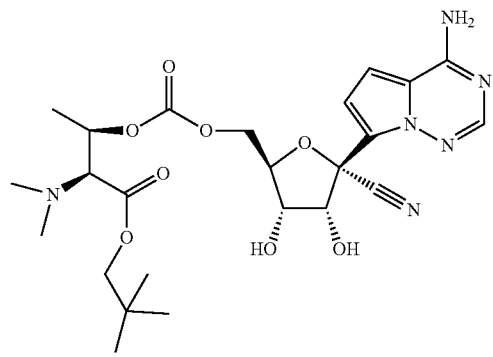 [SMILES: C[C@@H](OC(=O)OC[C@H]1O[C@@](C#N)(c2ccc3c(N)ncnn23)[C@H](O)[C@@H]1O)[C@@H](C(=O)OCC(C)(C)C)N(C)C] |
| Example 123 | 148 | 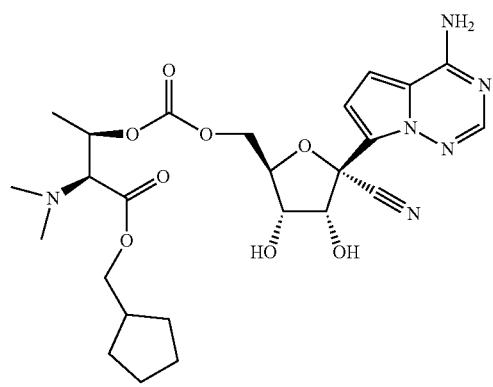 [SMILES: C[C@@H](OC(=O)OC[C@H]1O[C@@](C#N)(c2ccc3c(N)ncnn23)[C@H](O)[C@@H]1O)[C@@H](C(=O)OCC1CCCC1)N(C)C] |

-continued
| Example No. | Compound No. | Structure |
|---|---|---|
| Example 124 | 149 | 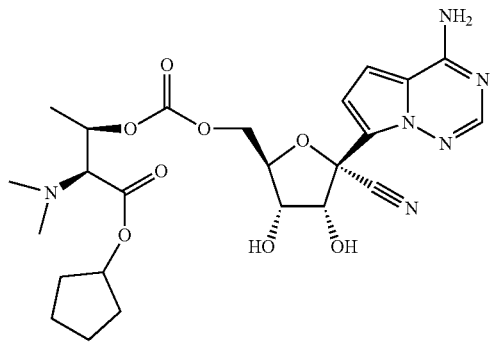 [SMILES: C[C@@H](OC(=O)OC[C@H]1O[C@@](C#N)(c2ccc3c(N)ncnn23)[C@H](O)[C@@H]1O)[C@@H](C(=O)OC1CCCC1)N(C)C] |
| Example 125 | 150 | 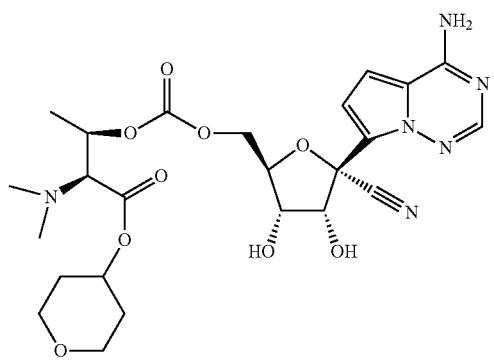 [SMILES: C[C@@H](OC(=O)OC[C@H]1O[C@@](C#N)(c2ccc3c(N)ncnn23)[C@H](O)[C@@H]1O)[C@@H](C(=O)OC1CCOCC1)N(C)C] |
| Example 126 | 151 | 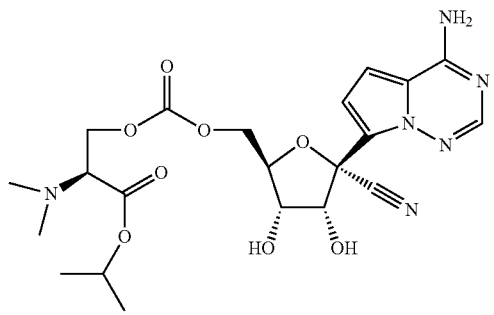 [SMILES: CC(C)OC(=O)[C@H](COC(=O)OC[C@H]1O[C@@](C#N)(c2ccc3c(N)ncnn23)[C@H](O)[C@@H]1O)N(C)C] |
| Example 127 | 152 | 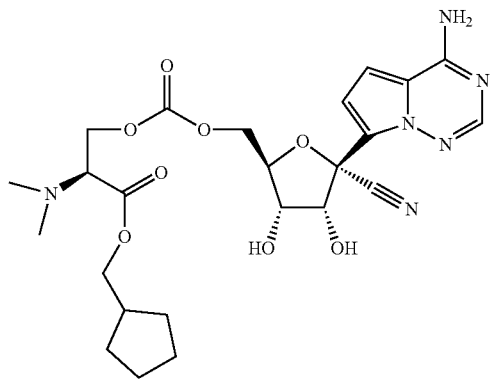 [SMILES: CN(C)[C@@H](COC(=O)OC[C@H]1O[C@@](C#N)(c2ccc3c(N)ncnn23)[C@H](O)[C@@H]1O)C(=O)OCC1CCCC1] |

| Example No. | Compound No. | Structure |
|---|---|---|
| Example 128 | 153 | 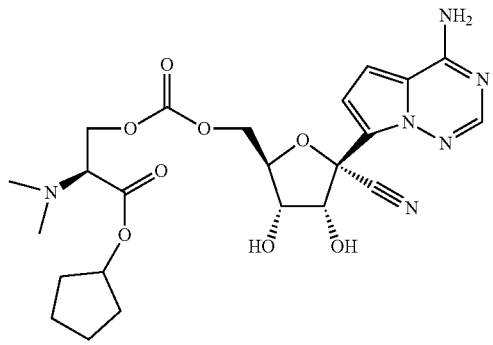 [SMILES: CN(C)[C@@H](COC(=O)OC[C@H]1O[C@@](C#N)(c2ccc3c(N)ncnn23)[C@H](O)[C@@H]1O)C(=O)OC1CCCC1] |
| Example 131 | 154 | 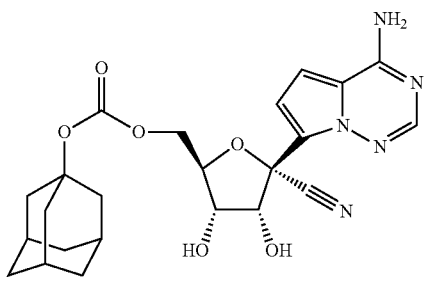 [SMILES: N#C[C@@]1(c2ccc3c(N)ncnn23)O[C@H](COC(=O)OC23CC4CC(CC(C4)C2)C3)[C@@H](O)[C@H]1O] |
| Example 132 | 155 | 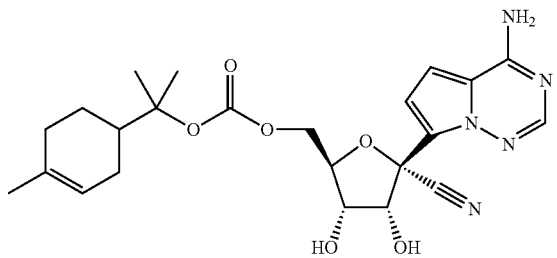 [SMILES: CC1=CCC(C(C)(C)OC(=O)OC[C@H]2O[C@@](C#N)(c3ccc4c(N)ncnn34)[C@H](O)[C@@H]2O)CC1] |
| Example 133 | 156 | 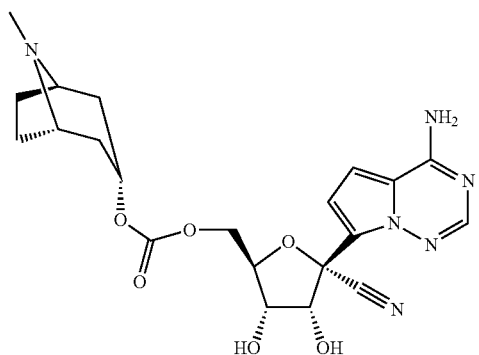 [SMILES: CN1[C@@H]2CC[C@H]1C[C@@H](OC(=O)OC[C@H]1O[C@@](C#N)(c3ccc4c(N)ncnn34)[C@H](O)[C@@H]1O)C2] | or a pharmaceutically acceptable salt thereof.

V. Pharmaceutical Formulations

The compounds disclosed herein may be formulated with conventional carriers and excipients. For example, tablets will contain excipients, glidants, fillers, binders and the like. Aqueous formulations are prepared in sterile form, and when intended for delivery by other than oral administration generally will be isotonic. All formulations may optionally comprise excipients such as those set forth in the "Handbook of Pharmaceutical Excipients" (1986). Pharmaceutically acceptable excipients include ascorbic acid and other anti-oxidants, chelating agents such as EDTA, carbohydrates such as dextran, hydroxyalkylcellulose, hydroxyalkylmethylcellulose, stearic acid and the like. In some embodiments, the formulations comprise one or more pharmaceutically acceptable excipients. The pH of the formulations ranges from about 3 to about 11, but is ordinarily about 7 to 10. In some embodiments, the pH of the formulations ranges from about 2 to about 5, but is ordinarily about 3 to 4.

While it is possible for the compounds of the disclosure ("the active ingredients") to be administered alone it may be preferable to present them as pharmaceutical formulations. The formulations, both for veterinary and for human use, of the invention comprise at least one active ingredient, as above defined, together with one or more acceptable carriers therefor and optionally other therapeutic ingredients, particularly those additional therapeutic ingredients as discussed herein. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any appropriate method known in the art of pharmacy. Techniques and formulations generally are found in Remington's Pharmaceutical Sciences (Mack Publishing Co., Easton, PA). Such methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then, if necessary, shaping the product.

In some embodiments, the pharmaceutical formulation is for subcutaneous, intramuscular, intravenous, oral, or inhalation administration.

In some embodiments, the compound described herein e.g., the compound of Formula I, or the pharmaceutically acceptable salt thereof, described herein have optimized/improved pharmacokinetic properties and are amenable to oral administration. For example, the compounds of Formula I have improved bioavailability and can therefore be administered by oral administration.

In some embodiments, the formulations of the present invention are suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

In some embodiments, the tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

For infections of the eye or other external tissues, e.g., mouth and skin, the formulations are applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate. Further emulgents and emulsion stabilizers suitable for use in the formulation of the invention include Tween® 80.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations according to the present invention comprise a compound according to the invention together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared.

Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcellulose, sodium alginate, polyvinylpyrrolidone, gum tragacanth and gum acacia, and dispersing or wetting agents such as a naturally-occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin. Further non-limiting examples of suspending agents include Cyclodextrin. In some examples, the suspending agent is Sulfobutyl ether beta-cyclodextrin (SEB-beta-CD), for example Captisol®.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally-occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water. Ringer's solution and isotonic sodium chloride solution. In addition, sterile fixed oils may conventionally be employed as a solvent or suspending medium. For this purpose, any bland fixed oil may be employed including synthetic mono- or diglycerides. In addition, fatty acids such as oleic acid may likewise be used in the preparation of injectables. Among the acceptable vehicles and solvents that may be employed are water, Ringer's solution isotonic sodium chloride solution, and hypertonic sodium chloride solution.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 mg of the active ingredient per milliliter of solution in order that infusion of a suitable volume at a rate of about 30 mL/hr can occur.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10%, and particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia, and mouthwashes comprising the active ingredient in a suitable liquid carrier.

Formulations for rectal administration may be presented as a suppository with a suitable base comprising for example cocoa butter or a salicylate.

In some embodiments, the compounds disclosed herein are administered by inhalation. In some embodiments, formulations suitable for intrapulmonary or nasal administration have a particle size for example in the range of 0.1 to 500 microns, such as 0.5, 1, 30, 35 etc., which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents. In some embodiments, the compounds used herein are formulated and dosed as dry powder. In some embodiments, the compounds used herein are formulated and dosed as a nebulized formulation. In some embodiments, the compounds used herein are formulated for delivery by a face mask. In some embodiments, the compounds used herein are formulated for delivery by a face tent.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier therefor.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention are used to provide controlled release pharmaceutical formulations containing as active ingredient one or more compounds of the invention ("controlled release formulations") in which the release of the active ingredient are controlled and regulated to allow less frequency dosing or to improve the pharmacokinetic or toxicity profile of a given active ingredient.

VI. Kits

Also provided herein are kits that includes a compound disclosed herein, a pharmaceutically acceptable salt, stereoisomer, mixture of stereoisomers or tautomer thereof. In some embodiments the kits described herein may comprise a label and/or instructions for use of the compound in the treatment of a disease or condition in a subject (e.g., human) in need thereof. In some embodiments, the disease or condition is viral infection.

In some embodiments, the kit may also comprise one or more additional therapeutic agents and/or instructions for use of additional therapeutic agents in combination with the compound of Formula I in the treatment of the disease or condition in a subject (e.g., human) in need thereof.

In some embodiments, the kits provided herein comprises individual dose units of a compound as described herein, or a pharmaceutically acceptable salt, racemate, enantiomer, diastereomer, tautomer, polymorph, pseudopolymorph, amorphous form, hydrate or solvate thereof. Examples of individual dosage units may include pills, tablets, capsules, prefilled syringes or syringe cartridges, IV bags, inhalers, nebulizers etc., each comprising a therapeutically effective amount of the compound in question, or a pharmaceutically acceptable salt, racemate, enantiomer, diastereomer, tautomer, polymorph, pseudopolymorph, amorphous form, hydrate or solvate thereof. In some embodiments, the kit may contain a single dosage unit and in others, multiple dosage units are present, such as the number of dosage units required for a specified regimen or period.

Also provided are articles of manufacture that include a compound of Formula I, or a pharmaceutically acceptable salt, stereoisomer, mixture of stereoisomers or tautomer thereof, and a container. In some embodiments, the container of the article of manufacture is a vial, jar, ampoule, preloaded syringe, blister package, tin, can, bottle, box, an intravenous bag, an inhaler, or a nebulizer.

VII. Administration

One or more compounds of the invention are administered by any route appropriate to the condition to be treated. Suitable routes include oral, rectal, inhalation, pulmonary, topical (including buccal and sublingual), vaginal and parenteral (including subcutaneous, intramuscular, intravenous, intradermal, intrathecal and epidural), and the like. In some embodiments, the compounds disclosed herein are administered by inhalation or intravenously. In some embodiments, the compounds disclosed herein are administered orally. It will be appreciated that the preferred route may vary with for example the condition of the recipient.

In the methods of the present invention for the treatment of a viral infection, the compounds of the present invention can be administered at any time to a human who may come into contact with the virus or is already suffering from the viral infection. In some embodiments, the compounds of the present invention can be administered prophylactically to humans coming into contact with humans suffering from the viral infection or at risk of coming into contact with humans suffering from the viral infection, e.g., healthcare providers. In some embodiments, administration of the compounds of the present invention can be to humans testing positive for the viral infection but not yet showing symptoms of the viral infection. In some embodiments, administration of the compounds of the present invention can be to humans upon commencement of symptoms of the viral infection.

In some embodiments, the methods disclosed herein comprise event driven administration of the compound described herein, e.g., the compound of Formula I, or a pharmaceutically acceptable salt thereof, to the subject.

As used herein, the terms "event driven" or "event driven administration" refer to administration of the compound described herein (e.g., the compound of Formula I), or a pharmaceutically acceptable salt thereof, (1) prior to an event (e.g., 2 hours, 1 day, 2 days, 5 day, or 7 or more days prior to the event) that would expose the individual to the virus (or that would otherwise increase the individual's risk of acquiring the viral infection); and/or (2) during an event (or more than one recurring event) that would expose the individual to the virus (or that would otherwise increase the individual's risk of acquiring the viral infection); and/or (3) after an event (or after the final event in a series of recurring events) that would expose the individual to the virus (or that would otherwise increase the individual's risk of acquiring the viral infection). In some embodiments, the event driven administration is performed pre-exposure of the subject to the virus. In some embodiments, the event driven administration is performed post-exposure of the subject to the virus.

In some embodiments, the event driven administration is performed pre-exposure of the subject to the virus and post-exposure of the subject to the virus.

In certain embodiments, the methods disclosed herein involve administration prior to and/or after an event that would expose the individual to the virus or that would otherwise increase the individual's risk of acquiring the viral infection, e.g., as pre-exposure prophylaxis (PrEP) and/or as post-exposure prophylaxis (PEP). In some embodiments, the methods disclosed herein comprise pre-exposure prophylaxis (PrEP). In some embodiments, methods disclosed herein comprise post-exposure prophylaxis (PEP).

In some embodiments, the compound of Formula I, or a pharmaceutically acceptable salt thereof, is administered before exposure of the subject to the virus.

In some embodiments, the compound of Formula I, or a pharmaceutically acceptable salt thereof, is administered before and after exposure of the subject to the virus.

In some embodiments, the compound of Formula I, or a pharmaceutically acceptable salt thereof, is administered after exposure of the subject to the virus.

An example of event driven dosing regimen includes administration of the compound of Formula I, or a pharmaceutically acceptable salt thereof, within 24 to 2 hours prior to the virus, followed by administration of the compound of Formula I, or a pharmaceutically acceptable salt, every 24 hours during the period of exposure, followed by a further administration of the compound of Formula I, or a pharmaceutically acceptable salt thereof, after the last exposure, and one last administration of the compound of Formula I, or a pharmaceutically acceptable salt thereof, 24 hours later.

A further example of an event driven dosing regimen includes administration of the compound of Formula I, or a pharmaceutically acceptable salt thereof, within 24 hours before the viral exposure, then daily administration during the period of exposure, followed by a last administration approximately 24 hours later after the last exposure (which may be an increased dose, such as a double dose).

The specific dose level of a compound of the present disclosure for any particular subject w % ill depend upon a variety of factors including the activity of the specific compound employed, the age, body weight, general health, sex, diet, time of administration, route of administration, and rate of excretion, drug combination and the severity of the particular disease in the subject undergoing therapy. For example, a dosage may be expressed as a number of milligrams of a compound described herein per kilogram of the subject's body weight (mg/kg). Dosages of between about 0.1 and 150 mg/kg may be appropriate. In some embodiments, about 0.1 and 100 mg/kg may be appropriate. In other embodiments a dosage of between 0.5 and 60 mg/kg may be appropriate. Normalizing according to the subject's body weight is particularly useful w % ben adjusting dosages between subjects of widely disparate size, such as occurs when using the drug in both children and adult humans or when converting an effective dosage in a non-human subject such as dog to a dosage suitable for a human subject.

The daily dosage may also be described as a total amount of a compound described herein administered per dose or per day. Daily dosage of a compound of Formula 1, or a pharmaceutically acceptable salt thereof, may be between about 1 mg and 4,000 mg, between about 2,000 to 4,000 mg/day, between about 1 to 2,000 mg/day, between about 1 to 1,000 mg/day, between about 10 to 500 mg/day, between about 20 to 500 mg/day, between about 50 to 300 mg/day, between about 75 to 200 mg/day, or between about 15 to 150 mg/day.

The dosage or dosing frequency of a compound of the present disclosure may be adjusted over the course of the treatment, based on the judgment of the administering physician.

The compounds of the present disclosure may be administered to an individual (e.g., a human) in a therapeutically effective amount. In some embodiments, the compound is administered once daily.

The compounds provided herein can be administered by any useful route and means, such as by oral or parenteral (e.g., intravenous) administration. Therapeutically effective amounts of the compound may include from about 0.00001 mg/kg body weight per day to about 10 mg/kg body weight per day, such as from about 0.0001 mg/kg body weight per day to about 10 mg/kg body weight per day, or such as from about 0.001 mg/kg body weight per day to about 1 mg/kg body weight per day, or such as from about 0.01 mg/kg body weight per day to about 1 mg/kg body weight per day, or such as from about 0.05 mg/kg body weight per day to about 0.5 mg/kg body weight per day. In some embodiments, a therapeutically effective amount of the compounds provided herein include from about 0.3 mg to about 30 mg per day, or from about 30 mg to about 300 mg per day, or from about 0.3 mg to about 30 mg per day, or from about 30 mg to about 300 mg per day.

A compound of the present disclosure may be combined with one or more additional therapeutic agents in any dosage amount of the compound of the present disclosure (e.g., from 1 mg to 1000 mg of compound). Therapeutically effective amounts may include from about 0.1 mg per dose to about 1000 mg per dose, such as from about 50 mg per dose to about 500 mg per dose, or such as from about 100 mg per dose to about 400 mg per dose, or such as from about 150 mg per dose to about 350 mg per dose, or such as from about 200 mg per dose to about 300 mg per dose, or such as from about 0.01 mg per dose to about 1000 mg per dose, or such as from about 0.01 mg per dose to about 100 mg per dose, or such as from about 0.1 mg per dose to about 100 mg per dose, or such as from about 1 mg per dose to about 100 mg per dose, or such as from about 1 mg per dose to about 10 mg per dose, or such as from about 1 mg per dose to about 1000 mg per dose. Other therapeutically effective amounts of the compound of Formula I are about 1 mg per dose, or about 2, 3, 4, 5, 6, 7, 8, 9, 10, 15, 20, 25, 30, 35, 40, 45, 50, 55, 60, 65, 70, 75, 80, 85, 90, 95, or about 100 mg per dose. Other therapeutically effective amounts of the compound of the present disclosure are about 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, or about 1000 mg per dose.

In some embodiments, the methods described herein comprise administering to the subject an initial daily dose of about 1 to 500 mg of a compound provided herein and increasing the dose by increments until clinical efficacy is achieved. Increments of about 5, 10, 25, 50, or 100 mg can be used to increase the dose. The dosage can be increased daily, every other day, twice per week, once per week, once every two weeks, once every three weeks, or once a month.

When administered orally, the total daily dosage for a human subject may be between about 1-4,000 mg/day, between about 1-3,000 mg/day, between 1-2,000 mg/day, about 1-1,000 mg/day, between about 10-500 mg/day, between about 50-300 mg/day, between about 75-200 mg/day, or between about 100-150 mg/day. In some embodiments, the total daily dosage for a human subject may be about 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, or 3000 mg/day administered in a single dose. In some embodiments, the total daily dosage for a human subject may be about 200, 300, 400, 500, 600, 700, or 800 mg/day administered in a single dose. In some embodiments, the total daily dosage for a human subject may be about 300, 400, 500, or 600 mg/day administered in a single dose. In some embodiments, the total daily dosage for a human subject may be about 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, or 4000 mg/day. In some embodiments, the total daily dosage for a human subject may be about 100-200, 100-300, 100-400, 100-500, 100-600, 100-700, 100-800, 100-900, 100-1000, 500-1100, 500-1200, 500-1300, 500-1400, 500-1500, 500-1600, 500-1700, 500-1800, 500-1900, 500-2000, 1500-2100, 1500-2200, 1500-2300, 1500-2400, 1500-2500, 2000-2600, 2000-2700, 2000-2800, 2000-2900, 2000-3000, 2500-3100, 2500-3200, 2500-3300, 2500-3400, 2500-3500, 3000-3600, 3000-3700, 3000-3800, 3000-3900, or 3000-4000 mg/day.

In some embodiments, the total daily dosage for a human subject may be about 100 mg/day administered in a single dose. In some embodiments, the total daily dosage for a human subject may be about 150 mg/day administered in a single dose. In some embodiments, the total daily dosage for a human subject may be about 200 mg/day administered in a single dose. In some embodiments, the total daily dosage for a human subject may be about 250 mg/day administered in a single dose. In some embodiments, the total daily dosage for a human subject may be about 300 mg/day administered in a single dose. In some embodiments, the total daily dosage for a human subject may be about 350 mg/day administered in a single dose. In some embodiments, the total daily dosage for a human subject may be about 400 mg/day administered in a single dose. In some embodiments, the total daily dosage for a human subject may be about 450 mg/day administered in a single dose. In some embodiments, the total daily dosage for a human subject may be about 500 mg/day administered in a single dose. In some embodiments, the total daily dosage for a human subject may be about 550 mg/day administered in a single dose. In some embodiments, the total daily dosage for a human subject may be about 600 mg/day administered in a single dose. In some embodiments, the total daily dosage for a human subject may be about 650 mg/day administered in a single dose. In some embodiments, the total daily dosage for a human subject may be about 700 mg/day administered in a single dose. In some embodiments, the total daily dosage for a human subject may be about 750 mg/day administered in a single dose. In some embodiments, the total daily dosage for a human subject may be about 800 mg/day administered in a single dose. In some embodiments, the total daily dosage for a human subject may be about 850 mg/day administered in a single dose. In some embodiments, the total daily dosage for a human subject may be about 900 mg/day administered in a single dose. In some embodiments, the total daily dosage for a human subject may be about 950 mg/day administered in a single dose. In some embodiments, the total daily dosage for a human subject may be about 1000 mg/day administered in a single dose. In some embodiments, the total daily dosage for a human subject may be about 1500 mg/day administered in a single dose. In some embodiments, the total daily dosage for a human subject may be about 2000 mg/day administered in a single dose. In some embodiments, the total daily dosage for a human subject may be about 2500 mg/day administered in a single dose. In some embodiments, the total daily dosage for a human subject may be about 3000 mg/day administered in a single dose. In some embodiments, the total daily dosage for a human subject may be about 4000 mg/day administered in a single dose.

A single dose can be administered hourly, daily, weekly, or monthly. For example, a single dose can be administered once every 1 hour, 2, 3, 4, 6, 8, 12, 16 or once every 24 hours. A single dose can also be administered once every 1 day, 2, 3, 4, 5, 6, or once every 7 days. A single dose can also be administered once every 1 week, 2, 3, or once every 4 weeks. In certain embodiments, a single dose can be administered once every week. A single dose can also be administered once every month. In some embodiments, a compound disclosed herein is administered once daily in a method disclosed herein. In some embodiments, a compound disclosed herein is administered twice daily in a method disclosed herein. In some embodiments, a compound disclosed herein is administered three times daily in a method disclosed herein.

In some embodiments, a compound disclosed herein is administered once daily in the total daily dose of 100-4000 mg/day. In some embodiments, a compound disclosed herein is administered twice daily in the total daily dose of 100-4000 mg/day. In some embodiments, a compound disclosed herein is administered three times daily in the total daily dose of 100-4000 mg/day.

The frequency of dosage of the compound of the present disclosure will be determined by the needs of the individual patient and can be, for example, once per day or twice, or more times, per day. Administration of the compound continues for as long as necessary to treat the viral infection. For example, a compound can be administered to a human being infected with the virus for a period of from 20 days to 180 days or, for example, for a period of from 20 days to 90 days or, for example, for a period of from 30 days to 60 days.

Administration can be intermittent, with a period of several or more days during which a patient receives a daily dose of the compound of the present disclosure followed by a period of several or more days during which a patient does not receive a daily dose of the compound. For example, a patient can receive a dose of the compound every other day, or three times per week. Again by way of example, a patient can receive a dose of the compound each day for a period of from 1 to 14 days, followed by a period of 7 to 21 days during which the patient does not receive a dose of the compound, followed by a subsequent period (e.g., from 1 to 14 days) during which the patient again receives a daily dose of the compound. Alternating periods of administration of the compound, followed by non-administration of the compound, can be repeated as clinically required to treat the patient.

The compounds of the present disclosure or the pharmaceutical compositions thereof may be administered once, twice, three, or four times daily, using any suitable mode described above. Also, administration or treatment with the compounds may be continued for a number of days; for example, commonly treatment would continue for at least 7 days, 14 days, or 28 days, for one cycle of treatment. Treatment cycles are well known in cancer chemotherapy, and are frequently alternated with resting periods of about 1 to 28 days, commonly about 7 days or about 14 days, between cycles. The treatment cycles, in other embodiments, may also be continuous.

VIII. Methods of Use

The present disclosure also provides a method of treating or preventing a viral infection in a subject (e.g., human) in need thereof, the method comprising administering to the subject a compound described herein.

In some embodiments, the present disclosure provides a method of treating a viral infection in a subject (e.g., human) in need thereof, the method comprising administering to a subject in need thereof a compound described herein.

In some embodiments, the compound described herein is administered to the human via oral, intramuscular, intravenous, subcutaneous, or inhalation administration.

In some embodiments, the present disclosure provides for methods of treating or preventing a viral infection in a subject (e.g., human) in need thereof, the method comprising administering to the subject a compound disclosed herein and at least one additional active therapeutic or prophylactic agent.

In some embodiments, the present disclosure provides for methods of treating a viral infection in a subject (e.g., human) in need thereof, the method comprising administering to the subject a compound disclosed herein, and at least one additional active therapeutic or prophylactic agent.

In one embodiment, the present disclosure provides for methods of inhibiting a viral polymerase in a cell, the methods comprising contacting the cell infected a virus with a compound disclosed herein, whereby the viral polymerase is inhibited.

In one embodiment, the present disclosure provides for methods of inhibiting a viral polymerase in a cell, the methods comprising contacting the cell infected a virus with a compound disclosed herein, and at least one additional active therapeutic agent, whereby the viral polymerase is inhibited.

Also provided here are the uses of the compounds disclosed herein for use in treating or preventing a viral infection in a subject in need thereof. For example, provided herein are uses of the compounds disclosed herein for use in treating a viral infection in a subject in need thereof.

In some embodiments, the viral infection is a paramyxoviridae virus infection. As such, in some embodiments, the present disclosure provides methods for treating a paramyxoviridae infection in a subject (e.g., a human) in need thereof, the method comprising administering to the subject a compound disclosed herein. Paramyxoviridae viruses include, but are not limited to Nipah virus. Hendra virus, measles, mumps, and parainfluenze virus.

In some embodiments, the viral infection is a human parainfluenza virus, Nipah virus, Hendra virus, measles, or mumps infection.

In some embodiments, the viral infection is a pneumoviridae virus infection. As such, in some embodiments, the present disclosure provides a method of treating a pneumoviridae virus infection in a human in need thereof, the method comprising administering to the human a compound provided herein. Pneumoviridae viruses include, but are not limited to, respiratory snycytial virus and human metapneumovirus. In some embodiments, the pneumoviridae virus infection is a respiratory syncytial virus infection. In some embodiments, the pneumoviridae virus infection is human metapneumovirus infection.

In some embodiments, the present disclosure provides a compound disclosed herein, for use in the treatment of a pneumoviridae virus infection in a human in need thereof. In some embodiments, the pneumoviridae virus infection is a respiratory syncytial virus infection. In some embodiments, the pneumoviridae virus infection is human metapneumovirus infection.

In some embodiments, the present disclosure provides methods for treating a RSV infection in a human in need thereof, the method comprising administering to the human a compound provided herein. In some embodiments, the human is suffering from a chronic respiratory syncytial viral infection. In some embodiments, the human is acutely infected with RSV.

In some embodiments, a method of inhibiting RSV replication is provided, wherein the method comprises administering to a human in need thereof, a compound disclosed herein, wherein the administration is by inhalation.

In some embodiments, the present disclosure provides a method for reducing the viral load associated with RSV infection, wherein the method comprises administering to a human infected with RSV a compound disclosed herein.

In some embodiments, the viral infection is a picornaviridae virus infection. As such, in some embodiments, the present disclosure provides a method of treating a picornaviridae virus infection in a human in need thereof, the method comprising administering to the human a compound of the present disclosure. Picornaviridae viruses are eneteroviruses causing a heterogeneous group of infections including herpangina, aseptic meningitis, a common-cold-like syndrome (human rhinovirus infection), a non-paralytic poliomyelitis-like syndrome, epidemic pleurodynia (an acute, febrile, infectious disease generally occurring in epidemics), hand-foot-mouth syndrome, pediatric and adult pancreatitis and serious myocarditis. In some embodiments, the Picornaviridae virus infection is human rhinovirus infection (HRV). In some embodiments, the Picornaviridae virus infection is HRV-A, HRV-B. or HRV-C infection.

In some embodiments, the viral infection is selected from the group consisting of Coxsackie A virus infection, Coxsackie A virus infection, enterovirus D68 infection, enterovirus B69 infection, enterovirus D70 infection, enterovirus A71 infection, and poliovirus infection.

In some embodiments, the present disclosure provides a compound, for use in the treatment of a picornaviridae virus infection in a human in need thereof. In some embodiments, the picornaviridae virus infection is human rhinovirus infection.

In some embodiments, the viral infection is a flaviviridae virus infection. As such, in some embodiments, the present disclosure provides a method of treating a flaviviridae virus infection in a human in need thereof, the method comprising administering to the human a compound described herein. Representative flaviviridae viruses include, but are not limited to, dengue, Yellow fever, West Nile, Zika, Japanese encephalitis virus, and Hepatitis C (HCV). In some embodiments, the flaviviridae virus infection is a dengue virus infection. In some embodiments, the flaviviridae virus infection is a yellow fever virus infection. In some embodiments, the flaviviridae virus infection is a West Nile virus infection. In some embodiments, the flaviviridae virus infection is a zika virus infection. In some embodiments, the flaviviridae virus infection is a Japanese ensephalitis virus infection. In some embodiments, the flaviviridae virus infection is a hepatitis C virus infection.

In some embodiments, the flaviviridae virus infection is a dengue virus infection, yellow fever virus infection, West Nile virus infection, tick borne encephalitis, Kunjin Japanese encephalitis, St. Louis encephalitis, Murray valley encephalitis. Omsk hemorrhagic fever, bovine viral diarrhea, zika virus infection, or a HCV infection.

In some embodiments, the present disclosure provides use of a compound disclosed herein for treatment of a flaviviridae virus infection in a human in need thereof. In some embodiments, the flaviviridae virus infection is a dengue virus infection. In some embodiments, the flaviviridae virus infection is a yellow fever virus infection. In some embodiments, the flaviviridae virus infection is a West Nile virus infection. In some embodiments, the flaviviridae virus infection is a zika virus infection. In some embodiments, the flaviviridae virus infection is a hepatitis C virus infection.

In some embodiments, the viral infection is a filoviridae virus infection. As such, in some embodiments, provided herein is a method of treating a filoviridae virus infection in a human in need thereof, the method comprising administering to the human a compound disclosed herein. Representative filoviridae viruses include, but are not limited to, ebola (variants Zaire, Bundibugio, Sudan, Tai forest, or Reston) and marburg. In some embodiments, the filovindae virus infection is an ebola virus infection. In some embodiments, the filoviridae virus infection is a marburg virus infection.

In some embodiments, the present disclosure provides a compound for use in the treatment of a filoviridae virus infection in a human in need thereof. In some embodiments, the filoviridae virus infection is an ebola virus infection. In some embodiments, the filovindae virus infection is a marburg virus infection.

In some embodiments, the viral infection is a coronavirus infection. As such, in some embodiments, provided herein is a method of treating a coronavirus infection in a human in need thereof, wherein the method comprises administering to the human a compound provided herein.

In some embodiments, the coronavirus infection is a Severe Acute Respiratory Syndrome (SARS-CoV) infection, Middle Eastern Respiratory Syndrome (MERS) infection, SARS-CoV-2 infection, other human coronavirus (229E, NL63, HKU1, or WIV1) infections, zoonotic coronavirus (PEDV or HKU CoV isolates such as HKU3, HKU5, or HKU9) infections. In some embodiments, the viral infection is a Severe Acute Respiratory Syndrome (SARS) infection. In some embodiments, the viral infection is a Middle Eastern Respiratory Syndrome (MERS) infection. In some embodiments, the viral infection is SARS-CoV-2 infection. In some embodiments, the viral infection is a zoonotic coronavirus infection, In some embodiments, the viral infection is caused by a virus having at least 70% sequence homology to a viral polymerase selected from the group consisting of SARS-CoV polymerase, MERS-CoV polymerase and SARS-CoV-2. In some embodiments, the viral infection is caused by a virus having at least 80% sequence homology to a viral polymerase selected from the group consisting of SARS-CoV polymerase, MERS-CoV polymerase and SARS-CoV-2. In some embodiments, the viral infection is caused by a virus having at least 90% sequence homology to a viral polymerase selected from the group consisting of SARS-CoV polymerase, MERS-CoV polymerase and SARS-CoV-2. In some embodiments, the viral infection is caused by a virus having at least 95% sequence homology to a viral polymerase selected from the group consisting of SARS-CoV polymerase, MERS-CoV polymerase and SARS-CoV-2.

In some embodiments, the viral infection is caused by a variant of SARS-CoV-2, for example by the B.1.1.7 variant (the UK variant), B.1.351 variant (the South African variant), P.1 variant (the Brazil variant), B.1.1.7 with E484K variant, B.1.1.207 variant, B.1.1.317 variant, B.1.1.318 variant, B.1.429 variant, B.1.525 variant, or P.3 variant. In some embodiments, the viral infection is caused by the B.1.1.7 variant of SARS-CoV-2. In some embodiments, the viral infection is caused by the B.1.351 variant of SARS-CoV-2. In some embodiments, the viral infection is caused by the P.1 variant of SARS-CoV-2.

In some embodiments, the present disclosure provides a compound for use in the treatment of a coronavirus virus infection in a human in need thereof. In some embodiments, the coronavirus infection is a Severe Acute Respiratory Syndrome (SARS) infection, Middle Eastern Respiratory Syndrome (MERS) infection, SARS-CoV-2 infection, other human coronavirus (229E, NL63, OC43, HKU1, or WIV1) infections, and zoonotic coronavirus (PEDV or HKU CoV isolates such as HKU3. HKU5, or HKU9) infections. In some embodiments, the viral infection is a Severe Acute Respiratory Syndrome (SARS) infection. In some embodiments, the viral infection is a Middle Eastern Respiratory Syndrome (MERS) infection. In some embodiments, the viral infection is SARS-CoV-2 infection (COVID19).

In some embodiments, the viral infection is an arenaviridae virus infection. As such, in some embodiments, the disclosure provides a method of treating an arenaviridae virus infection in a human in need thereof, the method comprising administering to the human a compound disclosed herein. In some embodiments, the arenaviridae virus infection is a Lassa infection or a Junin infection.

In some embodiments, the present disclosure provides a compound for use in the treatment of an arenaviridae virus infection in a human in need thereof. In some embodiments, the arenaviridae virus infection is a Lassa infection or a Junin infection.

In some embodiments, the viral infection is an orthomyxovirus infection, for example, an influenza virus infection. In some embodiments, the viral infection is an influenza virus A, influenza virus B, or influenza virus C infection.

As described more fully herein, the compounds described herein can be administered with one or more additional therapeutic agent(s) to an individual (e.g., a human) infected with a viral infection. The additional therapeutic agent(s) can be administered to the infected individual at the same time as the compound of the present disclosure or before or after administration of the compound of the present disclosure.

IX. Combination Therapy

The compounds described herein can also be used in combination with one or more additional therapeutic agents. As such, also provided herein are methods of treatment of a viral infection in a subject in need thereof, wherein the methods comprise administering to the subject a compound disclosed therein and a therapeutically effective amount of one or more additional therapeutic or prophylactic agents.

In some embodiments, the additional therapeutic agent is an antiviral agent. Any suitable antiviral agent can be used in the methods described herein. In some embodiments, the antiviral agent is selected from the group consisting of 5-substituted 2'-deoxyuridine analogues, nucleoside analogues, pyrophosphate analogues, nucleoside reverse transcriptase inhibitors, non-nucleoside reverse transcriptase inhibitors, protease inhibitors, integrase inhibitors, entry inhibitors, acyclic guanosine analogues, acyclic nucleoside phosphonate analogues, HCV NS5A/NS5B inhibitors, influenza virus inhibitors, interferons, immunostimulators, oligonucleotides, antimitotic inhibitors, and combinations thereof.

In some embodiments, the additional therapeutic agent is a 5-substituted 2'-deoxyuridine analogue. For example, in some embodiments, the additional therapeutic agent is selected from the group consisting of idoxuridine, trifluridine, brivudine [BVDU], and combinations thereof.

In some embodiments, the additional therapeutic agent is a nucleoside analogue. For example, in some embodiments, the additional therapeutic agent is selected from the group consisting of vidarabine, entecavir (ETV), telbivudine, lamivudine, adefovir dipivoxil, tenofovir disoproxil fumarate (TDF) and combinations thereof. In some embodiments, the additional therapeutic agent is favipiravir, ribavirin, galidesivir, β-D-N4-hydroxycytidine or a combination thereof.

In some embodiments, the additional therapeutic agent is a pyrophosphate analogue. For example, in some embodiments, the additional therapeutic agent is foscarnet or phosphonoacetic acid. In some embodiments, the additional therapeutic agent is foscarnet.

In some embodiments, the additional therapeutic agent is nucleoside reverse transcriptase inhibitor. In some embodiments, the antiviral agent is zidovudine, didanosine, zalcitabine, stavudine, lamivudine, abacavir, emtricitabine, and combinations thereof.

In some embodiments, the additional therapeutic agent is a non-nucleoside reverse transcriptase inhibitor. In some embodiments, the antiviral agent is selected from the group consisting of nevirapine, delavirdine, efavirenz, etravirine, rilpivirine, and combinations thereof.

In some embodiments, the additional therapeutic agent is a protease inhibitor. In some embodiments, the protease inhibitor is a HIV protease inhibitor. For example, in some embodiments, the antiviral agent is selected from the group consisting of saquinavir, ritonavir, indinavir, nelfinavir, amprenavir, lopinavir, atazanavir, fosamprenavir, darunavir, tipranavir, cobicistat, and combinations thereof. In some embodiments, the antiviral agent is selected from the group consisting of saquinavir, ritonavir, indinavir, nelfinavir, amprenavir, lopinavir, atazanavir, fosamprenavir, darunavir, tipranavir, and combinations thereof. In some embodiments, the protease inhibitor is a HCV NS3/4A protease inhibitor. For example, in some embodiments, the additional therapeutic agent is selected from the group consisting of voxilaprevir, asunaprevir, boceprevir, paritaprevir, simeprevir, telaprevir, vaniprevir, grazoprevir, ribavirin, danoprevir, faldaprevir, vedroprevir, sovaprevir, deldeprevir, narlaprevir and combinations thereof. In some embodiments, the additional therapeutic agent is selected from the group consisting of voxilaprevir, asunaprevir, boceprevir, paritaprevir, simeprevir, telaprevir, vaniprevir, grazoprevir, and combinations thereof.

In some embodiments, the additional therapeutic agent is an integrase inhibitor. For example, in some embodiments, the additional therapeutic agent is selected from the group consisting of raltegravir, dolutegravir, elvitegravir, abacavir, lamivudine, and combinations thereof. In some embodiments, the additional therapeutic agent is selected from the group consisting of bictegravir, raltegravir, dolutegravir, cabotegravir, elvitegravir, and combinations thereof. In some embodiments, the additional therapeutic agent is selected from the group consisting of bictegravir, dolutegravir, and cabotegravir, and combinations thereof. In some embodiments, the additional therapeutic agent is bictegravir.

In some embodiments, the additional therapeutic agent is an entry inhibitor. For example, in some embodiments, the additional therapeutic agent is selected from the group consisting of docosanol, enfuvirtide, maraviroc, ibalizumab, fostemsavir, leronlimab, ibalizumab, fostemsavir, leronlimab, palivizumab, respiratory syncytial virus immune globulin, intravenous [RSV-IGIV], varicella-zoster immunoglobulin [VariZIG], varicella-zoster immune globulin [VZIG]), and combinations thereof.

In some embodiments, the additional therapeutic agent is an acyclic guanosine analogue. For example, in some embodiments, the additional therapeutic agent is selected from the group consisting of acyclovir, ganciclovir, valacyclovir (also known as valaciclovir), valganciclovir, penciclovir, famciclovir, and combinations thereof.

In some embodiments, the additional therapeutic agent is an acyclic nucleoside phosphonate analogue. For example, in some embodiments, the additional therapeutic agent is selected from a group consisting of cidofovir, adefovir, adefovir dipivoxil, tenofovir, TDF, emtricitabine, efavirenz, rilpivirine, elvitegravir, and combinations thereof. In some embodiment, the additional therapeutic agent is selected from the group consisting of cidofovir, adefovir, adefovir dipivoxil, tenofovir, TDF, and combinations thereof. In some embodiment, the additional therapeutic agent is selected from the group consisting of cidofovir, adefovir dipivoxil, TDF, and combinations thereof.

In some embodiments, the additional therapeutic agent is a HCV NS5A/NS5B inhibitor. In some embodiments, the additional therapeutic agent is a NS3/4A protease inhibitor. In some embodiments, the additional therapeutic agent is a NS5A protein inhibitor. In some embodiments, the additional therapeutic agent is a NS5B polymerase inhibitor of the nucleoside/nucleotide type. In some embodiments, the additional therapeutic agent is a NS5B polymerase inhibitor of the nonnucleoside type. In some embodiments, the additional therapeutic agent is selected from the group consisting of daclatasvir, ledipasvir, velpatasvir, ombitasvir, elbasvir, sofosbuvir, dasabuvir, ribavirin, asunaprevir, simeprevir, paritaprevir, ritonavir, elbasvir, grazoprevir, AT-527, and combinations thereof. In some embodiments, the additional therapeutic agent is selected from the group consisting of daclatasvir, ledipasvir, velpatasvir, ombitasvir, elbasvir, sofosbuvir, dasabuvir, and combinations thereof.

In some embodiments, the additional therapeutic agent is an influenza virus inhibitor. In some embodiments, the additional therapeutic agent is a matrix 2 inhibitor. For example, in some embodiments, the additional therapeutic agent is selected from the group consisting of amantadine, rimantadine, and combinations thereof. In some embodiments, the additional therapeutic agent is a neuraminidase inhibitor. For example, in some embodiments, the additional therapeutic agent is selected from the group consisting of zanamivir, oseltamivir, peramivir, laninamivir octanoate, and combinations thereof. In some embodiments, the additional therapeutic agent is a polymerase inhibitor. For example, in some embodiments, the additional therapeutic agent is selected from the group consisting of ribavirin, favipiravir, and combinations thereof. In some embodiments, the additional therapeutic agent is selected from the group consisting of amantadine, rimantadine, arbidol (umifenovir), baloxavir marboxil, oseltamivir, peramivir, ingavirin, laninamivir octanoate, zanamivir, favipiravir, ribavirin, and combinations thereof. In some embodiments, the additional therapeutic agent is selected from the group consisting of amantadine, rimantadine, zanamivir, oseltamivir, peramivir, laninamivir octanoate, ribavirin, favipiravir, and combinations thereof.

In some embodiments, the additional therapeutic agent is an interferon. In some embodiments, the additional therapeutic agent is selected from the group consisting of interferon alfacon 1, interferon alfa 1b, interferon alfa 2a, interferon alfa 2b, pegylated interferon alfacon 1, pegylated interferon alfa 1 b, pegylated interferon alfa 2a (PegIFNα-2a), and PegIFNα-2b. e embodiments, the additional therapeutic agent is selected from the group consisting of interferon alfacon 1, interferon alfa 1b, interferon alfa 2a, interferon alfa 2b, pegylated interferon alfa 2a (PegIFNα-2a), and PegIFNα-2b. In some embodiments, the additional therapeutic agent is selected from the group consisting of interferon alfacon 1, pegylated interferon alfa 2a (PegIFNα-2a), PegIFNα-2b, and ribavirin. In some embodiments, the additional therapeutic agent is pegylated interferon alfa-2a, pegylated interferon alfa-2b, or a combination thereof.

In some embodiments, the additional therapeutic agent is an immunostimulatory agent. In some embodiments, the additional therapeutic agent is an oligonucleotide. In some embodiments, the additional therapeutic agent is an antimitotic inhibitor. For example, in some embodiments, the additional therapeutic agent is selected from the group consisting of fomivirsen, podofilox, imiquimod, sinecatechins, and combinations thereof.

In some embodiments, the additional therapeutic agent is selected from the group consisting of besifovir, nitazoxanide, REGN2222, doravirine, sofosbuvir, velpatasvir, daclatasvir, asunaprevir, beclabuvir, FV100, and letermovir, and combinations thereof.

In some embodiments, the additional therapeutic agent is an agent for treatment of RSV. For example, in some embodiments, the antiviral agent is ribavirin, ALS-8112 or presatovir. For example, in some embodiments, the antiviral agent is ALS-8112 or presatovir.

In some embodiments, the additional therapeutic agent is an agent for treatment of picornavirus. In some embodiments, the additional therapeutic agent is selected from the group consisting of hydantoin, guanidine hydrochloride, L-buthionine sulfoximine, Py-11, and combinations thereof. In some embodiments, the additional therapeutic agent is a picornavirus polymerase inhibitor. In some embodiments, the additional therapeutic agent is rupintrivir.

In some embodiments, the additional therapeutic agent is an agent for treatment of malaria. In some embodiments, the additional therapeutic agent is chloroquine.

In some embodiments, the additional therapeutic agent is selected from the group consisting of hydroxychloroquine, chloroquine, artemether, lumefantrine, atovaquone, proguanil, tafenoquine, pyronaridine, artesunate, artenimol, piperaquine, artesunate, amodiaquine, pyronaridine, artesunate, halofantrine, quinine sulfate, mefloquine, solithromycin, pyrimethamine, MMV-390048, ferroquine, artefenomel mesylate, ganaplacide, DSM-265, cipargamin, artemisone, and combinations thereof.

In some embodiments, the additional therapeutic agent is an agent for treatment of coronavirus. In some embodiments, the additional therapeutic agent is selected from a group consisting of IFX-1, FM-201, CYNK-001, DPP4-Fc, ranpimase, nafamostat, LB-2, AM-1, anti-viporins, and combinations thereof.

In some embodiments, the additional therapeutic agent is an agent for treatment of ebola virus. For example, in some embodiments, the additional therapeutic agent is selected from the group consisting of ribavirin, palivizumab, motavizumab, RSV-IGIV (RespiGam®), MEDI-557, A-60444, MDT-637, BMS-433771, amiodarone, dronedarone, verapamil, Ebola Convalescent Plasma (ECP), TKM-100201, BCX4430 ((2S,3S,4R,5R)-2-(4-amino-5H-pyrrolo[3,2-d]pyrimidin-7-yl)-5-(hydroxymethyl)pyrrolidine-3,4-diol), favipiravir (also known as T-705 or Avigan), T-705 monophosphate, T-705 diphosphate, T-705 triphosphate, FGI-106 (1-N,7-N-bis[3-(dimethylamino)propyl]-3,9-dimethylquinolino[8,7-h]quinolone-1,7-diamine), JK-05, TKM-Ebola, ZMapp, rNAPc2, VRC-EBOADC076-00-VP, OS-2966, MVA-BN filo, brincidofovir, Vaxart adenovirus vector 5-based ebola vaccine, Ad26-ZEBOV, FiloVax vaccine, GOVX-E301, GOVX-E302, ebola virus entry inhibitors (NPC1 inhibitors), rVSV-EBOV, and combinations thereof. In some embodiments, the additional therapeutic agent is ZMapp, mABI114, REGEN-EB3, and combinations thereof.

In some embodiments, the additional therapeutic agent is an agent for treatment of HCV. In some embodiments, the additional therapeutic agent is a HCV polymerase inhibitor. For example, in some embodiments, the additional therapeutic agent is selected from the group consisting of sofosbuvir, GS-6620, PSI-938, ribavirin, tegobuvir, radalbuvir, MK-0608, and combinations thereof. In some embodiments, the additional therapeutic agent is a HCV protease inhibitor. For example, in some embodiments, the additional therapeutic agent is selected from the group consisting of such as GS-9256, vedroprevir, voxilaprevir, and combinations thereof.

In some embodiments, the additional therapeutic agent is a NS5A inhibitor. For example, in some embodiments, the additional therapeutic agent is selected from the group consisting of ledipasvir, velpatasvir, and combinations thereof.

In some embodiments, the additional therapeutic agent is an anti HBV agent. For example, in some embodiments, the additional therapeutic agent is tenofovir disoproxil fumarate and emtricitabine, or a combination thereof. Examples of additional anti HBV agents include but are not limited to alpha-hydroxytropolones, amdoxovir, antroquinonol, beta-hydroxycytosine nucleosides, ARB-199, CCC-0975, ccc-R08, elvucitabine, ezetimibe, cyclosporin A, gentiopicrin (gentiopicroside), HH-003, hepalatide, JNJ-56136379, nitazoxanide, birinapant, NJK14047, NOV-205 (molixan, BAM-205), oligotide, mivotilate, feron, GST-HG-131, levamisole, Ka Shu Ning, alloferon, WS-007, Y-101 (Ti Fen Tai), rSIFN-co, PEG-IIFNm, KW-3, BP-Inter-014, oleanolic acid, HepB-nRNA, cTP-5 (rTP-5), HSK-II-2, HEISCO-106-1, HEISCO-106, Hepbama, IBPB-006IA, Hepuyinfen, DasKloster 0014-01, ISA-204, Jiangantai (Ganxikang), MIV-210, OB-AI-004, PF-06, picroside, DasKloster-0039, hepulantai, IMB-2613, TCM-800B, reduced glutathione, RO-6864018, RG-7834, QL-007sofosbuvir, ledipasvir, UB-551, and ZH-2N, and the compounds disclosed in US20150210682, (Roche), US 2016/0122344 (Roche), WO2015173164, WO2016023877, US2015252057A (Roche), WO16128335A1 (Roche), WO16120186A1 (Roche), US2016237090A (Roche), WO16107833A1 (Roche). WO16107832A1 (Roche), US2016176899A (Roche), WO16102438A1 (Roche), WO16012470A1 (Roche), US2016220586A (Roche), and US2015031687A (Roche). In some embodiments, the additional therapeutic agent is a HBV polymerase inhibitor. Examples of HBV DNA polymerase inhibitors include, but are not limited to, adefovir (HEPSERA®), emtricitabine (EMTRIVA®), tenofovir disoproxil fumarate (VIREAD®), tenofovir alafenamide, tenofovir, tenofovir disoproxil, tenofovir alafenamide fumarate, tenofovir alafenamide hemifumarate, tenofovir dipivoxil, tenofovir dipivoxil fumarate, tenofovir octadecyloxyethyl ester, CMX-157, tenofovir exalidex, besifovir, entecavir (BARACLUDE®), entecavir maleate, telbivudine (TYZEKA®), filocilovir, pradefovir, clevudine, ribavirin, lamivudine (EPIVIR-HBV®), phosphazide, famciclovir, fusolin, metacavir, SNC-019754, FMCA, AGX-1009, AR-II-04-26, HIP-1302, tenofovir disoproxil aspartate, tenofovir disoproxil orotate, and HS-10234. In some embodiments, the additional therapeutic agent is a HBV capsid inhibitor.

In some embodiments, the additional therapeutic agent is an agent for treatment of HIV. In some embodiments, the additional therapeutic agent is selected from the group consisting of HIV protease inhibitors, HIV integrase inhibitors, entry inhibitors, HIV nucleoside reverse transcriptase inhibitors, HIV nonnucleoside reverse transcriptase inhibitors, acyclic nucleoside phosphonate analogues, and combinations thereof.

In some embodiments, the additional therapeutic agent is selected from the group consisting of HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, immunomodulators, immunotherapeutic agents, antibody-drug conjugates, gene modifiers, gene editors (such as CRISPR/Cas9, zinc finger nucleases, homing nucleases, synthetic nucleases. TALENs), and cell therapies (such as chimeric antigen receptor T-cell, CAR-T, and engineered T cell receptors, TCR-T, autologous T cell therapies).

In some embodiments, the additional therapeutic agent is selected from the group consisting of combination drugs for HIV, other drugs for treating HIV. HIV protease inhibitors, HIV reverse transcriptase inhibitors, HIV integrase inhibitors, HIV non-catalytic site (or allosteric) integrase inhibitors. HIV entry (fusion) inhibitors. HIV maturation inhibitors, latency reversing agents, capsid inhibitors, immune-based therapies, PI3K inhibitors, HIV antibodies, and bispecific antibodies, and "antibody-like" therapeutic proteins, and combinations thereof.

In some embodiments, the additional therapeutic agent is a HIV combination drug.

Examples of the HIV combination drugs include, but are not limited to ATRIPLA® (efavirenz, tenofovir disoproxil fumarate, and emtricitabine); BIKTARVY® (bictegravir, emtricitabine, and tenofovir alafenamide); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); SYMTUZA® (darunavir, tenofovir alafenamide hemifumarate, emtricitabine, and cobicistat); SYMFI™ (efavirenz, lamivudine, and tenofovir disoproxil fumarate); CIMDU™ (lamivudine and tenofovir disoproxil fumarate); tenofovir and lamivudine; tenofovir alafenamide and emtricitabine; tenofovir alafenamide hemifumarate and emtricitabine; tenofovir alafenamide hemifumarate, emtricitabine, and rilpivirine; tenofovir alafenamide hemifumarate, emtricitabine, cobicistat, and elvitegravir; COMBIVIR® (zidovudine and lamivudine; AZT+3TC); EPZICOM® (LIVEXA®; abacavir sulfate and lamivudine; ABC+3TC); KALETRA® (ALUVIA®; lopinavir and ritonavir); TRIUMEQ® (dolutegravir, abacavir, and lamivudine); TRIZIVIR® (abacavir sulfate, zidovudine, and lamivudine; ABC+AZT+3TC); atazanavir and cobicistat; atazanavir sulfate and cobicistat; atazanavir sulfate and ritonavir; darunavir and cobicistat; dolutegravir and rilpivirine; dolutegravir and rilpivirine hydrochloride; dolutegravir, abacavir sulfate, and lamivudine; lamivudine, nevirapine, and zidovudine; raltegravir and lamivudine; doravirine, lamivudine, and tenofovir disoproxil fumarate; doravirine, lamivudine, and tenofovir disoproxil; dapivirine+levonorgestrel, dolutegravir+lamivudine, dolutegravir+emtricitabine+tenofovir alafenamide, elsulfavirine+emtricitabine+tenofovir disoproxil, lamivudine+abacavir+zidovudine, lamivudine+abacavir, lamivudine+tenofovir disoproxil fumarate, lamivudine+zidovudine+nevirapine, lopinavir+ritonavir, lopinavir+ritonavir+abacavir+lamivudine, lopinavir+ritonavir+zidovudine+lamivudine, tenofovir+lamivudine, and tenofovir disoproxil fumarate+emtricitabine+rilpivirine hydrochloride, lopinavir, ritonavir, zidovudine and lamivudine.

In some embodiments, the additional therapeutic agent is a HIV protease inhibitor. For example, in some embodiments the additional therapeutic agent is selected from the group consisting of saquinavir, ritonavir, indinavir, nelfinavir, amprenavir, lopinavir, atazanavir, fosamprenavir, darunavir, tipranavir, cobicistat, ASC-09, AEBL-2, MK-8718, GS-9500, GS-1156, and combinations thereof. For example, in some embodiments the additional therapeutic agent is selected from the group consisting of saquinavir, ritonavir, indinavir, nelfinavir, amprenavir, lopinavir, atazanavir, fosamprenavir, darunavir, tipranavir, cobicistat. In some embodiments, the additional therapeutic agent is selected from the group consisting of amprenavir, atazanavir, brecanavir, darunavir, fosamprenavir, fosamprenavir calcium, indinavir, indinavir sulfate, lopinavir, nelfinavir, nelfinavir mesylate, ritonavir, saquinavir, saquinavir mesylate, tipranavir, DG-17, TMB-657 (PPL-100), T-169, BL-008, MK-8122, TMB-607, TMC-310911, and combinations thereof.

In some embodiments, the additional therapeutic agent is a HIV integrase inhibitor. For example, in some embodiment, the additional therapeutic agent is selected from the group consisting of raltegravir, elvitegravir, dolutegravir, abacavir, lanivudine, bictegravir and combinations thereof. In some embodiment, the additional therapeutic agent is bictegravir. In some embodiments, the additional therapeutic agent is selected from a group consisting of bictegravir, elvitegravir, curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, raltegravir, dolutegravir, JTK-351, bictegravir, AVX-15567, BMS-986197, cabotegravir (long-acting injectable), diketo quinolin-4-1 derivatives, integrase-LEDGF inhibitor, ledgins, M-522, M-532, NSC-310217, NSC-371056, NSC-48240, NSC-642710, NSC-699171, NSC-699172, NSC-699173, NSC-699174, stilbenedisulfonic acid, T-169, VM-3500, cabotegravir, and combinations thereof.

In some embodiments, the additional therapeutic agent is a HIV entry inhibitor. For example, in some embodiments, the additional therapeutic agent is selected from the group consisting of enfuvirtide, maraviroc, and combinations thereof. Further examples of HIV entry inhibitors include, but are not limited to, cenicriviroc, CCR5 inhibitors, gp41 inhibitors, CD4 attachment inhibitors, DS-003 (BMS-599793), gp120 inhibitors, and CXCR4 inhibitors. Examples of CCR5 inhibitors include aplaviroc, vicriviroc, maraviroc, cenicriviroc, leronlimab (PRO-140), adaptavir (RAP-101), nifeviroc (TD-0232), anti-GP120/CD4 or CCR5 bispecific antibodies, B-07, MB-66, polypeptide C25P, TD-0680, and vMIP (Haimipu). Examples of CXCR4 inhibitors include plerixafor, ALT-1188, N15 peptide, and vMIP (Haimipu).

In some embodiments, the additional therapeutic agent is a HIV nucleoside reverse transcriptase inhibitors. In some embodiments, the additional therapeutic agent is a HIV nonnucleoside reverse transcriptase inhibitors. In some embodiments, the additional therapeutic agent is an acyclic nucleoside phosphonate analogue. In some embodiments, the additional therapeutic agent is a HIV capsid inhibitor.

In some embodiments, the additional therapeutic agent is a HIV nucleoside or nucleotide inhibitor of reverse transcriptase. For example, the additional therapeutic agent is selected from the group consisting of adefovir, adefovir dipivoxil, azvudine, emtricitabine, tenofovir, tenofovir alafenamide, tenofovir alafenamide fumarate, tenofovir alafenamide hemifumarate, tenofovir disoproxil, tenofovir disoproxil fumarate, tenofovir disoproxil hemifumarate, VIDEX® and VIDEX EC® (didanosine, ddI), abacavir, abacavir sulfate, alovudine, apricitabine, censavudine, didanosine, elvucitabine, festinavir, fosalvudine tidoxil, CMX-157, dapivirine, doravirine, etravirine, OCR-5753, tenofovir disoproxil orotate, fozivudine tidoxil, islatravir, lamivudine, phosphazid, stavudine, zalcitabine, zidovudine, rovafovir etalafenamide (GS-9131), GS-9148, MK-8504, MK-8591, MK-858, VM-2500, KP-1461, and combinations thereof.

In some embodiments, the additional therapeutic agent is a HIV non-nucleoside or non-nucleotide inhibitor of reverse transcriptase. For example, the additional agent is selected from the group consisting of dapivirine, delavirdine, delavirdine mesylate, doravirine, efavirenz, etravirine, lentinan, MK-8583, nevirapine, rilpivirine, TMC-278LA, ACC-007, AIC-292, KM-023, PC-1005, elsulfavirine rilp (VM-1500), combinations thereof.

In some embodiments, the additional therapeutic agents are selected from ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); adefovir; adefovir dipivoxil; cobicistat; emtricitabine; tenofovir; tenofovir disoproxil; tenofovir disoproxil fumarate; tenofovir alafenamide; tenofovir alafenamide hemifumarate; TRIUMEQ® (dolutegravir, abacavir, and lamivudine); dolutegravir, abacavir sulfate, and lamivudine; raltegravir; raltegravir and lamivudine; maraviroc; enfuvirtide; ALUVIA® (KALETRA®, lopinavir and ritonavir); COMBIVIR® (zidovudine and lamivudine; AZT+3TC); EPZICOM® (LIVEXA®; abacavir sulfate and lamivudine; ABC+3TC); TRIZIVIR® (abacavir sulfate, zidovudine, and lamivudine; ABC+AZT+3TC); rilpivirine; rilpivirine hydrochloride; atazanavir sulfate and cobicistat; atazanavir and cobicistat; darunavir and cobicistat; atazanavir; atazanavir sulfate; dolutegravir; elvitegravir; ritonavir; atazanavir sulfate and ritonavir; darunavir; lamivudine; prolastin; fosamprenavir; fosamprenavir calcium efavirenz; etravirine; nelfinavir; nelfinavir mesylate; interferon; didanosine; stavudine; indinavir; indinavir sulfate; tenofovir and lamivudine; zidovudine; nevirapine; saquinavir; saquinavir mesylate; aldesleukin; zalcitabine; tipranavir; amprenavir; delavirdine; delavirdine mesylate; Radha-108 (receptol); lamivudine and tenofovir disoproxil fumarate; efavirenz, lamivudine, and tenofovir disoproxil fumarate; phosphazid; lamivudine, nevirapine, and zidovudine; abacavir; and abacavir sulfate.

In some embodiments, the additional therapeutic agent is selected from the group consisting of colistin, valrubicin, icatibant, bepotastine, epirubicin, epoprosetnol, vapreotide, aprepitant, caspofungin, perphenazine, atazanavir, efavirenz, ritonavir, acyclovir, ganciclovir, penciclovir, prulifloxacin, bictegravir, nelfinavir, tegobuvi, nelfinavir, praziquantel, pitavastatin, perampanel, eszopiclone, and zopiclone.

In some embodiments, the additional therapeutic agent is an inhibitor of Bruton tyrosine kinase (BTK, AGMX1, AT, ATK, BPK, IGHD3, IMD1, PSCTK1, XLA; NCBI Gene ID: 695). For example, in some embodiments, the additional therapeutic agent is selected from the group consisting of (S)-6-amino-9-(1-(but-2-ynoyl)pyrrolidin-3-yl)-7-(4-phenoxyphenyl)-7H-purin-8(9H)-one, acalabrutinib (ACP-196), BGB-3111, CB988, HM71224, ibrutinib (Imbruvica), M-2951 (evobrutinib), M7583, tirabrutinib (ONO-4059), PRN-1008, spebrutinib (CC-292), TAK-020, vecabrutinib. ARQ-531, SHR-1459, DTRMWXHS-12, TAS-5315. AZD6738, calquence, danvatirsen, and combinations thereof. In some embodiments, the additional therapeutic agent is selected from a group consisting of tirabrutinib, ibrutinib, acalabrutinib, and combinations thereof. In some embodiments, the additional therapeutic agent is selected from a group consisting of tirabrutinib, ibrutinib, and combinations thereof. In some embodiments, the additional therapeutic agent is tyrphostin A9 (A9).

In some embodiments, the additional therapeutic agent is a KRAS inhibitor. For example, in some embodiments, the additional therapeutic agent is selected from the group consisting of AMG-510, COTI-219, MRTX-1257, ARS-3248, ARS-853, WDB-178, BI-3406, BI-1701963, ARS-1620 (G12C), SML-8-73-1 (G12C), Compound 3144 (G12D), Kobe0065/2602 (Ras GTP), RT11, MRTX-849 (G12C) and K-Ras(G12D)-selective inhibitory peptides, including KRpep-2 (Ac-RRCPLYISYDPVCRR-NH2), KRpep-2d (Ac-RRRRCPLYISYDPVCRRRR-NH2), and combinations thereof.

In some embodiments, the additional therapeutic agent is a proteasome inhibitor. For example, in some embodiments, the additional therapeutic agent is selected from a group consisting of ixazomib, carfilzomib, marizomib, bortezomib, and combinations thereof. In some embodiments, the additional therapeutic agent is carfilzomib.

In some embodiments, the additional therapeutic agent is a vaccine. For example, in some embodiments, the additional therapeutic agent is a DNA vaccine, RNA vaccine, live-attenuated vaccine, therapeutic vaccine, prophylactic vaccine, protein based vaccine, or a combination thereof. In some embodiments, the additional therapeutic agent is mRNA-1273. In some embodiments, the additional therapeutic agent is INO-4800 or INO-4700. In some embodiments, the additional therapeutic agent is live-attenuated RSV vaccine MEDI-559, human monoclonal antibody REGN2222 against RSV, palivizumab, respiratory syncytial virus immune globulin, intravenous [RSV-IGIV], and combinations thereof. In some embodiments, the additional therapeutic agent is a HBV vaccine, for example pediarix, engerix-B. and recombivax HB. In some embodiments, the additional therapeutic agent is a VZV vaccine, for example zostavax and varivax. In some embodiments, the additional therapeutic agent is a HPV vaccine, for example cervarix, gardasil 9, and gardasil. In some embodiments, the additional therapeutic agent is an influenza virus vaccine. For example, a (i) monovalent vaccine for influenza A (e.g., influenza A [H5N1] virus monovalent vaccine and influenza A [H1N1] 2009 virus monovalent vaccines), (ii) trivalent vaccine for influenza A and B viruses (e.g., Afluria, Agriflu, Fluad, Fluarix, Flublok, Flucelvax, FluLaval. Fluvirin, and Fluzone), and (iii) quadrivalent vaccine for influenza A and B viruses (FluMist, Fluarix, Fluzone, and FluLaval). In some embodiments, the additional therapeutic agent is a human adenovirus vaccine (e.g., Adenovirus Type 4 and Type 7 Vaccine, Live, Oral). In some embodiments, the additional therapeutic agent is a rotavirus vaccine (e.g., Rotarix for rotavirus serotype G1, G3, G4, or G9 and RotaTeq for rotavirus serotype G1, G2, G3, or G4). In some embodiments, the additional therapeutic agent is a hepatitis A virus vaccine (e.g., Havrix and Vaqta). In some embodiments, the additional therapeutic agent is poliovirus vaccines (e.g., Kinrix, Quadracel, and Ipol). In some embodiments, the additional therapeutic agent is a yellow fever virus vaccine (e.g., YF-Vax). In some embodiments, the additional therapeutic agent is a Japanese encephalitis virus vaccines (e.g., Ixiaro and JE-Vax). In some embodiments, the additional therapeutic agent is a measles vaccine (e.g., M-M-R II and ProQuad). In some embodiments, the additional therapeutic agent is a mumps vaccine (e.g., M-M-R II and ProQuad). In some embodiments, the additional therapeutic agent is a rubella vaccine (e.g., M-M-R II and ProQuad). In some embodiments, the additional therapeutic agent is a varicella vaccine (e.g., ProQuad). In some embodiments, the additional therapeutic agent is a rabies vaccine (e.g., Imovax and RabAvert). In some embodiments, the additional therapeutic agent is a variola virus (smallpox) vaccine (ACAM2000). In some embodiments, the additional therapeutic agent is a and hepatitis E virus (HEV) vaccine (e.g., HEV239). In some embodiments, the additional therapeutic agent is a 2019-nCov vaccine.

In some embodiments, the additional therapeutic agent is an antibody, for example a monoclonal antibody. For example, the additional therapeutic agent is an antibody against 2019-nCov selected from the group consisting of the Regeneron antibodies, the Wuxi Antibodies, the Vir Biotechnology Antibodies, antibodies that target the SARS-CoV-2 spike protein, antibodies that can neutralize SARS-CoV-2 (SARS-CoV-2 neutralizing antibodies), and combinations thereof. In some embodiments, the additional therapeutic agent is anti-SARS-CoV antibody CR-3022. In some embodiments, the additional therapeutic agent is aPD-1 antibody.

In some embodiments, the additional therapeutic agent is recombinant cytokine gene-derived protein injection.

In some embodiments, the additional therapeutic agent is a polymerase inhibitor. In some embodiments, the additional therapeutic agent is a DNA polymerase inhibitor. For example, in some embodiments, the additional therapeutic agent is cidofovir. In some embodiments, the additional therapeutic agent is a RNA polymerase inhibitor. For example, in some embodiments, the additional therapeutic agent is selected from the group consisting of ribavirin, favipiravir, lamivudine, pimodivir and combination thereof.

In some embodiments, the additional therapeutic agent is selected from the group consisting of lopinavir, ritonavir, interferon-alpha-2b, ritonavir, arbidol, hydroxychloroquine, darunavir and cobicistat, abidol hydrochloride, oseltamivir, litonavir, emtricitabine, tenofovir alafenamide fumarate, baloxavir marboxil, ruxolitinib, and combinations thereof.

In some embodiments, the additional therapeutic agent is selected from the group consisting of 6'-fluorinated aristeromycin analogues, acyclovir fleximer analogues, disulfiram, thiopurine analogues. ASC09F, GC376, GC813, phenylisoserine derivatives, neuroiminidase inhibitor analogues, pyrithiobac derivatives, bananins and 5-hydroxychromone derivatives, SSYA10-001, griffithsin, HR2P-M1, HR2P-M2, P21S10, Dihydrotanshinone E-64-C and E-64-D, OC43-HR2P, MERS-5HB, 229E-HR1P, 229E-HR2P, resveratrol, 1-thia-4-azaspiro[4.5] decan-3-one derivatives, gemcitabine hydrochloride, loperamide, recombinant interferons, cyclosporine A, alisporivir, imatinib mesylate, dasatinib, selumetinib, trametinib, rapamycin, saracatinib, chlorpromazine, triflupromazine, fluphenazine, thiethylperazine, promethazine, cyclophilin inhibitors, K11777, camostat, k22, teicoplanin derivatives, benzo-heterocyclic amine derivatives N30, mycophenolic acid, silvestrol, and combinations thereof.

In some embodiments, the additional therapeutic agent is an antibody. In some embodiments, the additional therapeutic agent is an antibody that binds to a coronavirus, for example an antibody that binds to SARS-CoV or MERS-CoV. In some embodiments, the additional therapeutic agent is a of 2019-nCoV virus antibody.

Compositions of the invention are also used in combination with other active ingredients. For the treatment of 2019-nCoV virus infections, preferably, the other active therapeutic agent is active against coronavirus infections, for example 2019-nCoV virus infections. The compounds and compositions of the present invention are also intended for use with general care provided patients with 2019-nCoV viral infections, including parenteral fluids (including dextrose saline and Ringer's lactate) and nutrition, antibiotic (including metronidazole and cephalosporin antibiotics, such as ceftriaxone and cefuroxime) and/or antifungal prophylaxis, fever and pain medication, antiemetic (such as metoclopramide) and/or antidiarrheal agents, vitamin and mineral supplements (including Vitamin K and zinc sulfate), anti-inflammatory agents (such as ibuprofen or steroids), corticosteroids such as methylprednisolone, immunomodulatory medications (e.g., interferon), other small molecule or biologics antiviral agents targeting 2019-nCoV (such as but not limited to lopinavir/ritonavir, EIDD-1931, favipiravir, ribavirine, neutralizing antibodies, etc.), vaccines, pain medications, and medications for other common diseases in the patient population, such anti-malarial agents (including artemether and artesunate-lumefantrine combination therapy), typhoid (including quinolone antibiotics, such as ciprofloxacin, macrolide antibiotics, such as azithromycin, cephalosporin antibiotics, such as ceftriaxone, or aminopenicillins, such as ampicillin), or shigellosis. In some embodiments, the additional therapeutic agent is dihydroartemisinin/piperaquine. In some embodiments, the additional therapeutic agent is EIDD-2801 (MH-4482, Molnupiravir).

In some embodiments, the additional therapeutic agent is an immunomodulator. Examples of immune-based therapies include toll-like receptors modulators such as tlr1, tlr2, tlr3, tlr4, tlr5, tlr6, tlr7, tlr8, tlr9, tlr10, tlr11, tlr12, and tlr13; programmed cell death protein 1 (Pd-1) modulators; programmed death-ligand 1 (Pd-L1) modulators; IL-15 modulators; DermaVir; interleukin-7; plaquenil (hydroxychloroquine); proleukin (aldesleukin, IL-2); interferon alfa; interferon alfa-2b; interferon alfa-n3; pegylated interferon alfa; interferon gamma; hydroxyurea; mycophenolate mofetil (MPA) and its ester derivative mycophenolate mofetil (MMF); ribavirin; polymer polyethyleneimine (PEI); gepon; IL-12; WF-10; VGV-1; MOR-22; BMS-936559; CYT-107, interleukin-15/Fc fusion protein, AM-0015, ALT-803, NIZ-985, NKTR-255, NKTR-262, NKTR-214, normferon, peginterferon alfa-2a, peginterferon alfa-2b, recombinant interleukin-15, Xmab-24306, RPI-MN, STING modulators, RIG-I modulators, NOD2 modulators, SB-9200, and IR-103. In some embodiments, the additional therapeutic agent is fingolimod, leflunomide, or a combination thereof. In some embodiments, the additional therapeutic agent is thalidomide.

In some embodiments, the additional therapeutic agent is an IL-6 inhibitor, for example tocilizumab, sarilumab, or a combination thereof.

In some embodiments, the additional therapeutic agent is an anti-TNF inhibitor. For example, the additional therapeutic agent is adalimumab, etanercept, golimumab, infliximab, or a combination thereof.

In some embodiments, the additional therapeutic agent is a JAK inhibitor, for example the additional therapeutic agent is baricitinib, filgotinib, olumiant, or a combination thereof.

In some embodiments, the additional therapeutic agent is an inflammation inhibitor, for example pirfenidone.

In some embodiments, the additional therapeutic agent is an antibiotic for secondary bacterial pneumonia. For example, the additional therapeutic agent is macrolide antibiotics (e.g., azithromycin, clarithromycin, and *Mycoplasma pneumoniae*), fluoroquinolones (e.g., ciprofloxacin and levofloxacin), tetracyclines (e.g., doxycycline and tetracycline), or a combination thereof.

In some embodiments, the compounds disclosed herein are used in combination with pneumonia standard of care (see e.g., Pediatric Community Pneumonia Guidelines, CID 2011:53 (1 October)). Treatment for pneumonia generally involves curing the infection and preventing complications. Specific treatment will depend on several factors, including the type and severity of pneumonia, age and overall health of the individuals. The options include: (i) antibiotics, (ii) cough medicine, and (iii) fever reducers/pain relievers (for e.g., aspirin, ibuprofen (Advil, Motrin IB, others) and acetaminophen (Tylenol, others)). In some embodiments, the additional therapeutic agent is bromhexine anti-cough.

In some embodiments, the compounds disclosed herein are used in combination with immunoglobulin from cured COVID-19 patients. In some embodiments, the compounds disclosed herein are used in combination with plasma transfusion. In some embodiments, the compounds disclosed herein are used in combination with stem cells.

In some embodiments, the additional therapeutic agent is an TLR agonist. Examples of TLR agonists include, but are not limited to, vesatolimod (GS-9620), GS-986, IR-103, lefitolimod, tilsotolimod, rintatolimod, DSP-0509, AL-034, G-100, cobitolimod, AST-008, motolimod, GSK-1795091, GSK-2245035, VTX-1463, GS-9688, LHC-165, BDB-001, RG-7854, telratolimod, and RO-7020531.

In some embodiments, the additional therapeutic agent is selected from the group consisting of bortezomid, flurazepam, ponatinib, sorafenib, paramethasone, clocortolone, flucloxacillin, sertindole, clevidipine, atorvastatin, cinolazepam, clofazimine, fosaprepitant, and combinations thereof.

In some embodiments, the additional therapeutic agent is carrimycin, suramin, triazavirin, dipyridamole, bevacizumab, meplazumab, GD31 (rhizobium), NLRP inflammasome inhibitor, or α-ketoamine. In some embodiments, the additional therapeutic agent is recombinant human angiotensin-converting enzyme 2 (rhACE2). In some embodiments, the additional therapeutic agent is viral macrophage inflammatory protein (vMIP).

In some embodiments, the additional therapeutic agent is an anti-viroporin therapeutic. For example, the additional therapeutic agent is BIT-314 or BIT-225. In some embodiments, the additional therapeutic agent is coronavirus E protein inhibitor. For example, the additional therapeutic agent is BIT-009. Further examples of additional therapeutic agents include those described in WO-2004112687, WO-2006135978, WO-2018145148, and WO-2009018609.

In some embodiments, the additional therapeutic or prophylactic agent is molnupiravir, oseltamivir, nirmatrelvir, or ritonavir. In some embodiments, the additional therapeutic or prophylactic agent is ritonavir or cobicistat.

It is possible to combine any compound of the invention with one of more additional active therapeutic agents. For example, the compound described herein can be combined with one, two, three, four, five, or more additional active therapeutic agents.

It is also possible to combine any compound of the invention with one or more additional active therapeutic agents in a unitary dosage form for simultaneous or sequential administration to a patient. The combination therapy may be administered as a simultaneous or sequential regimen. When administered sequentially, the combination may be administered in two or more administrations.

Co-administration of a compound of the invention with one or more other active therapeutic agents generally refers to simultaneous or sequential administration of a compound of the invention and one or more other active therapeutic agents, such that therapeutically effective amounts of the compound of the invention and one or more other active therapeutic agents are both present in the body of the patient.

Co-administration includes administration of unit dosages of the compounds of the invention before or after administration of unit dosages of one or more other active therapeutic agents, for example, administration of the compounds of the invention within seconds, minutes, or hours of the administration of one or more other active therapeutic agents. For example, a unit dose of a compound of the invention can be administered first, followed within seconds or minutes by administration of a unit dose of one or more other active therapeutic agents. Alternatively, a unit dose of one or more other therapeutic agents can be administered first, followed by administration of a unit dose of a compound of the invention within seconds or minutes. In some cases, it may be desirable to administer a unit dose of a compound of the invention first, followed, after a period of hours (e.g., 1-12 hours), by administration of a unit dose of one or more other active therapeutic agents. In other cases, it may be desirable to administer a unit dose of one or more other active therapeutic agents first, followed, after a period of hours (e.g., 1-12 hours), by administration of a unit dose of a compound of the invention.

The combination therapy may provide "synergy" and "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially. e.g., in separate tablets, pills or capsules, or by different injections in separate syringes. In general, during alternation therapy, an effective dosage of each active ingredient is administered sequentially, i.e., serially, whereas in combination therapy, effective dosages of two or more active ingredients are administered together. A synergistic anti-viral effect denotes an antiviral effect, which is greater than the predicted purely additive effects of the individual compounds of the combination.

1. Combination Therapy for the Treatment of Pneumoviridae

The compounds provided herein are also used in combination with other active therapeutic agents. For the treatment of Pneumoviridae virus infections, preferably, the other active therapeutic agent is active against Pneumoviridae virus infections, particularly respiratory syncytial virus infections and/or metapneumovirus infections. Non-limiting examples of these other active therapeutic agents active against RSV are ribavirin, palivizumab, motavizumab, RSV-IGIV (RespiGam®), MEDI-557, A-60444 (also known as RSV604), MDT-637, BMS-433771, ALN-RSVO, ALX-0171 and mixtures thereof. Other non-limiting examples of other active therapeutic agents active against respiratory syncytial virus infections include respiratory syncytial virus protein F inhibitors, such as AK-0529; RV-521, ALX-0171, JNJ-53718678, BTA-585, and presatovir; RNA polymerase inhibitors, such as lumicitabine and ALS-8112; anti-RSV G protein antibodies, such as anti-G-protein mAb; viral replication inhibitors, such as nitazoxanide.

In some embodiments, the other active therapeutic agent may be a vaccine for the treatment or prevention of RSV, including but not limited to MVA-BN RSV, RSV-F, MEDI-8897, JNJ-64400141, DPX-RSV, SynGEM, GSK-3389245A, GSK-300389-1A, RSV-MEDI deltaM2-2 vaccine, VRC-RSVRGP084-OOVP, Ad35-RSV-FA2, Ad26-RSV-FA2, and RSV fusion glycoprotein subunit vaccine.

Non-limiting examples of other active therapeutic agents active against metapneumovirus infections include sialidase modulators such as DAS-181; RNA polymerase inhibitors, such as ALS-8112; and antibodies for the treatment of Metapneumovirus infections, such as EV-046113.

In some embodiments, the other active therapeutic agent may be a vaccine for the treatment or prevention of metapneumovirus infections, including but not limited to mRNA-1653 and rHMPV-Pa vaccine.

2. Combination Therapy for the Treatment of Picornaviridae

The compounds provided herein are also used in combination with other active therapeutic agents. For the treatment of Picornaviridae virus infections, preferably, the other active therapeutic agent is active against Picornaviridae virus infections, particularly Enterovirus infections. Non-limiting examples of these other active therapeutic agents are capsid binding inhibitors such as pleconaril, BTA-798 (vapendavir) and other compounds disclosed by Wu, et al. (U.S. Pat. No. 7,078,403) and Watson (U.S. Pat. No. 7,166,604); fusion sialidase protein such as DAS-181; a capsid protein VPI inhibitor such as VVX-003 and AZN-001; a viral protease inhibitor such as CW-33; a phosphatidylinositol 4 kinase beta inhibitor such as GSK-480 and GSK-533; anti-EV71 antibody.

In some embodiments, the other active therapeutic agent may be a vaccine for the treatment or prevention of Picornaviridae virus infections, including but not limited to EV71 vaccines, TAK-021, and EV-D68 adenovector-based vaccine.

3. Combination Therapy for Respiratory Infections

Many of the infections of the Pneumoviridae, Picomaviridae, and Coronaviridae viruses are respiratory infections. Therefore, additional active therapeutics used to treat respiratory symptoms and sequelae of infection may be used in combination with the compounds provided herein. The additional agents are preferably administered orally or by direct inhalation. For example, other preferred additional therapeutic agents in combination with the compounds provided herein for the treatment of viral respiratory infections include, but are not limited to, bronchodilators and corticosteroids.

Glucocorticoids

Glucocorticoids, which were first introduced as an asthma therapy in 1950 (Carryer. Journal of Allergy, 21, 282-287, 1950), remain the most potent and consistently effective therapy for this disease, although their mechanism of action is not yet fully understood (Morris, J. Allergy Clin. Immunol., 75 (1 Pt) 1-13, 1985). Unfortunately, oral glucocorticoid therapies are associated with profound undesirable side effects such as truncal obesity, hypertension, glaucoma, glucose intolerance, acceleration of cataract formation, bone mineral loss, and psychological effects, all of which limit their use as long-term therapeutic agents (Goodman and Gilman, 10th edition, 2001). A solution to systemic side effects is to deliver steroid drugs directly to the site of inflammation. Inhaled corticosteroids (ICS) have been developed to mitigate the severe adverse effects of oral steroids. Non-limiting examples of corticosteroids that may be used in combinations with the compounds provided herein are dexamethasone, dexamethasone sodium phosphate, fluorometholone, fluorometholone acetate, loteprednol, loteprednol etabonate, hydrocortisone, prednisolone, fludrocortisones, triamcinolone, triamcinolone acetonide, betamethasone, beclomethasone diproprionate, methylprednisolone, fluocinolone, fluocinolone acetonide, flunisolide, fluocortin-21-butylate, flumethasone, flumetasone pivalate, budesonide, halobetasol propionate, mometasone furoate, fluticasone, AZD-7594, ciclesonide; or a pharmaceutically acceptable salts thereof.

Anti-Inflammatory Agents

Other anti-inflammatory agents working through anti-inflammatory cascade mechanisms are also useful as additional therapeutic agents in combination with the compounds provided herein for the treatment of viral respiratory infections. Applying "anti-inflammatory signal transduction modulators" (referred to in this text as AISTM), like phosphodiesterase inhibitors (e.g., PDE-4, PDE-5, or PDE-7 specific), transcription factor inhibitors (e.g., blocking NFκB through IKK inhibition), or kinase inhibitors (e.g., blocking P38 MAP, JNK, PI3K, EGFR or Syk) is a logical approach to switching off inflammation as these small molecules target a limited number of common intracellular pathways—those signal transduction pathways that are critical points for the anti-inflammatory therapeutic intervention (see review by P. J. Barnes, 2006). These non-limiting additional therapeutic agents include: 5-(2,4-Difluoro-phenoxy)-1-isobutyl-1H-indazole-6-carboxylic acid (2-dimethylamino-ethyl)-amide (P38 Map kinase inhibitor ARRY-797); 3-Cyclopropylmethoxy-N-(3,5-dichloro-pyridin-4-yl)-4-difluorormethoxy-benzamide (PDE-4 inhibitor Roflumilast); 4-[12-(3-cyclopentyloxy-4-methoxyphenyl)-2-phenyl-ethyl]-pyridine (PDE-4 inhibitor CDP-840); N-(3,5-dichloro-4-pyridinyl)-4-(difluoromethoxy)-8-[(methylsulfonyl)amino]-1-dibenzofurancarboxamide (PDE-4 inhibitor Oglemilast); N-(3,5-Dichloro-pyridin-4-yl)-2-[1-(4-fluorobenzyl)-5-hydroxy-1H-indol-3-yl]-2-oxo-acetamide (PDE-4 inhibitor AWD 12-281); 8-Methoxy-2-trifluoromethyl-quinoline-5-carboxylic acid (3,5-dichloro-1-oxy-pyridin-4-yl)-amide (PDE-4 inhibitor Sch 351591);

4-[5-(4-Fluorophenyl)-2-(4-methanesulfinyl-phenyl)-1H-imidazol-4-yl]-pyridine (P38 inhibitor SB-203850); 4-[4-(4-Fluoro-phenyl)-1-(3-phenyl-propyl)-5-pyridin-4-yl-1H-imidazol-2-yl]-but-3-yn-1-ol (P38 inhibitor RWJ-67657); 4-Cyano-4-(3-cyclopentyloxy-4-methoxy-phenyl)-cyclohexanecarboxylic acid 2-diethylanuno-ethyl ester (2-diethyl-ethyl ester prodrug of Cilomilast, PDE-4 inhibitor); (3-Chloro-4-fluorophenyl)-[7-methoxy-6-(3-morpholin-4-yl-propoxy)-quinazolin-4-yl]-amine (Gefitinib, EGFR inhibitor); and 4-(4-Methyl-piperazin-1-ylmethyl)-N-[4-methyl-3-(4-pyridin-3-yl-pyrimidin-2-ylamino)-phenyl]-benzamide (Imatinib, EGFR inhibitor).

β2-Adrenoreceptor Agonist Bronchodilators

Combinations comprising inhaled β2-adrenoreceptor agonist bronchodilators such as formoterol, albuterol or salmeterol with the compounds provided herein are also suitable, but non-limiting, combinations useful for the treatment of respiratory viral infections.

Combinations of inhaled β2-adrenoreceptor agonist bronchodilators such as formoterol or salmeterol with ICS's are also used to treat both the bronchoconstriction and the inflammation (Symbicort® and Advair®, respectively). The combinations comprising these ICS and β2-adrenoreceptor agonist combinations along with the compounds provided herein are also suitable, but non-limiting, combinations useful for the treatment of respiratory viral infections.

Other examples of Beta 2 adrenoceptor agonists are bedoradrine, vilanterol, indacaterol, olodaterol, tulobuterol, formoterol, abediterol, salbutamol, arformoterol, levalbuterol, fenoterol, and TD-5471.

Anticholinergics

For the treatment or prophylaxis of pulmonary bronchoconstriction, anticholinergics are of potential use and, therefore, useful as an additional therapeutic agent in combination with the compounds provided herein for the treatment of viral respiratory infections. These anticholinergics include, but are not limited to, antagonists of the muscarinic receptor (particularly of the M3 subtype) which have shown therapeutic efficacy in man for the control of cholinergic tone in COPD (Witek, 1999); 1-{4-Hydroxy-1-[3,3,3-tris-(4-fluoro-phenyl)-propionyl]-pyrrolidine-2-carbonyl}-pyrrolidine-2-carboxylic acid (1-methyl-piperidin-4-ylmethyl)-amide; 3-[3-(2-Diethylamino-acetoxy)-2-phenyl-propionyloxy]-8-isopropyl-8-methyl-8-azonia-bicyclo[3.2.1]octane (Ipratropium-N,N-diethylglycinate); 1-Cyclohexyl-3,4-dihydro-1H-isoquinoline-2-carboxylic acid 1-aza-bicyclo[2.2.2]oct-3-yl ester (Solifenacin); 2-Hydroxymethyl-4-methanesulfinyl-2-phenyl-butyric acid 1-aza-bicyclo[2.2.2]oct-3-yl ester (Revatropate); 2-{1-[2-(2,3-Dihydro-benzofuran-5-yl)-ethyl]-pyrrolidin-3-yl}-2,2-diphenyl-acetamide (Darifenacin); 4-Azepan-1-yl-2,2-diphenyl-butyramide (Buzepide); 7-[3-(2-Diethylamino-acetoxy)-2-phenyl-propionyloxy]-9-ethyl-9-methyl-3-oxa-9-azonia-tricyclo[3.3.1.02,4]nonane (Oxitropium-N,N-diethylglycinate); 7-[2-(2-Diethylamino-acetoxy)-2,2-di-thiophen-2-yl-acetoxy]-9,9-dimethyl-3-oxa-9-azonia-tricyclo[3.3.1.02,4]nonane (Tiotropium-N,N-diethylglycinate); Dimethylamino-acetic acid 2-(3-diisopropylamino-1-phenyl-propyl)-4-methyl-phenyl ester (Tolterodine-N,N-dimethylglycinate); 3-[4,4-Bis-(4-fluoro-phenyl)-2-oxo-imidazolidin-1-yl]-1-methyl-1-(2-oxo-2-pyridin-2-yl-ethyl)-pyrrolidinium; 1-[1-(3-Fluoro-benzyl)-piperidin-4-yl]-4,4-bis-(4-fluoro-phenyl)-imidazolidin-2-one; 1-Cyclooctyl-3-(3-methoxy-1-aza-bicyclo[2.2.2]oct-3-yl)-1-phenyl-prop-2-yn-1-ol; 3-[2-(2-Diethylamino-acetoxy)-2,2-di-thiophen-2-yl-acetoxy]-1-(3-phenoxy-propyl)-1-azonia-bicyclo[2.2.2]octane (Aclidinium-N,N-diethylglycinate); or (2-Diethylamino-acetoxy)-di-thiophen-2-yl-acetic acid 1-methyl-1-(2-phenoxy-ethyl)-piperidin-4-yl ester; revefenacin, glycopyrronium bromide, umeclidinium bromide, tiotropium bromide, aclidinium bromide, bencycloquidium bromide.

Mucolytic Agents

The compounds provided herein may also be combined with mucolytic agents to treat both the infection and symptoms of respiratory infections. A non-limiting example of a mucolytic agent is ambroxol. Similarly, the compounds may be combined with expectorants to treat both the infection and symptoms of respiratory infections. A non-limiting example of an expectorant is guaifenesin.

Nebulized hypertonic saline is used to improve immediate and long-term clearance of small airways in patients with lung diseases (Kuzik, *J. Pediatrics* 2007, 266). Thus, the compounds provided herein may also be combined with nebulized hypertonic saline particularly when the virus infection is complicated with bronchiolitis. The combination of the compound provided herein with hypertonic saline may also comprise any of the additional agents discussed above. In one embodiment, nebulized about 3% hypertonic saline is used.

4. Combination Therapy for the Treatment of Flaviviridae Virus Infections

The compounds and compositions provided herein are also used in combination with other active therapeutic agents. For the treatment of Flaviviridae virus infections, preferably, the other active therapeutic agent is active against Flaviviridae virus infections.

For treatment of the dengue virus infection, non-limiting examples of the other active therapeutic agents are host cell factor modulators, such as GBV-006; fenretinide ABX-220, BRM-211; alpha-glucosidase 1 inhibitors, such as celgosivir; platelet activating factor receptor (PAFR) antagonists, such as modipafant; cadherin-5/Factor Ia modulators, such as FX-06; NS4B inhibitors, such as JNJ-8359; viral RNA splicing modulators, such as ABX-202; a NS5 polymerase inhibitor; a NS3 protease inhibitor; and a TLR modulator.

In some embodiments, the other active therapeutic agent may be a vaccine for the treatment or prevention of dengue, including but not limited to TetraVax-DV, Dengvaxia®, DPIV-001, TAK-003, live attenuated dengue vaccine, tetravalent dengue fever vaccine, tetravalent DNA vaccine, rDEN2delta30-7169; and DENV-1 PIV.

5. Combination Therapy for the Treatment of Filoviridae Virus Infections

The compounds provided herein are also used in combination with other active therapeutic agents. For the treatment of Filoviridae virus infections, preferably, the other active therapeutic agent is active against Filoviridae virus infections, particularly Marburg virus, Ebola virus and Cueva virus infections. Non-limiting examples of these other active therapeutic agents are: ribavirin, amiodarone, dronedarone, verapamil, Ebola Convalescent Plasma (ECP), TKM-100201, BCX4430 ((2S,3S,4R,5R)-2-(4-amino-5H-pyrrolo[3,2-d]pyrimidin-7-yl)-5-(hydroxymethyl)pyrrolidine-3,4-diol), TKM-Ebola, T-705 monophosphate, T-705 diphosphate, T-705 triphosphate, FGI-106 (1-N,7-N-bis[3-(dimethylamino)propyl]-3,9-dimethylquinolino[8,7-h]quinolone-1,7-diamine), rNAPc2, OS-2966, brincidofovir, remdesivir; RNA polymerase inhibitors, such as galidesivir, favipiravir (also known as T-705 or Avigan), JK-05; host cell factor modulators, such as GMV-006; cadherin-5/factor Ia modulators, such as FX-06; and antibodies for the treatment of Ebola, such as REGN-3470-3471-3479 and ZMapp.

Other non-limiting active therapeutic agents active against Ebola include an alpha-glucosidase 1 inhibitor, a cathepsin B inhibitor, a CD29 antagonist, a dendritic ICAM-3 grabbing nonintegrin 1 inhibitor, an estrogen receptor antagonist, a factor VII antagonist HLA class II antigen modulator, a host cell factor modulator, a Interferon alpha ligand, a neutral alpha glucosidase AB inhibitor, a niemann-Pick C1 protein inhibitor, a nucleoprotein inhibitor, a polymerase cofactor VP35 inhibitor, a Serine protease inhibitor, a tissue factor inhibitor, a TLR-3 agonist, a viral envelope glycoprotein inhibitor, and an Ebola virus entry inhibitors (NPC1 inhibitors).

In some embodiments, the other active therapeutic agent may be a vaccine for the treatment or prevention of Ebola, including but not limited to VRC-EBOADC076-00-VP, adenovirus-based Ebola vaccine, rVSV-EBOV, rVSVN4CT1-EBOVGP, MVA-BN Filo+Ad26-ZEBOV regimen, INO-4212, VRC-EBODNA023-00-VP, VRC-EBOADC069-00-VP, GamEvac-combi vaccine, SRC VB Vector, HPiV3/EboGP vaccine, MVA-EBOZ. Ebola recombinant glycoprotein vaccine. Vaxart adenovirus vector 5-based Ebola vaccine, FiloVax vaccine, GOVX-E301, and GOVX-E302.

The compounds provided herein may also be used in combination with phosphoramidate morpholino oligomers (PMOs), which are synthetic antisense oligonucleotide analogs designed to interfere with translational processes by forming base-pair duplexes with specific RNA sequences. Examples of PMOs include but are not limited to AVI-7287, AVI-7288, AVI-7537, AVI-7539, AVI-6002, and AVI-6003.

The compounds provided herein are also intended for use with general care provided to patients with Filoviridae viral infections, including parenteral fluids (including dextrose saline and Ringer's lactate) and nutrition, antibiotic (including metronidazole and cephalosporin antibiotics, such as ceftriaxone and cefuroxime) and/or antifungal prophylaxis, fever and pain medication, antiemetic (such as metoclopramide) and/or antidiarrheal agents, vitamin and mineral supplements (including Vitamin K and zinc sulfate), anti-inflammatory agents (such as ibuprofen), pain medications, and medications for other common diseases in the patient population, such anti-malarial agents (including artemether and artesunate-lumefantrine combination therapy), typhoid (including quinolone antibiotics, such as ciprofloxacin, macrolide antibiotics, such as azithromycin, cephalosporin antibiotics, such as cefiriaxone, or aminopenicillins, such as ampicillin), or shigellosis.

The invention will be described in greater detail by way of specific examples. The following examples are offered for illustrative purposes and are not intended to limit the invention in any manner. Those of skill in the art will readily recognize a variety of non-critical parameters, which can be changed or modified to yield essentially the same results.

6. Combination Therapy for the Treatment of Coronaviridae Virus Infections

In some embodiments, the additional therapeutic agent a 2,5-Oligoadenylate synthetase stimulator, 5-HT 2a receptor antagonist, 5-Lipoxygenase inhibitor, ABL family tyrosine kinase inhibitor, Abl tyrosine kinase inhibitor, Acetaldehyde dehydrogenase inhibitor, Acetyl CoA carboxylase inhibitor, Actin antagonist, Actin modulator, Activity-dependent neuroprotector modulator, Adenosine A3 receptor agonist, Adrenergic receptor antagonist, Adrenomedullin ligand, Adrenomedullin ligand inhibitor, Advanced glycosylation product receptor antagonist. Advanced glycosylation product receptor modulator, AKT protein kinase inhibitor, Alanine proline rich secreted protein stimulator, Aldose reductase inhibitor, Alkaline phosphatase stimulator, Alpha 2 adrenoceptor antagonist, Alpha 2B adrenoceptor agonist, AMP activated protein kinase stimulator, AMPA receptor modulator, Amyloid protein deposition inhibitor, Androgen receptor antagonist, Angiotensin II AT-1 receptor antagonist, Angiotensin II AT-2 receptor agonist, Angiotensin II receptor modulator, Angiotensin converting enzyme 2 inhibitor, Angiotensin converting enzyme 2 modulator, Angiotensin converting enzyme 2 stimulator, Angiotensin receptor modulator, Annexin A5 stimulator, Anoctamin 1 inhibitor, Anti-coagulant. Anti-histamine, Anti-hypoxic, Anti-thrombotic, AP1 transcription factor modulator, Apelin receptor agonist, APOA1 gene stimulator, Apolipoprotein A1 agonist, Apolipoprotein B antagonist, Apolipoprotein B modulator, Apolipoprotein C3 antagonist, Aryl hydrocarbon receptor agonist, Aryl hydrocarbon receptor antagonist, ATP binding cassette transporter B5 modulator, Axl tyrosine kinase receptor inhibitor, Bactericidal permeability protein inhibitor, Basigin inhibitor, Basigin modulator, BCL2 gene inhibitor, BCL2L11 gene stimulator, Bcr protein inhibitor, Beta 1 adrenoceptor modulator, Beta 2 adrenoceptor agonist, Beta adrenoceptor agonist, Beta-arrestin stimulator, Blood clotting modulator, BMP10 gene inhibitor, BMP15 gene inhibitor, Bone morphogenetic protein-10 ligand inhibitor, Bone morphogenetic protein-15 ligand inhibitor, Bradykinin B2 receptor antagonist, Brain derived neurotrophic factor ligand, Bromodomain containing protein 2 inhibitor, Bromodomain containing protein 4 inhibitor, Btk tyrosine kinase inhibitor, C-reactive protein modulator, Ca2+ release activated Ca2+ channel 1 inhibitor, Cadherin-5 modulator, Calcium activated chloride channel inhibitor, Calcium channel modulator, Calpain-I inhibitor, Calpain-II inhibitor, Calpain-IX inhibitor, Cannabinoid CB2 receptor agonist, Cannabinoid receptor modulator, Casein kinase II inhibitor, CASP8-FADD-like regulator inhibitor, Caspase inhibitor, Catalase stimulator, CCL26 gene inhibitor, CCR2 chemokine antagonist, CCR5 chemokine antagonist, CD11a agonist, CD122 agonist, CD3 antagonist, CD4 agonist, CD40 ligand, CD40 ligand modulator. CD40 ligand receptor agonist, CD40 ligand receptor modulator, CD49d agonist, CD70 antigen modulator, CD73 agonist, CD73 antagonist, CD95 antagonist, CFTR inhibitor, CGRP receptor antagonist, Chemokine receptor-like 1 agonist, Chloride channel inhibitor, Chloride channel modulator, Cholera enterotoxin subunit B inhibitor, Cholesterol ester transfer protein inhibitor, Collagen modulator, Complement C1s subcomponent inhibitor, Complement C3 inhibitor, Complement C5 factor inhibitor, Complement C5a factor inhibitor, Complement Factor H stimulator, Complement cascade inhibitor, Complement factor C2 inhibitor, Complement factor D inhibitor. Connective tissue growth factor ligand inhibitor, Coronavirus nucleoprotein modulator, Coronavirus small envelope protein modulator, Coronavirus spike glycoprotein inhibitor, Coronavirus spike glycoprotein modulator. COVID19 envelope small membrane protein modulator, COVID19 non structural protein 8 modulator, COVID19 nucleoprotein modulator, COVID19 Protein 3a inhibitor, COVID19 replicase polyprotein 1a inhibitor, COVID19 replicase polyprotein 1a modulator, COVID19 replicase polyprotein 1ab inhibitor, COVID19 replicase polyprotein 1ab modulator, COVID19 Spike glycoprotein inhibitor, COVID19 Spike glycoprotein modulator, COVID19 structural glycoprotein modulator, CRF-2 receptor agonist, CSF-1 agonist, CSF-1 antagonist, CX3CR1 chemokine antagonist, CXC10 chemokine ligand inhibitor, CXC5 chemokine ligand inhibitor, CXCL1 gene modulator, CXCL2 gene modulator, CXCL3 gene modulator, CXCR1 chemokine antagonist, CXCR2 chemokine antagonist, CXCR4 chemokine antagonist, Cyclin D1 inhibitor, Cyclin E inhibitor, Cyclin-dependent kinase-1 inhibitor, Cyclin-dependent kinase-2 inhibitor, Cyclin-dependent kinase-5 inhibitor, Cyclin-dependent kinase-7 inhibitor, Cyclin-dependent kinase-9 inhibitor. Cyclooxygenase 2 inhibitor, Cyclooxygenase inhibitor, Cyclophilin inhibitor, Cysteine protease inhibitor, Cytochrome P450 3A4 inhibitor, Cytokine receptor antagonist, Cytotoxic T lymphocyte protein gene modulator, Cytotoxic T-lymphocyte protein-4 inhibitor, Cytotoxic T-lymphocyte protein-4 stimulator, DDX3 inhibitor, Dehydrogenase inhibitor, Dehydropeptidase-1 modulator, Deoxyribonuclease 1 stimulator, Deoxyribonuclease gamma stimulator, Deoxyribonuclease stimulator, Dihydroceramide delta 4 desaturase inhibitor, Dihydroorotate dehydrogenase inhibitor, Dipeptidyl peptidase 1 inhibitor, Dipeptidyl peptidase III inhibitor, Diuretic, DNA binding protein inhibitor, DNA methyltransferase inhibitor, Dopamine transporter inhibitor, E selectin antagonist, Ecto NOX disulfide thiol exchanger 2 inhibitor, EGFR gene inhibitor, Elongation factor 1 alpha 2 modulator, Endoplasmin modulator, Endoribonuclease DICER modulator. Endothelin ET-A receptor antagonist. Epidermal growth factor receptor antagonist. E-selectin antagonist, Estrogen receptor beta agonist, Estrogen receptor modulator, Eukaryotic initiation factor 4A-I inhibitor, Exo-alpha sialidase modulator, Exportin 1 inhibitor, Factor 1a modulator, Factor IIa modulator. Factor VII antagonist, Factor Xa antagonist, Factor XIa antagonist, FGF receptor antagonist, FGF-1 ligand, FGF-1 ligand inhibitor, FGF-2 ligand inhibitor, FGF1 receptor antagonist, FGF2 receptor antagonist, FGF3 receptor antagonist, Flt3 tyrosine kinase inhibitor, Fractalkine ligand inhibitor, Free fatty acid receptor 2 agonist, Free fatty acid receptor 3 agonist, furin inhibitors, Fyn tyrosine kinase inhibitor, FYVE finger phosphoinositide kinase inhibitor, G-protein coupled bile acid receptor 1 agonist, GABA A receptor modulator, Galectin-3 inhibitor, Gamma-secretase inhibitor, GDF agonist, Gelsolin stimulator, Glial cell neurotrophic factor ligand, Glucocorticoid receptor agonist. Glutathione peroxidase stimulator, GM-CSF ligand inhibitor, GM-CSF receptor agonist. GM-CSF receptor modulator, Griflithsin modulator, Growth regulated protein alpha ligand inhibitor, Grp78 calcium binding protein inhibitor, Heat shock protein HSP90 alpha inhibitor, Heat shock protein HSP90 beta inhibitor, Heat shock protein inhibitor, Heat shock protein stimulator, Hemagglutinin modulator, Hemoglobin modulator, Hemolysin alpha inhibitor, Heparanase inhibitor, Heparin agonist, Hepatitis B structural protein inhibitor, Hepatitis C virus NS5B polymerase inhibitor, HIF prolyl hydroxylase inhibitor. HIF prolyl hydroxylase-2 inhibitor, High mobility group protein BI inhibitor, Histamine H1 receptor antagonist, Histamine H2 receptor antagonist, Histone deacetylase-6 inhibitor, Histone inhibitor, HIV protease inhibitor, HIV-1 gp120 protein inhibitor, HIV-1 protease inhibitor, HIV-1 reverse transcriptase inhibitor, HLA class I antigen modulator, HLA class II antigen modulator, Host cell factor modulator. Hsp 90 inhibitor, Human papillomavirus E6 protein modulator, Human papillomavirus E7 protein modulator, Hypoxia inducible factor inhibitor gene inhibitor, Hypoxia inducible factor-2 alpha modulator, 1-kappa B kinase inhibitor, I-kappa B kinase inhibitor, ICAM-1 stimulator, IgG receptor FcRn large subunit p51 modulator, IL-12 receptor antagonist, IL-15 receptor agonist, IL-15 receptor modulator, IL-17 antagonist, IL-18 receptor accessory protein antagonist, IL-2 receptor agonist, IL-22 agonist, IL-23 antagonist, IL-6 receptor agonist, IL-6 receptor antagonist, IL-6 receptor modulator, IL-7 receptor agonist, IL-8 receptor antagonist, IL12 gene stimulator, IL8 gene modulator, Immunoglobulin G modulator, Immunoglobulin G1 agonist, Immunoglobulin GI modulator, Immunoglobulin agonist, Immunoglobulin gamma Fc receptor 1 modulator, Immunoglobulin kappa modulator, Inosine monophosphate dehydrogenase inhibitor, Insulin sensitizer, Integrin agonist, Integrin alpha-4/beta-7 antagonist, Integrin alpha-V/beta-1 antagonist, Integrin alpha-V/beta-6 antagonist, Interferon agonist, Interferon alpha 14 ligand, Interferon alpha 2 ligand, Interferon alpha 2 ligand modulator, Interferon alpha ligand, Interferon alpha ligand inhibitor. Interferon alpha ligand modulator, Interferon beta ligand, Interferon gamma ligand inhibitor, Interferon gamma receptor agonist. Interferon gamma receptor antagonist, Interferon receptor modulator, Interferon type I receptor agonist, Interleukin 17A ligand inhibitor, Interleukin 17F ligand inhibitor, Interleukin 18 ligand inhibitor, Interleukin 22 ligand. Interleukin-1 beta ligand inhibitor, Interleukin-1 beta ligand modulator, Interleukin-1 ligand inhibitor, Interleukin-2 ligand, Interleukin-29 ligand, Interleukin-6 ligand inhibitor, Interleukin-7 ligand, Interleukin-8 ligand inhibitor, IRAK-4 protein kinase inhibitor, JAK tyrosine kinase inhibitor, Jak1 tyrosine kinase inhibitor, Jak2 tyrosine kinase inhibitor, Jak3 tyrosine kinase inhibitor, Jun N terminal kinase inhibitor, Jun N terminal kinase modulator, Kallikrein modulator, Kelch like ECH associated protein 1 modulator, Kit tyrosine kinase inhibitor, KLKB1 gene inhibitor, Lactoferrin stimulator, Lanosterol-14 demethylase inhibitor, Lck tyrosine kinase inhibitor, Leukocyte Ig like receptor A4 modulator, Leukocyte elastase inhibitor, Leukotriene BLT receptor antagonist, Leukotriene D4 antagonist, Leukotriene receptor antagonist, Listeriolysin stimulator, Liver X receptor antagonist. Low molecular weight heparin. Lung surfactant associated protein B stimulator, Lung surfactant associated protein D modulator, Lyn tyrosine kinase inhibitor. Lyn tyrosine kinase stimulator, Lysine specific histone demethylase 1 inhibitor, Macrophage migration inhibitory factor inhibitor, Mannan-binding lectin serine protease inhibitor, Mannan-binding lectin serine protease-2 inhibitor, MAO B inhibitor, MAP kinase inhibitor, MAPK gene modulator, Matrix metalloprotease modulator, Maxi K potassium channel inhibitor, MCLI gene inhibitor, MEK protein kinase inhibitor, MEK-1 protein kinase inhibitor, Melanocortin MCI receptor agonist, Melanocortin MC3 receptor agonist, Metalloprotease-12 inhibitor, METTL3 gene inhibitor. Moesin inhibitor, Moesin modulator, Monocyte chemotactic protein 1 ligand inhibitor, Monocyte differentiation antigen CD14 inhibitor, mRNA cap guanine N7 methyltransferase modulator, mTOR complex 1 inhibitor, mTOR complex 2 inhibitor, mTOR inhibitor, Mucolipin modulator, Muscarinic receptor antagonist, Myeloperoxidase inhibitor, NACHT LRR PYD domain protein 3 inhibitor, NAD synthase modulator, NADPH oxidase inhibitor, Neuropilin 2 modulator, Neuroplastin inhibitor, NFE2L2 gene stimulator, NK cell receptor agonist, NK1 receptor antagonist, NMDA receptor antagonist, NMDA receptor epsilon 2 subunit inhibitor, Non receptor tyrosine kinase TYK2 antagonist, Non-nucleoside reverse transcriptase inhibitor. Nuclear erythroid 2-related factor 2 stimulator, Nuclear factor kappa B inhibitor, Nuclear factor kappa B modulator, Nuclease stimulator, Nucleolin inhibitor, Nucleoprotein inhibitor, Nucleoprotein modulator, Nucleoside reverse transcriptase inhibitor, Opioid receptor agonist, Opioid receptor antagonist, Opioid receptor mu modulator, Opioid receptor sigma antagonist 1, Ornithine decarboxylase inhibitor, Outer membrane protein inhibitor, OX40 ligand, p38 MAP kinase alpha inhibitor, p38 MAP kinase inhibitor, p38 MAP kinase modulator, p53 tumor suppressor protein stimulator, Palmitoyl protein thioesterase 1 inhibitor, Papain inhibitor, PARP inhibitor, PARP modulator, PDE 10 inhibitor, PDE 3 inhibitor, PDE 4 inhibitor, PDGF receptor alpha antagonist, PDGF receptor antagonist, PDGF receptor beta antagonist, Peptidyl-prolyl cis-trans isomerase A inhibitor, Peroxiredoxin 6 modulator, PGD2 antagonist, PGI2 agonist, P-glycoprotein inhibitor, Phosphoinositide 3-kinase inhibitor, Phosphoinositide-3 kinase delta inhibitor, Phosphoinositide-3 kinase gamma inhibitor, Phospholipase A2 inhibitor, Plasma kallikrein inhibitor, Plasminogen activator inhibitor 1 inhibitor, Platelet inhibitor, Platelet glycoprotein VI inhibitor, Polo-like kinase 1 inhibitor, Poly ADP ribose polymerase 1 inhibitor, Poly ADP ribose polymerase 2 inhibitor, Polymerase cofactor VP35 inhibitor, PPAR alpha agonist, Progesterone receptor agonist, Programmed cell death protein 1 modulator, Prolyl hydroxylase inhibitor, Prostaglandin E synthase-1 inhibitor. Protease inhibitor, Proteasome inhibitor, Protein arginine deiminase IV inhibitor, Protein tyrosine kinase inhibitor, Protein tyrosine phosphatase beta inhibitor, Protein tyrosine phosphatase-2C inhibitor, Proto-oncogene Mas agonist, Purinoceptor antagonist, Raf protein kinase inhibitor, RANTES ligand, Ras gene inhibitor, Retinoate receptor responder protein 2 stimulator, Rev protein modulator, Ribonuclease stimulator, RIP-1 kinase inhibitor, RNA helicase inhibitor, RNA polymerase inhibitor, RNA polymerase modulator, S phase kinase associated protein 2 inhibitor, SARS coronavirus 3C protease like inhibitor, Serine protease inhibitor, Serine threonine protein kinase ATR inhibitor, Serine threonine protein kinase TBK1 inhibitor, Serum amvloid A protein modulator, Signal transducer CD24 stimulator, Sodium channel stimulator, Sodium glucose transporter-2 inhibitor, Sphingosine kinase 1 inhibitor, Sphingosine kinase 2 inhibitor, Sphingosine kinase inhibitor, Sphingosine-1-phosphate receptor-1 agonist, Sphingosine-1-phosphate receptor-1 antagonist, Sphingosine-1-phosphate receptor-1 modulator, Sphingosine-1-phosphate receptor-5 agonist. Sphingosine-1-phosphate receptor-5 modulator, Spike glycoprotein inhibitor, Src tyrosine kinase inhibitor, STAT-1 modulator, STAT-3 inhibitor, STAT-5 inhibitor, STAT3 gene inhibitor, Stem cell antigen-1 inhibitor, Stimulator of interferon genes protein stimulator, Sulfatase inhibitor, Superoxide dismutase modulator, Superoxide dismutase stimulator, Syk tyrosine kinase inhibitor, T cell immunoreceptor Ig ITIM protein inhibitor, T cell receptor agonist, T cell surface glycoprotein CD28 inhibitor, T-cell differentiation antigen CD6 inhibitor, T-cell surface glycoprotein CD8 stimulator, T-cell transcription factor NFAT modulator, Tankyrase-1 inhibitor, Tankyrase-2 inhibitor, Tek tyrosine kinase receptor stimulator, Telomerase modulator, Tetanus toxin modulator, TGF beta receptor antagonist, TGFB2 gene inhibitor, Thymosin beta 4 ligand, Thyroid hormone receptor beta agonist, Tissue factor inhibitor, Tissue plasminogen activator modulator, Tissue plasminogen activator stimulator, TLR agonist, TLR modulator, TLR-2 agonist, TLR-2 antagonist, TLR-3 agonist, TLR-4 agonist, TLR-4 antagonist, TLR-6 agonist, TLR-7 agonist, TLR-7 antagonist, TLR-8 antagonist, TLR-9 agonist, TMPRSS2 gene inhibitor. TNF alpha ligand inhibitor, TNF alpha ligand modulator, TNF binding agent, TNF gene inhibitor, Topoisomerase inhibitor, Transcription factor EB stimulator, Transferrin modulator, Transketolase inhibitor, Translocation associated protein inhibitor, Transmembrane serine protease 2 inhibitor, Transthyretin modulator, TREM receptor 1 antagonist, TRP cation channel C1 modulator, TRP cation channel C6 inhibitor, TRP cation channel V6 inhibitor, Trypsin 1 inhibitor, Trypsin 2 inhibitor, Trypsin 3 inhibitor, Trypsin inhibitor, Tubulin alpha inhibitor, Tubulin beta inhibitor. Tumor necrosis factor 14 ligand inhibitor. TYK2 gene inhibitor, Type I IL-1 receptor antagonist, Tyrosine protein kinase ABL1 inhibitor, Ubiquinol cytochrome C reductase 14 kDa inhibitor, Ubiquitin ligase modulator, Unspecified GPCR agonist, Unspecified cytokine receptor modulator, Unspecified enzyme stimulator, Unspecified gene inhibitor, Unspecified receptor modulator. Urokinase plasminogen activator inhibitor, Vascular cell adhesion protein 1 agonist, Vasodilator, VEGF ligand inhibitor, VEGF receptor antagonist, VEGF-1 receptor antagonist, VEGF-1 receptor modulator, VEGF-2 receptor antagonist, VEGF-3 receptor antagonist, Vimentin inhibitor. Vimentin modulator, VIP receptor agonist, Viral envelope protein inhibitor, Viral protease inhibitor, Viral protease modulator, Viral protein target modulator, Viral ribonuclease inhibitor, Viral structural protein modulator, Vitamin D3 receptor agonist, X-linked inhibitor of apoptosis protein inhibitor, Xanthine oxidase inhibitor, or Zonulin inhibitor.

In some embodiments, the compounds and compositions of the present disclosure may be administered in combination with a Sars-Cov-2 treatment, such as parenteral fluids (including dextrose saline and Ringer's lactate), nutrition, antibiotics (including azithromycin, metronidazole, amphotericin B, amoxicillin/clavulanate, trimethoprim/sulfamethoxazole. R-327 and cephalosporin antibiotics, such as cefiriaxone and cefuroxime), antifungal prophylaxis, fever and pain medication, antiemetic (such as metoclopramide) and/or antidiarrheal agents, vitamin and mineral supplements (including Vitamin K, vitamin D, cholecalciferol, vitamin C and zinc sulfate), anti-inflammatory agents (such as ibuprofen or steroids), corticosteroids such as dexamethasone, methylprednisolone, prednisone, mometasone, immunomodulatory medications (eg interferon), vaccines, and pain medications.

In some embodiments, the additional therapeutic agent is an Abl tyrosine kinase inhibitor, such as radotinib or imatinib.

In some embodiments, the additional therapeutic agent is an acetaldehyde dehydrogenase inhibitor, such as ADX-629.

In some embodiments, the additional therapeutic agent is an adenosine A3 receptor agonist, such as piclidenoson.

In some embodiments, the additional therapeutic agent is an adrenomedullin ligand such as adrenomedullin.

In some embodiments, the additional therapeutic agent is a p38 MAPK+PPAR gamma agonist/insulin sensitizer such as KIN-001.

In some embodiments, the additional therapeutic agent is a PPAR alpha agonist such as DWTC-5101 (fenofibrate choline).

In some embodiments, the additional therapeutic agent is a cyclophilin inhibitor such as rencofilstat.

In some embodiments, the additional therapeutic is a p38 MAP kinase inhibitor such as PRX-201 or Gen-1124.

In some embodiments, the additional therapeutic agent is an aldose reductase inhibitor, such as caficrestat.

In some embodiments, the additional therapeutic agent is an AMPA receptor modulator, such as traneurocin.

In some embodiments, the additional therapeutic agent is an annexin A5 stimulator, such as AP-01 or SY-005.

In some embodiments, the additional therapeutic agent is an apelin receptor agonist, such as CB-5064MM.

In some embodiments, the additional therapeutic agent is an anti-coagulant, such as heparins (heparin and low molecular weight heparin), aspirin, apixaban, dabigatran, edoxaban, argatroban, enoxaparin, or fondaparinux.

In some embodiments, the additional therapeutic agent is an androgen receptor antagonist such as bicalutamide, enzalutamide, or prutelutamide (proxalutamide).

In some embodiments, the additional therapeutic agent is anti-hypoxic, such as trans-sodium crocetinate.

In some embodiments, the additional therapeutic agent is an anti-thrombotic, such as defibrotide, rivaroxaban, alteplase, tirofiban, clopidogrel, prasugrel, bemiparin, bivalirudin, sulodexide, or tenecteplase.

In some embodiments, the additional therapeutic agent is an antihistamine, such as cloroperastine or clemastine.

In some embodiments, the additional therapeutic agent is an apolipoprotein A1 agonist, such as CER-001.

In some embodiments, the additional therapeutic agent is a phospholipase A2 inhibitor, such as icosapent ethyl.

In some embodiments, the additional therapeutic agent is an axl tyrosine kinase receptor inhibitor, such as bemcentinib.

In some embodiments, the additional therapeutic agent is a corticosteroid/beta 2 adrenoceptor agonist, such as budesonide+formoterol fumarate.

In some embodiments, the additional therapeutic agent is a BET bromodomain inhibitor/APOA1 gene stimulator such as apabetalone.

In some embodiments, the additional therapeutic agent is a blood clotting modulator, such as lanadelumab.

In some embodiments, the additional therapeutic agent is a bradykinin B2 receptor antagonist, such as icatibant.

In some embodiments, the additional therapeutic agent is an EGFR gene inhibitor/Btk tyrosine kinase inhibitor, such as abivertinib.

In some embodiments, the additional therapeutic agent is a Btk tyrosine kinase inhibitor, such as ibrutinib or zanubrutinib.

In some embodiments, the additional therapeutic agent is a calpain-I/II/IX inhibitor, such as BLD-2660.

In some embodiments, the additional therapeutic agent is a cannabinoid CB2 receptor agonist, such as ontemabez or PPP-003.

In some embodiments, the additional therapeutic agent is a Ca2+ release activated Ca2+ channel 1 inhibitor, such as zegocractin (CM-4620).

In some embodiments, the additional therapeutic agent is an ATR inhibitor, such as berzosertib.

In some embodiments, the additional therapeutic agent is a cadherin-5 modulator, such as FX-06.

In some embodiments, the additional therapeutic agent is a casein kinase II inhibitor, such as silmitasertib.

In some embodiments, the additional therapeutic agent is a caspase inhibitor, such as emricasan.

In some embodiments, the additional therapeutic agent is a catalase stimulator/superoxide dismutase stimulator, such as MP-1032.

In some embodiments, the additional therapeutic agent is a CCR2 chemokine antagonist/CCR5 chemokine antagonist such as cenicriviroc.

In some embodiments, the additional therapeutic agent is a CCR5 chemokine antagonist, such as maraviroc or leronlimab.

In some embodiments, the additional therapeutic agent is a CD122 agonist/IL-2 receptor agonist, such as bempegaldesleukm.

In some embodiments, the additional therapeutic agent is a CD73 agonist/interferon beta ligand, such as FP-1201.

In some embodiments, the additional therapeutic agent is a cholesterol ester transfer protein inhibitor, such as dalcetrapib.

In some embodiments, the additional therapeutic agent is a Mannan-binding lectin serine protease/complement C1s subcomponent inhibitor/myeloperoxidase inhibitor, such as RLS-0071.

In some embodiments, the additional therapeutic agent is a complement C5 factor inhibitor/leukotriene BLT receptor antagonist, such as nomacopan.

In some embodiments, the additional therapeutic agent is a complement C5 factor inhibitor, such as eculizumab, STSA-1002, zilucoplan.

In some embodiments, the additional therapeutic agent is a CXCR4 chemokine antagonist, such as plerixafor or motixafortide.

In some embodiments, the additional therapeutic agent is a cytochrome P450 3A4 inhibitor/peptidyl-prolyl cis-trans isomerase A inhibitor, such as alisporivir.

In some embodiments, the additional therapeutic agent is a cysteine protease inhibitor, such as SLV-213.

In some embodiments, the additional therapeutic agent is a dihydroorotate dehydrogenase inhibitor, such as Meds-433, brequinar, RP-7214, or emvododstat.

In some embodiments, the additional therapeutic agent is a dehydropeptidase-1 modulator, such as Metablok.

In some embodiments, the additional therapeutic agent is a dihydroorotate dehydrogenase inhibitor/IL-17 antagonist, such as vidofludimus.

In some embodiments, the additional therapeutic agent is a diuretic, such as an aldosterone antagonist, such as spironolactone.

In some embodiments, the additional therapeutic agent is a deoxyribonuclease I stimulator, such as GNR-039 or dornase alfa.

In some embodiments, the additional therapeutic agent is a NET inhibitor, such as NTR-441.

In some embodiments, the additional therapeutic agent is a dihydroceramide delta 4 desaturase inhibitor/sphingosine kinase 2 inhibitor, such as opaganib.

In some embodiments, the additional therapeutic agent is a DNA methyltransferase inhibitor, such as azacytidine.

In some embodiments, the additional therapeutic agent is an LXR antagonist, such as larsucosterol.

In some embodiments, the additional therapeutic agent is a dipeptidyl peptidase I inhibitor, such as brensocatib.

In some embodiments, the additional therapeutic agent is a protein arginine deiminase IV inhibitor, such as JBI-1044.

In some embodiments, the additional therapeutic agent is an elongation factor 1 alpha 2 modulator, such as plitidepsin.

In some embodiments, the additional therapeutic agent is a eukaryotic initiation factor 4A-I inhibitor, such as zotatifin.

In some embodiments, the additional therapeutic agent is an exo-alpha sialidase modulator, such as DAS-181.

In some embodiments, the additional therapeutic agent is an exportin 1 inhibitor, such as selinexor.

In some embodiments, the additional therapeutic agent is a fractalkine ligand inhibitor, such as KAND-567.

In some embodiments, the additional therapeutic agent is a FYVE finger phosphoinositide kinase inhibitor/IL-12 receptor antagonist/IL-23 antagonist, such as apilimod dimesylate.

In some embodiments, the additional therapeutic agent is a GABA A receptor modulator, such as brexanolone.

In some embodiments, the additional therapeutic agent is a glucocorticoid receptor agonist, such as ciclesonide, hydrocortisone, dexamethasone, dexamethasone phosphate, or 101-PGC-005.

In some embodiments, the additional therapeutic agent is a GM-CSF receptor agonist, such as sargramostim.

In some embodiments, the additional therapeutic agent is a GPCR agonist, such as esuberaprost sodium.

In some embodiments, the additional therapeutic agent is a Griffithsin modulator, such as Q-Griffithsin.

In some embodiments, the additional therapeutic agent is a leukotriene D4 antagonist, such as montelukast.

In some embodiments, the additional therapeutic agent is a histamine H1 receptor antagonist, such as ebastine, tranilast, levocetirizine dihydrochloride.

In some embodiments, the additional therapeutic agent is a histamine H2 receptor antagonist, such as famotidine.

In some embodiments, the additional therapeutic agent is a heat shock protein stimulator/insulin sensitizer/PARP inhibitor, such as BGP-15.

In some embodiments, the additional therapeutic agent is a histone inhibitor, such as STC-3141.

In some embodiments, the additional therapeutic agent is a histone deacetylase-6 inhibitor, such as CKD-506.

In some embodiments, the additional therapeutic agent is a HIF prolyl hydroxylase-2 inhibitor, such as desidustat.

In some embodiments, the additional therapeutic agent is an HIF prolyl hydroxylase inhibitor, such as vadadustat.

In some embodiments, the additional therapeutic agent is an IL-8 receptor antagonist, such as reparixin.

In some embodiments, the additional therapeutic agent is an IL-7 receptor agonist, such as CYT-107.

In some embodiments, the additional therapeutic agent is an IL-7 receptor agonist/interleukin-7 ligand, such as efineptakin alfa.

In some embodiments, the additional therapeutic agent is an IL-22 agonist, such as efmarodocokin alfa.

In some embodiments, the additional therapeutic agent is an IL-22 agonist/interleukin 22 ligand, such as F-652.

In some embodiments, the additional therapeutic agent is targeted to IL-33, such as tozorakimab.

In some embodiments, the additional therapeutic is an IL-15 agonist such as nogapendekin alfa.

In some embodiments, the additional therapeutic agent is an integrin alpha-V/beta-1 antagonist/integrin alpha-V/beta-6 antagonist, such as bexotegrast.

In some embodiments, the additional therapeutic agent is an interferon alpha 2 ligand, such as interferon alfa-2b or Virafin.

In some embodiments, the additional therapeutic agent is an interferon beta ligand, such as interferon beta-1a follow-on biologic, interferon beta-1b, or SNG-001.

In some embodiments, the additional therapeutic agent is an interferon receptor modulator, such as peginterferon lambda-1a.

In some embodiments, the additional therapeutic agent is an interleukin-2 ligand, such as aldesleukin.

In some embodiments, the additional therapeutic agent is an IRAK-4 protein kinase inhibitor, such as zimlovisertib.

In some embodiments, the additional therapeutic agent is a JAK inhibitor, for example the additional therapeutic agent is baricitinib, filgotinib, jaktinib, tofacitinib, or nezulcitinib (TD-0903).

In some embodiments, the additional therapeutic agent is a neutrophil elastase inhibitor, such as alvelestat.

In some embodiments, the additional therapeutic agent is a lung surfactant associated protein D modulator, such as AT-100.

In some embodiments, the additional therapeutic agent is a plasma kallikrein inhibitor, such as donidalorsen.

In some embodiments, the additional therapeutic agent is a lysine specific histone demethylase 1/MAO B inhibitor, such as vafidemstat.

In some embodiments, the additional therapeutic agent is a Mannan-binding lectin serine protease inhibitor, such as conestat alfa.

In some embodiments, the additional therapeutic agent is a maxi K potassium channel inhibitor, such as ENA-001.

In some embodiments, the additional therapeutic agent is a MEK protein kinase inhibitor, such as zapnometinib.

In some embodiments, the additional therapeutic agent is a MEK-1 protein kinase inhibitor/Ras gene inhibitor, such as antroquinonol.

In some embodiments, the additional therapeutic agent is a melanocortin MCI receptor agonist, such as PL-8177.

In some embodiments, the additional therapeutic agent is a melanocortin MCI/MC3 receptor agonist, such as resomelagon acetate.

In some embodiments, the additional therapeutic agent is a matrix metalloprotease-12 inhibitor, such as FP-025.

In some embodiments, the additional therapeutic agent is a NACHT LRR PYD domain protein 3 inhibitor, such as dapansutrile, DFV-890, or ZYIL-1.

In some embodiments, the additional therapeutic agent is a NADPH oxidase inhibitor, such as isuzinaxib.

In some embodiments, the additional therapeutic agent is a neuropilin 2 modulator, such as efzofitimod.

In some embodiments, the additional therapeutic agent is an NK1 receptor antagonist, such as aprepitant or tradipitant.

In some embodiments, the additional therapeutic agent is an NMDA receptor antagonist, such as transcrocetin or ifenprodil.

In some embodiments, the additional therapeutic agent is a nuclear factor kappa B inhibitor/p38 MAP kinase inhibitor, such as zenuzolac.

In some embodiments, the additional therapeutic agent is an omithune decarboxylase inhibitor, such as eflomithine.

In some embodiments, the additional therapeutic agent is an opioid receptor sigma antagonist 1, such as MR-309.

In some embodiments, the additional therapeutic agent is a PGD2 antagonist, such as asapiprant.

In some embodiments, the additional therapeutic agent is a PDGF receptor antagonist/TGF beta receptor antagonist/p38 MAP kinase inhibitor, such as deupirfenidone.

In some embodiments, the additional therapeutic agent is a phospholipase A2 inhibitor, such as varespladib methyl.

In some embodiments, the additional therapeutic agent is a phosphoinositide 3-kinase inhibitor/mTOR complex inhibitor, such as dactolisib.

In some embodiments, the additional therapeutic agent is a mTOR inhibitor, such as sirolimus.

In some embodiments, the additional therapeutic agent is a phosphoinositide-3 kinase delta/gamma inhibitor, such as duvelisib.

In some embodiments, the additional therapeutic agent is a plasminogen activator inhibitor 1 inhibitor, such as TM-5614.

In some embodiments, the additional therapeutic agent is a protein tyrosine phosphatase beta inhibitor, such as razuprotafib.

In some embodiments, the additional therapeutic agent is a RIP-1 kinase inhibitor, such as DNL-758 or SIR-0365.

In some embodiments, the additional therapeutic agent is a Rev protein modulator, such as obefazimod.

In some embodiments, the additional therapeutic agent is an S phase kinase associated protein 2 inhibitor, such as niclosamide, SCAI-502 or DWRX-2003.

In some embodiments, the additional therapeutic agent is a signal transducer CD24 stimulator, such as EXO-CD24.

In some embodiments, the additional therapeutic agent is a sodium glucose transporter-2 inhibitor, such as dapagliflozin propanediol.

In some embodiments, the additional therapeutic agent is a sodium channel stimulator, such as solnatide.

In some embodiments, the additional therapeutic agent is a sphingosine-1-phosphate receptor-1 agonist/sphingosine-1-phosphate receptor-5 agonist, such as ozanimod.

In some embodiments, the additional therapeutic agent is a non-steroidal anti-inflammatory drug, such as Ampion.

In some embodiments, the additional therapeutic agent is a superoxide dismutase stimulator, such as avasopasem manganese.

In some embodiments, the additional therapeutic agent is a Syk tyrosine kinase inhibitor, such as fostamatinib disodium.

In some embodiments, the additional therapeutic agent is a Tie2 tyrosine kinase receptor agonist, such as AV-001.

In some embodiments, the additional therapeutic agent is a TGFB2 gene inhibitor, such as trabedersen.

In some embodiments, the additional therapeutic agent is a tissue factor inhibitor, such as AB-201.

In some embodiments, the additional therapeutic agent is a TLR-3 agonist, such as rintatolimod.

In some embodiments, the additional therapeutic agent is a TLR-4 antagonist, such as ApTLR-4FT, EB-05, or eritoran.

In some embodiments, the additional therapeutic agent is a TLR-7/8 antagonist, such as enpatoran.

In some embodiments, the additional therapeutic agent is a TLR-2/6 agonist, such as INNA-051.

In some embodiments, the additional therapeutic agent is a TLR-7 agonist, such as PRTX-007 or APR-002.

In some embodiments, the additional therapeutic agent is a TLR agonist, such as PUL-042.

In some embodiments, the additional therapeutic agent is a TLR-4 agonist, such as REVTx-99.

In some embodiments, the additional therapeutic agent is a TLR-2/4 antagonist, such as VB-201.

In some embodiments, the additional therapeutic agent is a TNF alpha ligand inhibitor, such as pegipanermin.

In some embodiments, the additional therapeutic agent is a type I IL-1 receptor antagonist, such as anakinra.

In some embodiments, the additional therapeutic agent is a TREM receptor 1 antagonist, such as nangibotide.

In some embodiments, the additional therapeutic agent is a trypsin inhibitor, such as ulinastatin.

In some embodiments, the additional therapeutic agent is a tubulin inhibitor such as sabizabulin, CCI-001, PCNT-13, CR-42-24, albendazole, entasobulin. SAR-132885, or ON-24160.

In some embodiments, the additional therapeutic agent is a VIP receptor agonist, such as aviptadil.

In some embodiments, the additional therapeutic agent is a xanthine oxidase inhibitor, such as oxypurinol.

In some embodiments, the additional therapeutic agent is a vasodilator, such as iloprost, epoprostenol (VentaProst), zavegepant, TXA-127, USB-002, ambrisentan, nitric oxide nasal spray (NORS), pentoxifylline, propranolol, RESP301, sodium nitrite, or dipyridamole.

In some embodiments, the additional therapeutic agent is a vitamin D3 receptor agonist, such as cholecalciferol.

In some embodiments, the additional therapeutic agent is a zonulin inhibitor, such as larazotide acetate.

In some embodiments, the additional therapeutic agent is a synthetic retinoid derivative, such as fenretinide.

In some embodiments, the additional therapeutic agent is a glucose metabolism inhibitor such as WP-1122 or WP-1096.

In some embodiments, the additional therapeutic agent is adalimumab, AT-H201, 2-deoxy-D-glucose, AD-17002, AIC-649, AMTX-100, astodrimer, AZD-1656, belapectin, bitespiramycin, bucillamine, budesonide, CNM-AgZn-17, Codivir, CT-38, danicopan, didodecyl methotrexate, DW-2008S (DW-2008), EDP-1815, EG-009A, Fabencov, Gamunex, genistein, GLS-1200, hzVSF-v13, imidazolyl ethanamide pentandioic acid, IMM-101, MAS-825, MRG-001, Nasitrol, Nylexa, olverembatinib, OP-101, OPN-019, Orynotide rhesus theta defensin-1, pyronaridine+artesunate, dapsone, RPH-104, sodium pyruvate, Sulforadex, tafenoquine, TB-006, telacebec, Tempol, TL-895, thimesoral, trimodulin, XC-221, XC-7, zunsemetinib, metformin glycinate, lucinactant. EOM-613, mosedipimod, ivermectin, leflunomide, ibudilast, RBT-9, raloxifene, prothione, gemcabene, or idronoxil.

In some embodiments, the additional therapeutic agent is a CD73 antagonist, such as AK-119.

In some embodiments, the additional therapeutic agent is a CD95 protein fusion, such as asunercept.

In some embodiments, the additional therapeutic agent is a complement factor C2 modulator, such as ARGX-117.

In some embodiments, the additional therapeutic agent is a complement C3 inhibitor, such as AMY-101 or NGM-621.

In some embodiments, the additional therapeutic agent is a CXC10 chemokine ligand inhibitor, such as EB-06.

In some embodiments, the additional therapeutic agent is a cytotoxic T-lymphocyte protein-4 fusion protein, such as abatacept.

In some embodiments, the additional therapeutic agent is an anti-S. *Aureus* antibody, such as tosatoxumab.

In some embodiments, the additional therapeutic agent is an anti-LPS antibody, such as IMM-124-E.

In some embodiments, the additional therapeutic agent is an adrenomedullin ligand inhibitor, such as enibarcimab.

In some embodiments, the additional therapeutic agent is a basigin inhibitor, such as meplazumab.

In some embodiments, the additional therapeutic agent is a CD3 antagonist, such as foralumab.

In some embodiments, the additional therapeutic agent is a connective tissue growth factor ligand inhibitor, such as PRS-220, pamrevlumab.

In some embodiments, the additional therapeutic agent is a complement C5a factor inhibitor, such as BDB-1 or vilobelimab.

In some embodiments, the additional therapeutic agent is a complement C5 factor inhibitor, such as ravulizumab.

In some embodiments, the additional therapeutic agent is a mannan-binding lectin serine protease-2 inhibitor, such as narsoplimab.

In some embodiments, the additional therapeutic agent is a GM-CSF modulator, such as STSA-1005, gimsilumab, nanilumab, plonmarlimab, otilimab, or lenzilumab.

In some embodiments, the additional therapeutic agent is a heat shock protein inhibitor/IL-6 receptor antagonist, such as siltuximab.

In some embodiments, the additional therapeutic agent is an IL-6 receptor antagonist, such as clazakizumab, levilimab, olokizumab, tocilizumab, or sirukumab.

In some embodiments, the additional therapeutic agent is an IL-8 receptor antagonist, such as BMS-986253.

In some embodiments, the additional therapeutic agent is an interleukin-1 beta ligand inhibitor, such as canakinumab.

In some embodiments, the additional therapeutic agent is an interferon gamma ligand inhibitor, such as emapalumab.

In some embodiments, the additional therapeutic agent is an anti-ILT7 antibody, such as daxdilimab.

In some embodiments, the additional therapeutic agent is a monocyte differentiation antigen CD14 inhibitor, such as atibuclimab.

In some embodiments, the additional therapeutic agent is a plasma kallikrein inhibitor, such as lanadelumab.

In some embodiments, the additional therapeutic agent is a platelet glycoprotein VI inhibitor, such as glenzocimab.

In some embodiments, the additional therapeutic agent is a T-cell differentiation antigen CD6 inhibitor, such as itolizumab.

In some embodiments, the additional therapeutic agent is a TNF alpha ligand inhibitor/TNF binding agent, such as infliximab.

In some embodiments, the additional therapeutic agent is an anti-LIGHT antibody, such as AVTX-002.

In some embodiments, the additional therapeutic agent is IMC-2 (valacyclovir+celecoxib), or AXA-1125.

In some embodiments, the additional therapeutic agent is COVID-HIG.

In some embodiments, a compound of the disclosure, or a pharmaceutically acceptable salt thereof, is co-administered with one or more agents useful for the treatment and/or prophylaxis of COVID-19.

Non-limiting examples of such agents include corticosteroids, such as dexamethasone, hydrocortisone, methylprednisolone, or prednisone; interleukin-6 (IL-6) receptor blockers, such as tocilizumab or sarilumab; Janus kinase (JAK) inhibitors, such as baricitinib, ruxolitinib, or tofacitinib; and antiviral agents, such as molnupiravir, sotrovimab, or remdesivir.

In further embodiments, a compound of the disclosure, or a pharmaceutically acceptable salt thereof, is co-administered with two or more agents useful for the treatment of COVID-19. Agents useful for the treatment and/or prophylaxis of COVID-19 include but are not limited to a compound of the disclosure and two additional therapeutic agents, such as nirmatrelvir and ritonavir, casirivimab and imdevimab, or ruxolitinib and tofacitinib.

In some embodiments, the additional therapeutic agent is an antiviral agent. In some embodiments, the antiviral agent is an entry inhibitor. In some embodiments, the antiviral agent is a protease inhibitor. In some embodiments, the antiviral agent is an RNA polymerase inhibitor. In some embodiments, the additional therapeutic agent is an RNA-dependent RNA polymerase (RdRp) inhibitor.

In some embodiments, the antiviral agent is selected from angiotensin converting enzyme 2 inhibitors, angiotensin converting enzyme 2 modulators, angiotensin converting enzyme 2 stimulators, angiotensin II AT-2 receptor agonists, angiotensin II AT-2 receptor antagonists, angiotensin II receptor modulators, coronavirus nucleoprotein modulators, coronavirus small envelope protein modulators, coronavirus spike glycoprotein inhibitors, coronavirus spike glycoprotein modulators, SARS-CoV-2 envelope small membrane protein inhibitors, SARS-CoV-2 envelope small membrane protein modulators, SARS-CoV-2 MPro inhibitors, SARS-CoV-2 non structural protein 8 modulators, SARS-CoV-2 nucleoprotein inhibitors, SARS-CoV-2 nucleoprotein modulators, SARS-CoV-2 protein 3a inhibitors, SARS-CoV-2 replicase polyprotein 1a inhibitors, SARS-CoV-2 replicase polyprotein 1a modulators, SARS-CoV-2 replicase polyprotein 1ab inhibitors, SARS-CoV-2 replicase polyprotein 1ab modulators, SARS-CoV-2 spike glycoprotein inhibitors, SARS-CoV-2 spike glycoprotein modulators, SARS-CoV-2 structural glycoprotein modulators, papain inhibitors, protease inhibitors, protease modulators, RNA polymerase inhibitors, RNA polymerase modulators, RNA-dependent RNA polymerase (RdRp) inhibitors. SARS coronavirus 3C protease like inhibitors, SARS-CoV-2 nsp14 methyltransferase enzyme inhibitor, 3CLpro/Mpro inhibitors, serine protease inhibitors, transmembrane serine protease 2 inhibitors, transmembrane serine protease 2 modulators, viral envelope protein inhibitors, viral protease inhibitors, viral protease modulators, viral protein target modulators, viral ribonuclease inhibitors, and viral structural protein modulators.

In some embodiments, the additional therapeutic agent is an entry inhibitor. For example, in some embodiments the additional therapeutic agent is an ACE2 inhibitor, a fusion inhibitor, or a protease inhibitor.

In some embodiments, the additional therapeutic agent is an angiotensin converting enzyme 2 inhibitor, such as SBK-001.

In some embodiments, the additional therapeutic agent is an angiotensin converting enzyme 2 modulator, such as neumifil or JN-2019.

In some embodiments, the additional therapeutic agent is an entry inhibitor such as MU-UNMC-1.

In some embodiments, the additional therapeutic agent is an angiotensin converting enzyme 2 stimulator, such as alunacedase alfa.

In some embodiments, the additional therapeutic agent is an angiotensin II AT-2 receptor agonist, such as VP-01.

In some embodiments, the additional therapeutic agent is an ACE II receptor antagonist, such as DX-600.

In some embodiments, the additional therapeutic agent is an angiotensin II receptor modulator, such as TXA-127.

In some embodiments, the additional therapeutic agent is a transmembrane serine protease 2 modulator, such as BC-201.

In some embodiments, the additional therapeutic agent is a viral envelope protein inhibitor, such as MXB-9 or MXB-004.

In some embodiments, the additional therapeutic agent is a RNAi agent such as ARO-COV or SNS-812.

In some embodiments, the additional therapeutic agent is a vaccine. For example, in some embodiments, the additional therapeutic agent is a DNA vaccine, RNA vaccine, live-attenuated vaccine, inactivated vaccine (i.e., inactivated SARS-CoV-2 vaccine), therapeutic vaccine, prophylactic vaccine, protein-based vaccine, viral vector vaccine, cellular vaccine, or dendritic cell vaccine.

In some embodiments, the additional therapeutic agent is a vaccine such as tozinameran, NVX-CoV2373, elasomeran, KD-414, Ad26.COV2-S, Vaxzevria, SCB-2019, AKS-452, VLA-2001, HDT-301, S-268019, MVC-COV1901, mRNA-1273.214, mRNA-1273.213, mRNA-1273.222, NVX-CoV2515, Covaxin, BBIBP-CorV, GBP-510, mRNA-1273.351+mRNA-1273.617 (SARS-CoV-2 multivalent mRNA vaccine, COVID-19), Ad5-nCoV, Omicron-based COVID-19 vaccine (mRNA vaccine, COVID-19), mRNA-1073, mRNA-1273.214, mRNA-1230, mRNA-1283, Omicron-based COVID-19 vaccine, SARS-CoV-2 Protein Subunit Recombinant Vaccine, Sputnik M, ZyCoV-D, COVID-19 XWG-03, mRNA-1273.529, mRNA-1010, CoronaVac, AZD-2816, Sputnik V, inactivated SARS-CoV-2 vaccine (Vero cell, COVID-19), DS-5670, PHH-1V, INO-4800, UB-612, coronavirus vaccine (whole-virion, inactivated/purified), ReCOV, MT-2766, ARCT-154, SP-0253, CORBEVAX, mRNA-1273.211, ZF-2001, Sputnik Light, recombinant protein vaccine (COVID-19/SARS-CoV-2 infection), VSV vector-based vaccine targeting spike glycoprotein (COVID-19), VLA-2101, GRT-R912, GRAd-COV2, VPM-1002, COViran Barekat, Ad5-nCoV-IH, ARCoV, Covax-19, recombinant SARS-CoV-2 vaccine (protein subunit/CHO cell, COVID-19), BBV-154, RAZI Cov Pars, COVID-19 vaccine (inactivated/Vero cells/intramuscular, SARS-CoV-2 infection), COVID-19 vaccine (inactivated, Vero cells/intramuscular), BNT-162b2s01, BNT-162b4, BNT-162b5, BNT-162b2 Omi, BNT-162b2 bivalent, CIGB-66, mRNA-1273.617, Mycobacterium w, ERUCOV-VAC, AG-0301-COVID19, fakhravac, AV-COVID-19, peptide vaccine (COVID-19), Nanocovax, SARS-CoV-2 vaccine (inactivated/Vero cells/intramuscular, COVID-19), QAZCOVID-IN, S-875670 nasal vaccine. VTP-500, or BNT162b5.

In some embodiments, the additional therapeutic agent is a protease inhibitor. For example, in some embodiments the additional therapeutic agent is a 3C-like cysteine protease inhibitor (3CLpro, also called Main protease, Mpro), a papain-like protease inhibitor (PLpro), serine protease inhibitor, or transmembrane serine protease 2 inhibitor (TMPRSS2).

In some embodiments, the additional therapeutic agent is a 3CLpro/Mpro inhibitor, such as CDI-873, GC-373, GC-376, PBI-0451, UCI-1, bofutrelvir (FB-2001, DC-402234), DC-402267, GDI-4405, RAY-1216, MPI-8, SH-879, SH-580, EDP-235, VV-993, CDI-988, MI-30, nirmatrelvir, ensitrelvir, ASC-11, EDDC-2214, SIM-0417, CDI-45205, COR-803, ALG-097111, TJC-642, CVD-0013943, eravacycline, cynarine, or prexasertib.

In some embodiments, the additional therapeutic agent is a papain-like protease inhibitor (PLpro), such as SBFM-PL4 or GRL-0617.

In some embodiments, the additional therapeutic agent is a SARS-CoV-2 helicase Nsp13 inhibitor, such as EIS-4363.

In some embodiments, the additional therapeutic agent is a SARS-CoV-2 helicase Nsp14 inhibitor, such as TO-507.

In some embodiments, the additional therapeutic agent is a SARS-CoV-2 spike (S) and protease modulator, such as EN U-200.

In some embodiments, the additional therapeutic agent is a protease inhibitor, such as ALG-097558 or MRX-18.

In some embodiments, the additional therapeutic agent is a serine protease inhibitor, such as upamostat, nafamostat, camostat mesylate, nafamostat mesylate, or camostat.

In some embodiments, the additional therapeutic agent is a 3CLpro/transmembrane serine protease 2 inhibitor, such as SNB-01 (pentarlandir) or SNB-02.

In some embodiments, the additional therapeutic agent is a viral protease inhibitor, such as Pan-Corona, Cov-X, or bepridil.

In some embodiments, the additional therapeutic agent is an RNA polymerase inhibitor. For example, in some embodiments, the additional therapeutic agent is an RNA polymerase inhibitor, or an RNA-dependent RNA polymerase (RdRp) inhibitor.

In some embodiments, the additional therapeutic agent is an RNA-dependent RNA polymerase (RdRp) inhibitor, such as remdesivir, NV-CoV-2-R, NV-CoV-1 encapsulated remdesivir. GS-621763. GS-5245, GS-441524, DEP remdesivir, ATV-006, VV-116, LGN-20, CMX-521 and compounds disclosed in WO2022142477, WO2021213288, WO2022047065.

In some embodiments, the additional therapeutic agent is an RNA polymerase inhibitor, such as molnupiravir (EIDD-2801), favipiravir, bemnifosbuvir, sofosbuvir, ASC-10, or galidesivir.

In some embodiments, the additional therapeutic agent is viral entry inhibitor, such as brilacidin.

In some embodiments, the additional therapeutic agent is an antibody that binds to a coronavirus, for example an antibody that binds to SARS or MERS.

In some embodiments, the additional therapeutic agent is an antibody, for example a monoclonal antibody. For example, the additional therapeutic agent is an antibody against SARS-CoV-2, neutralizing nanobodies, antibodies that target the SARS-CoV-2 spike protein, fusion proteins, multispecific antibodies, and antibodies that can neutralize SARS-CoV-2 (SARS-CoV-2 neutralizing antibodies).

In some embodiments, the additional therapeutic agent is an antibody that targets specific sites on ACE2. In some embodiments, the additional therapeutic agent is a polypeptide targeting SARS-CoV-2 spike protein (S-protein).

In some embodiments, the additional therapeutic agent is a SARS-CoV-2 virus antibody.

In some embodiments, the antibody is ABBV-47D11, COVI-GUARD (STI-1499), C144-LS+C135-LS, DXP-604, JMB-2002, LY-CovMab, bamlanivimab (LY-CoV555), GIGA-2050, IBI-314, S309, SAB-185, etesevimab (CB6), COR-101, JS016, VNAR, VIR-7832 and/or sotrovimab (VIR-7831), casirivimab+imdevimab (REGN-COV2 or REGN10933+RGN10987), BAT2020, BAT2019, 47D11, YBSW-015, or PA-001.

In some embodiments, the additional therapeutic agent is STI-9199 (COVI-SHIELD), STI-9167 or AR-701 (AR-703 and AR-720).

In some embodiments, the additional therapeutic agent is BRII-96, BRII-198, ADG-10, adintrevimab (ADG-20), ABP-300, BA-7208, BI-767551, BHV-1200, CT-P63, JS-026, sotrovimab (GSK-4182136), tixagevimab+cilgavimab (AZD-7442), regdanvimab, SAB-301, AOD-01, plutavimab (COVI-AMG), 9MW-3311 (MW-33), DXP-593, BSVEQAb, anti-SARS-CoV-2 IgY, COVID-EIG, CSL-760, F-61, REGN-3048-3051, SARS-CoV-2 monoclonal antibodies (COVID-19, ADM-03820), enuzovimab (HFB-30132A), INM-005, SCTA01, TY-027, XAV-19, amubarvimab+romlusevimab, SCTA-01, bebtelovimab, beludavimab, IBI-0123, IGM-6268. FYB-207, FS-2101, RBT-0813, REGN-14256, REGN-14284, SPKM-001, XVR-011, TB202-3, TB181-36, TB339-031, LMN-301, LQ-050, COVAB-36, MAD-0004J08, STI-2099, TATX-03, TZLS-501, ZCB-11 or ACV-200-17.

In some embodiments, the additional therapeutic agent is an engineered ACE-2-IgG1-Fc-fusion protein targeting SARS-Cov-2 RBD, such as EU-129, bivalent ACE2-IgG Fc null fusion protein (SI-F019).

In some embodiments, the additional therapeutic agent is an ACE2-Fc receptor fusion protein, such as HLX-71.

In some embodiments, the additional therapeutic agent is ensovibep.

In some embodiments, the additional therapeutic agent is SYZJ-001.

In some embodiments, the additional therapeutic agent is an HIV-1 protease inhibitor, such as ASC-09F (ASC-09+ritonavir) or lopinavir+ritonavir.

In some embodiments, the additional therapeutic agent is a non-nucleoside reverse transcriptase inhibitor, such as elsulfavirine.

In some embodiments, the additional therapeutic agent is a nucleoside reverse transcriptase inhibitor, such as azvudine.

In some embodiments, the additional therapeutic agent is Abbv-990, BAT-2022, NED-260, ALG-097431, bardoxolone, delcetravir, ESFAM-289. ENOB-CV-01, ENOB-CV-11, EIS-10700, beta-521, SIM-0417, molnupiravir, Pan-Corona, Tollovir, nirmatrelvir+ritonavir (Paxlovid®), favipiravir, GC-376, upamostat, LeSoleil-01, LeSoleil-02+, benfovir, VV-116, VV-993, SNB-01, EDP-235, Cov-X, ensitrelvir, MPI-8, masitinib, ALG-097558, ASC-11, PB-0451, nafamostat, nafamostat mesylate, CDI-45205, COR-803, ALG-097111. BC-201, SH-879, CDI-873, CDI-988, remdesivir, NV-CoV-2-R, NV-CoV-1 encapsulated remdesivir, NA-831+remdesivir, DEP remdesivir, GS-621763, GS-5245, GLS-5310, bemnifosbuvir, QLS-1128, ASC-10, SBFM-PL4, camostat mesylate, UCI-1, FB-2001 (DC-402234), ebselen, SH-580, LeSoleil-01, LeSoleil-02+, MRX-18, MXB-9, MI-09, MI-30, SNB-02, SJP-002C, TJC-642, ENU-200, CVD-0013943, GS-441524, bepridil, MXB-004, eravacycline, GRL-0617, camostat, GC-373, nitazoxanide, cynarine, prexasertib, RAY-1216, SACT-COVID-19, MP-18, EIDD-1931, EDDC-2214, nitric oxide, apabetalone, AnQlar, SBK-001, LQ-050, CG-Spike-Down, bamlanivimab. HLX-71, HT-002, HY-209, HY-3000, FYB-207, ensovibep, SYZJ-001. EU-129, neumifil, JN-2019, AR-701, vostesyl, PLM-402, PJS-539, CTB-ACE2, TB181-36, TB202-3, ABP-300. XVR-011, MSP-008-22, MU-UNMC-1, MU-UNMC-2, alunacedase alfa, VP-01, TRV-027, DX-600, TXA-127, NVX-CoV2515, riamilovir, tozinameran, elasomeran, Ad5-nCoV, BBIBP-CorV, CoronaVac, MVC-COV1901, NVX-CoV2373, sotrovimab, Sputnik V. TEE-001, Tyme-19, Vaxzevria, ZF-2001, or ZyCoV-D.

X. Examples

General Synthesis:

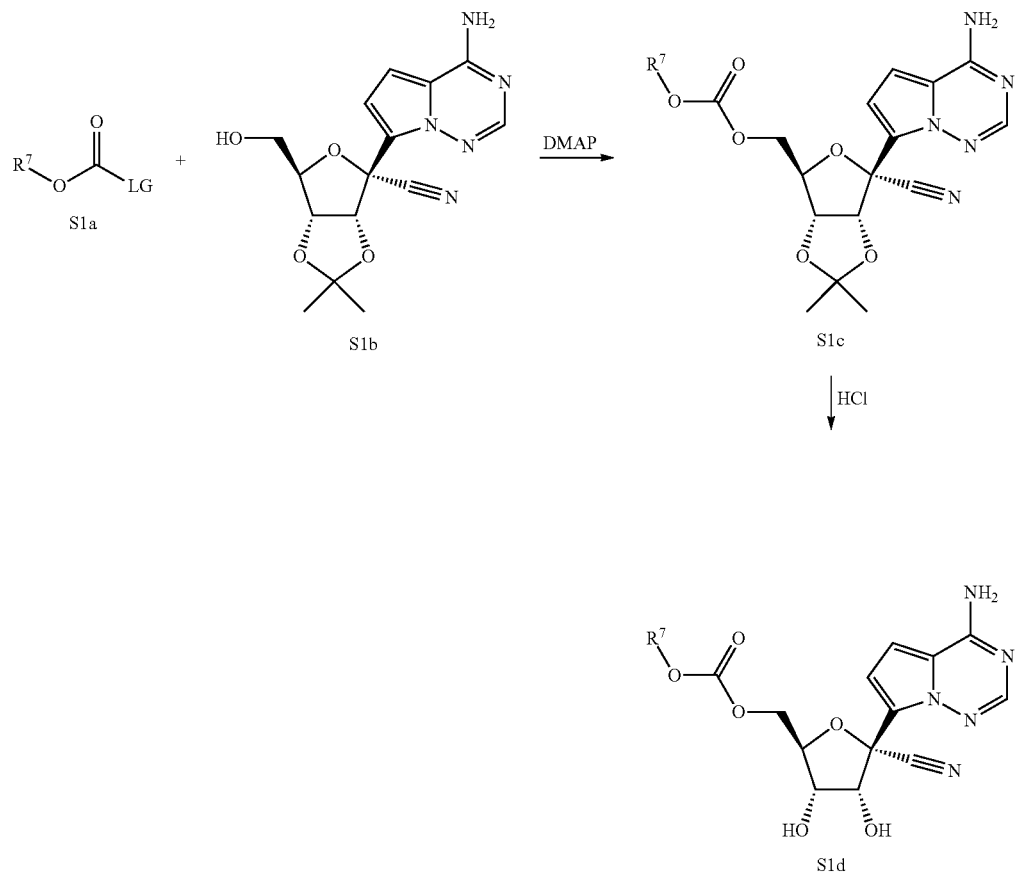

Scheme 1 shows the general synthesis of compounds of the present invention starting with the reaction of S1a and nucleoside S1b under basic conditions (e.g., 4-dimethylaminopyridine (DMAP)) to afford S1c. LG represents a leaving group. Example leaving groups include, but are not limited to, chloride, bromide, mesylate, tosylate, triflate, 4-nitrobenzenesulfonate, 4-chlorobenzenesulfonate, 4-nitrophenoxy, and pentafluorophenoxy. This reaction is followed by acetonide cleavage under acidic conditions (e.g., HCl) to afford the final compounds of the present invention of the type S1d.

Scheme 2

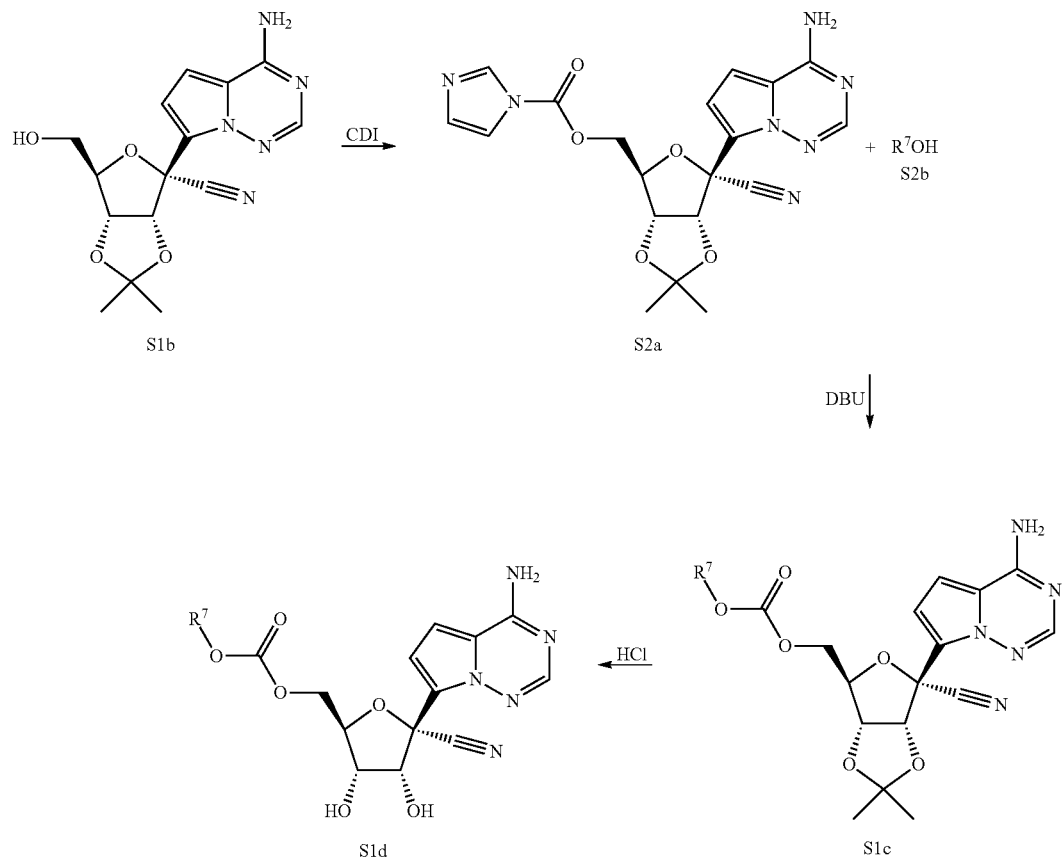

Scheme 2 shows a general synthesis of compounds of the present invention starting with the reaction of nucleoside S1b with 1,1'-carbonyldiimidazole (CDI) to generate intermediate S2a. Displacement of the imidazole with the alcohol S2b under basic conditions (e.g., 1,8-diazabicyclo[5.4.0]undec-7-ene (DBU)) generates the penultimate intermediate S1c. The acetonide is then cleaved under acidic conditions (e.g., HCl) to afford the final compounds of the present invention of the type S1d.

Scheme 3

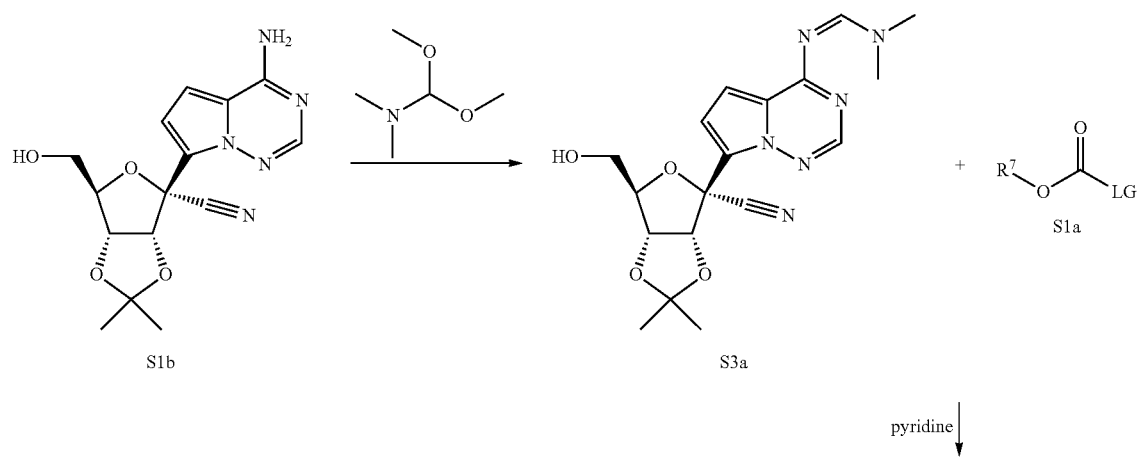

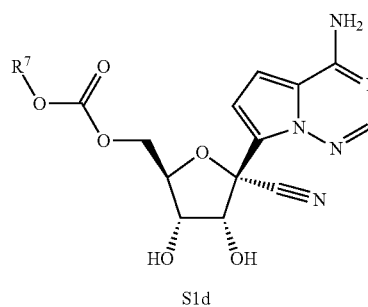

S1d

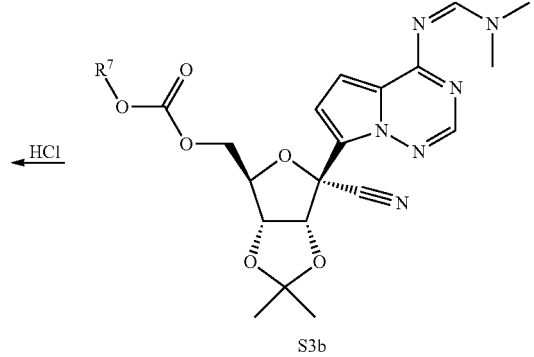

S3b

Scheme 3 shows a general synthesis of compounds of the present invention starting with the addition of a protecting group (e.g., dimethylformamidine) on N6 of nucleoside S1b to afford S3a. Reaction of S3a with S1a under basic conditions (e.g., pyridine) generates intermediate S3b, which is subsequently subjected to acidic conditions (e.g., HCl) to afford the final compounds of the present invention of the type S1d.

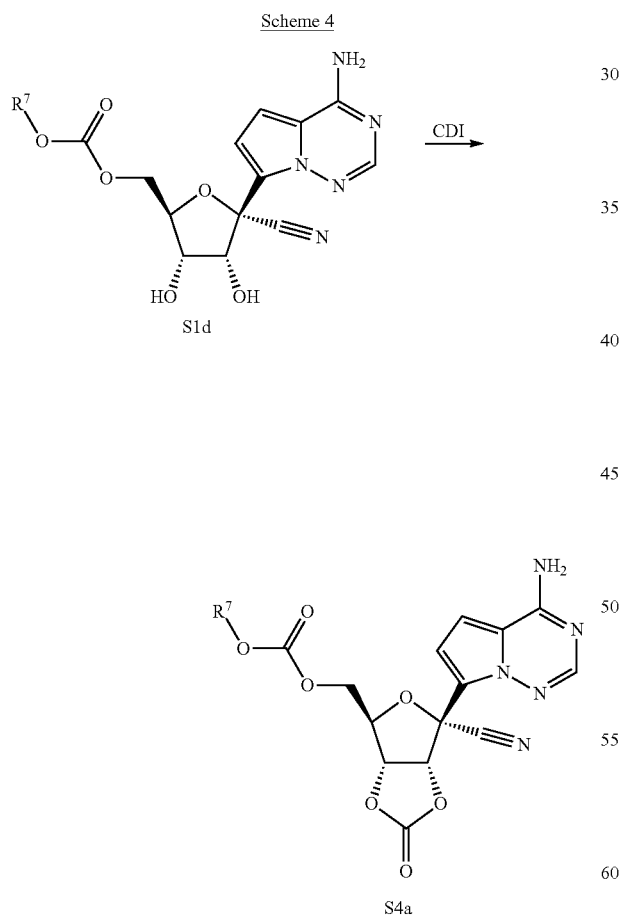

Scheme 4 shows a general synthesis of compounds of the present invention starting with the reaction of S1d with CDI or diphenyl carbonate to afford the final compounds of the present invention of the type S4a.

Scheme 5 shows a general synthesis of compounds of the present invention starting with the acetonide deprotection of S1b to generate the nucleoside S5a. Reaction of S5a with the anhydride S5b under basic conditions (e.g., DBU) affords the final compounds of the present invention of the type S1d.

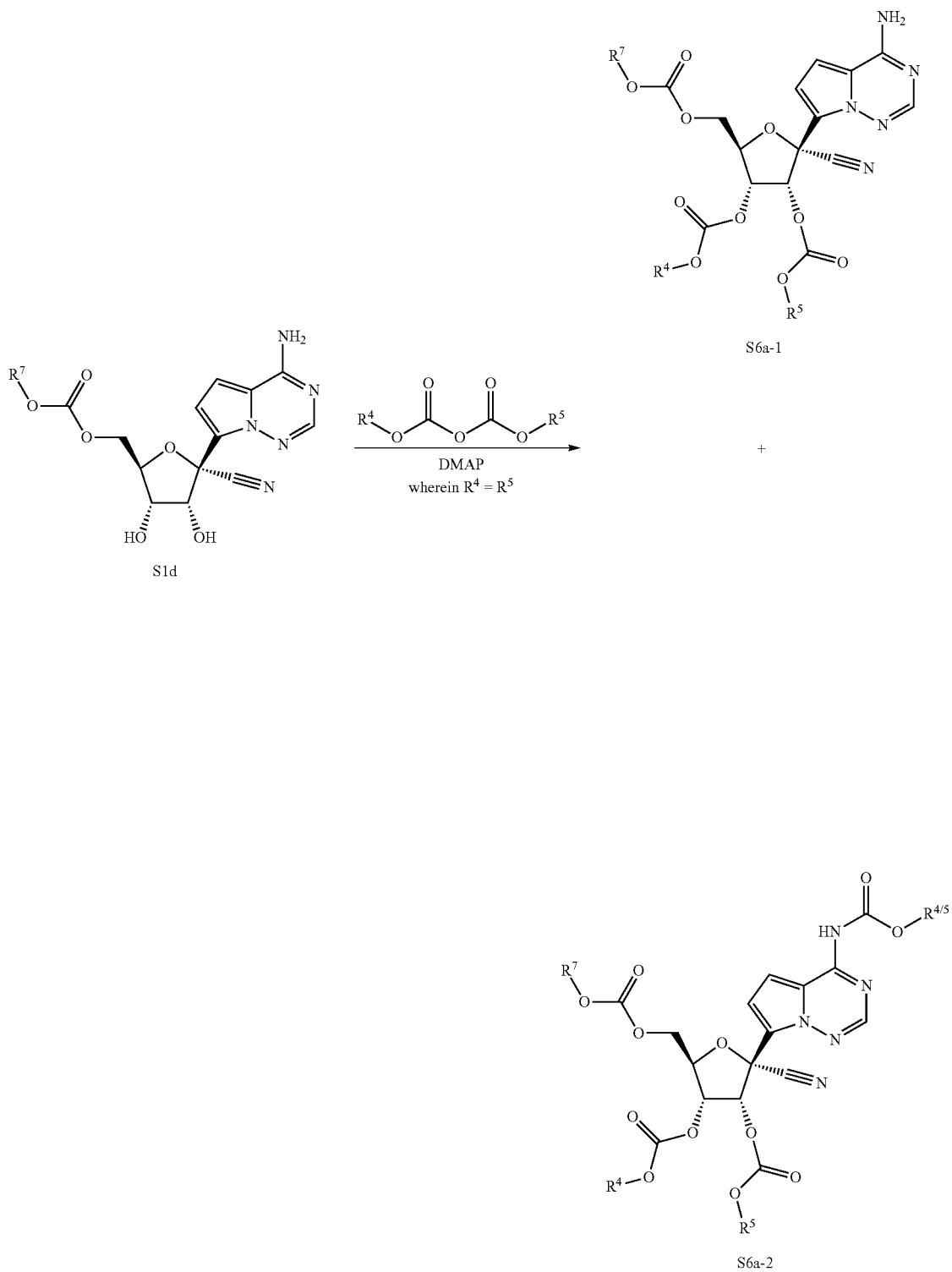
Scheme 6a shows a general synthesis of compounds of the present invention starting with S1d. Reaction of S1d with a dicarbonate in the presence DMAP in tetrahydrofuran (THF) affords the final compounds of the present invention of the type S6a-1 and S6a-2.

Scheme 7

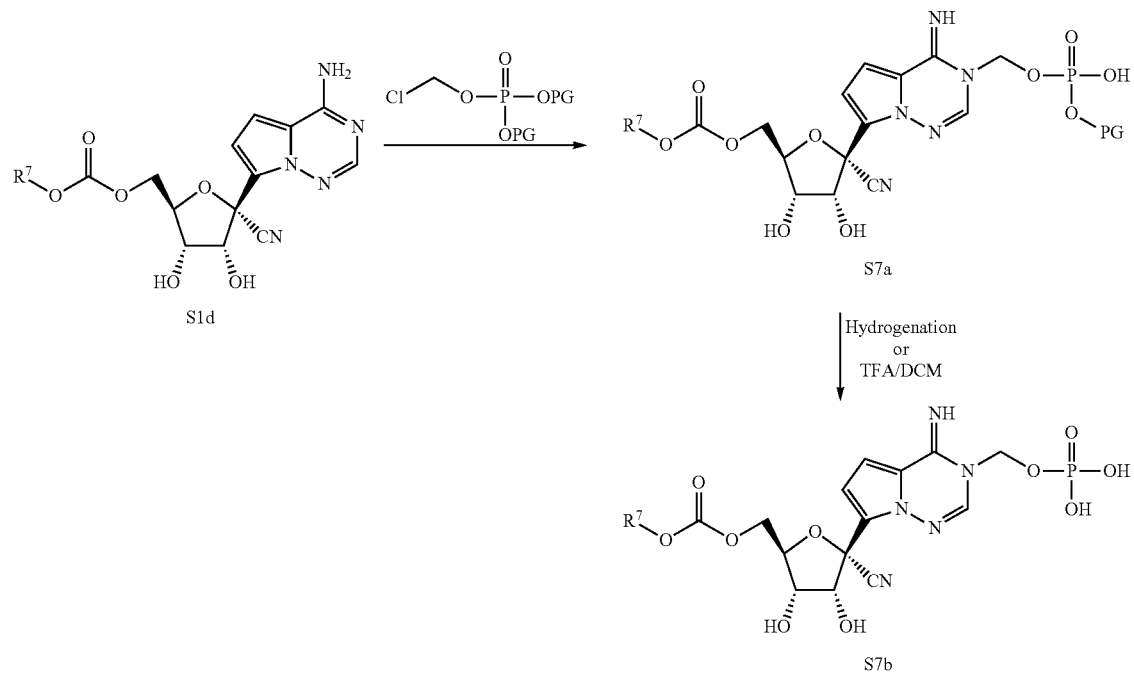

Scheme 7 describes the general synthesis of compounds of the present invention starting with S1d. Reacting compound S1d with chloromethyl disubstituted phosphate in the presence of sodium iodide in solvents (e.g., acetone) provides the intermediate S7a. PG is a protecting group. Example protecting groups include, but are not limited to, trimethylsilyl, dimethylhexylsilyl, t-butyldimethylsilyl, t-butyldiphenylsilyl, trityl, alkyl groups, and acyl groups such as acetyl and propionyl, methanesulfonyl, and p-toluenesulfonyl. Removal of the protecting group is achieved either by hydrogenation or treatment with an acid, which provides the compounds of the present invention of the type S7b.

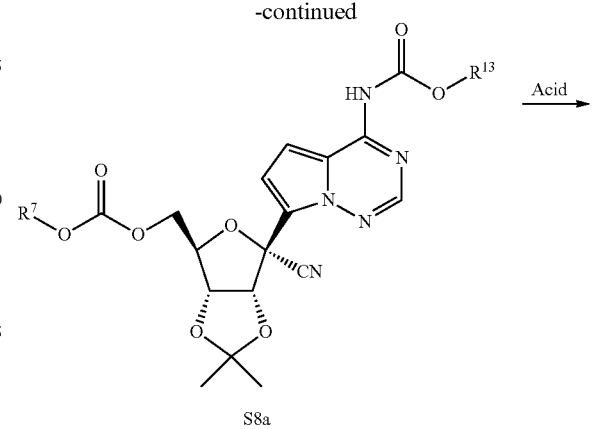

-continued

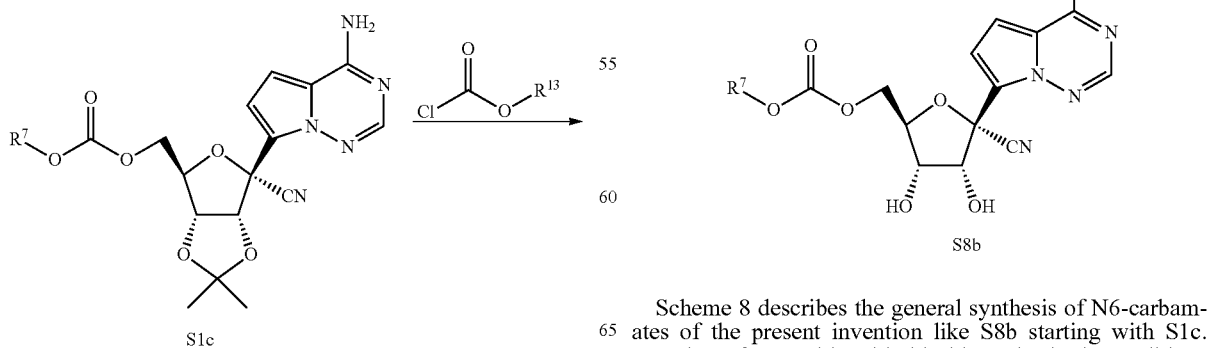

Scheme 8 describes the general synthesis of N6-carbamates of the present invention like S8b starting with S1c. Reaction of S1c with acid chloride under basic conditions (like pyridine) generates intermediate S8a, which is subsequently subjected to acidic conditions (e.g., HCl) to afford compounds of the present invention of the type S8b.

Scheme 9

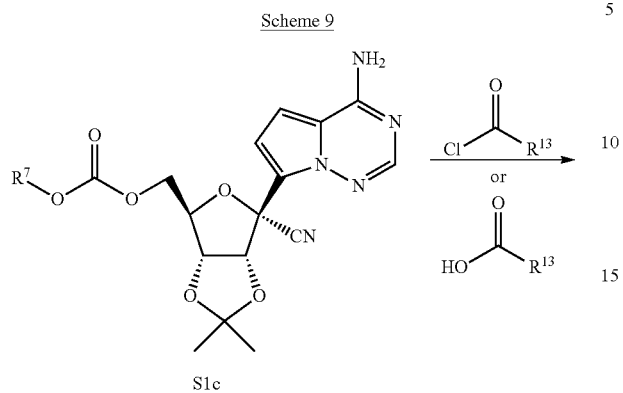

S1c

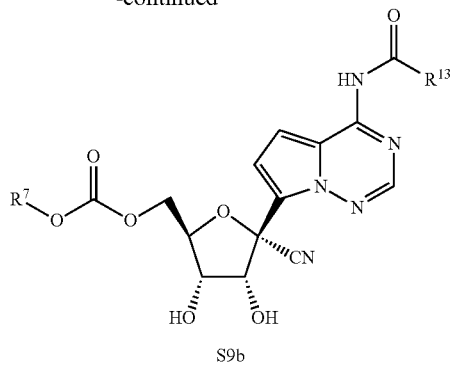

S9b

Scheme 9 describes the general synthesis of N6-amide analogs of the present invention like S9b starting with S1c. Reaction of S1c with acid chloride

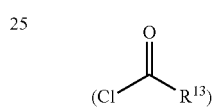

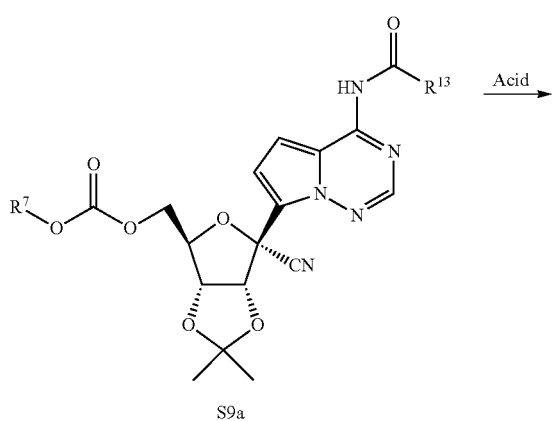

S9a under basic conditions (like pyridine) generates intermediate S9a, which is subsequently subjected to acidic conditions (e.g., HCl) to afford compounds of the present invention of the type S9b.

Compounds of the present invention like S9b can also be obtained by reaction of S1c with corresponding acid. Reaction of S1c with acid

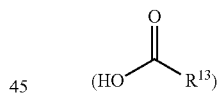

in the presence of 1-[bis(dimethylamino)methylene]-1H-1,2,3-triazolo[4,5-b]pyridinium 3-oxide hexafluorophosphate (HATU) or 1-ethyl-3-(3-dimethylaminopropyl)carbodiimide (EDCI) to generate intermediate S9a, which is subsequently subjected to acidic conditions (e.g., HCl) to afford compounds of the present invention of the type S9b.

Scheme 10

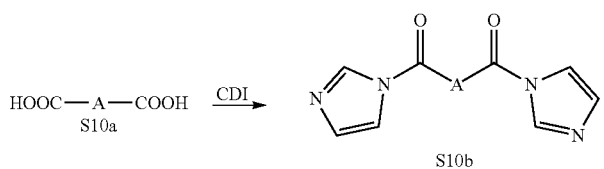

201

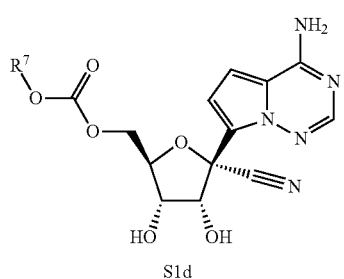

S1d

-continued

|DBU
wherein A is C₁-C₂₀ alkyl, (C₁-C₂₀ alkyl)-O-(C₁-C₆ alkyl), or (C₁-C₂₀ alkyl)-N(methyl)-(C₁-C₆ alkyl)

202

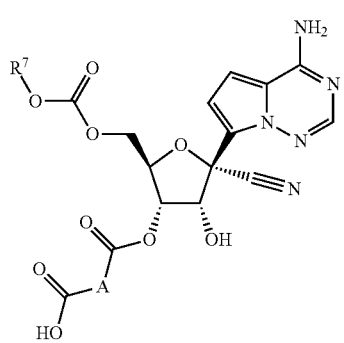

S10c

Scheme 10 shows a general synthesis of compounds of the present invention starting with the reaction of diacids S10a with 1,1'-carbonyldiimidazole to afford reagent S10b. Reaction between S10b and nucleoside S1d can further afford the final compounds of the present invention of the type S10c.

Scheme 11

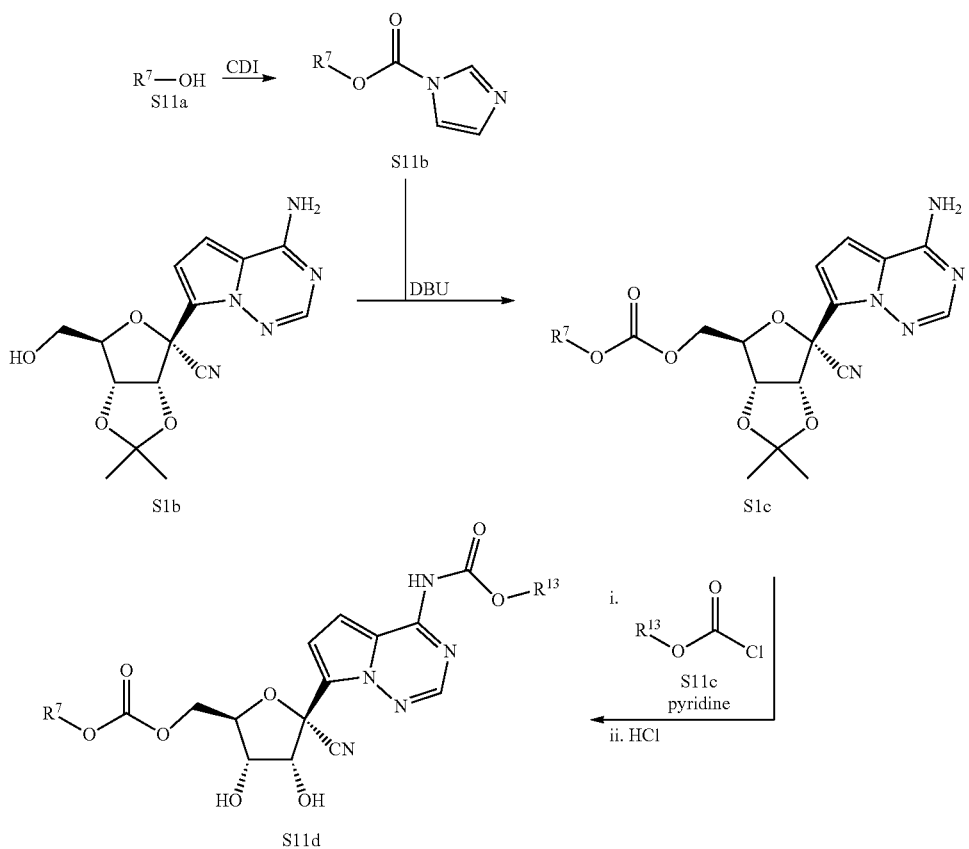

Scheme 11 shows a general synthesis of compounds of the present invention starting with acylation of alcohols S11a with 1,1'-carbonyldiimidazole (CDI) to afford reagent S11b. Reactions between S11b and S1b using 1,8-diazabicyclo[5.4.0]undec-7-ene (DBU) generates intermediate S1c. Reactions between S1c and S11c using pyridine as base followed by acidic treatment (e.g. HCl) then afford the final compounds of the present invention of the type S11d.

Scheme 12

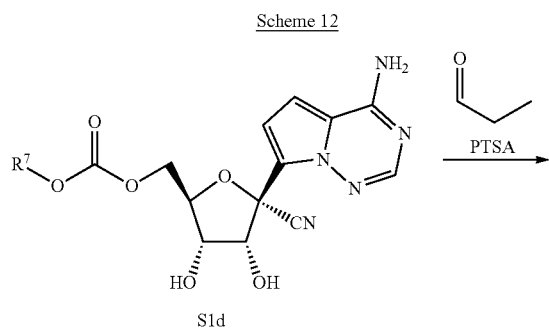

Scheme 12 shows a general synthesis of acetalization of alcohols S1d with propionaldehyde under acidic condition (e.g. PTSA) to afford the final compounds of the present invention of the type S12a.

Scheme 13

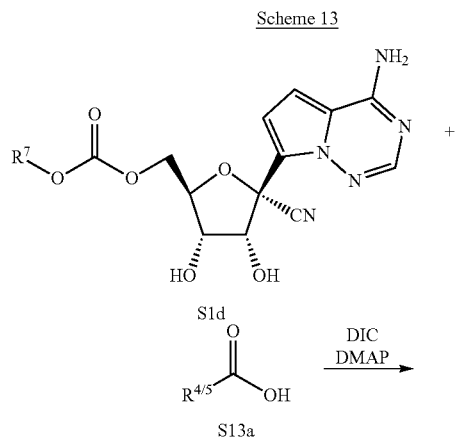

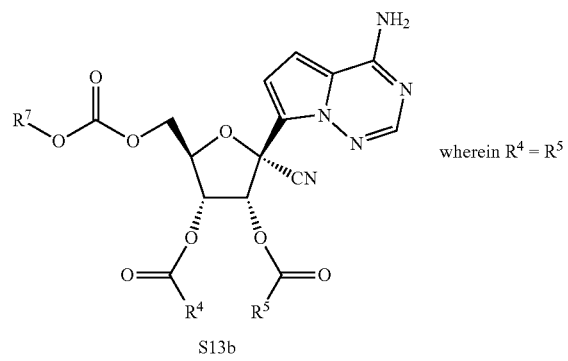

Scheme 13 shows a general synthesis of esterification of alcohols S1d with acid S13a using carbodiimide reaget (e.g. N,N'-diisopropylcarbodiimide (DIC)) and 4-dimethylaminopyridine (DMAP) to afford the final compounds of the present invention of the type S13b.

Scheme 14

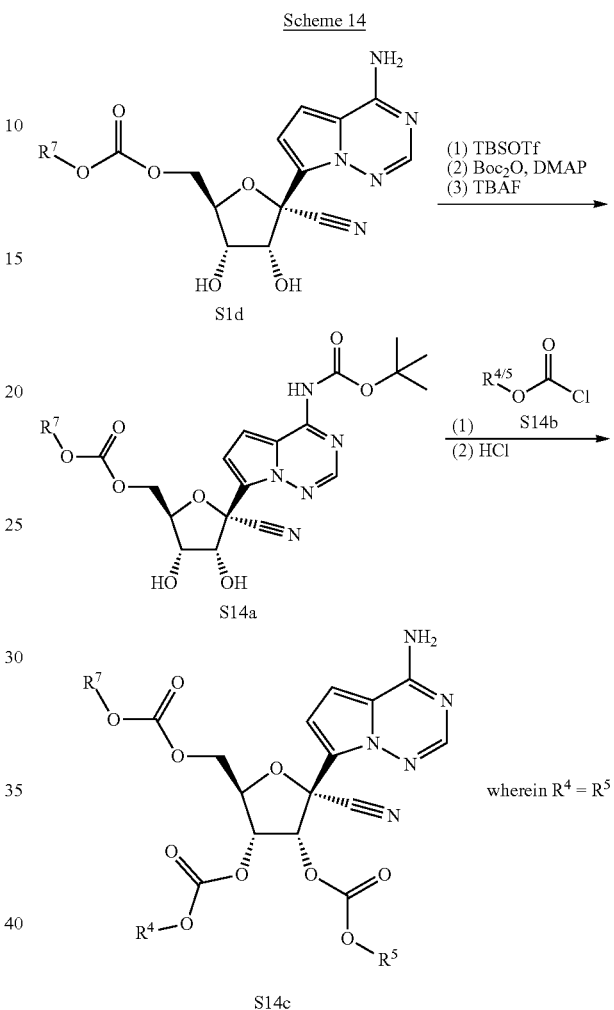

Scheme 14 shows a general synthesis of compounds of the present invention starting with the protecting group manipulation on the free amine of nucleoside S1d to afford S14a. Reactions of S14a with chloroformates S14b under basic conditions (e.g. pyridine) followed by acidic treatment (e.g. HCl) afford the final compounds of the present invention of the type S14c.

Synthesis of Intermediates Ia and Ib:

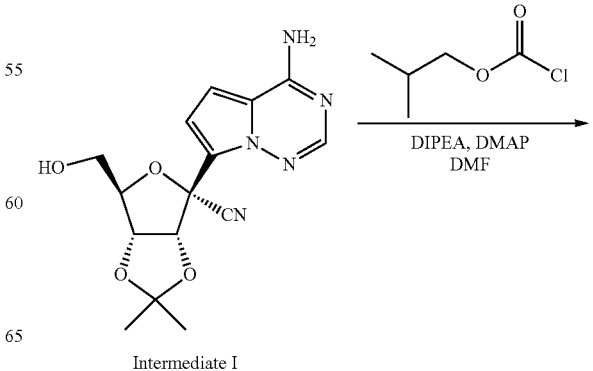

Intermediate I

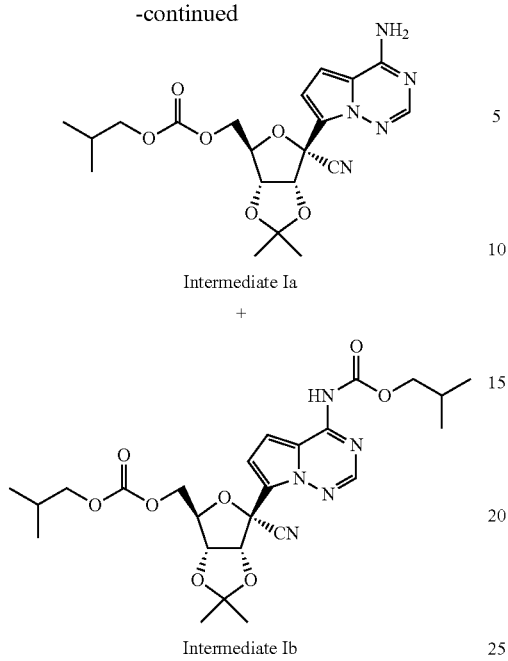

Intermediate Ia

+

Intermediate Ib

To a solution of (3aR,4R,6R,6aR)-4-(4-aminopyrrolo[2,1-q][1,2,4]triazin-7-yl)-6-(hydroxymethyl)-2,2-dimethyltetrahydrofuro[3,4-d][1,3]dioxole-4-carbonitrile, Intermediate I, (1000 mg, 3.0 mmol) (Siegel et. al. J. Med. Chem. 2017, 60, 1648-1661) in DMF (5 mL), diisopropyl ethyl amine (780 mg, 6 mmol) was added followed by 4-dimethyl aminopyridine (369 mg, 3 mmol). To the above solution at room temperature, isobutyl chloroformate (495 mg, 3.6 mmol) was added and stirred for 1 h. LC-MS shows formation two products 5'-cabonate and 5'-cabonate along with N6-carbamate. The reaction mixture was diluted with ethyl acetate (50 mL), washed with water, brine, dried over sodium sulfate and concentrated. The residue was purified by flash chromatography using dichloromethane and methanol as eluants and separated the two products. Intermediate Ia: ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl isobutyl carbonate. LCMS: MS m/z: 432.1 (M+1). Intermediate Ib: isobutyl (7-((3aR,4R,6R,6aR)-4-cyano-6-(((isobutoxycarbonyl)oxy)methyl)-2,2-dimethyltetrahydrofuro[3,4-d][1,3]dioxol-4-yl)pyrrolo[2,1-f][1,2,4]triazin-4-yl)carbamate. LCMS: MS m/z: 532.2 (M+1)
Synthesis of Intermediate II:

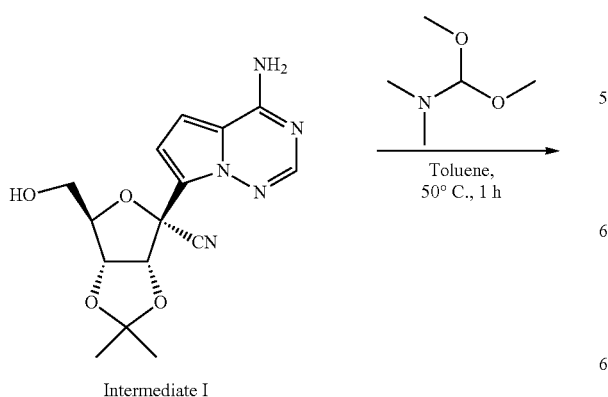

Intermediate I

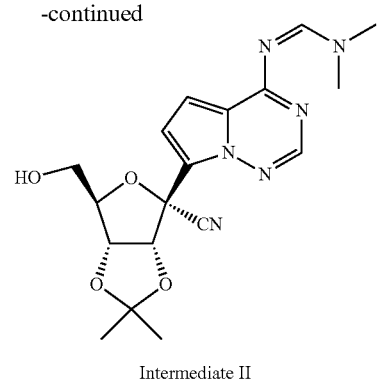

Intermediate II

To a solution of (3aR,4R,6R,6aR)-4-(4-aminopyrrolo[2,1-f][1,2,4]triazin-7-yl)-6-(hydroxymethyl)-2,2-dimethyltetrahydrofuro[3,4-d][1,3]dioxole-4-carbonitrile, Intermediate 1, (3000 mg, 9.0 mmol) (Siegel et. al. J. Med. Chem. 2017, 60, 1648-1661) in toluene (20 mL) N,N-Dimethylformamide dimethyl acetal (2158 mg, 18 mmol) was added and heated at 50° C. for 1 h. After the completion of the reaction, the solvent was evaporated under pressure, the residue was dissolved in ethyl acetate (100 mL). The solvent was washed with water (10 mL) and brine (10 mL) dried over sodium sulphate and concentrated to get the intermediate N'-[7-[(3aR,4R,6R,6aR)-4-cyano-6-(hydroxymethyl)-2,2-dimethyl-6,6a-dihydro-3aH-furo[3,4-d][1,3]dioxol-4-yl]pyrrolo[2,1-f][1,2,4]triazin-4-yl]-N,N-dimethyl-formamidine, Intermediate II. LCMS: MS m/z: 387.2

Example 1: ((2R,3S,4R,5R)-5-(4-aminopyrrolo[2,1-f][1,2,4]triazin-7-yl)-5-cyano-3,4-dihydroxytetrahydrofuran-2-yl)methyl isobutyl carbonate (Compound 1)

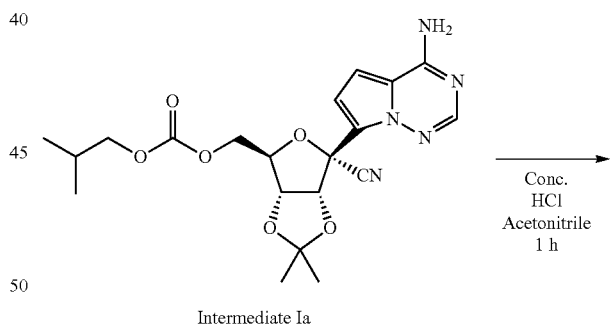

Intermediate Ia

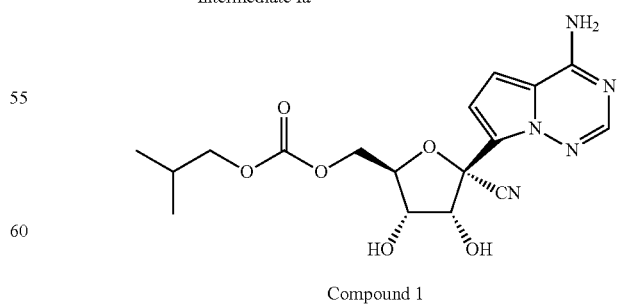

Compound 1

To a solution of ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl isobutyl carbonate: Intermediate Ia (1300 mg, 3 mmol) in acetonitrile (10 mL), conc. HCl (1.3 mL, 15 mmol) was added and stirred at room temperature for 1 h. After the completion of the reaction, the reaction mixture was diluted with ethyl acetate (50 mL), neutralized with saturated sodium bicarbonate, separated the organic layer, washed with water, brine, dried and concentrated. The residue was purified by flash chromatography using dichloromethane and methanol as eluants to obtain the title Compound 1. $^1$H NMR (400 MHz, DMSO-d6) δ 7.92 (s, 2H), 6.90 (d, J=4.6 Hz, 1H), 6.79 (d, J=4.5 Hz, 1H), 6.32 (d, J=6.0 Hz, 1H), 5.40 (d, J=5.8 Hz, 1H), 4.67 (dd, J=6.1, 4.9 Hz, 1H), 4.46-4.36 (m, 1H), 4.28-4.17 (m, 2H), 3.98-3.90 (m, 1H), 3.87 (d, J=6.5 Hz, 2H), 1.89 (dt, J=13.3, 6.7 Hz, 1H), 0.89 (d, J=6.7 Hz, 6H). LCMS: MS m/z: 392.1 (M+1)

Example 2: isobutyl (7-((2R,3R,4S,5R)-2-cyano-3,4-dihydroxy-5-(((isobutoxycarbonyl)oxy)methyl)tetrahydrofuran-2-yl)pyrrolo[2,1-f][1,2,4]triazin-4-yl)carbamate (Compound 2)

To a solution of isobutyl (7-((3aR,4R,6R,6aR)-4-cyano-6-(((isobutoxycarbonyl)oxy)methyl)-2,2-dimethyltetrahydrofuro[3,4-d][1,3]dioxol-4-yl)pyrrolo[2,1-f][1,2,4]triazin-4-yl)carbamate Intermediate Ib (650 mg, 1.2 mmol) in acetonitrile (10 mL), conc. HCl (0.6 mL, 6 mmol) was added and stirred at room temperature for 1 h. After the completion of the reaction, the reaction mixture was diluted with ethyl acetate (50 mL), neutralized with saturated sodium bicarbonate, separated the organic layer, washed with water, brine, dried and concentrated. The residue was purified by flash chromatography using dichloromethane and methanol as eluants to obtain Compound 2. $^1$H NMR (400 MHz, DMSO-d6) δ 10.88 (s, 1H), 8.37 (s, 1H), 7.31 (d, J=4.7 Hz, 1H), 7.02 (d, J=4.7 Hz, 1H), 6.42 (d, J=6.0 Hz, 1H), 5.45 (d, J=5.9 Hz, 1H), 4.66 (t, J=5.4 Hz, 1H), 4.42 (dd, J=11.6, 2.5 Hz, 1H), 4.34-4.13 (m, 2H), 3.96 (dd, J=16.0, 6.2 Hz, 3H), 3.86 (d, J=6.5 Hz, 2H), 1.97 (dq, J=13.6, 6.8 Hz, 1H), 1.88 (dt, J=13.3, 6.7 Hz, 1H), 0.96 (d, J=6.7 Hz, 6H), 0.88 (d, J=6.7 Hz, 6H). LCMS: MS m/z: 492.2 (M+1)

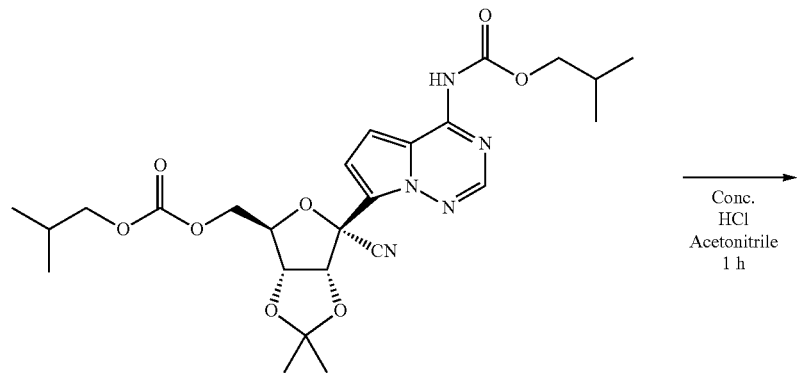

Intermediate Ib

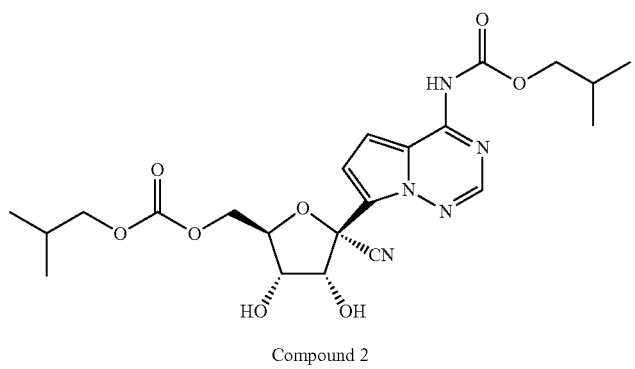

Compound 2

Example 3: ((2R,3S,4R,5R)-5-(4-aminopyrrolo[2,1-f][1,2,4]triazin-7-yl)-5-cyano-3,4-dihydroxytetrahydrofuran-2-yl)methyl neopentyl carbonate (Compound 3)

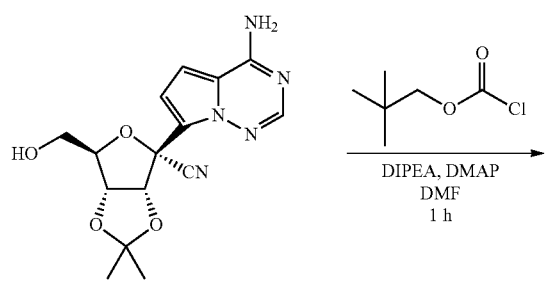

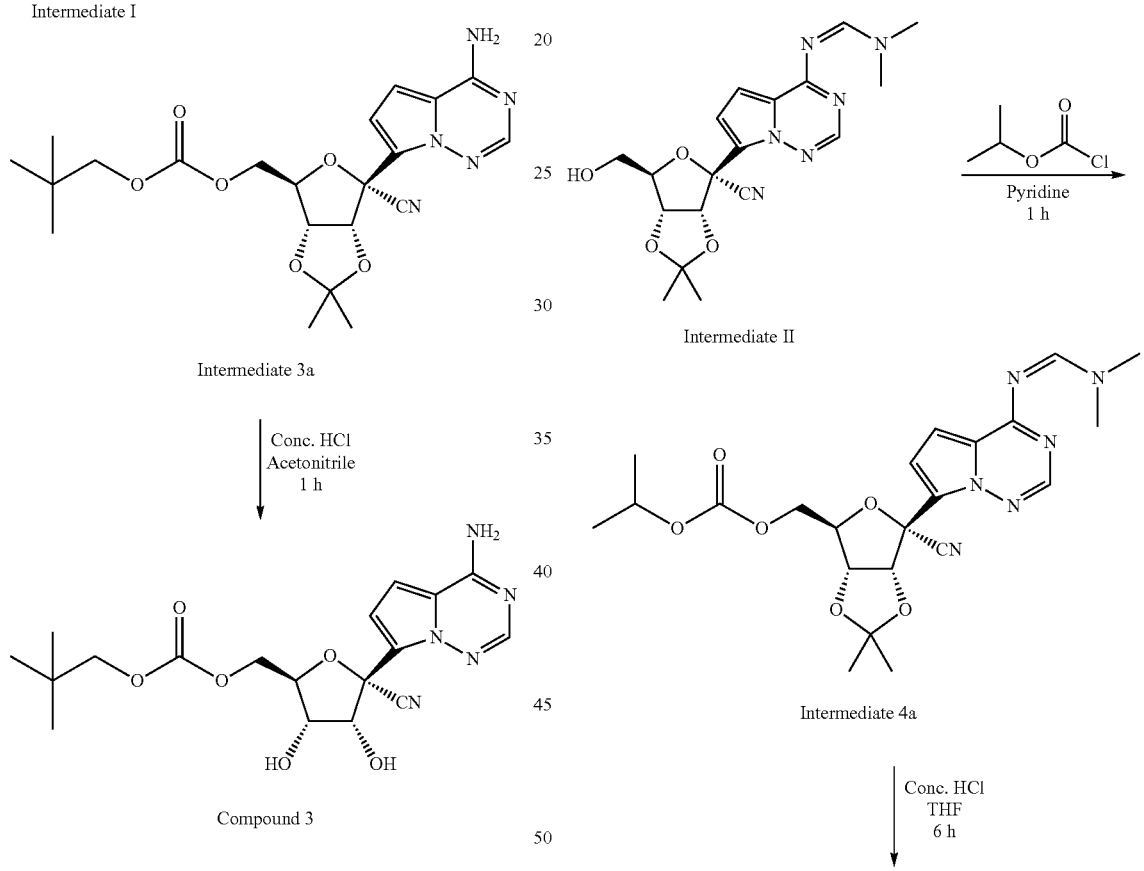

reaction mixture was diluted with ethyl acetate (50 mL), neutralized with saturated sodium bicarbonate, the organic layer separated, washed with water, brine, dried and concentrated. The residue was purified by flash chromatography using dichloromethane and methanol as eluants to obtain Compound 3. $^1$H NMR (400 MHz, DMSO-d6) δ 7.92 (s, 1H), 6.90 (d, J=4.5 Hz, 1H), 6.80 (d, J=4.5 Hz, 1H), 6.33 (d, J=6.0 Hz, 1H), 5.40 (d, J=5.8 Hz, 1H), 4.66 (dd, J=6.0, 4.9 Hz, 1H), 4.49-4.36 (m, 1H), 4.32-4.17 (m, 2H), 3.93 (ddd, J=8.8, 6.6, 4.4 Hz, 1H), 3.80 (d, J=1.7 Hz, 2H), 0.90 (s, 9H). LCMS: MS m/z: 406.2 (M+1).

Example 4: [(2R,3S,4R,5R)-5-(4-aminopyrrolo[2,1-f][1,2,4]triazin-7-yl)-5-cyano-3,4-dihydroxy-tetrahydrofuran-2-yl]methyl isopropyl carbonate (Compound 4)

To a solution of (3aR,4R,6R,6aR)-4-(4-aminopyrrolo[2,1-f][1,2,4]triazin-7-yl)-6-(hydroxymethyl)-2,2-dimethyltetrahydrofuro[3,4-d][1,3]dioxole-4-carbonitrile, Intermediate I, (2000 mg, 6.0 mmol) in DMF (5 mL), diisopropyl ethylamine (1560 mg, 12 mmol) was added followed by 4-dimethyl aminopyridine (737 mg, 6 mmol). To the above solution at room temperature, neopentyl chloroformate (1091 mg, 7.2 mmol) was added and stirred for 1 h. After the completion of the reaction, the reaction mixture was diluted with ethyl acetate (50 mL), washed with water, brine, dried over sodium sulfate and concentrated. The residue was purified by flash chromatography using dichloromethane and methanol to provide Intermediate 3a.

Intermediate 3a (2400 mg, 5.4 mmol) in acetonitrile (5 mL), was treated with conc. HCl (2.2 mL, 27 mmol) and stirred at r.t for 1 h. After the completion of the reaction, the To a solution of Intermediate II (850 mg, 2.2 mmol) in dichloromethane (20 mL), pyridine (1 mL) was added. The reaction mixture was cooled to 0° C., and the isopropyl chloroformate (270 mg, 2.2 mmol) in dichloromethane (5 mL) was slowly added, once the addition was complete, the cold bath was removed and stirred at room temperature for 1 h. After completion of the reaction, the reaction mixture was diluted with dichloromethane (50 mL), washed with water, brine and concentrated. The residue was purified by flash chromatography using ethyl acetate and dichloromethane as eluants to obtain the intermediate [(3aR,4R,6R,6aR)-4-cyano-4-[4-[(Z)-dimethylaminomethyleneamino]pyrrolo[2,1-f][1,2,4]triazin-7-yl]-2,2-dimethyl-6,6a-dihydro-3aH-furo[3,4-d][1,3]dioxol-6-yl]methyl isopropyl carbonate (and/or its (E)-isomer), Intermediate 4a. LCMS: MS m/z: 473.2 (M+1).

Note that compounds such as Intermediate 4a can be E or Z isomers. Although the Z isomer is drawn throughout the disclosure, the E isomer can also be generated and isolated.

To a solution of the Intermediate 4a (1300 mg, 2.8 mmol) in tetrahydrofuran (10 mL) cooled with an ice-bath, conc. HCl (1.3 mL, 43 mmol) was added slowly and the reaction mixture stirred for 6-18 h. After completion of the reaction, the reaction mixture was diluted with ethyl acetate (50 mL) and neutralized with saturated sodium bicarbonate. The organic layer was separated, washed with water, brine, and concentrated. The residue was purified by flash chromatography using dichloromethane and methanol as eluants to obtain the title compound, [(2R,3S,4R,5R)-5-(4-aminopyrrolo[2,1-f][1,2,4]triazin-7-yl)-5-cyano-3,4-dihydroxy-tetrahydrofuran-2-yl]methyl isopropyl carbonate, Compound 4. $^1$H NMR (400 MHz, Acetonitrile-d3) δ 7.94 (s, 1H), 6.84 (d, J=4.6 Hz, 1H), 6.78 (d, J=4.6 Hz, 1H), 6.33 (s, 3H), 4.83-4.69 (m, 3H), 4.45-4.31 (m, 2H), 4.26-4.14 (m, 2H), 3.67 (d, J=5.1 Hz, 1H), 1.22 (t, J=6.7 Hz, 6H). LCMS: MS m/z: 378.1

Example 5: ((2R,3S,4R,5R)-5-(4-aminopyrrolo[2,1-f][1,2,4]triazine-7-yl)-5-cyano-3,4-dihydroxytetrahydrofuran-2-yl)methyl methyl carbonate (Compound 5)

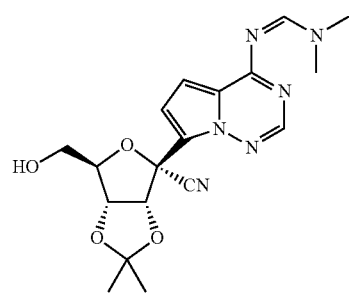

Intermediate II

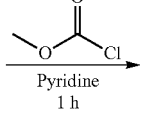

Pyridine
1 h

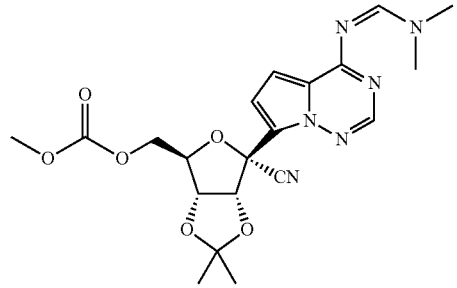

Intermediate 5a

Conc. HCl
THF
6 h

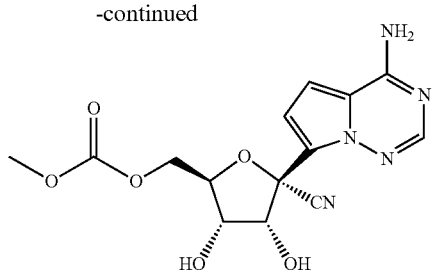

Compound 5

Compound 5 was synthesized as explained in Example 4 starting from methyl chloroformate instead of isopropyl chloroformate.

Intermediate 5a: [(3aR,4R,6R,6aR)-4-cyano-4-[4-[(Z)-dimethylaminomethyleneamino]pyrrolo[2,1-f][1,2,4]triazin-7-yl]-2,2-dimethyl-6,6a-dihydro-3aH-furo[3,4-d][1,3]dioxol-6-yl]methyl methyl carbonate (and/or its (E)-isomer); LCMS: MS m/z=445.1 (M+1)

Compound 5: $^1$H NMR (400 MHz, DMSO-d6) δ 7.92 (s, 1H), 6.91 (d, J=4.5 Hz, 1H), 6.79 (d, J=4.5 Hz, 1H), 6.30 (d, J=6.1 Hz, 1H), 5.75 (s, 0H), 5.40 (d, J=5.8 Hz, 1H), 4.68 (dd, J=6.1, 4.9 Hz, 1H), 4.47-4.32 (m, 1H), 4.30-4.16 (m, 2H), 3.94 (q, J=5.6 Hz, 1H), 3.70 (s, 3H). LCMS: MS m/z=350.1 (M+1)

Example 6: ((2R,3S,4R,5R)-5-(4-aminopyrrolo[2,1-f][,2,4]triazin-7-yl)-5-cyano-3,4-dihydroxytetrahydrofuran-2-yl)methyl ethyl carbonate (Compound 6)

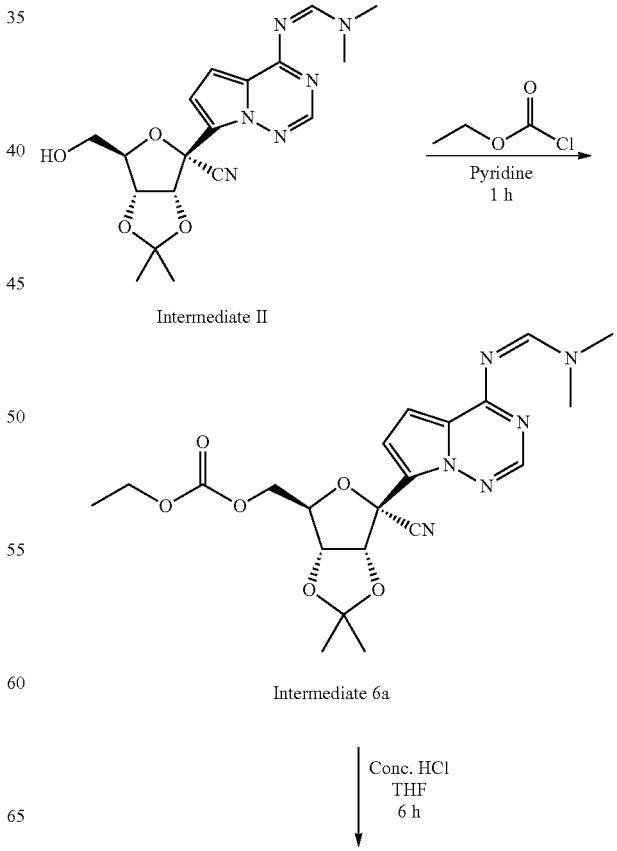

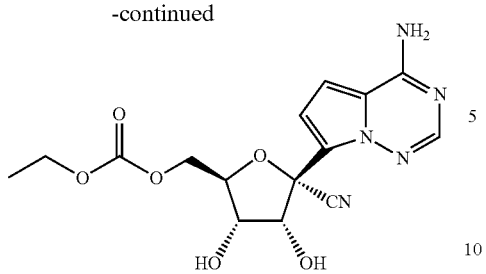

Compound 6

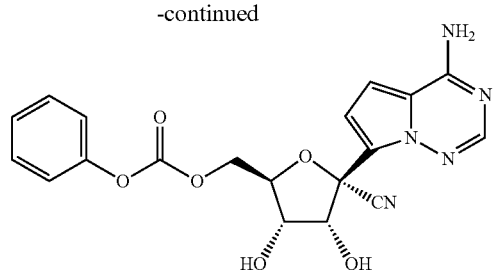

Compound 7

Compound 6 was synthesized as explained in Example 4 starting from ethyl chloroformate instead of isopropyl chloroformate.

Intermediate 6a: [(3aR,4R,6R,6aR)-4-cyano-4-[4-[(Z)-dimethylaminomethyleneamino]pyrrolo[2,1-f][1,2,4]triazin-7-yl]-2,2-dimethyl-6,6a-dihydro-3aH-furo[3,4-d][1,3]dioxol-6-yl]methyl ethyl carbonate (and/or its (E)-isomer). LCMS: MS m/z=459.2 (M+1)

Compound 6: $^1$H NMR (400 MHz, DMSO-d6) δ 7.92 (s, 3H), 6.91 (d, J=4.5 Hz, 1H), 6.79 (d, J=4.5 Hz, 1H), 6.30 (d, J=6.1 Hz, 1H), 5.40 (d, J=5.8 Hz, 1H), 4.69 (dd, J=6.1, 5.0 Hz, 1H), 4.39 (dd, J=10.3, 4.1 Hz, 1H), 4.29-4.17 (m, 2H), 4.11 (q, J=7.1 Hz, 2H), 3.94 (q, J=5.8 Hz, 1H), 1.20 (t, J=7.1 Hz, 3H). LCMS: MS m/z=363.9 (M+1)

Example 7: ((2R,3S,4R,5R)-5-(4-aminopyrrolo[2,1-f][1,2,4]triazin-7-yl)-5-cyano-3,4-dihydroxytetrahydrofuran-2-yl)methyl phenyl carbonate (Compound 7)

Compound 7 was synthesized as explained in Example 4 starting from phenyl chloroformate instead of isopropyl chloroformate.

Intermediate 7a: [(3aR,4R,6R,6aR)-4-cyano-4-[4-[(Z)-dimethylaminomethyleneamino]pyrrolo[2,1-f][1,2,4]triazin-7-yl]-2,2-dimethyl-6,6a-dihydro-3aH-furo[3,4-d][1,3]dioxol-6-yl]methyl phenyl carbonate (and/or its (E)-isomer). LCMS: MS m/z=507.1 (M+1)

Compound 7: $^1$H NMR (400 MHz, DMSO-d6) δ 7.93 (s, 1H), 7.48-7.37 (m, 2H), 7.35-7.25 (m, 1H), 7.25-7.14 (m, 2H), 6.92 (d, J=4.5 Hz, 1H), 6.82 (d, J=4.5 Hz, 1H), 6.34 (d, J=6.1 Hz, 1H), 5.45 (d, J=5.7 Hz, 1H), 4.71 (dd, J=6.1, 4.9 Hz, 1H), 4.53 (dd, J=11.5, 2.6 Hz, 1H), 4.44-4.23 (m, 2H), 4.01 (q, J=5.7 Hz, 1H). LCMS: MS m/z=412.1 (M+1)

Example 8: ((2R,3S,4R,5R)-5-(4-aminopyrrolo[2,1-f][1,2,4]triazin-7-yl)-5-cyano-3,4-dihydroxytetrahydrofuran-2-yl)methyl propyl carbonate (Compound 8)

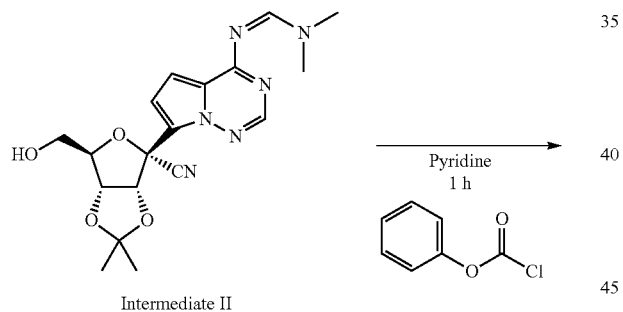

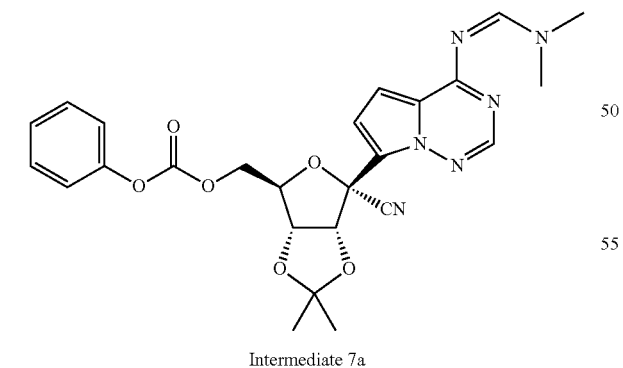

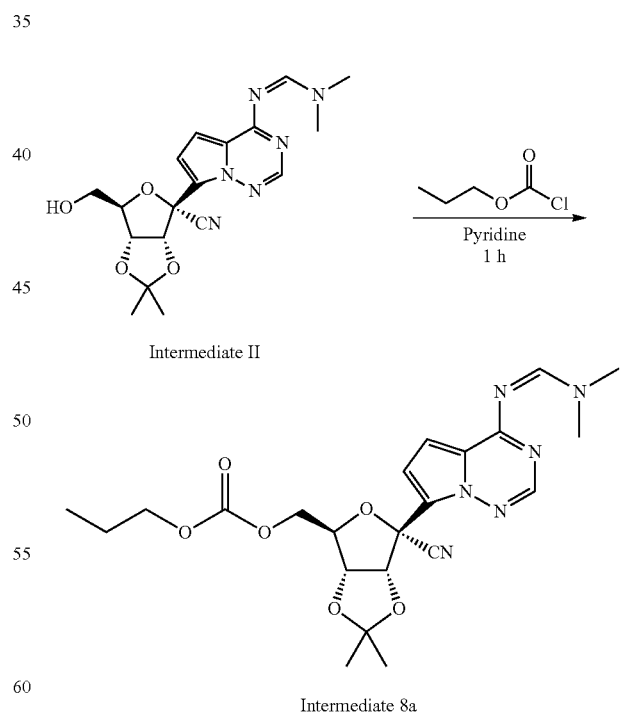

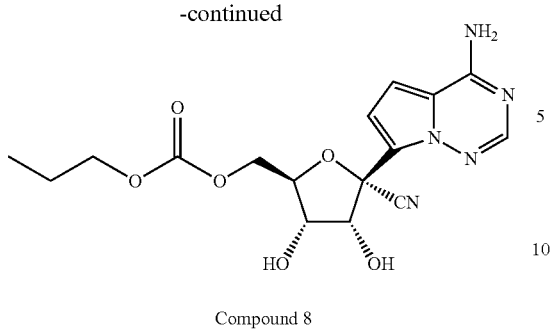

Compound 8

Compound 8 was synthesized as explained in Example 4 starting from propyl chloroformate instead of isopropyl chloroformate.

Intermediate 8a: [(3aR,4R,6R,6aR)-4-cyano-4-[4-[(Z)-dimethylaminomethyleneamino]pyrrolo[2,1-f][1,2,4]triazin-7-yl]-2,2-dimethyl-6,6a-dihydro-3aH-furo[3,4-d][1,3]dioxol-6-yl]methyl propyl carbonate (and/or its (E)-isomer). LCMS: MS m/z=473.1 (M+1)

Compound 8: $^1$H NMR (400 MHz, DMSO-d6) δ 7.92 (s, 1H), 6.90 (d, J=4.5 Hz, 1H), 6.79 (d, J=4.5 Hz, 1H), 6.31 (d, J=6.1 Hz, 1H), 5.40 (d, J=5.8 Hz, 1H), 4.68 (dd, J=6.1, 4.9 Hz, 1H), 4.50-4.30 (m, 1H), 4.30-4.14 (m, 2H), 4.03 (t, J=6.6 Hz, 2H), 3.98-3.85 (m, 2H), 1.60 (dt, J=7.5, 6.6 Hz, 2H), 0.88 (t, J=7.4 Hz, 3H). LCMS: MS m/z=378.1 (M+1)

Example 9: ((2R,3S,4R,5R)-5-(4-aminopyrrolo[2,1-f][1,2,4]triazin-7-yl)-5-cyano-3,4-dihydroxytetrahydrofuran-2-yl)methyl cyclopropyl carbonate (Compound 9)

Compound 9 was synthesized as explained in Example 4 starting from cyclopropyl chloroformate instead of isopropyl chloroformate.

Intermediate 9a: [(3aR,4R,6R,6aR)-4-cyano-4-[4-[(Z)-dimethylaminomethyleneamino]pyrrolo[2,1-f][1,2,4]triazin-7-yl]-2,2-dimethyl-6,6a-dihydro-3aH-furo[3,4-d][1,3]dioxol-6-yl]methyl cyclopropyl carbonate (and/or its (E)-isomer). LCMS: MS m/z=471.1 (M+1)

Compound 9: $^1$H NMR (400 MHz, DMSO-d6) δ 7.91 (s, 1H), 6.91 (d, J=4.5 Hz, 1H), 6.78 (d, J=4.5 Hz, 1H), 6.30 (d, J=6.1 Hz, 1H), 5.40 (d, J=5.7 Hz, 1H), 4.68 (dd, J=6.1, 5.0 Hz, 1H), 4.50-4.31 (m, 1H), 4.29-4.16 (m, 2H), 4.13-3.99 (m, 1H), 3.94 (q, J=5.5 Hz, 1H), 0.68 (m, 4H). LCMS: MS m/z=376.1 (M+1)

Example 10: ((2R,3S,4R,5R)-5-(4-aminopyrrolo[2,1-f][1,2,4]triazine-7-yl)-5-cyano-3,4-dihydroxytetrahydrofuran-2-yl)methyl (2-methoxyethyl) carbonate (Compound 10)

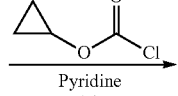

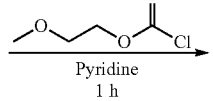

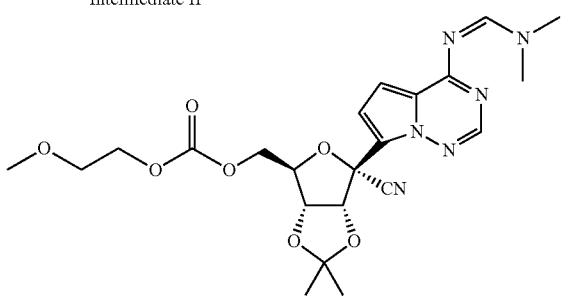

Intermediate 10a

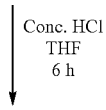

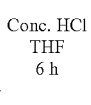

217

-continued

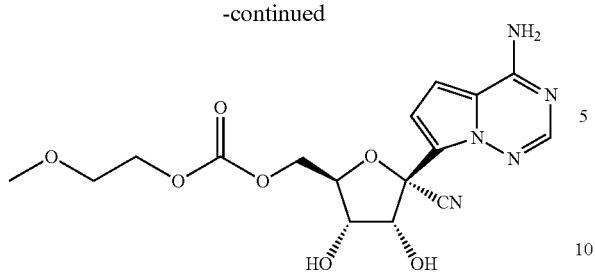

Compound 10

The Compound 10 was synthesized as explained in Example 4 starting from methoxy ethyl chloroformate instead of isopropyl chloroformate.

Intermediate 10a: [(3aR,4R,6R,6aR)-4-cyano-4-[4-[(Z)-dimethylaminomethyleneamino]pyrrolo[2,1-f][1,2,4]triazin-7-yl]-2,2-dimethyl-6,6a-dihydro-3aH-furo[3,4-d][1,3]dioxol-6-yl]methyl 2-methoxyethyl carbonate (and/or its (E)-isomer). LCMS: MS m/z=489.3 (M+1)

Compound 10: $^1$H NMR (400 MHz, DMSO-d6) δ 7.92 (s, 3H), 6.91 (d, J=4.5 Hz, 1H), 6.79 (d, J=4.5 Hz, 1H), 6.30 (d, J=6.1 Hz, 1H), 5.41 (d, J=5.7 Hz, 1H), 4.69 (dd, J=6.1, 5.0 Hz, 1H), 4.47-4.35 (m, 1H), 4.30-4.13 (m, 4H), 3.94 (q, J=5.5 Hz, 1H), 3.58-3.47 (m, 2H), 3.26 (s, 3H). LCMS: MS m/z=394.2 (M+1)

Example 11: ((2R,3S,4R,5R)-5-(4-aminopyrrolo[2,1-f][1,2,4]triazin-7-yl)-5-cyano-3,4-dihydroxytetrahydrofuran-2-yl)methyl (tetrahydrofuran-3-yl) carbonate (Compound 11)

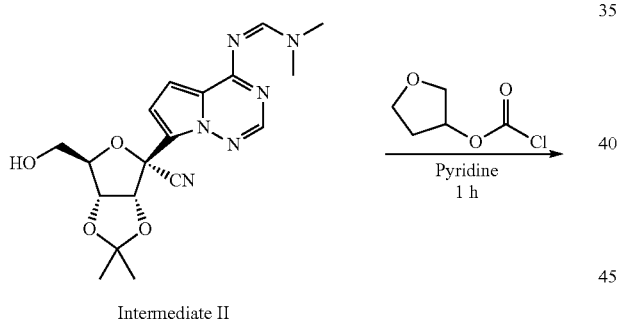

Intermediate II

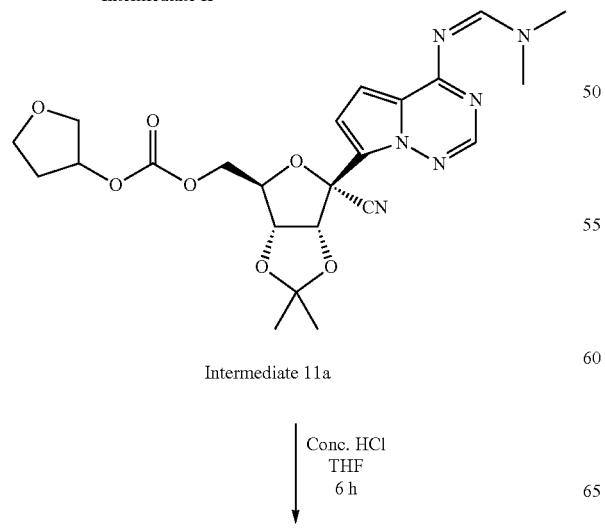

Intermediate 11a

| Conc. HCl
| THF
| 6 h

218

-continued

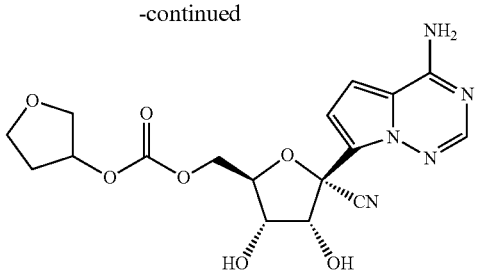

Compound 11

Compound 11 was synthesized as explained in Example 4 starting from tetrahydrofuran-3-yl chloroformate instead of isopropyl chloroformate.

Intermediate 11a: [(3aR,4R,6R,6aR)-4-cyano-4-[4-[(Z)-dimethylaminomethyleneamino]pyrrolo[2,1-f][1,2,4]triazin-7-yl]-2,2-dimethyl-6,6a-dihydro-3aH-furo[3,4-d][1,3]dioxol-6-yl]methyl tetrahydrofuran-3-yl carbonate (and/or its (E)-isomer). LCMS: MS m/z=501.3 (M+1)

Compound 11: $^1$H NMR (400 MHz, DMSO-d6) δ 7.92 (s, 1H), 6.92 (d, J=4.5 Hz, 1H), 6.80 (dd, J=4.5, 1.3 Hz, 1H), 6.32 (d, J=6.1 Hz, 1H), 5.41 (d, J=5.7 Hz, 1H), 5.15 (ddt, J=5.9, 3.7, 1.7 Hz, 1H), 4.70 (dd, J=6.1.4.9 Hz, 1H), 4.49-4.35 (m, 1H), 4.32-4.15 (m, 2H), 3.95 (q, J=4.9 Hz, 1H), 3.85-3.65 (m, 5H), 2.25-2.03 (m, 1H), 2.02-1.86 (m, 1H). LCMS: MS m/z=406.1 (M+1)

Example 12: ((2R,3S,4R,5R)-5-(4-aminopyrrolo[2,1-f][1,2,4]triazin-7-yl)-5-cyano-3,4-dihydroxytetrahydrofuran-2-yl)methyl cyclopentyl carbonate (Compound 12)

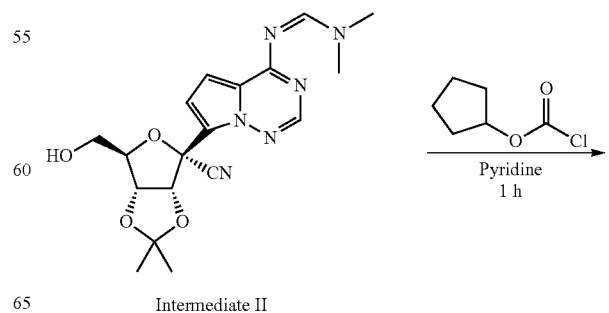

Intermediate II

219
-continued

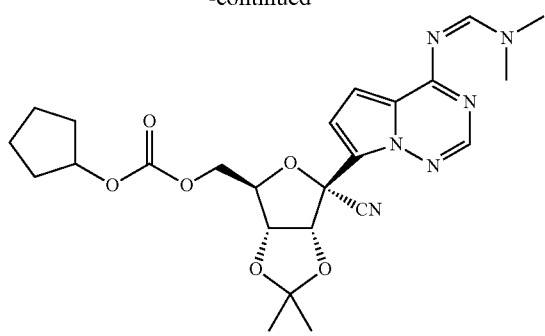

Intermediate 12a

| Conc. HCl
| THF
| 6 h

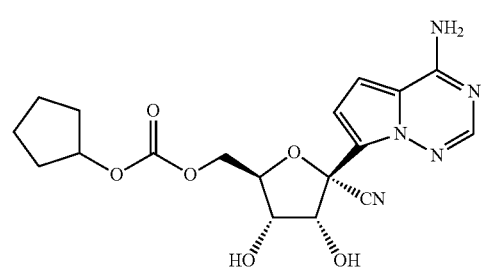

Compound 12

Compound 12 was synthesized as explained in Example 4 starting from cyclopentyl chloroformate instead of isopropyl chloroformate.

Intermediate 12a: [(3aR,4R,6R,6aR)-4-cyano-4-[4-[(Z)-dimethylaminomethyleneamino]pyrrolo[2,1-f][1,2,4]triazin-7-yl]-2,2-dimethyl-6,6a-dihydro-3aH-furo[3,4-d][1,3]dioxol-6-yl]methyl cyclopentyl carbonate (and/or its (E)-isomer). LCMS: MS m/z=499.3 (M+1)

Compound 12: $^1$H NMR (400 MHz, DMSO-d6) δ 7.92 (s, 2H), 6.91 (d, J=4.5 Hz, 1H), 6.78 (d, J=4.6 Hz, 1H), 6.31 (d, J=6.0 Hz, 1H), 5.39 (d, J=5.8 Hz, 1H), 4.98 (tt, J=6.0, 2.4 Hz, 1H), 4.67 (dd, J=6.0, 4.9 Hz, 1H), 4.49-4.32 (m, 1H), 4.29-4.11 (m, 2H), 3.93 (q, J=5.8 Hz, 1H), 1.95-1.71 (m, 4H), 1.74-1.45 (m, 4H). LCMS: MS m/z=404.2 (M+1)

220

Example 13: ((2R,3S,4R,5R)-5-(4-aminopyrrolo[2,1-f][1,2,4]triazin-7-yl)-5-cyano-3,4-dihydroxytetrahydrofuran-2-yl)methyl benzyl carbonate (Compound 13)

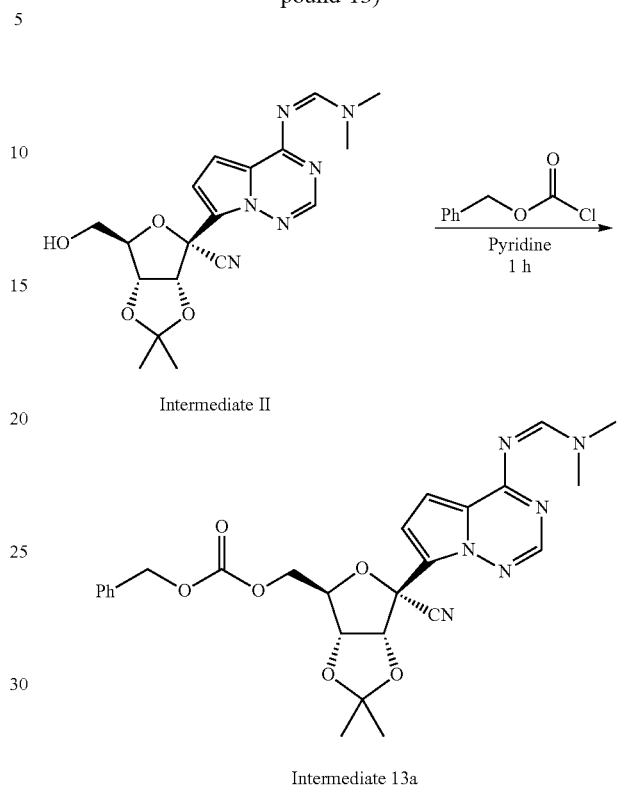

Intermediate 13a

| Conc. HCl
| THF
| 6 h

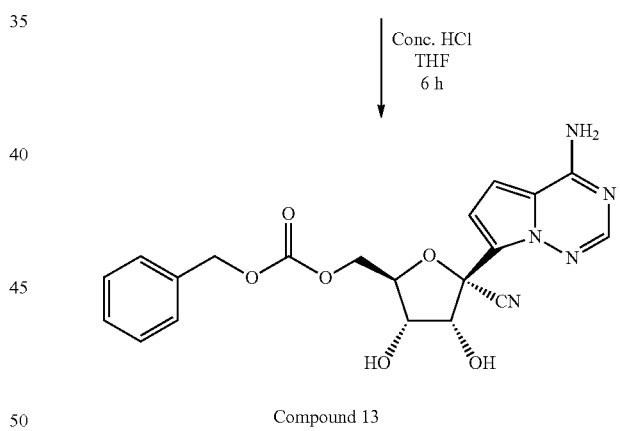

Compound 13

Compound 13 was synthesized as explained in Example 4 starting from benzyl chloroformate instead of isopropyl chloroformate.

Intermediate 13a: [(3aR,4R,6R,6aR)-4-cyano-4-[4-[(Z)-dimethylaminomethyleneamino]pyrrolo[2,1-f][1,2,4]triazin-7-yl]-2,2-dimethyl-6,6a-dihydro-3aH-furo[3,4-d][1,3]dioxol-6-yl]methyl benzyl carbonate (and/or its (E)-isomer). LCMS: MS m/z=521.3 (M+1)

Compound 13: $^1$H NMR (400 MHz, DMSO-d6) δ 7.91 (s, 1H), 7.46-7.29 (m, 5H), 6.90 (d, J=4.6 Hz, 1H), 6.78 (d, J=4.5 Hz, 1H), 6.31 (d, J=6.1 Hz, 1H), 5.40 (d, J=5.7 Hz, 1H), 5.14 (s, 2H), 4.68 (dd, J=6.1, 4.9 Hz, 1H), 4.51-4.37 (m, 1H), 4.34-4.17 (m, 2H), 3.94 (q, J=5.8 Hz, 1H). LCMS: MS m/z=426.2 (M+1)

Example 14: ((2R,3S,4R,5R)-5-(4-aminopyrrolo[2,1-f][1,2,4]triazin-7-yl)-5-cyano-3,4-dihydroxytetrahydrofuran-2-yl)methyl cyclooctyl carbonate (Compound 14)

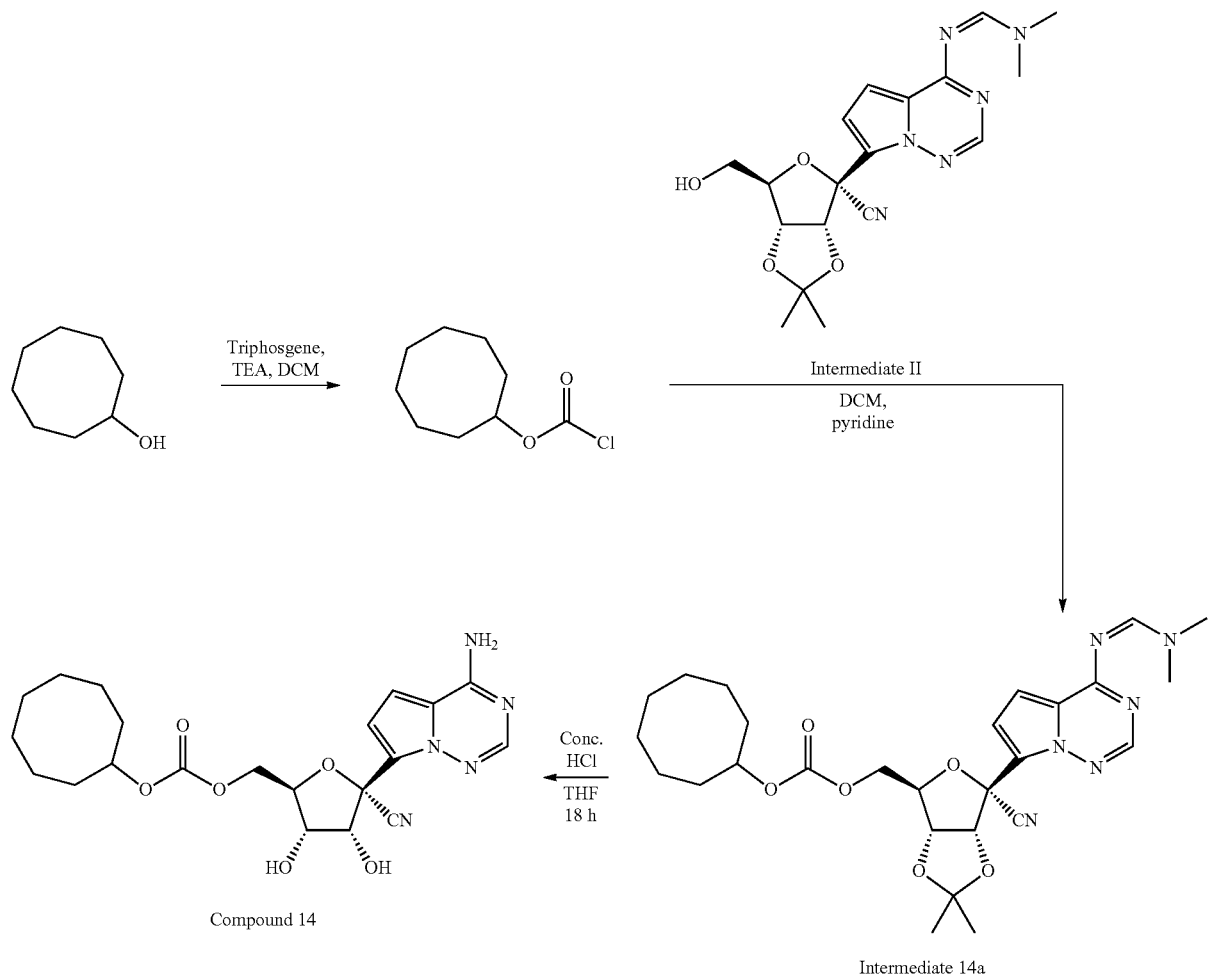

To a solution of triphosgene (393 mg, 1.3 mmol, 0.34 eq) in dichloromethane (20 mL) at 0° C., cyclooctanol (500 m, 3.9 mmol, 1 eq) was added. To the solution triethylamine (395 mg, 3.9 mmol) in dissolved in dichloromethane (5 mL) was added slowly at ice temperature. The reaction mixture was removed from the ice bath after 10 min and stirred at room temperature for 2 h. LCMS shows formation of the product cyclooctanyl chloroformate. The reaction mixture was used directly in the next step. LCMS: MS m/z=212.9 (M+Na)

A solution of Intermediate II (150 mg, 0.39 mmol) and pyridine (1 mL) in dichloromethane was cooled to 0° C. To this solution, the cyclooctanyl chloroformate reaction mixture was added and stirred at room temperature for 2 h. LCMS shows the formation of the product [(3aR,4R,6R,6aR)-4-cyano-4-|4-[(Z)-dimethylaminomethyleneamino]pyrrolo[2,1-f][1,2,4]triazin-7-yl]-2,2-dimethyl-6,6a-dihydro-3aH-furo[3,4-d[1,3]dioxol-6-yl]methyl cyclooctyl carbonate (and/or its (E)-isomer), Intermediate 14a. The reaction mixture was washed with water, brine and concentrated and purified by flash chromatography using dichloromethane and ethyl acetate as eluants. LCMS: MS m/z=541.2 (M+1)

To a solution of [(3aR,4R,6R,6aR)-4-cyano-4-[4-[(Z)-dimethylaminomethyleneamino]pyrrolo[2,1-f][1,2,4]triazin-7-yl]-2,2-dimethyl-6,6a-dihydro-3aH-furo[3,4-d][1,3]dioxol-6-yl]methyl cyclooctyl carbonate (and/or its (E)-isomer) 14a (190 mg, 0.35 mmol) in THF (5 mL) at 0° C. Conc. HCl (0.2 mL) was added and stirred at room temperature for 18 h. LCMS shows the complete conversion to the title compound.

After completion of the reaction, the reaction mixture was diluted with ethyl acetate (25 mL) and neutralized with saturated sodium bicarbonate. The organic layer was separated, washed with water, brine, and concentrated. The residue was purified by flash chromatography using dichloromethane and methanol as eluants to obtain Compound 14. $^1$H NMR (400 MHz, DMSO-d6) δ 7.91 (s, 3H), 6.90 (d, J=4.5 Hz, 1H), 6.78 (d, J=4.6 Hz, 1H), 6.30 (d, J=6.0 Hz, 1H), 5.38 (d, J=5.8 Hz, 1H), 4.67 (ddd, J=9.8, 7.1, 4.6 Hz, 2H), 4.45-4.34 (m, 1H), 4.29-4.11 (m, 2H), 3.93 (q, J=5.8 Hz, 1H), 1.78-1.58 (m, 7H), 1.49 (dt, J=11.3, 7.4 Hz, 8H). LCMS: MS m/z=446.2 (M+1)

Example 15: ((2R,3S,4R,5R)-5-(4-aminopyrrolo[2,1-f][1,2,4]triazin-7-yl)-5-cyano-3,4-dihydroxytetrahydrofuran-2-yl)methyl (2-ethylbutyl) carbonate (Compound 15)

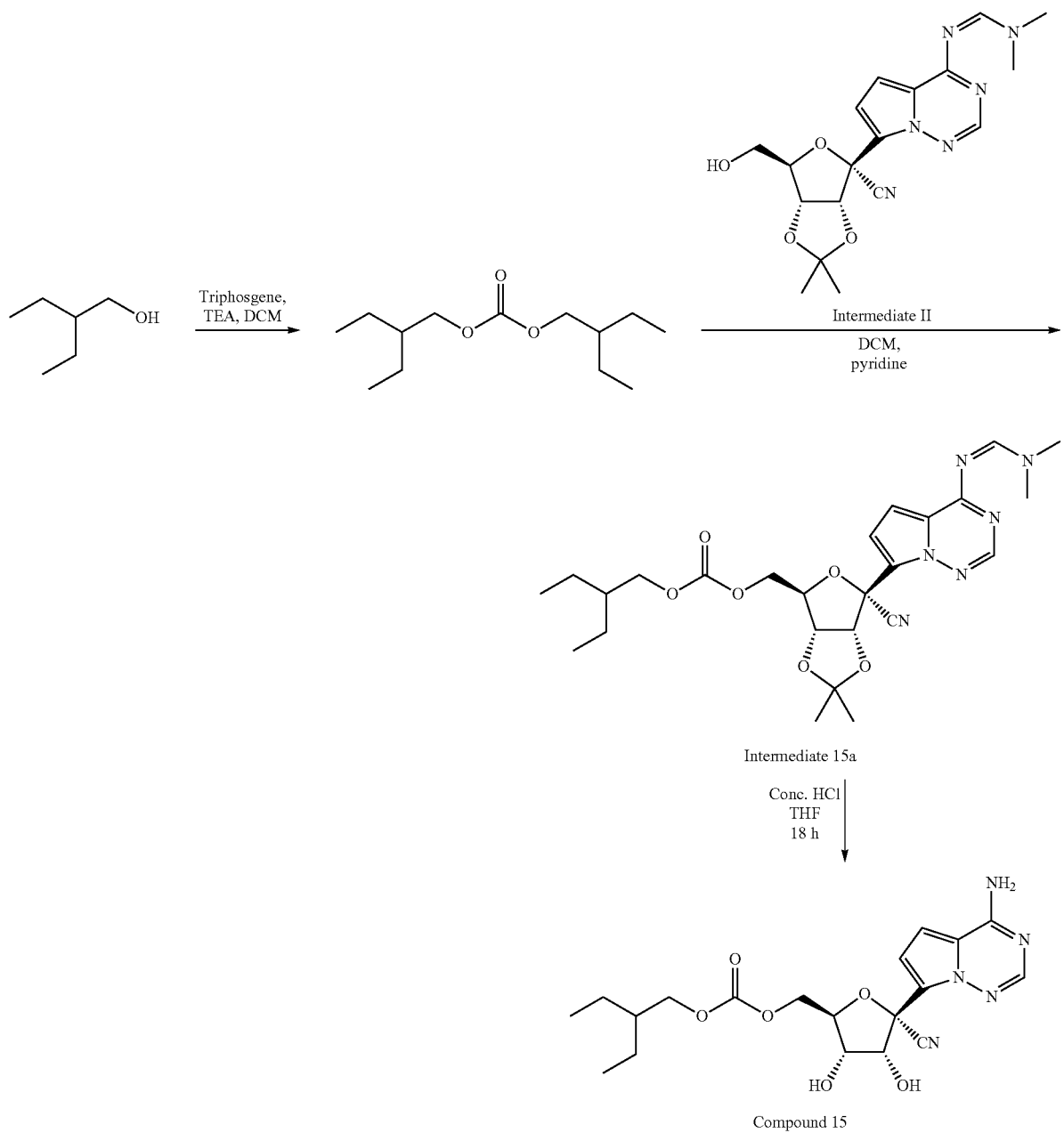

The bis(2-ethylbutyl) carbonate was synthesized using the conditions described for the preparation of cyclooctanyl chloroformate in Example 14 starting with 2-ethyl butanol instead of cyclooctanol. LCMS: MS m/z=230.3

The Intermediate 15a was synthesized as explained in Example 14 using the bis(2-ethylbutyl) carbonate and Intermediate II to obtain the intermediate [(3aR,4R,6R,6aR)-4-cyano-4-[4-[(Z)-dimethylaminomethyleneamino]pyrrolo[2,1-f][1,2,4]triazin-7-yl]-2,2-dimethyl-6,6a-dihydro-3aH-furo[3,4-d][1,3]dioxol-6-yl]methyl 2-ethylbutyl carbonate (and/or its (E)-isomer), Intermediate 15a. LCMS: MS m/z=515.3 (M+1)

Compound 15 was synthesized as explained in Example 14 using Intermediate 15a. Compound 15: $^1$H NMR (4(0) MHz, DMSO-d6) δ 7.92 (s, 3H), 6.90 (d, J=4.5 Hz, 1H), 6.79 (d, J=4.5 Hz, 1H), 6.32 (d, J=5.9 Hz, 1H), 5.39 (d, J=5.7 Hz, 1H), 4.66 (t, J=5.5 Hz, 1H), 4.48-4.38 (m, 1H), 4.30-4.17 (m, 2H), 4.01 (d, J=5.7 Hz, 2H), 3.93 (q, J=5.7 Hz, 1H), 1.49 (p, J=6.2 Hz, 1H), 1.30 (p, J=7.3 Hz, 4H), 0.85 (t, J=7.5 Hz, 6H). LCMS: MS m/z=420.2 (M+1)

Example 16: (2R,3R,4R,5R)-2-(4-aminopyrrolo[2,1-f][1,2,4]triazin-7-yl)-2-cyano-5-(((isobutoxycarbonyl)oxy)methyl)tetrahydrofuran-3,4-diyl bis(2-methylpropanoate) (Compound 16)

Compound 16

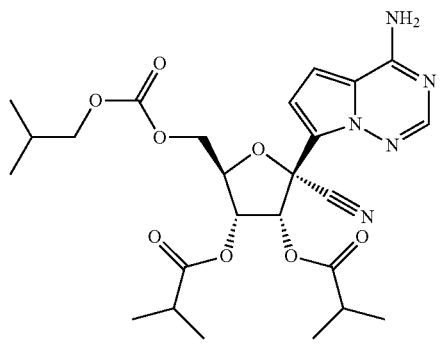

To a solution of Compound 1 (150 mg, 0.38 mmol) in THF (10 mL) isobutyric anhydride (78 mg, 0.77 mmol) was added followed by dimethyl aminopyridine (7 mg, 0.06 mmol). The reaction mixture was stirred at room temperature for 30 min. After the completion of the reaction, the mixture was concentrated and purified by flash chromatography using dichloromethane and ethyl acetate as eluants to provide Compound 16.: $^1$H NMR (400 MHz, DMSO-d6) δ 7.92 (s, 3H), 6.93 (d, J=4.6 Hz, 1H), 6.77 (d, J=4.6 Hz, 1H), 6.09 (d, J=5.8 Hz, 1H), 5.43 (dd, J=5.7, 4.1 Hz, 1H), 4.61 (dt, J=4.9, 3.6 Hz, 1H), 4.46 (dd, J=12.1, 3.4 Hz, 1H), 4.34 (dd, J=12.1, 5.0 Hz, 1H), 3.90-3.77 (m, 2H), 2.61 (dp, J=11.8, 7.0 Hz, 2H), 1.85 (hept, J=6.7 Hz, 1H), 1.15 (dd, J=8.1, 7.0 Hz, 6H), 1.10 (d, J=7.0 Hz, 6H), 0.85 (d, J=6.7 Hz, 6H). LCMS: MS m/z=532.3 (M+1)

Example 17: ((3aR,4R,6R,6aR)-6-(4-aminopyrrolo[2,1-f][1,2,4]triazin-7-yl)-6-cyano-2-oxotetrahydrofuro[3,4-d][1,3]dioxol-4-yl)methyl isobutyl carbonate (Compound 17)

Compound 17

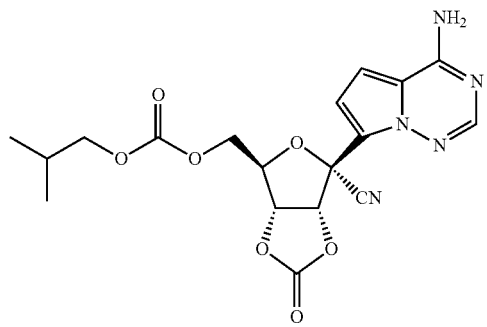

To a solution of Compound 1 (100 mg, 0.26 mmol) in DMF (2 mL), diphenyl carbonate (66 mg, 0.31 mmol) and triethylamine (26 mg, 0.26 mmol) were added and heated at 100° C. for 2 h. LCMS shows the complete conversion to the product. The reaction mixture was diluted with ethyl acetate, washed with bicarbonate, water, brine, dried over sodium sulphate and concentrated and purified by flash using dichloromethane and ethyl acetate as eluants to provide Compound 17.: $^1$H NMR (400 MHz, DMSO-d6) δ 8.04 (d, J=25.5 Hz, 2H), 7.96 (s, 1H), 6.97-6.89 (m, 2H), 5.98 (d, J=7.7 Hz, 1H), 5.50 (dd, J=7.7, 3.9 Hz, 1H), 4.82 (dt, J=5.8, 3.8 Hz, 1H), 4.43 (dd, J=12.0, 3.8 Hz, 1H), 4.28 (dd, J=12.0, 5.8 Hz, 1H), 3.81 (dd, J=6.6, 1.7 Hz, 2H), 1.83 (dt, J=13.4, 6.7 Hz, 2H), 0.84 (d, J=6.7 Hz, 6H). LCMS: MS m/z=418.1 (M+1).

Example 18: ((2R,3S,4R,5R)-5-(3-((((benzyloxy)(hydroxy)phosphoryl)oxy)methyl)-4-imino-3,4-dihydropyrrolo[2,1-f][1,2,4]triazin-7-yl)-5-cyano-3,4-dihydroxytetrahydrofuran-2-yl)methyl neopentyl carbonate (Compound 18)

Compound 18

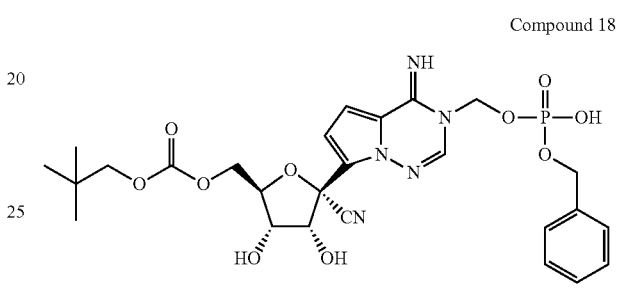

To a solution of Compound 3 (750 mg, 1.9 mmol) and sodium iodide (832 mg, 5.6 mmol) in acetone (20 mL), dibenzyl chloromethyl phosphate (1813 mg, 5.6 mmol) in acetone (5 mL) was added slowly and stirred at room temperature for 48 h. After completion of the reaction, the solvents were distilled off and charged the residue on flash column and eluted with dichloromethane and methanol as eluants to obtain Compound 18.: $^1$H NMR (400 MHz, DMSO-d6) δ 8.38 (d, J=1.5 Hz, 1H), 7.46 (d, J=4.7 Hz, 1H), 7.32 (d, J=4.1 Hz, 3H), 7.16 (d, J=4.5 Hz, 4H), 6.96 (d, J=4.8 Hz, 1H), 5.66 (d, J=12.0 Hz, 2H), 5.17 (t, J=14.2 Hz, 1H), 4.81 (d, J=7.0 Hz, 1H), 4.71 (d, J=7.1 Hz, 2H), 4.52 (d, J=4.8 Hz, 1H), 4.41 (dd, J=12.2, 2.7 Hz, 1H), 4.34-4.26 (m, 1H), 4.19 (dd, J=12.1, 5.1 Hz, 1H), 3.92 (dd, J=6.8, 4.9 Hz, 1H), 3.76 (d, J=3.4 Hz, 2H), 0.86 (s, 9H). $^{31}$P NMR (162 MHz, DMSO-d6) δ −1.89 (dt, J=15.2, 7.9 Hz). LCMS: MS m/z=606.1 (M+1)

Example 19: ((2R,3S,4R,5R)-5-cyano-3,4-dihydroxy-5-(4-imino-3-((phosphonooxy)methyl)-3,4-dihydropyrrolo[2,1-f][1,2,4]triazin-7-yl)tetrahydrofuran-2-yl)methyl neopentyl carbonate (Compound 19)

Compound 19

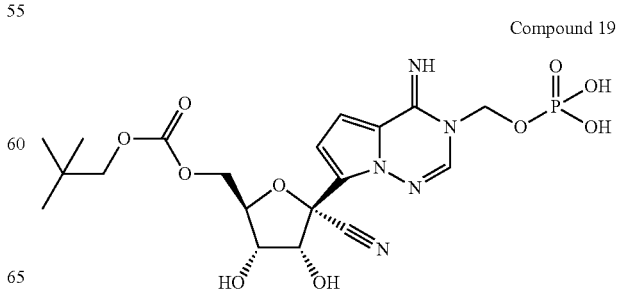

To a solution of Compound 18 (350 mg, 0.58 mmol) in ethanol, 5% Palladium on Carbon (30 mg) was added and stirred under hydrogen balloon for 48 h. The reaction was stopped, filtered washing with ethyl acetate, and the filtrate was concentrated. The residue was purified by prep HPLC using 0.1% TFA acetonitrile and 0.1% TFA water as eluants to obtain Compound 19 as a trifluoroacetate (TFA) salt. Compound 19: $^1$H NMR (400 MHz, DMSO-d6) δ 8.41 (s, 1H), 7.48 (d, J=4.8 Hz, 1H), 7.37-7.22 (m, 1H), 6.97 (d, J=4.8 Hz, 1H), 5.62 (d, J=10.7 Hz, 2H), 4.88-4.65 (m, 1H), 4.56 (d, J=4.8 Hz, 1H), 4.47-4.33 (m, 1H), 4.27 (ddd, J=7.3, 5.1, 2.6 Hz, 1H), 4.18 (dd, J=12.1, 5.1 Hz, 1H), 3.83-3.65 (m, 2H), 0.86 (s, 9H); $^{31}$P NMR (162 MHz, DMSO-d6) δ −0.30 (t, J=10.6 Hz). LCMS: MS m/z=516.2 (M+1).

Example 20: ((2R,3S,4R,5R)-5-(4-aminopyrrolo[2,1-f][1,2,4]triazin-7-yl)-5-cyano-3,4-dihydroxytetrahydrofuran-2-yl)methyl azetidin-3-yl carbonate (Compound 20)

tralization, the organic layer was separated, and the aqueous layer was concentrated and purified by prep HPLC using 0.1% TFA acetonitrile and 0.1% TFA water as eluants to obtain Compound 20 as TFA salt. Intermediate 20a: tert-butyl 3-(((((3aR,4R,6R,6aR)-6-cyano-6-(4-(((Z)-(dimethylamino)methylene)amino)pyrrolo[2,1-f][1,2,4]triazin-7-yl)-2,2-dimethyltetrahydrofuro[3,4-d][1,3]dioxol-4-yl)methoxy)carbonyl)oxy)azetidine-1-carboxylate. LCMS: MS m/z=586.3 (M+1). Compound 20: $^1$H NMR (400 MHz, DMSO-d$_6$) δ 9.25 (s, 1H), 9.02 (s, 1H), 8.03 (d, J=39.0 Hz, 1H), 7.94 (s, 1H), 6.97 (d, J=4.6 Hz, 1H), 6.83 (d, J=4.5 Hz, 1H), 5.18 (tt, J=6.9, 5.1 Hz, 1H), 4.71 (d, J=5.0 Hz, 1H), 4.46-4.37 (m, 1H), 4.27 (td, J=6.7, 6.0, 3.1 Hz, 6H), 3.98-3.91 (m, 1H). $^{19}$F NMR (376 MHz, DMSO-d6) 5-74.34. LCMS: MS m/z=391.2 (M+1)

Example 21: [(2R,3S,4R,5R)-5-[4-(butanoylamino)pyrrolo[2,1-f][1,2,4]triazin-7-yl]-5-cyano-3,4-dihydroxy-tetrahydrofuran-2-yl]methyl isobutyl carbonate (Compound 21)

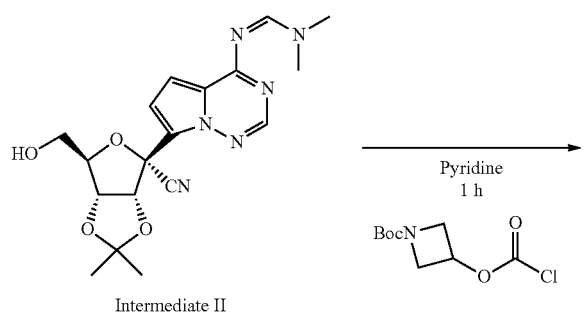

Intermediate II

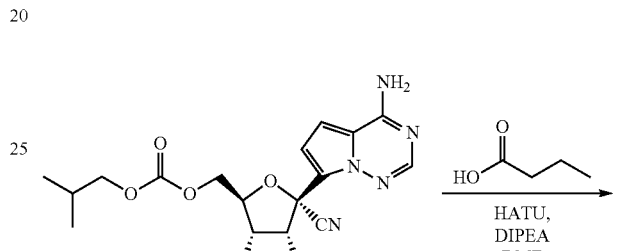

Intermediate Ia

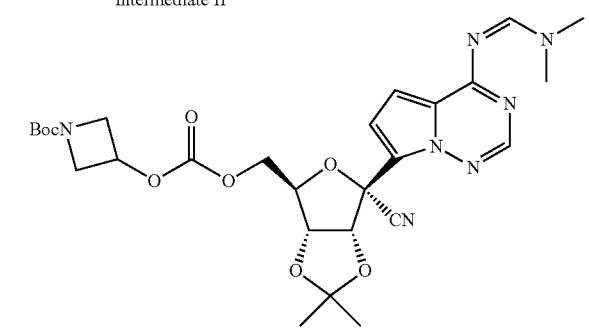

Intermediate 20a

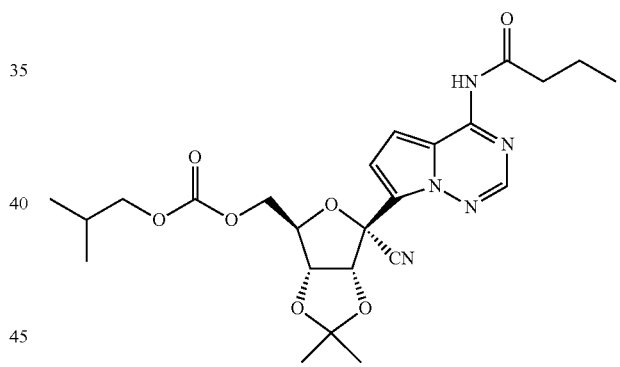

Intermediate 21a

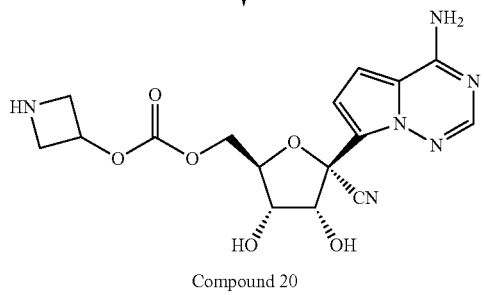

Compound 20

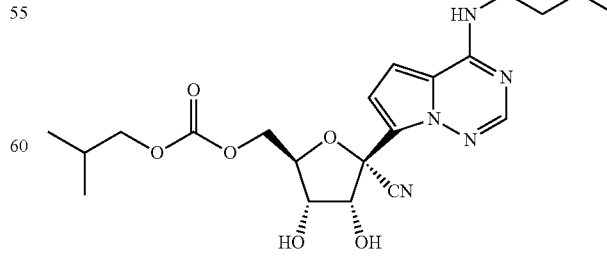

Compound 21

Compound 20 was synthesized as explained in Example 4 starting from tert-butyl 3-((chlorocarbonyl)oxy)azetidine-1-carboxylate instead of isopropyl chloroformate. After neu- To a solution of butyric acid (490 mg, 5.6 mmol), and HATU (1767 mg, 4.6 mmol) in DMF (5 mL), Intermediate 1a (2000 mg, 4.6 mmol) was added followed by diisopropyl ethyl amine (599 mg, 4.6 mmol) and stirred at room temperature for 48 h. The reaction mixture was diluted with ethyl acetate (100 mL), washed with water (5 mL) and brine (10 ml), dried, and concentrated to get [(3aR,4R,6R,6aR)-4-[4-(butanoylamino)pyrrolo[2,1-f][1,2,4]triazin-7-yl]-4-cyano-2,2-dimethyl-6,6a-dihydro-3aH-furo[3,4-d][1,3]dioxol-6-yl]methyl isobutyl carbonate, Intermediate 21a. LCMS: MS m/z=502.2 (M+1).

To a solution of Intermediate 21a (1550 mg, 3.1 mmol) in acetonitrile (10 mL), conc. HCl (1.4 mL, 15 mmol) was added and stirred at room temperature for 1 h. After the completion of the reaction, the reaction mixture was diluted with ethyl acetate (100 mL), neutralized with saturated sodium bicarbonate, separated the organic layer, washed with water and brine, dried, and concentrated. The residue was purified by flash chromatography using dichloromethane and methanol as eluents to obtain Compound 21. $^1$H NMR (400 MHz, DMSO-d6) δ 10.88 (s, 1H), 8.39 (s, 1H), 7.28 (d, J=4.8 Hz, 1H), 7.03 (d, J=4.7 Hz, 1H), 6.43 (d, J=6.0 Hz, 1H), 5.45 (d, J=5.3 Hz, 1H), 4.66 (t, J=5.2 Hz, 1H), 4.43 (dd, J=11.7, 2.4 Hz, 1H), 4.34-4.14 (m, 2H), 3.94 (d, J=5.6 Hz, 1H), 3.86 (d, J=6.5 Hz, 2H), 3.14 (qd, J=7.4, 4.2 Hz, 2H), 1.88 (dt, J=13.3, 6.7 Hz, 1H), 1.63 (p, J=7.3 Hz, 2H), 0.94 (t, J=7.4 Hz, 3H), 0.88 (d, J=6.7 Hz, 6H). LCMS: MS m/z=462.1 (M+1).

Example 22: ((2R,3S,4R,5R)-5-(4-aminopyrrolo[2,1-f][1,2,4]triazin-7-yl)-5-cyano-3,4-dihydroxytetrahydrofuran-2-yl)methyl tert-butyl carbonate (Compound 46)

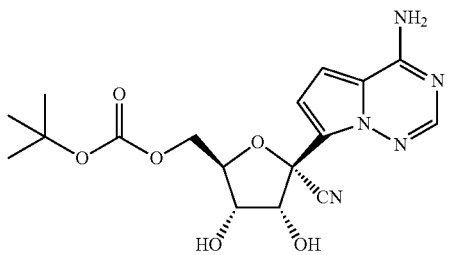 [SMILES: CC(C)(C)OC(=O)OC[C@H]1O[C@@](C#N)(c2ccc3c(N)ncnn23)[C@H](O)[C@@H]1O]

Step 1: Intermediate 22a—((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl tert-butyl carbonate Intermediate 22a

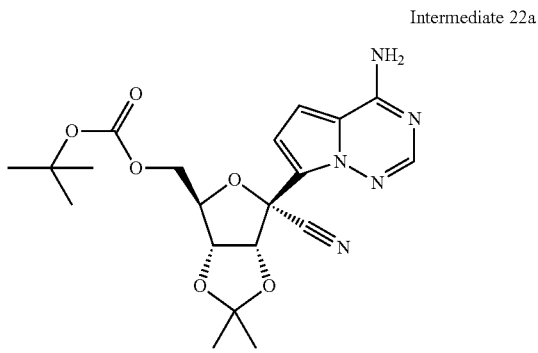 [SMILES: CC(C)(C)OC(=O)OC[C@H]1O[C@@](C#N)(c2ccc3c(N)ncnn23)[C@@H]2OC(C)(C)O[C@@H]21]

To a solution of (3aR,4R,6R,6aR)-4-(4-aminopyrrolo[2,1-f][1,2,4]triazin-7-yl)-6-(hydroxymethyl)-2,2-dimethyl-6,6a-dihydro-3aH-furo[3,4-d][1,3]dioxole-4-carbonitrile (Intermediate I, 3.0 g, 9.1 mmol) and di-tert-butyl dicarbonate (2.17 g, 10 mmol) in THF (30 mL) was added catalytic DMAP and the reaction mixture was stirred for 1.5 h. The reaction mixture was then concentrated in vacuo and purified by flash chromatography using dichloromethane and methanol as eluents to obtain Intermediate 22a. LCMS: MS m/z: 432.0 (M+1).

Step 2: Compound 46—((2R,3S,4R,5R)-5-(4-aminopyrrolo[2,1-f][1,2,4]triazin-7-yl)-5-cyano-3,4-dihydroxytetrahydrofuran-2-yl)methyl tert-butyl carbonate Compound 46

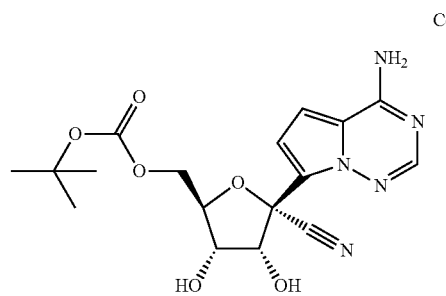

To a solution of ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl tert-butyl carbonate (Intermediate 22a, 3.2 g, 7.4 mmol) in THF (30 mL) at 0° C. was added conc. HCl (3.11 mL, 37 mmol). After ~10 min, the reaction mixture was brought to room temperature and stirred for 6 h.

The reaction mixture was diluted with ethyl acetate, neutralized with sat aq. NaHCO$_3$ solution, and the organics were separated and washed with water, brine, dried and concentrated in vacuo. The resulting residue was purified by flash chromatography using dichloromethane and methanol as eluents to obtain Compound 46. $^1$H NMR (400 MHz, DMSO-d6) δ 7.92 (s, 2H), 6.91 (d, J=4.6 Hz, 1H), 6.79 (d, J=4.5 Hz, 1H), 6.30 (d, J=6.1 Hz, 1H), 5.38 (d, J=5.8 Hz, 1H), 4.67 (dd, J=6.1, 5.0 Hz, 1H), 4.35 (dd, J=11.8, 2.9 Hz, 1H), 4.20 (td, J=6.2, 2.8 Hz, 1H), 4.12 (dd, J=11.8, 6.0 Hz, 1H), 3.92 (td, J=6.3, 5.1 Hz, 1H), 1.41 (s, 9H). LCMS: MS m/z: 392.0 (M+1).

Example 23: ((2R,3S,4R,5R)-5-(4-aminopyrrolo[2,1-f][1,2,4]triazin-7-yl)-5-cyano-3,4-dihydroxy tetrahydrofuran-2-yl)methyl (1-methylcyclohexyl) carbonate (Compound 47)

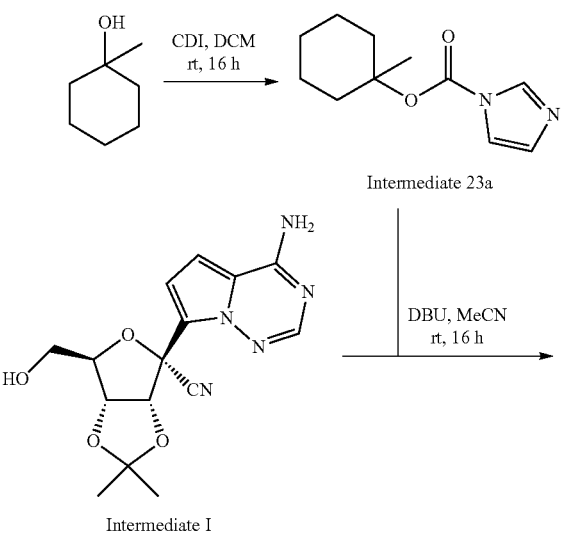

Intermediate 23a

Intermediate I

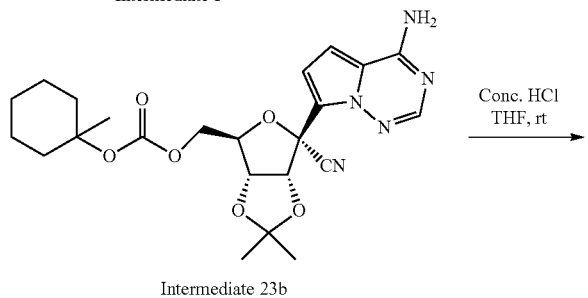

Intermediate 23b

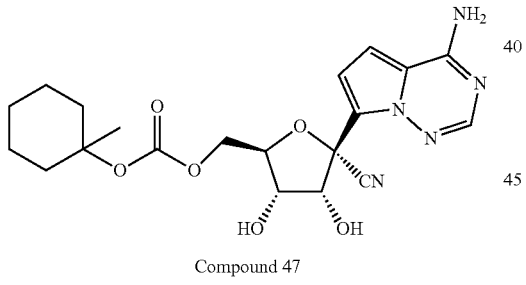

Compound 47

Step 1: Intermediate 23a

1-Methylcyclohexanol (2 mL, 16.1 mmol) was added dropwise to a stirring solution of 1,1'-carbonyldiimidazole (3.91 g, 24.1 mmol) in DCM (53 mL) at 0° C., then warmed to room temperature and stirred for 16 h. The reaction mixture was transferred to a separatory funnel, washed with water two times, dried over MgSO$_4$, and concentrated. Intermediate 23a was quantified using NMR and used without further purification.

Step 2. Intermediate 23b

Intermediate 23a (2.21 g, 10.6 mmol) and Intermediate I (3.2 g, 9.66 mmol) were dissolved in MeCN (27 mL) at room temperature, then was subsequently treated with 1,8-diazabicyclo[5.4.0]undec-7-ene (0.29 mL, 1.93 mmol). The resulting solution was stirred at room temperature for 16 h then was quenched with saturated aqueous ammonium chloride. The biphasic mixture was extracted using EtOAc three times, and the combined organic layers were dried over MgSO$_4$, concentrated. The crude Intermediate 23b was used without further purification assuming quantitative yield. LCMS: MS m/z 494.1 (M+23).

Step 3: Compound 47—((2R,3S,4R,5R)-5-(4-aminopyrrolo[2,1-f][1,2,4]triazin-7-yl)-5-cyano-3,4-dihydroxytetrahydrofuran-2-yl)methyl (1-methylcyclohexyl) carbonate A solution of Intermediate 23b (3.62 g, 1 mmol) in THF (77 mL) at 0° C. was treated with conc. HCl (6 mL, 72.6 mmol), then reaction was warmed to RT and stirred for 6.5 h. The resulting mixture was basified with saturated aqueous sodium bicarbonate, extracted with EtOAc three times, and the combined organic layers were dried over MgSO$_4$ then concentrated. The residue was purified by flash chromatography using dichloromethane and methanol as eluants to obtain Compound 47. $^1$H NMR (400 MHz, DMSO-d6) δ 8.17-7.68 (m, 3H), 7.04-6.87 (m, 1H), 6.85-6.78 (m, 1H), 6.40-6.27 (m, 1H), 5.51-5.32 (m, 1H), 4.77-4.56 (m, 1H), 4.44-4.33 (m, 1H), 4.26-4.07 (m, 2H), 3.99-3.88 (m, 1H), 2.04-1.92 (m, 2H), 1.55-1.13 (m, 11H). LCMS: MS m/z: 454.1 (M+23).

Example 24: ((2R,3S,4R,5R)-5-(4-aminopyrrolo[2,1-f][1,2,4]triazin-7-yl)-5-cyano-3,4-dihydroxytetrahydrofuran-2-yl)methyl (1,3,3-trimethylbicyclo[2.2.1]heptan-2-yl) carbonate (Compound 48)

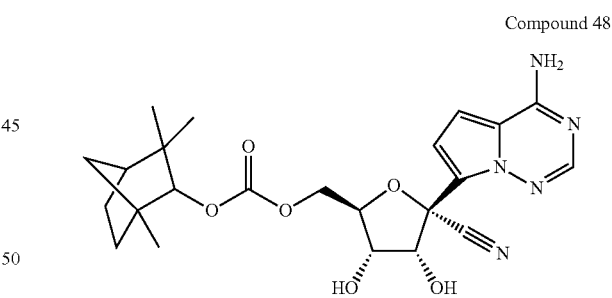

Compound 48

Compound 48 was synthesized in a manner similar to Compound 47 (((2R,3S,4R,5R)-5-(4-aminopyrrolo[2,1-f][1,2,4]triazin-7-yl)-5-cyano-3,4-dihydroxytetrahydrofuran-2-yl)methyl (1-methylcyclohexyl) carbonate), replacing 1-methylcyclohexanol with fenchyl alcohol (racemic). $^1$H NMR (400 MHz, DMSO-d6) δ 7.92 (s, 3H), 6.90 (d, J=4.6 Hz, 1H), 6.85-6.76 (m, 1H), 6.36 (d, J=6.0 Hz, 1H), 5.40 (d, J=5.8 Hz, 1H), 4.64 (dd, J=5.9, 4.8 Hz, 1H), 4.48-4.37 (m, 1H), 4.32-4.20 (m, 2H), 4.16 (t, J=3.1 Hz, 1H), 3.99-3.86 (m, 1H), 1.72-1.53 (m, 4H), 1.50-1.34 (m, 11H), 1.17 (dt, J=10.1, 2.1 Hz, 1H), 1.05 (s, 7H), 0.71 (s, 3H). LCMS: MS m/z: 472.1 (M+1).

Example 25: ((2R,3S,4R,5R)-5-(4-aminopyrrolo[2,1-f][1,2,4]triazin-7-yl)-5-cyano-3,4-dihydroxytetrahydrofuran-2-yl)methyl (2-(pyridin-4-yl)propan-2-yl) carbonate (Compound 49)

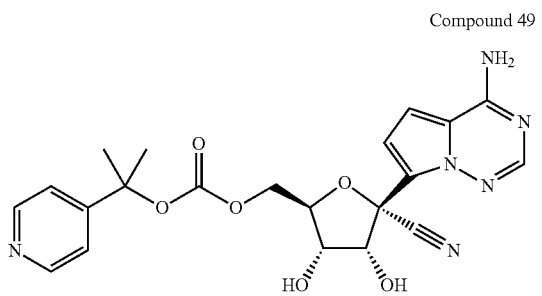 [SMILES: CC(C)(OC(=O)OC[C@H]1O[C@@](C#N)(c2ccc3c(N)ncnn23)[C@H](O)[C@@H]1O)c1ccncc1]

Compound 49

Compound 49 (((2R,3S,4R,5R)-5-(4-aminopyrrolo[2,1-f][1,2,4]triazin-7-yl)-5-cyano-3,4-dihydroxytetrahydrofuran-2-yl)methyl (2-(pyridin-4-yl)propan-2-yl) carbonate) was synthesized in a manner similar to Compound 47 (((2R,3S,4R,5R)-5-(4-aminopyrrolo[2,1-f][1,2,4]triazin-7-yl)-5-cyano-3,4-dihydroxytetrahydrofuran-2-yl)methyl (1-methylcyclohexyl) carbonate), replacing 1-methylcyclohexanol with 2-(pyridin-4-yl)propan-2-ol. $^1$H NMR (400 MHz, DMSO-d6) δ 8.53-8.42 (m, 2H), 7.93 (s, 3H), 7.31-7.19 (m, 2H), 6.93 (d, J=4.5 Hz, 1H), 6.82 (d, J=4.5 Hz, 1H), 6.33 (d, J=6.1 Hz, 1H), 5.40 (d, J=5.7 Hz, 1H), 4.69 (dd, J=6.1, 5.0 Hz, 1H), 4.33 (dd, J=11.6, 2.7 Hz, 1H), 4.25-4.09 (m, 2H), 3.97-3.86 (m, 1H), 1.69 (d, J=2.8 Hz, 6H). LCMS: MS m/z: 455.1 (M+1)

Example 26: ((2R,3S,4R,5R)-5-(4-aminopyrrolo[2,1-f][1,2,4]triazin-7-yl)-5-cyano-3,4-dihydroxytetrahydrofuran-2-yl)methyl (tetrahydro-2H-pyran-4-yl) carbonate (Compound 50)

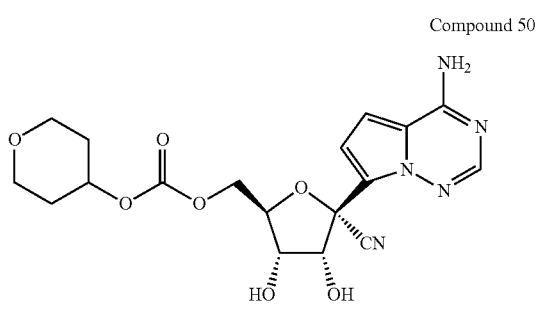 [SMILES: N#C[C@@]1(c2ccc3c(N)ncnn23)O[C@H](COC(=O)OC2CCOCC2)[C@@H](O)[C@H]1O]

Compound 50

Compound 50 was synthesized in a manner similar to ((2R,3S,4R,5R)-5-(4-aminopyrrolo[2,1-f][1,2,4]triazin-7-yl)-5-cyano-3,4-dihydroxytetrahydrofuran-2-yl)methyl cyclooctyl carbonate (Compound 14) in Example 41, using the 2-step procedure and replacing cyclooctanol with tetrahydro-2H-pyran-4-ol. $^1$H NMR (400 MHz, DMSO-d$_6$) δ 7.93 (s, 3H), 6.92 (d, J=4.5 Hz, 1H), 6.80 (d, J=4.5 Hz, 1H), 6.34 (d, J=6.0 Hz, 1H), 5.42 (d, J=5.8 Hz, 1H), 4.79-4.65 (m, 2H), 4.49-4.38 (m, 1H), 4.29-4.17 (m, 2H), 3.95 (q, J=5.9 Hz, 1H), 3.78 (dq, J=12.5, 4.4 Hz, 2H), 3.45 (tdd, J=9.0, 4.5, 3.0 Hz, 2H), 1.94-1.84 (m, 2H), 1.62-1.48 (m, 2H). LCMS: MS m/z: 420.01 (M+1).

Example 27. ((2R,3S,4R,5R)-5-(4-aminopyrrolo[2,1-f][1,2,4]triazin-7-yl)-5-cyano-3,4-dihydroxytetrahydrofuran-2-yl)methyl ((0R,2S,4R)-1,7,7-trimethylbicyclo[2.2.1]heptan-2-yl) carbonate (Compound 51)

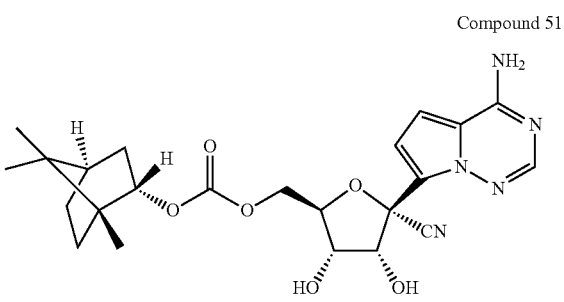 [SMILES: CC1(C)[C@@H]2CC[C@@]1(C)[C@@H](OC(=O)OC[C@H]1O[C@@](C#N)(c3ccc4c(N)ncnn34)[C@H](O)[C@@H]1O)C2]

Compound 51

Compound 51 was synthesized in a manner similar to ((2R,3S,4R,5R)-5-(4-aminopyrrolo[2,1-f][1,2,4]triazin-7-yl)-5-cyano-3,4-dihydroxytetrahydrofuran-2-yl)methyl cyclooctyl carbonate (Compound 14) in Example 41, using the 2-step procedure and replacing cyclooctanol with (+)-Borneol. The crude reaction mixture was concentrated in vacuo and resulting Intermediate 27a was used directly in the deprotection step. LCMS: MS m/z: 567.3 (M+1). Compound 51 was purified by silica gel chromatography (0-15% MeOH/DCM). $^1$H NMR (400 MHz, DMSO-d6) δ 7.92 (s, 3H), 6.90 (d, J=4.5 Hz, 1H), 6.79 (d, J=4.5 Hz, 1H), 6.35 (d, J=6.0 Hz, 1H), 5.41 (d, J=5.8 Hz, 1H), 4.73 (ddd, J=9.9, 3.4, 1.9 Hz, 1H), 4.65 (dd, J=6.0, 4.9 Hz, 1H), 4.45 (dd, J=11.4, 2.3 Hz, 1H), 4.27-4.16 (m, 2H), 3.94 (td, J=6.2, 4.9 Hz, 1H), 2.34-2.21 (m, 1H), 1.82 (ddd, J=13.0, 9.2, 4.2 Hz, 1H), 1.77-1.63 (m, 2H), 1.30 (tt, J=11.9, 2.8 Hz, 1H), 1.20 (ddd, J=11.3, 9.2.4.3 Hz, 1H), 0.99 (dd, J=13.7, 3.4 Hz, 1H), 0.87 (s, 3H), 0.85 (s, 3H), 0.82 (s, 3H). LCMS: MS m/z: 471.98 (M+1).

Example 28: ((2R,3S,4R,5R)-5-(4-aminopyrrolo[2,1-f][1,2,4]triazin-7-yl)-5-cyano-3,4-dihydroxytetrahydrofuran-2-yl)methyl (bicyclo[2.2.1]heptan-1-ylmethyl) carbonate (Compound 52)

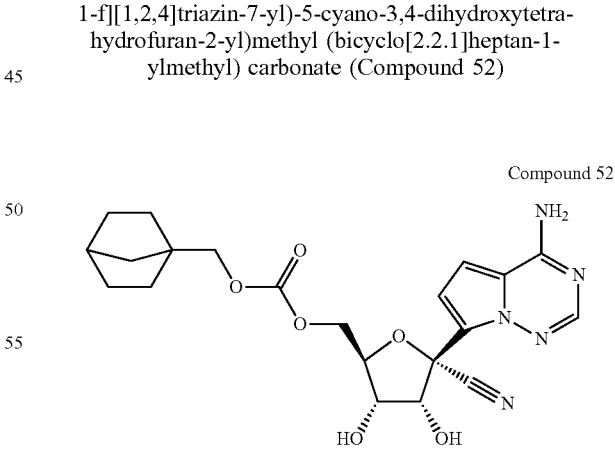

Compound 52

Compound 52 was synthesized in a manner similar to ((2R,3S,4R,5R)-5-(4-aminopyrrolo[2,1-f][1,2,4]triazin-7-yl)-5-cyano-3,4-dihydroxytetrahydrofuran-2-yl)methyl cyclooctyl carbonate (Compound 14) in Example 41, using the 2-step procedure and replacing cyclooctanol with bicyclo[2.2.1]heptan-1-ylmethanol. The crude reaction mixture was concentrated in vacuo and the intermediate was used directly in the deprotection step. LCMS: MS m/z: 444.10 (M+1). 1H NMR (400 MHz, DMSO-d6) δ 7.92 (s, 3H), 6.90 (d, J=4.6 Hz, 1H), 6.79 (d, J=4.6 Hz, 1H), 6.34 (d, J=6.0 Hz, 1H), 5.41 (d, J=5.8 Hz, 1H), 4.67 (dd, J=6.0, 4.9 Hz, 1H), 4.42 (d, J=9.0 Hz, 1H), 4.28-4.17 (m, 4H), 3.94 (q, J=5.8 Hz, 1H), 2.19 (dd, J=5.3, 3.6 Hz, 1H), 1.63-1.52 (m, 2H), 1.43 (tt, J=13.2, 3.1 Hz, 2H), 1.31-1.12 (m, 6H).

Example 29: ((2R,3S,4R,5R)-5-(4-aminopyrrolo[2,1-f][1,2,4]triazin-7-yl)-5-cyano-3,4-dihydroxytetrahydrofuran-2-yl)methyl (cyclobutylmethyl) carbonate (Compound 53)

Compound 53

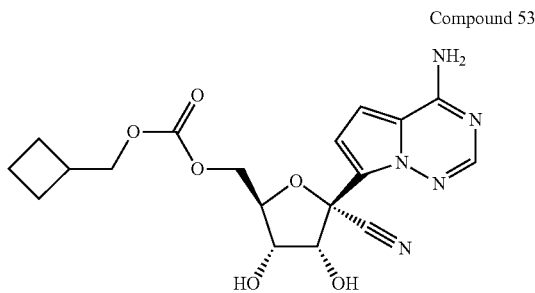 [SMILES: N#C[C@@]1(c2ccc3c(N)ncnn23)O[C@H](COC(=O)OCC2CCC2)[C@@H](O)[C@H]1O]

Compound 53 was synthesized in a manner similar to ((2R,3S,4R,5R)-5-(4-aminopyrrolo[2,1-f][1,2,4]triazin-7-yl)-5-cyano-3,4-dihydroxytetrahydrofuran-2-yl)methyl cyclooctyl carbonate (Compound 14) in Example 41, using the 2-step procedure and replacing cyclooctanol with cyclobutylmethanol. The crude reaction mixture was concentrated in vacuo and the intermediate was used directly in the deprotection step. LCMS: MS m/z: 404.10 (M+1). 1H NMR (400 MHz, DMSO-d6) δ 7.92 (s, 3H), 6.91 (d, J=4.6 Hz, 1H), 6.79 (d, J=4.5 Hz, 1H), 6.33 (s, 1H), 5.41 (s, 1H), 4.67 (t, J=3.5 Hz, 1H), 4.46-4.35 (m, 1H), 4.26-4.17 (m, 2H), 4.05 (d, J=6.7 Hz, 2H), 3.93 (t, J=5.6 Hz, 1H), 2.64-2.52 (m, 1H), 2.06-1.94 (m, 2H), 1.90-1.79 (m, 2H), 1.79-1.68 (m, 2H).

Example 30: ((2R,3S,4R,5R)-5-(4-aminopyrrolo[2,1-f][1,2,4]triazin-7-yl)-5-cyano-3,4-dihydroxy tetrahydrofuran-2-yl)methyl spiro[3.3]heptan-2-yl carbonate (Compound 29)

Compound 29

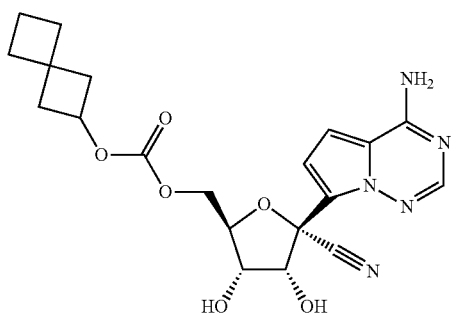

Compound 29 was synthesized in a manner similar to ((2R,3S,4R,5R)-5-(4-aminopyrrolo[2,1-f][1,2,4]triazin-7-yl)-5-cyano-3,4-dihydroxytetrahydrofuran-2-yl)methyl cyclooctyl carbonate (Compound 14) in Example 41, using the 2-step procedure and replacing cyclooctanol with spiro[3.3]heptan-2-ol. The crude reaction mixture was concentrated in vacuo and intermediate was used directly in the deprotection step. LCMS: MS m/z: 430.10 (M+1). 1H NMR (400 MHz, DMSO-d6) δ 7.91 (s, 3H), 6.91 (d, J=4.5 Hz, 1H), 6.78 (d, J=4.5 Hz, 1H), 6.31 (d, J=6.1 Hz, 1H), 5.40 (d, J=5.7 Hz, 1H), 4.77-4.64 (m, 2H), 4.44-4.33 (m, 1H), 4.28-4.11 (m, 2H), 3.93 (q, J=5.8 Hz, 1H), 2.44-2.33 (m, 2H), 2.02-1.87 (m, 6H), 1.85-1.72 (m, 2H).

Example 31: ((2R,3S,4R,5R)-5-(4-aminopyrrolo[2,1-f][1,2,4]triazin-7-yl)-5-cyano-3,4-dihydroxytetrahydrofuran-2-yl)methyl (2-methoxy-2-methylpropyl) carbonate (Compound 54)

Compound 54

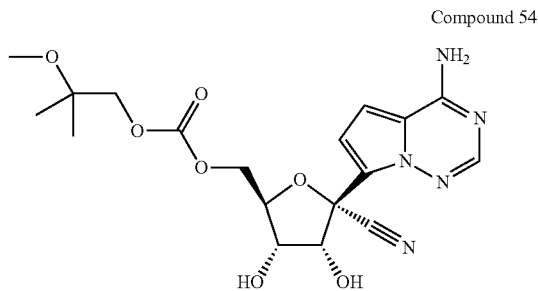 [SMILES: COC(C)(C)COC(=O)OC[C@H]1O[C@@](C#N)(c2ccc3c(N)ncnn23)[C@H](O)[C@@H]1O]

Compound 54 was synthesized in a manner similar to ((2R,3S,4R,5R)-5-(4-aminopyrrolo[2,1-f][1,2,4]triazin-7-yl)-5-cyano-3,4-dihydroxytetrahydrofuran-2-yl)methyl cyclooctyl carbonate (Compound 14) in Example 41, using the 2-step procedure and replacing cyclooctanol with 2-methoxy-2-methylpropan-1-ol. The crude reaction mixture was concentrated in vacuo and the intermediate was used directly in the deprotection step. LCMS: MS m/z: 422.10 (M+1). 1H NMR (400 MHz, DMSO-d6) δ 7.92 (s, 3H), 6.90 (d, J=4.5 Hz, 1H), 6.80 (d, J=4.5 Hz, 1H), 6.34 (d, J=6.0 Hz, 1H), 5.41 (d, J=5.8 Hz, 1H), 4.67 (dd, J=6.1, 4.9 Hz, 1H), 4.47-4.37 (m, 1H), 4.27-4.18 (m, 2H), 4.00 (d, J=1.0 Hz, 2H), 3.94 (q, J=5.7 Hz, 1H), 3.11 (s, 3H), 1.11 (s, 6H).

Example 32: ((2R,3S,4R,5R)-5-(4-aminopyrrolo[2,1-f][1,2,4]triazin-7-yl)-5-cyano-3,4-dihydroxytetrahydrofuran-2-yl)methyl (1-methylcycloheptyl) carbonate (Compound 55)

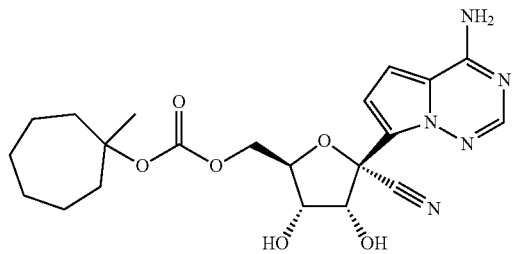 [SMILES: CC1(OC(=O)OC[C@H]2O[C@@](C#N)(c3ccc4c(N)ncnn34)[C@H](O)[C@@H]2O)CCCCCC1]

Step 1: Intermediate 32a—1,1-methylcycloheptyl 1H-imidazole-1-carboxylate

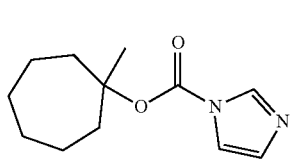

Intermediate 32a

A mixture of 1-methylcycloheptan-1-ol (0.272 mL, 1.95 mmol), 1,1'-carbonyldiimidazole (474 mg, 2.92 mmol), and potassium hydroxide (5.47 mg, 0.0975 mmol) in toluene (10.0 mL) was heated to 60° C. overnight. The reaction mixture was then diluted with DCM and washed twice with H$_2$O. The organic phase was dried over MgSO$_4$, filtered, and concentrated in vacuo. Intermediate 32a was quantified using NMR and used without further purification.

Step 2: Compound 55—((2R,3S,4R,5R)-5-(4-aminopyrrolo[2,1-f][1,2,4]triazin-7-yl)-5-cyano-3,4-dihydroxytetrahydrofuran-2-yl)methyl (1-methylcycloheptyl) carbonate

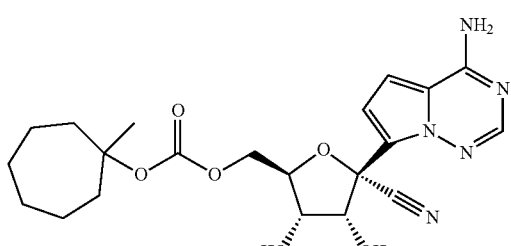

Compound 55

Compound 55 ((2R,3S,4R,5R)-5-(4-aminopyrrolo[2,1-f][1,2,4]triazin-7-yl)-5-cyano-3,4-dihydroxytetrahydrofuran-2-yl)methyl (1-methylcycloheptyl) carbonate was synthesized in a manner similar to Steps 2 and 3 of Example 23, ((2R,3S,4R,5R)-5-(4-aminopyrrolo[2,1-f][1,2,4]triazin-7-yl)-5-cyano-3,4-dihydroxytetrahydrofuran-2-yl)methyl (1-methylcyclohexyl) carbonate (Compound 47), replacing Intermediate 23a with Intermediate 32a. $^1$H NMR (400 MHz, DMSO-d6) δ 7.92 (s, 3H), 6.90 (d, J=4.6 Hz, 1H), 6.80 (d, J=4.5 Hz, 1H), 6.32 (d, J=6.0 Hz, 1H), 5.39 (d, J=5.9 Hz, 1H), 4.65 (dd, J=6.0, 4.9 Hz, 1H), 4.36 (dd, J=11.9, 2.9 Hz, 1H), 4.20 (td, J=6.2, 2.8 Hz, 1H), 4.12 (dd, J=11.9, 5.7 Hz, 1H), 3.92 (dt, J=6.9, 5.7 Hz, 1H), 2.01 (dt, J=15.0, 7.9 Hz, 2H), 1.79-1.60 (m, 2H), 1.58-1.45 (m, 6H), 1.44 (s, 3H), 1.42-1.31 (m, 2H). LCMS. MS m/z: 446.1 (M+1).

Example 33: ((2R,3S,4R,5R)-5-(4-aminopyrrolo[2,1-f][1,2,4]triazin-7-yl)-5-cyano-3,4-dihydroxytetrahydrofuran-2-yl)methyl (1-methylcyclopentyl) carbonate (Compound 56)

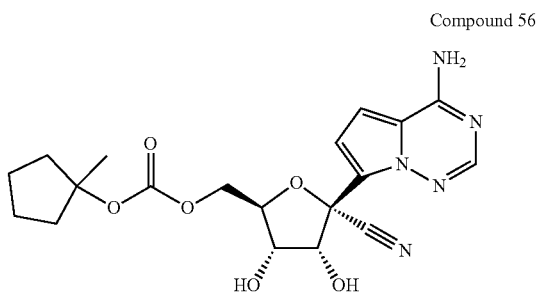 [SMILES: CC1(OC(=O)OC[C@H]2O[C@@](C#N)(c3ccc4c(N)ncnn34)[C@H](O)[C@@H]2O)CCCC1]

Compound 56

Compound 56 ((2R,3S,4R,5R)-5-(4-aminopyrrolo[2,1-f][1,2,4]triazin-7-yl)-5-cyano-3,4-dihydroxytetrahydrofuran-2-yl)methyl (1-methylcyclopentyl) carbonate was synthesized in a manner similar to Compound 55 ((2R,3S,4R,5R)-5-(4-aminopyrrolo[2,1-f][1,2,4]triazin-7-yl)-5-cyano-3,4-dihydroxytetrahydrofuran-2-yl)methyl (1-methylcycloheptyl) carbonate, replacing 1-methylcycloheptan-1-ol with 1-methylcyclopentan-1-ol. $^1$H NMR (4(0) MHz, DMSO-d6) δ 7.92 (s, 3H), 6.90 (d, J=4.5 Hz, 1H), 6.79 (d, J=4.5 Hz, 1H), 6.32 (d, J=6.0 Hz, 1H), 5.40 (d, J=5.8 Hz, 1H), 4.66 (t, J=5.5 Hz, 1H), 4.36 (dd, J=11.8, 2.8 Hz, 1H), 4.20 (td, J=6.2, 2.7 Hz, 1H), 4.13 (dd, J=11.8, 5.9 Hz, 1H), 3.92 (q, J=5.8 Hz, 1H), 2.06-1.93 (m, 2H), 1.63 (ttd, J=13.5, 9.1, 8.4, 3.8 Hz, 6H), 1.50 (s, 3H). LCMS: MS m/z: 418.1 (M+1).

Example 34: ((2R,3S,4R,5R)-5-(4-aminopyrrolo[2,1-f][1,2,4]triazin-7-yl)-5-cyano-3,4-dihydroxytetrahydrofuran-2-yl)methyl (1-methylcyclooctyl) carbonate (Compound 57)

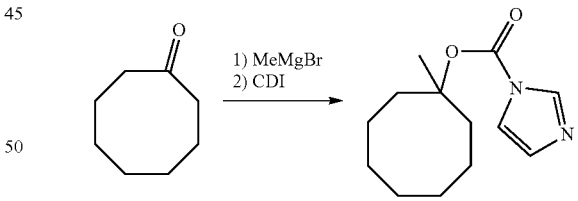

Intermediate 34a

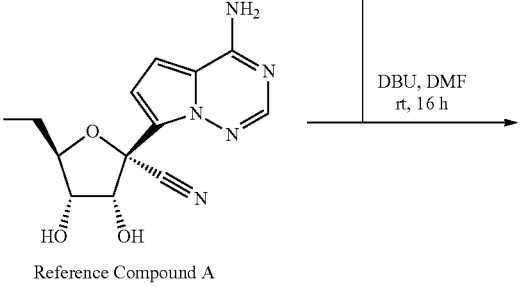

Reference Compound A

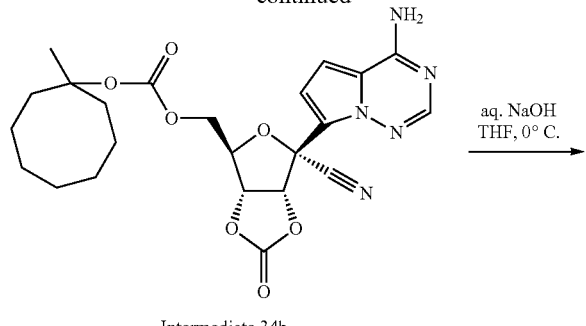

Intermediate 34b

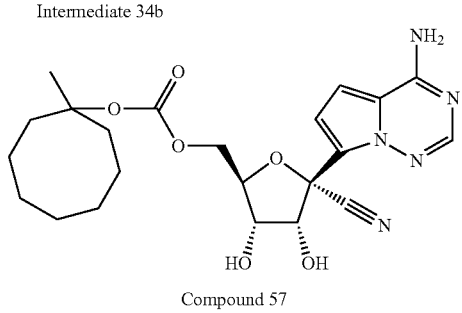

Compound 57

Step 1: Intermediate 34a

A stirred solution of cyclooctanone (10.5 mL, 79.7 mL) in diethyl ether (181 mL) was cooled to 0° C. then treated with MeMgBr (3 M in diethyl ether, 79.7 mL, 239 mmol). The resulting solution was warmed slowly to room temperature over 16 h before it was cooled to 0° C. and quenched by dropwise addition of saturated aqueous ammonium chloride solution. The organic layer was separated, and the aqueous layer was extracted three times with diethyl ether. The combined organic layers were dried over $MgSO_4$, concentrated, and the crude was purified by flash chromatography using hexanes and ethyl acetate as eluants to obtain 1-methylcyclooctanol.

1-Methylcyclooctanol (3.0 g, 21.1 mmol) was added dropwise to a stirring solution of 1,1'-carbonyldiimidazole (5.1 g, 31.6 mmol) in DCM (69 mL) at 0° C., then warmed to room temperature and stirred for 16 h. The reaction mixture was transferred to a separatory funnel, washed with water two times, dried over $MgSO_4$, and concentrated. Intermediate 34a was used without further purification.

Step 2: Intermediate 34b

A stirred solution of Reference Compound A (1.0 g, 3.43 mmol) and Intermediate 34a (1.78 g, 7.55 mmol) in DMF (17 mL) at room temperature was treated with 1,8-diazabicyclo[5.4.0]undec-7-ene (0.1 mL, 0.69 mmol). The resulting solution was stirred at room temperature for 16 h then was quenched with saturated aqueous ammonium chloride. The mixture was extracted using 1:1 Hexanes:EtOAc three times, and the combined organic layers were dried over $MgSO_4$, concentrated. Residual DMF was removed by azeotroping with heptanes. The resulting crude was purified by flash chromatography using dichloromethane and ethyl acetate as eluants to give Intermediate 34b. $^1$H NMR (400 MHz, DMSO-d6) δ 8.18-7.92 (m, 3H), 6.96 (d, J=4.6 Hz, 1H), 6.91 (d, J=4.6 Hz, 1H), 5.99 (d, J=7.7 Hz, 1H), 5.47 (dd, J=7.6, 3.9 Hz, 1H), 4.85-4.75 (m, 1H), 4.33 (dd, J=12.0, 4.0 Hz, 1H), 4.18 (dd, J=12.0, 5.9 Hz, 1H), 1.98 (q, J=9.7, 8.5 Hz, 2H), 1.72 (dd, J=15.0, 7.8 Hz, 2H), 1.40 (s, 13H).

Step 3: Compound 57—((2R,3S,4R,5R)-5-(4-aminopyrrolo[2,1-f][1,2,4]triazin-7-yl)-5-cyano-3,4-dihydroxytetrahydrofuran-2-yl)methyl (1-methylcyclooctyl) carbonate A stirred solution of Intermediate 34b (374 mg, 0.77 mmol) in THF (30.8 mL) was cooled to 0° C. and treated with aqueous NaOH (616 mg, 15.4 mmol, in 30.8 mL $H_2O$). After 30 minutes the reaction mixture was acidified with saturated aqueous ammonium chloride, and the organic layer was separated. The aqueous layer was extracted with EtOAc three times, the combined organic layers were dried over $MgSO_4$, and concentrated. The resulting crude was purified by flash chromatography using dichloromethane and ethyl acetate as eluants to give Compound 57. $^1$H NMR (400 MHz, DMSO-d6) δ 7.92 (s, 1H), 6.91 (d, J=4.6 Hz, 1H), 6.80 (d, J=4.5 Hz, 1H), 6.33 (d, J=6.0 Hz, 1H), 4.65 (t, J=5.4 Hz, 1H), 4.35 (dd, J=11.9, 2.9 Hz, 1H), 4.23-4.16 (m, 1H), 4.14-4.08 (m, 1H), 3.94-3.88 (m, 1H), 2.09-1.98 (m, 2H), 1.75 (dt, J=13.9, 8.7 Hz, 2H), 1.48 (d, J=40.7 Hz, 13H).

Example 35: (2R,3R,4R,5R)-2-(4-aminopyrrolo[2,1-f][1,2,4]triazin-7-yl)-5-(((tert-butoxycarbonyl)oxy)methyl)-2-cyanotetrahydrofuran-3,4-diyl bis(2-methylpropanoate) (Compound 58)

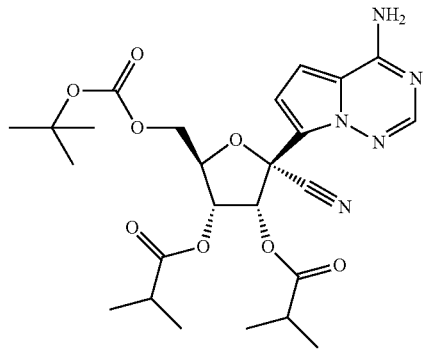

Compound 58

To a solution of [(2R,3S,4R,5R)-5-(4-aminopyrrolo[2,1-f][1,2,4]triazin-7-yl)-5-cyano-3,4-dihydroxy-tetrahydrofuran-2-yl]methyl tert-butyl carbonate (Compound 46, 1.00 g, 2.56 mmol) in DCM was added triethylamine (2.79 mL, 20.4 mmol). The reaction mixture was cooled to 0° C., and isobutyryl chloride was added dropwise in separate portions until full conversion of starting material was observed (a total of 3.0 equiv used). The reaction mixture was then concentrated in vacuo and purified by flash chromatography using dichloromethane and ethyl acetate as eluants to obtain Compound 58. $^1$H NMR (400 MHz, DMSO-d6) δ 8.14-7.95 (m, 2H), 7.93 (s, 1H), 6.94 (d, J=4.6 Hz, 1H), 6.78 (d, J=4.6 Hz, 1H), 6.08 (d, J=5.7 Hz, 1H), 5.40 (t, J=5.0 Hz, 1H), 4.57 (q, J=4.4 Hz, 1H), 4.39 (dd, J=12.2, 3.5 Hz, 1H), 4.26 (dd, J=12.1, 5.2 Hz, 1H), 2.70-2.53 (m, 2H), 1.36 (s, 9H), 1.22-1.02 (m, 12H). LCMS: MS m/z: 532.0 (M+1).

Example 36: (2R,3R,4R,5R)-2-(4-aminopyrrolo[2,1-f][1,2,4]triazin-7-yl)-2-cyano-5-(((isopropoxycarbonyl)oxy)methyl)tetrahydrofuran-3,4-diyl bis(2-methylpropanoate) (Compound 59)

Example 37: (2R,3R,4R,5R)-2-(4-aminopyrrolo[2,1-f][1,2,4]triazin-7-yl)-2-cyano-5-((((tert-pentyloxy)carbonyl)oxy)methyl)tetrahydrofuran-3,4-diyl di-tert-pentyl bis(carbonate) (Compound 60)

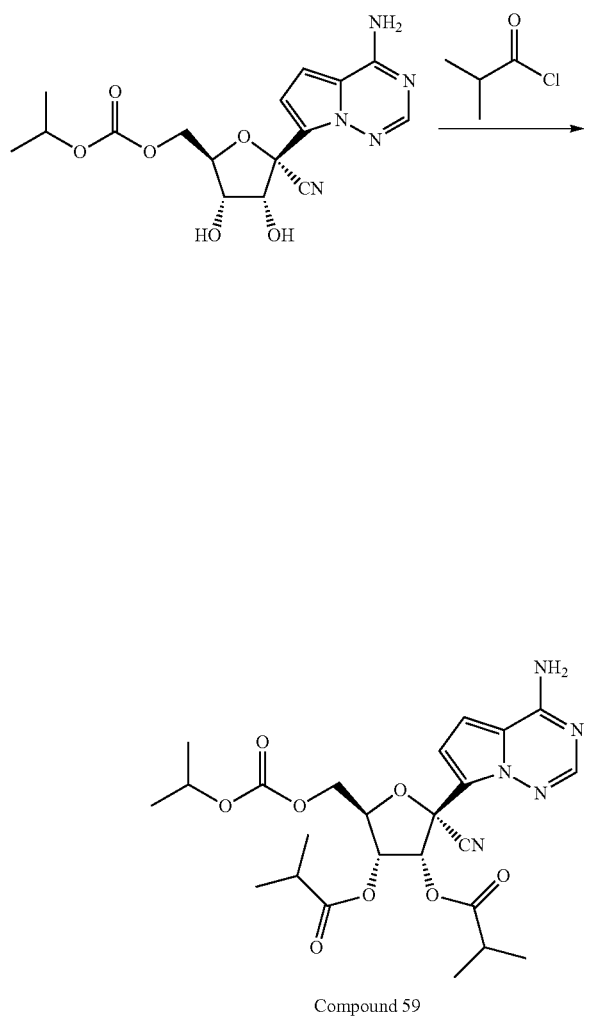

Compound 59

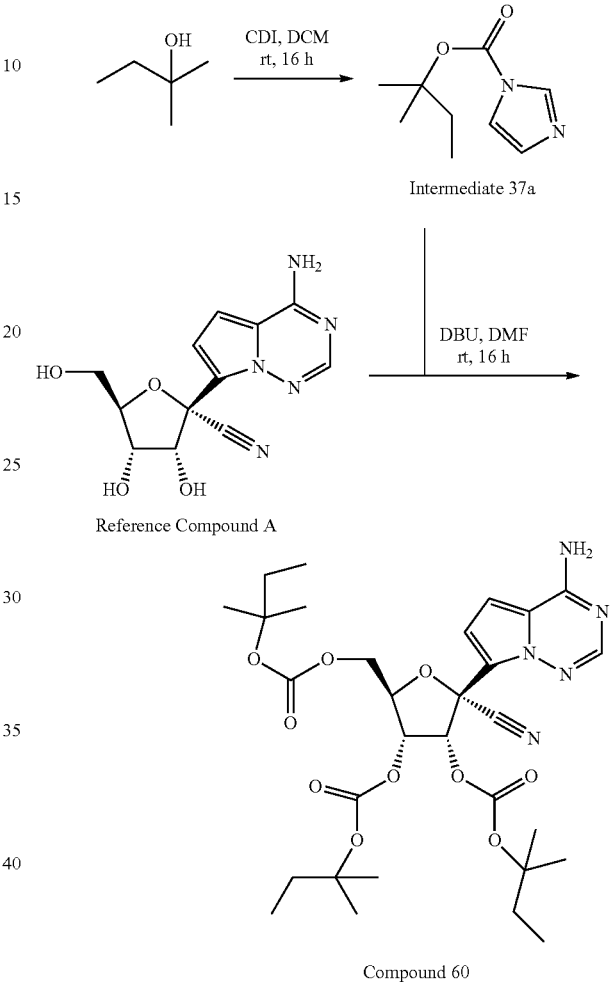

Compound 60

To ((2R,3S,4R,5R)-5-(4-aminopyrrolo[2,1-f][1,2,4]triazin-7-yl)-5-cyano-3,4-dihydroxytetrahydrofuran-2-yl)methyl isopropyl carbonate (Compound 4), (800 mg, 2.27 mmol) and N,N'-disuccinimidyl carbonate (133 mg, 0.52 mmol) in DCM (1 mL) was added 2-methylpropanoyl chloride (497 mg, 4.66 mmol) at 0° C. After 10 minutes, the reaction was purified by silica gel chromatography (0-10% MeOH in DCM) to afford Compound 59. LCMS: MS m/z: 518.2 (M+1). $^1$H NMR (400 MHz, DMSO-d6) δ 7.92 (s, 3H), 6.93 (d, J=4.6 Hz, 1H), 6.77 (d, J=4.6 Hz, 1H), 6.07 (d, J=5.8 Hz, 1H), 5.42 (dd, J=5.8, 4.1 Hz, 1H), 4.72 (p, J=6.2 Hz, 1H), 4.59 (dt, J=5.0, 3.7 Hz, 1H), 4.45 (dd, J=12.1, 3.5 Hz, 1H), 4.32 (dd, J=12.1, 5.1 Hz, 1H), 2.60 (ddq, J=13.9, 11.3, 7.0 Hz, 2H), 1.22-1.12 (m, 12H), 1.10 (d, J=7.0 Hz, 6H).

Step 1: Intermediate 37a

2-Methyl-2-butanol (1.0 mL, 9.13 mmol) was added dropwise to a stirring solution of 1,1'-carbonyldiimidazole (2.22 g, 13.7 mmol) in DCM (30 mL) at 0° C., then warmed to room temperature and stirred for 16 h. The reaction mixture was transferred to a separatory funnel, washed with water two times, dried over MgSO$_4$, and concentrated. Intermediate 37a was used without further purification.

Step 2: Compound 60

A stirred solution of Reference Compound A (210 mg, 0.721 mmol) and Intermediate 37a (657 mg, 3.6 mmol) in DMF (2 mL) at room temperature was treated with 1,8-diazabicyclo[5.4.0]undec-7-ene (22 mg, 0.144 mmol). The resulting solution was stirred at room temperature for 16 h then was quenched with saturated aqueous ammonium chloride. The mixture was extracted using 1:1 Hexanes:EtOAc three times, and the combined organic layers were dried over MgSO$_4$, concentrated. Residual DMF was removed by azeotroping with heptanes. The resulting crude was purified by flash chromatography using hexanes and ethyl acetate as eluants to give Compound 60. $^1$H NMR (400 MHz, DMSO-d6) δ 8.24 (s, 3H), 7.25 (d, J=4.6 Hz, 1H), 7.11 (d, J=4.6 Hz, 1H), 6.21 (d, J=5.9 Hz, 1H), 5.50 (t, J=5.9 Hz, 1H), 4.93-4.73 (m, 1H), 4.70 (dd, J=12.3, 3.3 Hz, 1H), 4.56 (dd, J=12.3, 4.9 Hz, 1H), 2.18-1.85 (m, 6H), 1.71-1.66 (m, 12H), 1.64-1.61 (m, 6H), 1.25-0.93 (m, 9H). LCMS: MS m/z 656.2 (M+23).

Example 38: ((2R,3S,4R,5R)-5-(4-aminopyrrolo[2,1-f][1,2,4]triazin-7-yl)-5-cyano-3,4-dihydroxytetrahydrofuran-2-yl)methyl cyclohexyl carbonate (Compound 35)

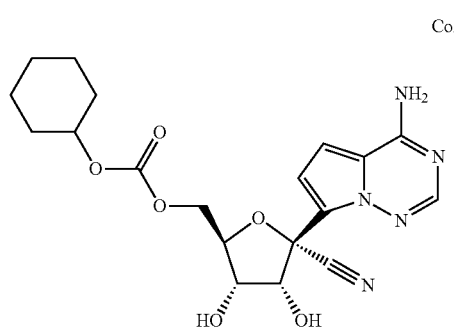

Compound 35

Compound 35 was synthesized in a manner similar to ((2R,3S,4R,5R)-5-(4-aminopyrrolo[2,1-f][1,2,4]triazin-7-yl)-5-cyano-3,4-dihydroxytetrahydrofuran-2-yl)methyl cyclooctyl carbonate (Compound 14) in Example 41, using the 2-step procedure and replacing cyclooctanol with cyclohexanol. $^1$H NMR (400 MHz, DMSO-d6) δ 7.92 (s, 3H), 6.91 (d, J=4.5 Hz, 1H), 6.79 (d, J=4.5 Hz, 1H), 6.33 (d, J=6.0 Hz, 1H), 5.41 (d, J=5.8 Hz, 1H), 4.67 (dd, J=6.0, 4.9 Hz, 1H), 4.52 (ddt, J=12.7, 8.7, 3.8 Hz, 1H), 4.46-4.36 (m, 1H), 4.28-4.16 (m, 2H), 3.93 (td, J=6.2, 4.9 Hz, 1H), 1.87-1.76 (m, 2H), 1.70-1.59 (m, 2H), 1.52-1.15 (m, 6H). LCMS: MS m/z 418.0 (M+1).

Example 39: isopropyl (7-((2R,3R,4S,5R)-2-cyano-3-hydroxy-4-((isopropoxycarbonyl)oxy)-5-(((isopropoxycarbonyl)oxy)methyl)tetrahydrofuran-2-yl)pyrrolo[2,1-f][1,2,4]triazin-4-yl)carbamate (Compound 62)

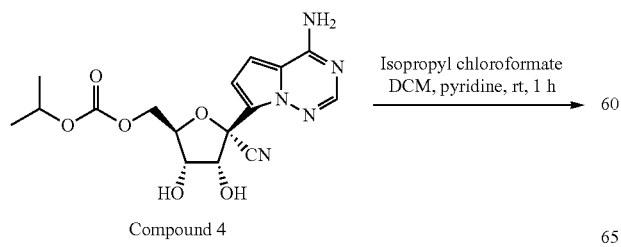

Compound 4

Isopropyl chloroformate
DCM, pyridine, rt, 1 h

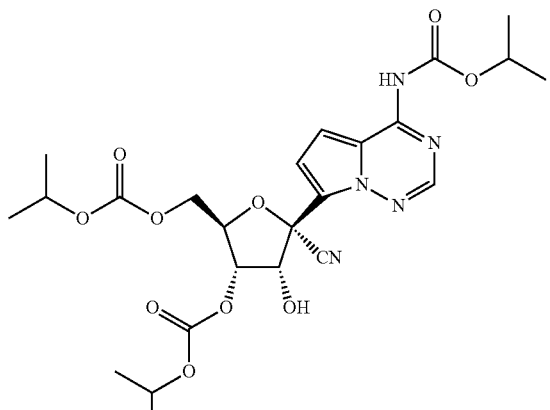

Compound 62

To a solution of ((2R,3S,4R,5R)-5-(4-aminopyrrolo[2,1-f][,2,4]triazin-7-yl)-5-cyano-3,4-dihydroxytetrahydrofuran-2-yl)methyl isopropyl carbonate, Compound 4 (1300 mg, 3.4 mmol) in dichloromethane (10 mL) was added pyridine (0.4 mL, 5.0 mmol). The mixture was then treated with isopropyl chloroformate (8.5 mL, 1.0 M in toluene, 8.5 mmol) and stirred at room temperature for 1 h. The reaction mixture was diluted with dichloromethane, washed with water, brine, dried over MgSO$_4$ and concentrated. The residue was purified by flash chromatography using dichloromethane and ethyl acetate as eluants to obtain Compound 62. $^1$H NMR (400 MHz, DMSO-d$_6$) δ 10.89 (s, 1H), 8.37 (s, 1H), 7.34 (s, 1H), 7.05 (d, J=4.9 Hz, 1H), 6.85 (d, J=6.0 Hz, 1H), 5.05-4.95 (m, 3H), 4.84-4.71 (m, 2H), 4.60-4.35 (m, 2H), 4.30-4.26 (m, 1H), 1.32-1.19 (m, 18H). LCMS: MS m/z: 550.02 (M+1).

Example 40: isopropyl (7-((2R,3R,4S,5R)-5-(((tert-butoxycarbonyl)oxy)methyl)-2-cyano-3,4-dihydroxytetrahydrofuran-2-yl)pyrrolo[2,1-f][1,2,4]triazin-4-yl)carbamate (Compound 63)

Compound 63

To a solution of ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl tert-butyl carbonate (Intermediate 22a, 1.9 g, 4.6 mmol, 1 equiv) in dichloromethane (16 mL) was added pyridine (0.56 mL, 6.9 mmol, 1.5 equiv). The reaction mixture was cooled to 0° C. and isopropyl chloroformate (5.5 mL of a 1N toluene solution, 5.5 mmol, 1.2 equiv) was added. The reaction mixture was slowly warmed to room temperature and stirred overnight. The reaction mixture was subsequently diluted with DCM/water, extracted twice with DCM, and the combined organics were dried over MgSO$_4$, filtered and concentrated in vacuo. The crude product, isopropyl (7-((3aR,4R,6R,6aR)-6-(((tert-butoxycarbonyl)oxy)methyl)-4-cyano-2,2-dimethyltetrahydrofuro[3,4-d][1,3]dioxol-4-yl)pyrrolo[2,1-f][1,2,4]triazin-4-yl)carbamate, was dissolved in THF (14 mL) and conc. HCl (1.9 mL, 23 mmol, 5.0 equiv) was added at 0° C. The reaction mixture was slowly warmed to room temperature and stirred for 5 hours before being quenched with sat. aq. NaHCO$_3$. The reaction mixture was diluted with EtOAc/water, extracted twice with EtOAc, and the combined organics were dried over MgSO$_4$, filtered and concentrated in vacuo. The resulting product was purified using silica gel chromatography (10-75% EtOAc/DCM). LCMS: MS m/z: 478.10 (M+1). 1H NMR (400 MHz, DMSO-d6) δ 10.83 (s, 1H), 8.36 (s, 1H), 7.32 (d, J=4.7 Hz, 1H), 7.00 (d, J=4.8 Hz, 1H), 6.41 (d, J=6.1 Hz, 1H), 5.44 (d, J=5.8 Hz, 1H), 4.98 (p, J=6.2 Hz, 1H), 4.65 (t, J=5.5 Hz, 1H), 4.36 (dd, J=11.9, 2.9 Hz, 1H), 4.23 (td, J=6.2, 2.8 Hz, 1H), 4.12 (dd, J=11.9, 5.7 Hz, 1H), 3.92 (q, J=5.9 Hz, 1H), 1.40 (s, 9H), 1.31 (d, J=6.3 Hz, 6H).

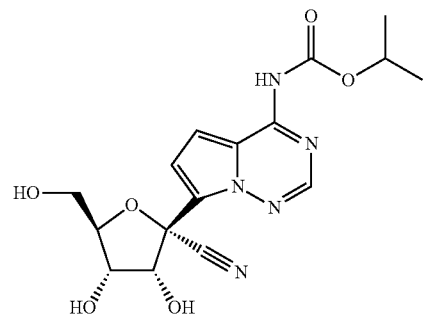 [SMILES: CC(C)OC(=O)Nc1ncnn2c([C@]3(C#N)O[C@H](CO)[C@@H](O)[C@H]3O)ccc12]

The corresponding 5' hydroxy compound, isopropyl (7-((2R,3R,4S,5R)-2-cyano-3,4-dihydroxy-5-(hydroxymethyl)tetrahydrofuran-2-yl)pyrrolo[2,1-f][1,2,4]triazin-4-yl)carbamate, was also isolated as a product from the deprotection reaction described above. LCMS: MS m/z: 378.10 (M+1). 1H NMR (400 MHz, DMSO-d6) δ 10.82 (s, 1H), 8.36 (s, 1H), 7.30 (d, J=4.8 Hz, 1H), 7.10 (d, J=4.8 Hz, 1H), 6.20 (d, J=6.3 Hz, 1H), 5.23 (d, J=5.4 Hz, 1H), 4.98 (p, J=6.3 Hz, 1H), 4.89 (t, J=5.6 Hz, 1H), 4.61 (t, J=5.6 Hz, 1H), 4.07 (dt, J=5.6, 3.9 Hz, 1H), 3.95 (q, J=5.4 Hz, 1H), 3.71-3.58 (m, 1H), 3.51 (dt, J=12.2, 5.0 Hz, 1H), 1.31 (d, J=6.3 Hz, 6H).

Example 41: ((2R,3S,4R,5R)-5-(4-aminopyrrolo[2,1-f][1,2,4]triazin-7-yl)-5-cyano-3,4-dihydroxytetrahydrofuran-2-yl)methyl cyclooctyl carbonate (Compound 14; alternate synthesis)

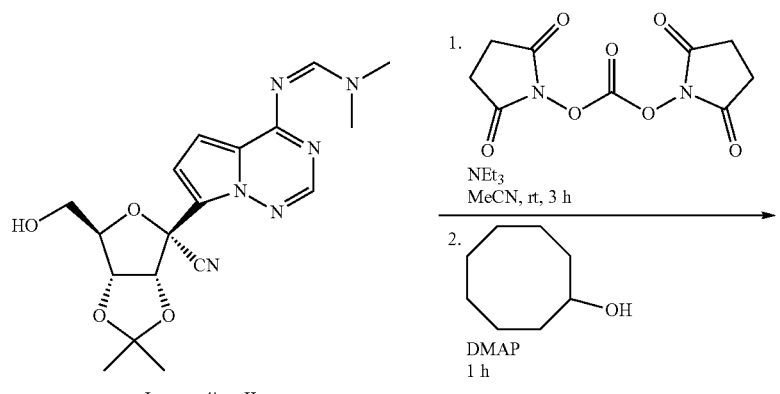

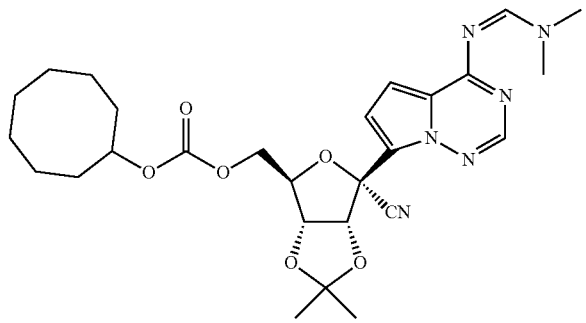

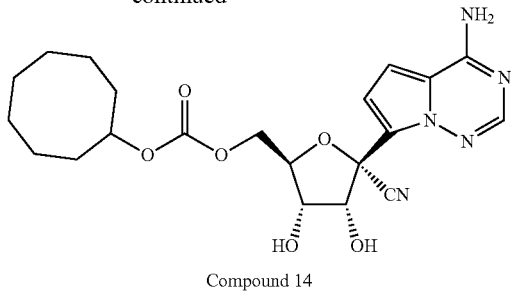

Compound 14

Step 1: Intermediate 14a

To a mixture of N'-(7-((3aR,4R,6R,6aR)-4-cyano-6-(hydroxymethyl)-2,2-dimethyltetrahydrofuro[3,4-d][1,3]dioxol-4-yl)pyrrolo[2,1-f][1,2,4]triazin-4-yl)-N,N-dimethyl-formimidamide, Intermediate II, (100 mg, 0.26 mmol) and N,N'-disuccinimidyl carbonate (133 mg, 0.52 mmol) in MeCN (1 mL) was added triethylamine (0.14 mL, 1.0 mmol). The mixture was stirred for 3 h, after which cyclooctanol (0.21 mL, 1.6 mmol) was added, and the mixture then stirred at rt for 1 h. After the completion of the reaction, the reaction mixture was diluted with ethyl acetate, washed with water, brine, dried over MgSO₄ and concentrated. Intermediate 14a was used without further purification. LCMS: MS m/z: 541.0 (M+1).

Step 2: Compound 14—((2R,3S,4R,5R)-5-(4-aminopyrrolo[2,1-f][1,2,4]triazin-7-yl)-5-cyano-3,4-dihydroxytetrahydrofuran-2-yl)methyl Cyclooctyl carbonate Intermediate 14a (140 mg, 0.26 mmol) was dissolved in THF (1.5 mL), and treated with conc. HCl (0.43 mL, 5.2 mmol) and stirred at room temperature overnight. After the completion of the reaction, the reaction mixture was diluted with ethyl acetate, neutralized with saturated sodium bicarbonate, the organic layer separated, washed with water, brine, dried over MgSO₄, filtered, and concentrated. The residue was purified by flash chromatography using dichloromethane and methanol as eluants to obtain Compound 14. ¹H NMR (400 MHz, DMSO-d6) δ 7.92 (s, 3H), 6.90 (d, J=4.6 Hz, 1H), 6.78 (d, J=4.5 Hz, 1H), 6.32 (d, J=6.1 Hz, 1H), 5.40 (d, J=5.8 Hz, 1H), 4.68 (ddd, J=10.9, 7.2, 4.6 Hz, 2H), 4.45-4.36 (m, 1H), 4.25-4.13 (m, 2H), 3.98-3.89 (m, 1H), 1.83-1.38 (m, 14H). LCMS: MS m/z: 446.0 (M+1).

Example 42: Allyl (((2R,3S,4R,5R)-5-(4-aminopyrrolo[2,1-f][1,2,4]triazin-7-yl)-5-cyano-3,4-dihydroxytetrahydrofuran-2-yl)methyl) carbonate (Compound 64)

To a solution of N'-[7-[(3aR,4R,6R,6aR)-4-cyano-6-(hydroxymethyl)-2,2-dimethyl-6,6a-dihydro-3aH-furo[3,4-d][1,3]dioxol-4-yl]pyrrolo[2,1-f][1,2,4]triazin-4-yl]-N,N-dimethyl-formamidine (Intermediate 11, 150 mg, 0.39 mmol) in dichloromethane (10 mL), allyl chloroformate (1170 mg, 9.7 mmol) followed by pyridine (0.78 mL, 9.7 mmol), was added and the mixture stirred at room temperature overnight. Reaction mixture was diluted with dichloromethane, washed with water, then brine, and combined organics were dried over MgSO₄, filtered, and concentrated in vacuo. The resulting residue was diluted with THF (2 mL), cooled to 0° C., and conc. HCl (0.32 mL, 3.9 mmol) was added. The mixture was stirred overnight, allowing to warm to room temperature. The mixture was then diluted with ethyl acetate, neutralized with sat. NaHCO₃ aq. solution, organics were separated and washed with water, followed by brine. Organics dried over MgSO₄, filtered, and concentrated in vacuo. The residue was then purified by flash chromatography using dichloromethane and methanol as eluents to obtain Compound 64. ¹H NMR (400 MHz, DMSO-d₆) δ 7.92 (s, 3H), 6.90 (d, J=4.6 Hz, 1H), 6.79 (d, J=4.5 Hz, 1H), 6.33 (d, J=6.1 Hz, 1H), 5.92 (ddt, J=17.2, 10.5, 5.5 Hz, 1H), 5.42 (d, J=5.8 Hz, 1H), 5.37-5.20 (m, 2H), 4.68 (dd, J=6.1, 5.0 Hz, 1H), 4.60 (dt, J=5.6, 1.4 Hz, 2H), 4.45-4.37 (m, 1H), 4.28-4.19 (m, 2H), 3.94 (q, J=5.6 Hz, 1H). LCMS: MS m/z: 376.0 (M+1).

Example 43: (2R,3R,4R,5R)-2-(4-aminopyrrolo[2,1-f][1,2,4]triazin-7-yl)-2-cyano-5-(((isopropoxycarbonyl)oxy)methyl)tetrahydrofuran-3,4-diyl diacetate (Compound 65)

Compound 64

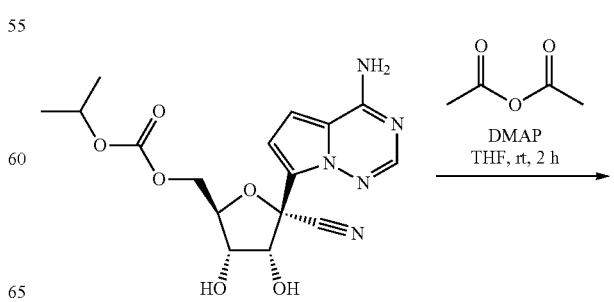

-continued

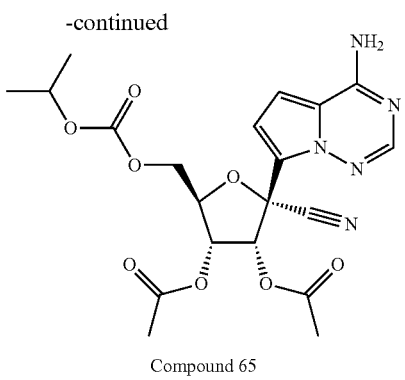

Compound 65

To a mixture of ((2R,3S,4R,5R)-5-(4-aminopyrrolo[2,1-f][1,2,4]triazin-7-yl)-5-cyano-3,4-dihydroxytetrahydrofuran-2-yl)methyl isopropyl carbonate, Compound 4, (200 mg, 0.53 mmol) and acetic anhydride (129 mg, 0.60 mmol) in THF (5 mL) was added 4-dimethylaminopyridine (9.7 mg, 0.08 mmol). The mixture was stirred at rt for 30 minutes. After the completion of the reaction, the reaction mixture was diluted with ethyl acetate, washed with water, brine, dried over MgSO$_4$ and concentrated. The residue was purified by flash chromatography using dichloromethane and ethyl acetate as eluants to obtain Compound 65. $^1$H NMR (400 MHz, DMSO-d$_6$) δ 8.05 (br, 1H), 7.99 (br, 1H), 7.95 (s, 1H), 6.95 (d, J=4.6 Hz, 1H), 6.80 (d, J=4.6 Hz, 1H), 6.06 (d, J=5.9 Hz, 1H), 5.39 (dd, J=5.9, 4.8 Hz, 1H), 4.73 (hept. J=6.3 Hz, 1H), 4.60 (td, J=4.9, 3.2 Hz, 1H), 4.47 (dd, J=12.1, 3.3 Hz, 1H), 4.31 (dd, J=12.2, 5.2 Hz, 1H), 2.12 (s, 6H), 1.21-1.18 (m, 6H). LCMS: MS m/z: 462.03 (M+1).

Example 44: ((3aR,4R,6R,6aR)-6-(4-aminopyrrolo[2,1-f][1,2,4]triazin-7-yl)-6-cyano-2-oxotetrahydrofuro[3,4-d][1,3]dioxol-4-yl)methyl isopropyl carbonate (Compound 66)

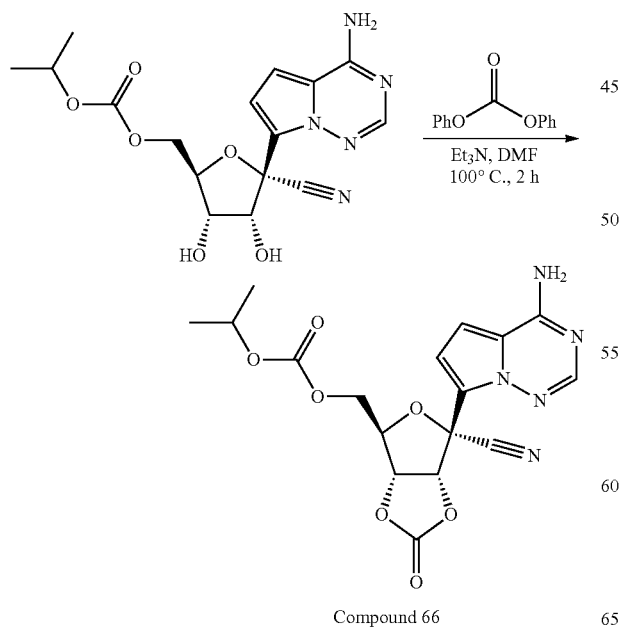

Compound 66

To a mixture of ((2R,3S,4R,5R)-5-(4-aminopyrrolo[2,1-f][1,2,4]triazin-7-yl)-5-cyano-3,4-dihydroxytetrahydrofuran-2-yl)methyl isopropyl carbonate, Compound 4, (189 mg, 0.5 mmol) and diphenyl carbonate (129 mg, 0.60 mmol) in DMF (3.6 mL) was added triethylamine (0.07 mL, 0.5 mmol). The mixture was heated to 100° C. and stirred for 2 h. After the completion of the reaction, the reaction mixture was diluted with ethyl acetate, washed with water, brine, dried over MgSO$_4$ and concentrated. The residue was purified by flash chromatography using dichloromethane and methanol as eluants to obtain Compound 66. $^1$H NMR (400 MHz, DMSO-d$_6$) δ 8.10 (br, 1H), 8.03 (br, 1H), 7.98 (s, 1H), 6.99-6.89 (m, 2H), 6.00 (d, J=7.7 Hz, 1H), 5.49 (dd, J=7.7, 3.9 Hz, 1H), 4.83-4.80 (m, 1H), 4.74-4.68 (m, 1H), 4.42 (dd, J=12.0, 3.9 Hz, 1H), 4.27 (dd, J=12.0, 5.7 Hz, 1H), 1.20 (d, J=6.2 Hz, 3H), 1.17 (d, J=6.2 Hz, 3H). LCMS: MS m/z: 404.01 (M+1).

Example 45: ((2R,3S,4R,5R)-5-(4-aminopyrrolo[2,1-f][1,2,4]triazin-7-yl)-5-cyano-3,4-dihydroxytetrahydrofuran-2-yl)methyl (1,1,1-trifluoro-2-methylpropan-2-yl) carbonate (Compound 67)

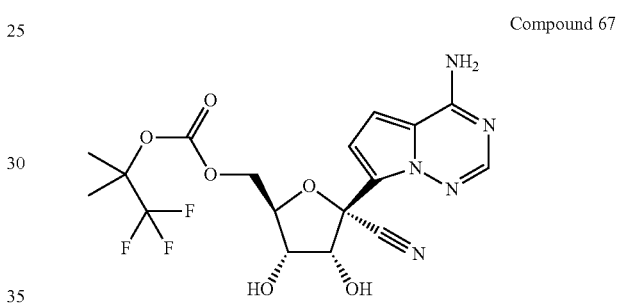

Compound 67

Compound 67 was synthesized in a manner similar to Example 23: ((2R,3S,4R,5R)-5-(4-aminopyrrolo[2,1-f][1,2,4]triazin-7-yl)-5-cyano-3,4-dihydroxytetrahydrofuran-2-yl)methyl (1-methylcyclohexyl) carbonate (Compound 47), replacing 1-methylcyclohexanol with 1,1,1-Trifluoro-2-methyl-2-propanol. 1H NMR (400 MHz, DMSO-d6) δ 7.92 (s, 1H), 6.90 (d, J=4.5 Hz, 1H), 6.78 (d, J=4.5 Hz, 1H), 6.35 (d, J=6.0 Hz, 1H), 5.42 (d, J=5.8 Hz, 1H), 4.67 (dd, J=6.1, 4.9 Hz, 1H), 4.51-4.40 (m, 1H), 4.27-4.18 (m, 2H), 3.94 (q, J=5.8 Hz, 1H), 1.67-0.6) (m, 6H). LCMS: MS m/z: 446.1 (M+1).

Example 46: ((2R,3S,4R,5R)-5-(4-aminopyrrolo[2,1-f][1,2,4]triazin-7-yl)-5-cyano-3,4-dihydroxytetrahydrofuran-2-yl)methyl (2,3-dimethylbutan-2-yl) carbonate (Compound 68)

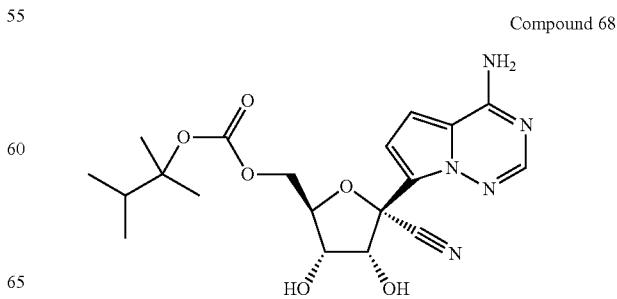

Compound 68

Compound 68 was synthesized in a manner similar to Example 23: ((2R,3S,4R,5R)-5-(4-aminopyrrolo[2,1-f][1,2,4]triazin-7-yl)-5-cyano-3,4-dihydroxytetrahydrofuran-2-yl)methyl (1-methylcyclohexyl) carbonate (Compound 47), replacing 1-methylcyclohexanol with 2,3-dimethyl-2-butanol. 1H NMR (400 MHz, DMSO-d6) δ 8.04-7.68 (m, 3H), 6.90 (d, J=4.6 Hz, 1H), 6.80 (d, J=4.5 Hz, 1H), 6.33 (d, J=6.0 Hz, 1H), 5.39 (d, J=5.9 Hz, 1H), 4.64 (t, J=5.4 Hz, 1H), 4.36 (dd, J=11.8, 2.8 Hz, 1H), 4.26-4.18 (m, 1H), 4.17-4.09 (m, 1H), 3.91 (q, J=5.6 Hz, 1H), 2.20-2.03 (m, 1H), 1.35 (s, 6H), 0.86 (d, J=6.8 Hz, 6H). LCMS: MS m/z: 442.1 (M+23).

Example 47: ((2R,3S,4R,5R)-5-(4-aminopyrrolo[2,1-f][1,2,4]triazin-7-yl)-5-cyano-3,4-dihydroxytetrahydrofuran-2-yl)methyl (3-methylpentan-3-yl) carbonate (Compound 69)

Compound 69

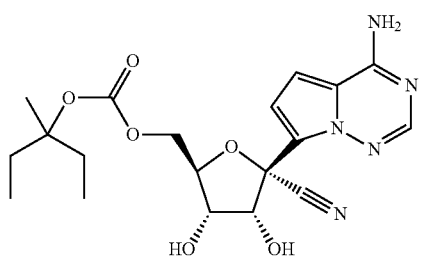

Compound 69 was synthesized in a manner similar to Example 23: ((2R,3S,4R,5R)-5-(4-aminopyrrolo[2,1-f][1,2,4]triazin-7-yl)-5-cyano-3,4-dihydroxytetrahydrofuran-2-yl)methyl (1-methylcyclohexyl) carbonate (Compound 47), replacing 1-methylcyclohexanol with 3-methyl-3-pentanol. 1H NMR (400 MHz, DMSO-d6) δ 8.08-7.77 (m, 3H), 6.91 (d, J=4.6 Hz, 1H), 6.81 (d, J=4.5 Hz, 1H), 6.33 (d, J=6.0 Hz, 1H), 5.40 (d, J=5.8 Hz, 1H), 4.69-4.60 (m, 1H), 4.36 (dd, J=11.7, 2.8 Hz, 1H), 4.21 (td, J=6.2, 2.7 Hz, 1H), 4.18-4.09 (m, 1H), 3.95-3.88 (m, 1H), 1.93-1.61 (m, 4H), 1.33 (s, 3H), 0.85-0.74 (m, 6H). LCMS: MS m/z: 442.1 (M+23).

Example 48: ((2R,3S,4R,5R)-5-(4-aminopyrrolo[2,1-f][1,2,4]triazin-7-yl)-5-cyano-3,4-dihydroxytetrahydrofuran-2-yl)methyl tert-pentyl carbonate (Compound 70)

Compound 70

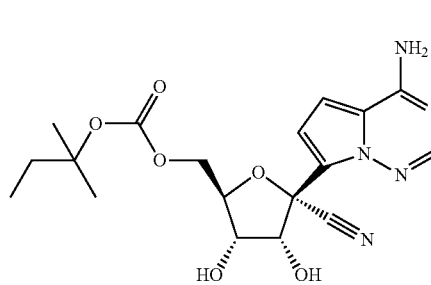

Compound 70 was synthesized in a manner similar to Example 23: ((2R,3S,4R,5R)-5-(4-aminopyrrolo[2,1-f][1,2,4]triazin-7-yl)-5-cyano-3,4-dihydroxytetrahydrofuran-2-yl)methyl (1-methylcyclohexyl) carbonate (Compound 47), replacing 1-methylcyclohexanol with 2-methyl-2-butanol. 1H NMR (400 MHz, DMSO-d6) δ 8.01-7.74 (m, 3H), 6.90 (d, J=4.5 Hz, 1H), 6.79 (d, J=4.5 Hz, 1H), 6.32 (d, J=6.0 Hz, 1H), 5.39 (d, J=5.8 Hz, 1H), 4.69-4.63 (m, 1H), 4.35 (dd, J=11.8, 2.8 Hz, 1H), 4.20 (td, J=6.2, 2.8 Hz, 1H), 4.12 (dd, J=11.7, 5.9 Hz, 1H), 3.95-3.88 (m, 1H), 1.80-1.67 (m, 2H), 1.37 (s, 6H), 0.83 (t, J=7.5 Hz, 3H). LCMS: MS m/z: 406.1 (M+1).

Example 49: ((2R,3S,4R,5R)-5-(4-aminopyrrolo[2,1-f][1,2,4]triazin-7-yl)-5-cyano-3,4-dihydroxytetrahydrofuran-2-yl)methyl (1,7,7-trimethylbicyclo[2.2.1]heptan-2-yl) carbonate (Compound 71)

Compound 71

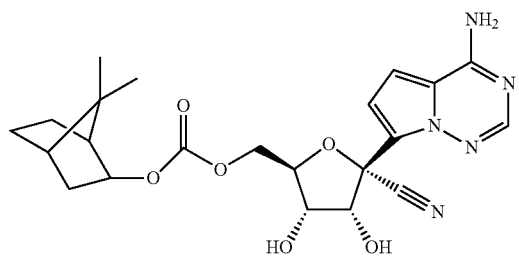

Compound 71 was synthesized in a manner similar to Example 23: ((2R,3S,4R,5R)-5-(4-aminopyrrolo[2,1-f][1,2,4]triazin-7-yl)-5-cyano-3,4-dihydroxytetrahydrofuran-2-yl)methyl (1-methylcyclohexyl) carbonate (Compound 47), replacing 1-methylcyclohexanol with isobomeol. 1H NMR (400 MHz, DMSO-d6) δ 8.10-7.70 (m, 3H), 6.89 (dd, J=4.6, 1.0 Hz, 1H), 6.79 (dd, J=5.9, 4.5 Hz, 1H), 6.36 (dd, J=5.9, 1.3 Hz, 1H), 5.39 (dd, J=5.9, 1.4 Hz, 1H), 4.61 (ddd, J=5.9, 4.8, 3.0 Hz, 1H), 4.51-4.38 (m, 2H), 4.27-4.13 (m, 2H), 3.97-3.87 (m, 1H), 1.83-1.57 (m, 4H), 1.51 (tt, J=10.2, 3.0 Hz, 1H), 1.16-1.01 (m, 2H), 0.93 (d, J=3.7 Hz, 3H), 0.87-0.76 (m, 6H). LCMS: MS m/z: 472.1 (M+1).

Example 50: ((2R,3S,4R,5R)-5-(4-aminopyrrolo[2,1-f][1,2,4]triazin-7-yl)-5-cyano-3,4-dihydroxytetrahydrofuran-2-yl)methyl (bicyclo[1.1.1]pentan-1-ylmethyl) carbonate (Compound 72)

Compound 72

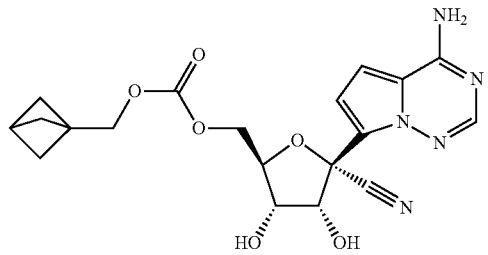

Compound 72 was synthesized in a manner similar to ((2R,3S,4R,5R)-5-(4-aminopyrrolo[2,1-f][1,2,4]triazin-7-yl)-5-cyano-3,4-dihydroxytetrahydrofuran-2-yl)methyl cyclooctyl carbonate (Compound 14) in Example 41, using the 2-step procedure and replacing cyclooctanol with bicyclo[1.1.1]pentan-1-ylmethanol. The crude reaction mixture was concentrated in vacuo and the resulting intermediate was used directly in the deprotection step. LCMS: MS m/z: 416.00 (M+1). 1H NMR (400 MHz, DMSO-d6) δ 7.93 (s, 3H), 6.92 (d, J=4.5 Hz, 1H), 6.80 (d, J=4.5 Hz, 1H), 6.33 (s, 1H), 5.41 (s, 1H), 4.67 (d, J=4.8 Hz, 1H), 4.41 (dd, J=9.4, 4.6 Hz, 1H), 4.27-4.18 (m, 2H), 4.02 (s, 2H), 3.97-3.90 (m, 1H), 2.49 (s, 1H), 1.72 (s, 6H).

Example 51: ((2R,3S,4R,5R)-5-(4-aminopyrrolo[2,1-f][1,2,4]triazin-7-yl)-5-cyano-3,4-dihydroxytetrahydrofuran-2-yl)methyl (3,3-difluorocyclobutyl) carbonate (Compound 73)

Compound 73

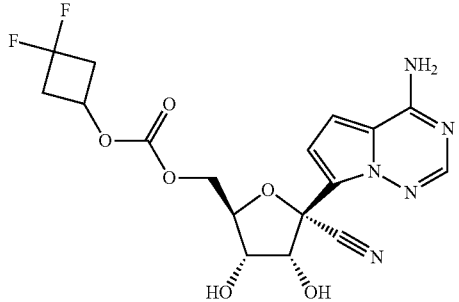

Compound 73 was synthesized in a manner similar to ((2R,3S,4R,5R)-5-(4-aminopyrrolo[2,1-f][1,2,4]triazin-7-yl)-5-cyano-3,4-dihydroxytetrahydrofuran-2-yl)methyl cyclooctyl carbonate (Compound 14) in Example 41, using the 2-step procedure and replacing cyclooctanol with 3,3-difluorocyclobutan-1-ol. The crude reaction mixture was concentrated in vacuo and the resulting intermediate was used directly in the deprotection step. LCMS: MS m/z: 425.90 (M+1). 1H NMR (400 MHz, DMSO-d6) δ 7.92 (s, 3H), 6.91 (d, J=4.5 Hz, 1H), 6.80 (d, J=4.5 Hz, 1H), 6.33 (d, J=6.1 Hz, 1H), 5.43 (d, J=5.7 Hz, 1H), 4.85 (dddd, J=12.2, 7.6, 4.7, 2.8 Hz, 1H), 4.70 (dd, J=6.1, 4.9 Hz, 1H), 4.50-4.37 (m, 1H), 4.33-4.17 (m, 2H), 3.96 (q, J=5.6 Hz, 1H), 3.06 (ddddd, J=19.3, 11.9, 7.4, 5.3, 2.5 Hz, 2H), 2.84-2.64 (m, 2H).

Example 52: ((2R,3S,4R,5R)-5-(4-aminopyrrolo[2,1-f][1,2,4]triazin-7-yl)-5-cyano-3,4-dihydroxytetrahydrofuran-2-yl)methyl (1-isopropyl-4-methylcyclohex-3-en-1-yl) carbonate (Compound 74)

Compound 74

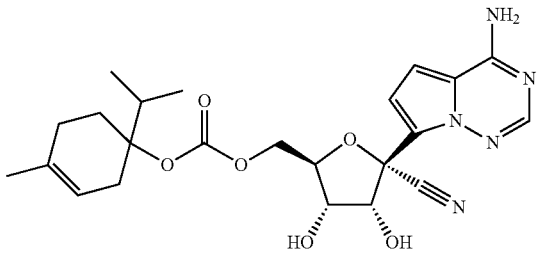

Compound 74 was synthesized in a manner similar to Example 32, ((2R,3S,4R,5R)-5-(4-aminopyrrolo[2,1-f][1,2,4]triazin-7-yl)-5-cyano-3,4-dihydroxytetrahydrofuran-2-yl)methyl (1-methylcycloheptyl) carbonate (Compound 55), replacing 1-methylcycloheptan-1-ol with 4-carvomenthenol. $^1$H NMR (400 MHz, DMSO-d6) δ 7.91 (s, 3H), 6.90 (dd, J=4.5, 2.7 Hz, 1H), 6.78 (dd, J=4.5, 3.4 Hz, 1H), 6.32 (d, J=6.0 Hz, 1H), 5.38 (dd, J=5.9, 1.0 Hz, 1H), 5.23 (d, J=12.0 Hz, 1H), 4.64 (dt, J=7.6, 5.7 Hz, 1H), 4.38-4.25 (m, 1H), 4.24-4.09 (m, 2H), 3.94-3.84 (m, 1H), 2.55 (q, J=6.9 Hz, 1H), 2.36-2.12 (m, 3H), 1.87 (s, 2H), 1.68-1.55 (m, 4H), 0.89-0.78 (m, 6H). LCMS: MS m/z: 472.1 (M+1).

Example 53: (2R,3R,4R,5R)-2-cyano-2-(4-isobutyramidopyrrolo[2,1-f][1,2,4]triazin-7-yl)-5-(((isopropoxycarbonyl)oxy)methyl)tetrahydrofuran-3,4-diyl bis(2-methylpropanoate) (Compound 75)

Compound 75

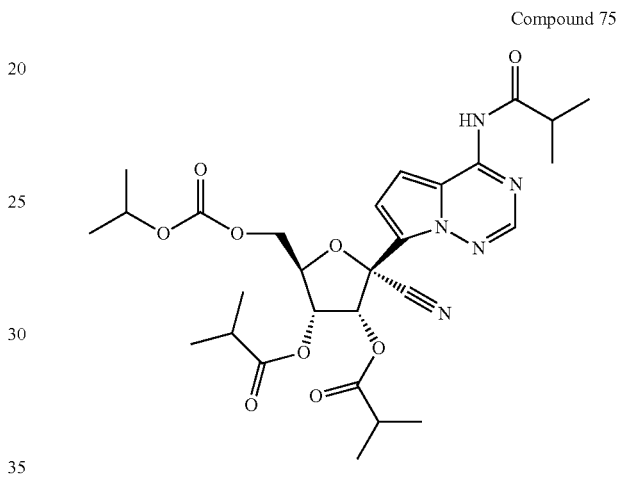

Compound 75 was synthesized in a manner similar to Example 36: (2R,3R,4R,5R)-2-(4-aminopyrrolo[2,1-f][1,2,4]triazin-7-yl)-2-cyano-5-(((isopropoxycarbonyl)oxy)methyl)tetrahydrofuran-3,4-diyl bis(2-methylpropanoate) (Compound 59), using 4.0 eq of 2-methylpropanoyl chloride instead of 2.1 eq. $^1$H NMR (400 MHz, Chloroform-d) δ 7.97 (s, 1H), 7.12 (br, 1H), 6.92 (d, J=4.7 Hz, 1H), 6.59 (d, J=4.7 Hz, 1H), 6.30 (d, J=5.9 Hz, 1H), 5.59-5.50 (m, 1H), 4.93-4.81 (m, 1H), 4.66-4.61 (m, 1H), 4.56-4.37 (m, 3H), 2.77-2.57 (m, 2H), 1.35-1.18 (m, 24H). LCMS: 1.15 min, MS m/z: 588.2 (M+1).

Example 54: ((2R,3S,4R,5R)-5-(4-aminopyrrolo[2,1-f][1,2,4]triazin-7-yl)-5-cyano-3,4-dihydroxytetrahydrofuran-2-yl)methyl (1,1-difluoro-2-methylpropan-2-yl) carbonate (Compound 76)

Compound 76

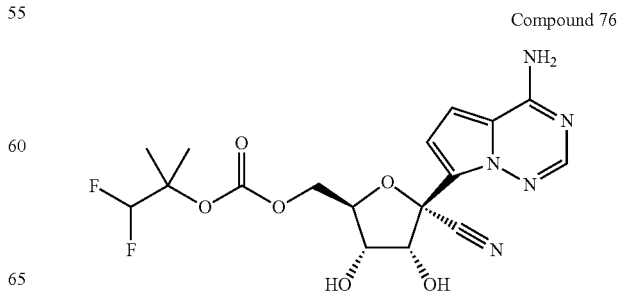

Step 1: Intermediate 54a
—1,1-difluoro-2-methylpropan-2-ol

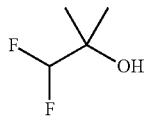

Intermediate 54a

To a mixture of 1,1-difluoropropan-2-one (0.172 mL, 2.13 mmol) in diethyl ether (2 mL) at −10° C. (brine bath) was added MeMgBr (3.00 mol/L, 0.851 mL, 2.55 mmol) dropwise. The mixture was stirred overnight, allowing to warm to room temperature. The mixture was then diluted with diethyl ether and quenched with 2 M HCL. Partitioned between water and ether, layers separated, and aqueous phase extracted with additional ether. The combined organics were dried over $MgSO_4$, filtered, and concentrated in vacuo. The resulting residue was used without further purification.

Step 2: Compound 76

Compound 76 was synthesized in a manner similar to Example 23: ((2R,3S,4R,5R)-5-(4-aminopyrrolo[2,1-f][1,2,4]triazin-7-yl)-5-cyano-3,4-dihydroxytetrahydrofuran-2-yl) methyl (1-methylcyclohexyl) carbonate (Compound 47), replacing 1-methylcyclohexanol with 1,1-difluoro-2-methylpropan-2-ol (Intermediate 54a). $^1$H NMR (400 MHz, DMSO-d6) δ 7.92 (s, 3H), 6.91 (d, J=4.5 Hz, 1H), 6.79 (d, J=4.5 Hz, 1H), 6.33 (d, J=6.0 Hz, 1H), 6.16 (t, J=55.5 Hz, 1H), 5.42 (d, J=5.7 Hz, 1H), 4.68 (dd, J=6.1, 4.9 Hz, 1H), 4.45-4.37 (m, 1H), 4.27-4.17 (m, 2H), 3.93 (q, J=5.7 Hz, 1H), 1.46 (d, J=1.7 Hz, 6H). $^{19}$F NMR (376 MHz, DMSO-d6) δ −132.88-−133.31 (m). LCMS: MS m/z: 428.0 (M+1).

Example 55: Ethyl 2-(((((2R,3S,4R,5R)-5-(4-aminopyrrolo[2,1-f][1,2,4]triazin-7-yl)-5-cyano-3,4-dihydroxytetrahydrofuran-2-yl)methoxy)carbonyl)oxy)-2-methylpropanoate (Compound 77)

Compound 77

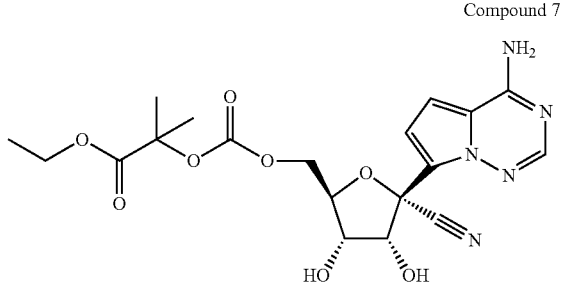

Compound 77 was synthesized in a manner similar to Example 23: ((2R,3S,4R,5R)-5-(4-aminopyrrolo[2,1-f][1,2,4]triazin-7-yl)-5-cyano-3,4-dihydroxytetrahydrofuran-2-yl) methyl (1-methylcyclohexyl) carbonate (Compound 47), replacing 1-methylcyclohexanol with ethyl 2-hydroxy-2-methylpropanoate. $^1$H NMR (400 MHz, DMSO-d$_6$) δ 7.93 (s, 3H), 6.92 (d, J=4.6 Hz, 1H), 6.81 (d, J=4.5 Hz, 1H), 6.35 (d, J=6.1 Hz, 1H), 5.43 (d, J=5.8 Hz, 1H), 4.75-4.67 (m, 1H), 4.45-4.34 (m, 1H), 4.31-4.20 (m, 2H), 4.16-4.05 (m, 2H), 3.96-3.89 (m, 1H), 1.51 (d, J=1.8 Hz, 6H), 1.14 (t, J=7.1 Hz, 3H). LCMS: 0.68 min, MS m/z: 450.0 (M+1).

Example 56: methyl O-((((2R,3S,4R,5R)-5-(4-aminopyrrolo[2,1-f][1,2,4]triazin-7-yl)-5-cyano-3,4-dihydroxytetrahydrofuran-2-yl)methoxy)carbonyl)-N,N-dimethyl-L-threoninate (Compound 78)

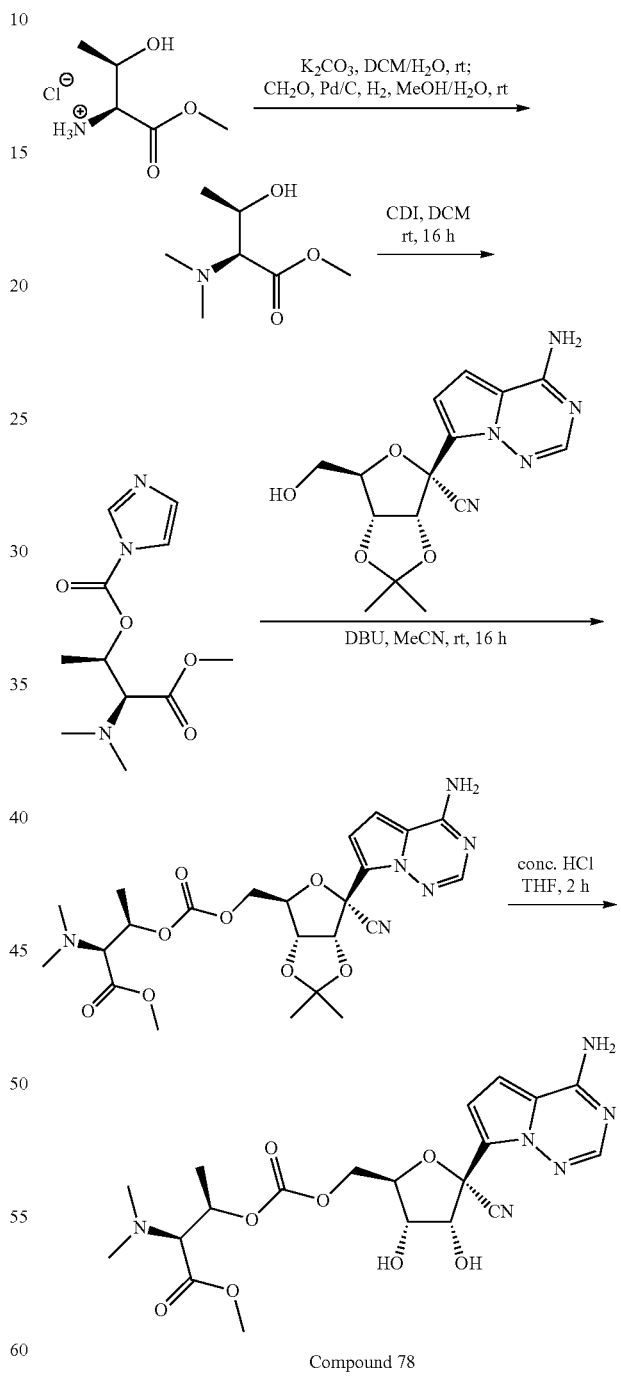

Compound 78

Step 1: methyl dimethyl-L-threoninate

A vigorously stirred solution of L-threonine methyl ester hydrochloride (2 g, 11.8 mmol) in DCM:H$_2$O (2:1, 50 mL)

was treated with potassium carbonate at room temperature. After continued stirring for 15 min, the two layers were separated, and the aqueous layer was extracted with DCM (30 mL×2). Combined organic layers were dried over magnesium sulfate and concentrated gently. The resulting free amine was dissolved in MeOH (20 mL), then formaldehyde (37 wt % in water, 5.3 mL, 70.8 mmol) and Pd/C (5 wt %, 3.02 g, 1.42 mmol) was added. The reaction apparatus was backfilled with $H_2$ then stirred vigorously for 72 h at room temperature. The reaction mixture was filtered over celite, and the filtrate was concentrated gently. The crude was purified by flash chromatography using EtOAc and hexanes as eluants to afford desired tertiary amine.

Step 2: (2R,3S)-3-(dimethylamino)-4-methoxy-4-oxobutan-2-yl 1H-imidazole-1-carboxylate A stirred solution of 1,1'-carbonyldiimidazole (691 mg, 4.26 mmol) in DCM (9.5 mL) was treated with tertiary amine (458 mg, 2.84 mmol). The resulting solution was stirred for 16 h at room temperature, then was transferred to separatory funnel and washed with H2O (10 mL×2). The organic layer was dried over magnesium sulfate and concentrated. The resulting crude carbamate was used directly without further purification.

Step 3: methyl O-((((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methoxy)carbonyl)-N,N-dimethyl-L-threoninate A stirred solution of nucleoside (700 mg, 2.11 mmol) and carbamate (593 mg, 2.32 mmol) in acetonitrile (7 mL) was treated with 1,8-Diazabicyclo[5.4.0]undec-7-ene (0.06 mL, 0.423 mmol) at room temperature, then was left to stir for 16 h. The resulting solution was quenched with saturated aqueous ammonium chloride (10 mL) then was extracted with EtOAc (20 mL×3). The combined organic layers were dried over magnesium sulfate and concentrated. The resulting crude carbonate was used directly without further purification.

Step 4: Compound 78—methyl O-((((2R,3S,4R,5R)-5-(4-aminopyrrolo[2,1-f][1,2,4]triazin-7-yl)-5-cyano-3,4-dihydroxytetrahydrofuran-2-yl)methoxy)carbonyl)-N,N-dimethyl-L-threoninate A stirred solution of carbonate (652 mg, 1.26 mmol) in THF (13 mL) was treated with conc. HCl (1.04 mL, 12.6 mmol) at room temperature. The resulting solution was stirred for 2 h then was quenched with saturated sodium bicarbonate until no gas evolution. The mixture was extracted with EtOAc (25 mL×3), the combined organic layers were dried over magnesium sulfate and concentrated. The resulting crude was purified by The crude was purified by flash chromatography using dichloromethane and methanol as eluants to afford final 5' carbonate nucleoside analogue Compound 78. 1H NMR (400 MHz, DMSO-d6) δ 7.92 (s, 3H), 6.90 (d, J=4.5 Hz, 1H), 6.78 (d, J=4.5 Hz, 1H), 6.33 (d, J=5.9 Hz, 1H), 5.39 (d, J=5.8 Hz, 1H), 5.03-4.93 (m, 1H), 4.70-4.63 (m, 1H), 4.42 (d, J=10.1 Hz, 1H), 4.32-4.17 (m, 2H), 3.98-3.87 (m, 1H), 3.64 (s, 3H), 2.23 (s, 6H), 1.20 (d, J=6.3 Hz, 3H). LCMS: MS m/z: 479.1 (M+1).

Example 57: (2R,3R,4R,5R)-2-(4-aminopyrrolo[2,1-f][1,2,4]triazin-7-yl)-2-cyano-5-(((((2-(pyridin-4-yl)propan-2-yl)oxy)carbonyl)oxy)methyl)tetrahydrofuran-3,4-diyl diacetate (Compound 79)

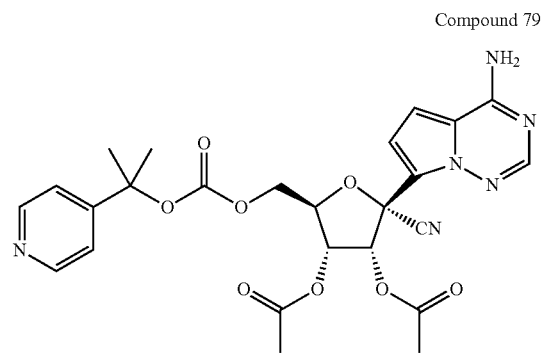 [SMILES: CC(=O)O[C@H]1[C@@H](OC(C)=O)[C@](C#N)(c2ccc3c(N)ncnn23)O[C@@H]1COC(=O)OC(C)(C)c1ccncc1]

Compound 79

Compound 79 was synthesized in a manner similar to (2R,3R,4R,5R)-2-(4-aminopyrrolo[2,1-f][1,2,4]triazin-7-yl)-2-cyano-5-(((isopropoxycarbonyl)ox)y)methyl)tetrahydrofuran-3,4-diyl diacetate (Compound 65), replacing ((2R,3S,4R,5R)-5-(4-aminopyrrolo[2,1-f][1,2,4]triazin-7-yl)-5-cyano-3,4-dihydroxytetrahydrofuran-2-y)methyl isopropyl carbonate (Compound 4) with ((2R,3S,4R,5R)-5-(4-aminopyrrolo[2,1-f][1,2,4]triazin-7-yl)-5-cyano-3,4-dihydroxytetrahydrofuran-2-yl)methyl (2-(pyridin-4-yl)propan-2-yl) carbonate (Compound 49). $^1$H NMR (400 MHz, DMSO-d$_6$) δ 8.49-8.42 (m, 2H), 8.07 (br, 1H), 8.00 (br, 1H), 7.96 (s, 1H), 7.26-7.20 (m, 2H), 6.97 (d, J=4.6 Hz, 1H), 6.83 (d, J=4.6 Hz, 1H), 6.09 (d, J=6.0 Hz, 1H), 5.40 (dd, J=6.0, 4.8 Hz, 1H), 4.57 (td, J=5.0, 3.2 Hz, 1H), 4.41 (dd, J=12.2, 3.2 Hz, 1H), 4.25 (dd, J=12.2, 5.1 Hz, 1H), 2.13 (s, 3H), 2.12 (s, 3H), 1.68 (s, 3H), 1.64 (s, 3H). LCMS: MS m/z: 539.02 (M+1).

Example 58: tert-butyl (7-((2R,3R,4R,5R)-2-cyano-3,4-bis((isopropoxycarbonyl)oxy)-5-(((isopropoxycarbonyl)oxy)methyl)tetrahydrofuran-2-yl)pyrrolo[2,1-f][1,2,4]triazin-4-yl)carbamate (Compound 80)

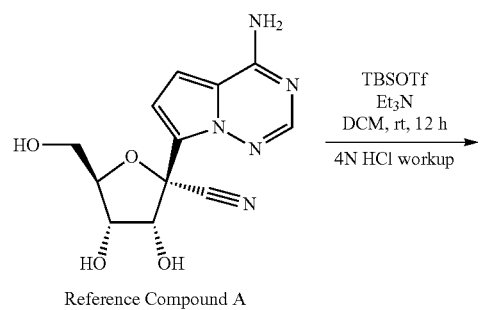

Reference Compound A

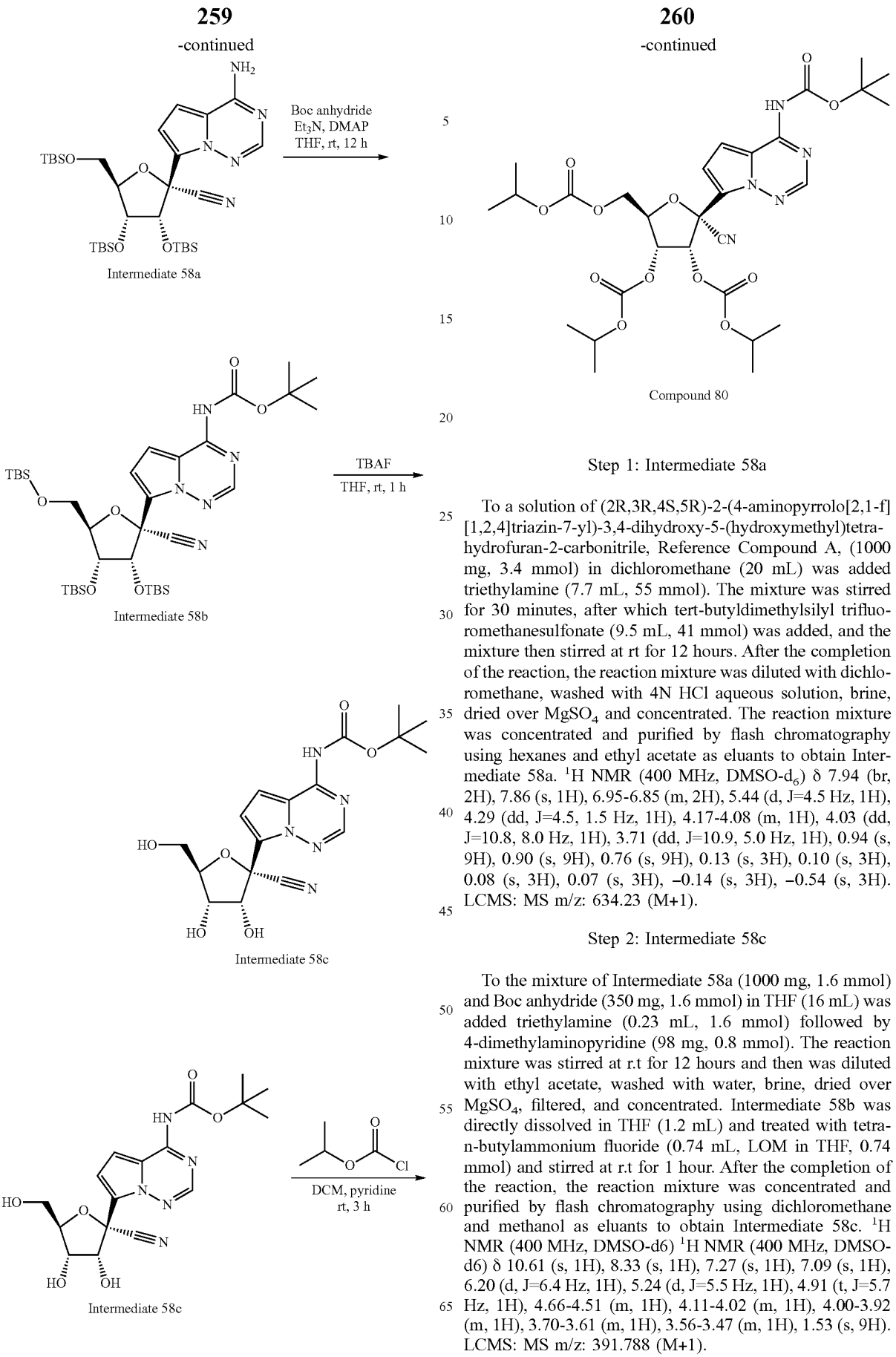

Step 1: Intermediate 58a

To a solution of (2R,3R,4S,5R)-2-(4-aminopyrrolo[2,1-f][1,2,4]triazin-7-yl)-3,4-dihydroxy-5-(hydroxymethyl)tetrahydrofuran-2-carbonitrile, Reference Compound A, (1000 mg, 3.4 mmol) in dichloromethane (20 mL) was added triethylamine (7.7 mL, 55 mmol). The mixture was stirred for 30 minutes, after which tert-butyldimethylsilyl trifluoromethanesulfonate (9.5 mL, 41 mmol) was added, and the mixture then stirred at rt for 12 hours. After the completion of the reaction, the reaction mixture was diluted with dichloromethane, washed with 4N HCl aqueous solution, brine, dried over MgSO$_4$ and concentrated. The reaction mixture was concentrated and purified by flash chromatography using hexanes and ethyl acetate as eluants to obtain Intermediate 58a. $^1$H NMR (400 MHz, DMSO-d$_6$) δ 7.94 (br, 2H), 7.86 (s, 1H), 6.95-6.85 (m, 2H), 5.44 (d, J=4.5 Hz, 1H), 4.29 (dd, J=4.5, 1.5 Hz, 1H), 4.17-4.08 (m, 1H), 4.03 (dd, J=10.8, 8.0 Hz, 1H), 3.71 (dd, J=10.9, 5.0 Hz, 1H), 0.94 (s, 9H), 0.90 (s, 9H), 0.76 (s, 9H), 0.13 (s, 3H), 0.10 (s, 3H), 0.08 (s, 3H), 0.07 (s, 3H), −0.14 (s, 3H), −0.54 (s, 3H). LCMS: MS m/z: 634.23 (M+1).

Step 2: Intermediate 58c

To the mixture of Intermediate 58a (1000 mg, 1.6 mmol) and Boc anhydride (350 mg, 1.6 mmol) in THF (16 mL) was added triethylamine (0.23 mL, 1.6 mmol) followed by 4-dimethylaminopyridine (98 mg, 0.8 mmol). The reaction mixture was stirred at r.t for 12 hours and then was diluted with ethyl acetate, washed with water, brine, dried over MgSO$_4$, filtered, and concentrated. Intermediate 58b was directly dissolved in THF (1.2 mL) and treated with tetra-n-butylammonium fluoride (0.74 mL, LOM in THF, 0.74 mmol) and stirred at r.t for 1 hour. After the completion of the reaction, the reaction mixture was concentrated and purified by flash chromatography using dichloromethane and methanol as eluants to obtain Intermediate 58c. $^1$H NMR (400 MHz, DMSO-d6) $^1$H NMR (400 MHz, DMSO-d6) δ 10.61 (s, 1H), 8.33 (s, 1H), 7.27 (s, 1H), 7.09 (s, 1H), 6.20 (d, J=6.4 Hz, 1H), 5.24 (d, J=5.5 Hz, 1H), 4.91 (t, J=5.7 Hz, 1H), 4.66-4.51 (m, 1H), 4.11-4.02 (m, 1H), 4.00-3.92 (m, 1H), 3.70-3.61 (m, 1H), 3.56-3.47 (m, 1H), 1.53 (s, 9H). LCMS: MS m/z: 391.788 (M+1).

Step 3: Compound 80

To a solution of Intermediate 58c (50 mg, 0.13 mmol) in dichloromethane (1 mL) was added pyridine (0.05 mL, 0.64 mmol). The mixture was then added isopropyl chloroformate (0.52 mL, 1.0 M in toluene, 0.52 mmol) and stirred at room temperature for 3 h. The reaction mixture was diluted with dichloromethane, washed with water, brine, dried over MgSO$_4$ and concentrated. The residue was purified by flash chromatography using dichloromethane and ethyl acetate as eluants to obtain Compound 80. $^1$H NMR (400 MHz, DMSO-d$_6$) δ 10.73 (s, 1H), 8.35 (s, 1H), 7.33 (s, 1H), 7.02 (s, 1H), 5.96 (d, J=6.1 Hz, 1H), 5.39-5.28 (m, 1H), 4.87-4.59 (m, 4H), 4.48 (dd, J=12.2, 3.4 Hz, 1H), 4.34 (dd, J=12.0, 4.8 Hz, 1H), 1.53 (s, 9H), 1.31-1.09 (m, 18H). LCMS: MS m/z: 649.80 (M+1).

Example 59: (2R,3R,4R,5R)-2-(4-aminopyrrolo[2,1-f][1,2,4]triazin-7-yl)-2-cyano-5-(((isopropoxycarbonyl)oxy)methyl)tetrahydrofuran-3,4-diyl diisopropyl bis(carbonate) (Compound 81)

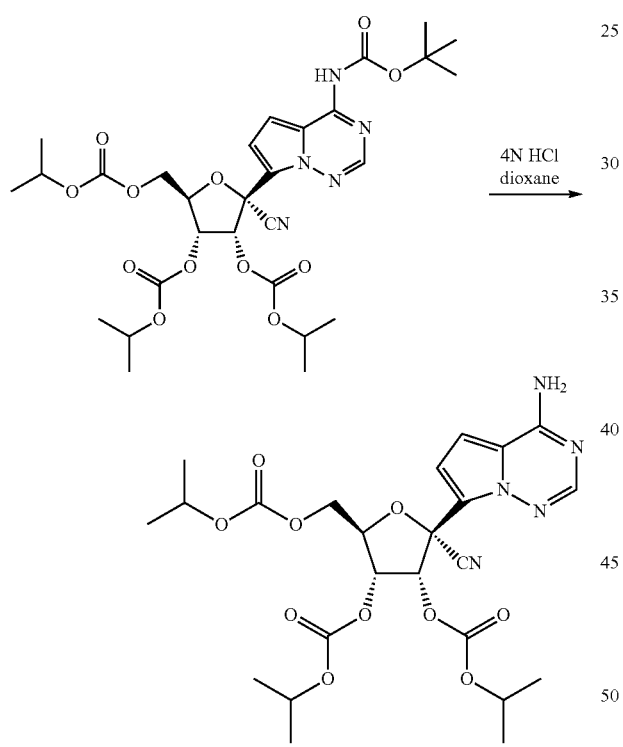

To Compound 80 (57 mg, 0.09 mmol) was added 4N HCl in dioxane (0.76 mL, 3.1 mmol). The reaction mixture was stirred at room temperature overnight. The reaction mixture was diluted with ethyl acetate, neutralized with saturated sodium bicarbonate, the organic layer separated, washed with water, brine, dried over MgSO$_4$, filtered, and concentrated. The residue was purified by flash chromatography using dichloromethane and ethyl acetate as eluants to obtain Compound 81. $^1$H NMR (400 MHz, DMSO-D6) δ 8.07 (br, 1H), 8.00 (br, 1H), 7.94 (s, 1H), 6.95 (d, J=4.6 Hz, 1H), 6.83 (d, J=4.6 Hz, 1H), 5.99 (d, J=6.0 Hz, 1H), 5.33 (dd, J=6.0, 5.0 Hz, 1H), 4.86-4.66 (m, 3H), 4.61 (td, J=5.0, 3.2 Hz, 1H), 4.48 (dd, J=12.2, 3.3 Hz, 1H), 4.33 (dd, J=12.2, 5.1 Hz, 1H), 1.30-1.16 (m, 18H). LCMS: MS m/z: 549.95 (M+1).

Example 60: ((2R,3S,4R,5R)-5-(4-aminopyrrolo[2,1-f][1,2,4]triazin-7-yl)-5-cyano-3,4-dihydroxytetrahydrofuran-2-yl)methyl (2-isopropyl-5-methylphenyl) carbonate (Compound 82)

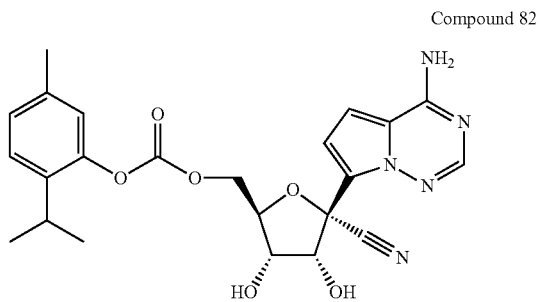 [SMILES: Cc1ccc(C(C)C)c(OC(=O)OC[C@H]2O[C@@](C#N)(c3ccc4c(N)ncnn34)[C@H](O)[C@@H]2O)c1]

Compound 82 was synthesized in manner similar to ((2R,3S,4R,5R)-5-(4-aminopyrrolo[2,1-f][1,2,4]triazin-7-yl)-5-cyano-3,4-dihydroxytetrahydrofuran-2-yl)methyl cyclooctyl carbonate (Compound 14) in Example 41, using the 2-step procedure and replacing cyclooctanol with 2-isopropyl-5-methylphenol. 1H NMR (400 MHz, DMSO-d6) δ 8.15-7.89 (m, 3H), 7.24 (d, J=7.9 Hz, 1H), 7.10-7.05 (m, 1H), 6.95 (d, J=4.6 Hz, 1H), 6.91-6.90 (m, 1H), 6.85 (d, J=4.5 Hz, 1H), 6.39 (s, 1H), 5.47 (s, 1H), 4.70 (d, J=4.9 Hz, 1H), 4.59-4.52 (m, 1H), 4.45-4.37 (m, 1H), 4.36-4.28 (m, 1H), 4.05-3.99 (m, 1H), 2.98-2.88 (m, 1H), 2.27 (s, 3H), 1.10 (dd, J=6.9, 2.7 Hz, 6H). LCMS: 0.86 min, MS m/z: 468.0 (M+1).

Example 61: ((2R,3S,4R,5R)-5-(4-aminopyrrolo[2,1-f][1,2,4]triazin-7-yl)-5-cyano-3,4-dihydroxytetrahydrofuran-2-yl)methyl ((1R,2S,5R)-2-isopropyl-5-methylcyclohexyl) carbonate (Compound 83)

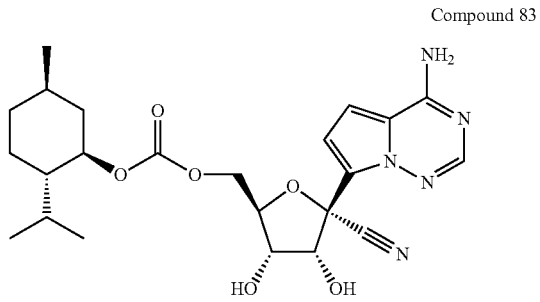 [SMILES: CC(C)[C@@H]1CC[C@@H](C)C[C@H]1OC(=O)OC[C@H]1O[C@@](C#N)(c2ccc3c(N)ncnn23)[C@H](O)[C@@H]1O]

Compound 83 was synthesized in manner similar to ((2R,3S,4R,5R)-5-(4-aminopyrrolo[2,1-f][1,2,4]triazin-7-yl)-5-cyano-3,4-dihydroxytetrahydrofuran-2-yl)methyl cyclooctyl carbonate (Compound 14) in Example 41, using the 2-step procedure and replacing cyclooctanol with (1R,2S,5R)-2-isopropyl-5-methylcyclohexan-1-ol. $^1$H NMR (400 MHz, DMSO-d6) δ 8.05-7.86 (m, 3H), 6.91 (d, J=4.5 Hz, 1H), 6.78 (t, J=3.9 Hz, 1H), 6.34 (s, 1H), 5.41 (s, 1H), 4.68-4.61 (m, 1H), 4.48-4.37 (m, 2H), 4.27-4.17 (m, 2H), 3.97-3.90 (m, 1H), 2.00-1.77 (m, 2H), 1.68-1.57 (m, 2H), 1.52-1.28 (m, 2H), 1.10-0.95 (m, 2H), 0.91-0.78 (m, 7H), 0.78-0.67 (m, 3H). LCMS: 0.94 min, MS m/z: 474.0 (M+1).

Example 62: ((2R,3S,4R,5R)-5-(4-aminopyrrolo[2,1-f][1,2,4]triazin-7-yl)-5-cyano-3,4-dihydroxytetrahydrofuran-2-yl)methyl (4,4-difluorocyclohexyl) carbonate (Compound 84)

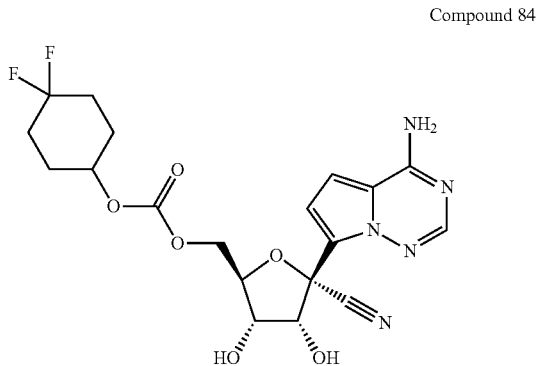 [SMILES: N#C[C@@]1(c2ccc3c(N)ncnn23)O[C@H](COC(=O)OC2CCC(F)(F)CC2)[C@@H](O)[C@H]1O]

Compound 84

Compound 84 was synthesized in a manner similar to ((2R,3S,4R,5R)-5-(4-aminopyrrolo[2,1-f][1,2,4]triazin-7-yl)-5-cyano-3,4-dihydroxytetrahydrofuran-2-yl)methyl cyclooctyl carbonate (Compound 14) in Example 41, using the 2-step procedure and replacing cyclooctanol with 4,4-difluorocyclohexanol. $^1$H NMR (400 MHz, DMSO-d6) δ 8.08-7.76 (m, 3H), 6.90 (d, J=4.5 Hz, 1H), 6.79 (d, J=4.5 Hz, 1H), 6.34 (d, J=6.0 Hz, 1H), 5.41 (d, J=5.8 Hz, 1H), 4.76 (tq, J=6.0, 2.7 Hz, 1H), 4.68 (dd, J=6.0, 4.9 Hz, 1H), 4.49-4.38 (m, 1H), 4.29-4.16 (m, 2H), 3.94 (q, J=5.8 Hz, 1H), 2.04-1.82 (m, 6H), 1.82-1.67 (m, 2H). LCMS: MS m/z 453.9 (M+1).

Example 63: ((2R,3S,4R,5R)-5-(4-aminopyrrolo[2,1-f][1,2,4]triazin-7-yl)-5-cyano-3,4-dihydroxytetrahydrofuran-2-yl)methyl (cyclopentylmethyl) carbonate (Compound 85)

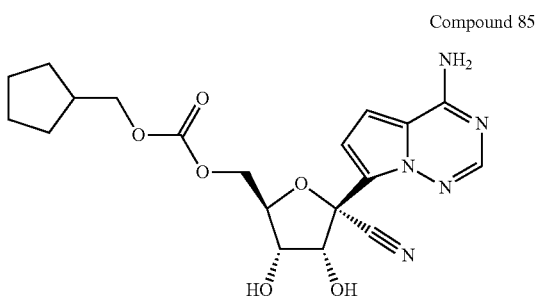 [SMILES: N#C[C@@]1(c2ccc3c(N)ncnn23)O[C@H](COC(=O)OCC2CCCC2)[C@@H](O)[C@H]1O]

Compound 85

Compound 85 was synthesized in a manner similar to ((2R,3S,4R,5R)-5-(4-aminopyrrolo[2,1-f][1,2,4]triazin-7-yl)-5-cyano-3,4-dihydroxytetrahydrofuran-2-yl)methyl cyclooctyl carbonate (Compound 14) in Example 41, using the 2-step procedure and replacing cyclooctanol with cyclopentylmethanol. $^1$H NMR (400 MHz, DMSO-d6) δ 7.92 (s, 3H), 6.90 (d, J=4.5 Hz, 1H), 6.79 (d, J=4.5 Hz, 1H), 6.33 (d, J=6.0 Hz, 1H), 5.41 (d, J=5.7 Hz, 1H), 4.67 (dd, J=6.0, 4.9 Hz, 1H), 4.45-4.36 (m, 1H), 4.27-4.17 (m, 2H), 3.95 (dd, J=9.8, 6.3 Hz, 3H), 2.14 (h, J=7.5 Hz, 1H), 1.75-1.62 (m, 2H), 1.61-1.42 (m, 4H), 1.21 (dq, J=11.0, 6.8 Hz, 2H). LCMS: MS m/z 418.0 (M+1).

Example 64: ((2R,3S,4R,5R)-5-(4-aminopyrrolo[2,1-f][1,2,4]triazin-7-yl)-5-cyano-3,4-dihydroxytetrahydrofuran-2-yl)methyl (cyclohexylmethyl) carbonate (Compound 86)

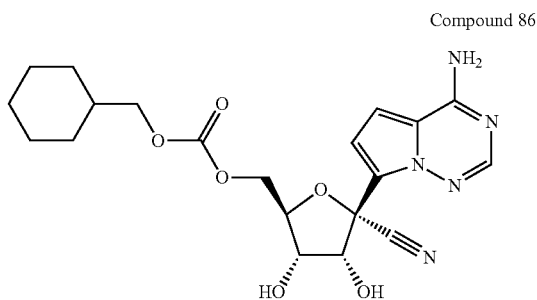 [SMILES: N#C[C@@]1(c2ccc3c(N)ncnn23)O[C@H](COC(=O)OCC2CCCCC2)[C@@H](O)[C@H]1O]

Compound 86

Compound 86 was synthesized in a manner similar to ((2R,3S,4R,5R)-5-(4-aminopyrrolo[2,1-f][1,2,4]triazin-7-yl)-5-cyano-3,4-dihydroxytetrahydrofuran-2-yl)methyl cyclooctyl carbonate (Compound 14) in Example 41, using the 2-step procedure and replacing cyclooctanol with cyclohexylmethanol. $^1$H NMR (400 MHz, DMSO-d6) δ 8.03-7.75 (m, 3H), 6.90 (d, J=4.5 Hz, 1H), 6.79 (d, J=4.5 Hz, 1H), 6.33 (d, J=6.0 Hz, 1H), 5.41 (d, J=5.8 Hz, 1H), 4.67 (dd, J=6.0, 4.9 Hz, 1H), 4.47-4.34 (m, 1H), 4.28-4.14 (m, 2H), 3.93 (q, J=5.6 Hz, 1H), 3.89 (d, J=6.3 Hz, 2H), 1.72-1.51 (m, 6H), 1.28-1.03 (m, 3H), 1.00-0.82 (m, 2H). LCMS: MS m/z 432.0 (M+1).

Example 65: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-1-phenylethyl) carbonate (Compound 87)

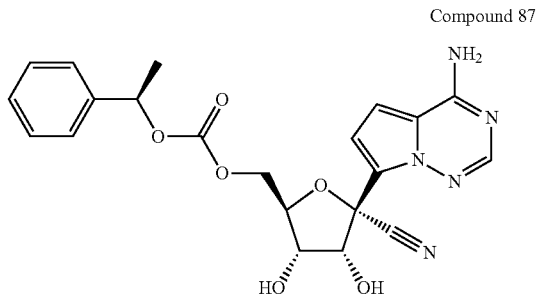 [SMILES: C[C@@H](OC(=O)OC[C@H]1O[C@@](C#N)(c2ccc3c(N)ncnn23)[C@H](O)[C@@H]1O)c1ccccc1]

Compound 87

Compound 87 was synthesized in a manner similar to ((2R,3S,4R,5R)-5-(4-aminopyrrolo[2,1-f][1,2,4]triazin-7-yl)-5-cyano-3,4-dihydroxytetrahydrofuran-2-yl)methyl cyclooctyl carbonate (Compound 14) in Example 41, using the 2-step procedure and replacing cyclooctanol with (1R)-1-phenylethanol. $^1$H NMR (400 MHz, DMSO-d6) δ 8.03-7.74 (m, 3H), 7.39-7.26 (m, 5H), 6.91 (d, J=4.5 Hz, 1H), 6.79 (d, J=4.5 Hz, 1H), 6.32 (d, J=6.0 Hz, 1H), 5.67 (q, J=6.5 Hz, 1H), 5.40 (d, J=5.8 Hz, 1H), 4.67 (dd, J=6.0.4.9 Hz, 1H), 4.43 (dd, J=11.4, 2.4 Hz, 1H), 4.27-4.13 (m, 2H), 3.92 (td, J=6.2, 5.0 Hz, 1H), 1.51 (d, J=6.6 Hz, 3H). LCMS: MS m/z 439.9 (M+1).

Example 66: ((2R,3S,4R,5R)-5-(4-aminopyrrolo[2,1-f][1,2,4]triazin-7-yl)-5-cyano-3,4-dihydroxytetrahydrofuran-2-yl)methyl ((S)-1-phenylethyl) carbonate (Compound 88)

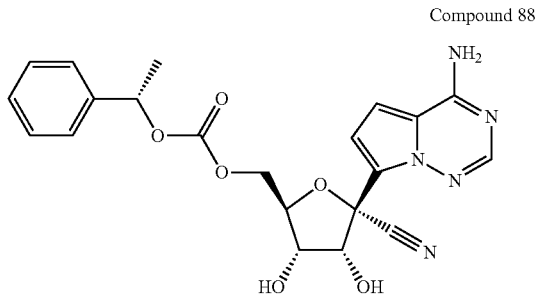 [SMILES: C[C@H](OC(=O)OC[C@H]1O[C@@](C#N)(c2ccc3c(N)ncnn23)[C@H](O)[C@@H]1O)c1ccccc1]

Compound 88

Compound 88 was synthesized in a manner similar to ((2R,3S,4R,5R)-5-(4-aminopyrrolo[2,1-f][1,2,4]triazin-7-yl)-5-cyano-3,4-dihydroxytetrahydrofuran-2-yl)methyl cyclooctyl carbonate (Compound 14) in Example 41, using the 2-step procedure and replacing cyclooctanol with (1S)-1-phenylethanol. $^1$H NMR (400 MHz, DMSO-d6) δ 8.04-7.79 (m, 3H), 7.41-7.25 (m, 5H), 6.91 (d, J=4.5 Hz, 1H), 6.77 (d, J=4.5 Hz, 1H), 6.32 (d, J=6.1 Hz, 1H), 5.67 (q, J=6.5 Hz, 1H), 5.40 (d, J=5.7 Hz, 1H), 4.67 (dd, J=6.1, 4.9 Hz, 1H), 4.41-4.30 (m, 1H), 4.23 (dd, J=8.8, 5.8 Hz, 2H), 3.93 (q, J=5.6 Hz, 1H), 1.50 (d, J=6.6 Hz, 3H). LCMS: MS m/z 440.0 (M+1).

Example 67: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-sec-butyl) carbonate (Compound 89)

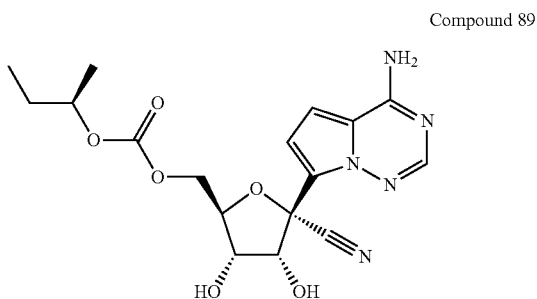 [SMILES: CC[C@@H](C)OC(=O)OC[C@H]1O[C@@](C#N)(c2ccc3c(N)ncnn23)[C@H](O)[C@@H]1O]

Compound 89

Compound 89 was synthesized in a manner similar to ((2R,3S,4R,5R)-5-(4-aminopyrrolo[2,1-f][1,2,4]triazin-7-yl)-5-cyano-3,4-dihydroxytetrahydrofuran-2-yl)methyl cyclooctyl carbonate (Compound 14) in Example 41, using the 2-step procedure and replacing cyclooctanol with (2R)-butan-2-ol. $^1$H NMR (400 MHz, DMSO-d6) δ 8.02-7.75 (m, 3H), 6.90 (d, J=4.5 Hz, 1H), 6.78 (d, J=4.5 Hz, 1H), 6.32 (d, J=6.0 Hz, 1H), 5.40 (d, J=5.8 Hz, 1H), 4.67 (dd, J=6.0, 4.9 Hz, 1H), 4.59 (h, J=6.2 Hz, 1H), 4.46-4.34 (m, 1H), 4.26-4.15 (m, 2H), 3.93 (q, J=5.8 Hz, 1H), 1.54 (dtd, J=13.3, 7.4, 3.0 Hz, 2H), 1.19 (d, J=6.2 Hz, 3H), 0.84 (t, J=7.4 Hz, 3H). LCMS: MS m/z 392.0 (M+1).

Example 68: ((2R,3S,4R,5R)-5-(4-aminopyrrolo[2,1-f][1,2,4]triazin-7-yl)-5-cyano-3,4-dihydroxytetrahydrofuran-2-yl)methyl ((S)-sec-butyl) carbonate (Compound 90)

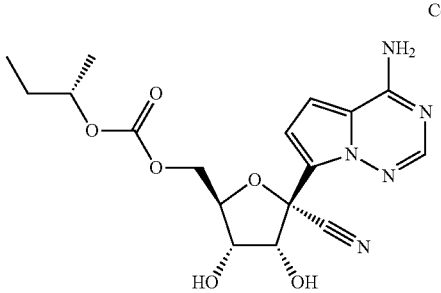

Compound 90

Compound 90 was synthesized in a manner similar to ((2R,3S,4R,5R)-5-(4-aminopyrrolo[2,1-f][1,2,4]triazin-7-yl)-5-cyano-3,4-dihydroxytetrahydrofuran-2-yl)methyl cyclooctyl carbonate (Compound 14) in Example 41, using the 2-step procedure and replacing cyclooctanol with (2S)-butan-2-ol. $^1$H NMR (400 MHz, DMSO-d6) δ 8.03-7.78 (m, 3H), 6.90 (d, J=4.5 Hz, 1H), 6.78 (d, J=4.5 Hz, 1H), 6.32 (d, J=6.0 Hz, 1H), 5.40 (d, J=5.8 Hz, 1H), 4.66 (dd, J=6.1, 4.9 Hz, 1H), 4.59 (p, J=6.2 Hz, 1H), 4.46-4.34 (m, 1H), 4.27-4.14 (m, 2H), 3.93 (q, J=5.8 Hz, 1H), 1.61-1.47 (m, 2H), 1.19 (d, J=6.3 Hz, 3H), 0.86 (t, J=7.5 Hz, 3H). LCMS: MS m/z 392.0 (M+1).

Example 69: ((2R,3S,4R,5R)-5-(4-aminopyrrolo[2,1-f][1,2,4]triazin-7-yl)-5-cyano-3,4-dihydroxytetrahydrofuran-2-yl)methyl (pyrimidin-2-ylmethyl) carbonate (Compound 91)

Compound 91

Compound 69 was synthesized in a manner similar to ((2R,3S,4R,5R)-5-(4-aminopyrrolo[2,1-f][1,2,4]triazin-7-yl)-5-cyano-3,4-dihydroxytetrahydrofuran-2-yl)methyl cyclooctyl carbonate (Compound 14) in Example 41, using the 2-step procedure and replacing cyclooctanol with pyrimidin-2-ylmethanol. $^1$H NMR (400 MHz, DMSO-d6) δ 8.81 (d, J=4.9 Hz, 2H), 8.05-7.74 (m, 3H), 7.46 (t, J=49 Hz, 1H), 6.90 (d, J=4.5 Hz, 1H), 6.83 (d, J=4.5 Hz, 1H), 6.33 (d, J=6.1 Hz, 1H), 5.44 (d, J=5.7 Hz, 1H), 5.29 (s, 2H), 4.70 (dd, J=6.1, 5.0 Hz, 1H), 4.50-4.36 (m, 1H), 4.33-4.19 (m, 2H), 3.97 (q, J=5.7 Hz, 1H). LCMS: MS m/z 427.9 (M+1).

Example 70: ((2R,3S,4R,5R)-5-(4-aminopyrrolo[2,1-f][1,2,4]triazin-7-yl)-5-cyano-3,4-dihydroxytetrahydrofuran-2-yl)methyl (2-morpholinoethyl) carbonate (Compound 92)

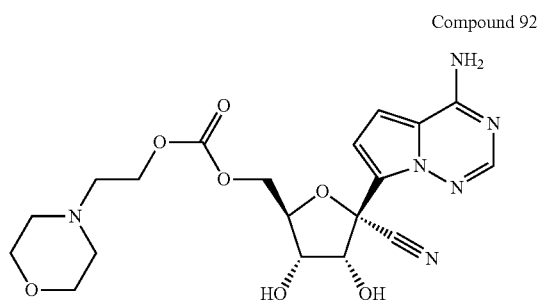 [SMILES: N#C[C@@]1(c2ccc3c(N)ncnn23)O[C@H](COC(=O)OCCN2CCOCC2)[C@@H](O)[C@H]1O]

Compound 92

Compound 92 was synthesized in a manner similar to ((2R,3S,4R,5R)-5-(4-aminopyrrolo[2,1-f][1,2,4]triazin-7-yl)-5-cyano-3,4-dihydroxytetrahydrofuran-2-yl)methyl cyclooctyl carbonate (Compound 14) in Example 41, using the 2-step procedure and replacing cyclooctanol with 4-(2-hydroxyethyl)morpholine. 1H NMR (400 MHz, DMSO-d6) δ 8.06-7.78 (m, 3H), 6.90 (d, J=4.5 Hz, 1H), 6.79 (d, J=4.5 Hz, 1H), 6.33 (d, J=6.0 Hz, 1H), 5.41 (d, J=5.7 Hz, 1H), 4.69 (dd, J=6.1, 4.9 Hz, 1H), 4.44-4.36 (m, 2H), 4.27-4.20 (m, 2H), 4.20-4.15 (m, 2H), 3.94 (q, J=5.6 Hz, 1H), 3.58-3.51 (m, 4H), 2.53 (t. J=5.6 Hz, 2H), 2.41-2.34 (m, 4H). LCMS: MS m/z: 449.1 (M+1).

Example 71: (2R,3R,4R,5R)-2-(4-aminopyrrolo[2,1-f][1,2,4]triazin-7-yl)-2-cyano-5-(((methoxycarbonyl)oxy)methyl)tetrahydrofuran-3,4-diyl dimethyl bis(carbonate) (Compound 93)

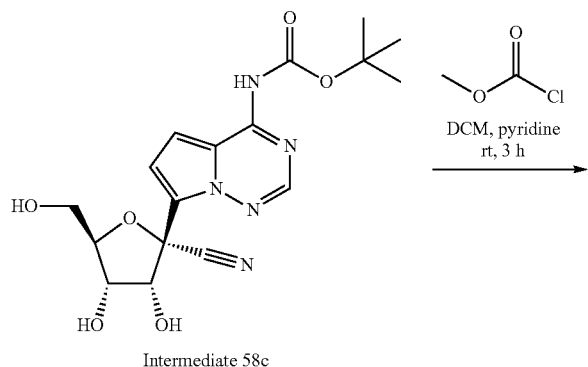

Intermediate 58c

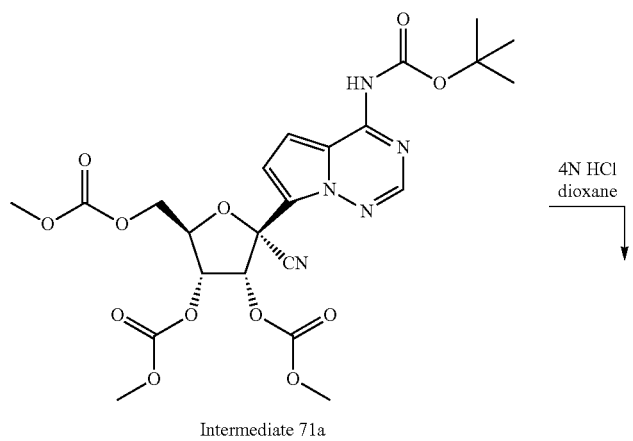

Intermediate 71a

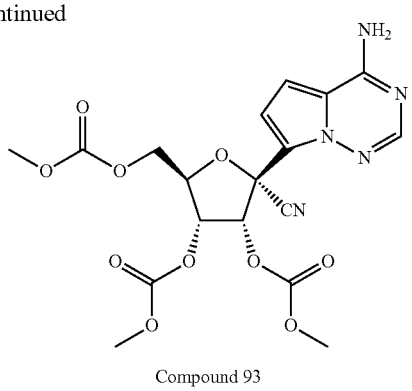

Compound 93

To a solution of Intermediate 58c (50 mg, 0.13 mmol) in dichloromethane (1 mL) was added pyridine (0.05 mL, 0.64 mmol). The mixture was then added methyl chloroformate (0.04 mL, 0.52 mmol) and stirred at room temperature for 3 h. The reaction mixture was diluted with dichloromethane, washed with water, brine, dried over MgSO₄ and concentrated to afford Intermediate 71a. To the crude Intermediate 71a was added 4N HCl in dioxane (0.76 mL, 3.1 mmol). The reaction mixture was stirred at room temperature overnight. The reaction mixture was diluted with ethyl acetate, neutralized with saturated sodium bicarbonate, the organic layer separated, washed with water, brine, dried over MgSO₄, filtered, and concentrated. The residue was purified by flash chromatography using dichloromethane and ethyl acetate as eluants to obtain Compound 93. $^1$H NMR (400 MHz, DMSO-d$_6$) δ 8.07 (br, 1H), 8.00 (br, 1H), 7.93 (s, 1H), 6.95 (d, J=4.6 Hz, 1H), 6.85 (d, J=4.6 Hz, 1H), 6.05 (d, J=6.0 Hz, 1H), 5.38 (dd, J=6.0, 4.1 Hz, 1H), 4.71-4.63 (m, 1H), 4.49 (dd, J=12.1, 3.3 Hz, 1H), 4.37 (dd, J=12.1, 5.0 Hz, 1H), 3.78 (s, 3H), 3.77 (s, 3H), 3.69 (s, 3H). LCMS: MS m/z: 466.03 (M+1).

Example 72: ((2R,3S,4R,5R)-5-(4-aminopyrrolo[2,1-f][1,2,4]triazin-7-yl)-5-cyano-3,4-dihydroxytetrahydrofuran-2-yl)methyl (3,3-dimethylcyclobutyl) carbonate (Compound 31)

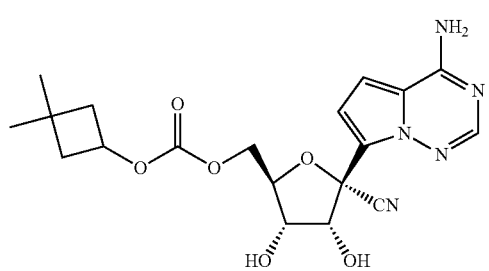

Compound 31

Compound 31 was synthesized in a manner similar to ((2R,3S,4R,5R)-5-(4-aminopyrrolo[2,1-f][1,2,4]triazin-7-yl)-5-cyano-3,4-dihydroxytetrahydrofuran-2-yl)methyl cyclooctyl carbonate (Compound 14) in Example 41, using the 2-step procedure and replacing cyclooctanol with 3,3-dimethylcyclobutan-1-ol. $^1$H NMR (400 MHz, DMSO-d$_6$) δ 7.92 (s, 3H), 6.92 (d, J=4.6 Hz, 1H), 6.79 (d, J=4.6 Hz, 1H), 6.32 (d, J=6.1 Hz, 1H), 5.41 (d, J=5.7 Hz, 1H), 4.91-4.84 (m, 1H), 4.69 (dd, J=6.1, 4.9 Hz, 1H), 4.45-4.33 (m, 1H), 4.27-4.15 (m, 2H), 3.94 (q, J=5.8 Hz, 1H), 2.23-2.11 (m, 2H), 1.87-1.77 (m, 2H), 1.12 (m, 6H). LCMS: MS m/z: 418.02 (M+1).

Example 73: ((2R,3S,4R,5R)-5-(4-aminopyrrolo[2,1-f][1,2,4]triazin-7-yl)-5-cyano-3,4-dihydroxytetrahydrofuran-2-yl)methyl (1,3-difluoropropan-2-yl) carbonate (Compound 94)

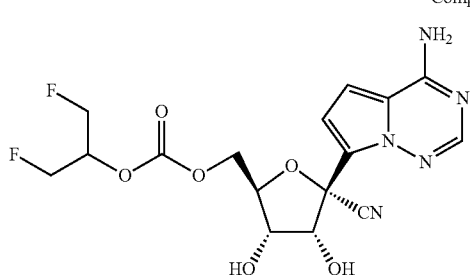

Compound 94

Compound 94 was synthesized in a manner similar to ((2R,3S,4R,5R)-5-(4-aminopyrrolo[2,1-f][1,2,4]triazin-7-yl)-5-cyano-3,4-dihydroxytetrahydrofuran-2-yl)methyl cyclooctyl carbonate (Compound 14) in Example 41, using the 2-step procedure and replacing cyclooctanol with 1,3-difluoropropan-2-ol. $^1$H NMR (400 MHz, DMSO-d$_6$) δ 7.93 (s, 3H), 6.92 (d, J=4.6 Hz, 1H), 6.80 (d, J=4.6 Hz, 1H), 6.35 (d, J=6.1 Hz, 1H), 5.44 (br, 1H), 5.20-5.07 (m, 1H), 4.79-4.74 (m, 1H), 4.72-4.62 (m, 3H), 4.59-4.55 (m, 1H), 4.51-4.45 (m, 1H), 4.34-4.22 (m, 2H), 3.96 (m, 1H). LCMS: MS m/z: 414.13 (M+1).

Example 74: ((2R,3S,4R,5R)-5-(4-aminopyrrolo[2,1-f][1,2,4]triazin-7-yl)-5-cyano-3,4-dihydroxytetrahydrofuran-2-yl)methyl pentyl carbonate (Compound 27)

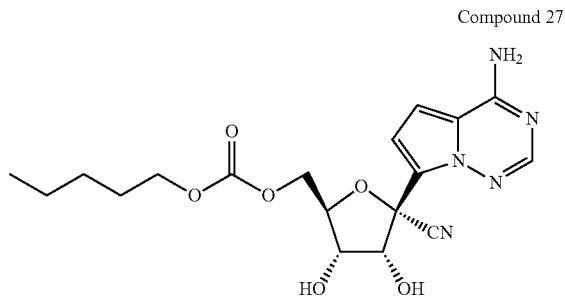 [SMILES: CCCCCOC(=O)OC[C@H]1O[C@@](C#N)(c2ccc3c(N)ncnn23)[C@H](O)[C@@H]1O]

Compound 27

Compound 27 was synthesized in a manner similar to ((2R,3S,4R,5R)-5-(4-aminopyrrolo[2,1-f][1,2,4]triazin-7-yl)-5-cyano-3,4-dihydroxytetrahydrofuran-2-yl)methyl cyclooctyl carbonate (Compound 14) in Example 41, using the 2-step procedure and replacing cyclooctanol with pentan-1-ol. $^1$H NMR (400 MHz, DMSO-d$_6$) δ 7.93 (s, 3H), 6.91 (d, J=4.5 Hz, 1H), 6.80 (d, J=4.6 Hz, 1H), 6.33 (d, J=6.1 Hz, 1H), 5.42 (d, J=5.8 Hz, 1H), 4.69 (dd, J=6.1, 5.0 Hz, 1H), 4.53-4.31 (m, 1H), 4.29-4.14 (m, 2H), 4.07 (t, J=6.6 Hz, 2H), 3.94 (q, J=5.8 Hz, 1H), 1.70-1.48 (m, 2H), 1.42-1.18 (m, 4H), 0.90-0.84 (m, 3H). LCMS: MS m/z: 406.04 (M+1).

Example 75: ((2R,3S,4R,5R)-5-(4-aminopyrrolo[2,1-f][1,2,4]triazin-7-yl)-5-cyano-3,4-dihydroxytetrahydrofuran-2-yl)methyl (1-methoxy-2-methylpropan-2-yl) carbonate (Compound 96)

Compound 96

NH$_2$

Compound 96 was synthesized in a manner similar to ((2R,3S,4R,5R)-5-(4-aminopyrrolo[2,1-f][1,2,4]triazin-7-yl)-5-cyano-3,4-dihydroxytetrahydrofuran-2-yl)methyl (1-methylcyclohexyl) carbonate (Compound 47) in Example 23, replacing 1-methylcyclohexanol with 1-methoxy-2-methyl-propan-2-ol. $^1$H NMR (400 MHz, DMSO-d$_6$) δ 7.94 (s, 3H), 6.92 (d, J=4.6 Hz, 1H), 6.81 (d, J=4.5 Hz, 1H), 6.33 (d, J=6.0 Hz, 1H), 5.42 (d, J=5.8 Hz, 1H), 4.69 (t, J=5.5 Hz, 1H), 4.37 (dd, J=11.7, 2.8 Hz, 1H), 4.22 (td, J=6.3, 2.8 Hz, 1H), 4.15 (dd, J=11.7, 6.1 Hz, 1H), 3.94 (q, J=5.8 Hz, 1H), 3.44 (s, 2H), 3.28 (s, 3H), 1.37 (s, 6H). LCMS: MS m/z: 421.90 (M+1).

Example 76: ethyl (S)-2-(((((2R,3S,4R,5R)-5-(4-aminopyrrolo[2,1-f][1,2,4]triazin-7-yl)-5-cyano-3,4-dihydroxytetrahydrofuran-2-yl)methoxy)carbonyl)oxy)propanoate (Compound 97)

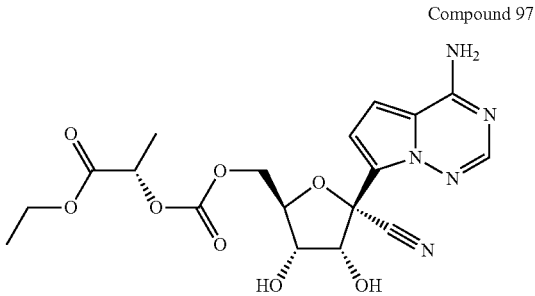 [SMILES: CCOC(=O)[C@H](C)OC(=O)OC[C@H]1O[C@@](C#N)(c2ccc3c(N)ncnn23)[C@H](O)[C@@H]1O]

Compound 97

Compound 97 was synthesized in a manner similar to Example 14: ((2R,3S,4R,5R)-5-(4-aminopyrrolo[2,1-f][1,2,4]triazin-7-yl)-5-cyano-3,4-dihydroxytetrahydrofuran-2-yl) methyl cyclooctyl carbonate (Compound 14), replacing cyclooctanol with ethyl (S)-(−)-lactate. $^1$H NMR (400 MHz, DMSO-d$_6$) δ 7.93 (s, 3H), 6.92 (d, J=4.5 Hz, 1H), 6.83 (d, J=4.5 Hz, 1H), 6.36 (d, J=5.5 Hz, 1H), 5.44 (d, J=5.7 Hz, 1H), 4.97 (q, J=7.0 Hz, 1H), 4.70 (t, J=5.2 Hz, 1H), 4.49-4.38 (m, 1H), 4.33-4.21 (m, 2H), 4.16 (qd, J=7.2, 2.9 Hz, 2H), 3.93 (q, J=5.6 Hz, 1H), 1.42 (d, J=7.0 Hz, 3H), 1.20 (t, J=7.1 Hz, 3H). LCMS: MS m/z: 436.04 (M+1).

Example 77: [(2R,3S,4R,5R)-5-(4-aminopyrrolo[2,1-f][1,2,4]triazin-7-yl)-5-cyano-3,4-dihydroxy-tetrahydrofuran-2-yl]methyl [1-methyl-1-(2-pyridyl)ethyl] carbonate (Compound 98)

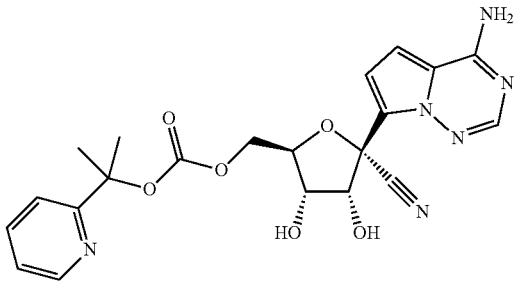

Compound 98

Compound 98 was synthesized in a manner similar to Example 23: ((2R,3S,4R,5R)-5-(4-aminopyrrolo[2,1-f][1,2,4]triazin-7-yl)-5-cyano-3,4-dihydroxytetrahydrofuran-2-yl) methyl (1-methylcyclohexyl) carbonate (Compound 47), replacing 1-methylcyclohexanol with 2-(2-pyridyl)propan-2-ol. 1H NMR (400 MHz, DMSO-d6) δ 8.52 (ddd, J=4.8, 1.8, 0.9 Hz, 1H), 8.03-7.85 (m, 3H), 7.75 (td, J=7.8, 1.9 Hz, 1H), 7.38 (dt, J=8.0, 1.0 Hz, 1H), 7.28 (ddd, J=7.6, 4.8, 1.1 Hz, 1H), 6.93 (d, J=4.6 Hz, 1H), 6.83 (d, J=4.5 Hz, 1H), 6.33 (d, J=5.9 Hz, 1H), 5.41 (d, J=5.7 Hz, 1H), 4.69 (t, J=5.4 Hz, 1H), 4.32 (dd, J=11.8, 2.8 Hz, 1H), 4.23-4.18 (m, 1H), 4.12 (dd, J=11.8, 6.0 Hz, 1H), 3.93 (q, J=5.7 Hz, 1H), 1.71 (s, 6H). LCMS: MS m/z 455.1 (M+1).

Example 78: [(2R,3S,4R,5R)-5-(4-aminopyrrolo[2,1-f][1,2,4]triazin-7-yl)-5-cyano-3,4-dihydroxy-tetrahydrofuran-2-yl]methyl [1-methyl-1-(3-pyridyl)ethyl] carbonate (Compound 99)

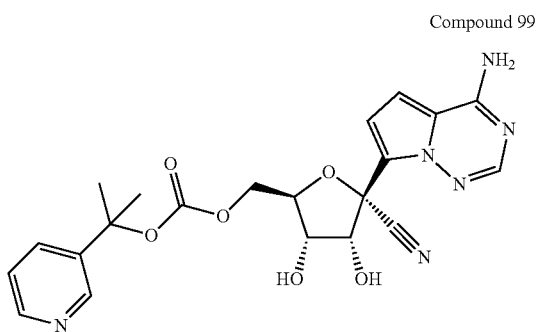 [SMILES: CC(C)(OC(=O)OC[C@H]1O[C@@](C#N)(c2ccc3c(N)ncnn23)[C@H](O)[C@@H]1O)c1cccnc1]

Compound 99

Compound 99 was synthesized in a manner similar to Example 23: ((2R,3S,4R,5R)-5-(4-aminopyrrolo[2,1-f][1,2,4]triazin-7-yl)-5-cyano-3,4-dihydroxytetrahydrofuran-2-yl)methyl (1-methylcyclohexyl) carbonate (Compound 47), replacing 1-methylcyclohexanol with 2-(3-pyridyl)propan-2-ol. 1H NMR (400 MHz, DMSO-d6) δ 8.61 (d, J=2.4 Hz, 1H), 8.55-8.46 (m, 1H), 8.03-7.82 (m, 3H), 7.80-7.65 (m, 1H), 7.35 (dd, J=8.0, 4.7 Hz, 1H), 6.93 (d, J=4.6 Hz, 1H), 6.81 (d, J=4.6 Hz, 1H), 6.32 (d, J=6.0 Hz, 1H), 5.40 (d, J=5.8 Hz, 1H), 4.78-4.62 (m, 1H), 4.32 (dd, J=11.7, 2.8 Hz, 1H), 4.24-4.17 (m, 1H), 4.13 (dd, J=11.7, 6.0 Hz, 1H), 3.92 (q, J=5.8 Hz, 1H), 1.75 (s, 6H). LCMS: MS m/z 455.1 (M+1).

Example 79: [(3aR,4R,6R,6aR)-4-(4-aminopyrrolo[2,1-f][1,2,4]triazin-7-yl)-4-cyano-2-phenyl-6,6a-dihydro-3aH-furo[3,4-d][1,3]dioxol-6-yl]methyl isopropyl carbonate (Compound 100)

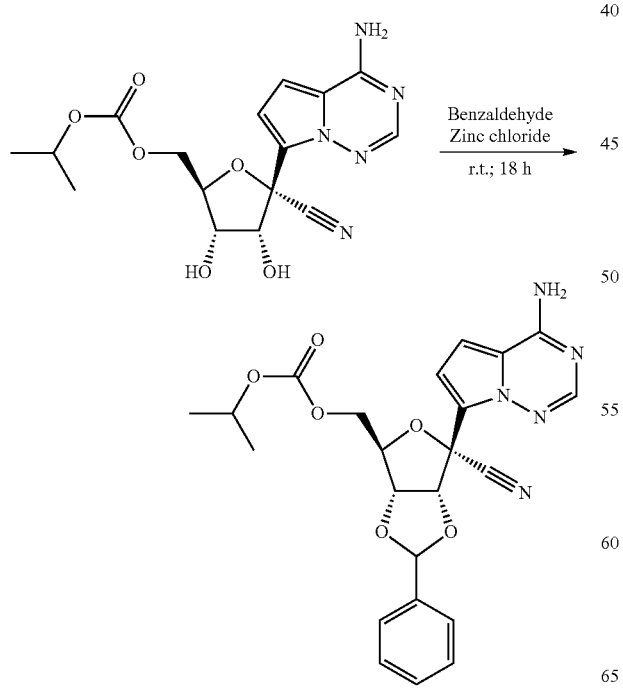

Benzaldehyde
Zinc chloride
r.t.; 18 h

To a solution of [(2R,3S,4R,5R)-5-(4-aminopyrrolo[2,1-f][1,2,4]triazin-7-yl)-5-cyano-3,4-dihydroxy-tetrahydrofuran-2-yl]methyl isopropyl carbonate Compound 4 (100 mg, 0.27 mmol) and benzaldehyde (84 mg, 0.8 mmol) in acetonitrile, Zinc chloride (36 mg, 0.27 mmol) was added and stirred at r.t for 18 h. The reaction mixture was then diluted with ethyl acetate, washed with saturated NaHCO3 and saturated brine. The organic layer was dried over Na2SO4, concentrated in vacuo and purified by column chromatography eluting with ethyl acetate in hexane (0%-50%) to give desired product Compound 100. $^1$H NMR (400 MHz, DMSO-d6) δ 7.96 (s, 3H), 7.69 (dd, J=6.8, 2.9 Hz, 2H), 7.47 (dd, J=5.0, 1.8 Hz, 3H), 6.93 (dd, J=4.6, 0.8 Hz, 1H), 6.85 (d, J=4.5 Hz, 1H), 6.11 (s, 1H), 5.55 (d, J=6.8 Hz, 1H), 5.04 (dd, J=6.8, 3.4 Hz, 1H), 4.69 (qd, J=7.4, 6.3, 4.3 Hz, 2H), 4.32 (dd, J=11.8, 4.2 Hz, 1H), 4.18 (dd, J=11.8, 62 Hz, 1H), 1.18 (dd, J=7.7, 6.3 Hz, 6H); LCMS: MS m/z: 466.2 (M+1)

Example 80: ((2R,3S,4R,5R)-5-(4-aminopyrrolo[2,1-f][1,2,4]triazin-7-yl)-5-cyano-3,4-dihydroxytetrahydrofuran-2-yl)methyl ((5-methyl-2-oxo-1,3-dioxol-4-yl)methyl) carbonate (Compound 26)

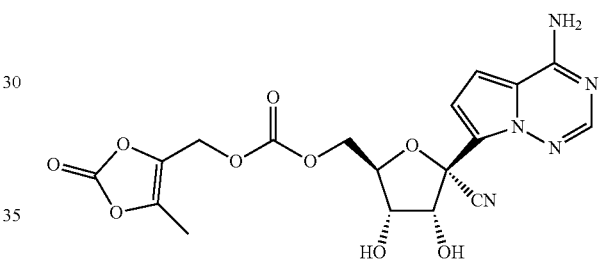

Compound 26 was synthesized in a manner similar to ((2R,3S,4R,5R)-5-(4-aminopyrrolo[2,1-f][1,2,4]triazin-7-yl)-5-cyano-3,4-dihydroxytetrahydrofuran-2-yl)methyl cyclooctyl carbonate (Compound 14) in Example 41, replacing cyclooctanol with 4-(hydroxymethyl)-5-methyl-1,3-dioxol-2-one. $^1$H NMR (400 MHz, DMSO-d$_6$) δ 7.92 (s, 3H), 6.91 (d, J=4.5 Hz, 1H), 6.79 (d, J=4.6 Hz, 1H), 6.33 (d, J=6.1 Hz, 1H), 5.43 (d, J=5.7 Hz, 1H), 5.03 (s, 2H), 4.69 (t, J=5.5 Hz, 1H), 4.48-4.39 (m, 1H), 4.33-4.21 (m, 2H), 3.95 (q, J=5.6 Hz, 1H), 2.17 (s, 3H). LCMS: MS m/z: 448.09 (M+1).

Example 81: ((2R,3S,4R,5R)-5-(4-aminopyrrolo[2,1-f][1,2,4]triazin-7-yl)-5-cyano-3,4-dihydroxy tetrahydrofuran-2-yl)methyl cyclobutyl carbonate (Compound 37)

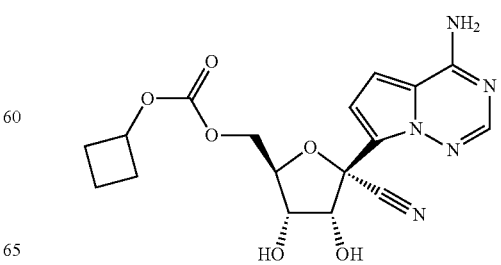

Compound 37 was synthesized in a manner similar to ((2R,3S,4R,5R)-5-(4-aminopyrrolo[2,1-f][1,2,4]triazin-7-yl)-5-cyano-3,4-dihydroxytetrahydrofuran-2-yl)methyl cyclooctyl carbonate (Compound 14) in Example 41, replacing cyclooctanol with cyclobutanol. $^1$H NMR (400 MHz, DMSO-d$_6$) δ 7.92 (s, 3H), 6.91 (d, J=4.5 Hz, 1H), 6.78 (d, J=4.6 Hz, 1H), 6.31 (d, J=6.1 Hz, 1H), 5.41 (d, J=5.7 Hz, 1H), 4.88-4.76 (m, 1H), 4.69 (dd, J=6.1, 4.9 Hz, 1H), 4.42-4.33 (m, 1H), 4.25-4.12 (m, 2H), 3.94 (q, J=5.8 Hz, 1H), 2.32-2.20 (m, 2H), 2.08-1.92 (m, 2H), 1.73 (ddddd, J=10.9, 9.9, 7.2, 2.7, 1.4 Hz, 1H), 1.62-1.47 (m, 1H). LCMS: MS m/z: 390.00 (M+1)

Example 82: ((3aR,4R,6R,6aR)-6-(4-aminopyrrolo[2,1-f][1,2,4]triazin-7-yl)-6-cyano-2-oxotetrahydrofuro[3,4-d][1,3]dioxol-4-yl)methyl methyl carbonate (Compound 127)

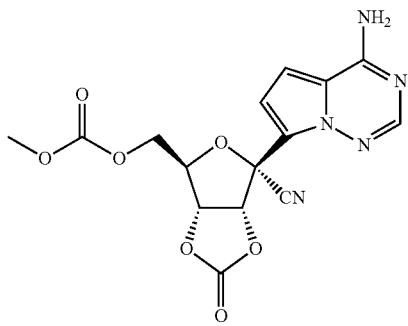 [SMILES: COC(=O)OC[C@H]1O[C@@](C#N)(c2ccc3c(N)ncnn23)[C@@H]2OC(=O)O[C@@H]21]

Compound 127 was synthesized in a manner similar to ((3aR,4R,6R,6aR)-6-(4-aminopyrrolo[2,1-f][1,2,4]triazin-7-yl)-6-cyano-2-oxotetrahydrofuro[3,4-d][1,3]dioxol-4-yl) methyl isopropyl carbonate (Compound 66) in Example 44, replacing ((2R,3S,4R,5R)-5-(4-aminopyrrolo[2,1-f][1,2,4]triazin-7-yl)-5-cyano-3,4-dihydroxytetrahydrofuran-2-yl) methyl isopropyl carbonate (Compound 4) with ((2R,3S,4R,5R)-5-(4-aminopyrrolo[2,1-f][1,2,4]triazin-7-yl)-5-cyano-3,4-dihydroxytetrahydrofuran-2-yl)methyl methyl carbonate (Compound 5). $^1$H NMR (400 MHz, DMSO-d6) δ 8.10 (br, 1H), 8.03 (br, 1H), 7.98 (s, 1H), 6.96 (d, J=4.6 Hz, 1H), 6.92 (d, J=4.6 Hz, 1H), 5.99 (d, J=7.8 Hz, 1H), 5.50 (dd, J=7.8, 4.0 Hz, 1H), 4.81 (dt, J=5.7, 4.0 Hz, 1H), 4.45 (dd, J=12.0, 3.8 Hz, 1H), 4.31 (dd, J=12.0, 5.7 Hz, 1H), 3.67 (s, 3H). LCMS: MS m/z: 376.04 (M+1).

Example 83: (2R,3R,4R,5R)-2-(4-aminopyrrolo[2,1-f][1,2,4]triazin-7-yl)-2-cyano-5-(((methoxycarbonyl)oxy)methyl)tetrahydrofuran-3,4-diyl diacetate (Compound 128)

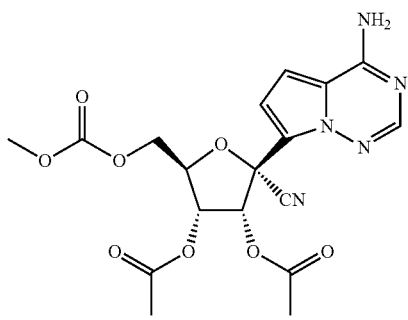 [SMILES: COC(=O)OC[C@H]1O[C@@](C#N)(c2ccc3c(N)ncnn23)[C@H](OC(C)=O)[C@@H]1OC(C)=O]

Compound 128 was synthesized in a manner similar to (2R,3R,4R,5R)-2-(4-aminopyrrolo[2,1-f][1,2,4]triazin-7-yl)-2-cyano-5-(((isopropoxycarbonyl)oxy)methyl)tetrahydrofuran-3,4-diyl diacetate (Compound 65) in Example 43, replacing ((2R,3S,4R,5R)-5-(4-aminopyrrolo[2,1-f][1,2,4]triazin-7-yl)-5-cyano-3,4-dihydroxytetrahydrofuran-2-yl) methyl isopropyl carbonate (Compound 4) with ((2R,3S,4R,5R)-5-(4-aminopyrrolo[2,1-f][1,2,4]triazin-7-yl)-5-cyano-3,4-dihydroxytetrahydrofuran-2-yl)methyl methyl carbonate (Compound 5). $^1$H NMR (400 MHz, DMSO-d6) δ 8.04 (br, 1H), 7.98 (br, 1H), 7.94 (s, 1H), 6.94 (d, J=4.6 Hz, 1H), 6.80 (d, J=4.6 Hz, 1H), 6.07 (d, J=5.9 Hz, 1H), 5.41 (dd, J=5.9, 4.5 Hz, 1H), 4.61 (td, J=4.7, 3.2 Hz, 1H), 4.47 (dd, J=12.1, 3.2 Hz, 1H), 4.34 (dd, J=12.1, 5.0 Hz, 1H), 3.68 (s, 3H), 2.13 (s, 3H), 2.12 (s, 3H). LCMS: MS m/z: 434.02 (M+1).

Example 84: (2R,3R,4R,5R)-2-(4-aminopyrrolo[2,1-f][1,2,4]triazin-7-yl)-2-cyano-5-(((ethoxycarbonyl)oxy)methyl)tetrahydrofuran-3,4-diyl diacetate (Compound 129)

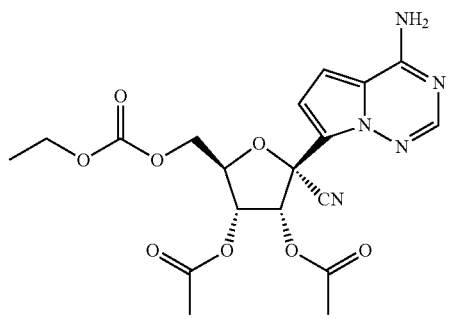 [SMILES: CCOC(=O)OC[C@H]1O[C@@](C#N)(c2ccc3c(N)ncnn23)[C@H](OC(C)=O)[C@@H]1OC(C)=O]

Compound 129 was synthesized in a manner similar to (2R,3R,4R,5R)-2-(4-aminopyrrolo[2,1-f][1,2,4]triazin-7-yl)-2-cyano-5-(((isopropoxycarbonyl)oxy)methyl)tetrahydrofuran-3,4-diyl diacetate (Compound 65) in Example 43, replacing ((2R,3S,4R,5R)-5-(4-aminopyrrolo[2,1-f][1,2,4]triazin-7-yl)-5-cyano-3,4-dihydroxytetrahydrofuran-2-yl) methyl isopropyl carbonate (Compound 4) with ((2R,3S,4R,5R)-5-(4-aminopyrrolo[2,1-f][1,2,4]triazin-7-yl)-5-cyano-3,4-dihydroxytetrahydrofuran-2-yl)methyl ethyl carbonate (Compound 6). $^1$H NMR (400 MHz, DMSO-d6) δ 7.95 (s, 3H), 6.95 (d, J=4.7 Hz, 1H), 6.81 (d, J=4.6 Hz, 1H), 6.08 (d, J=5.9 Hz, 1H), 5.41 (dd, J=6.0, 4.6 Hz, 1H), 4.61 (td, J=4.9, 3.2 Hz, 1H), 4.48 (dd, J=12.2, 3.2 Hz, 1H), 4.33 (dd, J=12.2, 5.1 Hz, 1H), 4.14-4.06 (m, 2H), 2.12 (d, J=1.5 Hz, 6H), 1.19 (t, J=7.1 Hz, 3H). LCMS: MS m/z: 447.99 (M+1).

Example 85: 8-(((2R,3S,4R,5R)-5-(4-aminopyrrolo[2,1-f][,2,4]triazin-7-yl)-5-cyano-4-hydroxy-2-(((isopropoxycarbonyl)oxy)methyl)tetrahydrofuran-3-yl)oxy)-8-oxooctanoic acid (Compound 130)

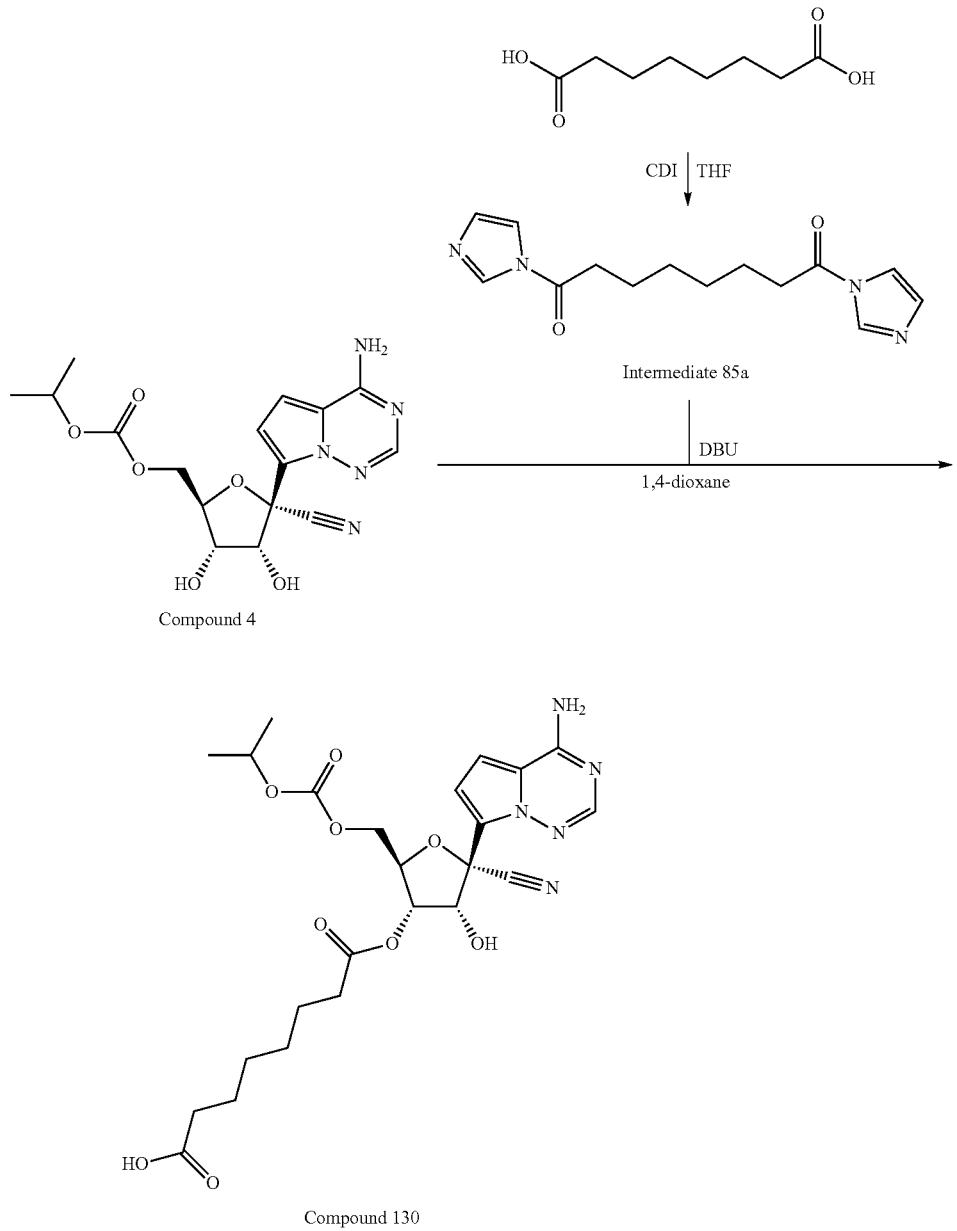

To a stirring solution of suberic acid (2.0 g, 11 mmol) in THF (30 mL) was added 1,1'-carbonyldiimidazole (5.0 g, 31 mmol) at room temperature. The reaction mixture was stirred overnight. Intermediate 85a will precipitate as white solid, which was then filtered and air dried.

To a suspension of Intermediate 85a (604 mg, 2.2 mmol) in anhydrous 1,4-dioxane (100 mL) was added (Compound 4) (755 mg, 2.0 mmol) at room temperature with intense stirring. The catalysis of 1,8-diazabicyclo[5.4.0]undec-7-ene (3 drops) was added to the reaction medium, and the mixture was reacted at 80° C. for 15-20 hours. After the completion of the reaction, the reaction mixture was diluted with ethyl acetate, washed with water, brine, dried over $MgSO_4$, and concentrated. The residue was purified by high-performance liquid chromatography using water and acetonitrile as eluants to obtain Compound 130. $^1$H NMR (400 MHz, DMSO-$d_6$) δ 11.98 (br, 1H), 7.93 (s, 3H), 6.93 (d, J=4.5 Hz, 1H), 6.84 (d, J=4.6 Hz, 1H), 5.12 (t, J=5.1 Hz, 1H), 5.04 (d, J=5.6 Hz, 1H), 4.78-4.69 (m, 1H), 4.46 (q, J=4.6 Hz, 1H), 4.39 (dd, J=12.0, 3.6 Hz, 1H), 4.26 (dd, J=11.8, 5.6 Hz, 1H), 2.38 (t, J=7.3 Hz, 2H), 2.18 (t, J=7.4 Hz, 2H), 1.58 (t, =7.4 Hz, 2H), 1.48 (q, J=7.2 Hz, 2H), 1.29 (dq, J=14.2, 8.3, 7.3 Hz, 4H), 1.21 (t, J=6.1 Hz, 6H). LCMS: MS m/z: 534.06 (M+1).

Example 86: benzyl (7-((2R,3R,4S,5R)-2-cyano-5-(((ethoxycarbonyl)oxy)methyl)-3,4-dihydroxytetrahydrofuran-2-yl)pyrrolo[2,1-f][1,2,4]triazin-4-yl)carbamate (Compound 131)

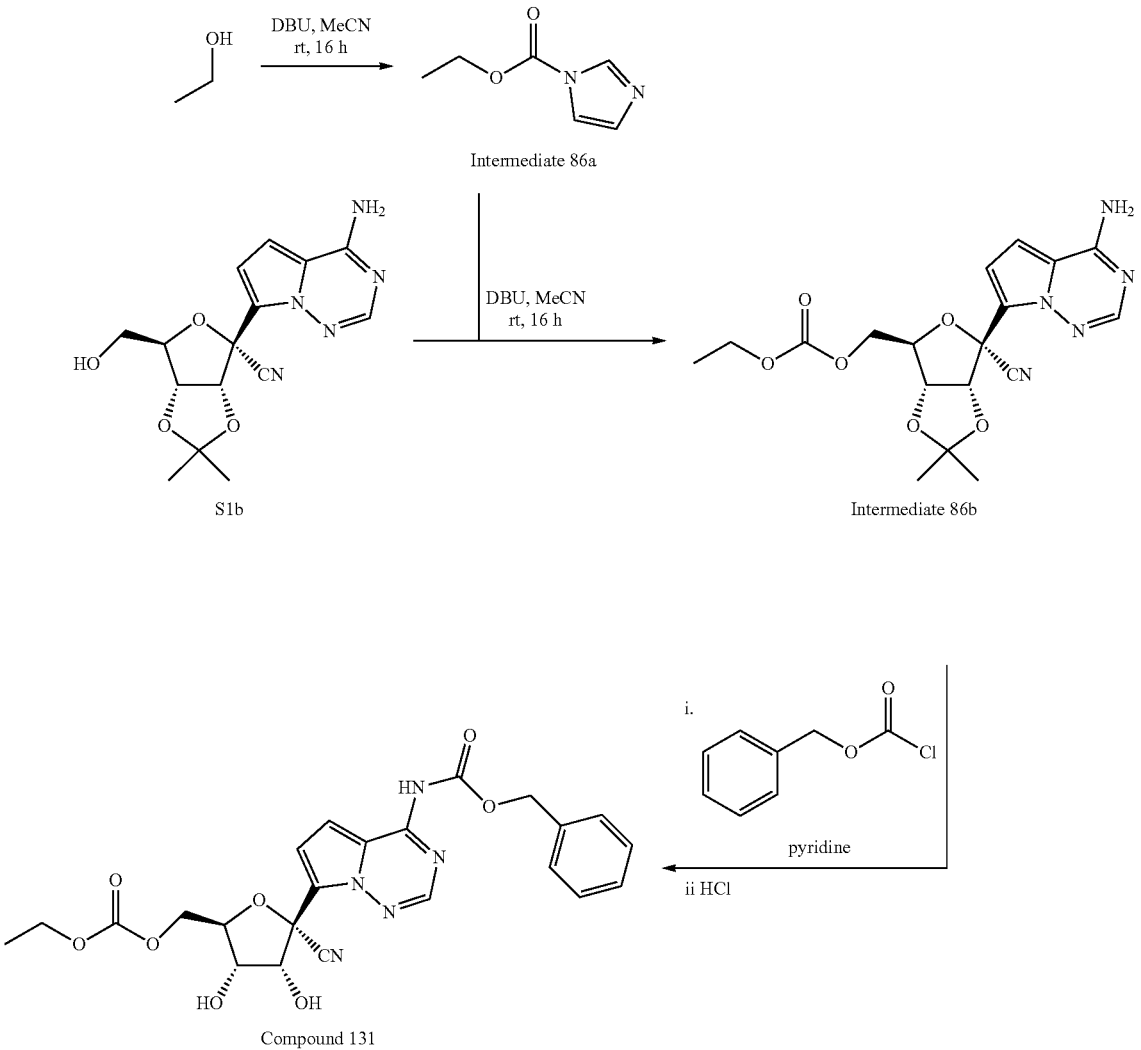

Ethanol (1.46 mL, 25 mmol) was added dropwise to a stirring solution of 1,1'-carbonyldiimidazole (6.08 g, 37.5 mmol) in DCM (80 mL) at 0° C., then warmed to room temperature and stirred for 16 h. The reaction mixture was transferred to a separatory funnel, washed with water twice, dried over MgSO$_4$, and concentrated. Intermediate 86a was used without further purification.

Intermediate 86a (1.40 g, 10.0 mmol) and S1b (3.0 g, 9.0 mmol) were dissolved in MeCN (27 mL) at room temperature, then was subsequently treated with 1,8-diazabicyclo[5.4.0]undec-7-ene (0.27 mL, 1.81 mmol). The resulting solution was stirred at room temperature for 16 h then was quenched with saturated aqueous ammonium chloride. The biphasic mixture was extracted using EtOAc three times, and the combined organic layers were dried over MgSO$_4$ and concentrated. The crude Intermediate 86b was used without further purification assuming quantitative yield.

To a solution of Intermediate 86b (4.0 g, 10 mmol) in DCM (100 mL) at 0° C. was added pyridine (2.46 mL, 30 mmol) followed by benzyl chloroformate (6.1 mL, 18 mmol). The reaction mixture was warmed at RT and stirred overnight. The reaction mixture was then washed with saturated aqueous sodium bicarbonate and the organic layer was concentrated. The crude product was then directly treated with 4N HCl in 1,4-dioxane (24 mL) at RT overnight. The resulting mixture was then basified with saturated aqueous sodium bicarbonate and extracted with EtOAc three times. The combined organic layers were dried over MgSO$_4$ then concentrated. The residue was purified by flash chromatography using dichloromethane and methanol as eluants to obtain Compound 131. $^1$H NMR (400 MHz, DMSO-d6) δ 11.04 (s, 1H), 8.39 (s, 1H), 7.51-7.46 (m, 2H), 7.46-7.36 (m, 3H), 7.32 (d, J=4.5 Hz, 1H), 7.02 (d, J=4.8 Hz, 1H), 6.43 (d, J=6.1 Hz, 1H), 5.46 (d, J=5.9 Hz, 1H), 5.27 (s, 2H), 4.67 (t, J=5.5 Hz, 1H), 4.44-4.35 (m, 1H), 4.31-4.17 (m, 2H), 4.11 (q, J=7.1 Hz, 2H), 3.94 (q, J=5.8 Hz, 1H), 1.19 (t, J=7.1 Hz, 3H). LCMS: MS m/z: 497.99 (M+1).

Example 87: ((3aR,4R,6R,6aR)-6-(4-aminopyrrolo[2,1-f][1,2,4]triazin-7-yl)-6-cyano-2-ethyltetrahydrofuro[3,4-d][1,3]dioxol-4-yl)methyl ethyl carbonate (Compound 132)

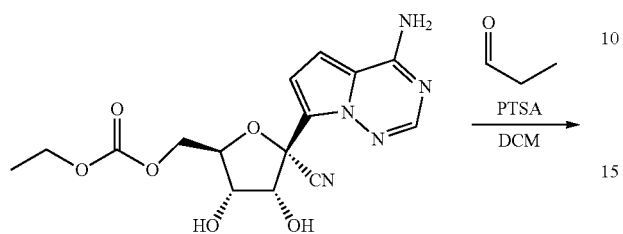

Compound 6

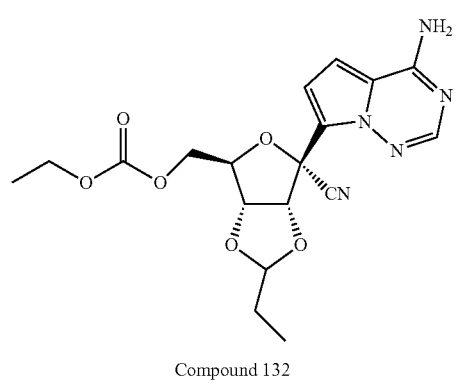

Compound 132

Propionaldehyde (1.6 mL, 22 mmol) and Compound 6 (1080 mg, 3.0 mmol) were added into DCM (30 mL). Under an ice bath, p-methylbenzenesulfonic acid (PTSA, 1131 mg, 2.0 mmol) was added to the reaction mixture and stir for 10 min. The reaction mixture was then warmed up to room temperature and was stirred overnight. The reaction solution was then poured into sat. NaHCO$_3$ solution and extracted with DCM. Ammonia ethanol solution was added to the organic layer and concentrated resulting in a crude oil. The crude oil was then dissolved in ethyl acetate and washed with brine. The organic layer was then dried and purified by flash chromatography using dichloromethane and methanol as eluants to obtain Compound 132. $^1$H NMR (400 MHz, DMSO-d6) δ 8.01 (br, 2H), 7.95 (s, 1H), 6.92 (d, J=4.6 Hz, 1H), 6.85 (d, J=4.6 Hz, 1H), 5.41 (d, J=6.5 Hz, 1H), 5.17 (t, J=4.9 Hz, 1H), 4.87 (dd, J=6.6, 3.0 Hz, 1H), 4.59 (dt, J=6.9, 3.8 Hz, 1H), 4.31 (dd, J=11.8, 4.1 Hz, 1H), 4.18 (dd, J=11.8.5.9 Hz, 1H), 4.06 (qd, J=7.1, 1.4 Hz, 2H), 1.86 (qd, J=7.5, 4.8 Hz, 2H), 1.16 (t, J=7.1 Hz, 3H), 0.99 (t, J=7.5 Hz, 3H). LCMS: MS m/z: 403.98 (M+1).

Example 88: ((3aR,4R,6R,6aR)-6-(4-aminopyrrolo[2,1-f][1,2,4]triazin-7-yl)-6-cyano-2-ethyltetrahydrofuro[3,4-d][1,3]dioxol-4-yl)methyl isopropyl carbonate (Compound 133)

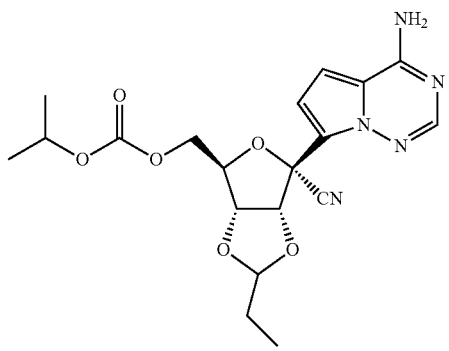

Compound 133 was synthesized in a manner similar to ((3aR,4R,6R,6aR)-6-(4-aminopyrrolo[2,1-f][1,2,4]triazin-7-yl)-6-cyano-2-ethyltetrahydrofuro[3,4-d][1,3]dioxol-4-yl)methyl ethyl carbonate (Compound 132) in Example 87, replacing ((2R,3S,4R,5R)-5-(4-aminopyrrolo[2,1-f][1,2,4]triazin-7-yl)-5-cyano-3,4-dihydroxytetrahydrofuran-2-yl)methyl ethyl carbonate (Compound 6) with ((2R,3S,4R,5R)-5-(4-aminopyrrolo[2,1-f][1,2,4]triazin-7-yl)-5-cyano-3,4-dihydroxytetrahydrofuran-2-yl)methyl isopropyl carbonate (Compound 4). $^1$H NMR (400 MHz, DMSO-d6) δ 7.96 (s, 3H), 6.92 (d, J=4.5 Hz, 1H), 6.84 (d, J=4.6 Hz, 1H), 5.40 (d, J=6.5 Hz, 1H), 5.17 (t, J=4.9 Hz, 1H), 4.87 (dd, J=6.6, 3.0 Hz, 1H), 4.69 (hept, J=6.3 Hz, 1H), 4.59 (dt, J=6.7, 3.8 Hz, 1H), 4.29 (dd, J=11.8, 4.2 Hz, 1H), 4.16 (dd, J=11.7, 6.1 Hz, 1H), 1.86 (qd, J=7.5, 4.8 Hz, 2H), 1.19 (d, J=6.2 Hz, 3H), 1.17 (d, J=6.2 Hz, 3H), 0.99 (t, J=7.5 Hz, 3H). LCMS: MS m/z: 418.02 (M+1).

Example 89: (2R,3R,4R,5R)-2-(4-aminopyrrolo[2,1-f][1,2,4]triazin-7-yl)-2-cyano-5-(((isopropoxycarbonyl)oxy)methyl)tetrahydrofuran-3,4-diyl bis(pent-4-enoate) (Compound 134)

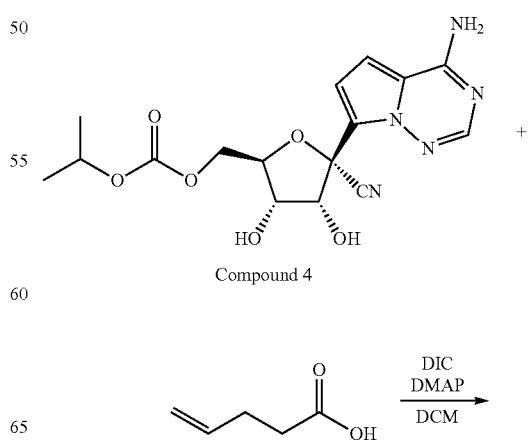

Compound 4

-continued

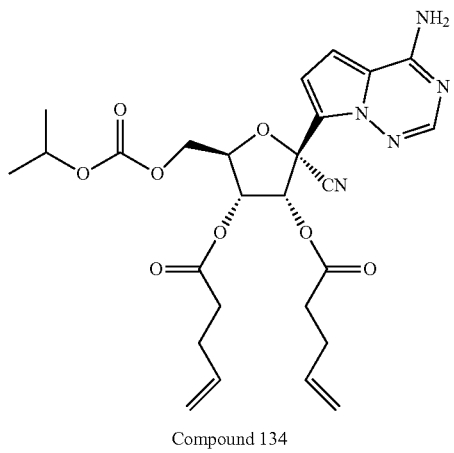

Compound 134

To a suspension of ((2R,3S,4R,5R)-5-(4-aminopyrrolo[2,1-f][1,2,4]triazin-7-yl)-5-cyano-3,4-dihydroxytetrahydrofuran-2-yl)methyl isopropyl carbonate (Compound 4) (377 mg, 1.0 mmol) in DCM (5 mL) was added 4-pentenoic acid (200 mg, 2.0 mmol), N,N'-diisopropylcarbodiimide (DIC, 252 mg, 2.0 mmol) and 4-dimethylaminopyridine (61 mg, 0.5 mmol). The reaction was stirred at room temperature overnight. The reaction solution was then poured into a sat. NaHCO₃ solution and extracted with DCM three times. The organic layers were then combined, dried, concentrated, and purified by flash chromatography using dichloromethane and ethyl acetate as eluants to obtain Compound 134. $^1$H NMR (400 MHz, DMSO-d6) δ 7.94 (s, 3H), 6.94 (d, J=4.6 Hz, 1H), 6.79 (d, J=4.6 Hz, 1H), 6.11 (d, J=5.8 Hz, 1H), 5.82 (dddt, J=25.0, 16.7, 10.3, 6.3 Hz, 2H), 5.43 (dd, J=5.9, 4.4 Hz, 1H), 5.14-4.91 (m, 4H), 4.73 (hept, J=6.3 Hz, 1H), 4.60 (q, J=4.4 Hz, 1H), 4.46 (dd, J=12.2, 3.4 Hz, 1H), 4.31 (dd, J=12.1, 5.2 Hz, 1H), 2.61-2.51 (m, 2H), 2.50-2.42 (m, 2H), 2.41-2.24 (m, 4H), 1.22-1.18 (m, 6H). LCMS: MS m/z: 542.07 (M+1).

Example 90: (2R,3R,4R,5R)-2-(4-aminopyrrolo[2,1-f][1,2,4]triazin-7-yl)-2-cyano-5-(((isopropoxycarbonyl)oxy)methyl)tetrahydrofuran-3,4-diyl dimethyl bis(carbonate) (Compound 135)

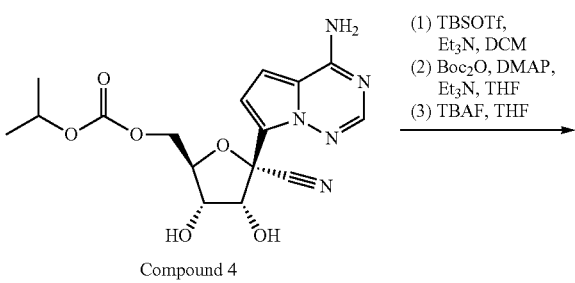

Compound 4

-continued

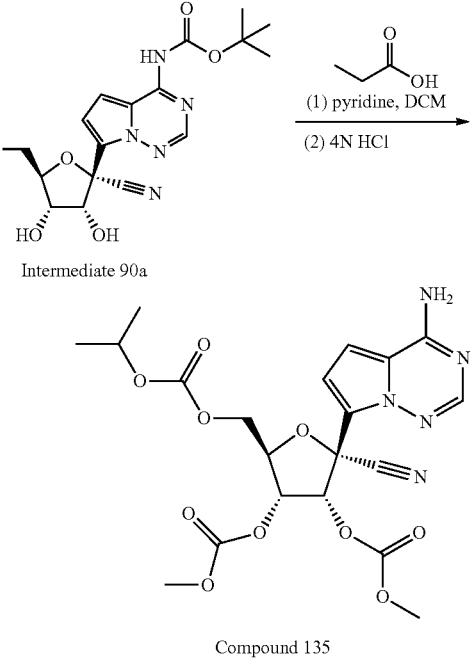

Intermediate 90a

Compound 135

To a solution of ((2R,3S,4R,5R)-5-(4-aminopyrrolo[2,1-f][1,2,4]triazin-7-yl)-5-cyano-3,4-dihydroxytetrahydrofuran-2-yl)methyl isopropyl carbonate (Compound 4) (1.1 g, 3.0 mmol) in dichloromethane (35 mL) was added triethylamine (4.2 mL, 30 mmol). The mixture was stirred for 30 minutes, after which tert-butyldimethylsilyl trifluoromethanesulfonate (4.8 mL, 21 mmol) was added. The mixture then stirred at rt for 12 hours. After the completion of the reaction, the reaction mixture was diluted with dichloromethane, washed with 4N HCl aqueous solution and brine, dried over MgSO₄, and concentrated. The crude product was then dissolved in 30 mL of THF followed by the addition of Boc anhydride (2.0 g, 9 mmol), triethylamine (2.1 mL, 15 mmol), and 4-dimethylaminopyridine (367 mg, 3 mmol). The reaction mixture was stirred at r.t for 12 hours and then was diluted with ethyl acetate, washed with water, brine, dried over MgSO₄, filtered, and concentrated. The concentrated residue was then dissolved in THF (30 mL), treated with tetra-n-butylammonium fluoride (13 mL, 1.0M in THF, 13 mmol), and stirred at r.t for 3 hours. After the completion of the reaction, the reaction mixture was concentrated to obtain Intermediate 90a. LCMS: MS m/z: 477.71 (M+1).

To a solution of Intermediate 90a (111 mg, 0.23 mmol) in dichloromethane (2 mL) was added pyridine (0.1 mL, 1.2 mmol). The mixture was then added methyl chloroformate (0.08 mL, 0.1 mmol) and stirred at room temperature for 3 h. The reaction mixture was diluted with dichloromethane, washed with water, brine, dried over MgSO₄ and concentrated. To the residue was then added 4N HCl in dioxane (1 mL, 4 mmol). The reaction mixture was stirred at room temperature overnight. The reaction mixture was diluted with ethyl acetate and neutralized with saturated sodium bicarbonate. The organic layer was separated, washed with water and brine, dried over MgSO₄, filtered, and concentrated. The resulting residue was purified by flash chromatography using dichloromethane and ethyl acetate as eluants to obtain Compound 135. $^1$H NMR (400 MHz, DMSO-d6) δ 8.08 (br, 2H), 8.00 (s, 1H), 6.95-6.93 (m, 1H) 6.89 (d, J=4.6 Hz, 1H), 6.27 (d, J=5.0 Hz, 1H), 5.38 (dd, J=6.3, 5.0

Hz, 1H), 4.84-4.77 (m, 1H), 4.63 (td, J=5.5, 3.0 Hz, 1H), 44.48 (dd, J=12.3, 3.0 Hz, 1H), 4.35-4.27 (m, 1H), 3.76 (s, 3H), 3.71 (s, 3H), 1.28-1.20 (m, 6H). LCMS: MS m/z: 493.98 (M+1).

Example 91: (2R,3R,4R,5R)-2-(4-aminopyrrolo[2,1-f][1,2,4]triazin-7-yl)-2-cyano-5-(((isopropoxycarbonyl)oxy)methyl)tetrahydrofuran-3,4-diyl di(but-3-en-1-yl) bis(carbonate) (Compound 136)

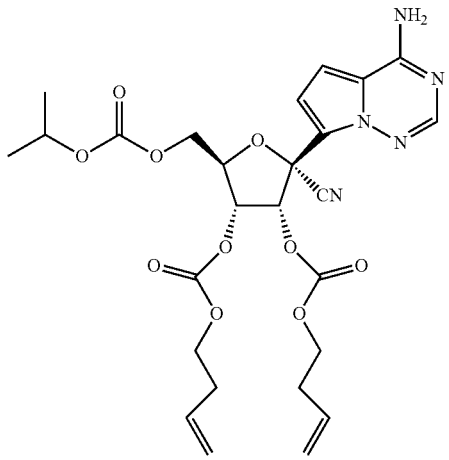 [SMILES: C=CCCOC(=O)O[C@H]1[C@@H](OC(=O)OCCC=C)[C@](C#N)(c2ccc3c(N)ncnn23)O[C@@H]1COC(=O)OC(C)C]

Compound 136 was synthesized in a manner similar to (2R,3R,4R,5R)-2-(4-aminopyrrolo[2,1-f][1,2,4]triazin-7-yl)-2-cyano-5-(((isopropoxycarbonyl)oxy)methyl)tetrahydrofuran-3,4-diyl dimethyl bis(carbonate) (Compound 135) in Example 90, replacing methyl chloroformate with 3-butenyl chloroformate. $^1$H NMR (400 MHz, DMSO-d6) δ 8.08 (br, 1H), 8.02 (br, 1H), 7.94 (s, 1H), 6.95 (d, J=4.6 Hz, 1H), 6.90-6.87 (m, 1H), 5.92 (d, J=6.7 Hz, 1H), 5.48-5.36 (m, 3H), 4.73 (p, J=6.3 Hz, 1H), 4.56-4.44 (m, 4H), 4.28 (dd, J=12.3, 5.1 Hz, 1H), 4.10 (dq, J=10.9, 5.9 Hz, 2H), 2.49-2.40 (m, 2H), 2.39-2.28 (m, 2H), 1.21 (d, J=6.2 Hz, 3H), 1.18 (d, J=6.2 Hz, 3H). LCMS: MS m/z: 546.02 (M+1).

Example 92: (2R,3R,4R,5R)-2-(4-aminopyrrolo[2,1-f][1,2,4]triazin-7-yl)-2-cyano-5-(((ethoxycarbonyl)oxy)methyl)tetrahydrofuran-3,4-diyl diethyl bis(carbonate) (Compound 106)

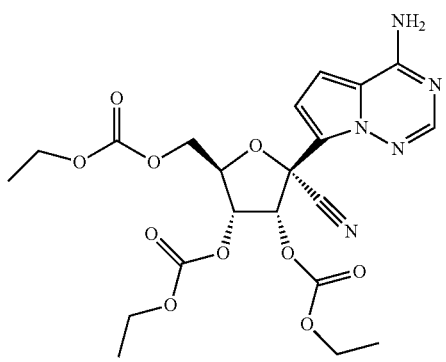 [SMILES: CCOC(=O)OC[C@H]1O[C@@](C#N)(c2ccc3c(N)ncnn23)[C@H](OC(=O)OCC)[C@@H]1OC(=O)OCC]

Compound 106 was synthesized in a manner similar to Compound 81, replacing isopropyl chloroformate with ethyl chloroformate. $^1$H NMR (400 MHz, DMSO-d6) δ 8.07 (br, 1H), 8.00 (br, 1H), 7.93 (s, 1H), 6.95 (d, J=4.6 Hz, 1H), 6.84 (d, J=4.6 Hz, 1H), 6.03 (d, J=6.0 Hz, 1H), 5.36 (dd, J=6.0, 4.5 Hz, 1H), 4.65 (td, J=4.7, 3.3 Hz, 1H), 4.49 (dd, J=12.2, 3.3 Hz, 1H), 4.35 (dd, J=12.2, 5.0 Hz, 1H), 4.18 (qd, J=7.1, 5.2 Hz, 4H), 4.10 (qd, J=7.1, 1.9 Hz, 2H), 1.26 (t, J=7.1 Hz, 3H), 1.23 (t, J=7.1 Hz, 3H), 1.19 (t, J=7.1 Hz, 3H). LCMS: MS m/z: 507.96 (M+1).

Example 93: ((2R,3S,4R,5R)-5-(4-aminopyrrolo[2,1-f][1,2,4]triazin-7-yl)-5-cyano-3,4-dihydroxytetrahydrofuran-2-yl)methyl (chloromethyl) carbonate (Compound 101)

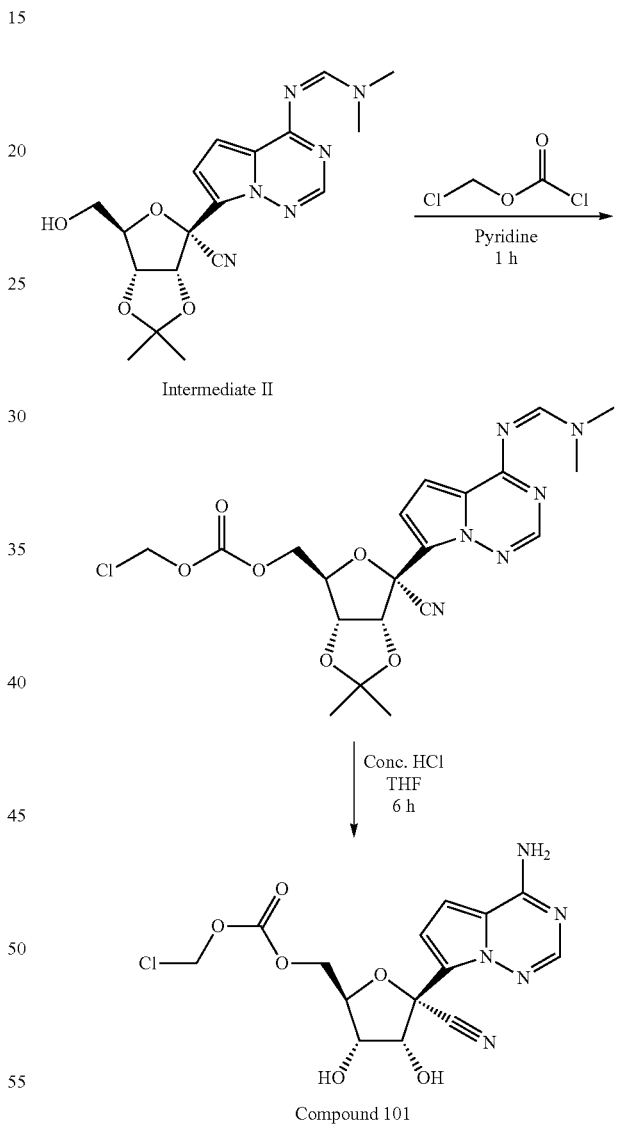

Compound 101 was synthesized in a manner similar to Compound 4 in Example 4 starting from chloromethyl chloroformate instead of isopropyl chloroformate. $^1$H NMR (400 MHz, DMSO-d6) δ 7.92 (s, 3H), 6.91 (d, J=4.5 Hz, 1H), 6.79 (d, J=4.5 Hz, 1H), 6.34 (d, J=6.1 Hz, 1H), 6.00-5.82 (m, 2H), 5.44 (s, 1H), 4.69 (t, J=4.9 Hz, 1H), 4.52 (dd, J=11.9, 2.9 Hz, 1H), 4.36 (dd, J=11.9, 5.9 Hz, 1H), 4.27 (td, J=6.2, 2.8 Hz, 1H), 3.95 (t, J=5.9 Hz, 1H). LCMS: MS m/z=384.1 (M+1).

Example 94: ((2R,3S,4R,5R)-5-(4-aminopyrrolo[2,1-f][1,2,4]triazin-7-yl)-5-cyano-3,4-dihydroxytetrahydrofuran-2-yl)methyl (((di-tert-butoxyphosphoryl)oxy)methyl) carbonate (Compound 110)

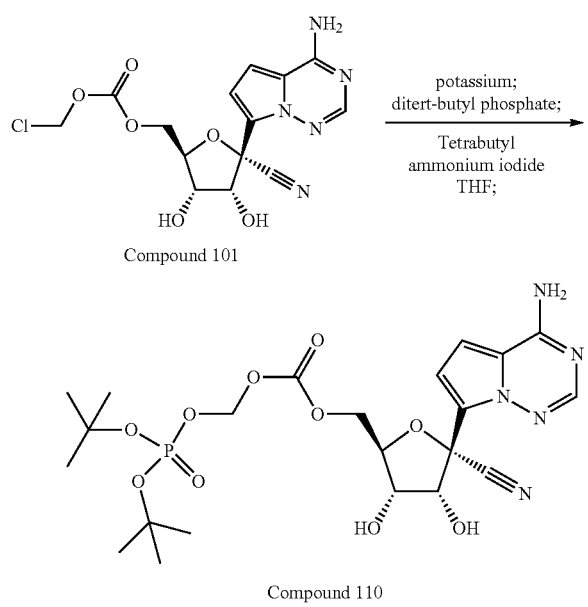

Compound 101

Compound 110

To a solution of Compound 101 (200 mg, 0.52 mmol) in THF (10 mL) tetrabutyl ammonium iodide (77 mg, 0.21 mmol) was added followed by potassium ditert-butyl phosphate (259 mg, 1 mmol) and heated at 70° C. overnight. The reaction mixture was concentrated, diluted with dichloromethane, washed with water and brine, dried, and purified by prep HPLC using acetonitrile/Water as eluents to get the title Compound 110. $^1$H NMR (400 MHz, DMSO-d6) δ 7.92 (s, 3H), 6.91 (d, J=4.5 Hz, 1H), 6.80 (d, J=4.5 Hz, 1H), 5.51 (d, J=13.6 Hz, 2H), 4.69 (t, J=5.0 Hz, 1H), 4.45 (dd, J=11.9, 2.9 Hz, 1H), 4.38-4.20 (m, 2H), 4.03-3.89 (m, 1H), 1.43-1.35 (m, 18H). LCMS: MS m/z=446.0 (M-112, deprotection).

Example 95: ((2R,3S,4R,5R)-5-(4-aminopyrrolo[2,1-f][1,2,4]triazin-7-yl)-5-cyano-3,4-dihydroxytetrahydrofuran-2-yl)methyl ((phosphonooxy)methyl) carbonate (Compound 40)

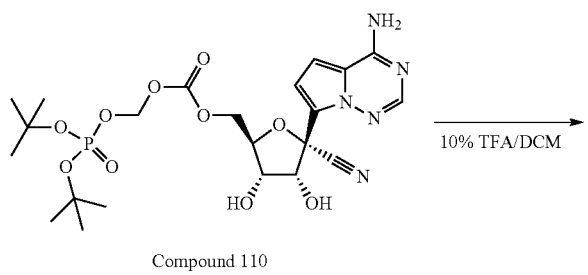

Compound 110

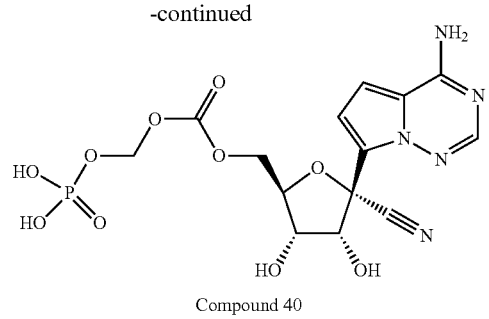

Compound 40

A solution of Compound 110 (100 mg, 0.18 mmol) in 10 mL of 10% TFA/DCM was stirred at r.t for 2 h. After completion of the starting material, the solvents were distilled off, and the residue was purified by prep HPLC using acetonitrile (0.1% TFA) and water (0.1% TFA) as eluents to get the title Compound 40 as a TFA salt. $^1$H NMR (400 MHz, DMSO-d6) δ 9.25-9.10 (m, 2H), 8.22 (dd, J=4.6, 1.4 Hz, 1H), 8.04 (d, J=4.6 Hz, 1H), 6.67 (d, J=13.6 Hz, 2H), 5.87 (d, J=5.0 Hz, 1H), 5.67-5.57 (m, 1H), 5.55-5.40 (m, 2H), 5.21-5.09 (m, 1H). LCMS: MS m/z=446.0 (M+1)

Example 96: methyl (7-((2R,3R,4R,5R)-2-cyano-3,4-bis((methoxycarbonyl)oxy)-5-((((neopentyloxy)carbonyl)oxy)methyl)tetrahydrofuran-2-yl)pyrrolo[2,1-f][1,2,4]triazin-4-yl)carbamate (Compound 103)

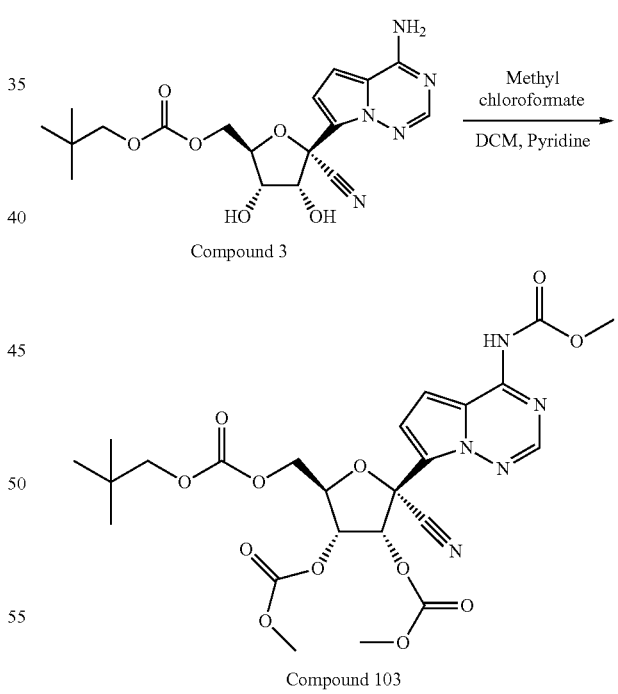

Compound 3

Compound 103

To a solution of Compound 3 (100 mg, 0.25 mmol) in dichloromethane (10 mL), methyl chloroformate (250 mg, 1.25 mml) was added followed by pyridine (0.1 mL). The resulting mixture was stirred at room temperature for 1 h. After completion of starting material, the mixture was diluted with DCM, washed with water, brine, concentrated, and purified by flash chromatography using EtOAc/DCM as eluents to get the title Compound 103. $^1$H NMR (400 MHz, DMSO-d6) δ 11.03 (s, 1H), 8.38 (s, 1H), 7.35 (d, J=4.8 Hz, 1H), 7.04 (d, J=4.8 Hz, 1H), 6.00 (d, J=5.8 Hz, 1H), 5.39 (dd, J=5.8, 4.2 Hz, 1H), 4.72 (td, J=4.6, 3.2 Hz, 1H), 4.50 (dd, J=12.2, 3.2 Hz, 1H), 4.36 (dd, J=12.2, 4.9 Hz, 1H), 3.78 (d, J=2.8 Hz, 9H), 3.75 (s, 2H), 0.86 (s, 9H). LCMS: MS m/z=522.1 (M+1).

Example 97: ((3aR,4R,6R,6aR)-6-(4-aminopyrrolo[2,1-f][1,2,4]triazin-7-yl)-6-cyano-2-methoxytetrahydrofuro[3,4-d][1,3]dioxol-4-yl)methyl isopropyl carbonate (Compound 107)

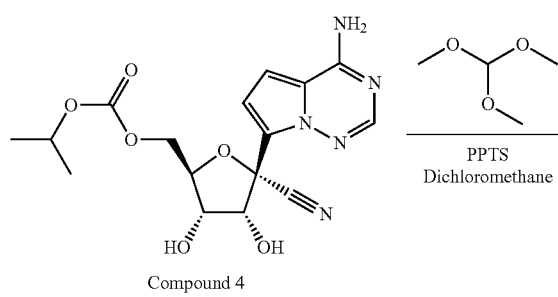

Compound 4

Example 98: ((2R,3S,4R,5R)-5-(4-aminopyrrolo[2,1-f][1,2,4]triazin-7-yl)-5-cyano-3,4-dihydroxytetrahydrofuran-2-yl)methyl (cyclopropylmethyl) carbonate (Compound 125)

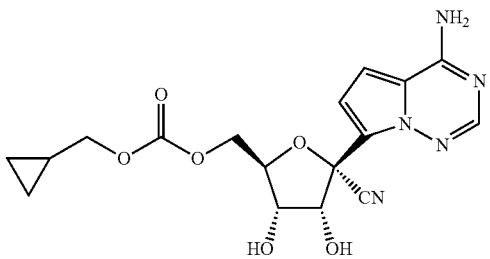 [SMILES: N#C[C@@]1(c2ccc3c(N)ncnn23)O[C@H](COC(=O)OCC2CC2)[C@@H](O)[C@H]1O]

Compound 125 was synthesized in a manner similar to ((2R,3S,4R,5R)-5-(4-aminopyrrolo[2,1-f][1,2,4]triazin-7-yl)-5-cyano-3,4-dihydroxytetrahydrofuran-2-yl)methyl cyclooctyl carbonate (Compound 14) in Example 41, replacing cyclooctanol with cyclopropylmethanol. $^1$H NMR (400 MHz, DMSO-d6) δ 7.92 (s, 3H), 6.91 (d, J=4.6 Hz, 1H), 6.79 (d, J=4.5 Hz, 1H), 6.32 (d, J=6.1 Hz, 1H), 5.41 (d, J=5.7 Hz, 1H), 4.68 (dd, J=6.1, 5.0 Hz, 1H), 4.46-4.35 (m, 1H), 4.28-4.14 (m, 2H), 3.93 (dd, J=9.9, 6.3 Hz, 3H), 1.18-1.03 (m, 1H), 0.57-0.48 (m, 2H), 0.33-0.23 (m, 2H). LCMS: MS m/z: 390.0 (M+1).

Example 99: ((2R,3S,4R,5R)-5-(4-aminopyrrolo[2,1-f][1,2,4]triazin-7-yl)-5-cyano-3,4-dihydroxytetrahydrofuran-2-yl)methyl ((1-(trifluoromethyl)cyclopropyl)methyl) carbonate (Compound 120)

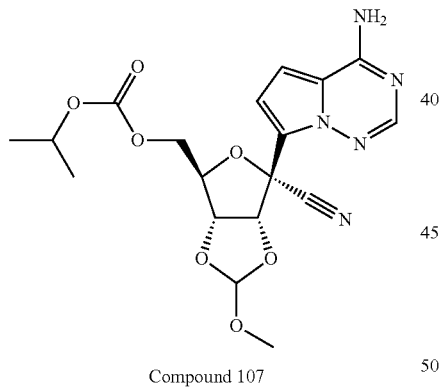

Compound 107

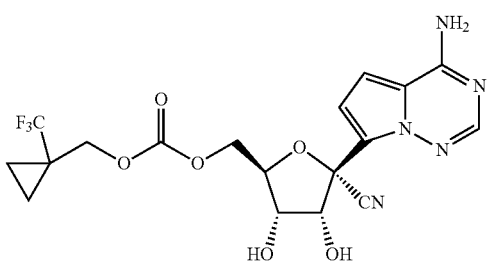 [SMILES: N#C[C@@]1(c2ccc3c(N)ncnn23)O[C@H](COC(=O)OCC2(C(F)(F)F)CC2)[C@@H](O)[C@H]1O]

To a solution of Compound 4 (100 mg, 0.27 mmol) in dichloromethane (10 mL), trimethyl orthoformate (84 mg, 0.87 mmol) was added followed by PPTS (67 mg, 0.27 mmol), and the reaction mixture was stirred at room temperature overnight. The reaction mixture was diluted with dichloromethane, washed with bicarbonate, water, and brine, dried, and purified by flash chromatography using ethyl acetate and dichloromethane as eluents. $^1$H NMR (400 MHz, DMSO-d6) δ 7.95 (s, 4H), 6.91 (d, J=4.5 Hz, 1H), 6.79 (d, J=4.5 Hz, 1H), 6.15 (s, 1H), 5.40 (d, J=6.9 Hz, 1H), 5.04 (dd, J=7.0,4.8 Hz, 1H), 4.72 (p, J=6.3 Hz, 1H), 4.65 (dt, J=6.9, 4.5 Hz, 1H), 4.29 (dd, J=11.8, 4.4 Hz, 1H), 4.11 (dd, J=11.8, 6.9 Hz, 1H), 3.43 (s, 3H), 1.20 (dd, J=6.2, 2.4 Hz, 6H). LCMS: MS m/z=420.1 (M+1)

Compound 120 was synthesized in a manner similar to ((2R,3S,4R,5R)-5-(4-aminopyrrolo[2,1-f][1,2,4]triazin-7-yl)-5-cyano-3,4-dihydroxytetrahydrofuran-2-yl)methyl cyclooctyl carbonate (Compound 14) in Example 41, replacing cyclooctanol with (1-(trifluoromethyl)cyclopropyl) methanol. $^1$H NMR (400 MHz, DMSO-d6) δ 7.92 (s, 3H), 6.90 (d, J=4.5 Hz, 1H), 6.79 (d, J=4.6 Hz, 1H), 6.34 (d, J=6.0 Hz, 1H), 5.42 (d, J=5.8 Hz, 1H), 4.67 (dd, J=6.0, 4.9 Hz, 1H), 4.48-4.39 (m, 1H), 4.31-4.20 (m, 4H), 3.93 (q, J=5.7 Hz, 1H), 1.10-1.04 (m, 2H), 1.04-0.96 (m, 2H). 19F NMR (376 MHz, DMSO-d6) S -68.66. LCMS: MS m/z: 457.90 (M+1).

Example 100. ((2R,3S,4R,5R)-5-(4-aminopyrrolo[2,1-f][1,2,4]triazin-7-yl)-5-cyano-3,4-dihydroxytetrahydrofuran-2-yl)methyl ((3-cyanobicyclo[1.1.1]pentan-1-yl)methyl) carbonate (Compound 121)

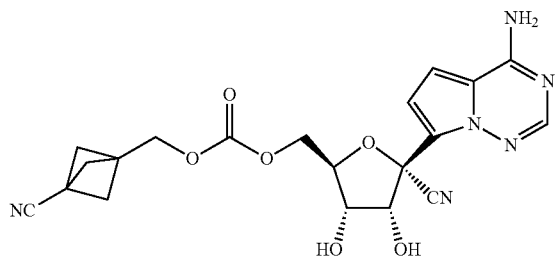 [SMILES: N#CC12CC(COC(=O)OC[C@H]3O[C@@](C#N)(c4ccc5c(N)ncnn45)[C@H](O)[C@@H]3O)(C1)C2]

Compound 121 was synthesized in a manner similar to ((2R,3S,4R,5R)-5-(4-aminopyrrolo[2,1-f][1,2,4]triazin-7-yl)-5-cyano-3,4-dihydroxytetrahydrofuran-2-yl)methyl cyclooctyl carbonate (Compound 14) in Example 41, replacing cyclooctanol with 3-(hydroxymethyl)bicyclo[1.1.1]pentane-1-carbonitrile. $^1$H NMR (400 MHz, DMSO-$d_6$) δ 7.93 (s, 3H), 6.92 (d, J=4.6 Hz, 1H), 6.80 (d, J=4.5 Hz, 1H), 6.34 (s, 1H), 5.42 (s, 1H), 4.73-4.64 (m, 1H), 4.47-4.34 (m, 1H), 4.29-4.15 (m, 2H), 4.08 (s, 2H), 3.93 (t, J=5.5 Hz, 1H), 2.20 (s, 6H). MS m/z: 440.97 (M+1)

Example 101: ((2R,3S,4R,5R)-5-(4-aminopyrrolo[2,1-f][1,2,4]triazin-7-yl)-5-cyano-3,4-dihydroxytetrahydrofuran-2-yl)methyl (4-methoxyphenethyl) carbonate (Compound 112)

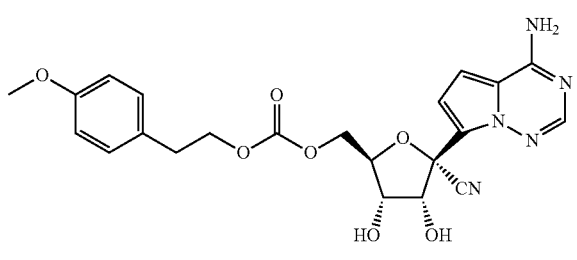 [SMILES: COc1ccc(CCOC(=O)OC[C@H]2O[C@@](C#N)(c3ccc4c(N)ncnn34)[C@H](O)[C@@H]2O)cc1]

Compound 112 was synthesized in a manner similar to ((2R,3S,4R,5R)-5-(4-aminopyrrolo[2,1-f][1,2,4]triazin-7-yl)-5-cyano-3,4-dihydroxytetrahydrofuran-2-yl)methyl cyclooctyl carbonate (Compound 14) in Example 41, replacing cyclooctanol with 2-(4-methoxyphenyl)ethan-1-ol. $^1$H NMR (400 MHz, DMSO-$d_6$) δ 7.93 (s, 3H), 7.56-7.03 (m, 2H), 6.93 (d, J=4.5 Hz, 1H), 6.89-6.83 (m, 2H), 6.80 (d, J=4.5 Hz, 1H), 6.33 (d, J=6.1 Hz, 1H), 5.42 (d, J=5.8 Hz, 1H), 4.69 (dd, J=6.1, 4.9 Hz, 1H), 4.38 (dd, J=9.8, 4.4 Hz, 1H), 4.23 (td, J=6.0, 5.0, 3.5 Hz, 4H), 3.93 (q, J=5.8 Hz, 1H), 3.72 (s, 3H), 2.85 (t, J=6.8 Hz, 2H). LCMS: MS m/z: 470.04 (M+1).

Example 102: ((2R,3S,4R,5R)-5-(4-aminopyrrolo[2,1-f][1,2,4]triazin-7-yl)-5-cyano-3,4-dihydroxytetrahydrofuran-2-yl)methyl ((1-methylcyclopropyl)methyl) carbonate (Compound 114)

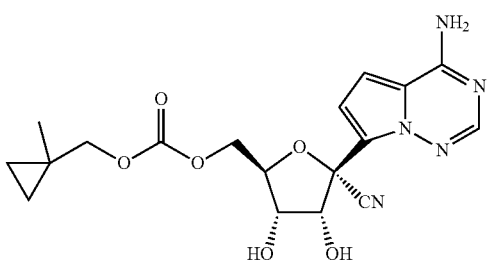 [SMILES: CC1(COC(=O)OC[C@H]2O[C@@](C#N)(c3ccc4c(N)ncnn34)[C@H](O)[C@@H]2O)CC1]

Compound 114 was synthesized in a manner similar to ((2R,3S,4R,5R)-5-(4-aminopyrrolo[2,1-f][1,2,4]triazin-7-yl)-5-cyano-3,4-dihydroxytetrahydrofuran-2-yl)methyl cyclooctyl carbonate (Compound 14) in Example 41, replacing cyclooctanol with (1-methylcyclopropyl)methanol. $^1$H NMR (400 MHz, DMSO-$d_6$) δ 7.93 (s, 3H), 6.92 (d, J=4.6 Hz, 1H), 6.80 (d, J=4.5 Hz, 1H), 6.34 (d, J=6.0 Hz, 1H), 5.42 (d, J=5.8 Hz, 1H), 4.69 (dd, J=6.0, 4.9 Hz, 1H), 4.48-4.37 (m, 1H), 4.29-4.15 (m, 2H), 3.87-3.97 (m, 3H), 1.08 (s, 3H), 0.55-0.43 (m, 2H), 0.43-0.26 (m, 2H). LCMS: MS m/z: 403.97 (M+1).

Example 103: ((2R,3S,4R,5R)-5-(4-aminopyrrolo[2,1-f][1,2,4]triazin-7-yl)-5-cyano-3,4-dihydroxytetrahydrofuran-2-yl)methyl ((3,3-difluorocyclobutyl)methyl) carbonate (Compound 115)

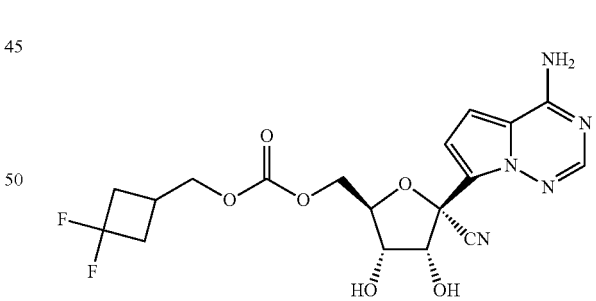

Compound 115 was synthesized in a manner similar to ((2R,3S,4R,5R)-5-(4-aminopyrrolo[2,1-f][1,2,4]triazin-7-yl)-5-cyano-3,4-dihydroxytetrahydrofuran-2-yl)methyl cyclooctyl carbonate (Compound 14) in Example 41, replacing cyclooctanol with (3,3-difluorocyclobutyl)methanol. $^1$H NMR (400 MHz, DMSO-$d_6$) δ 7.93 (s, 3H), 6.91 (d, J=4.5 Hz, 1H), 6.80 (d, J=4.5 Hz, 1H), 6.34 (d, J=6.1 Hz, 1H), 5.42 (d, J=5.8 Hz, 1H), 4.69 (dd, J=6.1, 4.9 Hz, 1H), 4.48-4.38 (m, 1H), 4.29-4.19 (m, 2H), 4.15 (d, J=6.2 Hz, 2H), 3.95 (q, J=5.6 Hz, 1H), 2.73-2.60 (m, 2H), 2.49-2.32 (m, 3H). LCMS: MS m/z: 440.06 (M+1).

Example 104: ((2R,3S,4R,5R)-5-(4-aminopyrrolo[2,1-f][1,2,4]triazin-7-yl)-5-cyano-3,4-dihydroxytetrahydrofuran-2-yl)methyl ((1-phenylcyclopropyl)methyl) carbonate (Compound 116)

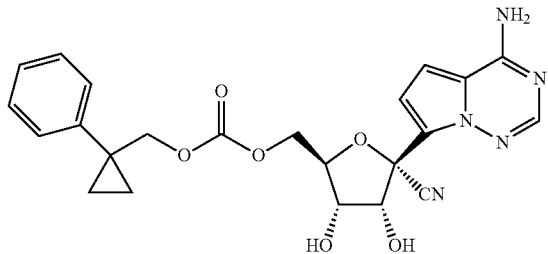 [SMILES: N#C[C@@]1(c2ccc3c(N)ncnn23)O[C@H](COC(=O)OCC2(c3ccccc3)CC2)[C@@H](O)[C@H]1O]

Compound 116 was synthesized in a manner similar to ((2R,3S,4R,5R)-5-(4-aminopyrrolo[2,1-f][1,2,4]triazin-7-yl)-5-cyano-3,4-dihydroxytetrahydrofuran-2-yl)methyl cyclooctyl carbonate (Compound 14) in Example 41, replacing cyclooctanol with (1-phenylcyclopropyl)methanol. $^1$H NMR (400 MHz, DMSO-$d_6$) δ 7.92 (s, 3H), 7.30 (d, J=4.3 Hz, 4H), 7.20 (dt, J=8.6, 4.1 Hz, 1H), 6.92 (d, J=4.6 Hz, 1H), 6.78 (d, J=4.5 Hz, 1H), 6.32 (d, J=6.0 Hz, 1H), 5.40 (d, J=5.8 Hz, 1H), 4.67 (dd, J=6.1, 4.9 Hz, 1H), 4.42-4.31 (m, 1H), 4.26-4.14 (m, 4H), 3.91 (q. J=5.7 Hz, 1H), 1.03-0.94 (m, 2H), 0.94-0.83 (m, 2H). LCMS: MS m/z: 466.01 (M+1).

Example 105. ((2R,3S,4R,5R)-5-(4-aminopyrrolo[2,1-f][1,2,4]triazin-7-yl)-5-cyano-3,4-dihydroxytetrahydrofuran-2-yl)methyl ((3,3-dimethylcyclobutyl)methyl) carbonate (Compound 117)

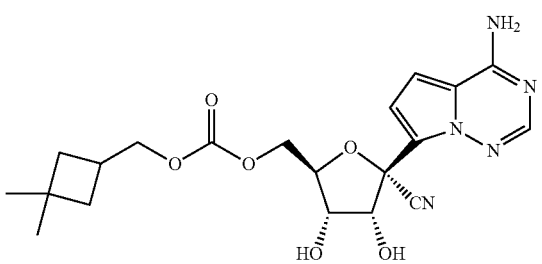 [SMILES: CC1(C)CC(COC(=O)OC[C@H]2O[C@@](C#N)(c3ccc4c(N)ncnn34)[C@H](O)[C@@H]2O)C1]

Compound 117 was synthesized in a manner similar to ((2R,3S,4R,5R)-5-(4-aminopyrrolo[2,1-f][1,2,4]triazin-7-yl)-5-cyano-3,4-dihydroxytetrahydrofuran-2-yl)methyl cyclooctyl carbonate (Compound 14) in Example 41, replacing cyclooctanol with (3,3-dimethylcyclobutyl)methanol. $^1$H NMR (400 MHz, DMSO-$d_6$) δ 7.93 (s, 3H), 6.91 (d, J=4.6 Hz, 1H), 6.79 (d, J=4.6 Hz, 1H), 6.33 (d, J=6.1 Hz, 1H), 5.41 (d, J=5.8 Hz, 1H), 4.68 (dd, J=6.1, 4.9 Hz, 1H), 4.46-4.35 (m, 1H), 4.28-4.18 (m, 2H), 4.04 (d, J=6.7 Hz, 2H), 3.94 (q, J=5.8 Hz, 1H), 2.50-2.44 (m, 1H), 1.82-1.71 (m, 2H), 1.57-1.52 (m, 2H), 1.12 (s, 3H), 1.04 (s, 3H). LCMS: MS m/z: 432.02 (M+1).

Example 106: ((2R,3S,4R,5R)-5-(4-aminopyrrolo[2,1-f][1,2,4]triazin-7-yl)-5-cyano-3,4-dihydroxytetrahydrofuran-2-yl)methyl ((1-cyanocyclopropyl)methyl) carbonate (Compound 118)

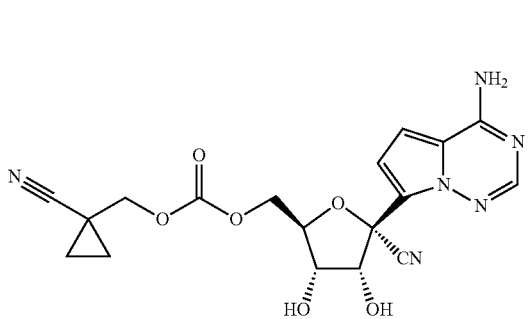

Compound 118 was synthesized in a manner similar to ((2R,3S,4R,5R)-5-(4-aminopyrrolo[2,1-f][1,2,4]triazin-7-yl)-5-cyano-3,4-dihydroxytetrahydrofuran-2-yl)methyl cyclooctyl carbonate (Compound 14) in Example 41, replacing cyclooctanol with 1-(hydroxymethyl)cyclopropane-1-carbonitrile. $^1$H NMR (400 MHz, DMSO-$d_6$) δ 7.93 (s, 3H), 6.92 (d, J=4.5 Hz, 1H), 6.81 (d, J=4.5 Hz, 1H), 6.34 (d, J=6.1 Hz, 1H), 5.44 (d, J=5.7 Hz, 1H), 4.71 (dd, J=6.1, 4.9 Hz, 1H), 4.45 (dd, J=9.6, 5.1 Hz, 1H), 4.31-4.24 (m, 2H), 4.15 (s, 2H), 3.97 (q, J=5.6 Hz, 1H), 1.39-1.32 (m, 2H), 1.22-1.13 (m, 2H). LCMS: MS m/z: 415.11 (M+1).

Example 107: ((2R,3S,4R,5R)-5-(4-aminopyrrolo[2,1-f][1,2,4]triazin-7-yl)-5-cyano-3,4-dihydroxytetrahydrofuran-2-yl)methyl ((1-(cyanomethyl)cyclopropyl)methyl) carbonate (Compound 119)

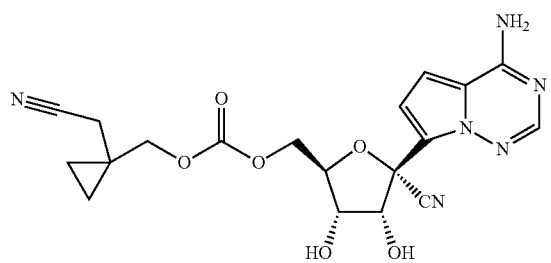 [SMILES: N#CCC1(COC(=O)OC[C@H]2O[C@@](C#N)(c3ccc4c(N)ncnn34)[C@H](O)[C@@H]2O)CC1]

Compound 119 was synthesized in a manner similar to ((2R,3S,4R,5R)-5-(4-aminopyrrolo[2,1-f][1,2,4]triazin-7-yl)-5-cyano-3,4-dihydroxytetrahydrofuran-2-yl)methyl cyclooctyl carbonate (Compound 14) in Example 41, replacing cyclooctanol with 2-(1-(hydroxymethyl)cyclopropyl)acetonitrile. $^1$H NMR (400 MHz, DMSO-$d_6$) δ 7.93 (s, 3H), 6.92 (d, J=4.5 Hz, 1H), 6.81 (d, J=4.5 Hz, 1H), 6.34 (d, J=6.1 Hz, 1H), 5.43 (d, J=5.8 Hz, 1H), 4.69 (dd, J=6.1, 4.9 Hz, 1H), 4.47-4.39 (m, 1H), 4.29-4.21 (m, 2H), 4.04 (s, 2H), 3.95 (q, J=5.6 Hz, 1H), 2.68 (s, 2H), 0.73-0.66 (m, 2H), 0.66-0.59 (m, 2H). LCMS: MS m/z: 429.15 (M+1).

Example 108: ((2R,3S,4R,5R)-5-(4-aminopyrrolo[2,1-f][1,2,4]triazin-7-yl)-5-cyano-3,4-dihydroxytetrahydrofuran-2-yl)methyl ((1-methylcyclobutyl)methyl) carbonate (Compound 122)

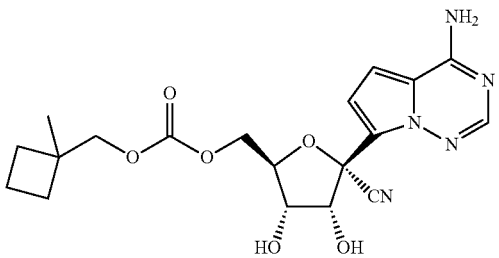 [SMILES: CC1(COC(=O)OC[C@H]2O[C@@](C#N)(c3ccc4c(N)ncnn34)[C@H](O)[C@@H]2O)CCC1]

Compound 122 was synthesized in a manner similar to ((2R,3S,4R,5R)-5-(4-aminopyrrolo[2,1-f][1,2,4]triazin-7-yl)-5-cyano-3,4-dihydroxytetrahydrofuran-2-yl)methyl cyclooctyl carbonate (Compound 14) in Example 41, replacing cyclooctanol with (1-methylcyclobutyl)methanol. $^1$H NMR (400 MHz, DMSO-$d_6$) δ 7.93 (s, 3H), 6.91 (d, J=4.5 Hz, 1H), 6.80 (d, J=4.5 Hz, 1H), 6.35 (d, J=6.0 Hz, 1H), 5.42 (d, J=5.8 Hz, 1H), 4.67 (dd, J=6.0, 4.9 Hz, 1H), 4.49-4.39 (m, 1H), 4.29-4.18 (m, 2H), 4.03-3.90 (m, 3H), 1.94-1.76 (m, 4H), 1.72-1.60 (m, 2H), 1.11 (s, 3H). LCMS: MS m/z: 418.04 (M+1).

Example 109: ((2R,3S,4R,5R)-5-(4-aminopyrrolo[2,1-f][1,2,4]triazin-7-yl)-5-cyano-3,4-dihydroxytetrahydrofuran-2-yl)methyl ((1-methylcyclopentyl)methyl) carbonate (Compound 123)

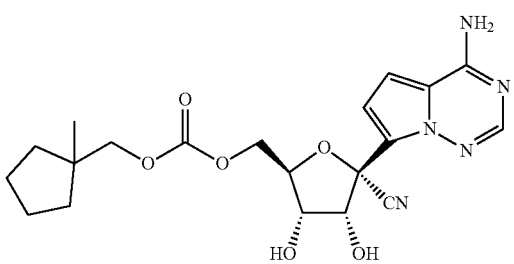 [SMILES: CC1(COC(=O)OC[C@H]2O[C@@](C#N)(c3ccc4c(N)ncnn34)[C@H](O)[C@@H]2O)CCCC1]

Compound 123 was synthesized in a manner similar to ((2R,3S,4R,5R)-5-(4-aminopyrrolo[2,1-f][1,2,4]triazin-7-yl)-5-cyano-3,4-dihydroxytetrahydrofuran-2-yl)methyl cyclooctyl carbonate (Compound 14) in Example 41, replacing cyclooctanol with (1-methylcyclopentyl)methanol. $^1$H NMR (400 MHz, DMSO-$d_6$) δ 7.93 (s, 3H), 6.91 (d, J=4.5 Hz, 1H), 6.80 (d, J=4.5 Hz, 1H), 6.35 (d, J=6.0 Hz, 1H), 5.41 (d, J=5.8 Hz, 1H), 4.70-4.63 (m, 1H), 4.49-4.39 (m, 1H), 4.29-4.18 (m, 2H), 4.00-3.84 (m, 3H), 1.63-1.56 (m, 4H), 1.51-1.44 (m, 2H), 1.32-1.24 (m, 2H), 0.98 (s, 3H). LCMS: MS m/z: 432.06 (M+1).

Example 110: isopropyl (7-((2R,3R,4S,5R)-2-cyano-3,4-dihydroxy-5-(((isopropoxycarbonyl)oxy)methyl)tetrahydrofuran-2-yl)pyrrolo[2,1-f][1,2,4]triazin-4-yl)carbamate (Compound 137)

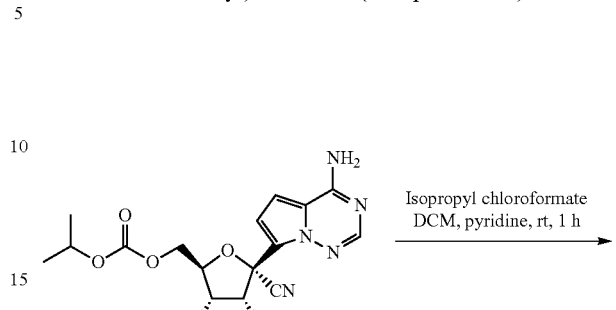

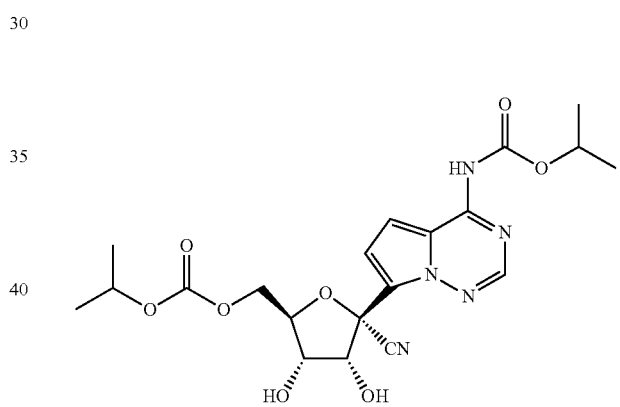

To a solution of ((2R,3S,4R,5R)-5-(4-aminopyrrolo[2,1-f][1,2,4]triazin-7-yl)-5-cyano-3,4-dihydroxytetrahydrofuran-2-yl)methyl isopropyl carbonate (Compound 4) (1300 mg, 3.4 mmol) in dichloromethane (10 mL) was added pyridine (0.4 mL, 5.0 mmol). To the mixture was added isopropyl chloroformate (3.4 mL, 1.0 M in toluene, 3.4 mmol). The mixture stirred at room temperature for 1 h. The reaction mixture was diluted with dichloromethane, washed with water and brine, dried over MgSO$_4$, and concentrated. The residue was purified by flash chromatography using dichloromethane and ethyl acetate as eluants to obtain Compound 137. $^1$H NMR (400 MHz, DMSO-d6) δ 10.85 (s, 1H), 8.36 (s, 1H), 7.42-7.20 (m, 1H), 7.00 (d, J=4.7 Hz, 1H), 6.43 (d, J=6.1 Hz, 1H), 5.46 (d, J=5.8 Hz, 1H), 5.00-4.97 (m, 1H), 4.78-4.72 (m, 1H), 4.67 (dd, J=6.0, 4.9 Hz, 1H), 4.42 (dd, J=11.8, 2.6 Hz, 1H), 4.27 (td, J=6.2, 2.6 Hz, 1H), 4.21 (dd, J=11.7, 5.8 Hz, 1H), 3.95 (q, J=5.8 Hz, 1H), 1.32-1.21 (m, 12H). LCMS: MS m/z: 464.02 (M+1).

Example 111: tert-butyl 2-[[(2R,3S,4R,5R)-5-(4-aminopyrrolo[2,1-f][1,2,4]triazin-7-yl)-5-cyano-3,4-dihydroxy-tetrahydrofuran-2-yl]methoxycarbonyloxy]-2-methyl-propanoate (Compound 138)

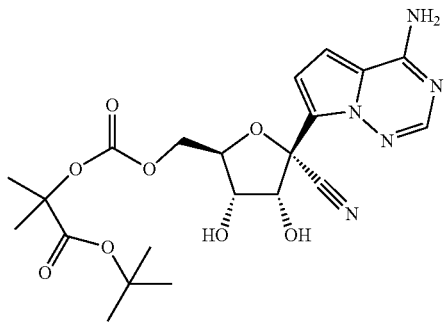 [SMILES: CC(C)(C)OC(=O)C(C)(C)OC(=O)OC[C@H]1O[C@@](C#N)(c2ccc3c(N)ncnn23)[C@H](O)[C@@H]1O]

Compound 138 was synthesized in a manner similar to ((2R,3S,4R,5R)-5-(4-aminopyrrolo[2,1-f][1,2,4]triazin-7-yl)-5-cyano-3,4-dihydroxytetrahydrofuran-2-yl)methyl (1-methylcyclohexyl) carbonate (Compound 47) in Example 23, replacing 1-methylcyclohexanol with tert-butyl 2-hydroxy-2-methyl-propanoate and purifying by flash column chromatography using C18 column, and water and acetonitrile with 0.1% trifluoroacetic acid. $^1$H NMR (400 MHz, DMSO-d6) δ 8.81-8.30 (m, 2H), 8.06 (s, 1H), 7.14-7.02 (m, 1H), 6.96-6.83 (m, 1H), 4.73-4.61 (m, 1H), 4.48-4.34 (m, 1H), 4.34-4.19 (m, 2H), 4.00-3.82 (m, 1H), 3.45-3.28 (m, 1H), 1.55-1.29 (m, 15H). LCMS: MS m/z: 478.1 (M+1).

Example 112. (2R,3S,4R,5R)-5-(4-aminopyrrolo[2,1-f][1,2,4]triazin-7-yl)-5-cyano-3,4-dihydroxy-tetrahydrofuran-2-yl]methyl [3-(trifluoromethyl)-1-bicyclo[1.1.1]pentanyl] carbonate (Compound 139)

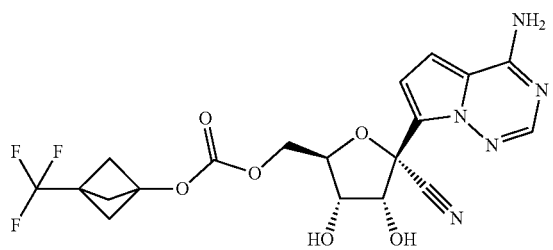 [SMILES: N#C[C@@]1(c2ccc3c(N)ncnn23)O[C@H](COC(=O)OC23CC(C(F)(F)F)(C2)C3)[C@@H](O)[C@H]1O]

Compound 139 was synthesized in a manner similar to ((2R,3S,4R,5R)-5-(4-aminopyrrolo[2,1-f][1,2,4]triazin-7-yl)-5-cyano-3,4-dihydroxytetrahydrofuran-2-yl)methyl (1-methylcyclohexyl) carbonate (Compound 47) in Example 23, replacing 1-methylcyclohexanol with 3-(trifluoromethyl)bicyclo[1.1.1]pentan-1-ol and purifying by flash column chromatography using dichloromethane and methanol as eluents. $^1$H NMR (400 MHz, DMSO-d6) δ 8.01-7.78 (m, 3H), 6.92 (d, J=4.5 Hz, 1H), 6.78 (d, J=4.5 Hz, 1H), 6.34 (d, J=6.1 Hz, 1H), 5.43 (d, J=5.7 Hz, 1H), 4.73-4.66 (m, 1H), 4.50-4.40 (m, 1H), 4.29-4.21 (m, 2H), 3.96 (q, J=5.5 Hz, 1H), 2.41 (s, 6H). LCMS: MS m/z: 470.0 (M+1).

Example 113: ((2R,3S,4R,5R)-5-(4-aminopyrrolo[2,1-f][1,2,4]triazin-7-yl)-5-cyano-3,4-dihydroxytetrahydrofuran-2-yl)methyl decyl carbonate (Compound 124)

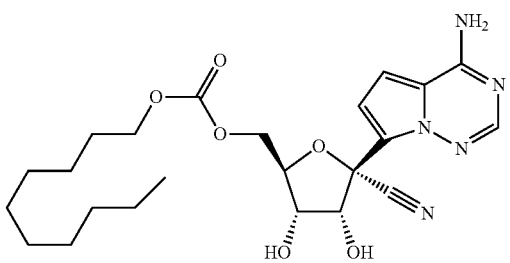 [SMILES: CCCCCCCCCCOC(=O)OC[C@H]1O[C@@](C#N)(c2ccc3c(N)ncnn23)[C@H](O)[C@@H]1O]

Compound 124 was synthesized in a manner similar to ((2R,3S,4R,5R)-5-(4-aminopyrrolo[2,1-f][1,2,4]triazin-7-yl)-5-cyano-3,4-dihydroxytetrahydrofuran-2-yl)methyl cyclooctyl carbonate (Compound 14) in Example 41, replacing cyclooctanol with 1-decanol. $^1$H NMR (400 MHz, DMSO-d6) δ 7.92 (s, 3H), 6.91 (d, J=4.5 Hz, 1H), 6.79 (d, J=4.5 Hz, 1H), 6.34 (d, J=6.0 Hz, 1H), 5.42 (d, J=5.8 Hz, 1H), 4.68 (m, 1H), 4.46-4.35 (m, 1H), 4.28-4.17 (m, 2H), 4.07 (t, J=6.6 Hz, 2H), 3.93 (q, J=5.6 Hz, 1H), 1.58 (m, 2H), 1.25 (m, 16H), 0.97-0.73 (m, 3H). LCMS: MS m/z 476.20 (M+1).

Example 114: ((2R,3S,4R,5R)-5-(4-aminopyrrolo[2,1-f][1,2,4]triazin-7-yl)-5-cyano-3,4-dihydroxytetrahydrofuran-2-yl)methyl octadecyl carbonate (Compound 126)

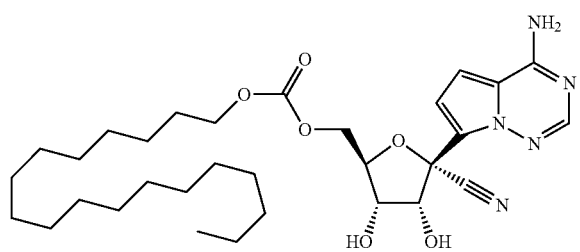 [SMILES: CCCCCCCCCCCCCCCCCCOC(=O)OC[C@H]1O[C@@](C#N)(c2ccc3c(N)ncnn23)[C@H](O)[C@@H]1O]

Compound 126 was synthesized in a manner similar to ((2R,3S,4R,5R)-5-(4-aminopyrrolo[2,1-f][1,2,4]triazin-7-yl)-5-cyano-3,4-dihydroxytetrahydrofuran-2-yl)methyl cyclooctyl carbonate (Compound 14) in Example 41, replacing cyclooctanol with 1-octadecanol. $^1$H NMR (400 MHz, DMSO-d6) δ 8.04-7.74 (m, 3H), 6.90 (d, J=4.5 Hz, 1H), 6.78 (d, J=4.5 Hz, 1H), 6.33 (d, J=6.0 Hz, 1H), 5.41 (d, J=5.8 Hz, 1H), 4.67 (t, J=5.4 Hz, 1H), 4.44-4.35 (m, 1H), 4.27-4.18 (m, 2H), 4.05 (t, J=6.6 Hz, 2H), 3.93 (q, J=5.7 Hz, 1H), 1.66-1.49 (m, 2H), 1.32-1.14 (m, 32H), 0.91-0.78 (m, 3H).

Example 115: 6-(((((2R,3S,4R,5R)-5-(4-aminopyrrolo[2,1-f][1,2,4]triazin-7-yl)-5-cyano-3,4-dihydroxytetrahydrofuran-2-yl)methoxy)carbonyl)oxy)hexanoic acid (Compound 140)

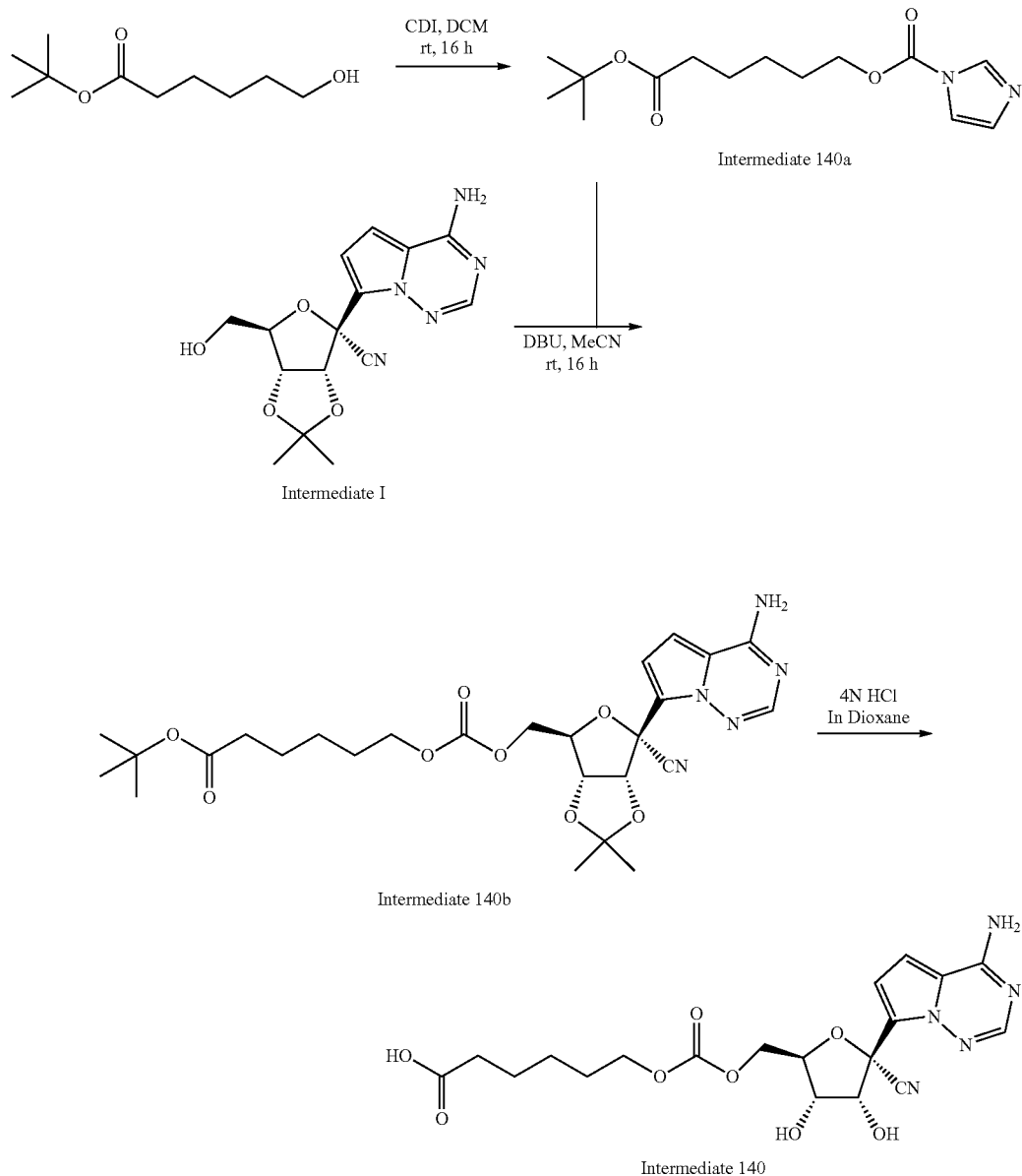

tert-Butyl 6-hydroxyhexanoate (584 mg, 3.1 mmol) was added to a stirring solution of 1,1'-carbonyldiimidazole (0.754 g, 4.65 mmol) in DCM (10 mL) at rt, and the reaction mixture was stirred for 16 h. The reaction mixture was then transferred to a separatory funnel, washed with water two times, dried over MgSO$_4$, and concentrated to afford Intermediate 140a, which was directly used into next step without further purification.

To the solution of Intermediate 140a (870 mg, 3.1 mmol) in MeCN (8 mL) was added Intermediate I (928 mg, 2.8 mmol) at room temperature followed by 1,8-diazabicyclo[5.4.0]undec-7-ene (85.3 mg, 0.56 mmol). The resulting solution was stirred at room temperature for 16 h then was quenched with saturated aqueous ammonium chloride. The biphasic mixture was extracted using EtOAc three times, and the combined organic layers were dried over MgSO$_4$, concentrated to afford Intermediate 140b, which was directly treated with 4N HCl in dioxane (14 mL) overnight. The reaction mixture was then concentrated and purified by HPLC using (ACN+0.1% TFA/water+0.1% TFA) to afford Compound 140 as TFA salt. $^1$H NMR (400 MHz, DMSO-d6) δ 11.99 (br, 1H), 8.49 (br, 1H), 8.27 (br, 1H), 8.02 (s, 1H), 7.05 (s, 1H), 6.85 (d, J=4.6 Hz, 1H), 6.34 (br, 2H), 4.67 (d, J=4.9 Hz, 1H), 4.40 (d, J=9.8 Hz, 1H), 4.29-4.17 (m, 2H), 4.07 (t, J=6.6 Hz, 2H), 3.94 (t, J=5.6 Hz, 1H), 2.21 (t, J=7.4 Hz, 2H), 1.63-48 (m, 4H), 1.37-1.27 (m, 2H). LCMS: MS m/z: 449.98 (free base, M+1).

Example 116: 4-(((((2R,3S,4R,5R)-5-(4-aminopyrrolo[2,1-f][1,2,4]triazin-7-yl)-5-cyano-3,4-dihydroxytetrahydrofuran-2-yl)methoxy)carbonyl)oxy)butanoic acid (Compound 141)

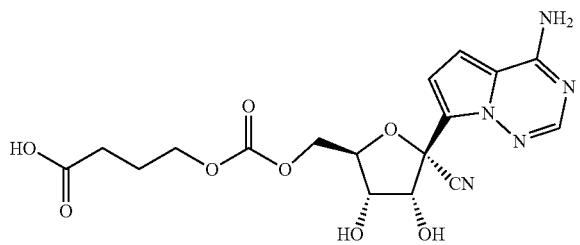 [SMILES: N#C[C@@]1(c2ccc3c(N)ncnn23)O[C@H](COC(=O)OCCCC(=O)O)[C@@H](O)[C@H]1O]

Compound 141 as a TFA salt was synthesized in a manner similar to 6-(((((2R,3S,4R,5R)-5-(4-aminopyrrolo[2,1-f][1,2,4]triazin-7-yl)-5-cyano-3,4-dihydroxytetrahydrofuran-2-yl)methoxy)carbonyl)oxy)hexanoic acid (Compound 140) in Example 115, replacing tert-butyl 6-hydroxyhexanoate with tert-butyl 4-hydroxybutanoate. $^1$H NMR (400 MHz, DMSO-$d_6$) δ 10.87 (br, 3H), 9.09 (br, 1H), 8.84 (br, 1H), 8.14 (s, 1H), 7.20 (d, J=4.6 Hz, 1H), 6.91 (d, J=4.6 Hz, 1H), 4.65 (d, J=4.8 Hz, 1H), 4.40 (dd, J=11.4, 2.2 Hz, 1H), 4.29-4.20 (m, 2H), 4.10 (t, J=6.5 Hz, 2H), 3.94 (dd, J=6.3, 4.9 Hz, 1H), 2.30 (t, J=7.3 Hz, 2H), 1.83 (p, J=6.9 Hz, 2H). LCMS: MS m/z: 421.99 (M+1).

Example 117: 5-(((((2R,3S,4R,5R)-5-(4-aminopyrrolo[2,1-f][1,2,4]triazin-7-yl)-5-cyano-3,4-dihydroxytetrahydrofuran-2-yl)methoxy)carbonyl)oxy)pentanoic acid (Compound 142)

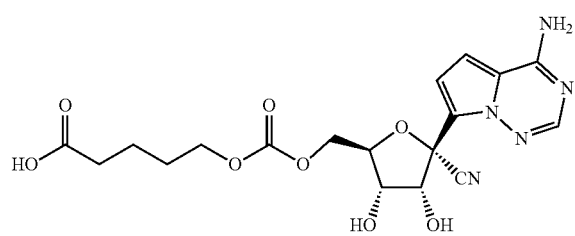 [SMILES: N#C[C@@]1(c2ccc3c(N)ncnn23)O[C@H](COC(=O)OCCCCC(=O)O)[C@@H](O)[C@H]1O]

Compound 142 as a TFA salt was synthesized in a manner similar to 6-(((((2R,3S,4R,5R)-5-(4-aminopyrrolo[2,1-f][1,2,4]triazin-7-yl)-5-cyano-3,4-dihydroxytetrahydrofuran-2-yl)methoxy)carbonyl)oxy)hexanoic acid (Compound 140) in Example 115, replacing tert-butyl 6-hydroxyhexanoate with tert-butyl 5-hydroxypentanoate. $^1$H NMR (400 MHz, DMSO-$d_6$) δ 11.94 (br, 1H), 8.51 (br, 1H), 8.29 (br, 1H), 8.04 (s, 1H), 7.07 (d, J=4.6 Hz, 1H), 6.86 (d, J=4.6 Hz, 1H), 6.33 (br, 2H), 4.65 (d, J=4.8 Hz, 1H), 4.41 (d, J=11.1 Hz, 1H), 4.24 (t, J=10.1 Hz, 2H), 4.08 (t, J=6.1 Hz, 2H), 3.94 (t, J=5.5 Hz, 1H), 2.25 (t, J=6.9 Hz, 2H), 1.65-1.50 (m, 4H). LCMS: MS m/z: 435.99 (M+1).

Example 118: 7-(((((2R,3S,4R,5R)-5-(4-aminopyrrolo[2,1-f][1,2,4]triazin-7-yl)-5-cyano-3,4-dihydroxytetrahydrofuran-2-yl)methoxy)carbonyl)oxy)heptanoic acid (Compound 143)

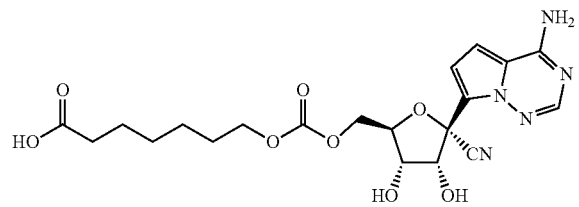 [SMILES: N#C[C@@]1(c2ccc3c(N)ncnn23)O[C@H](COC(=O)OCCCCCCC(=O)O)[C@@H](O)[C@H]1O]

Compound 143 as a TFA salt was synthesized in a manner similar to 6-(((((2R,3S,4R,5R)-5-(4-aminopyrrolo[2,1-f][1,2,4]triazin-7-yl)-5-cyano-3,4-dihydroxytetrahydrofuran-2-yl)methoxy)carbonyl)oxy)hexanoic acid (Compound 140) in Example 115, replacing tert-butyl 6-hydroxyhexanoate with tert-butyl 7-hydroxyheptanoate. $^1$H NMR (400 MHz, DMSO-$d_6$) δ 8.62 (br, 1H), 8.38 (br, 1H), 8.05 (s, 1H), 7.08 (d, J=4.5 Hz, 1H), 6.86 (d, J=4.6 Hz, 1H), 6.26 (br, 3H), 4.66 (d, J=4.9 Hz, 1H), 4.44-4.37 (m, 1H), 4.28-4.18 (m, 2H), 4.06 (t, J=6.6 Hz, 2H), 3.94 (dd, J=6.3, 4.9 Hz, 1H), 2.20 (t, J=7.3 Hz, 2H), 1.62-1.44 (m, 4H), 1.29 (h, J=3.2 Hz, 4H). LCMS: MS m/z: 464.02 (M+1).

Example 119: [(2R,3S,4R,5R)-5-(4-aminopyrrolo[2,1-f][1,2,4]triazin-7-yl)-5-cyano-3-[ethoxy(hydroxy)phosphoryl]oxy-4-hydroxy-tetrahydrofuran-2-yl]methyl isopropyl carbonate (Compound 144)

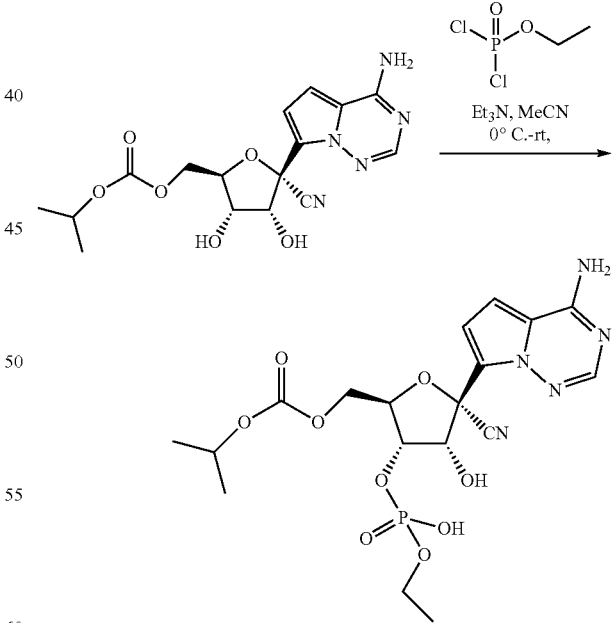

A stirred solution of [(2R,3S,4R,5R)-5-(4-aminopyrrolo[2,1-f][1,2,4]triazin-7-yl)-5-cyano-3,4-dihydroxy-tetrahydrofuran-2-yl]methyl isopropyl carbonate (Compound 4) (100 mg, 0.265 mmol) and triethylamine (0.2 mL, 1.46 mmol) in MeCN (2.6 mL) at 0° C. was treated with ethyl dichlorophosphate (0.04 mL, 0.32 mmol) and was warmed to room temperature over 2 hours. The reaction mixture was quenched with saturated aqueous ammonium chloride (3 mL) and extracted with EtOAc (5 mL×3). The combined organic layers were dried over MgSO$_4$ and concentrated, and the crude residue was purified by flash column chromatography using C18 column using acetonitrile and water as eluents to give Compound 144. $^1$H NMR (400 MHz, DMSO-d6) δ 8.06-7.79 (m, 3H), 6.95-6.87 (m, 1H), 6.87-6.74 (m, 1H), 4.83-4.68 (m, 2H), 4.45-4.31 (m, 2H), 4.25-4.13 (m, 1H), 3.88-3.68 (m, 2H), 1.15-1.03 (m, 3H). LCMS: MS: m/z 486.0 (M+1).

Example 120: isopropyl (2S,3R)-3-[[(2R,3S,4R,5R)-5-(4-aminopyrrolo[2,1-f][1,2,4]triazin-7-yl)-5-cyano-3,4-dihydroxy-tetrahydrofuran-2-yl]methoxycarbonyloxy]-2-(dimethylamino)butanoate (Compound 145)

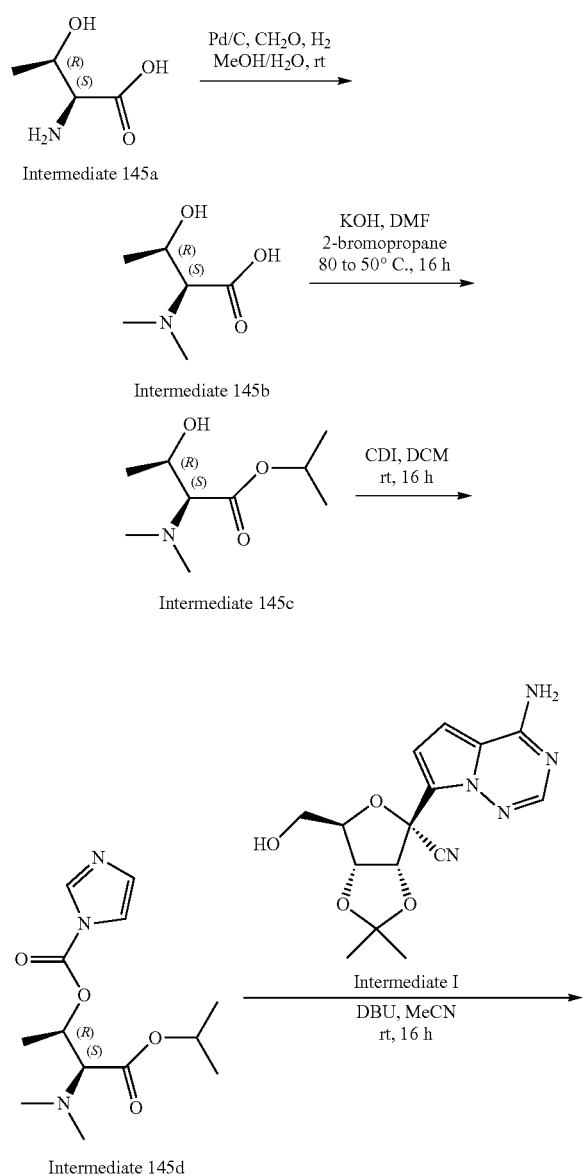

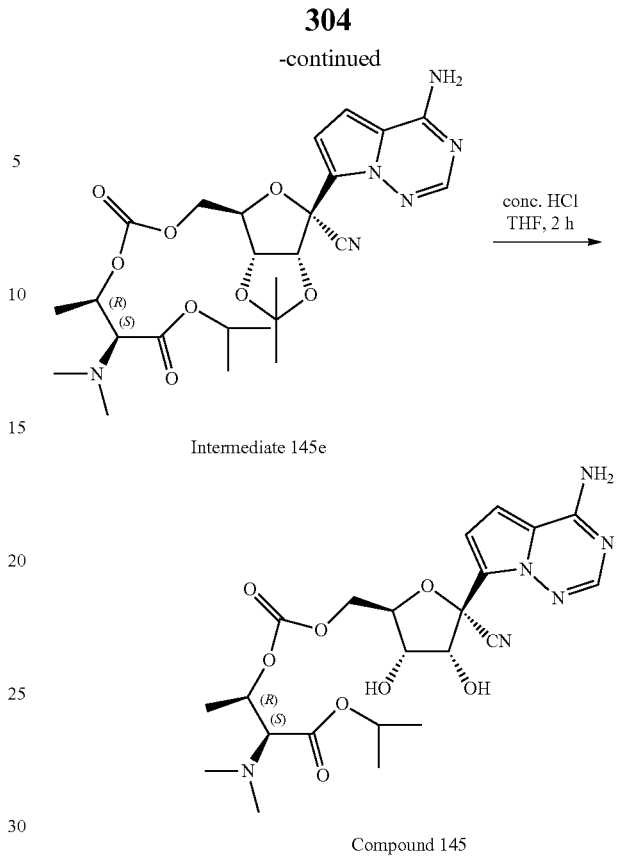

A solution of L-threonine (Intermediate 145a, 5 g, 42 mmol) in MeOH (70 mL) was treated with formaldehyde (37 wt % in water, 18.7 mL, 252 mmol) and Pd/C (5 wt % on carbon, 10.7 g, 5.04 mmol). The reaction apparatus was backfilled with H2 then the reaction mixture was stirred vigorously for 72 hours. The resulting mixture was filtered over Celite®, and the filtrate was concentrated to dryness to give desired N-methylated L-threonine (Intermediate 145b).

A solution of Intermediate 145b (2 g, 13.6 mmol) in DMF (136 mL) was treated with KOH (762 mg, 13.6 mmol), then reaction mixture was heated to 80° C. and stirred for 4 hours. The resulting solution was cooled to 50° C., then 2-bromopropane (1.4 mL, 14.9 mmol) was added, and the reaction mixture was stirred for 16 hours. The resulting white suspension was cooled to room temperature and H$_2$O (150 mL) was added, and then was extracted with diethyl ether (100 mL×3). The combined organic layers were washed with H2O (100 mL×3), dried over MgSO$_4$, and concentrated gently to give N-dimethyl-O-iPr-L-threonine (Intermediate 145c). This was used directly in next step without further purification A solution of 1,1'-carbonyldiimidazole (2.4 g, 14.7 mmol) in DCM (35 mL) was treated with Intermediate 145c (1.86 g, 9.82 mmol), then was left to stir for 16 hours. The resulting solution was washed with H$_2$O (50 mL×2), and the organic layer was dried over MgSO$_4$ then concentrated to dryness to give desired carbamate. This was used directly in next step without further purification.

A solution of Intermediate 1 (1.5 g, 4.53 mmol) and Intermediate 145d in MeCN (16 mL) was treated with 1,8-diazabicyclo[5.4.0]undec-7-ene (138 mg, 0.905 mmol) then was stirred for 16 hours. The resulting yellow solution was quenched with saturated aqueous ammonium chloride (20 mL) and extracted with EtOAc (30 mL×3). The combined organic layers were dried over MgSO₄ and concentrated to dryness. The resulting crude Intermediate 145e was used in next step without further purification, assuming quantitative yield.

A solution of crude Intermediate 145e (2.48 g, 4.53 mmol) in THF (45 mL) was treated with conc. HCl (3.74 mL, 45.3 mmol), then was stirred for 2 hours before being quenched with saturated aqueous sodium bicarbonate until basic. The mixture was extracted with EtOAc (50 mL×3), and the combined organic layers were dried over MgSO₄ then concentrated to dryness. The resulting crude residue was purified by flash column chromatography using dichloromethane and methanol as eluents to give Compound 145. ¹H NMR (400 MHz, DMSO-d6) δ 8.14-7.75 (m, 3H), 6.90 (d, J=4.4 Hz, 1H), 6.78 (d, J=4.5 Hz, 1H), 6.33 (d, J=6.1 Hz, 1H), 5.39 (d, J=5.8 Hz, 1H), 4.97 (dp, J=12.6, 6.5 Hz, 2H), 4.70-4.61 (m, 1H), 4.48-4.37 (m, 1H), 4.30-4.16 (m, 2H), 4.02-3.84 (m, 1H), 3.25 (d, J=8.2 Hz, 1H), 2.26 (s, 6H), 1.34-1.02 (m, 9H). LCMS: MS m/z: 507.2 (M+1).

Example 121: isopropyl (2S)-4-[[(2R,3S,4R,5R)-5-(4-aminopyrrolo[2,1-f][1,2,4]triazin-7-yl)-5-cyano-3,4-dihydroxy-tetrahydrofuran-2-yl]methoxycarbonyloxy]-2-(dimethylamino)butanoate (Compound 146)

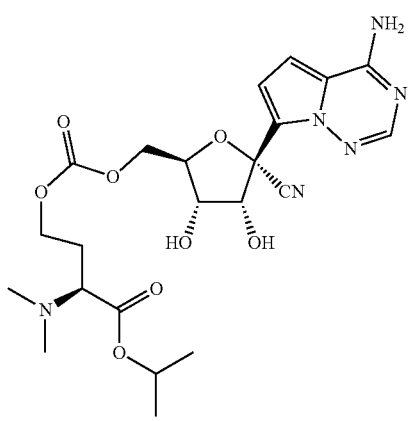 [SMILES: CC(C)OC(=O)[C@H](CCOC(=O)OC[C@H]1O[C@@](C#N)(c2ccc3c(N)ncnn23)[C@H](O)[C@@H]1O)N(C)C]

Compound 146 was synthesized in a manner similar to isopropyl (2S,3R)-3-[[(2R,3S,4R,5R)-5-(4-aminopyrrolo[2,1-f][1,2,4]triazin-7-yl)-5-cyano-3,4-dihydroxy-tetrahydrofuran-2-yl]methoxycarbonyloxy]-2-(dimethylamino)butanoate (Compound 145) in Example 120, replacing L-threonine with L-homoserine. ¹H NMR (400 MHz, DMSO-d6) δ 8.05-7.78 (m, 3H), 6.91 (d, J=4.6 Hz, 1H), 6.80 (d, J=4.6 Hz, 1H), 6.32 (d, J=6.1 Hz, 1H), 5.42 (d, J=5.8 Hz, 1H), 4.94 (p, J=6.3 Hz, 1H), 4.74-4.64 (m, 1H), 4.44-4.33 (m, 1H), 4.27-4.19 (m, 2H), 4.12 (t, J=6.5 Hz, 2H), 3.93 (q, J=5.6 Hz, 1H), 3.25-3.19 (m, 1H), 2.25 (s, 6H), 1.98-1.84 (m, 2H), 1.25-1.16 (m, 6H). LCMS: MS m/z: 507.1 (M+1).

Example 122: neopentyl O-((((2R,3S,4R,5R)-5-(4-aminopyrrolo[2,1-f][1,2,4]triazin-7-yl)-5-cyano-3,4-dihydroxytetrahydrofuran-2-yl)methoxy)carbonyl)-N,N-dimethyl-L-threoninate (Compound 147)

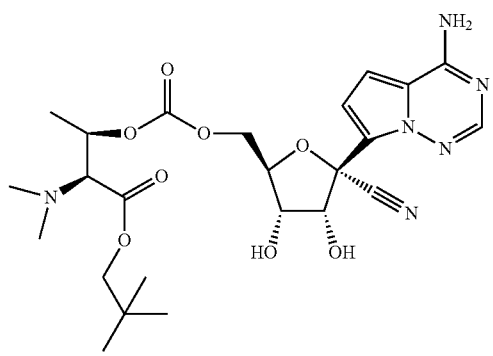 [SMILES: C[C@@H](OC(=O)OC[C@H]1O[C@@](C#N)(c2ccc3c(N)ncnn23)[C@H](O)[C@@H]1O)[C@@H](C(=O)OCC(C)(C)C)N(C)C]

Compound 147 was synthesized in a manner similar to isopropyl (2S,3R)-3-[[(2R,3S,4R,5R)-5-(4-aminopyrrolo[2,1-f][1,2,4]triazin-7-yl)-5-cyano-3,4-dihydroxy-tetrahydrofuran-2-yl]methoxycarbonyloxy]-2-(dimethylamino)butanoate (Compound 145) in Example 120, replacing 2-bromopropane with 1-bromo-2,2-dimethylpropane and purified by HPLC using 10 mM aqueous ammonium formate and acetonitrile as eluents. ¹H NMR (500 MHz, DMSO) δ 7.97-7.80 (m, 3H), 6.90 (d, J=4.5 Hz, 1H), 6.77 (d, J=4.5 Hz, 1H), 6.33 (d, J=6.1 Hz, 1H), 5.38 (d, J=5.9 Hz, 1H), 5.06-4.97 (m, 1H), 4.65 (dd, J=5.8, 5.1 Hz, 1H), 4.44-4.38 (m, 1H), 4.26-4.17 (m, 2H), 3.92 (dd, J=11.1, 5.8 Hz, 1H), 3.76 (q, J=10.5 Hz, 2H), 3.37 (d, J=7.8 Hz, 1H), 2.29 (s, 6H), 1.23 (d, J=6.3 Hz, 3H), 0.90 (d, J=13.0 Hz, 9H). LCMS: MS m/z: 535.5 (M+1).

Example 123: (2S,3R)-cyclopentylmethyl 3-(((((2R,3S,4R,5R)-5-(4-aminopyrrolo[2,1-f][1,2,4]triazin-7-yl)-5-cyano-3,4-dihydroxytetrahydrofuran-2-yl)methoxy)carbonyl)oxy)-2-(dimethylamino)butanoate (Compound 148)

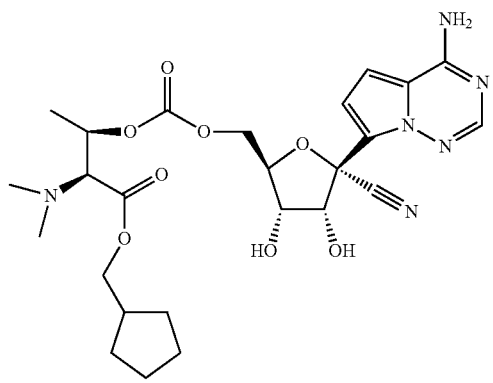 [SMILES: C[C@@H](OC(=O)OC[C@H]1O[C@@](C#N)(c2ccc3c(N)ncnn23)[C@H](O)[C@@H]1O)[C@@H](C(=O)OCC1CCCC1)N(C)C]

Compound 148 was synthesized in a manner similar to isopropyl (2S,3R)-3-[[(2R,3S,4R,5R)-5-(4-aminopyrrolo[2,1-f][1,2,4]triazin-7-yl)-5-cyano-3,4-dihydroxy-tetrahydrofuran-2-yl]methoxycarbonyloxy]-2-(dimethylamino)butanoate (Compound 145) in Example 120, replacing 2-bromopropane with (bromomethyl)cyclopentane and purified by HPLC using 10 mM aqueous ammonium formate and acetonitrile as eluents. $^1$H NMR (500 MHz, DMSO) δ 7.92 (s, 3H), 6.89 (d, J=4.5 Hz, 1H), 6.77 (d, J=4.5 Hz, 1H), 6.55-6.40 (m, 1H), 5.60-5.45 (m, 1H), 5.03-4.92 (m, 1H), 4.70-4.61 (m, 1H), 4.49-4.37 (m, 1H), 4.21 (s, 2H), 3.95 (d, J=7.0 Hz, 2H), 3.93-3.85 (m, 1H), 2.54-2.51 (m, 1H), 2.27 (s, 6H), 2.08 (s, 1H), 1.71-1.61 (m, 2H), 1.52 (s, 2H), 1.50-1.43 (m, 2H), 1.22 (d, J=6.3 Hz, 3H), 1.20-1.13 (m, 2H). LCMS: MS m/z: 547.4 (M+1).

Example 124: cyclopentyl O-((((2R,3S,4R,5R)-5-(4-aminopyrrolo[2,1-f][1,2,4]triazin-7-yl)-5-cyano-3,4-dihydroxytetrahydrofuran-2-yl)methoxy)carbonyl)-N,N-dimethyl-L-threoninate (Compound 149)

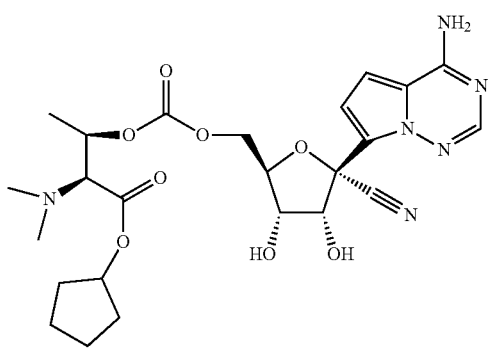 [SMILES: C[C@@H](OC(=O)OC[C@H]1O[C@@](C#N)(c2ccc3c(N)ncnn23)[C@H](O)[C@@H]1O)[C@@H](C(=O)OC1CCCC1)N(C)C]

Compound 149 was synthesized in a manner similar to isopropyl (2S,3R)-3-[[(2R,3S,4R,5R)-5-(4-aminopyrrolo[2,1-f][1,2,4]triazin-7-yl)-5-cyano-3,4-dihydroxy-tetrahydrofuran-2-yl]methoxycarbonyloxy]-2-(dimethylamino)butanoate (Compound 145) in Example 120, replacing 2-bromopropane with bromocyclopentane and purifying by HPLC using 10 mM aqueous ammonium formate and acetonitrile as eluents. $^1$H NMR (500 MHz, DMSO) δ 7.99-7.80 (m, 3H), 6.89 (d, J=4.5 Hz, 1H), 6.77 (d, J=4.5 Hz, 1H), 6.37 (d, J=6.0 Hz, 1H), 5.41 (d, J=6.0 Hz, 1H), 5.12 (s, 1H), 4.98 (dd, J=7.9, 6.4 Hz, 1H), 4.65 (dd, J=5.6, 5.2 Hz, 1H), 4.41 (dd, J=14.2, 5.2 Hz, 1H), 4.27-4.18 (m, 2H), 3.91 (d, J=5.4 Hz, 1H), 3.27 (d, J=7.9 Hz, 1H), 2.27 (s, 6H), 1.85-1.71 (m, 2H), 1.66-1.57 (m, >99.5% 4H), 1.56-1.48 (m 2H), 1.20 (d, J=6.4 Hz, 3H). LCMS: MS m/z: 533.4 (M+1).

Example 125: tetrahydro-2H-pyran-4-yl O-((((2R,3S,4R,5R)-5-(4-aminopyrrolo[2,1-f][1,2,4]triazin-7-yl)-5-cyano-3,4-dihydroxytetrahydrofuran-2-yl)methoxy)carbonyl)-N,N-dimethyl-L-threoninate (Compound 150)

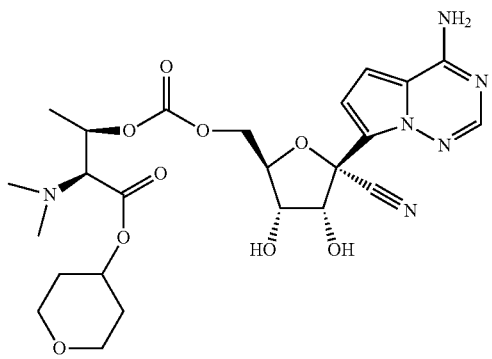 [SMILES: C[C@@H](OC(=O)OC[C@H]1O[C@@](C#N)(c2ccc3c(N)ncnn23)[C@H](O)[C@@H]1O)[C@@H](C(=O)OC1CCOCC1)N(C)C]

Compound 150 was synthesized in a manner similar to isopropyl (2S,3R)-3-[[(2R,3S,4R,5R)-5-(4-aminopyrrolo[2,1-f][1,2,4]triazin-7-yl)-5-cyano-3,4-dihydroxy-tetrahydrofuran-2-yl]methoxycarbonyloxy]-2-(dimethylamino)butanoate (Compound 145) in Example 120, replacing 2-bromopropane with 4-bromotetrahydropyran and purifying by HPLC using 10 mM aqueous ammonium formate and acetonitrile as eluents. $^1$H NMR (500 MHz, DMSO) δ 7.99-7.82 (m, 3H), 6.90 (d, J=4.4 Hz, 1H), 6.77 (d, J=4.4 Hz, 1H), 6.37 (d, J=6.0 Hz, 1H), 5.40 (d, J=5.8 Hz, 1H), 5.06-4.99 (m, 1H), 4.97-4.92 (m, 1H), 4.64 (t, J=5.4 Hz, 1H), 4.41 (d, J=9.3 Hz, 1H), 4.28-4.17 (m, 2H), 3.91 (d, J=5.2 Hz, 1H), 3.80-3.66 (m, 2H), 3.49-3.37 (m, 2H), 2.29 (s, 6H), 1.90-1.74 (m, 2H), 1.59-1.45 (m, 2H), 1.22 (d, J=6.3 Hz, 3H). LCMS: MS m/z: 549.4 (M+1).

Example 126: isopropyl O-((((2R,3S,4R,5R)-5-(4-aminopyrrolo[2,1-f][1,2,4]triazin-7-yl)-5-cyano-3,4-dihydroxytetrahydrofuran-2-yl)methoxy)carbonyl)-N,N-dimethyl-L-serinate (Compound 151)

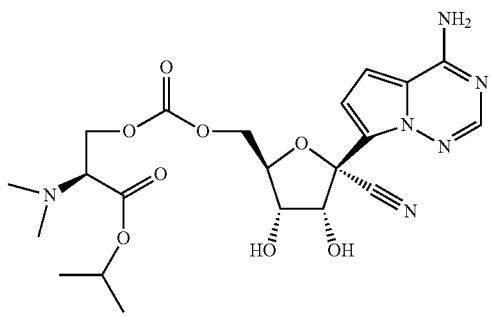 [SMILES: CC(C)OC(=O)[C@H](COC(=O)OC[C@H]1O[C@@](C#N)(c2ccc3c(N)ncnn23)[C@H](O)[C@@H]1O)N(C)C]

Compound 151 was synthesized in a manner similar to isopropyl (2S,3R)-3-[[(2R,3S,4R,5R)-5-(4-aminopyrrolo[2,1-f][1,2,4]triazin-7-yl)-5-cyano-3,4-dihydroxy-tetrahydrofuran-2-yl]methoxycarbonyloxy]-2-(dimethylamino)butanoate (Compound 145) in Example 120, replacing L-threonine with L-serine and purifying by HPLC using 0.1% v/v trifluoro acetic acid in water and acetonitrile as eluents to afford the corresponding TFA salt. ¹H NMR (500 MHz, DMSO) δ 8.24-8.01 (m, J=61.2 Hz, 2H), 7.96 (s, 1H), 6.96 (d, J=4.6 Hz, 1H), 6.81 (d, J=4.6 Hz, 1H), 6.39 (br. s, 1H), 5.58-5.36 (m, 1H), 5.08-4.99 (m, 1H), 4.72-4.63 (m, 3H), 4.59 (br.s, 1H), 4.43 (dd, J=11.7, 2.6 Hz, 1H), 4.34-4.27 (m, 1H), 4.25 (td, J=6.8, 2.5 Hz, 1H), 3.92 (dd, J=6.6, 5.0 Hz, 1H), 2.83 (s, J=29.0 Hz, 6H), 1.22 (d, J=6.3 Hz, 3H), 1.13 (d, J=6.2 Hz, 3H). LCMS: MS m/z: 493.4 (M+1).

Example 127: cyclopentylmethyl O-((((2R,3S,4R,5R)-5-(4-aminopyrrolo[2,1-f][1,2,4]triazin-7-yl)-5-cyano-3,4-dihydroxytetrahydrofuran-2-yl)methoxy)carbonyl)-N,N-dimethyl-L-serinate (Compound 152)

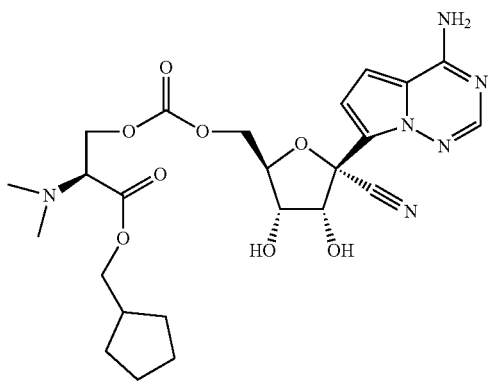 [SMILES: CN(C)[C@@H](COC(=O)OC[C@H]1O[C@@](C#N)(c2ccc3c(N)ncnn23)[C@H](O)[C@@H]1O)C(=O)OCC1CCCC1]

Compound 152 was synthesized in a manner similar to isopropyl (2S,3R)-3-[[(2R,3S,4R,5R)-5-(4-aminopyrrolo[2,1-f][1,2,4]triazin-7-yl)-5-cyano-3,4-dihydroxy-tetrahydrofuran-2-yl]methoxycarbonyloxy]-2-(dimethylamino)butanoate (Compound 145) in Example 120, replacing L-threonine with L-serine and 2-bromopropane with (bromomethyl)cyclopentane, and purifying by HPLC using 0.1% v/v trifluoro acetic acid in water and acetonitrile as eluents to afford the corresponding TFA salt. ¹H NMR (500 MHz, DMSO) δ 8.21-7.98 (m, 2H), 7.96 (s, 1H), 6.95 (d, J=4.6 Hz, 1H), 6.80 (d, J=4.6 Hz, 1H), 6.41 (br. s, 1H), 5.40 (br. s, 1H), 4.72-4.57 (m, 4H), 4.43 (dd, J=11.4, 2.1 Hz, 1H), 4.32-4.22 (m, 2H), 4.15-4.08 (m, 1H), 4.03 (dd, J=10.6, 7.0 Hz, 1H), 3.91 (dd, J=6.6, 5.0 Hz, 1H), 2.83 (s, J=15.1 Hz, 6H), 2.16-2.08 (m, 1H), 1.66-1.57 (m, J=13.0, 8.1 Hz, 2H), 1.53-1.36 (m, 4H), 1.21-1.10 (m, 2H). LCMS: MS m/z: 533.5 (M+1).

Example 128: cyclopentyl O-((((2R,3S,4R,5R)-5-(4-aminopyrrolo[2,1-f][1,2,4]triazin-7-yl)-5-cyano-3,4-dihydroxytetrahydrofuran-2-yl)methoxy)carbonyl)-N,N-dimethyl-L-serinate (Compound 153)

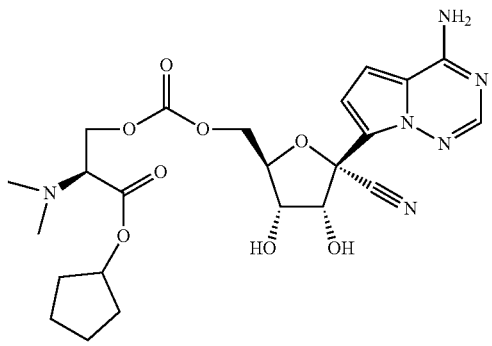 [SMILES: CN(C)[C@@H](COC(=O)OC[C@H]1O[C@@](C#N)(c2ccc3c(N)ncnn23)[C@H](O)[C@@H]1O)C(=O)OC1CCCC1]

Compound 153 was synthesized in a manner similar to isopropyl (2S,3R)-3-[[(2R,3S,4R,5R)-5-(4-aminopyrrolo[2,1-f][1,2,4]triazin-7-yl)-5-cyano-3,4-dihydroxy-tetrahydrofuran-2-yl]methoxycarbonyloxy]-2-(dimethylamino)butanoate (Compound 145) in Example 120, replacing L-threonine with L-serine and 2-bromopropane with bromocyclopentane, and purifying by HPLC using 0.1% v/v trifluoro acetic acid in water and acetonitrile as eluents to afford the corresponding TFA salt. ¹H NMR (400 MHz, DMSO) δ 8.36-8.04 (m, J=54.1 Hz, 2H), 7.97 (s, 1H), 6.96 (d, J=4.5 Hz, 1H), 6.81 (d, J=4.6 Hz, 1H), 6.42 (br. s, 1H), 5.42 (br. s, 1H), 5.26-5.18 (m, 1H), 4.74-4.56 (m, 4H), 4.46-4.38 (m, 1H), 4.33-4.21 (m, 2H), 3.91 (dd, J=6.1, 5.2 Hz, 1H), 2.84 (s, J=13.1 Hz, 6H), 1.90-1.41 (m, 8H). LCMS: MS m/z: 519.3 (M+1).

Example 129: ((2R,3S,4R,5R)-5-(4-aminopyrrolo[2,1-f][1,2,4]triazin-7-yl)-5-cyano-3,4-dihydroxytetrahydrofuran-2-yl)methyl (4-methoxyphenyl) carbonate (Compound 111)

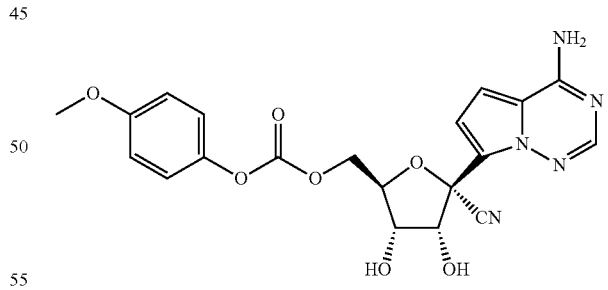

Compound 111 was synthesized in a manner similar to [(2R,3S,4R,5R)-5-(4-aminopyrrolo[2,1-f][1,2,4]triazin-7-yl)-5-cyano-3,4-dihydroxy-tetrahydrofuran-2-yl]methyl isopropyl carbonate (Compound 4) in Example 4, replacing isopropyl chloroformate with 4-methoxyphenyl carbonochloridate. ¹H NMR (400 MHz, DMSO-d6) δ 7.93 (s, 3H), 7.15-7.08 (m, 2H), 6.97-6.89 (m, 3H), 6.82 (d, J=4.5 Hz, 1H), 6.36 (d, J=6.1 Hz, 1H), 5.46 (d, J=5.7 Hz, 1H), 4.71 (dd, J=6.1, 4.9 Hz, 1H), 4.56-4.46 (m, 1H), 4.38-4.26 (m, 2H), 4.00 (q, J=5.6 Hz, 1H), 3.75 (s, 3H). LCMS: MS m/z: 441.93 (M+1)

Example 130: (2R,3R,4R,5R)-2-(4-aminopyrrolo[2,1-f][1,2,4]triazin-7-yl)-2-cyano-5-(((ethoxycarbonyl)oxy)methyl)tetrahydrofuran-3,4-diyl diacetate (Compound 129)

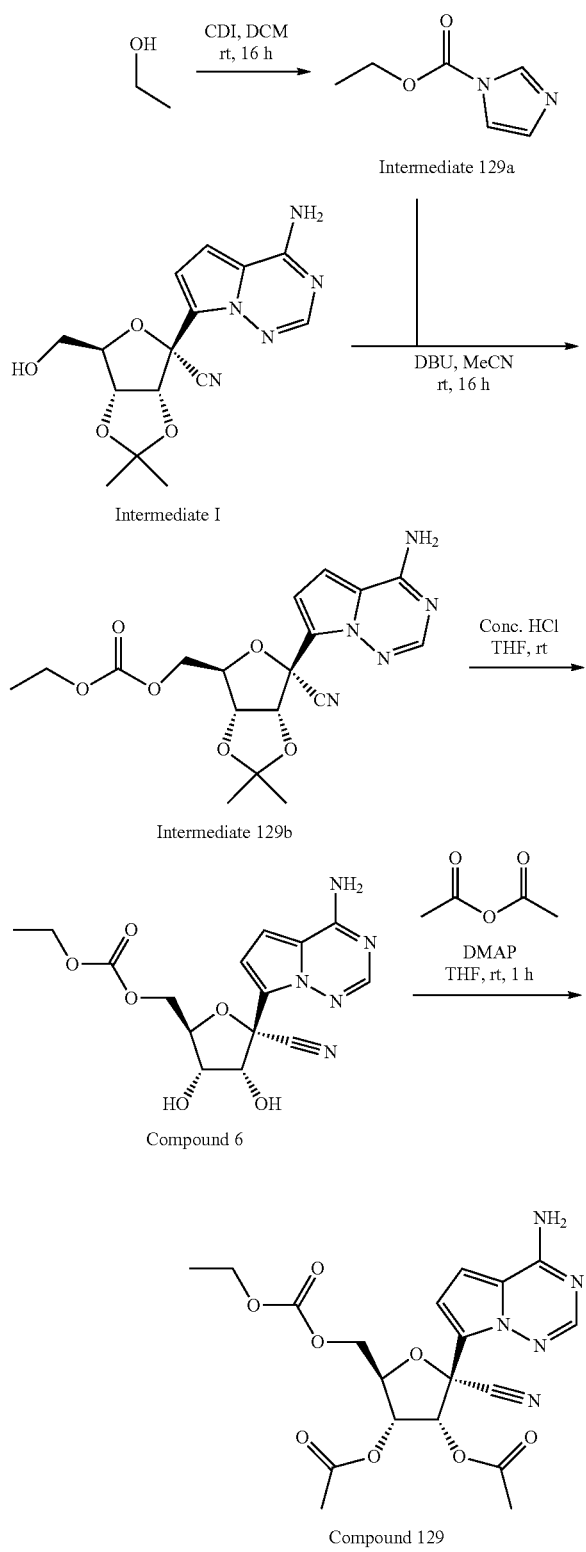

Ethanol (1 equiv) was added to a stirring solution of 1,1'-carbonyldiimidazole (1.5 equiv) in DCM (1 M with respect to 1,1'-carbonyldiimidazole) at rt, and the reaction mixture was stirred for 16 h. The reaction mixture was then transferred to a separatory funnel, washed with water two times, dried over MgSO$_4$, and concentrated to afford Intermediate 129a, which was directly used into next step without further purification.

To the solution of Intermediate 129a (1.1 equiv) in MeCN (0.4 M with respect to Intermediate 129a) was added Intermediate I (1 equiv) at room temperature followed by 1,8-diazabicyclo[5.4.0]undec-7-ene (0.2 equiv). The resulting solution was stirred at room temperature for 16 h and then was quenched with saturated aqueous ammonium chloride. The biphasic mixture was extracted using EtOAc three times, and the combined organic layers were dried over MgSO$_4$ and concentrated to afford Intermediate 129b, which was directly used in the next step without further purification.

To a solution of Intermediate 129b (1 equiv) in THF (1.2 M with respect to Intermediate 129b) at rt was added conc. HCl (5 equiv) slowly over ten minutes. The reaction was then stirred for 6.5 h. The resulting mixture was basified with saturated aqueous sodium bicarbonate and extracted with EtOAc three times, and the combined organic layers were dried over MgSO$_4$ then concentrated. The crude product was redissolved into ethanol, and the total volume was adjusted to approximately 7 mL/g. Slurry formation was observed at rt, and then heptane (7 mL/g) was added slowly. The slurry was agitated overnight and then the solids were filtered and rinsed with a mixture of ethanol (1.5 mL/g) and heptane (1.5 mL/g). The solids were dried under vacuum to afford Compound 6 (73% yield). $^1$H NMR (400 MHz, DMSO-d6) δ 7.92 (br, 3H), 6.91 (d, J=4.5 Hz, 1H), 6.79 (d, J=4.5 Hz, 1H), 6.30 (d, J=6.1 Hz, 1H), 5.40 (d, J=5.8 Hz, 1H), 4.69 (dd, J=6.1, 5.0 Hz, 1H), 4.39 (dd, J=10.3, 4.1 Hz, 1H), 4.29-4.17 (m, 2H), 4.11 (q, J=7.1 Hz, 2H), 3.94 (q, J=5.8 Hz, 1H), 1.20 (t, J=7.1 Hz, 3H). LCMS: MS m/z: 363.9 (M+23).

To a mixture of Compound 6 (1 equiv) and acetic anhydride (2 equiv) in THF (0.5 M with respect to Compound 6) was added 4-dimethylaminopyridine (0.15 equiv). The mixture was stirred at rt for 1 hr. After the completion of the reaction, the reaction mixture was diluted with ethyl acetate, washed with water and brine, dried over MgSO$_4$, and concentrated. The residue was purified by flash chromatography using dichloromethane and ethyl acetate as eluants to obtain Compound 129. $^1$H NMR (400 MHz, DMSO-d6) δ 7.95 (br, 3H), 6.95 (d, J=4.7 Hz, 1H), 6.81 (d, J=4.6 Hz, 1H), 6.08 (d, J=5.9 Hz, 1H), 5.41 (dd, J=6.0, 4.6 Hz, 1H), 4.61 (td, J=4.9, 3.2 Hz, 1H), 4.48 (dd, J=12.2, 3.2 Hz, 1H), 4.33 (dd, J=12.2, 5.1 Hz, 1H), 4.14-4.06 (m, 2H), 2.12 (d, J=1.5 Hz, 6H), 1.19 (t, J=7.1 Hz, 3H). LCMS: MS m/z: 447.99 (M+1).

Example 131: (3S,5S,7S)-adamantan-1-yl (((2R,3S,4R,5R)-5-(4-aminopyrrolo[2,1-f][1,2,4]triazin-7-yl)-5-cyano-3,4-dihydroxytetrahydrofuran-2-yl)methyl) carbonate (Compound 154)

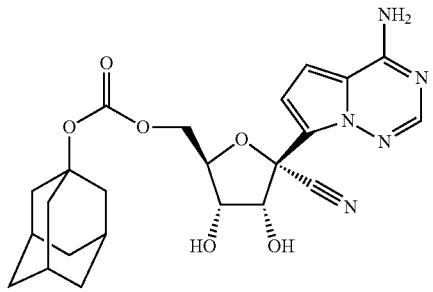 [SMILES: N#C[C@@]1(c2ccc3c(N)ncnn23)O[C@H](COC(=O)OC23CC4CC(CC(C4)C2)C3)[C@@H](O)[C@H]1O]

Compound 154 was synthesized in a manner similar to Compound 47 (((2R,3S,4R,5R)-5-(4-aminopyrrolo[2,1-f][1,2,4]triazin-7-yl)-5-cyano-3,4-dihydroxytetrahydrofuran-2-yl)methyl (1-methylcyclohexyl) carbonate) in Example 23, replacing 1-methylcyclohexanol with 1-adamantol. 1H NMR (400 MHz, DMSO-d6) δ 8.11-7.63 (m, 3H), 6.91 (d, J=4.5 Hz, 1H), 6.79 (d, J=4.5 Hz, 1H), 6.31 (d, J=6.1 Hz, 1H), 5.39 (d, J=5.8 Hz, 1H), 4.75-4.60 (m, 1H), 4.35 (dd, J=11.9, 2.9 Hz, 1H), 4.19 (td, J=6.1, 2.9 Hz, 1H), 4.15-4.05 (m, 1H), 3.96-3.87 (m, 1H), 2.16-2.09 (m, 4H), 2.03-1.92 (m, 6H), 1.65-1.48 (m, 6H).). LCMS: MS m/z: 492.1 (M+23).

Example 132: ((2R,3S,4R,5R)-5-(4-aminopyrrolo[2,1-f][1,2,4]triazin-7-yl)-5-cyano-3,4-dihydroxytetrahydrofuran-2-yl)methyl (2-(4-methylcyclohex-3-en-1-yl)propan-2-yl) carbonate (Compound 155)

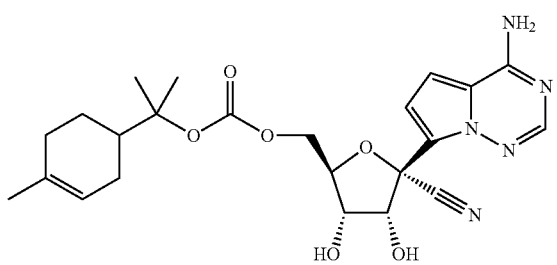 [SMILES: CC1=CCC(C(C)(C)OC(=O)OC[C@H]2O[C@@](C#N)(c3ccc4c(N)ncnn34)[C@H](O)[C@@H]2O)CC1]

Compound 155 was synthesized in a manner similar to Compound 55 ((2R,3S,4R,5R)-5-(4-aminopyrrolo[2,1-f][1,2,4]triazin-7-yl)-5-cyano-3,4-dihydroxytetrahydrofuran-2-yl)methyl (1-methylcycloheptyl) carbonate in Example 32, replacing 1-methylcycloheptan-1-ol with 2-(4-methylcyclohex-3-en-1-yl)propan-2-ol. $^1$H NMR (400 MHz, DMSO-d6) δ 7.92 (s, 3H), 6.90 (d, J=4.5 Hz, 1H), 6.79 (d, J=4.5 Hz, 1H), 6.32 (d, J=6.0 Hz, 1H), 5.39 (d, J=5.8 Hz, 1H), 5.36-5.28 (m, 1H), 4.65 (dd, J=6.0, 4.9 Hz, 1H), 4.35 (dd, J=11.8, 2.8 Hz, 1H), 4.20 (td, J=6.2, 2.7 Hz, 1H), 4.12 (dd, J=11.8, 5.8 Hz, 1H), 3.92 (q, J=5.7 Hz, 1H), 2.02-1.67 (m, 6H), 1.64-1.56 (m, 3H), 1.37 (d, J=11.8 Hz, 6H), 1.28-1.13 (m, 1H). LCMS: MS m/z: 472.1 (M+1).

Example 133: ((2R,3S,4R,5R)-5-(4-aminopyrrolo[2,1-f][1,2,4]triazin-7-yl)-5-cyano-3,4-dihydroxytetrahydrofuran-2-yl)methyl ((1R,3r,5S)-8-methyl-8-azabicyclo[3.2.1]octan-3-yl) carbonate (Compound 156)

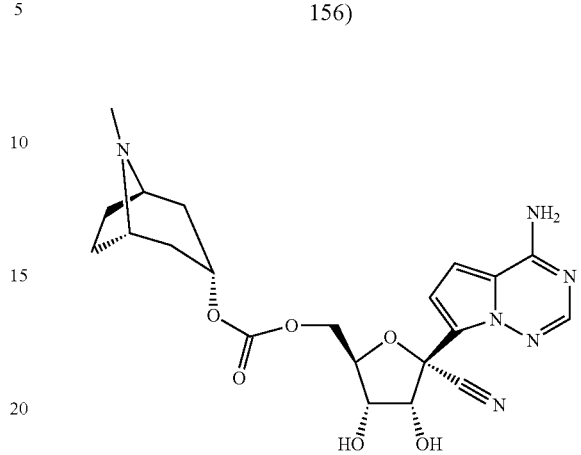

Compound 156 was synthesized in a manner similar to Compound 47 (((2R,3S,4R,5R)-5-(4-aminopyrrolo[2,1-f][1,2,4]triazin-7-yl)-5-cyano-3,4-dihydroxytetrahydrofuran-2-yl)methyl (1-methylcyclohexyl) carbonate) in Example 23, replacing 1-methylcyclohexanol with tropine and was purified by flash chromatography using dichloromethane, methanol, and triethylamine. 1H NMR (400 MHz, DMSO-d6) δ 7.92 (s, 3H), 6.91 (d, J=4.6 Hz, 1H), 6.82 (d, J=4.5 Hz, 1H), 6.39 (s, 1H), 5.42 (s, 1H), 4.73 (t, J=5.2 Hz, 1H), 4.62 (d, J=4.7 Hz, 1H), 4.48-4.34 (m, 1H), 4.29-4.15 (m, 2H), 3.93 (t, J=5.5 Hz, 1H), 3.17 (s, 2H), 2.26 (s, 3H), 2.17-2.04 (m, 2H), 1.98 (dd, J=8.1, 4.2 Hz, 2H), 1.89-1.80 (m, 2H). LCMS: MS m/z: 459.1 (M+1).

Example A: HEp-2 RSV-Luc5 384-Well Assay

HEp-2 cell line was purchased from ATCC (Manassas, VA Cat #CCL-23) and maintained in Dulbecco's Minimum Essential Medium (DMEM) (Corning, New York, NY, Cat #15-018CM) supplemented with 10% fetal bovine serum (FBS) (Hyclone, Logan, UT, Cat #SH30071-03) and 1× Penicillin-Streptomycin-L-Glutamine (Corning, New York, NY, Cat #30-009-CI). Cells were passaged 2 times per week to maintain sub-confluent densities and were used for experiments at passage 5-20. Respiratory syncytial virus recombinant with luciferase (RSV-Luc5) (≥0.1×107 TCID50/ml) was purchased from Microbiologics (Saint Cloud, MN). Viral replication was determined in HEp-2 cells in the following manner.

Compounds are prepared in 100% DMSO in 384-well polypropylene plates (Greiner, Monroe. NC, Cat #784201) with 8 compounds per plate in grouped replicates of 4 at 10 serially diluted concentrations (1:3). The serially diluted compounds were transferred to low dead volume Echo plates (Labcyte, Sunnyvale, CA, Cat #LP-0200).

The test compounds were spotted to 384-well assay plates (Greiner. Monroe, NC, Cat #781091) at 200 nL per well. HEp-2 cells were harvested and suspended in DMEM (supplemented with 10% FBS and 1× Penicillin-Streptomycin-L-Glutamine) and seeded to the pre-spotted assay plates at 4,000 cells per well in 30 μL. RSV-Luc5 viruses were diluted in DMEM (supplemented with 10% FBS and 1× Penicillin-Streptomycin-L-Glutamine) at 200,000 Infectious Units (IU) per mL and 10 μL per well was added to the assay plates containing cells and compounds, for an MOI=0.5. The assay plates were incubated for 3 days at 37° C. and 5% $CO_2$. At the end of incubation, One-Glo reagent (Promega, Madison, WI, Cat #E6120) was prepared. The assay plates and One-Glo reagent were equilibrated to room temperature for at least 15 minutes. 40 μL per well of One-Glo reagent was added and the plates were incubated at room temp for 15 minutes before reading the luminescence signal on an EnVision multimode plate reader (Perkin Elmer. Waltham, MA). Remdesivir was used as positive control and DMSO was used as negative control. Values were normalized to the positive and negative controls (as 0% and 100% replication, respectively) and data was fitted using non-linear regression analysis by Gilead's dose response tool. The $EC_{50}$ value for each compound was then determined as the concentration reducing the viral replication by 50%.

Remdesivir

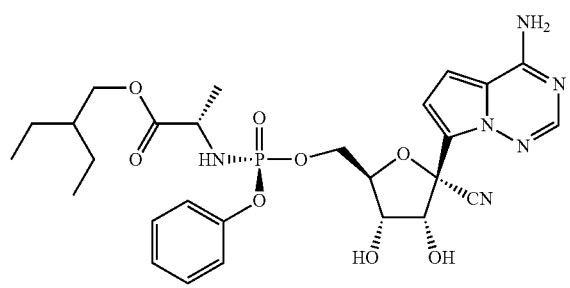 [SMILES: CCC(CC)COC(=O)[C@H](C)N[P@](=O)(OC[C@H]1O[C@@](C#N)(c2ccc3c(N)ncnn23)[C@H](O)[C@@H]1O)Oc1ccccc1]

Example B: A549-hACE2 SARS-CoV2-NLuc 384-Well Assay

A549-hACE2 cell line was maintained in Dulbecco's Minimum Essential Medium (DMEM) (Corning, New York, NY, Cat #15-018CM) supplemented with 10% fetal bovine serum (FBS) (Hyclone, Logan, UT, Cat #SH30071-03), 1× Penicillin-Streptomycin-L-Glutamine (Corning, New York, NY, Cat #30-009-CI) and 10 μg/mL blasticidin (Life Technologies Corporation. Carlsbad, CA, Cat #A11139-03). Cells were passaged 2 times per week to maintain sub-confluent densities and were used for experiments at passage 5-20. SARS Coronavirus 2 recombinant with NanoLuc (SARS-CoV2-NLuc) was obtained from University of Texas Medical Branch (Galveston, TX). Viral replication was determined in A549-hACE2 cells in the following manner.

Compounds are prepared in 100% DMSO in 384-well polypropylene plates (Greiner, Monroe, NC, Cat #784201) with 8 compounds per plate in grouped replicates of 4 at 10 serially diluted concentrations (1:3). The serially diluted compounds were transferred to low dead volume Echo plates (Labcyte. Sunnyvale, CA, Cat #LP-0200).

The test compounds were spotted to 384-well assay plates (Greiner, Monroe, NC, Cat #781091) at 200 nL per well using an Echo acoustic dispenser (Labcyte, Sunnyvale, CA). A549-hACE2 cells were harvested and suspended in DMEM (supplemented with 2% FBS and 1× Penicillin-Streptomycin-L-Glutamine) and seeded to the pre-spotted assay plates at 10,000 cells per well in 30 μL. SARS-CoV2-NLuc virus was diluted in DMEM (supplemented with 2% FBS and 1× Penicillin-Streptomycin-L-Glutamine) at 350,000 Infectious Units (IU) per mL and 10 μL per well was added to the assay plates containing cells and compounds, for an MOI of 0.35. The assay plates were incubated for 2 days at 37° C. and 5% $CO_2$. At the end of incubation. Nano-Glo reagent (Promega, Madison, WI, Cat #N1150) was prepared. The assay plates and Nano-Glo reagent were equilibrated to room temperature for at least 15 minutes. 40 μL per well of Nano-Glo reagent was added and the plates were incubated at room temperature for 15 minutes before reading the luminescence signal on an EnVision multimode plate reader (Perkin Elmer. Waltham, MA). Remdesivir was used as positive control and DMSO was used as negative control. Values were normalized to the positive and negative controls (as 0% and 100% replication, respectively) and data was fitted using non-linear regression analysis by Gilead's dose response tool. The $EC_{50}$ value for each compound was defined as the concentration reducing the viral replication by 50%.

Example C: NHBE RSV-Luc5 384-Well Assay

Normal Human Bronchial Epithelial (NHBE) cells were purchased from Lonza (Walkersville, MD Cat #CC2540) and maintained in BEGM Bronchial Epithelial Cell Growth Medium BulletKit (Lonza CC-3170).

Cells were thawed, expanded, and were used for experiments at passage 2. Respiratory syncytial virus recombinant with luciferase (RSV-Luc5) ($\geq 0.1 \times 10^7$ Infectious Units/ml (IU/ml) determined by $TCID_{50}$) was purchased from Microbiologics (Saint Cloud, MN). Viral replication was determined in NHBE cells in the following manner.

Compounds are prepared in 100% DMSO in 384-well polypropylene plates (Greiner, Monroe, NC, Cat #784201) with 8 compounds per plate in grouped replicates of 4 at 10 serially diluted concentrations (1:3). The serially diluted compounds were transferred to low dead volume Echo plates (Labcyte, Sunnyvale, CA, Cat #LP-0200).

The test compounds were spotted to 384-well assay plates (Greiner, Monroe. NC. Cat #781091) at 200 nL per well. NHBE cells were harvested and suspended in BEGM Bronchial Epithelial Cell Growth Medium BulletKit and seeded to the pre-spotted assay plates at 5,000 cells per well in 30 μL. RSV-Luc5 virus was diluted in BEGM Bronchial Epithelial Cell Growth Medium BulletKit at 500,000 Infectious Units (IU) per mL and 10 μL per well was added to the assay plates containing cells and compounds, for an MOI of 1. The assay plates were incubated for 3 days at 37° C. and 5% $CO_2$. At the end of incubation, One-Glo reagent (Promega, Madison, WI, Cat #E6120) was prepared. The assay plates and One-Glo reagent were equilibrated to room temperature for at least 15 minutes. 40 μL per well of One-Glo reagent was added and the plates were incubated at room temperature for 15 minutes before reading the luminescence signal on an EnVision multimode plate reader (Perkin Elmer, Waltham, MA). Remdesivir was used as positive control and DMSO was used as negative control. Values were normalized to the positive and negative controls (as 0% and 100% replication, respectively) and data was fitted using non-linear regression analysis by Gilead's dose response tool. The $EC_{50}$ value for each compound was defined as the concentration reducing the viral replication by 50%.

Example D: CC50 MT4

Cytotoxicity of the compounds was determined in uninfected cells using the cell viability reagent in a similar fashion as described before for other cell types (Cihlar et al., Antimicrob Agents Chemother. 2008, 52(2):655-65). HEp-2 (1.5×103 cells/well) and MT-4 (2×103 cells/well) cells were plated in 384-well plates and incubated with the appropriate medium containing 3-fold serially diluted compound ranging from 15 nM to 100,000 nM. Cells were cultured for 4-5 days at 37° C. Following the incubation, the cells were allowed to equilibrate to 25° C., and cell viability was determined by adding Cell-Titer Glo viability reagent. The mixture was incubated for 10 min, and the luminescence signal was quantified using an Envision plate reader. Untreated cell and cells treated at 2 μM puromycin (Sigma, St. Louis, MO) serve as 100% and 0% cell viability control, respectively. The percent of cell viability was calculated for each tested compound concentration relative to the 0% and 100% controls and the $CC_{50}$ value was determined by non-linear regression as a compound concentration reducing the cell viability by 50%.

TABLE D1

| Example | Compound No. | RSV Hep2 $EC_{50}$ (nM) | RSV NHBE $EC_{50}$ (nM) | SARS-CoV2 $EC_{50}$ (nM) | MT4 $CC_{50}$ (μM) |
|---|---|---|---|---|---|
| Example 1 | 1 | 422 | 2184 | 1871 | >46443 |
| Example 2 | 2 | 6608 | 9599 | >50000 | >50000 |
| Example 3 | 3 | 545 | 1597 | 796 | >50000 |
| Example 4 | 4 | 606 | 774 | 2672 | >50000 |
| Example 5 | 5 | 2903 | 3550 | 13227 | >50000 |
| Example 6 | 6 | 1115 | 1008 | 4416 | >50000 |
| Example 7 | 7 | 416 | 1341 | 915 | 47440 |
| Example 8 | 8 | 301 | 1838 | 1014 | >50000 |
| Example 9 | 9 | 784 | 1809 | 2276 | >50000 |
| Example 10 | 10 | 3965 | 2990 | 14065 | >50000 |
| Example 11 | 11 | 4940 | 2920 | 20589 | >50000 |
| Example 12 | 12 | 659 | 1584 | 2349 | >50000 |
| Example 13 | 13 | 444 | 1533 | 1249 | 39140 |
| Example 14 | 14 | 350 | 380 | 1557 | >50000 |
| Example 15 | 15 | 530 | 900 | 1236 | >50000 |
| Example 16 | 16 | 1151 | 981 | 2570 | 27787 |
| Example 17 | 17 | 412 | 1902 | 814 | >50000 |
| Example 18 | 18 | 2872 | 12124 | 12375 | >50000 |
| Example 19 | 19 | 1241 | 5402 | 7701 | >50000 |
| Example 20 | 20 | 2019 | 4354 | 8985 | >50000 |
| Example 21 | 21 | 2383 | 2253 | 12903 | >50000 |

TABLE D2

| Example No. | Compound No. | RSV Hep2 $EC_{50}$ (nM) | RSV NHBE $EC_{50}$ (nM) | SARS-CoV2 $EC_{50}$ (nM) | MT4 $CC_{50}$ (μM) |
|---|---|---|---|---|---|
| Example 22 | 46 | 2324 | 1182 | 4297 | >50000 |
| Example 23 | 47 | 2331 | 1476 | 3358 | >50000 |
| Example 24 | 48 | 2348 | 167 | 14195 | 25480 |
| Example 25 | 49 | >50000 | 17653 | 14251 | >50000 |
| Example 26 | 50 | 1916 | 1371 | 20444 | >50000 |
| Example 27 | 51 | 2140 | 727 | 7834 | 38296 |
| Example 28 | 52 | 100 | 919 | 574 | 38813 |
| Example 29 | 53 | 98 | 833 | 662 | >50000 |
| Example 30 | 29 | 109 | 1305 | 835 | >50000 |
| Example 31 | 54 | 587 | 1015 | 5691 | >50000 |
| Example 32 | 55 |  | 1336 | 2895 | >50000 |
| Example 33 | 56 | 1262 | 1212 | 2521 | >50000 |
| Example 34 | 57 |  | 2451 | 2291 | >50000 |
| Example 35 | 58 | 1359 | 1067 | 2241 | 27077 |
| Example 36 | 59 | 786 | 811 | 4164 | >50000 |
| Example 37 | 60 |  | 1582 | 2685 | 32945 |
| Example 38 | 35 | 650.55 | 1007 | 1907.3 | >50000 |
| Example 39 | 62 | >50000 | 5000 | 5000 | >50000 |
| Example 40 | 63 |  | 41618 | >50000 | >50000 |
| Example 42 | 64 |  | 2656.4 | 4205.4 | >50000 |
| Example 43 | 65 | 1080.1 | 184.94 | 3639.6 | >50000 |
| Example 44 | 66 | 847.01 | 499.24 | 3207.5 | >50000 |
| Example 45 | 67 |  | 1516.4 | 12832 | >50000 |
| Example 46 | 68 |  | 1302.5 | 3134.8 | >50000 |
| Example 47 | 69 | 1047 | 987.97 | 2830.7 | >50000 |
| Example 48 | 70 | 1721.9 | 2183.9 | 2813.1 | >50000 |
| Example 49 | 71 | 3014.8 | 531.5 | 7821.4 | 47754 |
| Example 50 | 72 | 779.49 | 1823.9 | 1125.9 | >50000 |
| Example 51 | 73 | 206.06 | 1104.6 | 1899.7 | >50000 |
| Example 52 | 74 |  | 955.83 | 2401.3 | >50000 |
| Example 53 | 75 | 1029.6 | 321.26 | 5061 | >50000 |
| Example 54 | 76 |  | 3398.6 | >50000 | >50000 |
| Example 55 | 77 |  | >50000 | >50000 | >50000 |
| Example 56 | 78 |  | 3599.4 | 3579.7 | >50000 |
| Example 57 | 79 |  | >50000 | >50000 | >50000 |
| Example 58 | 80 |  | 2043.8 | >50000 | >50000 |
| Example 59 | 81 |  | 996.33 | 24444 | 48302 |

TABLE D2-continued

| Example No. | Compound No. | RSV Hep2 EC$_{50}$ (nM) | RSV NHBE EC$_{50}$ (nM) | SARS-CoV2 EC$_{50}$ (nM) | MT4 CC$_{50}$ (µM) |
|---|---|---|---|---|---|
| Example 60 | 82 | | 2410.6 | 1550.3 | >50000 |
| Example 61 | 83 | | 2322.7 | 24534 | 20973 |
| Example 62 | 84 | 311.46 | 205.36 | 1540.3 | >50000 |
| Example 63 | 85 | 165.82 | 776.15 | 416.99 | >50000 |
| Example 64 | 86 | 371.12 | 1219.1 | 623.01 | >50000 |
| Example 65 | 87 | 344.61 | 559.34 | 1052.8 | >50000 |
| Example 66 | 88 | 381.87 | 70.228 | 1627.6 | >50000 |
| Example 67 | 89 | 664.66 | 977.86 | 2689.6 | >50000 |
| Example 68 | 90 | 248.91 | 180.43 | 1842.9 | >50000 |
| Example 69 | 91 | 3641.3 | 5837.2 | 14745 | >50000 |
| Example 70 | 92 | 1804.2 | 3044.8 | 5630.6 | >50000 |
| Example 71 | 93 | | 11095 | 10611 | 31711 |
| Example 72 | 31 | 321.66 | 802.6 | 1083.1 | >50000 |
| Example 73 | 94 | 1018.6 | 922.57 | 3630.3 | >50000 |
| Example 74 | 27 | 144.96 | 1007.7 | 657.85 | >50000 |
| Example 75 | 96 | | >50000 | | >50000 |
| Example 76 | 97 | | 6158 | | |
| Example 77 | 98 | | 8999 | | |
| Example 78 | 99 | | 3153 | | |
| Example 79 | 100 | >50000 | 16023 | | >50000 |
| Example 81 | 37 | | 4746 | 3152 | >50000 |
| Example 80 | 26 | 942 | 844 | 2389 | >50000 |
| Example 82 | 127 | | 5059.8 | 13659 | >50000 |
| Example 83 | 128 | | 2038.1 | 7232 | >50000 |
| Example 84 | 129 | | 672.72 | 5831.3 | >50000 |
| Example 85 | 130 | | 2961.7 | 9042.9 | >50000 |
| Example 86 | 131 | | 4786.5 | 8260.1 | >50000 |
| Example 87 | 132 | | >50000 | >50000 | >50000 |
| Example 88 | 133 | | >50000 | >50000 | >50000 |
| Example 89 | 134 | | 1403.6 | 5134 | >50000 |
| Example 90 | 135 | | >50000 | >50000 | >50000 |
| Example 91 | 136 | | 2033 | 4695.8 | >50000 |
| Example 92 | 106 | | 1396 | 4560.4 | >50000 |

TABLE D3

| Example No. | Compound No. | EC50 SARS CoV2 NanoLuc A549 384 | EC50 RSVFluc-NHBE 384 V2 | EC50 RSVFluc-Hep2 384 V2 | CC50 MT4 384 | DM logD |
|---|---|---|---|---|---|---|
| 93 | 101 | 3208.9 | 1961.1 | 1844.5 | >50000 | 0.9 |
| 94 | 110 | | 20370 | 10833 | >50000 | 1.7 |
| 95 | 40 | | 3691.5 | 3552.2 | >50000 | <0.3 |
| 96 | 103 | >50000 | 17666 | 20673 | >50000 | 3.2 |
| 97 | 107 | >50000 | >50000 | >50000 | >50000 | 2.5 |
| 98 | 125 | 1789.8 | 645.07 | 219.77 | >50000 | 1.1 |
| 99 | 120 | 1412.7 | 1255.6 | 816.34 | >50000 | 1.6 |
| 100 | 121 | 7965.6 | 1556.7 | 1506 | >50000 | 1.1 |
| 101 | 112 | 2110.6 | 453.83 | 181.13 | >50000 | 1.8 |
| 102 | 114 | 1116.1 | 965.54 | 122.66 | >50000 | 1.5 |
| 103 | 115 | 1756.1 | 989.53 | 227.55 | >50000 | 1.4 |
| 104 | 116 | 822.27 | 864.47 | 320.84 | >50000 | 2.1 |
| 105 | 117 | 777.79 | 1376.3 | 493.91 | >50000 | 2.3 |
| 106 | 118 | 6803.9 | 1819.5 | 1763.4 | >50000 | 0.7 |
| 107 | 119 | 8824.9 | 2193.2 | 2204.4 | >50000 | 0.9 |
| 108 | 122 | 707.08 | 1044.3 | 289.92 | >50000 | 1.9 |
| 109 | 123 | 1161.1 | 1805.6 | 719.86 | >50000 | 2.2 |
| 110 | 137 | >50000 | 9519.7 | >50000 | >50000 | 2 |
| 111 | 138 | 21191 | >50000 | | >50000 | 2 |
| 112 | 139 | 808.09 | 1638.9 | | >50000 | 2.2 |
| 113 | 124 | 1140.4 | 624.88 | 723.04 | 27580.7 | 3.7 |
| 114 | 126 | 1608.8 | 517.37 | | 27659.6 | >5.7 |
| 115 | 140 | >50000 | >50000 | | >50000 | <0.3 |
| 116 | 141 | >50000 | >50000 | | >50000 | <0.3 |
| 117 | 142 | >50000 | >50000 | | >50000 | <0.3 |
| 118 | 143 | 35388 | >50000 | | >50000 | <0.3 |
| 119 | 144 | >50000 | 3056.6 | | >50000 | 0.4 |
| 120 | 145 | 3484.7 | 3148.8 | | >50000 | 1.85 |
| 121 | 146 | 7678.9 | 8252.4 | | >50000 | 1.5 |
| 122 | 147 | 2849.4 | 2467.2 | | >50000 | 2.5 |
| 123 | 148 | 2050.9 | 2104.7 | | >50000 | 2.7 |

TABLE D3-continued

| Example No. | Compound No. | EC50 SARS CoV2 NanoLuc A549 384 | EC50 RSVFluc-NHBE 384 V2 | EC50 RSVFluc-Hep2 384 V2 | CC50 MT4 384 | DM logD |
|---|---|---|---|---|---|---|
| 124 | 149 | 2420.7 | 2548 | | >50000 | 2.2 |
| 125 | 150 | 2368.9 | 3075.3 | | >50000 | 1.3 |
| 126 | 151 | 2756.1 | 2892.3 | | >50000 | 1.3 |
| 127 | 152 | 1280.5 | 3633.4 | | >50000 | 2.2 |
| 128 | 153 | 2673.9 | 3237.3 | | >50000 | 1.7 |
| 129 | 111 | 3424.1 | 1298 | 220.04 | >50000 | 1.5 |
| 131 | 154 | 33999 | 10998 | 11717 | >50000 | 2.6 |
| 133 | 156 | 31442 | 49847 | | >50000 | 0.3 |
| 132 | 155 | 3186.1 | 1123.3 | 1566.7 | >50000 | 2.8 |

Example E. Rat Pharmacokinetics Assay

Ester Reference Compound, Compounds 1 to 4, Compound 6, and Compound 10 were dosed orally by gavage to male Sprague-Dawley rats (n=3/group); Ester Reference Compound at 6 mg/kg in 2.5% Dimethyl sulfoxide; 10% Kolliphor HS-15; 10% Labrasol; 2.5% Propylene glycol and 75% water, pH 2.5; Compound 1 at 6.7 mg/kg and Compound 3 at 7.0 mg/kg in 2.5% Dimethyl sulfoxide; 10% Kolliphor HS-15; 10% Labrasol; 2.5% Propylene glycol and 75% water, pH 5.9; Compound 2 at 8.4 mg/kg in 10% Dimethyl sulfoxide, 40% Kolliphor HS-15; 40% Labrasol and 10% Propylene glycol and $3^{rd}$ Ester Reference Compound at 6.7 mg/kg, Compound 4 at 6.5 mg/kg, Compound 6 at 6.2 mg/kg, Compound 10 at 6.8 mg/kg and Compound 128 and Compound 129 at 75 mg/kg in 2.5% Dimethyl sulfoxide; 10% Kolliphor HS-15; 10% Labrasol; 2.5% Propylene glycol and 75% water, pH 5.8. Blood samples were collected into pre-chilled collection tubes containing $K_2EDTA$ and processed to plasma at 10 time points over a span of pre-dose to 24 h post-administration. Plasma samples were subject to protein precipitation with a 12.5-fold volume of methanol, vortexed and centrifuged. Supernatants were transferred and evaporated to dryness under nitrogen and reconstituted with 5% acetonitrile in water. Separation was achieved on a Phenomenex Synergi Polar-RP column, a mobile phase A of 10 mM ammonium formate with 0.1% formic acid in water and a mobile phase B of 0.1% formic acid in acetonitrile with a step-wise linear gradient from 5 to 95% mobile phase B. An LCMS/MS method was used to measure the concentrations of the Reference Compound A and either Ester Reference Compound, $3^{rd}$ Ester Reference Compound, Compounds 1-4, Compound 6, Compound 10, Compound 128 or Compound 129 in plasma. Data for Reference Compound A following oral administration of either Ester Reference Compound, $3^{rd}$ Ester Reference Compound, Compounds 1 to 4, Compound 6, Compound 10, Compound 128 or Compound 129 is tabulated below.

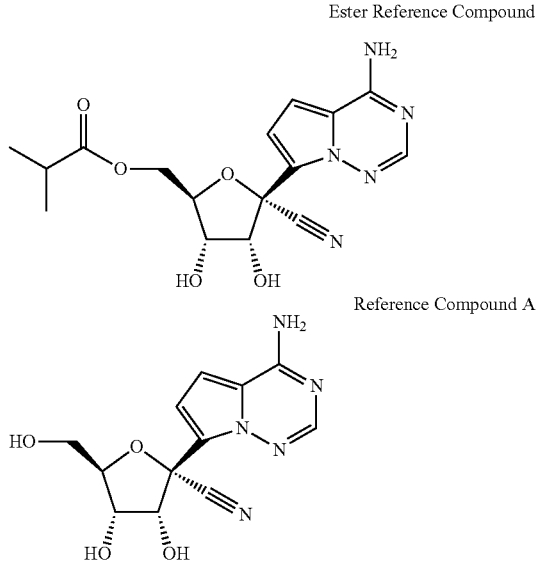

TABLE E1

| Compound No. | Oral Dose mg/kg | Oral Dose (mg-eq Reference Compound A)/kg | Reference Compound A $C_{max}$ (nM) | Reference Compound A $AUC_{inf.}$ (nM.h) | Reference Compound A F%[a] |
|---|---|---|---|---|---|
| Ester Reference Compound | 6 | 4.8 | 2100 | 7570 | 63.6 |
| $3^{rd}$ Ester Reference Compound | 6.7 | 5 | 4910 | 12000 | 101 |
| 1 | 6.7 | 5 | 2760 | 9720 | 77.1 |
| 2 | 8.4 | 5 | 2000 | 8620 | 68.4 |
| 3 | 7.0 | 5 | 5330 | 12200 | 96.6 |
| 4 | 6.5 | 5 | 5470 | 10200 | 81.0 |

TABLE E1-continued

| Compound No. | Oral Dose mg/kg | Oral Dose (mg-eq Reference Compound A)/kg | Reference Compound A $C_{max}$ (nM) | Reference Compound A $AUC_{inf.}$ (nM.h) | Reference Compound A F%[a] |
|---|---|---|---|---|---|
| 6 | 6.2 | 5 | 2130 | 7630 | 60.6 |
| 10 | 6.8 | 5 | 1790 | 6320 | 50.1 |
| 128 | 75 | 50.4 | 37600 | 136000 | 107 |
| 129 | 75 | 48.8 | 29300 | 132000 | 107 |

[a]based on reference compound A mg-eq/kg dose; using IV data from 1 mg/kg dose of reference compound A Example F: Monkey Pharmacokinetics Assay Ester Reference Compound, Compounds 1 to 4, Compound 6, and Compound 10 were dosed orally by gavage to male rhesus monkeys (n=3/group); Ester Reference Compound at 12.4 mg/kg in 2.5% DMSO; 10% Kolliphor HS-15; 10% Labrasol; 2.5% Propylene glycol and 75% water, pH 2.2; Compound 1 at 13.4 mg/kg and Compound 3 at 13.9 mg/kg in 2.5% DMSO; 10% Kolliphor HS-15, 10% Labrasol; 2.5% Propylene glycol and 75% water, Compound 2 at 16.9 mg/kg in 10% Dimethyl sulfoxide; 40% Kolliphor HS-15: 40% Labrasol and 10% Propylene glycol and Compound 4 at 13.0 mg/kg, Compound 6 at 12.5 mg/kg and Compound 10 at 13.5 mg/kg in 2.5% Dimethyl sulfoxide; 10% Kolliphor HS-15: 10% Labrasol; 2.5% Propylene glycol and 75% water, pH 5.8. Blood samples were collected into pre-chilled collection tubes containing $K_2EDTA$ with dichlorvos (2 mM final concentration with blood added) and processed to plasma at 10 timepoints over a span of pre-dose to 24 h post-administration. Plasma samples were subject to protein precipitation with a 12.5-fold volume of methanol, vortexed and centrifuged. Supernatants were transferred and evaporated to dryness under nitrogen and reconstituted with 5% acetonitrile in water. Separation was achieved on a Phenomenex Synergi Polar-RP column, a mobile phase A of 10 mM ammonium formate with 0.1% formic acid in water and a mobile phase B of 0.1% formic acid in acetonitrile with a step-wise linear gradient from 5 to 95% mobile phase B. An LC-MS/MS method was used to measure the concentrations of the Reference Compound A and either Ester Reference Compound, Compounds 1 to 4. Compound 6, or Compound 10 in plasma. Data for Reference Compound A following oral administration of either Ester Reference Compound, Compounds 1 to 4, Compound 6, or Compound 10 is tabulated below.

Ester Reference Compound

-continued

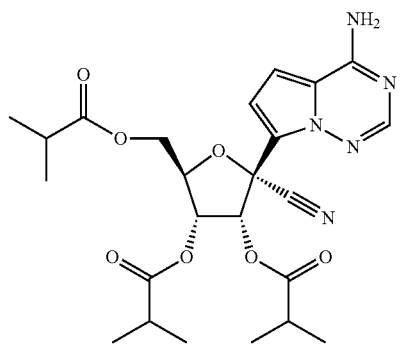

2nd Ester Reference Compound

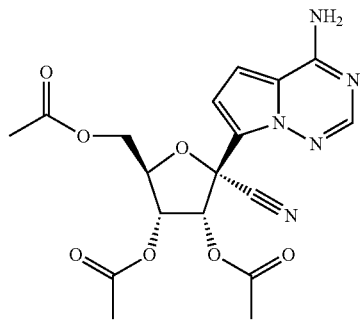

3rd Ester Reference Compound

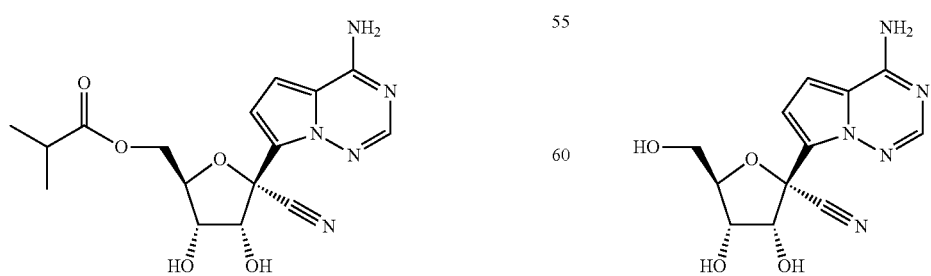

Reference Compound A

TABLE F1

| Compound No: | Oral Dose mg/kg | Oral Dose (mg-eq Reference Compound A)/kg | Reference Compound A $C_{max}$ (nM) | Reference Compound A $AUC_{inf.}$ (nM.h) | Reference Compound A F %[a] |
|---|---|---|---|---|---|
| Ester Reference Compound | 12.4 | 10 | 4100 | 11300 | 18.9 |
| 1 | 13.4 | 10 | 5770 | 21900 | 36.4 |
| 2 | 16.9 | 10 | 1600 | 12500 | 20.8 |
| 3 | 13.9 | 10 | 10500 | 26400 | 43.9 |
| 4 | 13.0 | 10 | 6650 | 25700 | 42.8 |
| 6 | 12.5 | 10 | 7790 | 27300 | 45.6 |
| 10 | 13.5 | 10 | 3300 | 11600 | 19.3 |

| Compound No. | Example No. | Oral Dose (mg-eq Reference Compound A)/kg | Reference Compound A $C_{max}$ (nM) | Reference Compound A $AUC_{inf.}$ (nM.h) | Reference Compound A F %[a] |
|---|---|---|---|---|---|
| 4 | 4 | 25.5 | 14900 | 74800 | 47 |
| 48 | 24 | 31.3 | 8270 | 44100 | 23 |
| 145 | 120 | 31.8 | 6510 | 25200 | 13 |
| 97 | 76 | 28.2 | 10900 | 44500 | 25 |
| 128 | 83 | 26.5 | 20500 | 78900 | 48 |
| 129 | 84 | 25.2 | 32200 | 90200 | 58 |
| Reference Ester Compound | — | 9.43 | 7570 | 21800 | 37 |
| 2nd Reference Ester Compound | — | 11.6 | 7830 | 34300 | 48 |
| 3rd Reference Ester Compound | — | 11.6 | 10500 | 37900 | 53 |

[a]based on reference compound A mg-eq/kg dose; using IV data from 1 mg/kg dose of reference compound A.PK for Compound 4, Compound 48, Compound 97, Compound 128, Compound 129, Compound 145, Ester Reference Compound, 2nd Ester Reference Compound, and 3rd Ester Reference Compound was determined in cynomolgus monkeys by analogus procedure described above for rhesus monkeys.

Example G: GI S9 Stability

Duplicate aliquots of test compound or positive control substrate (GS-7340) were added to S9 stock diluted with 100 mM phosphate buffered saline, pH 7.4, to obtain a protein concentration of 1.0 mg/mL. The S9 metabolic reactions were initiated by the addition of the substrates to the S9 reaction mixture to a final concentration of 2 µM. At 0, 10, 20, 30, 60 and 120 min, 25 mL aliquots of the reaction mixture were transferred to plates containing 225 ml of IS/Q solution. After quenching, the plates were centrifuged at 3000 g for 30 minutes, and 150 µL aliquots of each supernatant were diluted with 150 µL water. Aliquots (10 mL) of the diluted supernatant were analyzed on a Thermo Q-Exactive mass spectrometer as described below.

GI S9 Stability—No phenylmethylsulfonyl fluoride (PMSF): Similar to the procedure described above, test compounds were incubated at 2 µM with 1 mg/mL PMSF-free Intestinal S9 fractions. Samples are removed at 6 time points over the course of a 120 min experiment and the parent compound disappreance and reference compound A formation is determined by mass spectrometry.

G1 stability data for select compounds is presented in Table K1 below and in FIG. 1.

Example H: Plasma Stability

Duplicate aliquots of plasma were warmed to 37° C. and the metabolic reactions initiated by the addition of test compound (6 mL of 0.1 mM DMSO stock) or plasma stability standard (GS-7340) to obtain a final substrate concentration of 2 µM. At 0.05, 0.5, 1, 2, 3 and 4 hr, 25 mL aliquots of the reaction mixture were transferred to plates containing 225 ml of IS/Q quenching solution. After quenching, the plates were centrifuged at 3000 g for 30 minutes, and 150 µL supernatant was diluted with 150 µL water. Aliquots (10 mL) of the diluted supernatant were analyzed on a Thermo Q-Exactive mass spectrometer as described below.

Example I: CES1/2 Stability

Test compounds or positive control substrates (oseltamivir for CES1 enzymes or procaine for CES2) were incubated with individual Supersome preparations (final CES concentration 1.5 mg/ml) in 0.1 M potassium phosphate buffer (pH 7.4) at 37° C. Substrates were added to a final concentration of 2 µM to initiate the reaction. The final incubation volume was 250 mL. Aliquots were removed after incubation for 0, 10, 30, 60 and 120 min. The reactions were stopped by the addition of IS/Q. Following protein precipitation and centrifugation, 150 mL of supernatant was diluted with an equal volume of water prior to LC-MS analysis. For procaine 150 mL of supernatant was dried down and reconstituted with 250 mL water. All samples were analyzed by LC-MS and the PAR values were used for quantification.

Example J: Hepatic S9 Stability

Duplicate aliquots of test compound or positive control substrate (GS-7340) were added to S9 stock diluted with 100 mM potassium phosphate buffer, pH 7.4, to obtain a protein concentration of 2.4 mg/mL. The S9 metabolic reactions were initiated by the addition of the substrates to the S9 reaction mixture to a final concentration of 2 μM. At 2, 12, 25, 45, 65 and 90 min, 25 mL aliquots of the reaction mixture were transferred to plates containing 225 ml of IS/Q solution. After quenching, the plates were centrifuged at 3000 g for 30 minutes, and 150 μL aliquots of each supernatant were diluted with 150 μL water. Aliquots (10 mL) of the diluted supernatant were analyzed on a Thermo Q-Exactive mass spectrometer as described below.

Example K: Liquid Chromatography/Mass Spectroscopy Methods for S9 and Plasma Stability Quantification of test compounds, Reference Compound A (S9 stability assay nucleoside metabolite), and controls was performed by analyte/internal standard peak area ratio (PAR) values measured on a Thermo Q-Exactive mass spectrometer coupled to a Dionex UtiMate 3000 HPLC with a Leap Technologies HTC PAL autosampler. The column used for analysis of test compounds and Reference Compound A was a Waters Acquity BEH C18 (1.7 mm particle size, 2.1'50 mm). The column used for control (GS-7340) was a Thermo Hypersil GOLD (1.9 mm particle size, 2.1'50 mm). Mobile phase A consisted of 0.1% (v/v) formic acid in water. Mobile phase B consisted of 0.1% (v/v) formic acid in acetonitrile. Elution of analytes was achieved by a series of linear gradients of acetonitrile in water containing 0.1% (v/v) formic acid. The mass spectrometer was calibrated on a weekly basis and mass tolerance of 5 ppm was used.

TABLE K1

| Example No. | Compound No. | GIS9 Human T1/2 | GIS9-HUMAN-NOPMSF T1/2 | STA Human Plasma 37 |
|---|---|---|---|---|
| 1 | 1 | 112.79 | 1.45 | 28.434 |
| 2 | 2 | 156.56 | | 344.3 |
| 3 | 3 | 81.045 | 0.8 | 82.745 |
| 4 | 4 | 252.67 | 0.903 | 107.92 |
| 5 | 5 | 789 | 74.831 | 1388.9 |
| 6 | 6 | 712.67 | 4.085 | 55.852 |
| 7 | 7 | 53.99 | | 6.563 |
| 8 | 8 | 159.49 | 0.58 | 11.698 |
| 9 | 9 | 311.41 | | 156.68 |
| 10 | 10 | 789 | | 43.569 |
| 11 | 11 | 789 | | 135.19 |
| 12 | 12 | 57.974 | | 35.623 |
| 13 | 13 | 35.305 | | 3 |
| 14 | 14 | 56.255 | 1.067 | 262.42 |
| 15 | 15 | 33.113 | | 40.503 |
| 16 | 16 | 1.007 | | 30.6 |
| 17 | 17 | | | |
| 18 | 18 | | | |
| 19 | 19 | 27.405 | | 1584 |
| 20 | 20 | | | |
| 21 | 21 | | | |
| 22 | 46 | 439.12 | 144.53 | 553.13 |
| 23 | 47 | | 151.4 | 1584 |
| 24 | 48 | | 10.1 | 1584 |
| 25 | 49 | | 521.7 | 1584 |
| 26 | 50 | | 15.231 | 430.4 |
| 27 | 51 | | 10.969 | 1366.8 |
| 28 | 52 | | 0.655 | 85 |
| 29 | 53 | | 0.636 | 13 |
| 30 | 29 | | 0.617 | 139 |
| 31 | 54 | 692.28 | 4.325 | 108 |
| 32 | 55 | | 0.596 | 75.665 |
| 33 | 56 | | 16.5 | 77.644 |
| 34 | 57 | | | 317.5 |
| 35 | 58 | | 1.191 | 1584 |
| 36 | 59 | 1.435 | 0.869 | 84.318 |
| 37 | 60 | | 44.853 | 1584 |
| 38 | 35 | | 0.593 | 139.6 |
| 39 | 62 | 31.066 | | 488.7 |
| 40 | 63 | | 181.47 | 1584 |
| 42 | 64 | | 0.993 | 3 |
| 43 | 65 | | 0.621 | 14.9 |
| 44 | 66 | | 0.491 | 24.2 |
| 45 | 67 | | 10.467 | 1177.1 |
| 46 | 68 | | 46.06 | 266.43 |
| 47 | 69 | | 48.7 | 294.49 |
| 48 | 70 | | 72.972 | 1399.3 |
| 49 | 71 | | 25.8 | 1584 |
| 50 | 72 | | 0.623 | 31.1 |
| 51 | 73 | | 0.588 | 70 |
| 52 | 74 | | 30.32 | 205.11 |
| 53 | 75 | | 0.884 | 277.1 |
| 54 | 76 | | 38.86 | 1584 |
| 55 | 77 | | 792 | 383.67 |
| 56 | 78 | | 72.07 | 336.23 |
| 57 | 79 | | 0.681 | 17.837 |
| 58 | 80 | | 0.847 | 604.23 |
| 59 | 81 | | 0.688 | 195.87 |
| 60 | 82 | | 2 | 193.22 |
| 61 | 83 | | 12.1 | 1584 |
| 62 | 84 | | 0.955 | 327.2 |
| 63 | 85 | | 0.621 | 38.6 |
| 64 | 86 | | 0.684 | 48.6 |
| 65 | 87 | | 1.248 | 28.7 |
| 66 | 88 | | 4.912 | 1584 |
| 67 | 89 | | 0.59 | 188.5 |
| 68 | 90 | | 0.591 | 169.9 |
| 69 | 91 | | 41.971 | 285 |
| 70 | 92 | | 237.8 | 139.9 |
| 71 | 93 | | 1.017 | 28.444 |
| 72 | 31 | | 0.857 | 32.4 |
| 73 | 94 | | 1.13 | 105.4 |
| 74 | 113 | | 0.605 | 35.4 |
| 75 | 96 | | 789 | 1584 |
| 76 | 97 | | 3.645 | 6.669 |
| 77 | 98 | | 789 | 884.09 |
| 78 | 99 | | 96.647 | 173.49 |
| 79 | 100 | | | |
| 80 | 26 | | 0.487 | 33.7 |
| 81 | 37 | | 0.589 | 53 |
| 82 | 127 | | 0.957 | 12.071 |
| 83 | 128 | | 0.59 | 9.735 |
| 84 | 129 | | 0.623 | 3 |
| 85 | 130 | | 1.586 | 409.28 |
| 86 | 131 | | 2.64 | 150.92 |
| 87 | 132 | | 0.624 | 12.304 |
| 88 | 133 | | 0.623 | 73.357 |
| 89 | 134 | | | 65.405 |
| 90 | 135 | | 0.653 | 96.462 |
| 91 | 136 | | 1.013 | 463.08 |
| 92 | 106 | | 0.66 | 30.917 |
| 98 | 125 | | 0.582 | 12.2 |
| 99 | 120 | | 0.605 | 38.7 |
| 100 | 121 | | 1.583 | 107.7 |
| 101 | 112 | | 1.774 | 28.8 |
| 102 | 114 | | 1.212 | 26.8 |
| 103 | 115 | | 0.581 | 41.2 |
| 104 | 116 | | 0.63 | 26.4 |
| 105 | 117 | | 0.616 | 86 |
| 106 | 118 | | 4.115 | 59.4 |
| 107 | 119 | | 2.982 | 40.7 |
| 108 | 122 | | 0.637 | 34.1 |
| 109 | 123 | | 0.615 | 96.5 |
| 110 | 137 | | 8.055 | 676.3 |
| 112 | 139 | | 1.368 | 150.07 |
| 113 | 124 | | 0.744 | 192.3 |
| 114 | 126 | | 97.584 | 79.1 |
| 115 | 140 | | 783.41 | 1322.1 |
| 116 | 141 | | 789 | 902.37 |
| 117 | 142 | | 789 | 1584 |
| 118 | 143 | | 789 | 800.58 |
| 120 | 145 | | 32.763 | 299.49 |
| 121 | 146 | | 174.12 | 497.93 |
| 129 | 111 | 53.11 | 3.928 | 35 |

TABLE K1-continued

| Example No. | Compound No. | GIS9 Human T1/2 | GIS9-HUMAN-NOPMSF T1/2 | STA Human Plasma 37 |
|---|---|---|---|---|
| 131 | 154 | | 278.9 | 1584 |
| 133 | 156 | | 789 | 248.79 |
| 132 | 155 | | 77.5 | 1584 |

Example L: CACO-2 Permeability

Pre-plated Caco-2 cells (clone C2BBe1) were obtained from Sigma-Aldrich, Inc. (Atlanta, GA). Cell monolayers were grown to confluence on collagen-coated, microporous, polycarbonate membranes in 24-well transwell plates for 21 days. The permeability assay buffer in donor wells was Hanks' balanced salt solution (HBSS) containing 10 mM HEPES and 15 mM glucose at a pH of 6.5 containing 200 µM BNPP. The receiver wells used HBSS buffer containing 10 mM HEPES and 15 mM glucose at a pH of 7.4 and supplemented with 1% BSA. After an initial equilibration with transport buffer, TEER values were read to test membrane integrity. The experiment was started by the addition of buffers containing test compounds, 200 µl and 1000 µl in the apical and basolateral chamber, respectively. At 0- and 2-hour post dose, 10 µL was sampled from donor compartment and was immediately diluted in 190 µL of 20% methanol. At 1 and 2 hours post dose, 100 µl of solution was taken from the receiver compartments and was immediately diluted in 100 µl of 20% methanol. Removed buffer was replaced with fresh buffer and a correction was applied to all calculations for the removed material. Each compound was tested in 2 separate replicate wells for each condition. All samples were then extracted with 400 µl 110M % acetonitrile with internal standard to precipitate protein. Cells were dosed on the apical or basolateral side to determine forward (A to B) and reverse (B to A) permeability. To test for non-specific binding and compound instability, the total amount of drug was quantitated at the end of the experiment and compared to the material present in the original dosing solution as a percent recovery. Formation of the parent compound (GS-441524; Reference Compound A) was monitored in assay wells dosed with the prodrug. Samples were analyzed by LC-MS/MS.

TABLE L1

| Example No | Compound No. | DM Caco2 A to B | DM Caco2 B to A |
|---|---|---|---|
| 1 | 1 | 0.275 | 3.853 |
| 2 | 2 | 1.17 | 8.69 |
| 3 | 3 | 1.23 | 9.8 |
| 4 | 4 | 0.545 | 5.29 |
| 5 | 5 | | |
| 6 | 6 | 0.21 | 2.77 |
| 7 | 7 | 0.52 | 8.98 |
| 8 | 8 | | |
| 9 | 9 | 0.39 | 5.17 |
| 10 | 10 | 0.08 | 1.39 |
| 11 | 11 | | |
| 12 | 12 | 1.15 | 13.73 |
| 13 | 13 | 0.59 | 8.8 |
| 14 | 14 | 1.84 | 21.7 |
| 15 | 15 | 1.46 | 12 |
| 16 | 16 | | |
| 17 | 17 | | |
| 18 | 18 | | |
| 19 | 19 | | |
| 20 | 20 | | |
| 21 | 21 | 1.36 | 8.33 |
| 22 | 46 | 0.76 | 10.66 |
| 23 | 47 | 1.68 | 11.38 |
| 24 | 48 | 6.19 | 12.52 |
| 25 | 49 | 0.13 | 3.48 |
| 26 | 50 | 0.13 | 2.76 |
| 27 | 51 | 4.35 | 17.19 |
| 28 | 52 | 6.95 | 13.04 |
| 29 | 53 | 2.34 | 10.58 |
| 30 | 29 | 1.91 | 12.29 |
| 31 | 54 | 0.25 | 3.8 |
| 32 | 55 | 0.38 | 1.89 |
| 33 | 56 | 0.35 | 1.83 |
| 34 | 57 | | |
| 35 | 58 | 5.67 | 6.86 |
| 36 | 59 | 11.61 | 17.7 |
| 37 | 60 | 0.12 | 0.32 |
| 38 | 35 | 0.95 | 10.64 |
| 39 | 62 | 4.19 | 12.12 |
| 40 | 63 | 1.18 | 12.46 |
| 42 | 64 | 0.39 | 4.6 |
| 43 | 65 | 3.07 | 7.23 |
| 44 | 66 | | |
| 45 | 67 | 0.99 | 9.76 |
| 46 | 68 | 0.98 | 7.09 |
| 47 | 69 | 1 | 4.74 |
| 48 | 70 | 0.88 | 6.91 |
| 49 | 71 | 4.02 | 13.65 |
| 50 | 72 | 2.52 | 10.69 |
| 51 | 73 | 0.48 | 4.69 |
| 52 | 74 | 3.25 | 9.88 |
| 53 | 75 | | |
| 54 | 76 | 2.13 | 12.17 |
| 55 | 77 | 0.27 | 5.58 |
| 56 | 78 | 0.2 | 4.2 |
| 57 | 79 | 0.61 | 9.26 |
| 58 | 80 | 1.35 | 0.95 |
| 59 | 81 | 7.77 | 14.74 |
| 60 | 82 | 2.73 | 20.67 |
| 61 | 83 | 5.3 | 25.42 |
| 62 | 84 | 0.27 | 6.99 |
| 63 | 85 | | |
| 64 | 86 | | |
| 65 | 87 | 1.79 | 10.98 |
| 66 | 88 | 2.72 | 12.82 |
| 67 | 89 | | |
| 68 | 90 | 0.9 | 7.41 |
| 69 | 91 | 0.02 | 0.5 |
| 70 | 92 | 0.07 | 0.48 |
| 71 | 93 | 1.2 | 8.3 |
| 72 | 31 | 0.68 | 13 |
| 73 | 94 | 0.13 | 2.19 |
| 74 | 113 | 5.21 | 13.91 |
| 75 | 96 | 0.09 | 4.05 |
| 76 | 97 | 0.04 | 2.15 |
| 77 | 98 | 0.02 | 5.65 |
| 78 | 99 | 0.11 | 2.47 |
| 79 | 100 | 11.73 | 22.71 |
| 80 | 26 | 0.07 | 0.36 |
| 81 | 37 | 0.5 | 7.54 |
| 82 | 127 | | |
| 83 | 128 | 3.35 | 5.69 |
| 84 | 129 | 3.505 | 6.635 |
| 85 | 130 | 0.12 | 2.54 |
| 86 | 131 | 2.01 | 15.52 |
| 87 | 132 | 12.34 | 13.86 |
| 88 | 133 | 17.25 | 16.82 |
| 89 | 134 | | |
| 90 | 135 | 3.87 | 18.05 |
| 91 | 136 | 4.33 | 5.7 |
| 92 | 106 | 4.975 | 9.5 |
| 99 | 120 | 0.77 | 8.35 |
| 100 | 121 | 0.08 | 4.15 |
| 101 | 112 | 2.53 | 15.81 |
| 102 | 114 | 2.07 | 11.26 |
| 103 | 115 | 0.91 | 8.32 |

TABLE L1-continued

| Example No | Compound No. | DM Caco2 A to B | DM Caco2 B to A |
|---|---|---|---|
| 104 | 116 | 4.18 | 17.53 |
| 105 | 117 | 6.18 | 10.53 |
| 106 | 118 | 0.07 | 1.67 |
| 107 | 119 | 0.07 | 1.91 |
| 109 | 123 | 3.18 | 9.88 |
| 110 | 137 | 0.98 | 11.37 |
| 112 | 139 | 0.99 | 12.98 |
| 113 | 124 | 0.08 | 7.35 |
| 114 | 126 | 0.01 | 0.03 |
| 115 | 140 | 0.04 | 0.12 |
| 116 | 141 | 0.05 | 0.08 |
| 117 | 142 | 0.02 | 0.07 |
| 120 | 145 | 0.2 | 8.475 |
| 121 | 146 | 0.06 | 7.15 |
| 129 | 111 | 0.625 | 11.22 |
| 131 | 154 | 2.08 | 14.67 |
| 133 | 156 | 0.12 | 0.13 |
| 132 | 155 | 3.06 | 10.35 |
| Reference Ester Compound | | 0.12 | 0.62 |
| 2$^{nd}$ Reference Ester Compound | | 11.97 | 6.74 |
| 3$^{rd}$ Reference Ester Compound | | 5.07 | 8.91 |
| Reference Compound A | | 0.12 | 1.52 |

Example M: Thermodynamic Solubility in pH7 Buffered Solution

The aqueous solubility of compounds over a time of 24 hours was assessed. Solubility was determined at ambient temperature in a 50 mM phosphate buffered pH7 solution with 150 mM NaCl (to achieve isotonicity). Solids were added to the buffered solution in 1.5-mL Eppendorf tubes, vortexed for 1 minute, then agitated for 24 hours in an Eppendorf ThermoMixer C. To determine concentration in solution, the suspensions were centrifuged for 15 min at 15,000 rpm. Supernatants were diluted to a volume of 1 mL with 30:70 v/v acetonitrile:water. All diluted supernatants were analyzed by UPLC using a Waters Acquity UPLC with a PDA UV detector.

TABLE M1

Solubility of Exemplary and Reference Compounds

| Example No. | Compound No. | Sol pH 7 |
|---|---|---|
| 4 | 4 | 1.85 |
| 6 | 6 | 3.02 |
| 13 | 13 | 0.12 |
| 14 | 14 | 0.21 |
| 15 | 15 | 0.26 |
| 21 | 21 | — |
| 36 | 59 | 0.01 |
| 39 | 62 | 0.1 |
| 22 | 46 | 0.45 |
| 53 | 75 | — |
| 27 | 51 | 0.08 |
| 110 | 137 | 0.13 |
| 44 | 66 | — |
| 35 | 58 | 0.02 |
| 43 | 65 | 0.045 |
| 23 | 47 | 0.1 |
| 25 | 49 | 2.03 |
| 24 | 48 | 0.19 |
| 37 | 60 | — |
| 40 | 63 | 0.82 |
| 59 | 81 | 0.06 |
| 57 | 79 | 0.26 |
| 45 | 67 | — |
| 56 | 78 | 0.89 |
| 54 | 76 | 0.37 |
| 55 | 77 | 4.64 |
| 120 | 145 | 2.35 |
| 71 | 93 | 0.62 |
| 75 | 96 | 1.25 |
| 76 | 97 | 6.02 |
| 88 | 133 | 0.24 |
| 83 | 128 | 1.42 |
| 84 | 129 | 0.72 |
| 92 | 106 | 0.08 |
| N/A | Ester Reference Compound | 0.96 |
| N/A | 2$^{nd}$ Ester Reference Compound | 0.01 |
| N/A | 3$^{rd}$ Ester Reference Compound | 1.38 |

Example N: Stability in pH2 and pH7 Buffered Solutions

The aqueous stability of compounds over a time of 24 hours at 40° C. was assessed. Stability was determined in 50 mM phosphate buffered solutions at both pH2 and pH7, with 150 mM NaCl (to achieve isotonicity). 3-5 mg of solid compounds were added to 7 mL scintillation vials. Acetonitrile was added to each vial to produce a 1 mg/ml, stock solution. Stock solutions were diluted to 50 µg/mL in either pH2 or pH7 phosphate buffer, to a volume of 1 mL. For each compound and pH condition, 50 µg/mL samples were prepped in duplicate. One sample was placed on the UPLC tray at 40° C. for analysis and the second sample was placed in a 40° C. oven for storage. Sample preps for each compound were offset by 40 minutes to account for run time on UPLC.

Samples in the UPLC tray were analyzed by UPLC using a Waters Acquity UPLC with a PDA UV detector. Concentration timepoints were measured at 0, 3, 6, 9, and 12 hrs. After 24 hrs, samples in the 40° C. oven were removed and analyzed by UPLC.

Figure 2:
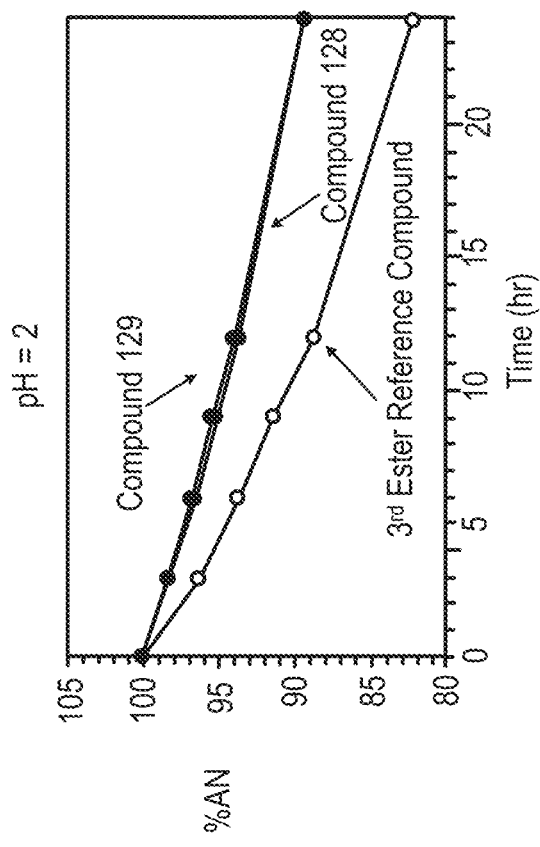
FIG. 2: Shows the Stability of Compound 128, Compound 129, Ester Reference Compound, $2^{nd}$ Ester Reference Compound, and $3^{rd}$ Ester Reference Compound.
Figure 2:
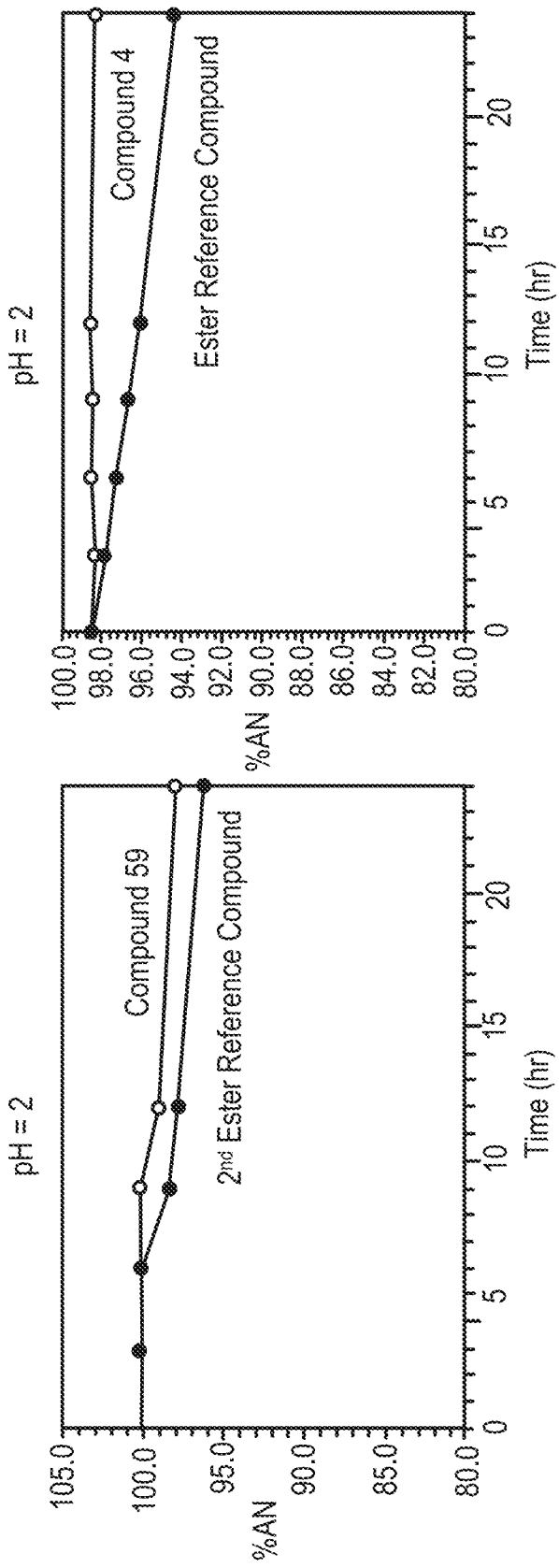

The results for exemplary compounds are summarized in the Tables N1 and N2 below and also presented in FIG. 2. In FIG. 2, % AN stands for % area normalized. That is. % AN is the area of the compound peak relative to the sum of areas of all the peaks in the UPLC chromatogram. For example, if there were two peaks, compound peak with an area of 9 and another peak with an area of 1, then the % AN of the compound peak would be 90%.

TABLE N1

Stability of exemplary and reference compounds at pH2.

| | Compound 129 of Example 84 | Compound 128 of Example 83 | $3^{rd}$ Ester Reference Compound | Compound 59 of Example 36 | $2^{nd}$ Ester Reference Compound | Compound 4 of Example 4 | Ester Reference Compound |
|---|---|---|---|---|---|---|---|
| 0 hr | 100.0 | 100.0 | 100.0 | 100.0 | 100.0 | 98.5 | 98.5 |
| 3 hr | 98.4 | 98.3 | 96.3 | 100.0 | 100.0 | 98.3 | 97.8 |
| 6 hr | 96.9 | 96.7 | 93.8 | 100.0 | 100.0 | 98.5 | 97.3 |
| 9 hr | 95.5 | 95.2 | 91.5 | 100.0 | 98.3 | 98.4 | 96.7 |
| 12 hr | 94.0 | 93.8 | 88.7 | 98.9 | 97.7 | 98.5 | 96.1 |
| 24 hr | 89.4 | 89.3 | 82.1 | 97.9 | 96.2 | 98.3 | 94.4 |

All values listed are % AN values.

TABLE N2

Stability of exemplary and reference compounds as pH2 and pH7.

| Compound No. | pH2 Stability 24 h % AN | pH7 Stability 24 h % AN |
|---|---|---|
| $3^{rd}$ Ester Reference Compound | 82 | 79 |
| 4 | 98 | 97 |
| 6 | 100 | 100 |
| 13 | 98 | 97 |
| 14 | 97 | 97 |
| 15 | 98 | 97 |
| 21 | 0 | 92 |
| 46 | 4 | 8 |
| 47 | 1 | 3 |
| 48 | 100 | 99 |
| 49 | 97 | 94 |
| 51 | 98 | 97 |
| 58 | 2 | 7 |
| 59 | 98 | 93 |
| 60 | 0 | 0 |
| 62 | 61 | 10 |
| 63 | 3 | 0 |
| 65 | 90 | 80 |
| 66 | 2 | 0 |
| 67 | 95 | 91 |
| 75 | 0 | — |
| 76 | 92 | 91 |
| 77 | 98 | 95 |
| 78 | 90 | 0 |
| 79 | 88 | 77 |
| 81 | 100 | 98 |
| 93 | 94 | 75 |
| 96 | 96 | 95 |
| 97 | 98 | 85 |
| 106 | 100 | 91 |
| 128 | 89 | 78 |
| 129 | 89 | 78 |
| 133 | 95 | 98 |
| 137 | 80 | 97 |
| 145 | 93 | 0 |

Example O: Monkey Pharmacokinetics Assay (Solid/Suspension)

Ester Reference Compound, Compound 4, Compound 128 and Compound 129 were dosed orally as tablets to male and/or female cynomolgus monkeys (n=3/group) at 100 mg-eq fixed in 4% crospovidone; 1% magnesium stearate and 45% cellulose; $3^{rd}$ Ester Reference Compound by oral gavage as a suspension at 100 mg-eq fixed in 1% poloxamer 188; 99% water; Compounds 13-15, Compound 46. Compounds 4849, Compounds 58-59, Compounds 62-63, Compound 76, Compound 79, Compound 93 and Compound 106 at 100 mg-eq fixed and Compound 65 at 20 mg-eq fixed by oral gavage as a suspension in 0.5% methylcellulose 0.1% polysorbate 80; 99.4% water. Blood samples were collected into pre-chilled collection tubes containing $K_2$EDTA with dichlorvos (2 mM final concentration with blood added) and processed to plasma at 10 timepoints over a span of pre-dose to 24 h post-administration. Plasma samples were subject to protein precipitation with a 12.5-fold volume of methanol, vortexed and centrifuged. Supernatants were transferred and evaporated to dryness under nitrogen and reconstituted with 5% acetonitrile in water. Separation was achieved on a Phenomenex Synergi Polar-RP column, a mobile phase A of 10 mM ammonium formate with 0.1% formic acid in water and a mobile phase B of 0.1% formic acid in acetonitrile with a step-wise linear gradient from 5 to 95% mobile phase B. An LC-MS/MS method was used to measure the concentrations of the Reference Compound A and either Ester Reference Compound, $3^{rd}$ Ester Reference Compound, Compound 4, Compounds 13-15, Compound 46, Compounds 48-49, Compounds 58-59, Compounds 62-63, Compound 65, Compound 76, Compound 79, Compound 93, Compound 106, Compound 128 or Compound 129 in plasma. Data for Reference Compound A following oral administration of either Ester Reference Compound, $3^{rd}$ Ester Reference Compound, Compound 4, Compounds 13-15, Compound 46, Compounds 48-49, Compounds 58-59. Compounds 62-63, Compound 65. Compound 76, Compound 79, Compound 93, Compound 106, Compound 128 or Compound 129 is tabulated below.

TABLE O1

PK Data for Exemplary and Reference Compounds

| Compound No: | Oral Dose mg/kg | Oral Dose (mg-eq Reference Compound A) | Reference Compound A $C_{max}$ (nM) | Reference Compound A $AUC_{inf}$ (nM.h) | Reference Compound A F %[a] |
|---|---|---|---|---|---|
| Ester Reference Compound | 29 | 100 | 5540 | 27100 | 18 |
| 3rd Ester Reference Compound | 33 | 100 | 15800 | 45000 | 32 |
| 4 | 32 | 100 | 10600 | 29500 | 19 |
| 14 | 40 | 100 | 8640 | 50000 | 27 |
| 65 | 8 | 20 | 4490 | 12500 | 37 |
| 128 | 38 | 100 | 13600 | 65500 | 41 |
| 129 | 46 | 100 | 27400 | 87400 | 51 |

[a]based on reference compound A mg-eq/kg dose; using IV data from 1 mg/kg dose of reference compound A.

TABLE O2

F % for Additional Exemplary Compounds

| Compound No. | Cyno F % suspension (unless noted) |
|---|---|
| 13 | 10 |
| 15 | 18 |
| 46 | 30 |
| 48 | 12 |
| 49 | 6 |
| 58 | 6 |
| 59 | 5 |
| 62 | 18 |
| 63 | 12 |
| 76 | 34 |
| 79 | 8 |
| 93 | 47 |
| 106 | 13 |

All references, including publications, patents, and patent documents are incorporated by reference herein, as though individually incorporated by reference. The present disclosure provides reference to various embodiments and techniques. However, it should be understood that many variations and modifications may be made while remaining within the spirit and scope of the present disclosure. The description is made with the understanding that it is to be considered an exemplification of the claimed subject matter and is not intended to limit the appended claims to the specific embodiments illustrated.

The invention claimed is:

1. A compound of the following formula:

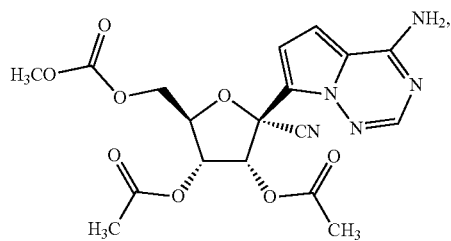

or a pharmaceutically acceptable salt thereof.

2. A pharmaceutical composition comprising one or more pharmaceutically acceptable excipients and the compound of claim 1, or a pharmaceutically acceptable salt thereof.

3. The pharmaceutical composition of claim 2, wherein the pharmaceutical composition is formulated for oral administration.

4. A method for treating a coronavirus infection in a human in need thereof, wherein the method comprises administering to the human a therapeutically effective amount of the compound of claim 1, or a pharmaceutically acceptable salt thereof.

5. The method of claim 4, wherein the coronavirus infection is a zoonotic cornavirus infection.

6. The method of claim 4, wherein the coronavirus infection is a severe acute respiratory syndrome coronavirus 2 (SARS-CoV-2) infection.

7. The method of claim 4, wherein the method comprises orally administering to the human a therapeutically effective amount of the compound of claim 1, or a pharmaceutically acceptable salt thereof.

8. The method of claim 4, wherein the method further comprises administering to the human a therapeutically effective amount of at least one additional therapeutic agent or prophylactic agent.

9. A compound of the following formula:

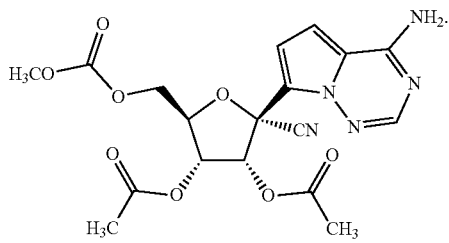 [SMILES: COC(=O)OC[C@H]1O[C@@](C#N)(c2ccc3c(N)ncnn23)[C@H](OC(C)=O)[C@@H]1OC(C)=O]

10. A pharmaceutical composition comprising one or more pharmaceutically acceptable excipients and the compound of claim 9.

11. The pharmaceutical composition of claim 10, wherein the pharmaceutical composition is formulated for oral administration.

12. A method for treating a coronavirus infection in a human in need thereof, wherein the method comprises administering to the human a therapeutically effective amount of the compound of claim 9.

13. The method of claim 12, wherein the coronavirus infection is a zoonotic coronavirus infection.

14. The method of claim 12, wherein the coronavirus infection is a severe acute respiratory syndrome coronavirus 2 (SARS-CoV-2) infection.

15. The method of claim 12, wherein the method comprises orally administering to the human a therapeutically effective amount of the compound of claim 9.

16. The method of claim 12, wherein the method further comprises administering to the human a therapeutically effective amount of at least one additional therapeutic agent or prophylactic agent.

* * * * *

UNITED STATES PATENT AND TRADEMARK OFFICE
CERTIFICATE OF CORRECTION

PATENT NO. : 11,851,438 B2
APPLICATION NO. : 18/117878
DATED : December 26, 2023
INVENTOR(S) : Mark J. Bartlett et al.

Page 1 of 1

It is certified that error appears in the above-identified patent and that said Letters Patent is hereby corrected as shown below:

In the Claims

Column 336, Line 5, Claim 5, delete "cornavirus" and insert --coronavirus--.

Signed and Sealed this
Twenty-sixth Day of November, 2024

Katherine Kelly Vidal
*Director of the United States Patent and Trademark Office*